(12) United States Patent
Han et al.

(10) Patent No.: US 12,416,001 B2
(45) Date of Patent: Sep. 16, 2025

(54) NUCLEOBASE EDITORS AND METHODS OF USE THEREOF

(71) Applicant: Ohio State Innovation Foundation, Columbus, OH (US)

(72) Inventors: Renzhi Han, Columbus, OH (US); Li Xu, Bedford, MA (US); Yandi Gao, Powell, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 629 days.

(21) Appl. No.: 17/799,440

(22) PCT Filed: Feb. 12, 2021

(86) PCT No.: PCT/US2021/017868
§ 371 (c)(1),
(2) Date: Aug. 12, 2022

(87) PCT Pub. No.: WO2021/163492
PCT Pub. Date: Aug. 19, 2021

(65) Prior Publication Data
US 2023/0116627 A1    Apr. 13, 2023

Related U.S. Application Data

(60) Provisional application No. 62/976,590, filed on Feb. 14, 2020.

(51) Int. Cl.
*C12N 15/00* (2006.01)
*C12N 9/22* (2006.01)
(Continued)

(52) U.S. Cl.
CPC ............ *C12N 15/102* (2013.01); *C12N 9/22* (2013.01); *C12N 9/78* (2013.01); *C12N 15/11* (2013.01);
(Continued)

(58) Field of Classification Search
None
See application file for complete search history.

(56) References Cited

U.S. PATENT DOCUMENTS

2018/0127780 A1    5/2018  Liu et al.
2018/0237787 A1*   8/2018  Maianti .................. A61P 3/10
(Continued)

FOREIGN PATENT DOCUMENTS

CN         110029096 A      7/2019
CN         110526993 A     12/2019
(Continued)

OTHER PUBLICATIONS

International Searching Authority (ISA/US). International Search Report and Written Opinion, issued n PCT Application No. PCT/US2021/017868 on May 7, 2021. 13 pages.
(Continued)

*Primary Examiner* — Aaron A Priest
(74) *Attorney, Agent, or Firm* — Meunier Carlin & Curfman LLC

(57) ABSTRACT

The present disclosure relates to nucleobase editors and methods of use thereof. Disclosed herein are fusion proteins, systems, and compositions for editing disease-associated mutations and methods of use thereof. In some aspects, disclosed herein is a fusion protein comprising a Cas9 nickase and a nucleotide deaminase, wherein the Cas9 nickase comprises a first amino acid substitution at a position selected from the group consisting of 262, 324, 409, 480, 543, 694, and 1219 when compared to SEQ ID NO: 11, and wherein the Cas9 nickase comprises a second amino acid substitution at a position selected from the group consisting of 1111, 1135, 1218, 1219, 1322, 1335, and 1337 when compared to SEQ ID NO: 11.

15 Claims, 63 Drawing Sheets
Specification includes a Sequence Listing.

(51) Int. Cl.
   *C12N 9/78*   (2006.01)
   *C12N 15/10*  (2006.01)
   *C12N 15/11*  (2006.01)
   *C12N 15/86*  (2006.01)

(52) U.S. Cl.
   CPC .......... *C12N 15/86* (2013.01); *C12N 2310/20* (2017.05); *C12N 2750/14143* (2013.01); *C12N 2800/40* (2013.01); *C12Y 305/04002* (2013.01); *C12Y 305/04005* (2013.01)

(56) References Cited

U.S. PATENT DOCUMENTS

| | | | | |
|---|---|---|---|---|
| 2020/0308571 | A1* | 10/2020 | Joung | C12N 15/102 |
| 2021/0196809 | A1* | 7/2021 | Maianti | A61K 39/00113 |
| 2021/0301269 | A1* | 9/2021 | Sanjana | C12N 15/1082 |
| 2021/0380955 | A1* | 12/2021 | Bryson | A61K 48/0025 |
| 2022/0127594 | A1* | 4/2022 | Gaudelli | C12N 15/1137 |
| 2022/0136012 | A1* | 5/2022 | Gaudelli | C12N 9/78 435/462 |
| 2022/0290121 | A1* | 9/2022 | Joung | C12N 9/78 |
| 2022/0401530 | A1* | 12/2022 | Bryson | C12N 9/22 |

FOREIGN PATENT DOCUMENTS

| | | |
|---|---|---|
| WO | 2018/218166 A1 | 11/2018 |
| WO | 2019/092042 A1 | 5/2019 |
| WO | 2019/120283 A1 | 6/2019 |
| WO | 2019/139645 A2 | 7/2019 |
| WO | 2019/168953 A1 | 9/2019 |
| WO | 2019/217943 A1 | 11/2019 |
| WO | 2019/226953 A1 | 11/2019 |
| WO | 2020/010083 A1 | 1/2020 |
| WO | 2020/028823 B1 | 2/2020 |
| WO | 2020/033083 A1 | 2/2020 |

OTHER PUBLICATIONS

European Patent Office. Extended European Search Report issued in EP Application No. 21753734.9 on Jan. 29, 2024. 15 pages.

* cited by examiner

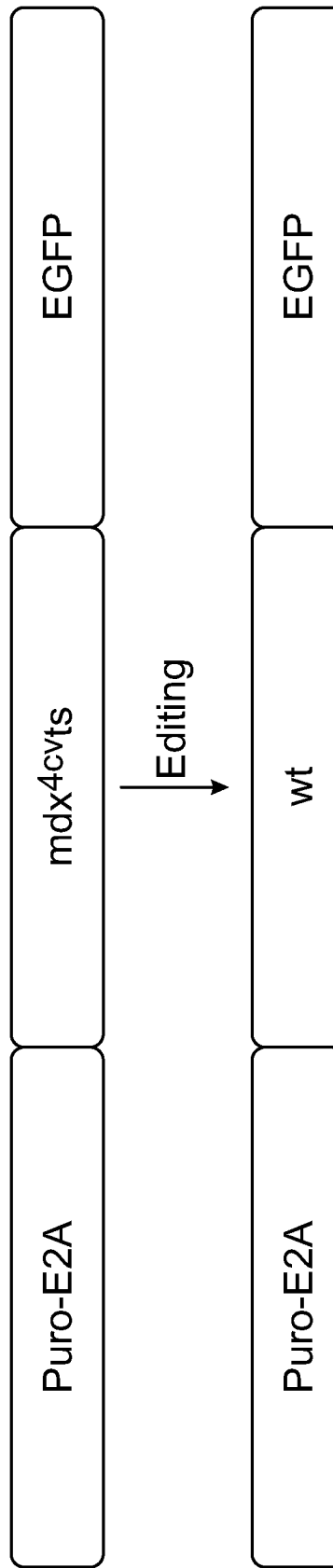

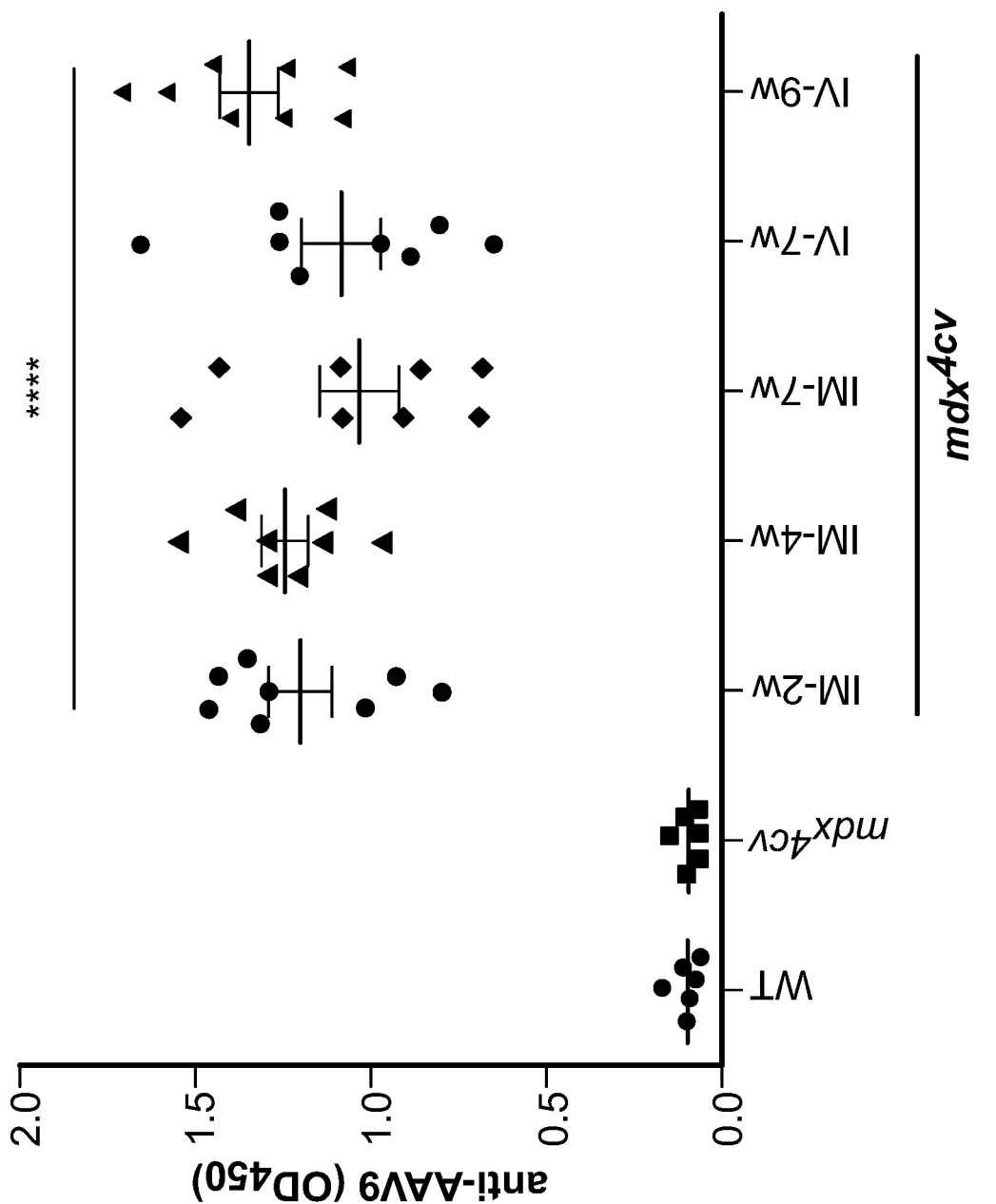

| Mismatches | Number of Targets |
|---|---|
| 1 | 1 |
| 2 | 2 |
| 3 | 55 |
| 4 | 562 |

```
ChrX:  GTTATCTCCTGTTCTGCAGC TGT
Chr16: GTTATCTCCTGCTCTGCAGC AGA
Chr1:  GATATCTCCTGTTCTGCAGG AGA
```

FIG. 28

Mouse1

| | G | T | T | T | A⁴ | T | C⁶ | T | C | C | T | G | T | T | C | T | G | A | C | G | T | G | T |
|---|---|---|---|---|---|---|---|---|---|---|---|---|---|---|---|---|---|---|---|---|---|---|---|
| A | 0.05 | 0.01 | 0.00 | 0.00 | 13.64 | 0.01 | 0.03 | 0.03 | 0.05 | 0.02 | 0.03 | 0.02 | 0.01 | 0.01 | 0.00 | 0.03 | 0.08 | 99.90 | 0.02 | 0.01 | 0.01 | 0.03 | 0.01 |
| C | 0.00 | 0.03 | 0.07 | 0.01 | 0.01 | 0.03 | 97.93 | 0.04 | 99.86 | 99.96 | 0.02 | 0.09 | 0.00 | 0.03 | 0.02 | 99.96 | 0.00 | 0.00 | 99.96 | 0.07 | 99.97 | 0.00 | 0.02 |
| G | 99.95 | 0.00 | 0.00 | 0.00 | 86.34 | 0.00 | 0.19 | 0.00 | 0.02 | 0.00 | 99.97 | 0.01 | 99.97 | 0.00 | 99.96 | 0.00 | 99.92 | 0.08 | 0.00 | 0.05 | 0.00 | 99.96 | 0.00 |
| T | 0.00 | 99.96 | 99.92 | 99.95 | 0.02 | 99.95 | 1.84 | 99.93 | 0.06 | 0.02 | 0.00 | 99.89 | 0.00 | 99.97 | 0.03 | 99.86 | 0.00 | 0.01 | 0.02 | 99.87 | 0.01 | 0.01 | 99.97 |

(PAM indicated over last three columns; arrows at C⁶ and A⁴)

Mouse2

| | G | T | T | T | A⁴ | T | C⁶ | T | C | C | T | G | T | T | C | T | G | A | C | G | T | G | T |
|---|---|---|---|---|---|---|---|---|---|---|---|---|---|---|---|---|---|---|---|---|---|---|---|
| A | 0.07 | 0.01 | 0.00 | 0.00 | 14.04 | 0.02 | 0.04 | 0.03 | 0.04 | 0.03 | 0.02 | 0.02 | 0.01 | 0.01 | 0.01 | 0.01 | 0.07 | 99.90 | 0.01 | 0.04 | 0.01 | 0.03 | 0.01 |
| C | 0.00 | 0.03 | 0.06 | 0.02 | 0.00 | 0.02 | 98.27 | 0.04 | 99.90 | 99.92 | 0.03 | 0.09 | 0.00 | 0.03 | 0.02 | 99.97 | 0.00 | 0.01 | 99.94 | 0.00 | 99.97 | 0.00 | 0.02 |
| G | 99.92 | 0.00 | 0.00 | 0.00 | 85.93 | 0.00 | 0.21 | 0.00 | 0.00 | 0.03 | 0.96 | 0.01 | 99.96 | 0.00 | 99.93 | 0.00 | 99.93 | 0.08 | 0.00 | 99.94 | 0.00 | 99.96 | 0.00 |
| T | 0.00 | 99.95 | 99.94 | 99.95 | 0.02 | 99.96 | 1.48 | 99.92 | 0.05 | 0.02 | 99.88 | 99.88 | 0.00 | 99.96 | 0.02 | 99.82 | 0.00 | 0.02 | 0.04 | 0.02 | 0.89 | 0.01 | 99.97 |

(PAM indicated over last three columns; arrows at C⁶ and A⁴)

Mouse3

| | T | G | T | C | G | A | C | G | T | C | T | T | G | T | C | C | T | C⁶ | T | A⁴ | T | T | G |
|---|---|---|---|---|---|---|---|---|---|---|---|---|---|---|---|---|---|---|---|---|---|---|---|
| A | 0.01 | 0.03 | 0.01 | 0.01 | 0.02 | 99.88 | 0.00 | 0.07 | 0.04 | 0.01 | 0.01 | 0.02 | 0.03 | 0.02 | 0.04 | 0.02 | 0.03 | 0.04 | 0.02 | 7.94 | 0.01 | 0.01 | 0.08 |
| C | 0.02 | 0.00 | 0.09 | 99.96 | 0.00 | 0.01 | 99.95 | 0.00 | 0.15 | 99.98 | 0.03 | 0.02 | 0.00 | 0.09 | 99.94 | 99.97 | 0.07 | 97.74 | 0.05 | 0.01 | 0.06 | 0.06 | 0.00 |
| G | 0.01 | 99.96 | 0.01 | 0.00 | 99.97 | 0.10 | 0.00 | 99.92 | 0.01 | 0.00 | 0.00 | 0.00 | 99.97 | 0.01 | 0.01 | 0.00 | 0.01 | 0.36 | 0.00 | 92.03 | 0.00 | 0.00 | 99.91 |
| T | 99.96 | 0.01 | 99.89 | 0.02 | 0.01 | 0.01 | 0.05 | 0.00 | 99.81 | 0.02 | 99.95 | 99.96 | 0.00 | 99.89 | 0.02 | 0.01 | 99.89 | 1.86 | 99.93 | 0.02 | 99.93 | 99.93 | 0.00 |

Mouse4

| | T | G | T | C | G | A | C | G | T | C | T | T | G | T | C | C | T | C⁶ | T | A⁴ | T | T | G |
|---|---|---|---|---|---|---|---|---|---|---|---|---|---|---|---|---|---|---|---|---|---|---|---|
| A | 0.01 | 0.04 | 0.01 | 0.01 | 0.03 | 99.87 | 0.01 | 0.08 | 0.03 | 0.01 | 0.01 | 0.01 | 0.05 | 0.02 | 0.04 | 0.03 | 0.04 | 0.03 | 0.02 | 19.63 | 0.00 | 0.01 | 0.10 |
| C | 0.02 | 0.00 | 0.12 | 99.96 | 0.00 | 0.01 | 99.93 | 0.00 | 0.17 | 99.97 | 0.04 | 0.03 | 0.00 | 0.10 | 99.94 | 99.93 | 0.06 | 98.51 | 0.02 | 0.01 | 0.06 | 0.04 | 0.00 |
| G | 0.00 | 99.94 | 0.02 | 0.00 | 99.95 | 0.10 | 0.00 | 99.91 | 0.01 | 0.00 | 0.00 | 0.00 | 99.95 | 0.01 | 0.00 | 0.00 | 0.00 | 0.19 | 0.01 | 80.32 | 0.00 | 0.00 | 99.89 |
| T | 99.96 | 0.01 | 99.84 | 0.03 | 0.02 | 0.02 | 0.06 | 0.01 | 99.79 | 0.02 | 99.95 | 99.96 | 0.00 | 99.87 | 0.02 | 0.04 | 99.89 | 1.28 | 99.96 | 0.04 | 99.94 | 99.95 | 0.00 |

FIG. 28 (Cont'd)

```
SMN1 Exon7:  GGTTTCAGACAAAATCAAAAAGAAGGAAGGTGCTCACATTCCTTAAATTAAGGA
                  6                                36
SMN2 Exon7:  GGTTTTAGACAAAATCAAAAAGAAGGAAGGTGCTCACATTCCTTAAATTAAGGA gRNA1;  GTGCTCACATTCCTTAAATTA AGG
gRNA2;  gGCTCACATTCCTTAAATTAA GGA
```

NUCLEOBASE EDITORS AND METHODS OF USE THEREOF

CROSS-REFERENCE TO RELATED APPLICATIONS

This application is a national stage application filed under 35 U.S.C. § 371 of PCT/US2021/017868, filed Feb. 12, 2021, which claims the benefit of U.S. Provisional Application No. 62/976,590, filed Feb. 14, 2020, which are expressly incorporated herein by reference.

STATEMENT REGARDING FEDERALLY SPONSORED RESEARCH

This invention was made with government support under Grant No. R01 HL116546 awarded by the National Institutes of Health. The government has certain rights in the invention.

FIELD

The present disclosure relates to nucleobase editors and methods of use thereof.

BACKGROUND

Many genetic diseases arise from single nucleotide alterations. Duchenne muscular dystrophy (DMD) is a fatal genetic muscle disease affecting approximately 1 in ~5000 male births worldwide, which is caused by mutations in the DMD gene. Most of the DMD mutations are due to deletions or duplications with over 500 point mutations accounting for ~10% of the cases. DMD codes for the dystrophin protein, a cytoskeletal protein that functions in the muscle force transmission and sarcolemmal stability of muscle fibers. Loss of dystrophin leads to progressive muscle weakness and wasting, loss of ambulation, respiratory impairment, cardiomyopathy, and eventual death. Previous studies showed that exon deletion through CRISPR genome editing can restore dystrophin expression and function. Although promising, this strategy has safety concerns as it relies on repair of the double strand DNA break (DSB) created by CRISPR/Cas9, which can cause unwanted large deletion and even chromosomal rearrangement.

Therefore, what is needed are compositions for precise correction of disease-associated mutations.

SUMMARY

Disclosed herein are fusion proteins, systems, and compositions for editing disease-associated mutations and methods of use thereof.

In some aspects, disclosed herein is a fusion protein comprising a Cas9 nickase and a nucleotide deaminase, wherein the Cas9 nickase comprises a first amino acid substitution at a position selected from the group consisting of 262, 324, 409, 480, 543, 694, and 1219 when compared to SEQ ID NO: 11, and wherein the Cas9 nickase comprises a second amino acid substitution at a position selected from the group consisting of 1111, 1135, 1218, 1219, 1322, 1335, and 1337 when compared to SEQ ID NO: 11.

In some embodiments, the first amino acid substitution is selected from the group consisting of A262T, R324L, S409I, E480K, E543D, M694I, and E1219V when compared to SEQ ID NO: 11. In some embodiments, the second amino acid substitution is selected from the group consisting of L1111R, D1135V, G1218R, E1219F, A1322R, R1335V, R1335Q, R1335E, and T1337R when compared to SEQ ID NO: 11.

In some embodiments, the Cas9 nickase comprises the amino acid sequence selected from the group consisting of SEQ ID NOs: 12-20.

In some embodiments, the Cas9 nickase when in conjunction with a bound guide RNA (gRNA) specifically binds to a target nucleic acid sequence.

In some embodiments, the Cas9 nickase recognizes a NG protospacer adjacent motif (PAM) sequence.

In some embodiments, the nucleotide deaminase is a cytidine deaminase or an adenine deaminase. In some embodiments, the adenine deaminase is a dimeric adenine deaminase or a monomeric adenine deaminase domain. In some embodiments, the monomeric adenine deaminase comprises amino acid substitutions A56G and V82G when compared to SEQ ID NO: 47. In some embodiments, the adenine deaminase comprises the amino acid sequence set forth in SEQ ID NO: 22 or 23.

In some aspects, disclosed herein is a system for base editing comprising:
a first nucleotide sequence encoding a N-terminal portion of a Cas9 nickase fused at its C-terminus to an intein-N; and
a second nucleotide sequence encoding an intein-C fused to the N-terminus of a C-terminal portion of the Cas9 nickase;
wherein the first nucleotide sequence further comprises a nucleotide sequence encoding a nucleotide deaminase fused to the N-terminus of the N-terminal portion of the Cas9 nickase,
wherein the Cas9 nickase comprises a first amino acid substitution at a position selected from the group consisting of 262, 324, 409, 480, 543, 694, and 1219 when compared to SEQ ID NO: 11, and
wherein the Cas9 nickase comprises a second amino acid substitution at a position selected from the group consisting of 1111, 1135, 1218, 1219, 1322, 1335, and 1337 when compared to SEQ ID NO: 11.

In some embodiments, the N-terminal portion of the Cas9 nickase comprises the amino acid positions 2-573 of the amino acid sequence selected from the group consisting of SEQ ID NOs: 12-20 and the C-terminal portion of the Cas9 nickase comprises the amino acid positions 574-1368 of the amino acid sequence selected from the group consisting of SEQ ID NOs: 12-20.

In some embodiments, the first nucleotide sequence or the second nucleotide sequence further comprises a nucleotide encoding a guide RNA (gRNA).

In some aspects, disclosed herein is a composition comprising:
a first recombinant adeno-associated virus (AAV) particle comprising a first nucleotide sequence encoding a N-terminal portion of a Cas9 nickase fused at its C-terminus to an intein-N; and
a second recombinant AAV particle comprising a second nucleotide sequence encoding an intein-C fused to the N-terminus of a C-terminal portion of the Cas9 nickase;
wherein the first nucleotide sequence further comprises a nucleotide sequence encoding a nucleotide deaminase fused to the N-terminus of the N-terminal portion of the Cas9 nickase,
wherein the Cas9 nickase comprises a first amino acid substitution at a position selected from the group consisting of 262, 324, 409, 480, 543, 694, and 1219 when compared to SEQ ID NO: 11, and wherein the Cas9 nickase comprises a second amino acid substitution at a position selected from the group consisting of 1111, 1135, 1218, 1219, 1322, 1335, and 1337 when compared to SEQ. ID NO: 11.

In some embodiments, the first nucleotide sequence comprises the sequence as set forth in SEQ ID NO: 3 or SEQ ID NO: 5. In some embodiments, the second nucleotide sequence comprises the sequence as set forth in SEQ ID NO: 4 or SEQ ID NO: 6.

In some aspects, disclosed herein is a method of treating a genetic disease or disorder in a subject, comprising administering a therapeutically effective amount of the composition of any preceding aspect. In some embodiments, the genetic disease or disorder is Duchenne muscular dystrophy, dysferlinopathy, or spinal muscular atrophy. In some embodiments, the genetic disease or disorder is due to a point mutation in a causative gene from a G:C pair to an A:T pair.

BRIEF DESCRIPTION OF THE DRAWINGS

The accompanying figures, which are incorporated in and constitute a part of this specification, illustrate several aspects described below.

FIGS. 1a-1e show in vitro studies of mdx$^{4cv}$ mutation correction using ABE-NG. FIG. 1a shows genomic DNA, encoded amino acids and guide RNA with PAM (highlighted in blue) sequences at the stop codon mutation site (red). FIG. 1b shows the reporter construct containing a puromycin resistance cassette fused with E2A peptide, mdx$^{4cv}$ target sequence and ATG-removed. EGFP. Correction of the stop codon within the target sequence would allow EGFP expression. FIG. 1c shows fluorescence microscopy images of HEK293 cells transfected with reporter alone, or reporter, gRNA and one of the base editors (ABEmax, ABE-x and ABE-NG). Scale bar: 500 µm. FIGS. 1d-1e shows flow cytometry analysis of EGFP expression in HEK293 cells transfected as described in FIG. 1c. *$p<0.05$; ****$p<0.0001$ (one-way ANOVA). The sequences in FIG. 1 are GAACAGCTGCAGAACAGGAGATAACAG (SEQ ID NO: 620), GTTASTCTCCTGTTCTG CAGCTGT (SEQ ID NO: 621).

FIGS. 2a-2f show measurements of the base editing efficiencies of different ABE variants on a NGG-PAM site and five different sites with NGH or GAT PAM. The gRNA sequences are listed on the top of each graph with the PAM sequences in red and the target adenines in blue ns, not significant; $p<0.01$; *$p<0.001$; ****$p<0.0001$ (one-way ANOVA). The sequences in FIG. 2 are ATGACAGGCAGGGGCACCGCGG (SEQ ID NO: 622), GAGCGAGCAGCGTCTTCGAGAGT (SEQ ID NO: 623), GCAGACGGCA GTCACTAGGGGGC (SEQ ID NO: 624), GTCGCAGGACAGCTTTTCCTAGA (SEQ ID NO: 625), GGGAAGCTGGGTGAATGGAGCGA (SEQ ID NO: 626), GATCCAGGT GCTGCAGAAGGGAT (SEQ ID NO: 627).

FIG. 3a shows schematics of the adenine deaminase domain used in ABE-NG editors. FIG. 3b shows quantification of the editing efficiency of different ABE-NG variants with modified TadA* domain at the mdx$^{4cv}$ target site. **$p<0.0001$ (one-way ANOVA). FIG. 3c shows the number of off-target RNA editing events in Neuro-2a cells transfected with different ABE-NG variants. *$p<0.05$; *$p<0.001$ (one-way ANOVA). FIG. 3d shows quantification of the off-target RNA editing (A-to-I) activities on four RNA adenines previously identified as being efficiently modified by ABEmax in HEK293 cells. **$p<0.0001$ (one-way ANOVA).

FIG. 5a shows schematics showing the two halves of intein-split ABEmax. The TadA-TadA* was fused with Npu intein N-terminal fragment and SpCas9 nickase (nSpCas9) was fused with Npu intein C-terminal fragment. FIG. 5b shows genomic DNA PCR analysis of HEK293 cells at 5 days after transfection with S2-gRNA and different versions of ABEs.

FIG. 6a shows schematics of the intein split ABE-NG. The N-terminal and C-terminal intein sequences reconstitute the full-length protein when co-expressed within cells. FIG. 6b shows Western blot analysis of HEK293 cell lysates transfected with different versions of ABEs. FIG. 6c shows fluorescence microscopy images of HEK293 cells transfected with reporter alone, or reporter, gRNA and one of the base editors (ABE-NG, split_v1 N+C or Split_v2 N+C). Scale bar: 500 µm. FIG. 6d shows flow cytometry analysis of EGFP expression in HEK293 cells transfected as described in FIG. 6c. FIG. 6e shows Western blot analysis of HEK293 cell lysates transfected with full-length iABE-NGA, Gp41-1 or Npu split of iABE-NGA. FL, the full-length iABE-NGA band; N, the N-terminal fragment of the iABE-NGA. FIG. 6f shows densitometry quantification of the Western blot data shown in FIG. 6e, FIG. 6g shows the assembly efficiency of the Gp41-1 and Npu split of iABE-NGA (defined as the percentage of the full-length iABE-NGA bands). FIG. 6h shows quantification of the editing efficiency of full-length iABE-NGA, Gp41-1 split and Npu split of iABE-NGA at the mdx$^{4cv}$ target site, Npu Split_1g is same as Npu Split except that only the C-terminal construct carries the gRNA. ns, not significant; *$p<0.05$; *$p<0.001$; **$p<0.0001$; (one-way ANOVA).

FIG. 8a shows dystrophin and laminin-α2 co-immunostaining of heart sections from WT and mdx$^{4cv}$ mice (10 weeks or 10 months of age) with or without tail vein injection of AAV9-iNG (a total of $1\times10^{14}$ vg/kg, 1:1 of the N and C-terminal halt). Scale bar: 100 µm. FIGS. 8b-8d show quantification of dystrophin-positive fibers in the heart (FIG. 8b), gastrocnemius (GA, FIG. 8c) and diaphragm (Diaph, FIG. 8d) muscles. 10 w, 10 weeks old; 10 m, 10 months old. $p<0.01$; **$p<0.0001$ (Student's t-test). FIG. 8e shows Western blot analysis of heart homogenates from 10-week-old mice with anti-dystrophin, Cas9 and Gapdh antibodies. The WT muscle lysates were loaded at 5 µg/lane while the mdx$^{4cv}$ muscle lysates were loaded at 25 µg/lane. FIG. 8f shows densitometry quantification of Western blot data shown in FIG. 8e. *p<0.05 (one-way ANOVA). FIG. 8g shows Western blot analysis of heart homogenates from 10-month-old mice with anti-dystrophin and Gapdh antibodies. FIG. 8h shows densitometry quantification of Western blot data in FIG. 8g, p<0.01; p<0.0001 (one-way ANOVA). FIG. 8i shows representative sequencing trace of dystrophin transcripts of WT and mdx$^{4cv}$ mouse hearts (10 weeks or 10 months old) with or without AAV9-iNG treatment. FIGS. 8j and 8k show quantification of the targeted T-to-C editing efficiency in the mdx$^{4cv}$ mouse hearts (FIG. 8j, 10 weeks; FIG. 8k, 10 months) as assayed by sequencing of dystrophin transcripts. **p<0.0001 (Student's t-test).

FIG. 10 shows stitched large images showing dystrophin and laminin-α2 immunostaining of the entire heart sections of a control mdx$^{4cv}$ mouse at 10 weeks of age. Scale bars: 0.5 mm.

FIG. 24a shows immunofluorescence staining of dystrophin in diaphragm and gastrocnemius muscles of WT and mdx$^{4cv}$ mice with or without systemic AAV9-iNG delivery. FIG. 24b shows Western blot of dystrophin expression in gastrocnemius muscles. FIG. 24c shows quantification of Western blot data.

FIGS. 25a-25m show systemic delivery of AAV9-iNG improved histopathology and contractility in mdx$^{4cv}$ mice. FIG. 25a shows trichrome staining of muscle and heart sections showing the extensive fibrosis in diaphragm and gastrocnemius (GA) muscles of mdx$^{4cv}$ mice (10 months of age), which were substantially reduced following systemic AAV9-iNG delivery. The mdx$^{4cv}$ mouse heart had little fibrosis at 10 months of age. Scale bar: 200 µm. FIGS. 25b-25d show quantification of fibrotic area of the diaphragm, gastrocnemius and heart muscles. ns, not significant; *p<0.05; p<0.01; *p<0.001; **p<0.0001 (one-way ANOVA). FIGS. 25e-25h show measurement of CNF in the diaphragm (FIGS. 25e and 25f) and gastrocnemius (FIGS. 25g and 25h) muscles of mdx$^{4cv}$ mice with or without AAV9-iNG treatment at 10 weeks (FIGS. 25e and 25g) or 10 months (FIGS. 25f and 25h) of age (two-tailed, unpaired Student's t-test). FIGS. 25i-25l show muscle fiber size measurement and distribution in diaphragm and gastrocnemius muscles of the mice (WT and mdx$^{4cv}$ with or without AAV9-iNG) at 10 weeks of age. ns, not significant; p<0.01 (one-way ANOVA). FIG. 25m shows tetanic torque measurements of the posterior compartment muscles. *p<0.05; ****p<0.0001 (one-way ANOVA).

FIGS. 26a-26b show average CSA of diaphragm (FIG. 26a) and gastrocnemius (FIG. 26b) muscle fibers. c, d, Distribution of diaphragm (FIG. 26c) and gastrocnemius (FIG. 26d) muscle fiber areas. ns, not significant; *p<0.05 (one-way ANOVA).

FIGS. 27a-27j show host immune response, toxicity and off-target studies of AAV9-iNG therapy in mdx$^{4cv}$ mice. FIGS. 27a and 27b show host immune response to AAV9 capsid and the base editor transgene (anti-Cas9). IM, intramuscular injection; IV, intravenous injection. **p<0.0001 (one-way ANOVA) compared to WT or mdx$^{4cv}$. FIGS. 27c-27e show measurements of serum AST (FIG. 27c), ALT (FIG. 27d) and BUN (FIG. 27e) of mice treated with or without AAV9-iNG. ns, not statistically significant (one-way ANOVA). FIG. 27f shows predicted off-target sites with different number of mismatches from the mdx$^{4cv}$ target gRNA, and the sequences of two most similar off-target sites located on chromosome 16 and 1, respectively. FIGS. 27g and 27h show quantification of deep sequencing reads of the genomic DNA PCR amplicons of the chromosome 16 off-target site (FIG. 27g) or the chromosome 1 off-target site (FIG. 27h) from Neuro-2a cells transfected with ABE-NG, iABE-NGA or control plus the gRNA. ns, not significant (one-way ANOVA). FIG. 27i shows quantification of the $A^4$-to-G editing in mdx$^{4cv}$ mice treated with or without AAV9-iNG. p<0.0001 (student's t-test). FIG. 27j shows quantification of the bystander $C^6$-to-T editing in mdx$^{4cv}$ mice treated with or without AAV9-iNG. *p<0.001 (student's t-test). The sequences in FIG. 27 are GTTATCTCCTGTTCTGCAGCTGT (SEQ ID NO: 621), GTTATCTCCTGCTCTGCAGCAGA (SEQ ID NO: 628), GATATCTCCTGT TCTGCAGGAGA (SEQ ID NO: 629).

FIG. 28 shows off-target activities of AAV9-iNG. The nucleotide frequency at the on-target site of the four mdx$^{4cv}$ mice at 10 months after treatment with AAV9-iNG. The desired edit at $A^4$ is highlighted in green and the bystander $C^6$ edit in red. The sequence in FIG. 28 is GTTATCTCCTGTTCTGCAGCTGT (SEQ ID NO: 621), FIG. 29a shows the number of RNA SNVs in three AAV9-iNG treated mouse hearts after filtering the RNA SNVs in three control mouse hearts. FIG. 29b shows the A-to-I editing rate of all RNA SNVs. FIG. 29c shows the A-to-I editing rate of the common RNA SNVs in the three AAV9-iNG treated mouse hearts.

FIG. 30a shows Sanger sequencing showing that iABE-NGA mediated efficient conversion of A to G at the splice acceptor site of human DMD exon 55. FIG. 30b shows RT-PCR analysis showing that iABE-NGA editing led to skipping of exon 55 in ΔE48-54 DMD-hiPSC-derived cardiomyocytes. The WT, ΔE48-54 (green arrow) and E55 skipped transcript (red arrow) were clearly discernable.

FIG. 31a shows sequences of SMN1 and SMN2 exon 7 with the different nucleotides at position 6 highlighted in red. Two gRNAs were designed to edit A36 to G with the PAM highlighted in purple. FIG. 31b shows RT-PCR analysis of Neuro-2a cells transfected with a SMN2 reporter gene plus or minus the base editors and gRNAs. The exon 7 inclusion (FL) or exclusion (Δ7) transcripts were measured. FIG. 31c shows quantification of the RT-PCR products. p<0.01; p<0.0001; ns, not significant when compared with the control group, using one-way ANOVA with Turkey post test. The sequences in FIG. 31a are GGTTTCAGACAAAATCA AAAAGAAGGAAG-GTGCTCACATTCCTTAAATTAAGGA (SEQ ID NO: 632), GGTTTT AGACAAAATCAAAAAGAAG-GAAGGTGCTCACATTCCTTAAATTAAGGA (SEQ ID NO: 633), GTGCTCACATTCCTTAAATTAAGG (SEQ ID NO: 634), gGCTCACATTCCTTA AATTAAGGA (SEQ ID NO: 635)

DETAILED DESCRIPTION

Figure 1C:
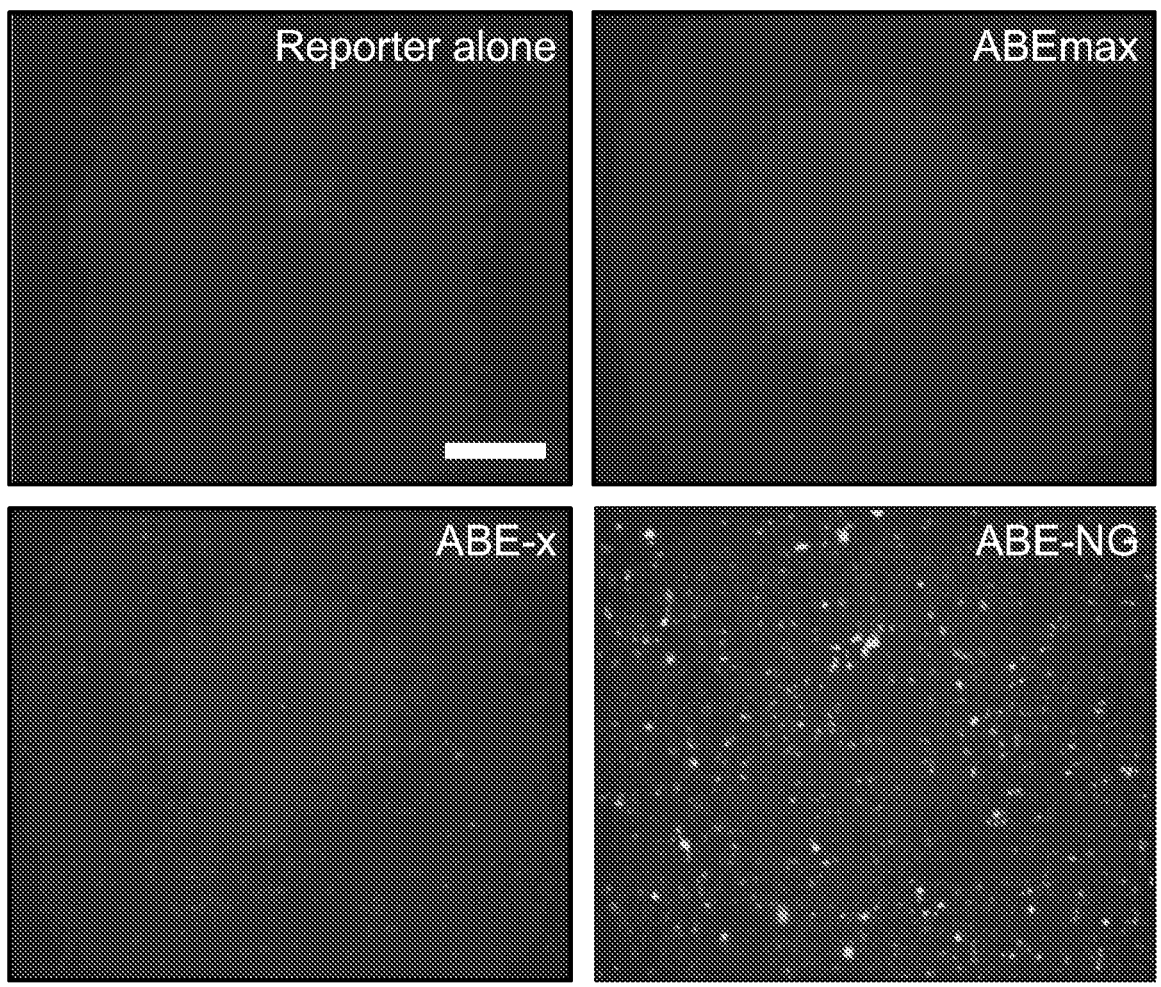

Fusing the CRISPR-Cas9 nickase with nucleobase deaminases (e.g. cytidine or adenine deaminase), a new paradigm-shifting class of genome editing technology, termed "base editors", have recently been developed. DNA base editors, via catalyzing the conversion of one base to another, directly and precisely install point mutations into chromosomal DNA without making DSBs. Therefore, base editing can be developed as promising therapeutics to correct the genetic diseases without DNA cleavage. In particular, the adenine base editors (ABEs) show remarkable fidelity in mouse embryos and rice as compared to cytosine base editors (CBEs), making them highly attractive in therapeutic development. Moreover, nearly half of the point mutations causing human diseases are G-to-A or C-to-T, highlighting the potential of ABEs in correcting a large number of human diseases. In particular, 174 out of 508 pathogenic point mutations for DMD are due to G:C to A:T conversion (Table 5), which can be targeted by ABE editing.

In vivo base editing can correct a custom-made mouse model of Duchenne muscular dystrophy (DMD), which carries a nonsense mutation in exon 20 with a classical 5'-TGG protospacer adjacent motif (PAM) sequence in the noncoding strand for recognition by the Cas9 from *Streptococcus pyogenes* (SpCas9). In silico analysis of the ClinVar database showed that about 42.8% of the 53469 human disease-causing mutations can be potential targets for base editing correction; however, the majority (~72.4%) of these potential targets cannot be suitable for SpCas9 base editing due to the lack of the 5'-NGG PAM sequence within the suitable distance from the mutations. Several variants of SpCas9 have recently been engineered with relaxed PAM (such as xCas9-3.7, SpCas9-NG and ScCas9) and non-G PAM. These enzymes greatly increase the target scope for correcting human mutations. However, their performance to correct genetic mutations in preclinical animal models remains to be determined. Here, the efficacy of correcting a commonly used mouse model of DMD, mdx$^{4cv}$ mice were explored, using NG-targeting base editors.

The present disclosure provides fusion proteins, systems, and compositions for editing disease-associated mutations and uses thereof for treating a disease (for example, Duchenne muscular dystrophy).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

Terminology

Terms used throughout this application are to be construed with ordinary and typical meaning to those of ordinary skill in the art. However, Applicant desires that the following terms be given the particular definition as defined below.

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

The term "Cas9" or "Cas9 nuclease" refers to an RNA-guided nuclease comprising a Cas9 protein, or a fragment thereof (e.g., a protein comprising an active, inactive, or partially active DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. Science 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but not limited to, *S. pyogenes* and *S. thermophiles*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

A "composition" is intended to include a combination of active agent and another compound or composition, inert (for example, a fusion protein, nucleic acid, or virus) or active, such as an adjuvant.

Dystrophinopathies are a group of muscular dystrophies resulting from mutations in the dystrophin gene, located on the short arm of the X chromosome in the Xp21 region (Kunkel et al. 1985; Monaco et al. 1985; Ray et al. 1985). Of these, "Duchenne muscular dystrophy" or "DMD" is the most common dystrophinopathy resulting from complete absence of the dystrophin gene product, the subsarcolemmal protein dystrophin (Hoffman et al. 1987a; Koenig et al. 1987; Hoffman et al. 1988). While dystrophin deficiency can be a primary cause of DMD, multiple secondary pathways are responsible for the progression of muscle necrosis, abnormal fibrosis and failure of regeneration that results in a progressively worsening clinical status. There is evidence supporting oxidative radical damage to myofibers (Rando 2002), inflammation (Spencer and Tidball 2001; Porter et al. 2002), abnormal calcium homeostasis (Allen 2010; Millay 2009), myonuclear apoptosis (Rando 2001b; Sandri et al. 2001; Tews 2002), abnormal fibrosis and failure of regeneration (Rando 2001b; Bernasconi 1995); (Melone 2000; Morrison 2000; Luz 2002). This body of literature has been validated by cross sectional genome-wide approaches that allow an overall analysis of multiple defective mechanisms in DMD (Chen et al. 2000; Porter 2003). The main symptom of DMD is muscle weakness associated with muscle wasting first with the voluntary muscles, e.g., the hips, pelvic area, thighs, shoulders, and calf muscles.

As used herein, the term "effective amount" refers to an amount of a composition necessary or sufficient to realize a desired biologic effect. An effective amount of the composition would be the amount that achieves a selected result, and such an amount could be determined as a matter of routine experimentation by a person skilled in the art. For example, an effective amount of the composition could be that amount necessary for preventing, treating and/or ameliorating Duchenne muscular dystrophy in a subject. The term is also synonymous with "sufficient amount."

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams R. Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, NJ), polyethylene glycol (PEG), and PLURONICS™ (BASF; Florham Park, NJ), To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

A gRNA is a component of the CRISPR/Cas system. A "gRNA" (guide ribonucleic acid) herein refers to a fusion of a CRISPR-targeting RNA (crRNA) and a trans-activation crRNA (tracrRNA), providing both targeting specificity and scaffolding/binding ability for Cas9 nuclease. A "crRNA" is a bacterial RNA that confers target specificity and requires tracrRNA to bind to Cas9, A "tracrRNA" is a bacterial RNA that links the crRNA to the Cas9 nuclease and typically can bind any crRNA. The sequence specificity of a Cas DNA-binding protein is determined by gRNAs, which have nucleotide base-pairing complementarity to target DNA sequences. The native gRNA comprises a Specificity Determining Sequence (SDS), which specifies the DNA sequence to be targeted. At least a portion of the target DNA sequence is complementary to the SDS of the gRNA. For Cas9 to successfully bind to the DNA target sequence, a region of the target sequence is complementary to the SDS of the gRNA sequence and is immediately followed by the correct protospacer adjacent motif (PAM) sequence (e.g., NGG or NG for Cas9 used herein). In some embodiments, an SDS is 100% complementary to its target sequence. In some embodiments, the SDS sequence is less than 100% complementary to its target sequence and is, thus, considered to be partially complementary to its target sequence. For example, a targeting sequence may be 99%, 98%, 97%, 96%, 95%, 94%, 93%, 92%, 91%, or 90% complementary to its target sequence.

The term "linker," as used herein, refers to a chemical group or a molecule linking two molecules or moieties, e.g., two domains of a fusion protein, such as, for example, a Cas9 domain and a nucleic acid editing domain (e.g., a deaminase domain). In some embodiments, a linker joins a gRNA binding domain of an RNA-programmable nuclease, including a Cas9 nuclease domain, and the catalytic domain of a nucleic acid editing protein. In some embodiments, a linker joins a Cas9 and a nucleic acid editing protein. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, Molecular Cloning: A Laboratory Manual (4th ed., Cold Spring Harbor Laboratory Press, Cold Spring Harbor, N.Y. (2012)).

The term "nickase" as used herein, refers to a nuclease that cleaves only a single DNA strand, either due to its natural function or because it has been engineered to cleave only a single DNA strand, Jinek et al., "A programmable dual-RNA-guided DNA endonuclease in adaptive bacterial immunity" Science 337(6096):816-821 (2012) and Cong et at. Multiplex genome engineering using CRISPR/Cas systems Science 339(6121):819-823 (2013).

The term "nucleic acid editing domain," as used herein refers to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain comprises a deaminase (e.g., a cytidine deaminase or an adenine deaminase).

An "adenine deaminase" is an enzyme involved in purine metabolism. It is needed for the breakdown of adenosine from food and for the turnover of nucleic acids in tissues. Its primary function in humans is the development and maintenance of the immune system. An adenine deaminase catalyzes hydrolytic deamination of adenosine (forming inosine, which base pairs as G) in the context of DNA.

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage. For example, Duchenne muscular dystrophy, may result in e.g., a slowing of muscle degeneration, decreased fatigue, increased muscle strength, reduced blood levels of creatine kinase (CK), decreased difficulty with motor skills, decreased muscle fiber deformities, decreased inflammation or fibrotic tissue infiltration in the muscle, stabilization of the progression of the disease (e.g., by halting progressive muscle weakness) etc.

"Therapeutically effective amount" or "therapeutically effective dose" of a composition (e.g. a fusion protein, a nucleic acid, or virus) refers to an amount that is effective to achieve a desired therapeutic result. In some embodiments, a desired therapeutic result is the prevention of Duchenne muscular dystrophy. In some embodiments, a desired therapeutic result is the treatment of Duchenne muscular dystrophy. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, lentiviral vectors, adenoviral vectors, adeno-associated virus vectors, retroviral vectors, and the like.

An "adeno-associated virus" or "AAV" is a virus which infects humans and some other primate species. The wild-type AAV genome is a single-stranded deoxyribonucleic acid (ssDNA), either positive- or negative-sensed. The genome comprises two inverted terminal repeats (ITRs), one at each end of the DNA strand, and two open reading frames (ORFs): rep and cap between the ITRs. The rep ORF comprises four overlapping genes encoding Rep proteins required for the AAV life cycle. The cap ORF comprises overlapping genes encoding capsid proteins: VP1, VP2 and VP3, which interact together to form the viral capsid. VP1, VP2 and VP3 are translated from one mRNA transcript, which can be spliced in two different manners: either a longer or shorter intron can be excised resulting in the formation of two isoforms of mRNAs: a ~2.3 kb- and a ~2.6 kb-long mRNA isoform. The capsid forms a supraniolecular assembly of approximately 60 individual capsid protein subunits into a non-enveloped, T-1 icosahedral lattice capable of protecting the AAV genome. The mature capsid is composed of VP1, VP2, and VP3 (molecular masses of approximately 87, 73, and 62 kDa respectively) in a ratio of about 1:1:10.

The term "nucleic acid" as used herein means a polymer composed of nucleotides, deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22: 1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers.

The term "polypeptide" refers to a compound made up of a single chain of D- or L-amino acids or a mixture of D- and L-amino acids joined by peptide bonds.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g. NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) nucleotide sequence identity is defined as the percentage of amino acids in a candidate sequence that are identical to the nucleotides in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology information (www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=-4, and a comparison of both strands.

The BLAST algorithm also performs a statistical analysis of the similarity between two sequences (see, e.g., Karlin and Altschul (1993) *Proc. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The term "increased" or "increase" as used herein generally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "reduced", "reduce", "reduction", or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

In some aspects, disclosed herein is a fusion protein comprising a Cas9 nickase and a nucleotide deaminase, wherein the Cas9 nickase comprises a first amino acid substitution at a position selected from the group consisting of 262, 324, 409, 480, 543, 694, and 1219 when compared to SEQ ID NO: 11, and wherein the Cas9 nickase comprises a second amino acid substitution at a position selected from the group consisting of 1111, 1135, 1218, 1219, 1322, 1335, and 1337 when compared to SEQ ID NO: 11. In some embodiments, the Cas9 nickase and the nucleotide deaminase are operably linked.

In some embodiments, the first amino acid substitution is selected from the group consisting of A262T, R324L, S409I, E480K, E543D, M694I, and E1219V when compared to SEQ ID NO: 11. In some embodiments, the second amino acid substitution is selected from the group consisting of L1111R, D1135V, G1218R, E1219F, A1322R, R1335V, R1335Q, R1335E, and T1337R when compared to SEQ ID NO: 11.

In some embodiments, the fusion protein comprises a Cas9 nickase fused to a deaminase and further fused to a Uracil DNA glycosylase inhibitor (UGI) domain.

In some embodiments, the Cas9 nickase comprises an amino acid sequence at least 80% identity (at least 80%, at least 85%, at least 90%, at least 95%, at least 96%, at least 97%, at least 98%, at least 99%, or at least 99.5%) to the amino acid sequence selected from the group consisting of SEQ ID NOs: 12-20. In some embodiments, the Cas9 nickase comprises the amino acid sequence selected from the group consisting of SEQ ID NOs: 12-20.

In some embodiments, the Cas9 nickase when in conjunction with a bound guide RNA (gRNA) specifically binds to a target nucleic acid sequence.

In some embodiments, the Cas9 nickase recognizes a NG protospacer adjacent motif (PAM) sequence.

In some embodiments, the nucleotide deaminase is a cytidine deaminase or an adenine deaminase. In some embodiments, the nucleotide deaminase is a cytidine deaminase. In some embodiments, the nucleotide deaminase is an adenine deaminase. In some embodiments, the adenine deaminase is a dimeric adenine deaminase or a monomeric adenine deaminase domain. In some embodiments, the dimeric adenine deaminase comprises an amino acid sequence at least 80% identity (at least 80%, at least 85%, at least 90%, at least 95%, at least 96%, at least 97%, at least 98%, at least 99%, or at least 99.5%) to SEQ ID NOs: 22. In some embodiments, the monomeric adenine deaminase comprises an amino acid sequence at least 80% identity (at least 80%, at least 85%, at least 90%, at least 95%, at least 96%, at least 97%, at least 98%, at least 99%, or at least 99.5%) to SEQ NOs: 23. In some embodiments, the monomeric adenine deaminase comprises amino acid substitutions A56G and V82G when compared to SEQ ID NO: 47. In some embodiments, the adenine deaminase comprises the amino acid sequence set forth in SEQ ID NO: 22 or 23.

In some embodiments, the adenine deaminase is encoded by a nucleotide sequence at least 80% identity (at least 80%, at least 85%, at least 90%, at least 95%, at least 96%, at least 97%, at least 98%, at least 99%, or at least 99.5%) to SEQ ID NO: 41 or 42. In some embodiments, the adenine deaminase is encoded by the nucleotide sequence as set forth in SEQ ID NO: 41 or 42.

In some embodiments, the Cas9 nickase comprising the monomeric adenine deaminase domain has a lower off-target RNA editing activity than a Cas9 nickase comprising a dimeric adenine deaminase domain (e.g., at least 10% lower, at least 20% lower, at least 30% lower, at least 40% lower, at least 50% lower, at least 60% lower, at least 70% lower, at least 80% lower, at least 90% lower, at least 95% lower, at least 99% lower, or at least 2 times lower, at least 3 times lower, at least 4 times lower, at least 5 times lower, at least 6 times lower, at least 7 times lower, at least 8 times lower, at least 9 times lower, at least 10 times lower, at least 20 times lower, at least 50 times lower, at least 100 times lower, at least 150 times lower, at time 200 times lower, at least 500 times lower, or at least 1000 times lower).

In some aspects, disclosed herein is a construct comprising a nucleotide sequence encoding the fusion protein of any preceding aspect. In some embodiments, the construct further comprises a promoter operably linked to the nucleotide sequence, wherein the promoter is a CMV promoter. Accordingly, in some embodiments, the nucleotide sequence of any preceding aspect is at least 80% identity (at least 80%, at least 85%, at least 90%, at least 95%, at least 96%, at least 97%, at least 98%, at least 99%, or at least 99.5%) to SEQ ID NO: 1 or SEQ ID NO: 2.

In some aspects, disclosed herein is a system for base editing comprising:
  a first nucleotide sequence encoding a N-terminal portion of a Cas9 nickase fused at its C-terminus to an intein-N; and
  a second nucleotide sequence encoding an intein-C fused to the N-terminus of a C-terminal portion of the Cas9 nickase;
  wherein the first nucleotide sequence further comprises a nucleotide sequence encoding a nucleotide deaminase fused to the N-terminus of the N-terminal portion of the Cas9 nickase,
  wherein the Cas9 nickase comprises a first amino acid substitution at a position selected from the group consisting of 262, 324, 409, 480, 543, 694, and 1219 when compared to SEQ ID NO: 11, and
  wherein the Cas9 nickase comprises a second amino acid substitution at a position selected from the group consisting of 1111, 1135, 1218, 1219, 1322, 1335, and 1337 when compared to SEQ ID NO: 11.

In some embodiments, the Cas9 nickase comprises an amino acid sequence at least 80% identity (at least 80%, at least 85%, at least 90%, at least 95%, at least 96%, at least 97%, at least 98%, at least 99%, or at least 99.5%) to the amino acid sequence selected from the group consisting of SEQ ID NOs: 12-20. In some embodiments, the Cas9 nickase comprises the amino acid sequence selected from the group consisting of SEQ ID NOs: 12-20.

Accordingly, in some embodiments, the Cas9 nickase is encoded by a nucleotide sequence at least 80% identity (at least 80%, at least 85%, at least 90%, at least 95%, at least 96%, at least 97%, at least 98%, at least 99%, or at least 99.5%) to the nucleotide sequence selected from the group consisting of SEQ ID NOs: 31-39. In some embodiments, the Cas9 nickase is encoded by a nucleotide sequence selected from the group consisting of SEQ ID NOs:

In some embodiments, the N-terminal portion of the Cas9 nickase comprises the amino acid positions 2-560, 2-561, 2-562, 2-563, 2-564, 2-565, 2-566, 2-567, 2-568, 2-569, 2-570, 2-571, 2-572, 2-573, 2-574, 2-575, 2-576, 2-577, 2-578, 2-579, or 2-580 of the amino acid sequence selected from the group consisting of SEQ ID NOs: 12-20. In some embodiments, the C-terminal portion of the Cas9 nickase comprises the amino acid positions 574-1368 of the amino acid sequence selected from the group consisting of SEQ ID NOs: 12-20.

An "intein" is a segment of a protein that is able to excise itself and join the remaining portions (the exteins) with a peptide bond in a process known as protein splicing. Inteins are also referred to as "protein introns." The process of an intein excising itself and joining the remaining portions of the protein is herein termed "protein splicing" or "intein-mediated protein splicing." In some embodiments, an intein of a precursor protein (an intein containing protein prior to intein-mediated protein splicing) comes from two genes. Such intein is referred to herein as a split intein. The inteins used herein can be, for example, Npu DnaE intein, Cfa, DnaE intein or pg41-1 intein. The intein encoded by the DnaE-n gene is herein referred as "intein-N." The intein encoded by the DnaE-c gene is herein referred as "intein-C."

Other intein systems may also be used. For example, a synthetic intein based on the dnaE intein, the Cfa-N and Cfa-C intein pair, has been described (e.g., in Stevens et al., J Am Chem Soc. 2016 Feb. 24; 138(7):2162-5, incorporated herein by reference). Non-limiting examples of intein pairs that may be used in accordance with the present disclosure include: Ssp GyrB intein, Ssp DnaX intein, Ter DnaE3 intein, Ter ThyX intein, Rma DnaB intein and Cne Prp8 intein (e.g., as described in U.S. Pat. No. 8,394,604, incorporated herein by reference.

In some embodiments, the intein-N is a Cfa intein-N or a gp41-1 intein-N. Accordingly, in some embodiments, the intein-N comprises the amino acid sequence of SEQ ID NO: 24 or 26. In some embodiments, the intein-N is encoded by the nucleotide sequence of SEQ ID NO: 43 or 45. Accordingly, the first nucleotide sequence of any preceding aspects comprises SEQ ID NO: 43 or 45.

In some embodiments, the intein-C is a Cfa intein-C or a gp41-1 intein-C. Accordingly, in some embodiments, the intein-C comprises the amino acid sequence of SEQ ID NO: 25 or 27. In some embodiments, the intein-C is encoded by the nucleotide sequence of SEQ ID NO: 44 or 46. Accordingly, the second nucleotide sequence of any preceding aspects comprises SEQ ID NO: 44 or 46.

In some embodiments, the first nucleotide sequence or the second nucleotide sequence further comprises a nucleotide encoding a guide RNA (gRNA).

In some embodiments, the first nucleotide sequence comprises an N terminal portion of SEQ ID NO: 1 or 2. In some embodiments, the first nucleotide comprises a portion of SEQ ID NO: 1 or 2.

In some embodiments, the second nucleotide sequence comprises a C terminal portion of SEQ ID NO: 1 or 2. In some embodiments, the second nucleotide comprises a portion of SEQ ID NO: 1 or 2.

In some aspects, disclosed herein is a composition comprising:
 a first recombinant viral particle comprising a first nucleotide sequence encoding a N-terminal portion of a Cas9 nickase fused at its C-terminus to an intein-N; and
 a second recombinant viral particle comprising a second nucleotide sequence encoding an intein-C fused to the N-terminus of a C-terminal portion of the Cas9 nickase;
 wherein the first nucleotide sequence further comprises a nucleotide sequence encoding a nucleotide deaminase fused to the N-terminus of the N-terminal portion of the Cas9 nickase,
 wherein the Cas9 nickase comprises a first amino acid substitution at a position selected from the group consisting of 262, 324, 409, 480, 543, 694, and 1219 when compared to SEQ ID NO: 11, and
 wherein the Cas9 nickase comprises a second amino acid substitution at a position selected from the group consisting of 1111, 1135, 1218, 1219, 1322, 1335, and 1337 when compared to SEQ ID NO: 11.

In some embodiments, the Cas9 nickase comprises an amino acid sequence at least 80% identity (at least 80%, at least 85%, at least 90%, at least 95%, at least 96%, at least 97%, at least 98%, at least 99%, or at least 99.5%) to the amino acid sequence selected from the group consisting of SEQ ID NOs: 12-20. In some embodiments, the Cas9 nickase comprises the amino acid sequence selected from the group consisting of SEQ ID NOs: 12-20.

Accordingly, in some embodiments, the Cas9 nickase is encoded by a nucleotide sequence at least 80% identity (at least 80%, at least 85%, at least 90%, at least 95%, at least 96%, at least 97%, at least 98%, at least 99%, or at least 99.5%) to the nucleotide sequence selected from the group consisting of SEQ ID NOs: 31-39. In some embodiments, the Cas9 nickase is encoded by a nucleotide sequence selected from the group consisting of SEQ ID NOs: 31-39.

In some embodiments, the N-terminal portion of the Cas9 nickase comprises the amino acid positions 2-560, 2-561, 2-562, 2-563, 2-564, 2-565, 2-566, 2-567, 2-568, 2-569, 2-570, 2-571, 2-572, 2-573, 2-574, 2-575, 2-576, 2-577, 2-578, 2-579, or 2-580 of the amino acid sequence selected from the group consisting of SEQ ID NOs: 12-20. In some embodiments, the C-terminal portion of the Cas9 nickase comprises the amino acid positions 574-1368 of the amino acid sequence selected from the group consisting of SEQ ID NOs: 12-20.

In some embodiments, the intein-N is a Cfa intein-N or a gp41-1 intein-N. Accordingly, in some embodiments, the intein-N comprises the amino acid sequence of SEQ ID NO: 24 or 26. In some embodiments, the intein-N is encoded by the nucleotide sequence of SEQ ID NO: 43 or 45. Accordingly, the first nucleotide sequence of any preceding aspects comprises SEQ ID NO: 43 or 45.

In some embodiments, the intein-C is a Cfa intein-C or a gp41-1 intein-C. Accordingly, in some embodiments, the intein-C comprises the amino acid sequence of SEQ ID NO: 25 or 27. In some embodiments, the intein-C is encoded by the nucleotide sequence of SEQ ID NO: 44 or 46. Accordingly, the second nucleotide sequence of any preceding aspects comprises SEQ ID NO: 44 or 46.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used AAV is a preferred vector because it can infect many cell types and is nonpathogenic to humans. AAV type vectors can transport about 4 to 5 kb and wild type AAV is known to stably insert into chromosome 19. Vectors which contain this site-specific integration property are preferred. In some embodiments, the AAV vector of any preceding aspect further a herpes simplex virus thymidine kinase gene, HSV-tk, and/or a marker gene, such as the gene encoding the green fluorescent protein, GFP.

Accordingly, in some aspects, disclosed herein is a composition comprising:
 a first recombinant adeno-associated virus (AAV) particle comprising a first nucleotide sequence encoding a N-terminal portion of a Cas9 nickase fused at its C-terminus to an intein-N; and
 a second recombinant AAV particle comprising a second nucleotide sequence encoding an intein-C fused to the N-terminus of a C-terminal portion of the Cas9 nickase;
 wherein the first nucleotide sequence further comprises a nucleotide sequence encoding a nucleotide deaminase fused to the N-terminus of the N-terminal portion of the Cas9 nickase,
 wherein the Cas9 nickase comprises a first amino acid substitution at a position selected from the group consisting of 262, 324, 409, 480, 543, 694, and 1219 when compared to SEQ ID NO: 11, and
 wherein the Cas9 nickase comprises a second amino acid substitution at a position selected from the group consisting of 1111, 1135, 1218, 1219, 1322, 1335, and 1337 when compared to SEQ ID NO: 11.

In some embodiments, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus. Typically the AAV and B19 coding regions have been deleted, resulting in a safe, noncytotoxic vector. The AAV ITRs, or modifications thereof, confer infectivity and site-specific integration. U.S. Pat. No. 6,261,834 is herein incorporated by reference for material related to the AAV vector.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

The spacing between promoter elements frequently is flexible, so that promoter function is preserved when elements are inverted or moved relative to one another. Depending on the promoter, it appears that individual elements can function either cooperatively or independently to activate transcription.

The term "promoter" as used herein is defined as a DNA sequence recognized by the synthetic machinery of the cell, or introduced synthetic machinery, required to initiate the specific transcription of a polynucleotide sequence. One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1 alpha (EF-1α). However, other promoter sequences may also be used, including, but not limited to the simian virus 40 (SV40), early promoter, mouse mammary tumor virus (MMTV), human immunodeficiency virus (HIV) long terminal repeat (LTR) promoter, promoter, PGK-1 promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter as well as synthetic protein, such as a CAG promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. In some embodiments, the AAV of any preceding aspect comprises a constitutive promoter or a muscle tissue specific promoter, e.g., a muscle-specific MHP1 promoter.

In some embodiments, the promoter is a CMV promoter. In some embodiments, the CMV promoter comprises the nucleotide sequence of SEQ ID NO: 28. Accordingly, in some embodiments, the first recombinant adeno-associated virus (AAV) particle of any preceding aspect comprises a first nucleotide sequence that is at least 80% identity (at least 80%, at least 85%, at least 90%, at least 95%, at least 96%, at least 97%, at least 98%, at least 99%, or at least 99.5%) to SEQ ID NO: 3 or SEQ ID NO: 5, wherein the second recombinant adeno-associated virus (AAV) particle of any preceding aspect comprises a first nucleotide sequence that is at least 80% identity (at least 80%, at least 85%, at least 90%, at least 95%, at least 96%, at least 97%, at least 98%, at least 99%, or at least 99.5%) to SEQ ID NO: 4 or SEQ ID NO: 6.

In some embodiments, the promoter is a MHP1 promoter. In some embodiments, the MHP1 promoter comprises the nucleotide sequence of SEQ ID NO: 29. Accordingly, in some embodiments, the first recombinant adeno-associated virus (AAV) particle of any preceding aspect comprises a first nucleotide sequence that is at least 80% identity (at least 80%, at least 85%, at least 90%, at least 95%, at least 96%, at least 97%, at least 98%, at least 99%, or at least 99.5%) to SEQ ID NO: 7, wherein the second recombinant adeno-associated virus (AAV) particle of any preceding aspect comprises a first nucleotide sequence that is at least 80% identity (at least 80%, at least 85%, at least 90%, at least 95%, at least 96%, at least 97%, at least 98%, at least 99%, or at least 99.5%) to SEQ ID NO: 8.

In some embodiments, viral vector is a lentivirus vector. Accordingly, disclosed herein is a composition comprising:
a first recombinant lentivirus particle comprising a first nucleotide sequence encoding a N-terminal portion of a Cas9 nickase fused at its C-terminus to an intein-N; and
a second recombinant lentivirus particle comprising a second nucleotide sequence encoding an intein-C fused to the N-terminus of a C-terminal portion of the Cas9 nickase;
wherein first nucleotide sequence further comprises a nucleotide sequence encoding a nucleotide deaminase fused to the N-terminus of the N-terminal portion of the Cas9 nickase,
wherein the Cas9 nickase comprises a first amino acid substitution at a position selected from the group consisting of 262, 324, 409, 480, 543, 694, and 1219 when compared to SEQ ID NO: 11, and
wherein the Cas9 nickase comprises a second amino acid substitution at a position selected from the group consisting of 1111, 1135, 1218, 1219, 1322, 1335, and 1337 when compared to SEQ ID NO: 11.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. See, e.g., WO2012079000A1, incorporated by reference herein in their entireties.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to mod late promoter-driven transcription. In some embodiments, the recombinant nucleic acid of any preceding aspect further comprises a reporter gene. In some embodiments, the reporter gene in invention is GFP.

In some embodiments, the fusion protein, nucleotide, system, or composition of any preceding aspect can be further formulated in a pharmaceutically acceptable carrier.

Genetic Diseases and Methods of Treatment

It is estimated that over 10,000 human diseases are caused by genetic disorders, which are abnormalities in genes or chromosomes, See, e.g., McClellan, J. and M. C. King, Genetic heterogeneity in human disease. Cell. 141(2): p. 210-7; Leachman, S. A., et al., Therapeutic siRNAs for dominant genetic skin disorders including pachyonychia congenita. J Dermatol Sci, 2008. 51(3): p. 151-7. The compositions disclosed herein can be used to treat a number of these genetic disorders.

In some aspects, disclosed herein is a method of treating a genetic disease in a subject, comprising administering to the subject a therapeutically effective amount of the fusion protein, system, or composition of any preceding aspect.

In some embodiments, the genetic disease is a muscular dystrophy. Muscular dystrophies are a group of muscle diseases caused by mutations in a person's genes. Over time, muscle weakness decreases mobility, making everyday tasks difficult. The methods and compositions disclosed herein can be used for treating a muscular dystrophy, including, for example, Duchenne muscular dystrophy, Becker muscular dystrophy, myotonic dystrophy, limb-girdle muscular dystrophy, facioscapulohumeral dystrophy, congenital muscular dystrophy, distal muscular dystrophy, oculopharyngeal muscular dystrophy, or Emery-Dreifuss muscular dystrophy.

In some embodiments, the genetic disease or disorder is Duchenne muscular dystrophy, dysferlinopathy, or spinal muscular atrophy. In some embodiments, the methods and compositions disclosed herein can be used for treating Duchenne muscular dystrophy. In some embodiments, the genetic disease is spinal muscular atrophy.

In some embodiments, the genetic disease or disorder is hypercholesterolemia. For treating hypercholesterolemia, iABE-NGA is used to create a protective silent mutation in functional genes, for example ANGPTL3, APOC3, PCSK9, or ASGR1, to lower plasma cholesterol levels.

In some embodiments, the genetic disease or disorder is due to a point mutation in a causative gene from a G:C pair to an A:T pair.

In some aspects, disclosed herein is a method of treating a genetic disease in a subject, comprising administering to the subject a therapeutically effective amount of the fusion protein, system, and composition of any preceding aspect.

The disclosed methods can be performed any time prior to the onset of a genetic disease, even prior to the apparent of any symptom. In one aspect, the disclosed methods can be employed 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 years; 12, 11, 10, 9, 8, 7, 6, 5, 4, 3, 2, or 1 months; 30, 29, 28, 27, 26, 25, 24, 23, 22, 21, 20, 19, 18, 17, 16, 15, 14, 13, 12, 11, 10, 9, 8, 7, 6, 5, 4, or 3 days; 60, 48, 36, 30, 24, 18, 15, 12, 10, 9, 8, 7, 6, 5, 4, 3, or 2 hours prior to the onset of the genetic disease or any symptom thereof; or 1, 2, 3, 4, 5, 6, 7, 8, 9, 10, 11, 12, 15, 18, 24, 30, 36, 48, 60 hours; 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days; 4, 5, 6, 7, 8, 9, 10, 11, 12 or more months; 1, 3, 4, 5, 6, 7, 8, 9, 10, 11, 12, 13, 14, 15, 16, 17, 18, 19, 20, 21, 22, 23, 24, 25, 26, 27, 28, 29, 30, 45, or 60 years after the onset of the genetic disease or any symptom thereof.

Dosing frequency for the composition of any preceding aspects, includes, but is not limited to, at least once every year, once every two years, once every three years, once every four years, once every five years, once every six years, once every seven years, once every eight years, once every nine years, once every ten year, at least once every two months, once every three months, once every four months, once every five months, once every six months, once every seven months, once every eight months, once every nine months, once every ten months, once every eleven months, at least once every month, once every three weeks, once every two weeks, once a week, twice a week, three times a week, four times a week, five times a week, six times a week, daily, two times per day, three times per day, four times per day, five times per day, six times per day, eight times per day, nine times per day, ten times per day, eleven times per day, twelve times per day, once every 12 hours, once every 10 hours, once every 8 hours, once every 6 hours, once every 5 hours, once every 4 hours, once every 3 hours, once every 2 hours, once every hour, once every 40 min, once every 30 min, once every 20 min, once every 10 min, once every 5 min, or once per min. Administration can also be continuous and adjusted to maintaining a level of the compound within any desired and specified range.

The compositions of the present invention can be administered to the appropriate subject in any manner known in the art, e.g., orally, intramuscularly, intravenously, sublingual mucosal, intraarterially, intrathecally, intradermally, intraperitoneally, intranasally, intrapulmonarily, intraocularly, intravaginally, intrarectally, subcutaneously, or through by inhalation. Parenteral administration, if used, is generally characterized by injection. Injectables can be prepared in conventional forms, either as liquid solutions or suspensions, solid forms suitable for solution or suspension in liquid prior to injection, or as emulsions.

EXAMPLES

The following examples are set forth below to illustrate the compounds, systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Figure 1D:
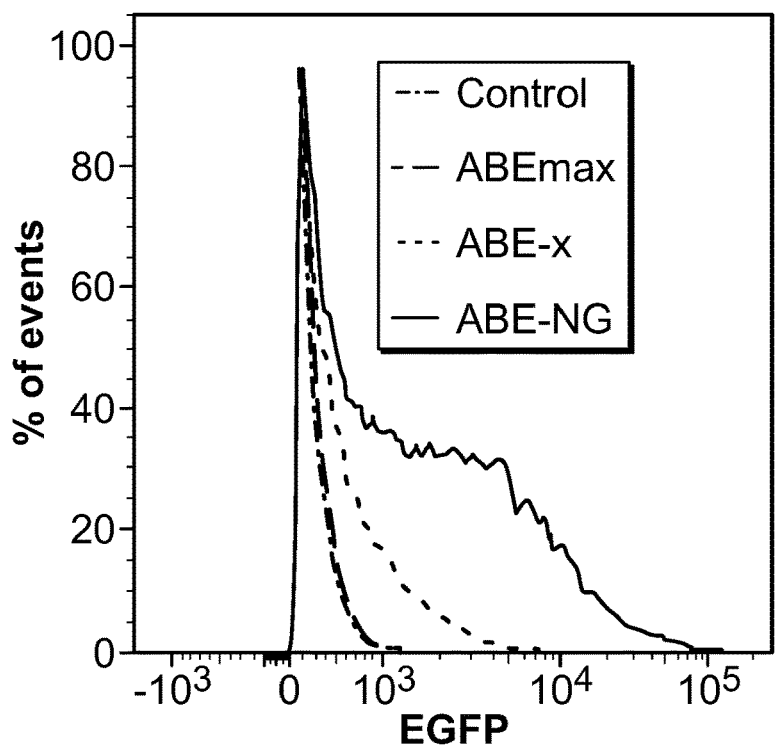
Figure 1E:
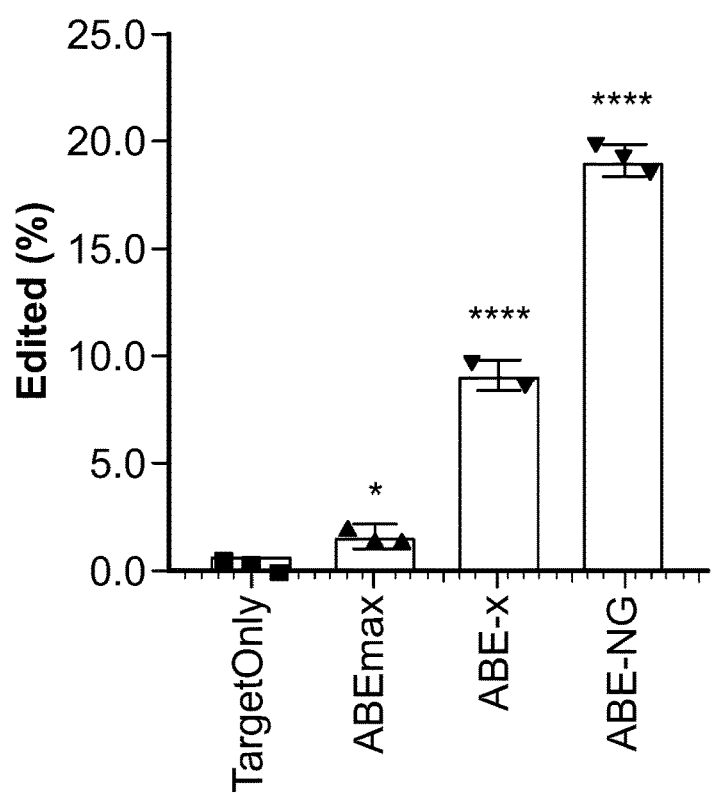

Example 1. In Vitro Reporter Assay Demonstrates the Feasibility to Correct the mdx$^{4cv}$ Mutation Using ABE-NG The mdx$^{4cv}$ mouse carries a premature stop codon (CAA-to-TAA) in the exon 53 of Dmd gene, which disrupts the expression of dystrophin and leads to the development of muscular dystrophy. Targeting the noncoding strand with ABEs can correct this nonsense mutation. However, in the noncoding strand, there is a lack of 5'-NGG sequence at the downstream of this mutation within the suitable editing window, but a 5'-TGT PAM is present with the mutated A located at position 4 in the guide RNA (gRNA) (FIG. 1a), making it feasible to correct the stop codon with the NG-targeting base editors in this widely used mouse model of DMD. A reporter plasmid with the targeting sequence from the mdx$^{4cv}$ mice was first constructed (FIG. 1b). The nonsense mutation in the mdx$^{4cv}$ targeting sequence disrupts the expression of downstream EGFP and successful editing of the nonsense mutation is indicated by the restoration of EGFP expression. As shown in FIG. 1c, transfection with the reporter alone resulted in minimal background fluorescence. Similarly, co-transfection with the reporter, mdx$^{4cv}$-gRNA and ABEmax failed to restore EGFP expression. However, ABE-NG (based on SpCas9-NG) successfully restored EGFP expression in this reporter assay. In contrast, ABE-x (based on xCas9-3.7) was found to be less efficient in restoring EGFP expression even though xCas9-3.7 was also engineered to target 5'-NG PAM, consistent with previous reports that xCas9-3.7 is generally less efficient than SpCas9-NG. FACS analysis showed that ABE-x and ABE-NG restored EGFP expression in 10% and 20% cells, respectively (FIGS. 1d, 1e). These in vitro studies showed that ABE-NG corrects the nonsense mdx$^{4cv}$ mutation.

Example 2. Improvements in the Editing Efficiency and Specificity of ABE-NG

The relative low efficiency of ABE-NG, together with the recently reported off-target RNA editing activity, prompted the re-design of ABE-NG in order to improve the editing efficiency and specificity. First, the targeting efficiency of ABE-NG at the sites with 5'-NG PAM can be improved by optimizing the PAM-interacting domain. The targeting property of ABE-NG can be modified by combining the mutations in SpCas9-NG (R1335V/L1111R/D1135V/G1218R/E1219F/A1322R/T1337R) with other mutations designed to target different PAM sequences such as those in xCas9(3.7) (A262T/R324L/S409I/E480K/E543D/M694I/E1219V), VQR (D1135V/R1335Q/T1337R), VRER (D1135V/G1218R/R1335E/T1337R) and the loop sequence in ScCas9 (amino acids 367-376). Seven new ABE variants were generated with different combinations of the aforementioned variants (Table 1) and compared their base editing activities at six different loci with those of ABE-NG and ABEmaxSC. While all variants except ABE-NGC (containing all NG mutations plus R1335E) performed similarly at the NGG site (FIG. 2a), it was observed that ABE-NGA (carrying all NG mutations plus R1335Q) had a small improvement in editing the NGH sites as compared to ABE-NG (FIGS. 2b-2e). ABE-NGA and ABE-NGX-NGC (carrying the xCas9(3.7) mutations, NG mutations and R1335E) worked equally well at the NGC site (FIG. 2c). The ABE-NG and ABE-NGA also edited the site containing a 5'-GAT PAM with high efficiency (FIG. 2f), with similar efficiency as compared to the ABE-NGX variant carrying both the xCas9 (3.7) mutations and ABE-NG mutations, which was previously reported to have the broadest targeting scope active in plant. However, the efficiency of ABE-NGX at the NGH sites was lower than ABE-NGA (FIG. 2b). Since ABE-NGA is generally superior to other variants tested at NGH sites, ABE-NGA was chosen for further in vitro and in vivo studies.

Figure 3A:
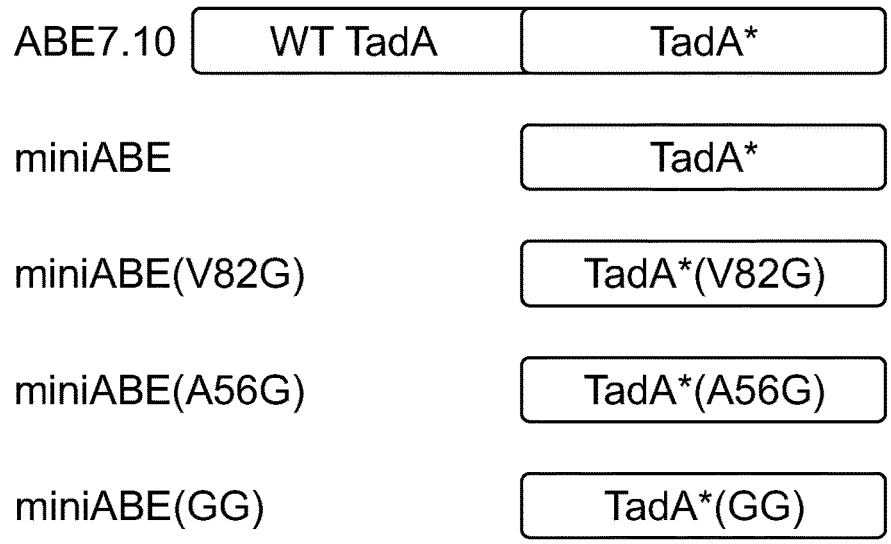
FIGS. 3a-3d show re-engineering of the adenine deaminase domain to improve the efficiency and specificity of ABE-NG.
Figure 3B:
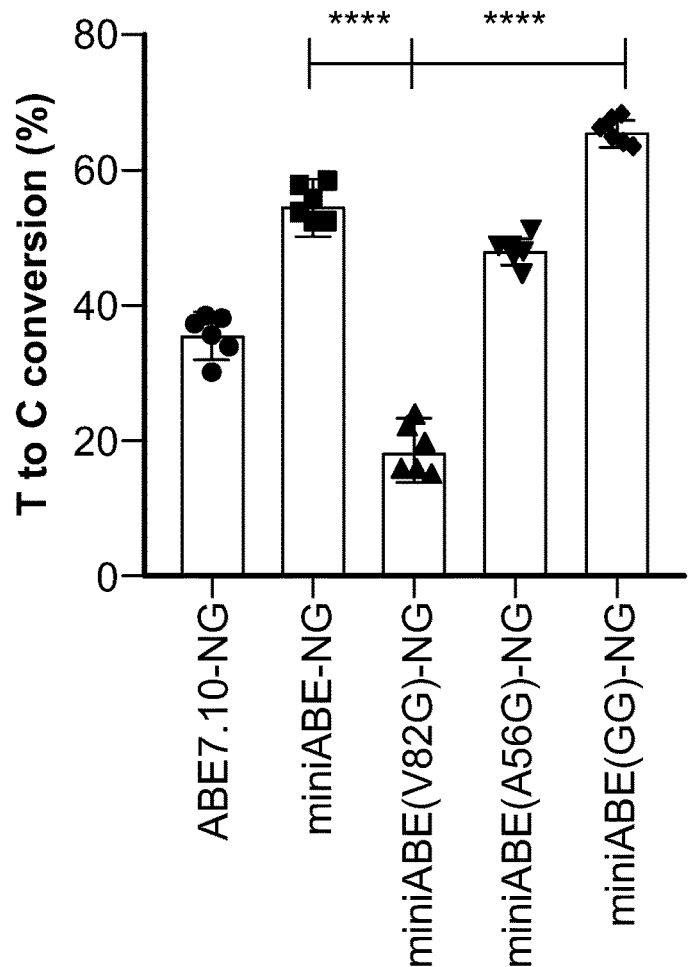

Previous studies showed that the deaminase domain in the ABEs can elicit transcriptome-wide RNA off-target editing activity, and that the off-target RNA editing activity can be substantially reduced by removing the WT ecTadA domain and mutating the evolved ecTadA domain. The dimeric adenine deaminase domain (ecTadA-ecTadA*) in ABE-NG was replaced with the originally evolved ecTadA* monomer or its high-fidelity version (ecTadA*-V82G) (FIG. 3a) in order to minimize the off-target RNA editing activity. The miniABE-NG (the mononeric TadA* fused with SpCas9-NG nickase) performed slightly better at the mdx$^{4cv}$ target site as compared to ABE7.10-NG (FIG. 3b). However, the on-target DNA editing activity of miniABE(V82G)-NG was remarkably reduced by over 50% when compared to ABE7.10-NG (FIG. 3b). Then the next experiment attempted to improve the on-target DNA editing efficiency of the high-fidelity mini ABE(V82G)-NG without compromising its low off-target RNA editing activity. The V82G is one of the 26 amino acid residue positions in ecTadA that reside near the enzymatic pocket around the substrate tRNA, inferred from the S. aureus TadA-tRNA co-crystal structure. The V82G mutation does not only affect the non-specific affinity to RNA substrates, but can also reduce its affinity to the DNA substrates. It was noticed that the A56G mutation (which is also inferred to lie near the enzymatic pocket around the tRNA substrate) had higher on-target DNA editing activity without affecting the off-target RNA editing activity as compared to miniABEmax. Installing the A56G mutation into miniABE(V82G)-NG can improve its on-target DNA editing activity without compromising its off-target RNA editing profile. Indeed, it was observed that adding the A56G mutation into miniABE(V82G)-NG (named miniABE(GG)-NG) completely restored its on-target DNA editing activity (FIG. 3b).

Figure 3C:
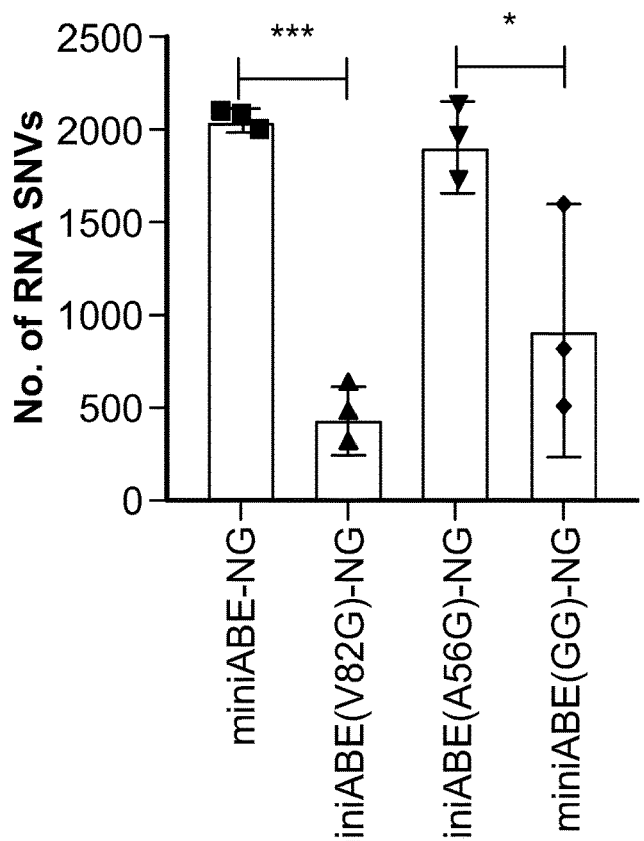
Figure 3D:
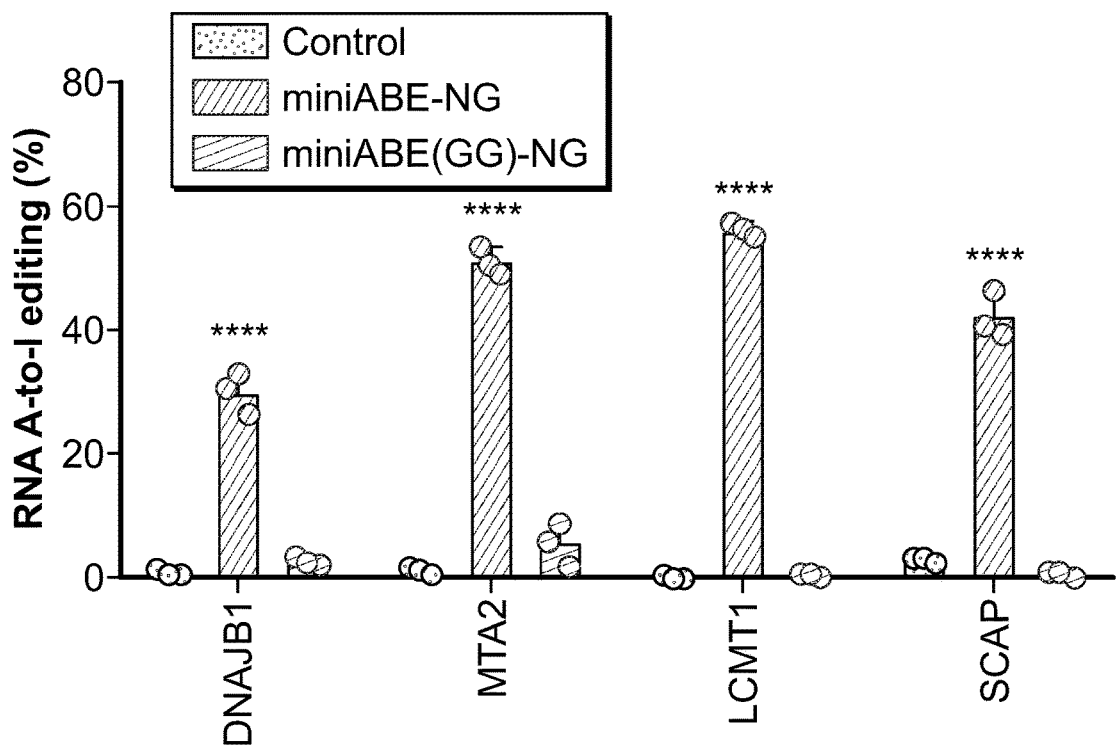

RNA-seq was used to compare the transcriptome-wide off-target RNA editing activities of miniABE(GG)-NG to other ABE variants in mouse Neuro2a cells. These studies were performed in triplicate. Edited RNA adenines were identified from RNA-sect experiments by filtering out background editing observed with read-count-matched controls. MiniABE-NG and miniABE(A56G)-NG induced much higher numbers of adenine editing as compared to miniABE (V82G)-NG or miniABE(GG)-NG (FIG. 3c). There was no statistical difference between miniABE(V82G)-NG and miniABE(GG)-NG. To further verify the off-target RNA editing activity of mini ABE(GG)-NG, four RT-PCR amplicons were amplified and sequenced, which were shown to be highly modified by ABEmax in human cells. Transfection of HEK293 cells with mini ABE-NG induced high levels of A-to-I RNA editing in all these transcripts (FIG. 3d); however, such A-to-I RNA editing was essentially eliminated in cells transfected with miniABE(GG)-NG (FIG. 3d). Taken together, these results showed that miniABE(GG)-NG does not only have increased DNA editing activity, but also inherits the high fidelity of miniABE(V82G)-NG. Hereafter, the improved ABE-NG carrying the miniABE(GG) domain and Cas9-NGA nickase was referred to as iABE-NGA.

Figure 4A:
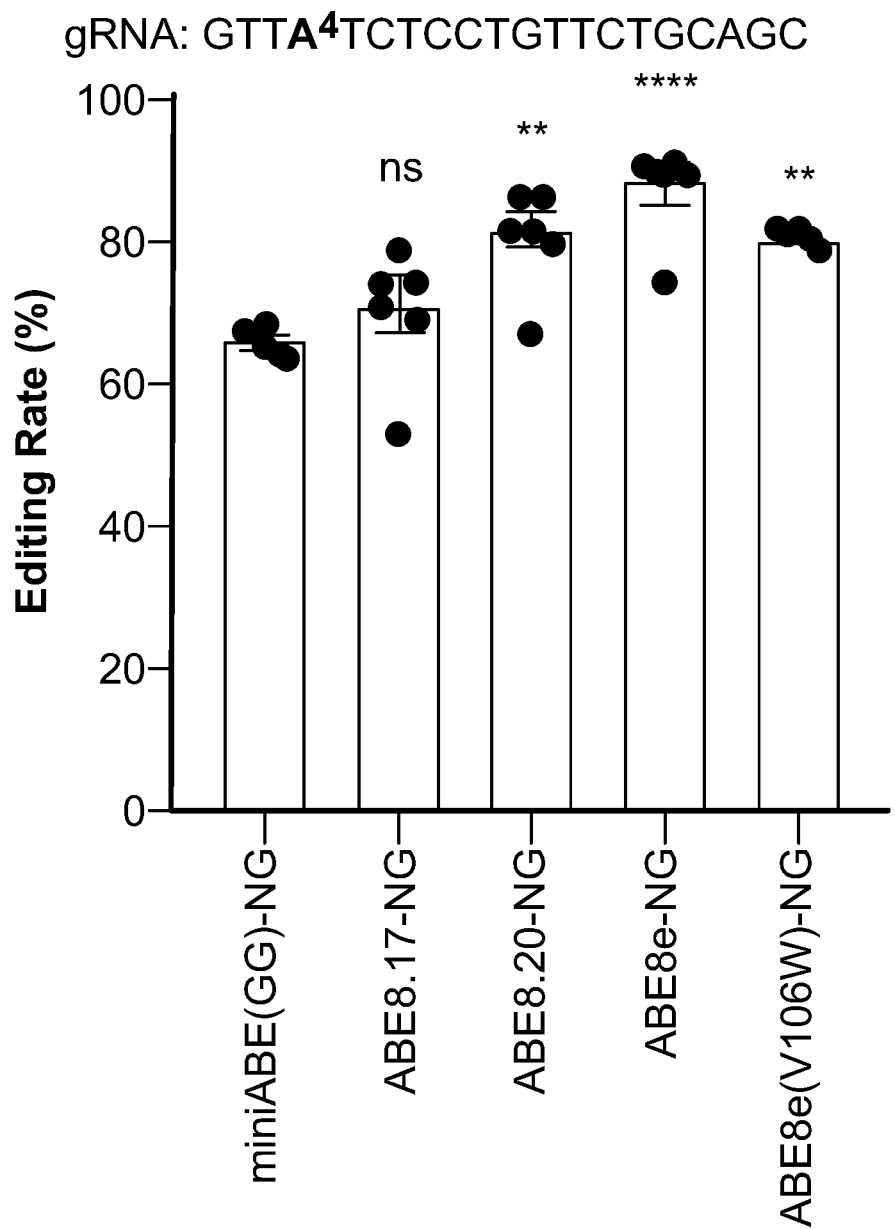
FIGS. 4a-4b show comparison of the editing efficiency of different ABEs at the mdx$^{4cv}$ target site (FIG. 4a) and human dysferlin Q605X site (FIG. 4b). All base editors carry the SpCas9-NG and differ at the adenine deaminase domain. ns, not statistically significant; $p<0.01$; **$p<0.0001$ (one-way ANOVA for FIG. 4a; two-way ANOVA for FIG. 4b). The sequence in FIG. 4 is GTTATCTCCTGTTCTGCAGC (SEQ ID NO: 570) and ATCCTACAGCATGGTGGCTG (SEQ ID NO: 590).
Figure 4B:
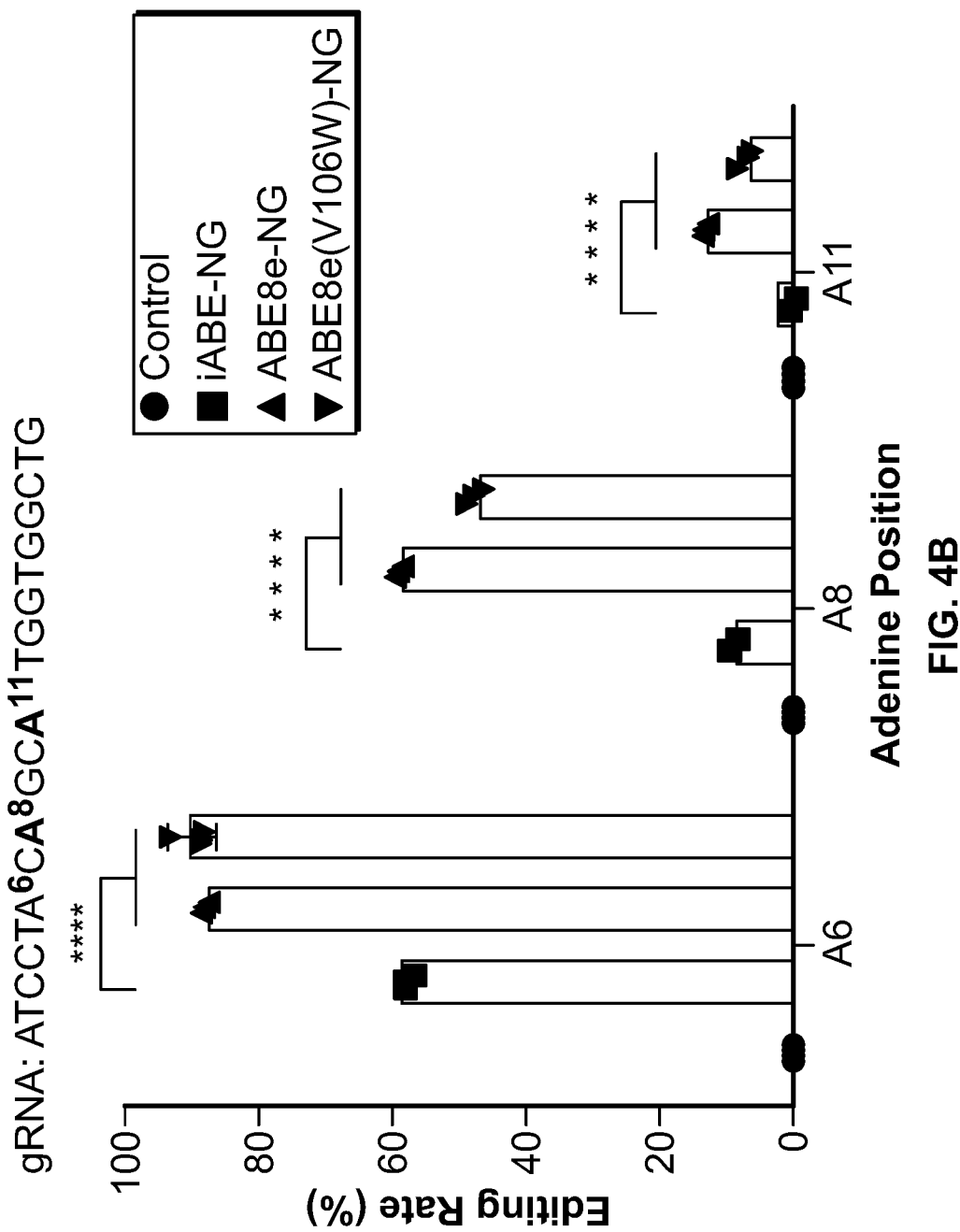

A new generation of ABEs were developed through directed evolution, namely, ABE8s (such as ABE8.17 and ABE8.20) and ABE8e. To directly compare miniABE(GG) with ABE8.17, ABE8.20 and ABE8e, each of them was fused with SpCas9-NG and tested their activities for editing the mdx$^{4cv}$ target site using the reporter assay in Neuro2A cells. All these editors showed above 60% editing efficiency with the ABE8e-NG exhibiting the highest activity (FIG. 4a). ABE8e can have also increased bystander activity than miniABE(GG). Since the mdx$^{4cv}$ target site has no extra adenine within the editing window, the bystander editing activity of ABE8e and miniABE(GG) was compared by testing their performance to edit a nonsense mutation in human DYSF gene (encoding dysferlin) that causes limb girdle muscular dystrophy. The target A$^6$ was edited with ~58% and 88% efficiency by iABE-NG and ABE8e-NG, respectively (FIG. 4b). The two bystander adenines at positions 8 and 11 were also edited at substantially higher (quantitative numbers) rates by ABE8e-NG than miniABE (GG)-NG. Even the ABE8e with V106W mutation still displayed very high bystander editing activity at position 8. Thus, for in vivo applications that require not only efficiency but also precision, the use of miniABE(GG) was recommended.

Figure 5A:
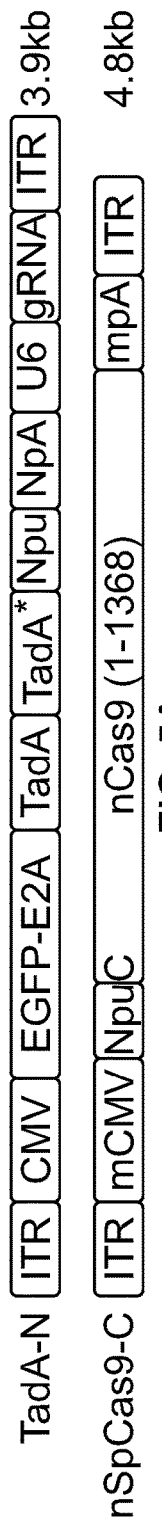
FIGS. 5a-5b show the intein split of ABEmax had relatively low editing activity.
Figure 5B:
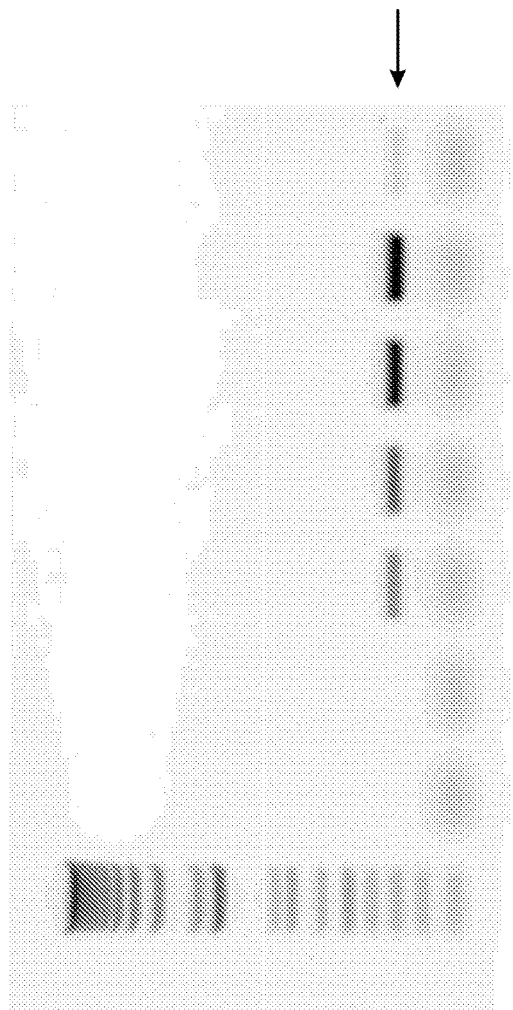
Figure 6A:
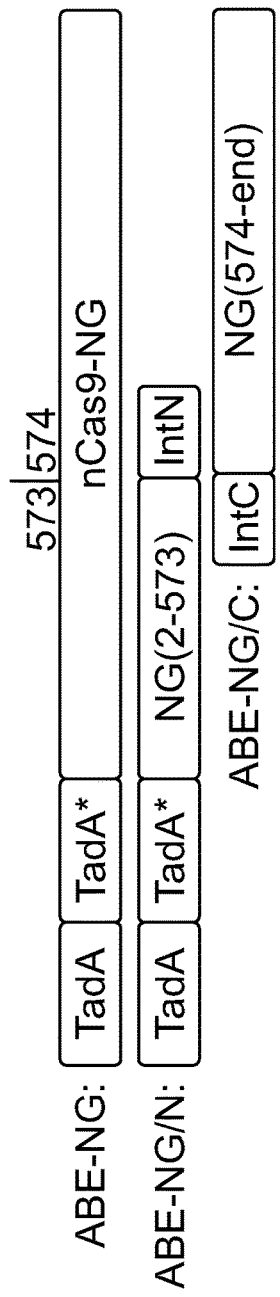
FIGS. 6a-6h show intein-mediated assembly of full-length ABE-NG.
Figure 6B:
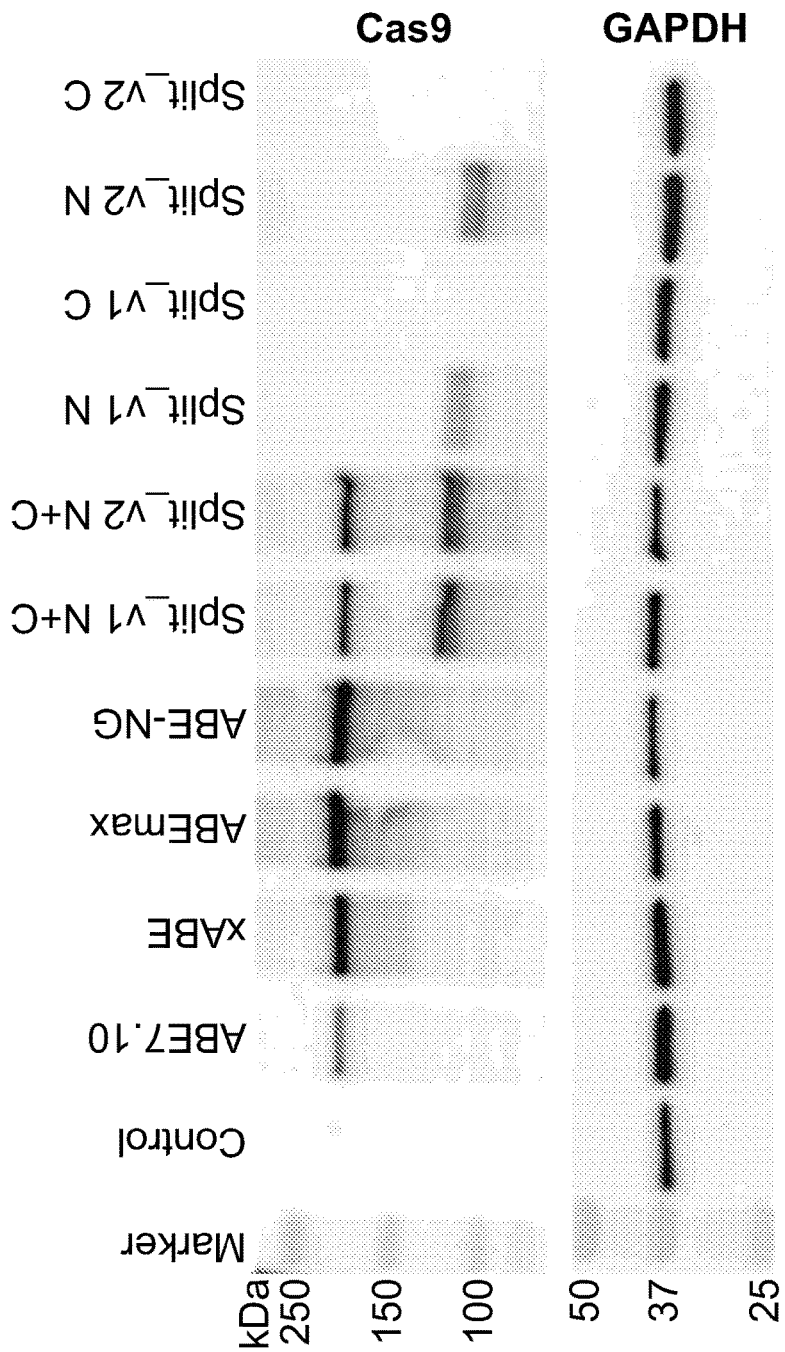
Figure 6C:
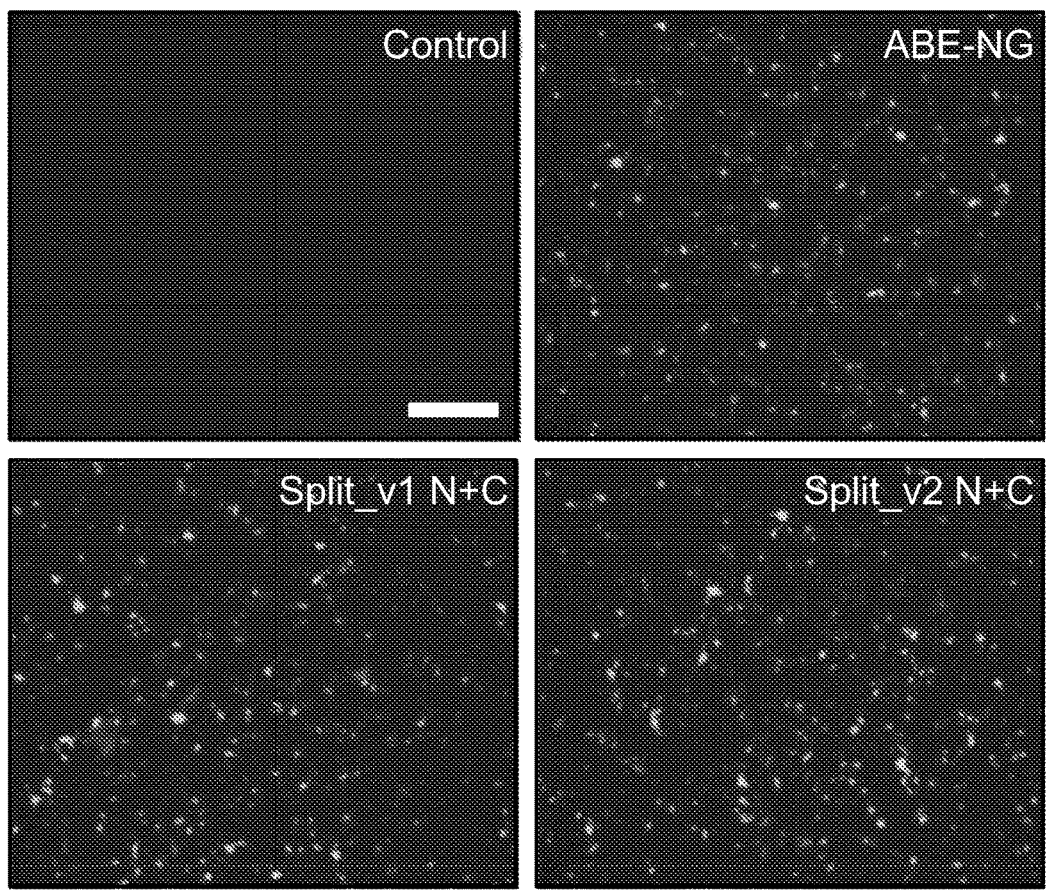
Figure 6D:
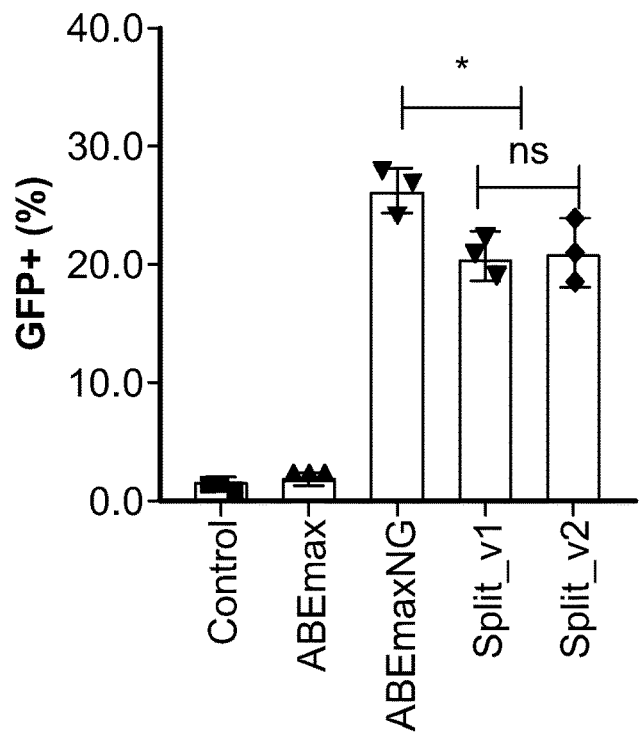

Example 3. Intein-Split Allows Efficient Assembly of Full-Length ABE-NG and Editing The large size of the ABE-NG and other base editors poses a major challenge for viral packaging and in vivo delivery. A dual trans-splicing adeno-associated virus (AAV) approach was used to deliver ABE and a dual protein trans-splicing (PTS) approach using the split-intein moiety from Nostoc punctiforme (Npu) was used to deliver CBE. The PTS approach was adopted to deliver ABE. The ABE was split between the ecTad-ecTadA* and the Cas9 nickase with Npu intein moieties, and this split renders low editing efficiency (FIG. 5). To improve the editing efficiency of the split ABE, the amino acid position 573 and 574 of the Cas9 nickase were chose as the splitting site because previous studies showed that 573/574 split Cas9 exhibited near the full-length Cas9 activity. Moreover, split at this site would produce a roughly equal size of the two halves for AAV packaging (FIG. 4a). the split ABE can be further improved by using inteins with fast rate of PTS. Two inteins were selected with the remarkably fast rate of PTS: Cfa (t½=20 s at 30° C.) and Gp41-1 ($t_{1/2}$=5 s at 37° C.), which are ~2.5-fold and ~10-fold faster than the rate reported for the Npu DnaE intein ($t_{1/2}$=50 s at 37° C.), respectively. Transfection of both split versions into HEK293 cells resulted in robust expression of full-length ABEs as detected by the anti-Cas9 antibody (FIG. 6b), although the expression level was generally lower than the ABEmax but higher than the original ABE7.10. Co-transfection with the split ABH-NG, mdx$^{4cv}$-gRNA and the mdx$^{4cv}$ reporter restored EGFP expression to a similar level as the full-length ABE-NG (FIG. 6c). There was no significant difference between the Cfa and Gp41-1 intein splits (FIG. 6d). The Gp41-1 version was chosen for further studies.

Figure 6E:
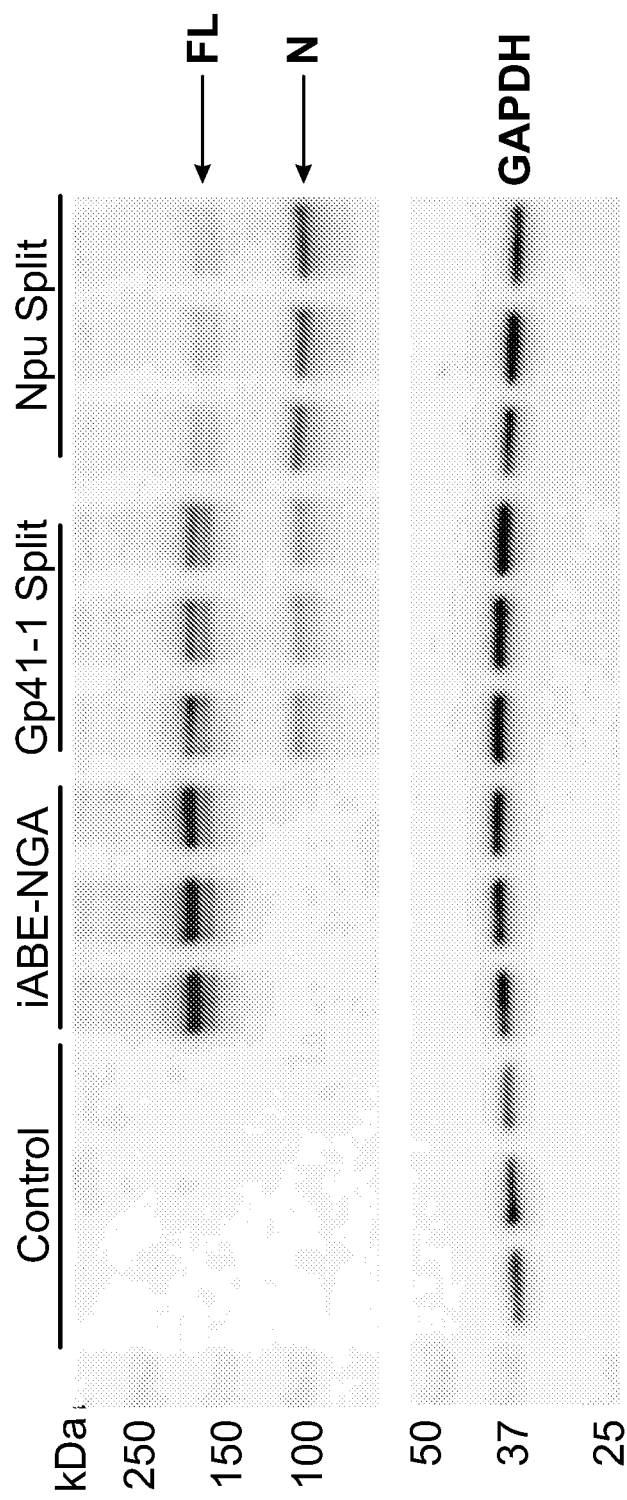
Figure 6F:
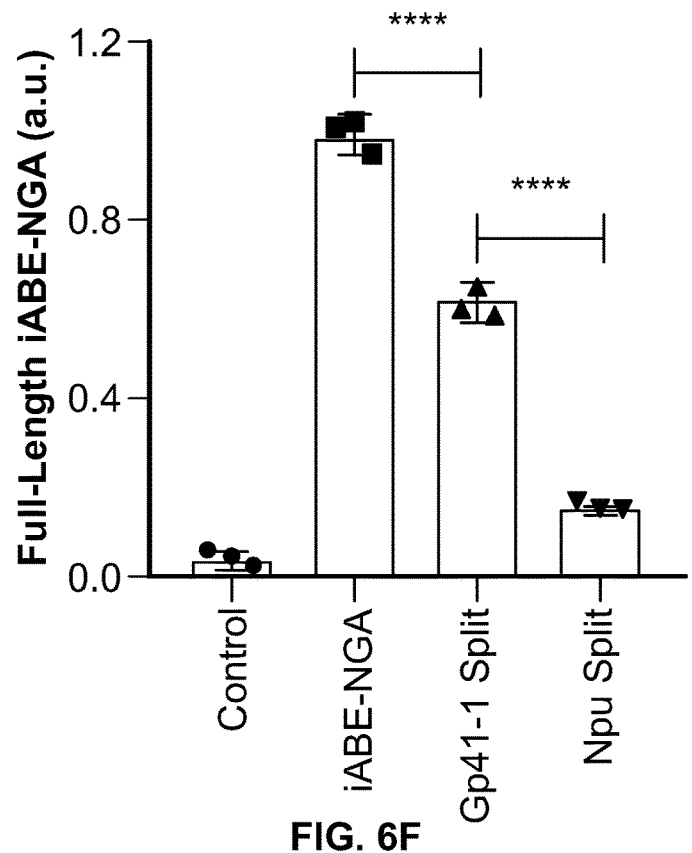
Figure 6G:
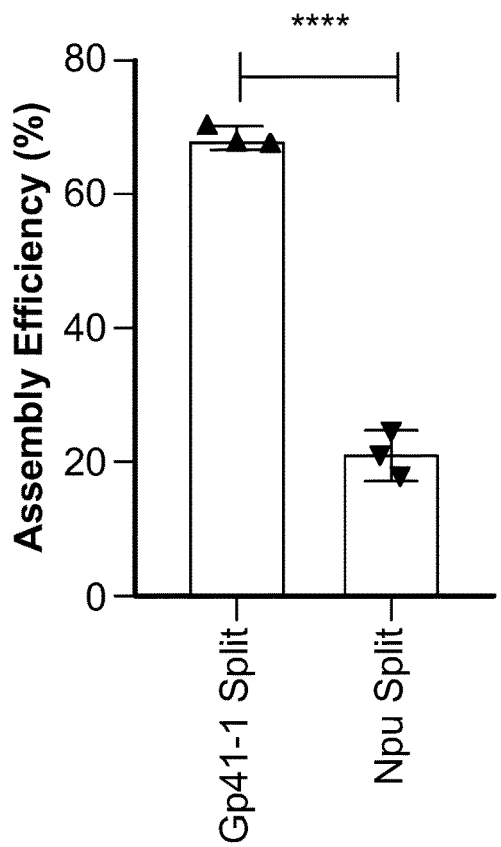
Figure 6H:
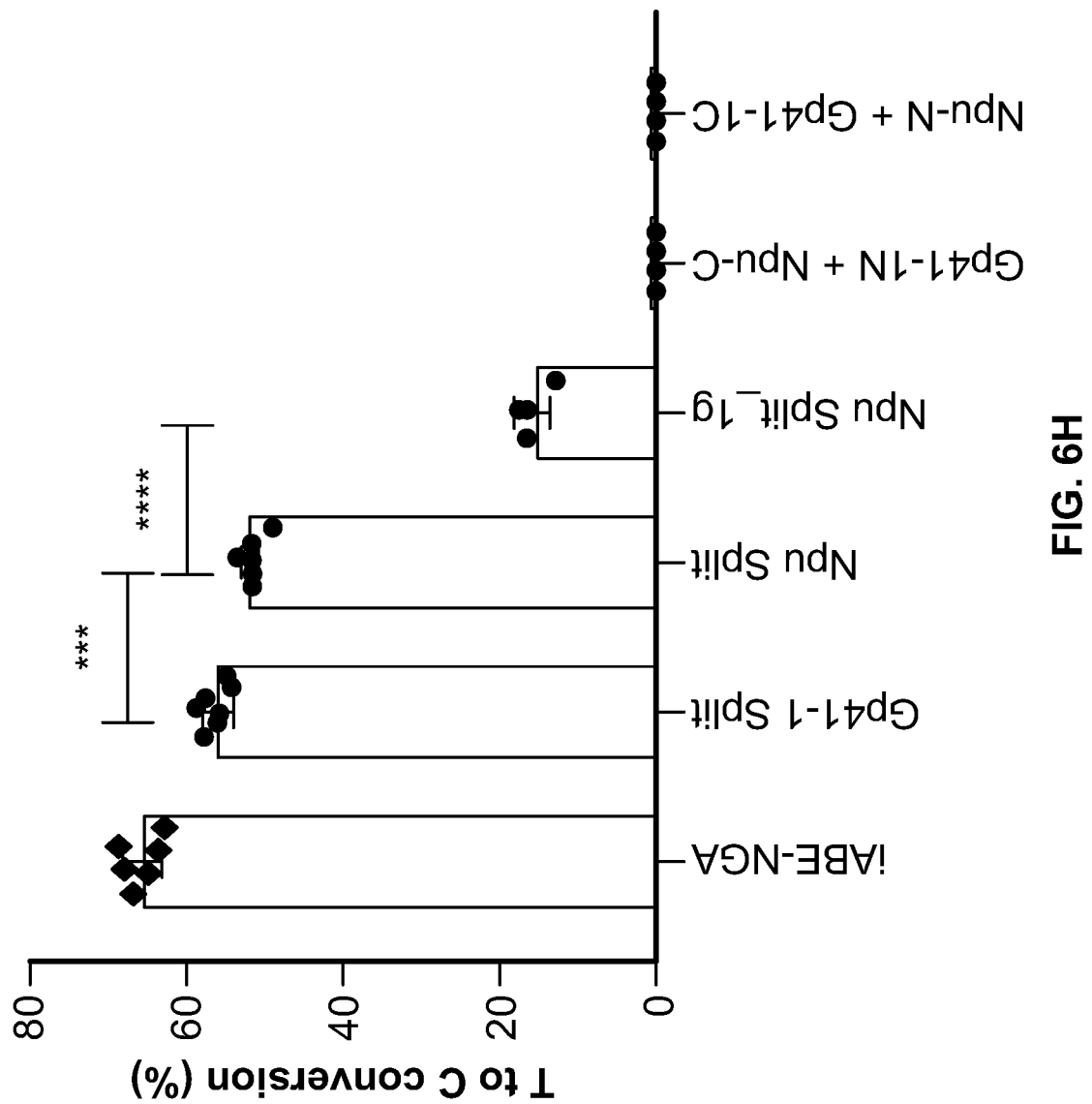

It was shown that the Npu intein split of ABE worked well in vivo and in vivo. The Gp41-1 split and Npu split was directly compared. While both the Gp41-1 split and Npu split allowed the assembly of full-length iABE-NGA, Western blotting analysis showed that the Gp41-1 split rendered significantly more full-length iABE-NGA protein as compared to the Npu split (FIGS. 6e, 6f). The assembly efficiency (as measured by the percentage of the full-length band) of the Gp41-1 split was about 70%, while the Npu split resulted in only 21% (FIG. 6g). To further compare the editing efficiency of the Gp41-1 split and Npu split, the T-to-C conversion of the mdx$^{4cv}$ stop codon was quantified quantified in Neuro2A cells using the reporter assay. As compared to the full-length iABE-NGA, the Gp41-1 split and Npu split retained about 85.5% and 78.8% of its activity, respectively (FIG. 6h). The difference in the editing efficiency between the Gp41-1 split and Npu split was small but statistically significant (p=0.009) (FIG. 6h). In the Gp41-1 split and Npu split shown herein, each half carries a U6-gRNA expression cassette, while only the C-terminal half of the Npu split reported by the Liu group carries the U6-gRNA expression cassette. To test if the double U6-gRNA cassette has higher editing activity than a single U6-gRNA cassette, the U6-gRNA cassette was removed from the N-terminal construct of the Npu split used herein, which resulted in greatly reduced editing (FIG. 6h), indicating that the gRNA dosage is a limiting factor for ancient Cas9-mediated editing. Moreover, to test the specificity of intein-mediated assembly of iABE-NGA, the N and C-terminal fragments of the Gp41-1 and Npu splits were swapped, and observed no editing (FIG. 6h), indicating that the intein-mediated protein splicing and assembly of full-length iABE-NGA are required for efficient editing.

Figure 7:
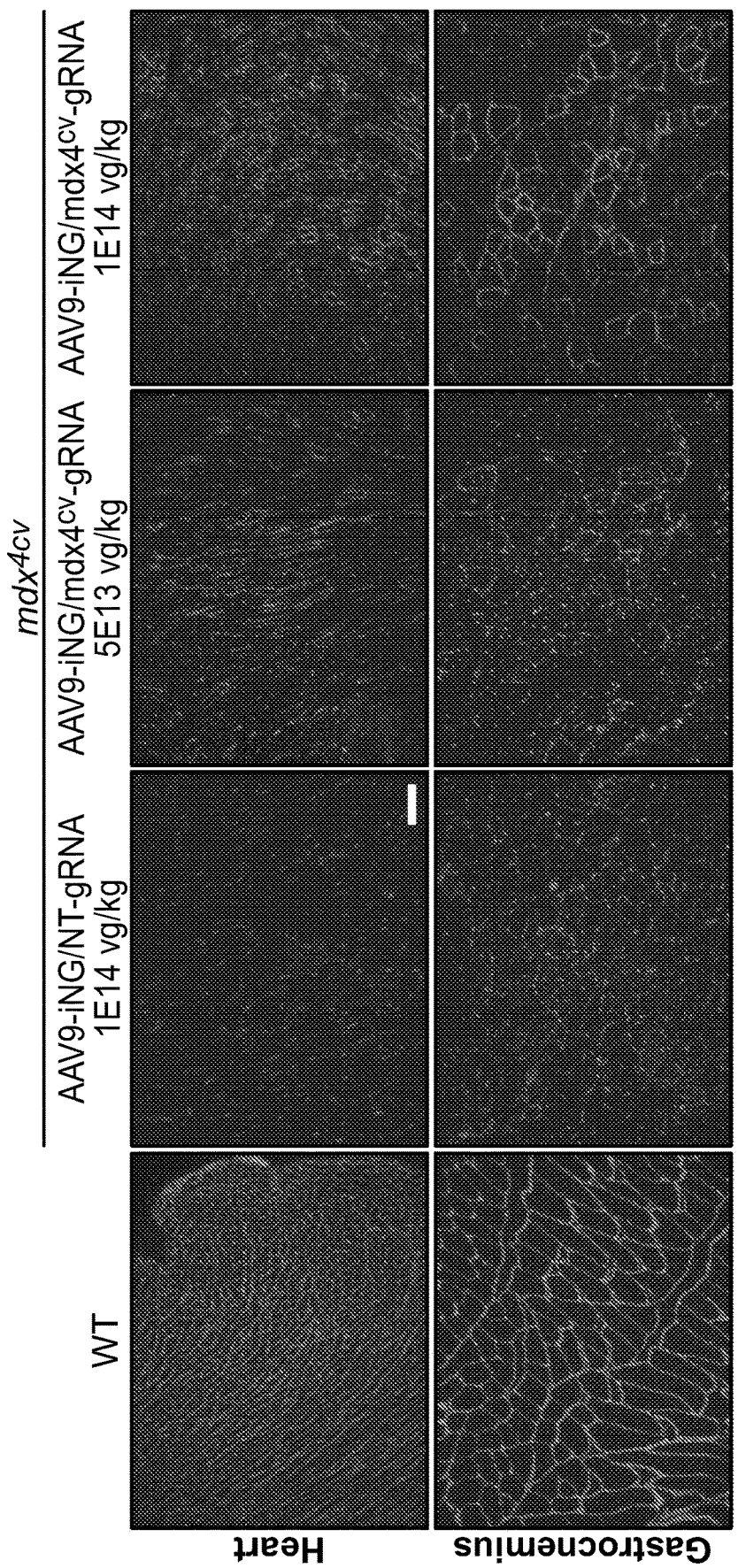
FIG. 7. Immunofluorescence staining of heart and gastrocnemius muscle sections with anti-dystrophin antibody and DAPI. The mdx$^{4cv}$ mice at 5 weeks of age received either $5\times10^{13}$, $1\times10^{14}$ AAV9-iNG/mdx$^{4cv}$-gRNA or $1\times10^{14}$ vg/kg AAV9-iNG/non-targeting-gRNA (NT-gRNA) through tail vein injection, and sacrificed at 10 weeks of age for immunofluorescence staining analysis. Scale bar: 100 µm.

Example 4. Systematic Delivery of AAV9-iNG Leads to Widespread Dystrophin Restoration The two Gp41 intein split halves of the iABE-NGA were packaged into AAV9 (hereafter referred to as AAV9-iNG) and tested if in vivo delivery of iABE-NG-A could correct the mutation in mdx$^{4cv}$ mice. A truncated MHCK7 promoter was used to drive the expression of two halves of iABE-NGA. A preliminary testing of two dosages (a total of $5 \times 10^{13}$ or $1 \times 10^{14}$ vg/kg, 1:1 of the N and C-terminal half) showed that the higher dose appeared to increase the dystrophin-positive myocytes in the mdx$^{4cv}$ mouse heart (FIG. 7). The higher dose ($1 \times 10^{14}$ vg/kg, 1:1 of the N and C-terminal half) was chosen for the rest of the study. In addition, the study also showed that injection of AAV9-iNG carrying a non-targeting gRNA failed to induce dystrophin rescue (FIG. 7).

Figure 8A:
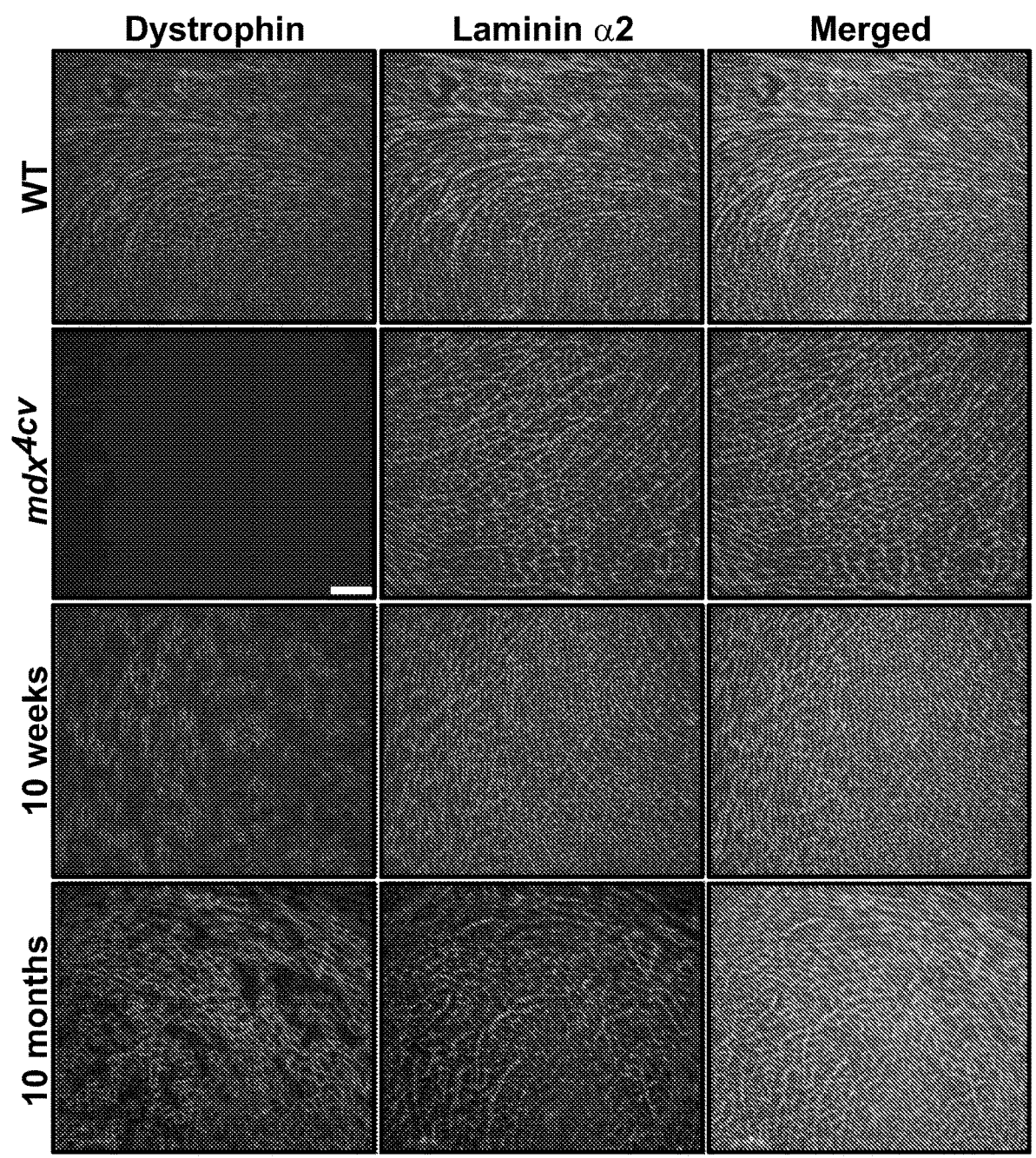
FIGS. 8a-8k show widespread restoration of dystrophin expression in mdx$^{4cv}$ mice following systemic administration of AAV9-iNG.
Figure 8C:
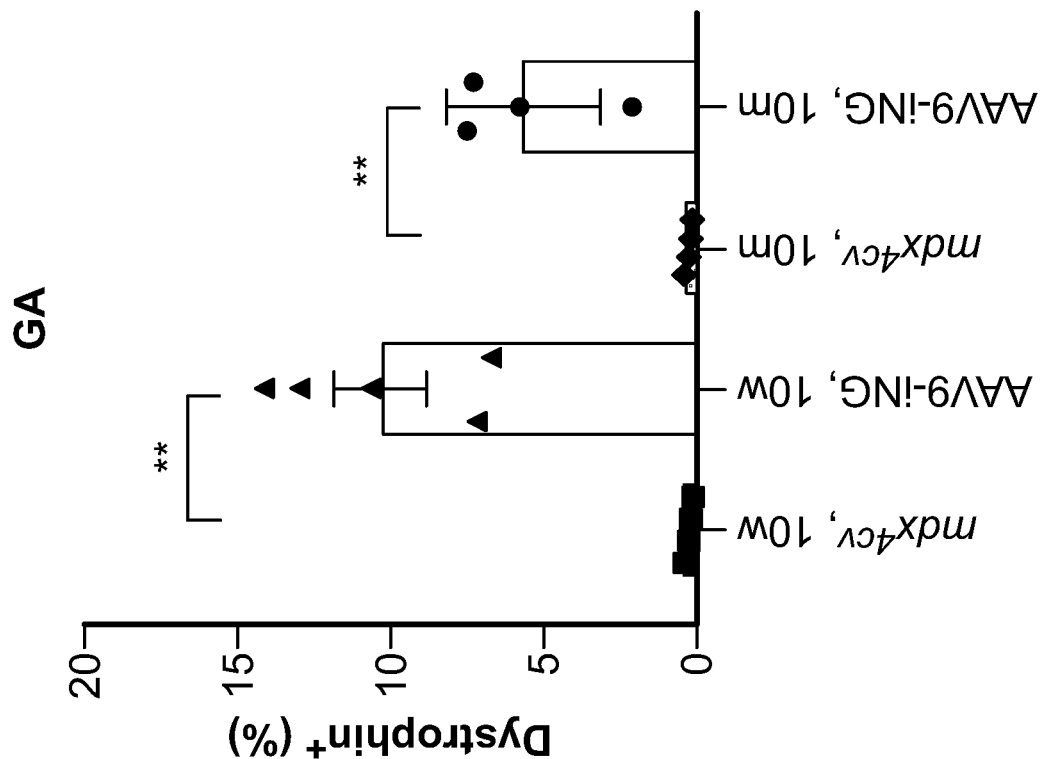
Figure 8B:
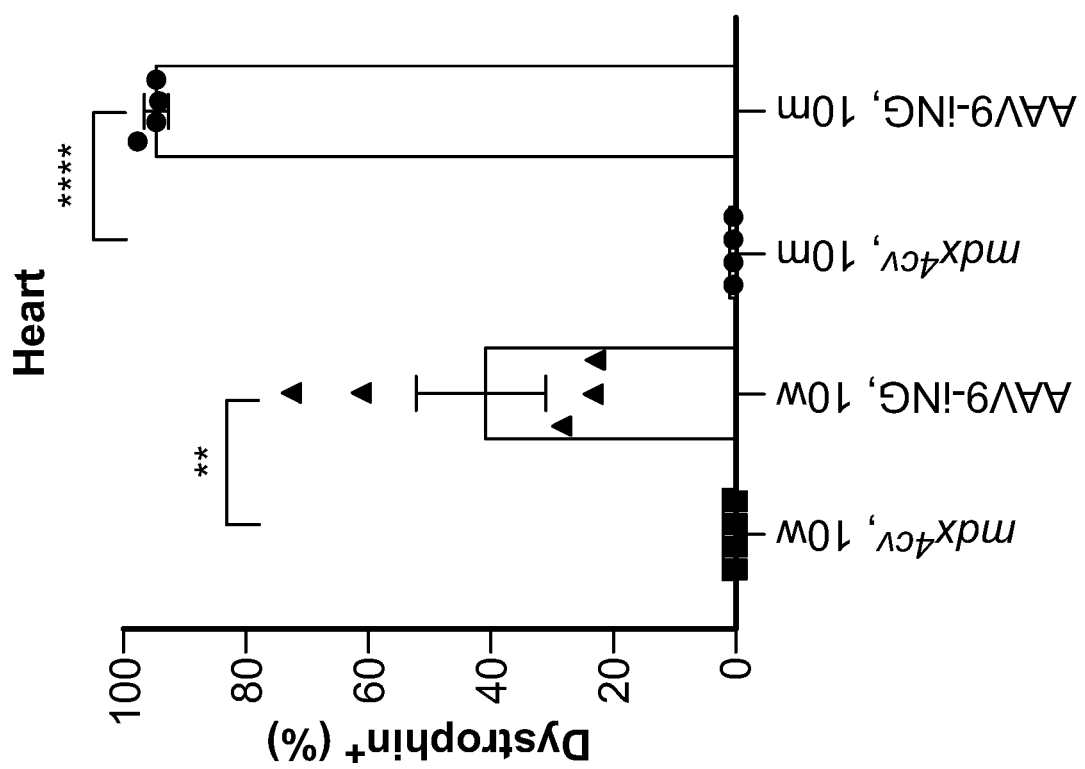
Figure 8D:
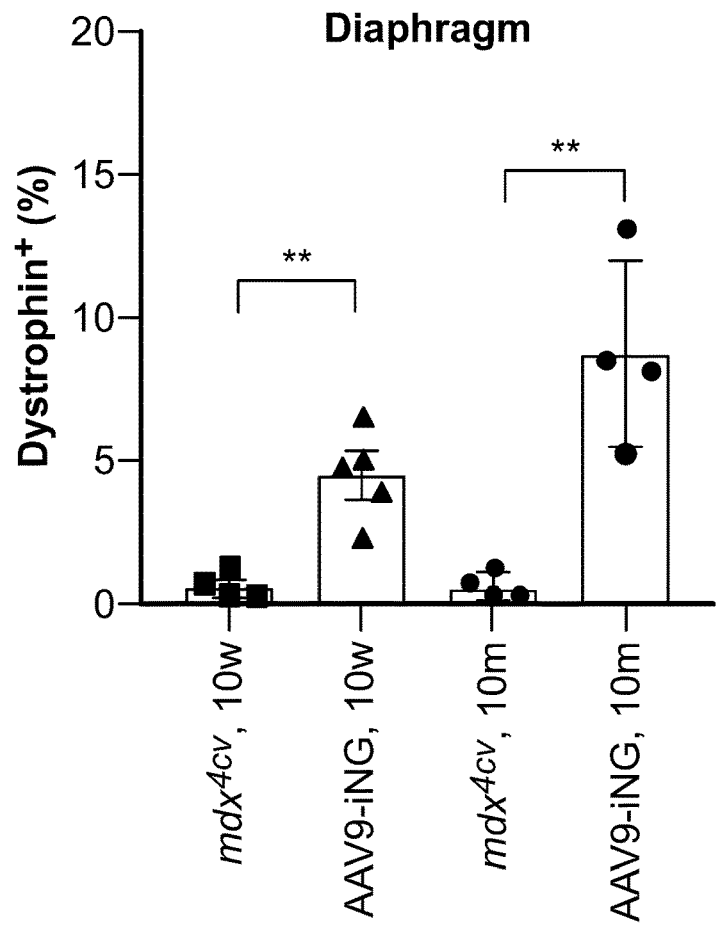
Figure 8E:
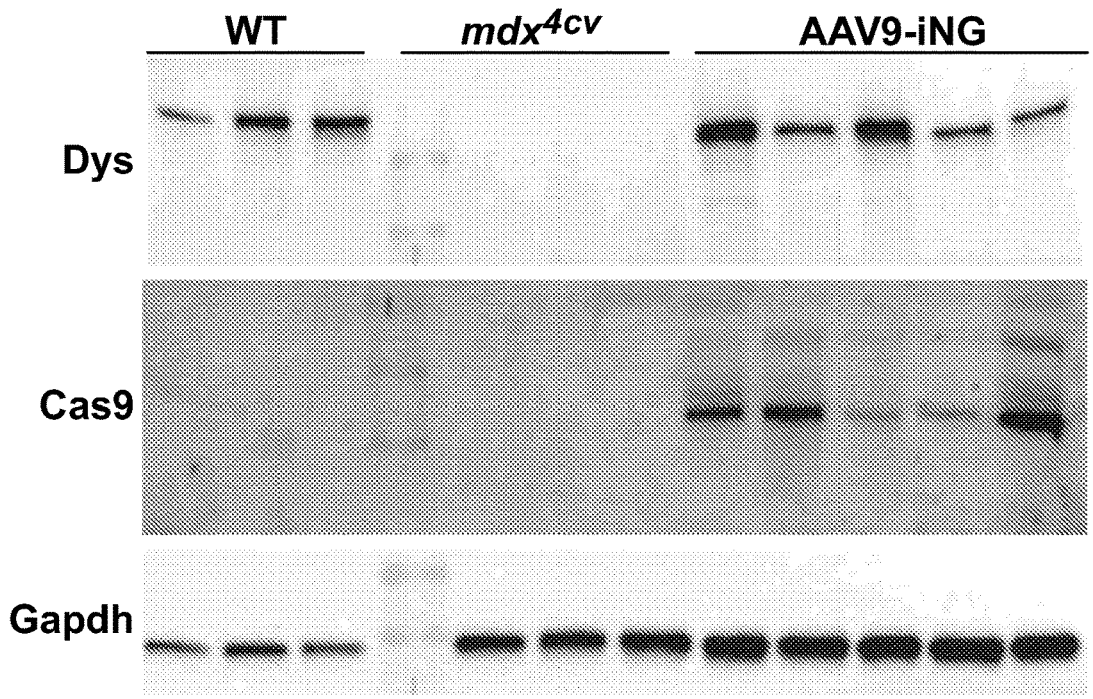
Figure 8F:
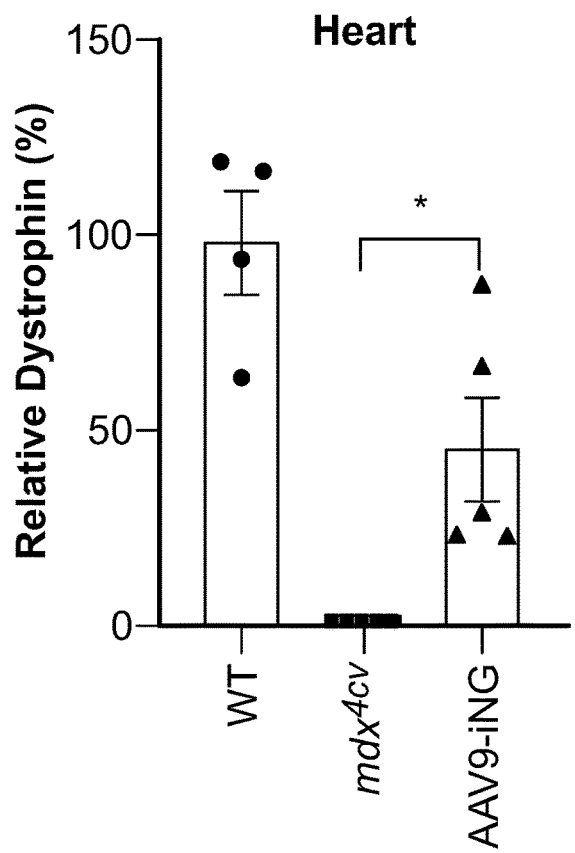
Figure 16A:
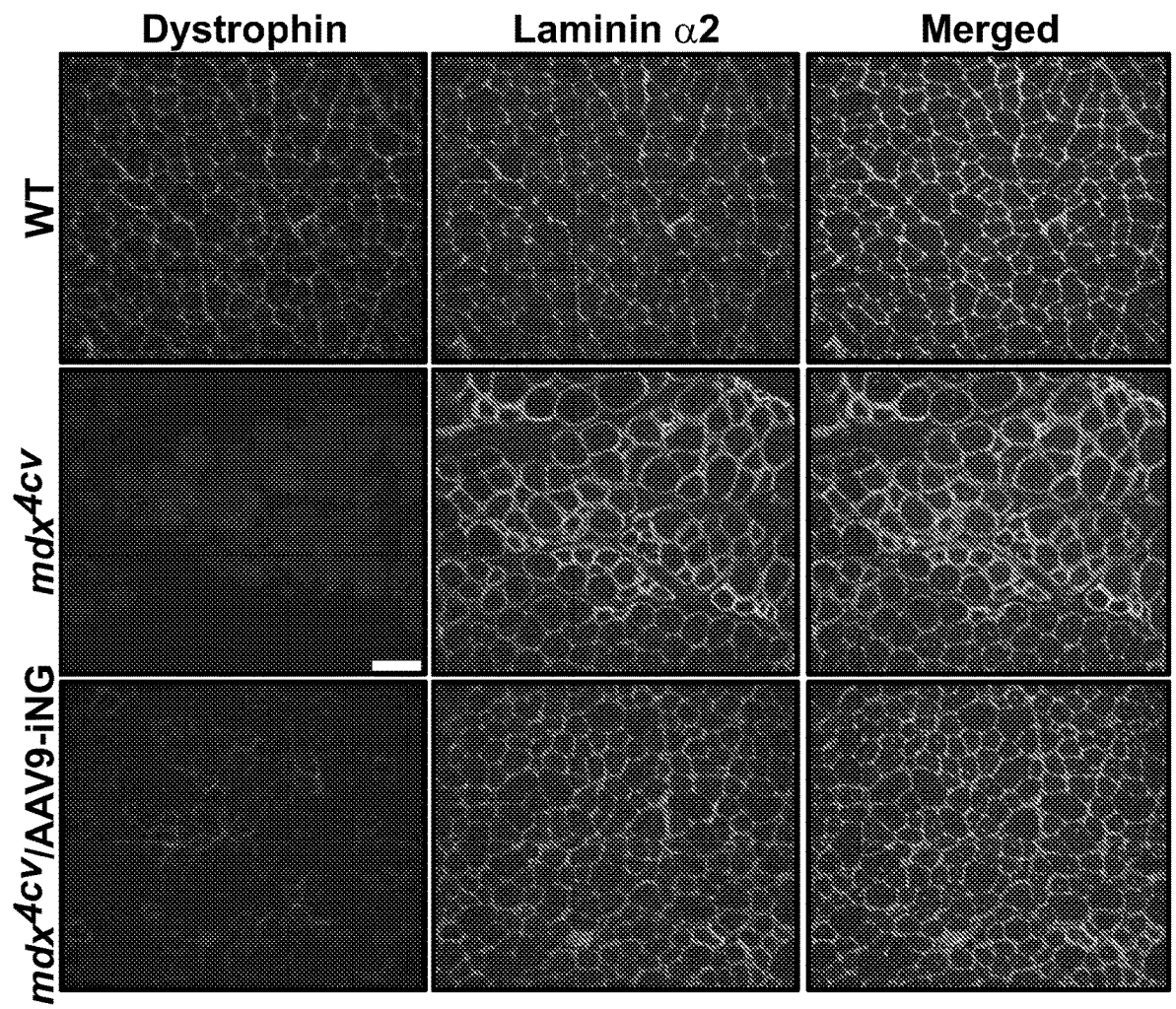
FIGS. 16a-16b show immunofluorescence staining of dystrophin and laminin α2 in the gastrocnemius (FIG. 16a) and diaphragm (FIG. 16b) muscles from WT and mdx$^{4cv}$ (10 weeks of age) treated with or without tail vein injection of AAV9-iNG. Scale bar: 100 µm.
Figure 16B:
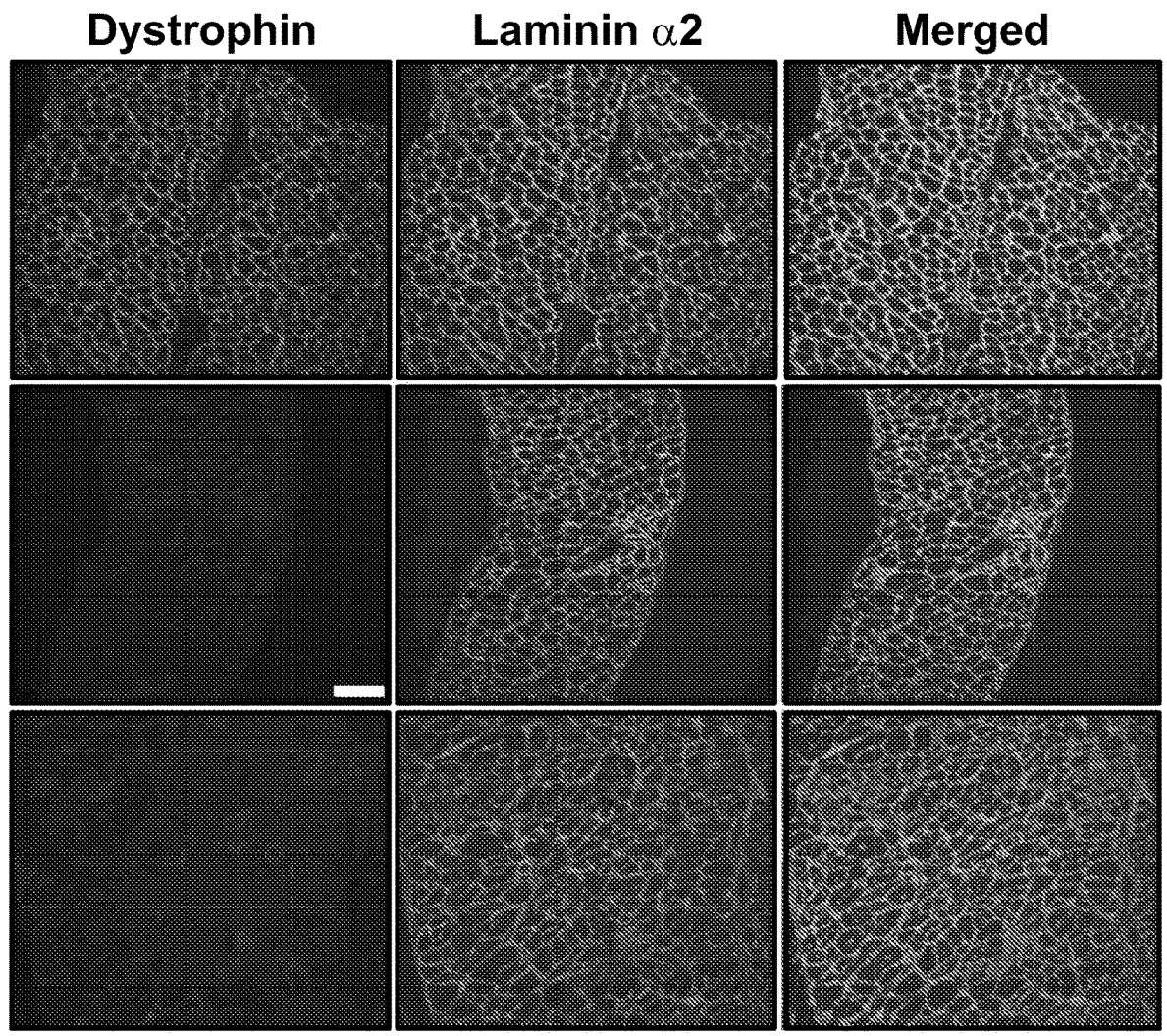
Figure 17:
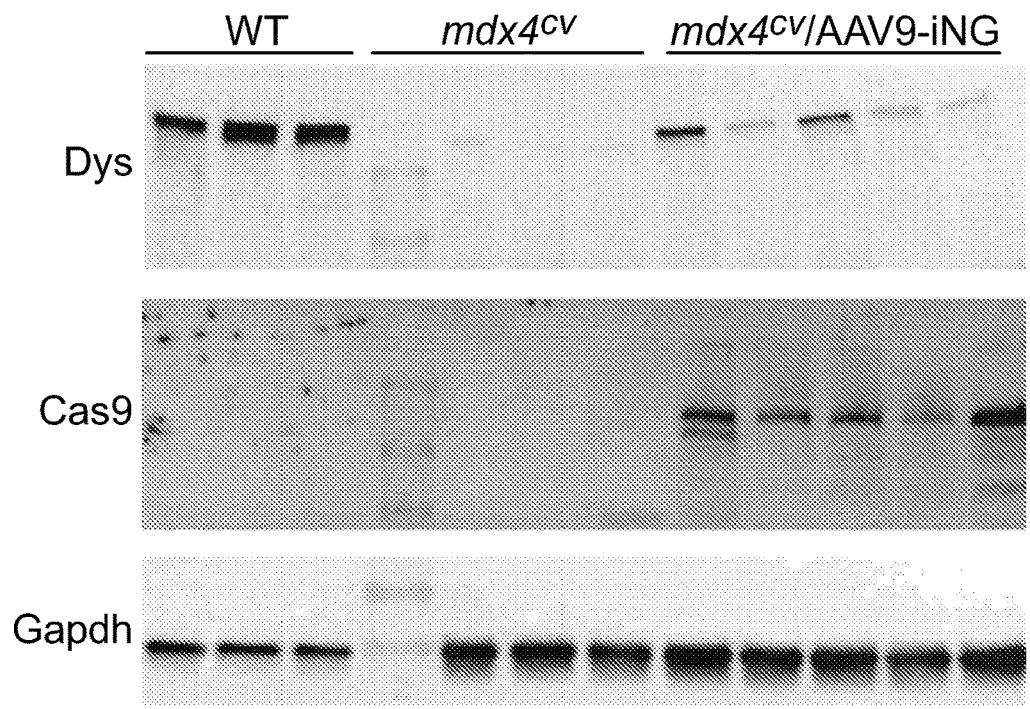
FIG. 17 shows Western blot analysis of gastrocnemius muscles from WT and mdx$^{4cv}$ (10 weeks of age) treated with or without tail vein injection of AAV9-iNG.
Figure 17:
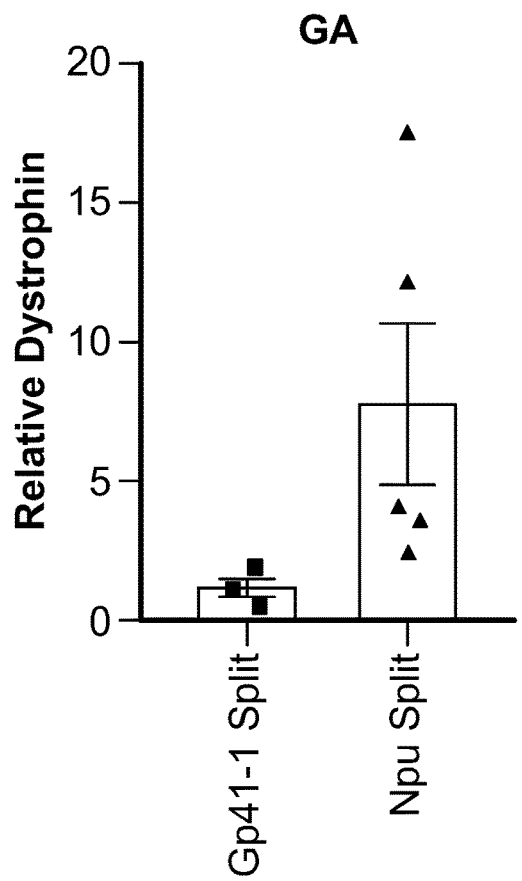
Figure 18:
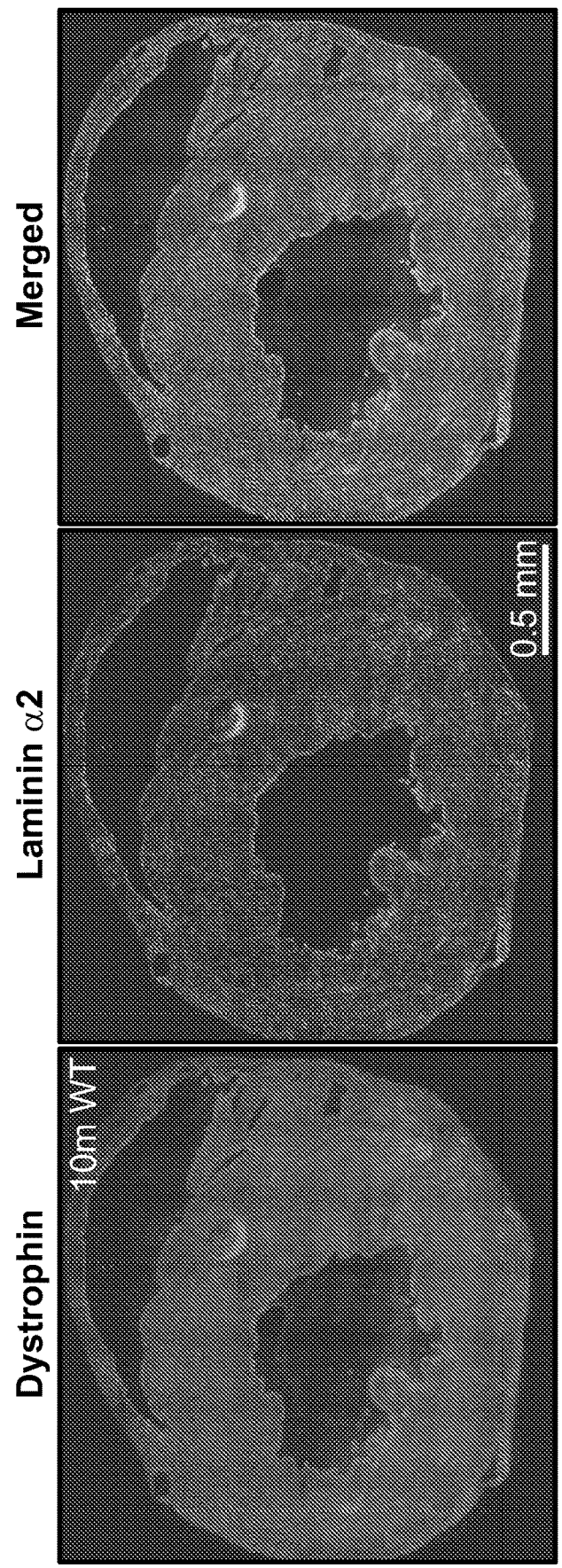
FIG. 18 shows stitched large images showing dystrophin and laminin-α2 immunostaining of the entire heart sections of a WT mouse at 10 months of age. Scale bars: 0.5 mm.
Figure 19:
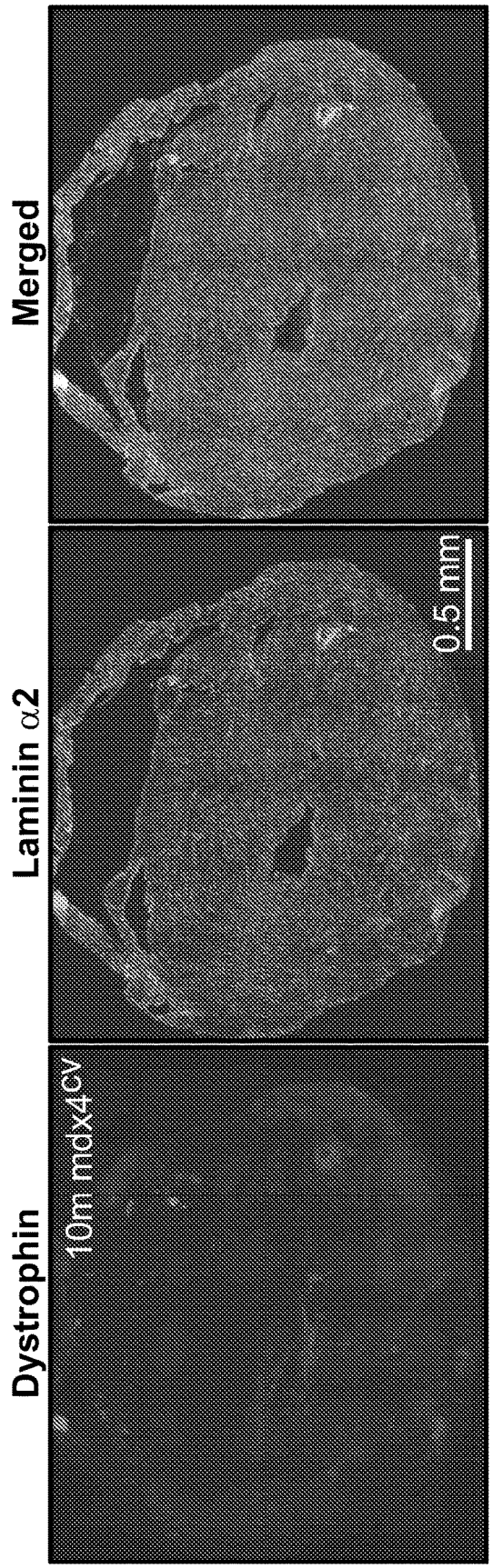
FIG. 19 shows stitched large images showing dystrophin and laminin-α2 immunostaining of the entire heart sections of a control mdx$^{4cv}$ mouse at 10 months of age. Scale bars: 0.5 mm.
Figure 20:
FIG. 20 shows stitched large images showing dystrophin and laminin-α2 immunostaining of the entire heart sections mdx$^{4cv}$ mouse #1976 9-10 months after intravenous injection of AAV9-iNG at 5 weeks of age. Mouse number is shown in yellow, Scale bars: 0.5 mm.
Figure 21:
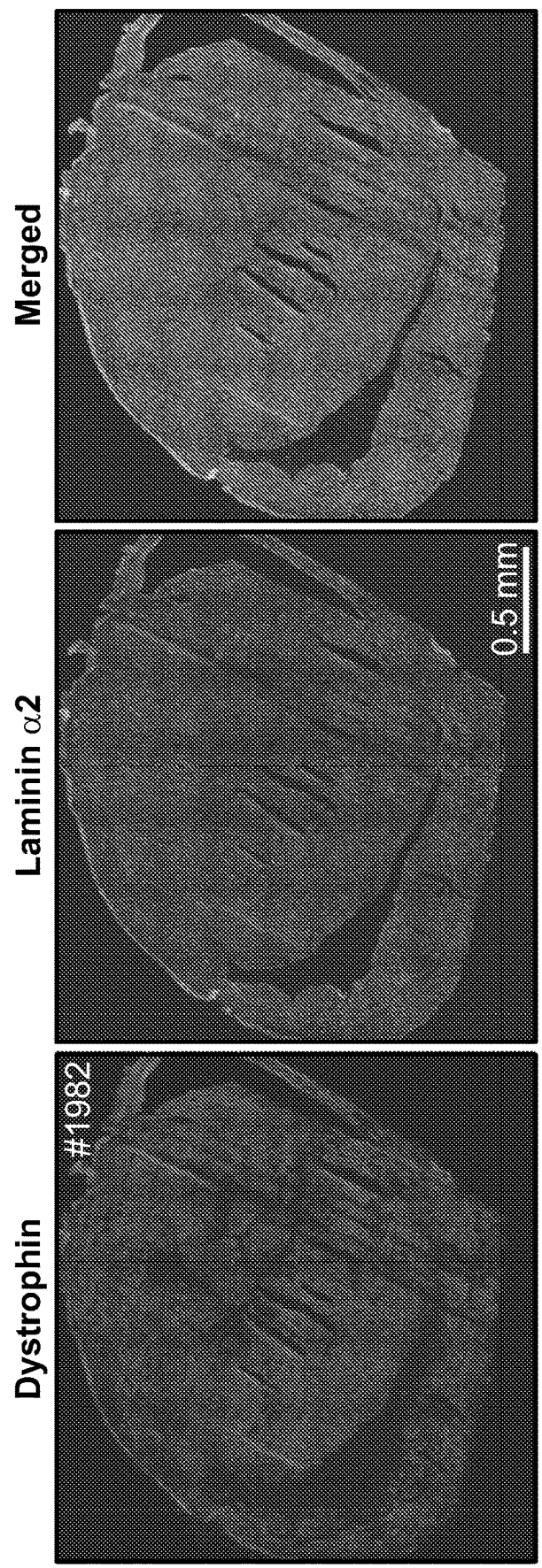
FIG. 21 shows stitched large images showing dystrophin and laminin-α2 immunostaining of the entire heart sections mdx$^{4cv}$ mouse #1982 9-10 months after intravenous injection of AAV9-iNG at 5 weeks of age. Mouse number is shown in yellow. Scale bars: 0.5 mm.
Figure 22:
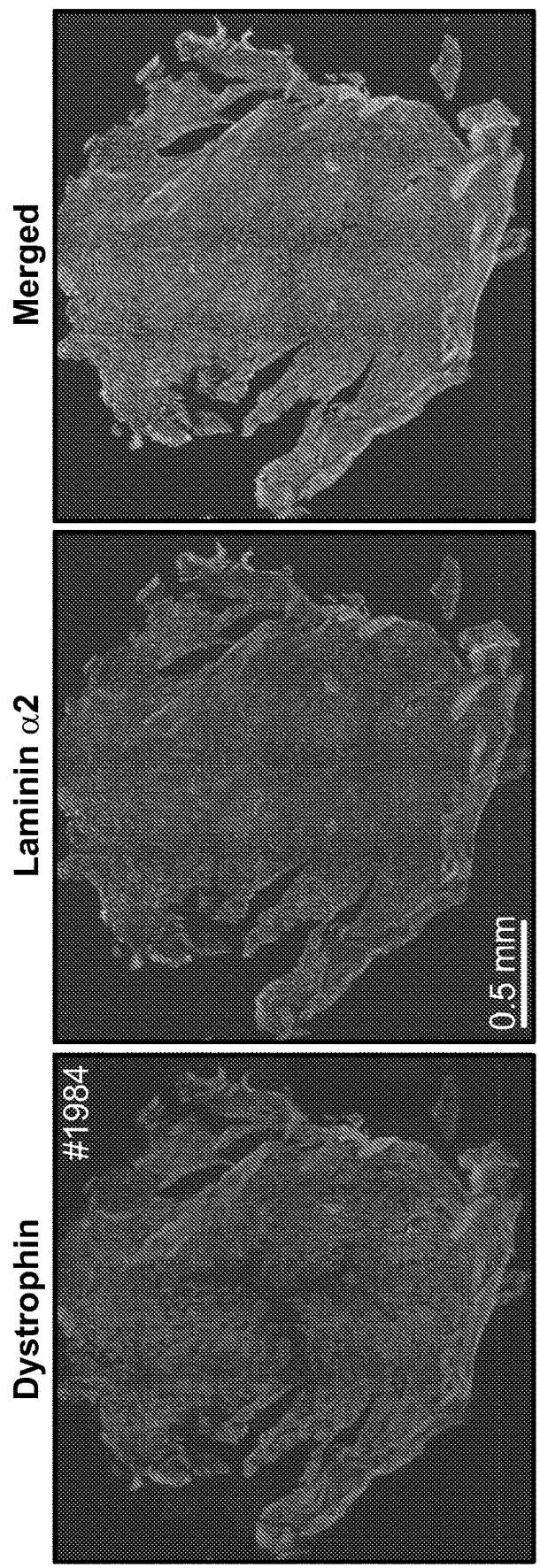
FIG. 22 shows stitched large images showing dystrophin and laminin-α2 immunostaining of the entire heart sections mdx$^{4cv}$ mouse #1985 9-10 months after intravenous injection of AAV9-iNG at 5 weeks of age. Mouse number is shown in yellow. Scale bars: 0.5 mm.
Figure 23:
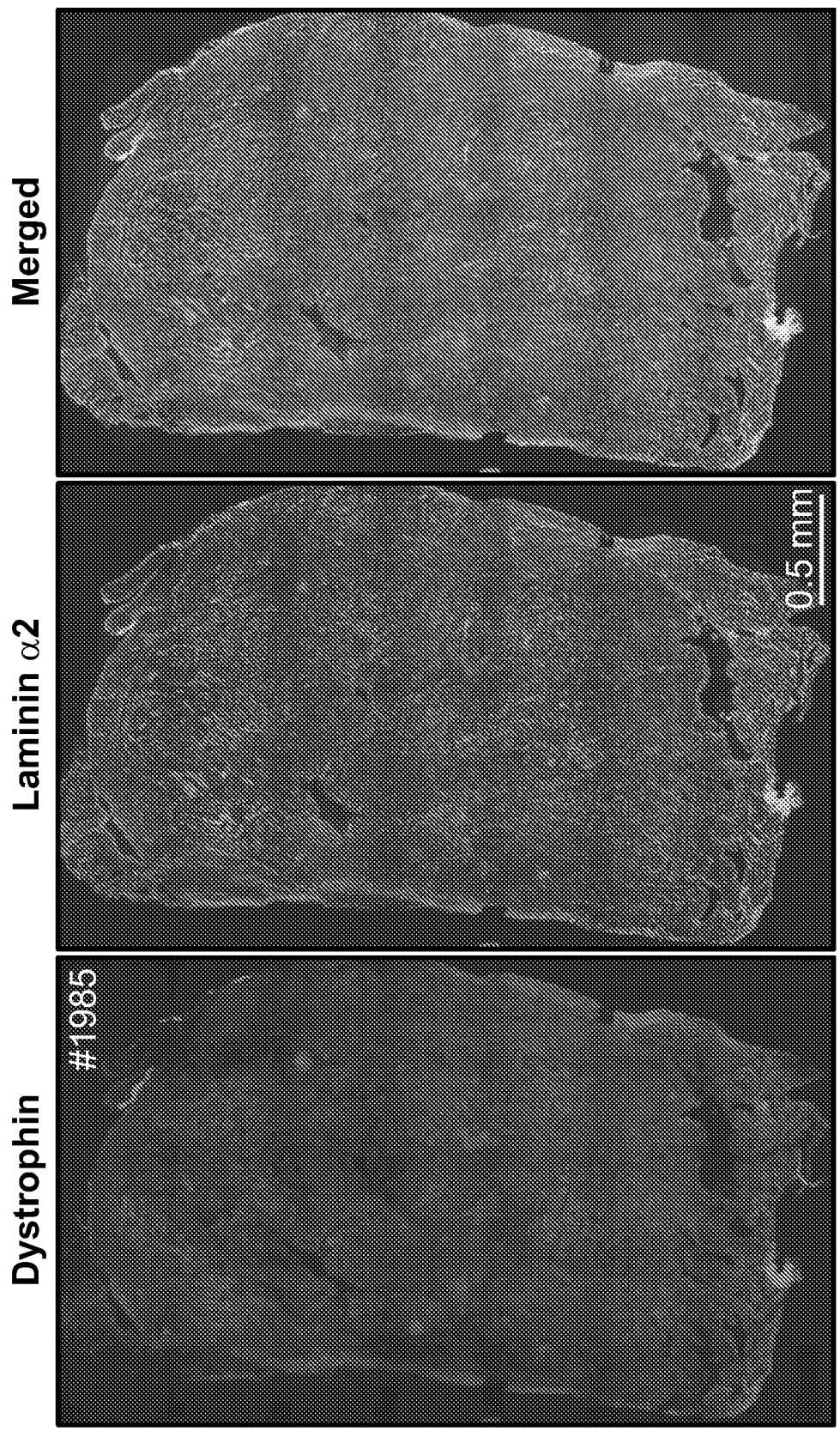
FIG. 23 shows stitched large images showing dystrophin and laminin-α2 immunostaining of the entire heart sections mdx$^{4cv}$ mouse #1984 9-10 months after intravenous injection of AAV9-iNG at 5 weeks of age. Mouse number is shown in yellow, Scale bars: 0.5 mm.

A cohort of nine mdx$^{4cv}$ mice were treated with AAV9-iNG (a total of $1 \times 10^{14}$ vg/kg, 1:1 of the N and C-terminal halt) through a single tail vein injection at 5 weeks of age. A subset of the mice was sacrificed at 5 weeks after AAV9-iNG administration. Dystrophin was found to be widely rescued in mdx$^{4cv}$ heart (FIG. 8a and FIGS. 9-15). Quantification of the entire heart sections showed that 41.9±10.5% cardiomyocytes of mdx$^{4cv}$ mice became dystrophin positive at 10 weeks of age after systematic AAV9-iNG treatment (N=5) while the control mdx$^{4cv}$ hearts were essentially dystrophin negative (0.03±0.02%, N=4) (FIG. 8b). Dystrophin was also rescued in skeletal muscles (diaphragm and gastrocnemius) of mdx$^{4cv}$ mice treated with AAV9-iNG, albeit the recovery was less efficient as compared to that in the heart (FIGS. 8c, 8d, and FIG. 16). Western blot analysis showed that dystrophin was rescued in mdx$^{4cv}$ mouse heart to 45.9±11.7% of the WT level following systemic AAV9-iNG treatment (FIGS. 8e, 8f). Consistent with the immunofluorescence data, Western blot showed dystrophin was restored to about 8.0±2.6% of the WT level in the gastrocnemius muscle of mdx$^{4cv}$ mice (FIG. 17).

Figure 8G:
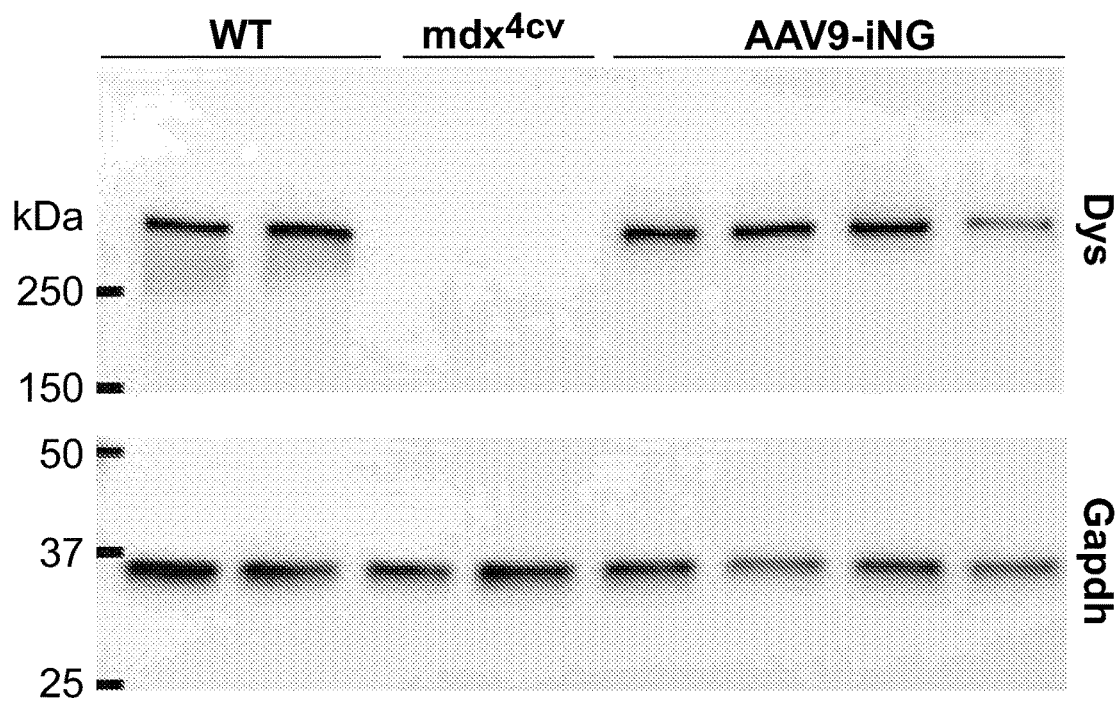
Figure 8H:
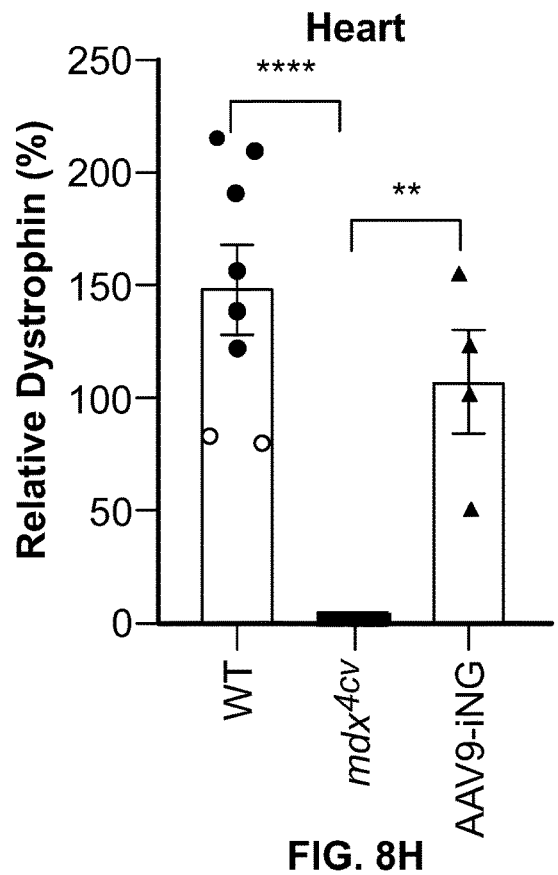
Figure 24A:
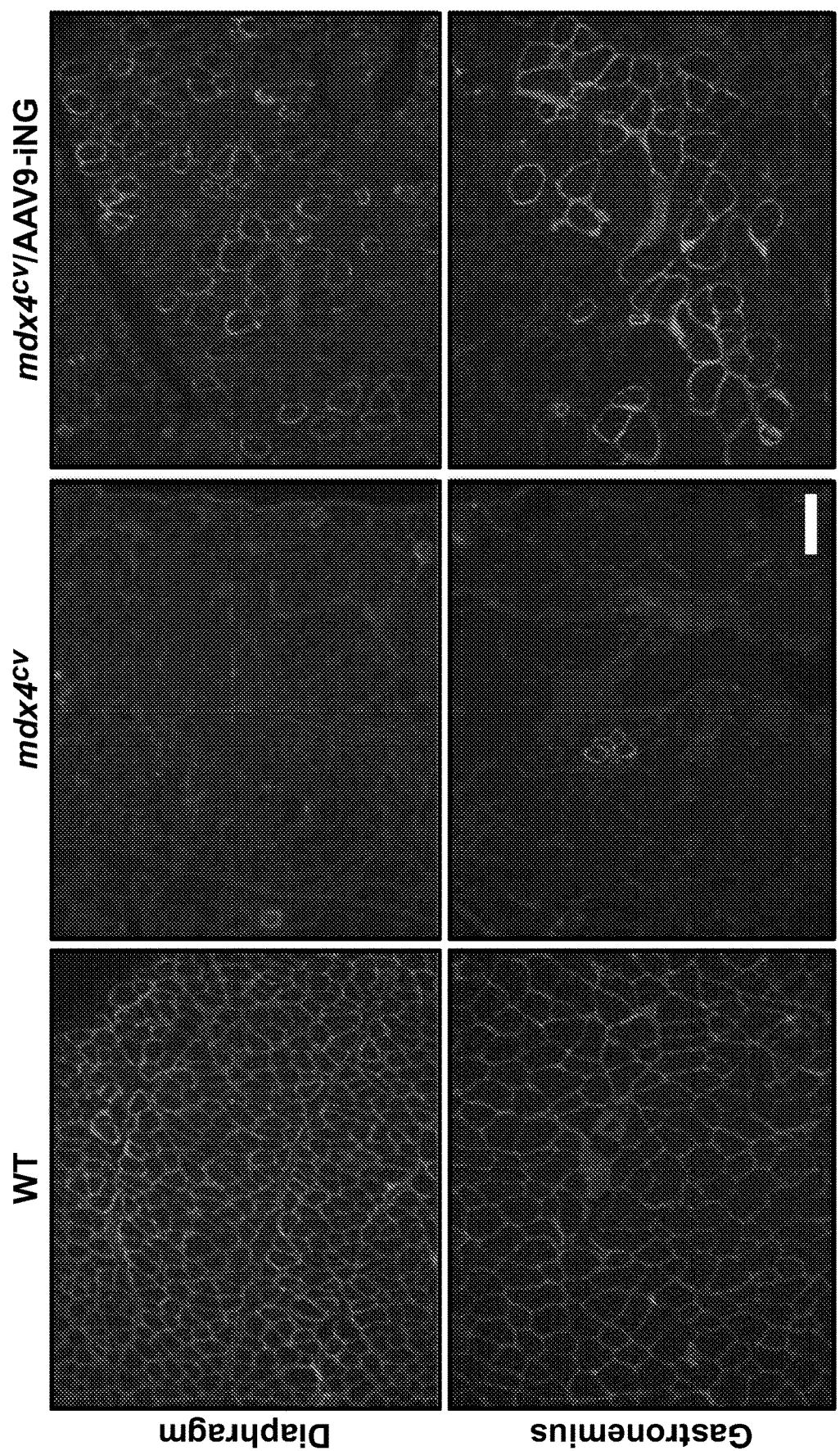
FIGS. 24a-24c show restoration of dystrophin expression in the skeletal muscles of 10-month-old mdx$^{4cv}$ mice after tail vein injection of AAV9-iNG at 5 weeks of age.
Figure 24B:
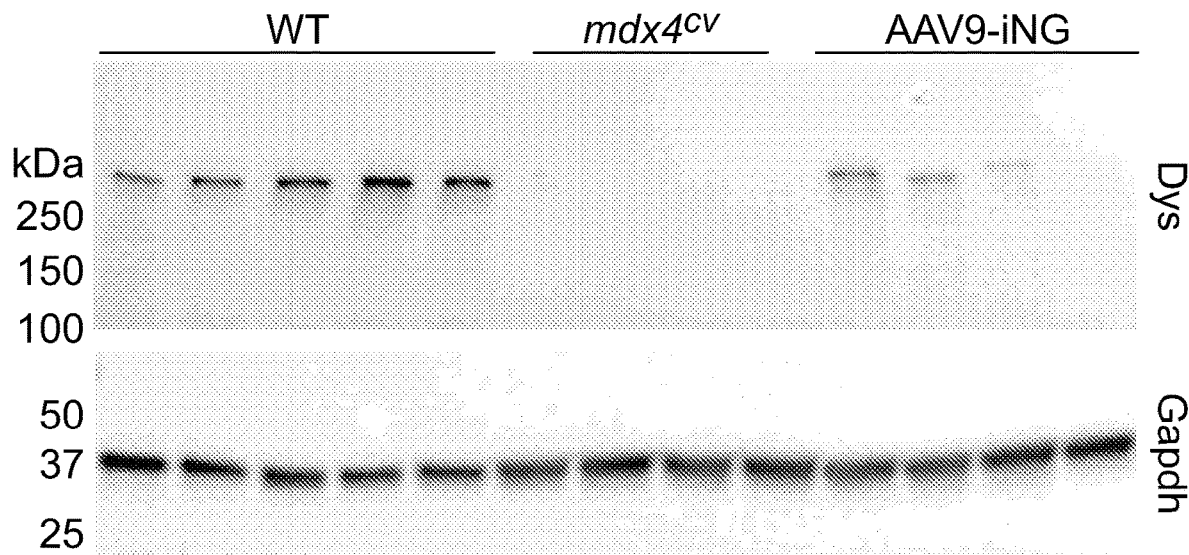
Figure 24C:
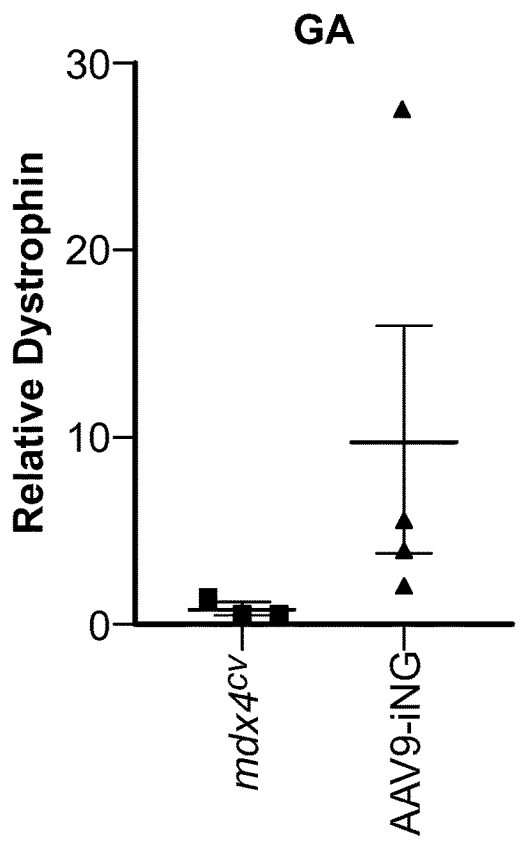

A group of mdx$^{4cv}$ mice treated with intravenous administration of AAV9-iNG at 5 weeks of age were kept for 10 months to study the long-term impact of systemic ABE editing therapy. A near complete dystrophin restoration was observed in the hearts of all four treated mdx$^{4cv}$ mice at 10 months of age (FIGS. 8a, 8b and FIGS. 18-23). Dystrophin was also rescued in the skeletal muscles of these older animals with a similar percentage of dystrophin-positive muscle fibers as analyzed at the 10 weeks of age (FIGS. 5c, 5d and FIG. 24). Western blot analysis showed near WT levels of dystrophin expression in the hearts of the 10-month-old mdx$^{4cv}$ mice treated with AAV9-iNG (FIGS. 8g, 8h).

Figure 8I:
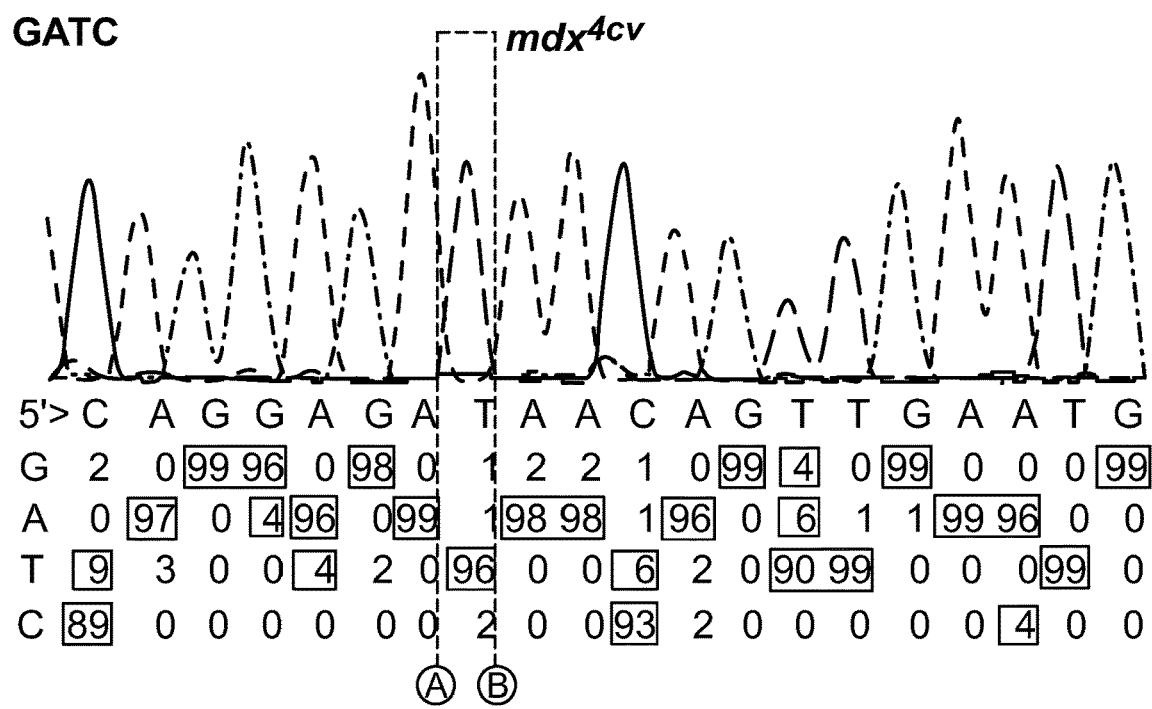
Figure 8I:
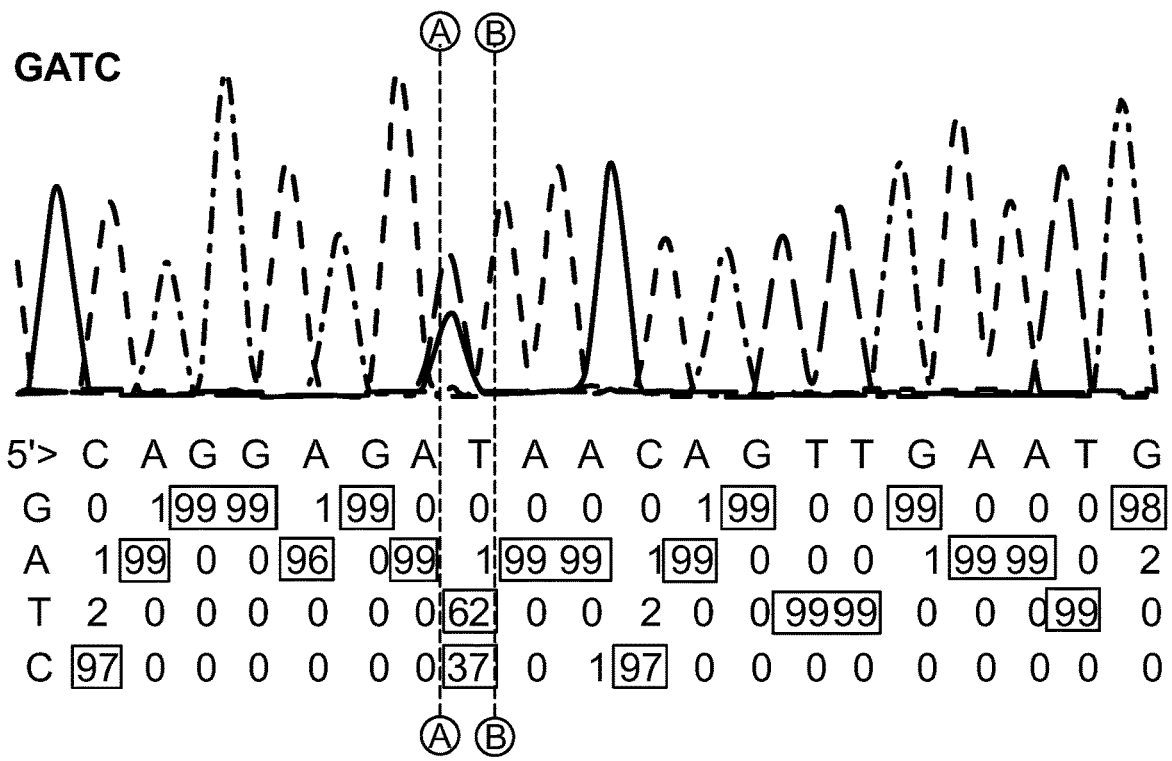
Figure 8I:
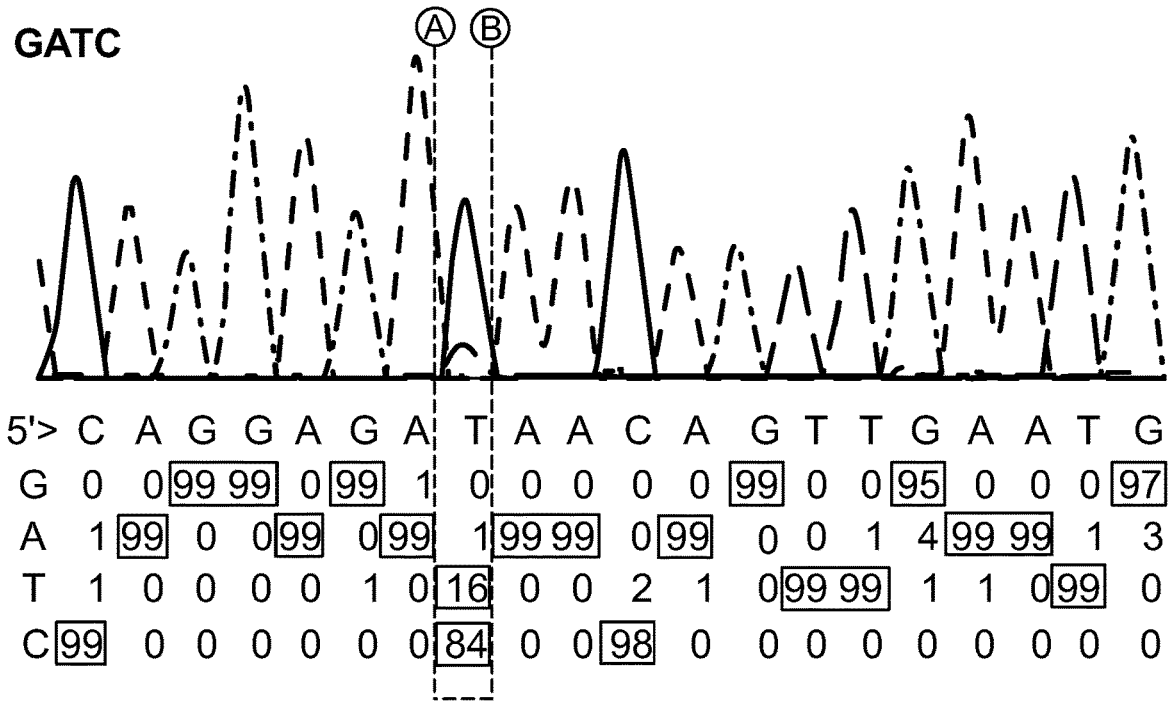
Figure 8J:
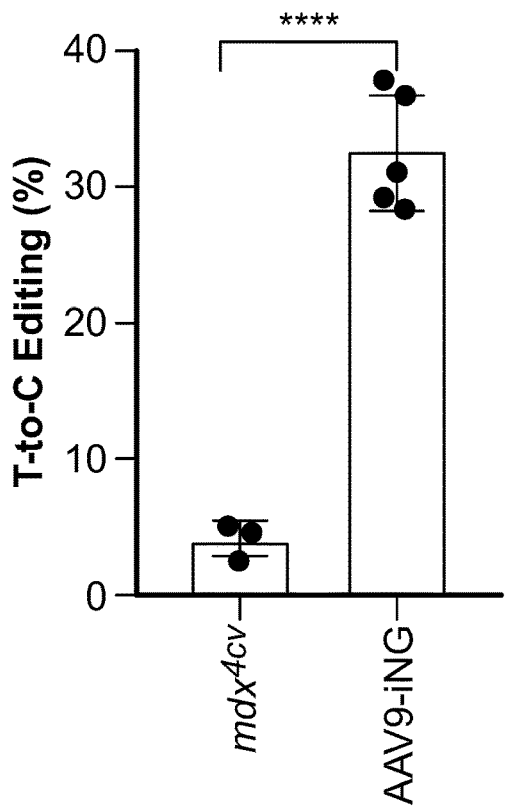
Figure 8K:
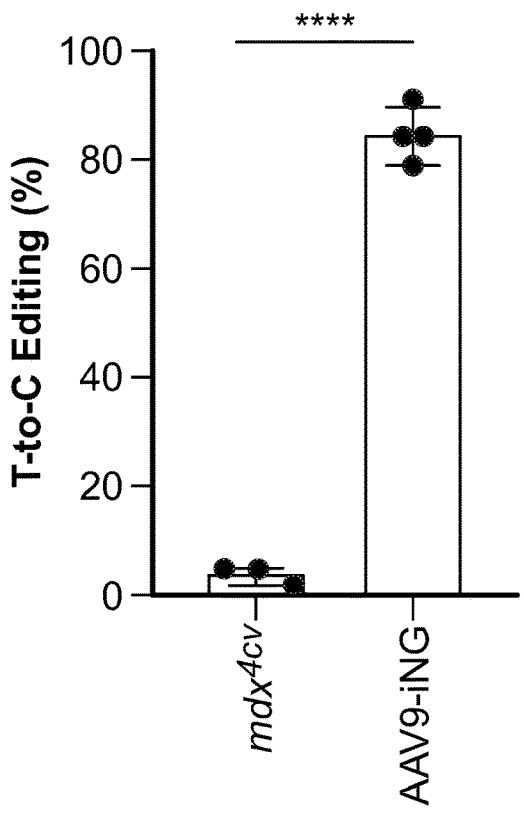
Figure 9:
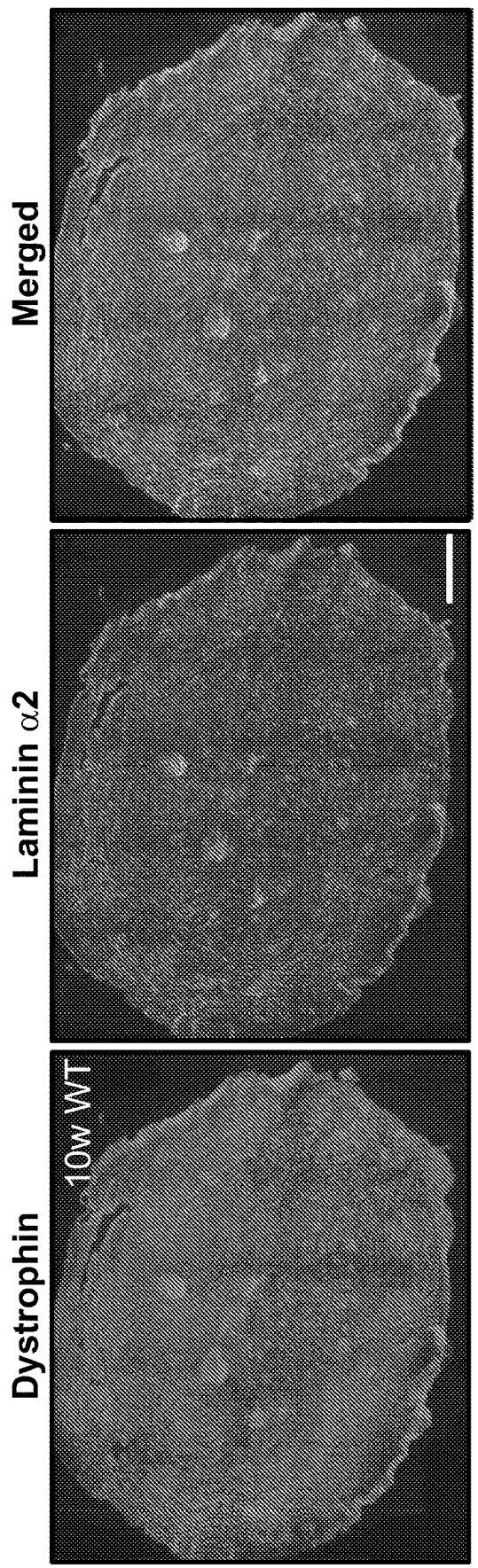
FIG. 9 shows stitched large images showing dystrophin and laminin-α2 immunostaining of the entire heart sections of a WT mouse at 10 weeks of age. Scale bars: 0.5 mm.
Figure 10:
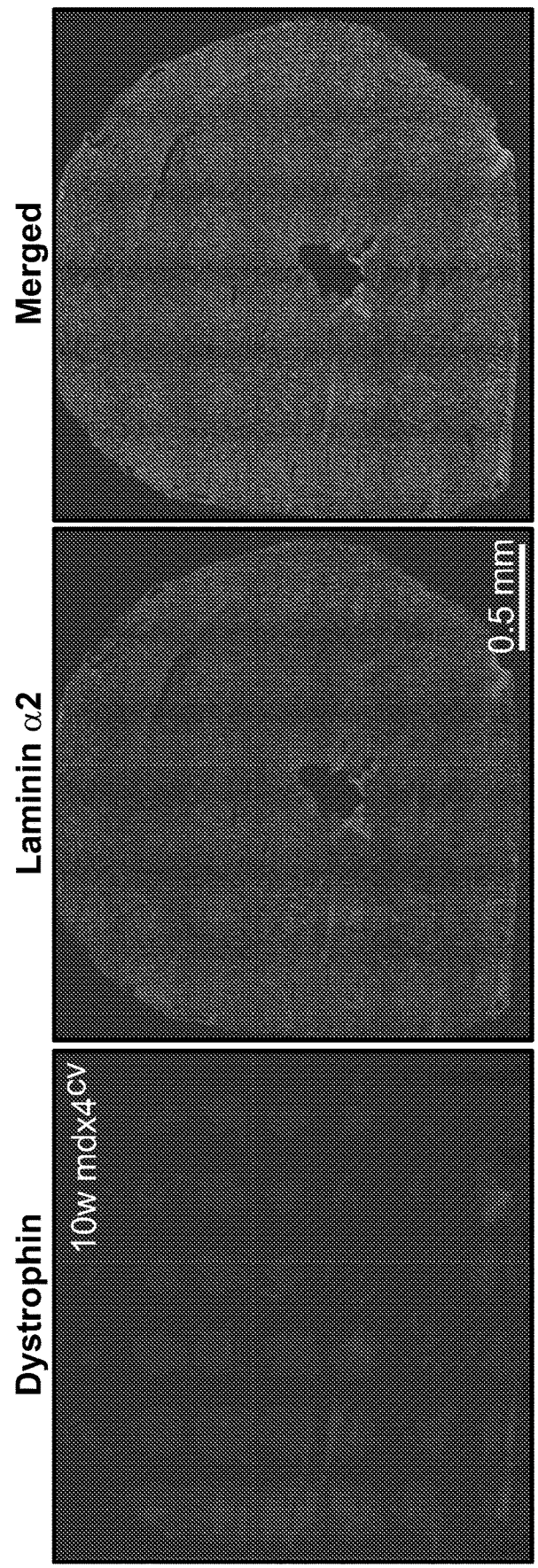
Figure 11:
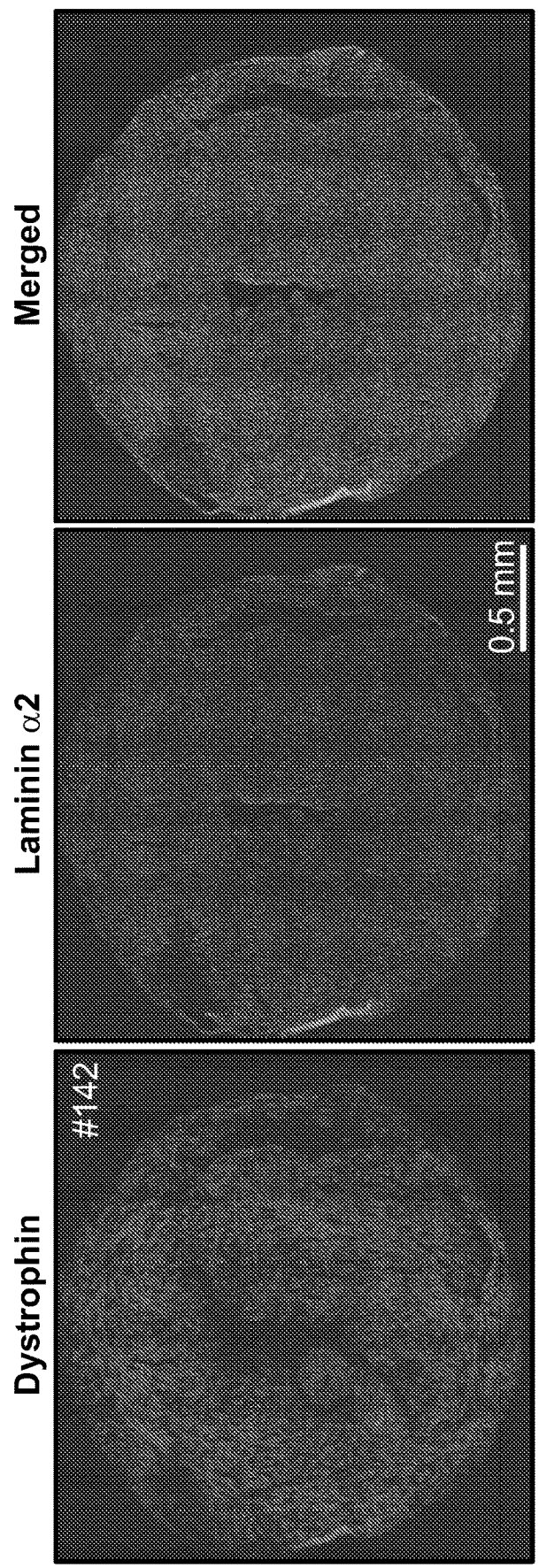
FIG. 11 shows stitched large images showing dystrophin and laminin-α2 immunostaining of the entire heart sections mdx$^{4cv}$ mouse #142 five weeks after intravenous injection of AAV9-iNG at 5 weeks of age. Mouse number is shown in yellow. Scale bars: 0.5 mm.
Figure 12:
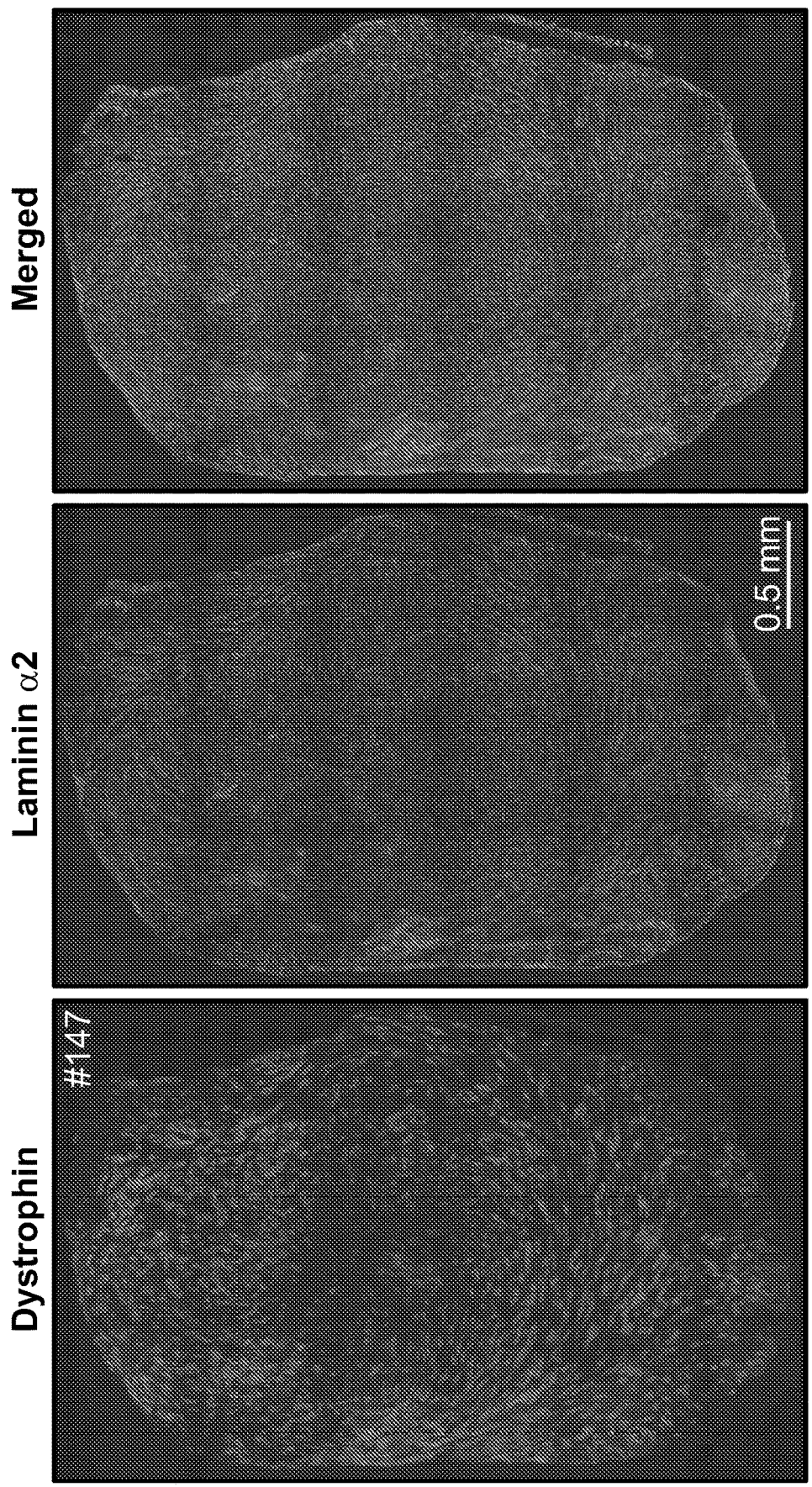
FIG. 12 shows stitched large images showing dystrophin and laminin-α2 immunostaining of the entire heart sections mdx$^{4cv}$ mouse #147 five weeks after intravenous injection of AAV9-iNG at 5 weeks of age. Mouse number is shown in yellow. Scale bars: 0.5 mm.
Figure 13:
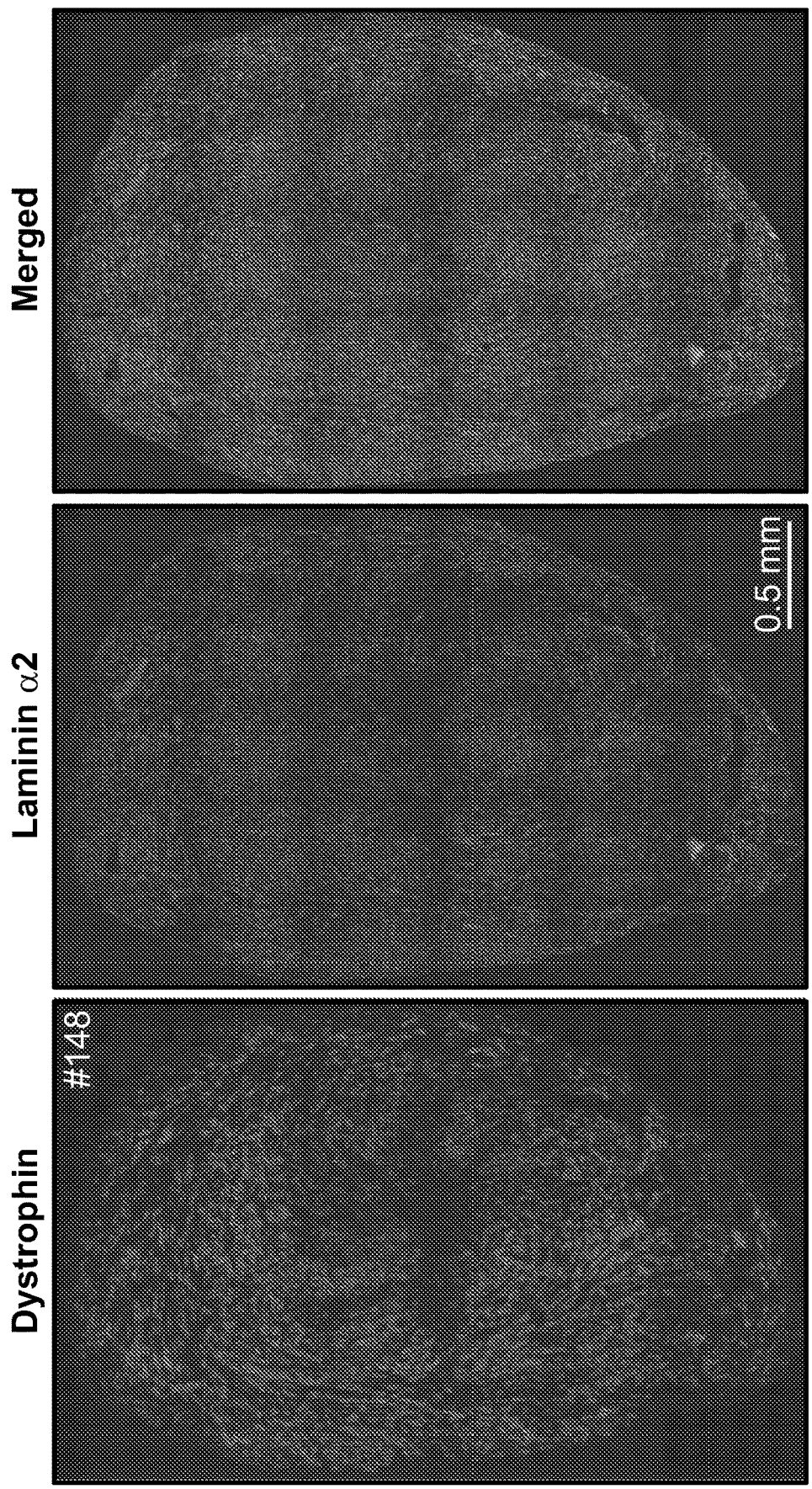
FIG. 13 shows stitched large images showing dystrophin and laminin-α2 immunostaining of the entire heart sections mdx$^{4cv}$ mouse #148 five weeks after intravenous injection of AAV9-iNG at 5 weeks of age. Mouse number is shown in yellow. Scale bars: 0.5 mm.
Figure 14:
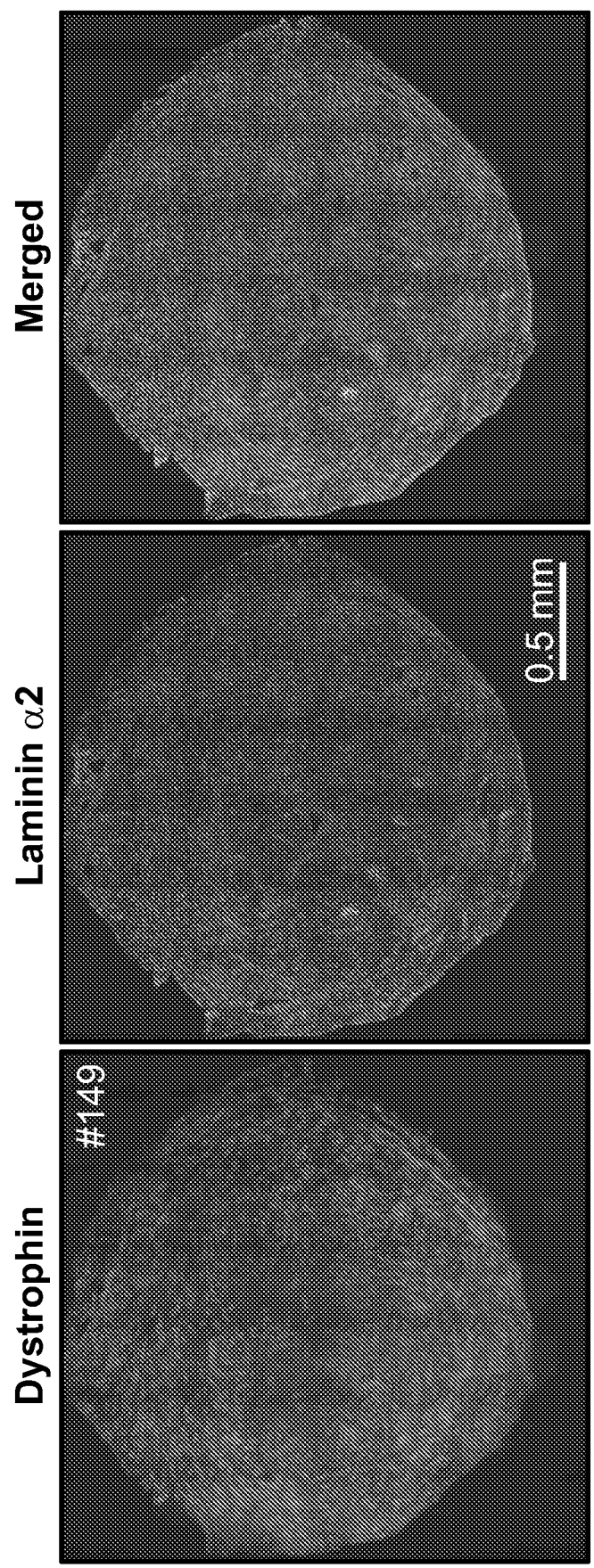
FIG. 14 shows stitched large images showing dystrophin and laminin-α2 immunostaining of the entire heart sections mdx$^{4cv}$ mouse #149 five weeks after intravenous injection of AAV9-iNG at 5 weeks of age. Mouse number is shown in yellow. Scale bars: 0.5 mm.
Figure 15:
FIG. 15 shows stitched large images showing dystrophin and laminin-α2 immunostaining of the entire heart sections mdx$^{4cv}$ mouse #150 five weeks after intravenous injection of AAV9-iNG at 5 weeks of age. Mouse number is shown in yellow. Scale bars: 0.5 mm.

The heart and muscle tissues contain many different types of cells, which makes it challenging to precisely determine the DNA editing efficiency in myocytes. To estimate the editing efficiency of the Dmd gene, the total RNA was extracted from the heart tissues treated with or without AAV9-iNG, amplified the target region by RT-PCR, and analyzed the resulting amplicons by Sanger sequencing and BEAT program. The AAV9-iNG treated mdx$^{4cv}$ hearts showed an average 32.6±2.0% T-to-C editing at 10 weeks of age (FIGS. 8i, 8j) and 84.6±2.6% at 10 months of age (FIGS. 8i, 8k).

Figure 25A:
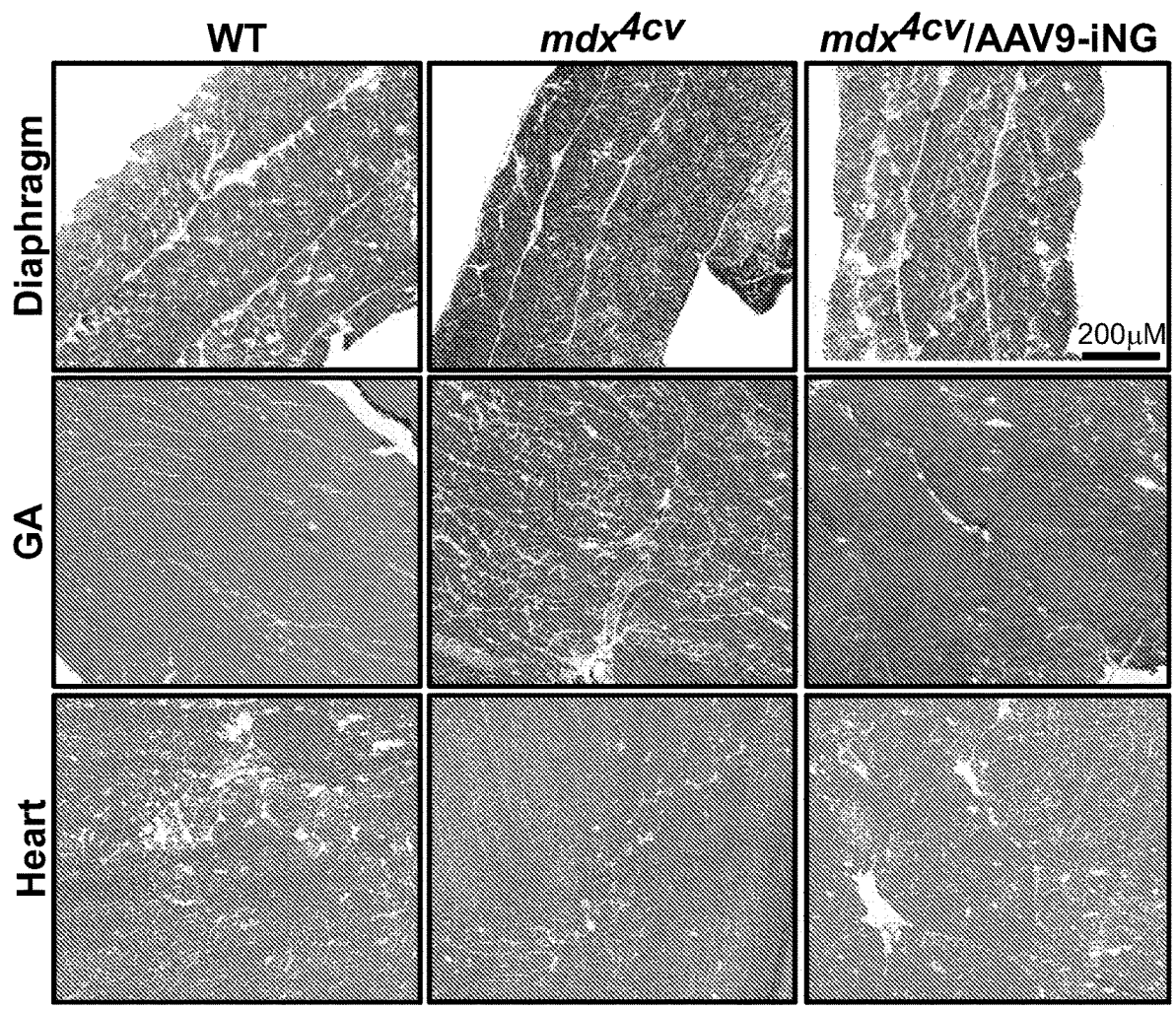
Figure 25B:
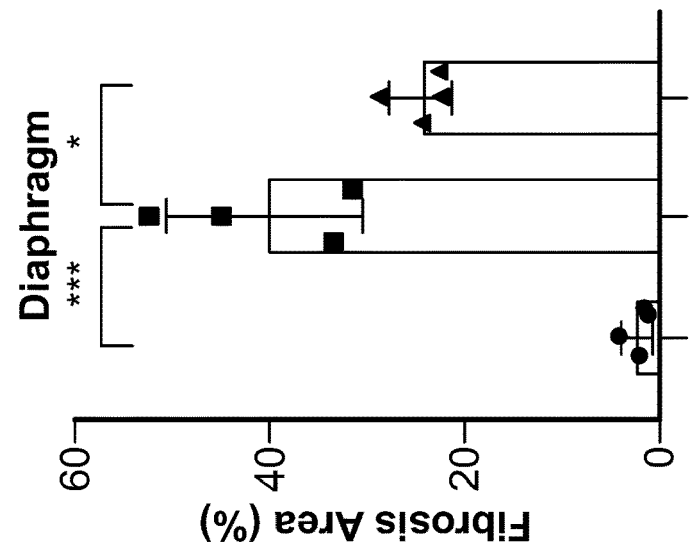
Figure 25C:
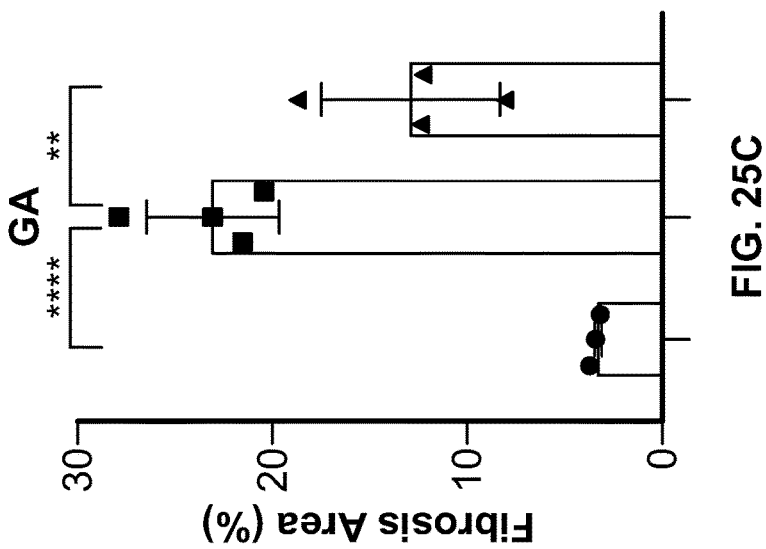
Figure 25D:
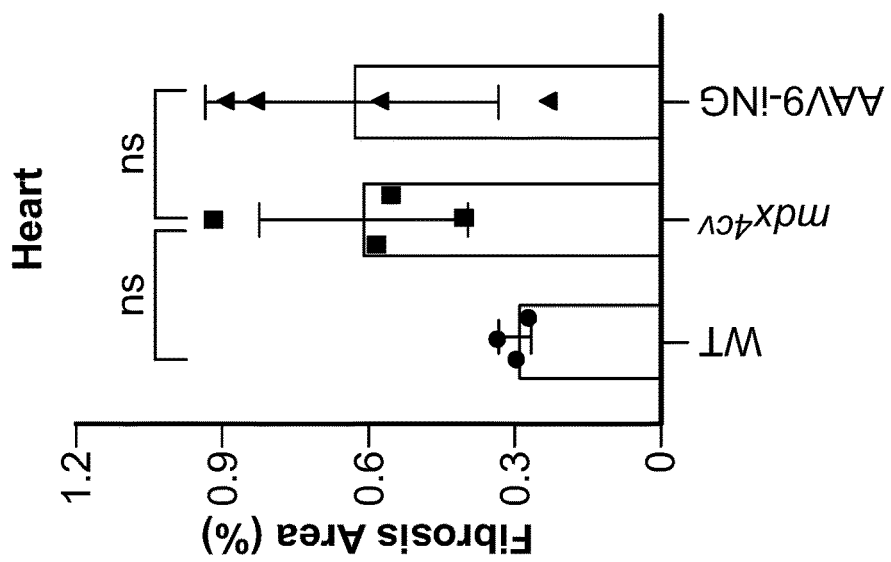
Figure 25G:
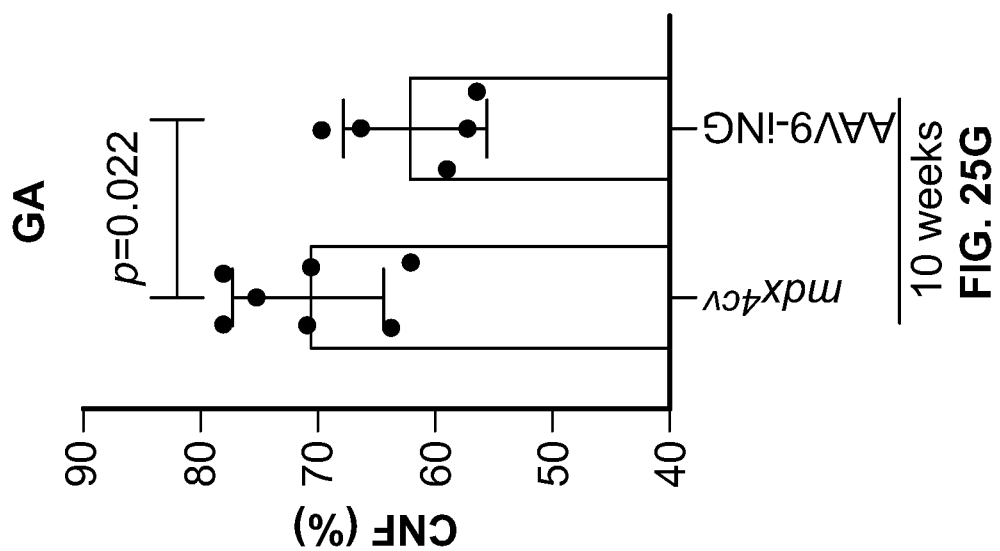
Figure 25F:
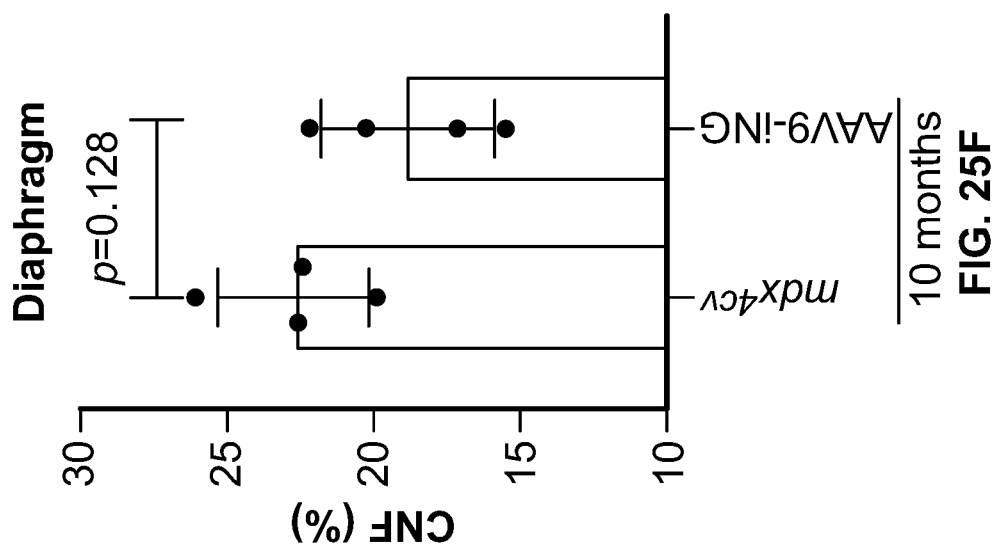
Figure 25E:
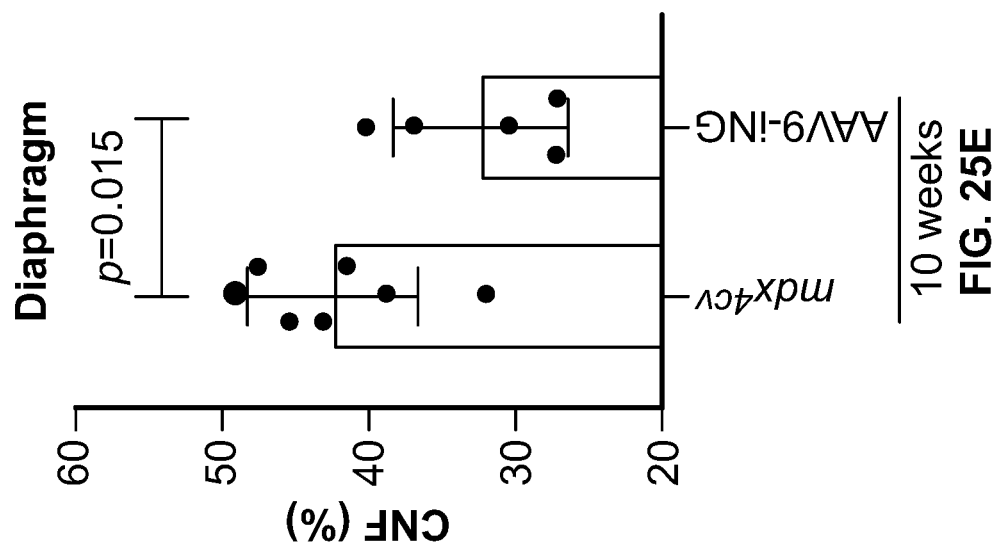
Figure 25H:
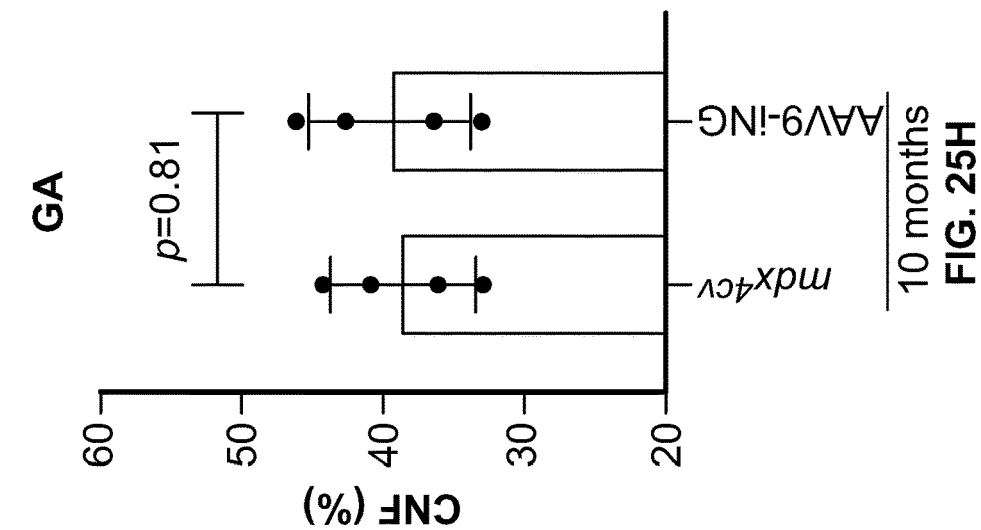
Figure 25I:
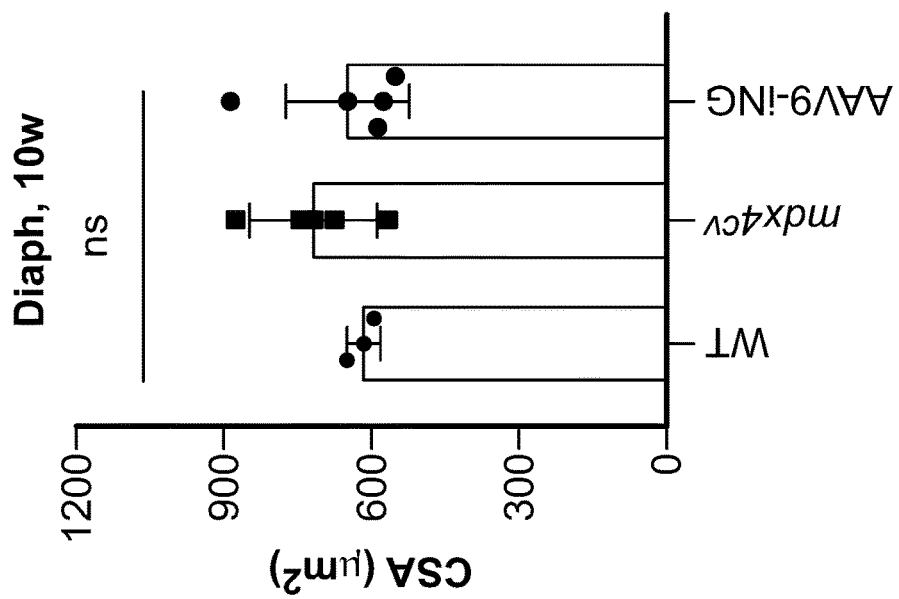
Figure 25J:
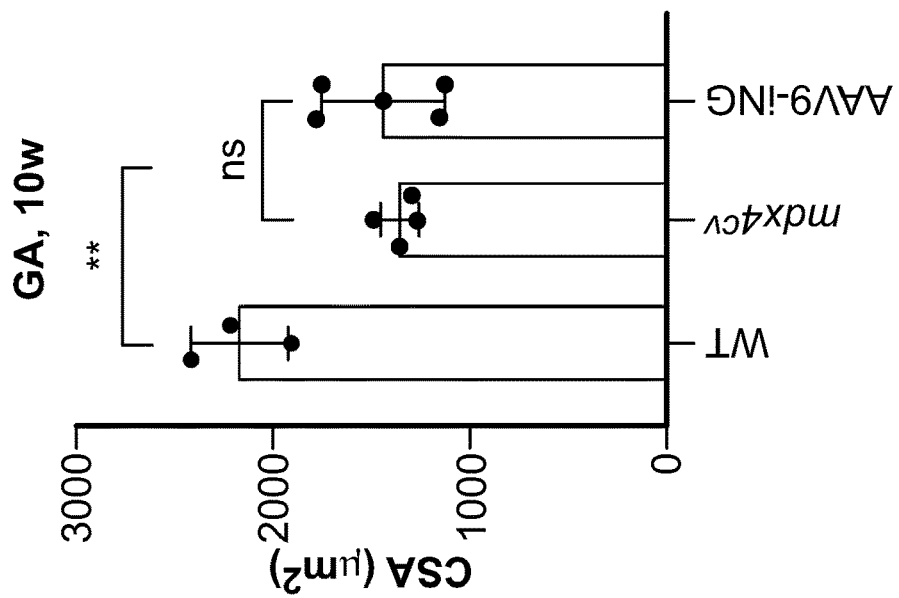
Figure 25K:
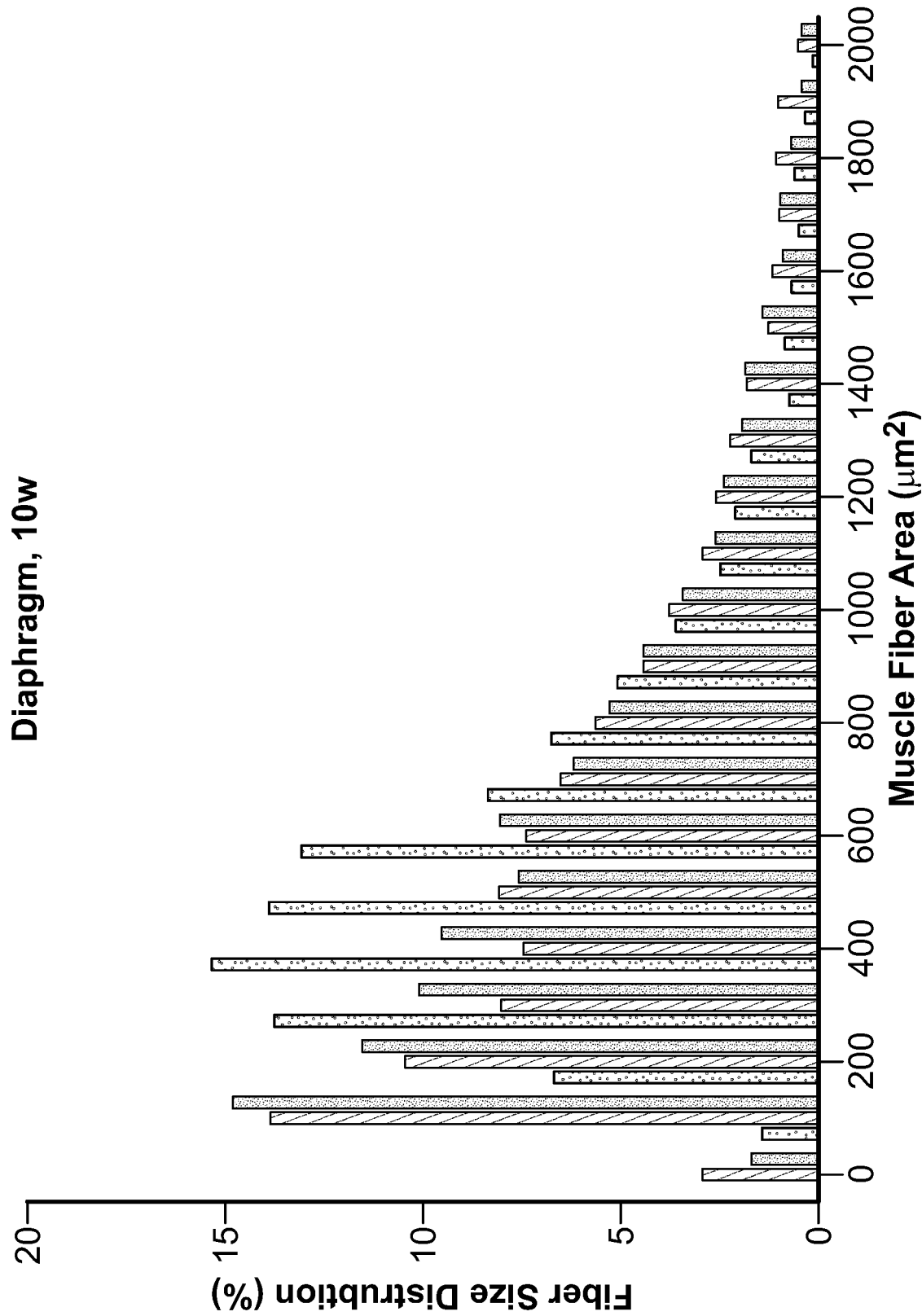
Figure 25I:
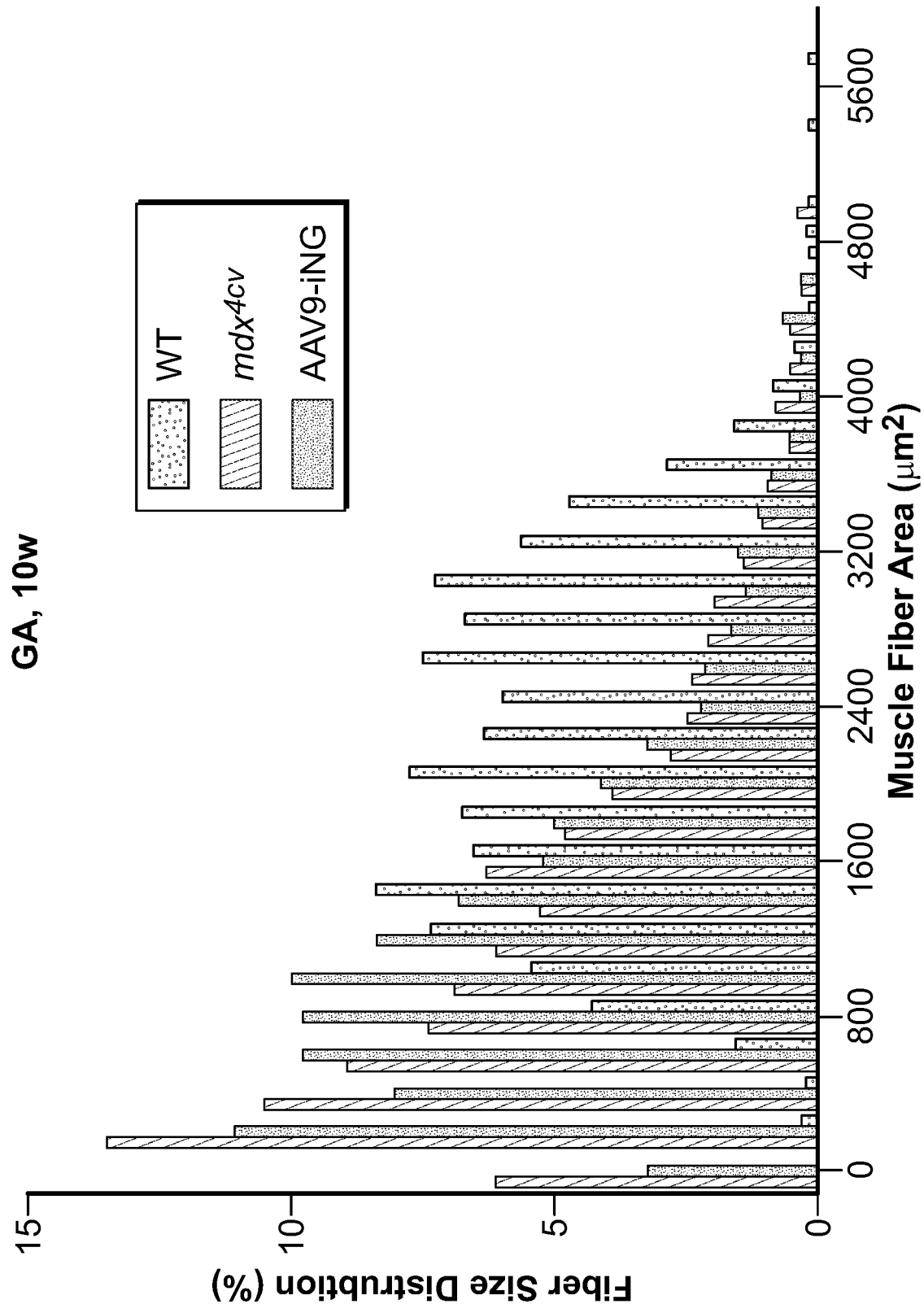
Figure 26B:
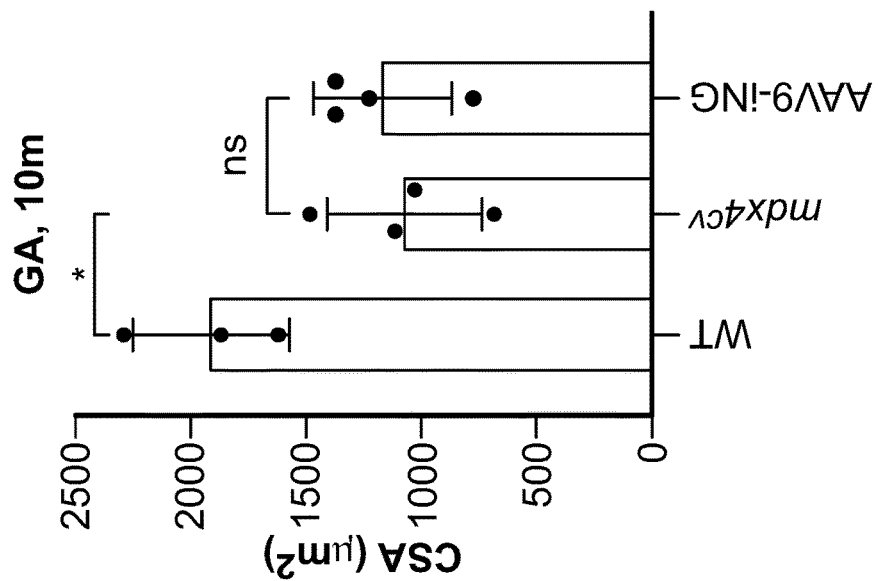
FIGS. 26a-26d show measurement of muscle fiber size in diaphragm and gastrocnemius muscles at 10 months of age.
Figure 26A:
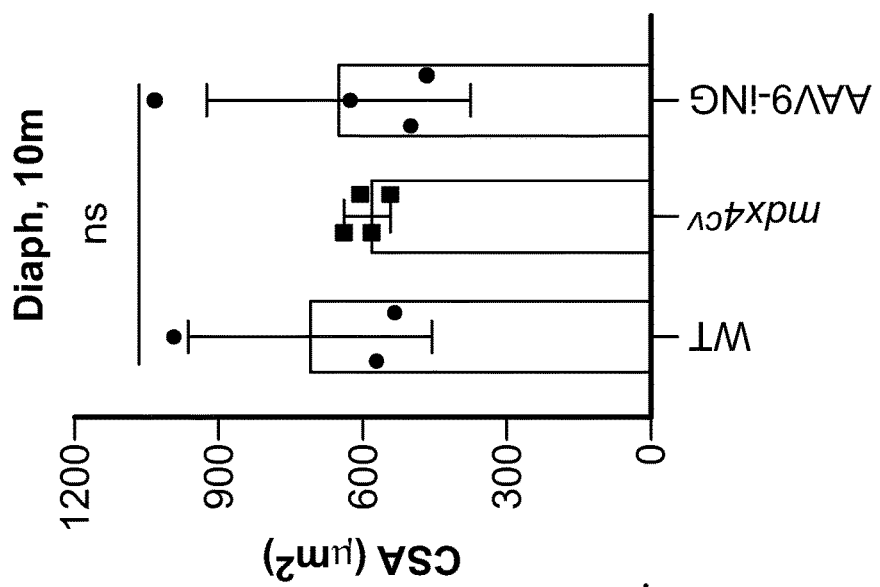

Repeated cycles of muscle degeneration and regeneration in muscular dystrophy result in muscle fibrosis. To examine if systemic AAV9-iNG delivery can improve the histopathology of mdx$^{4cv}$ mice, Trichrome staining was performed in 10-month-old mice. As compared to WT mice, the mdx$^{4cv}$ mice showed significantly elevated fibrosis in both diaphragm and gastrocnemius muscles and the fibrotic areas in these muscles were significantly reduced in the mdx$^{4cv}$ mice treated with AAV9-iNG (FIGS. 25a-25c). Consistent with previous studies that the mdx mice do not develop overt cardiomyopathy before one year old, there were no significant changes in cardiac fibrosis in mdx$^{4cv}$ mice with or without AAV9-iNG treatment at 10 months of age as compared to the WT controls (FIG. 25d). AAV9-iNG treatment also significantly reduced the percentage of centrally nucleated fibers (CNF) in both diaphragm and gastrocnemius muscles at 10 weeks of age (FIGS. 25e, 25g). By 10 months of age, the effects of AAV9-iNG treatments on CNF were blunted (FIGS. 25f, 25h). Although a significant difference in cross-sectional area (CSA) of muscle fibers was not observe following AAV9-iNG treatment (FIGS. 25i, 25j, and FIGS. 26a, 26b), the AAV9-iNG treatment appeared to shift the fiber size distribution towards those of the WT muscles (FIGS. 25k, 25l, and FIGS. 26c, 26d), particularly in gastrocnemius muscles at 10 weeks of age.

Figure 25M:
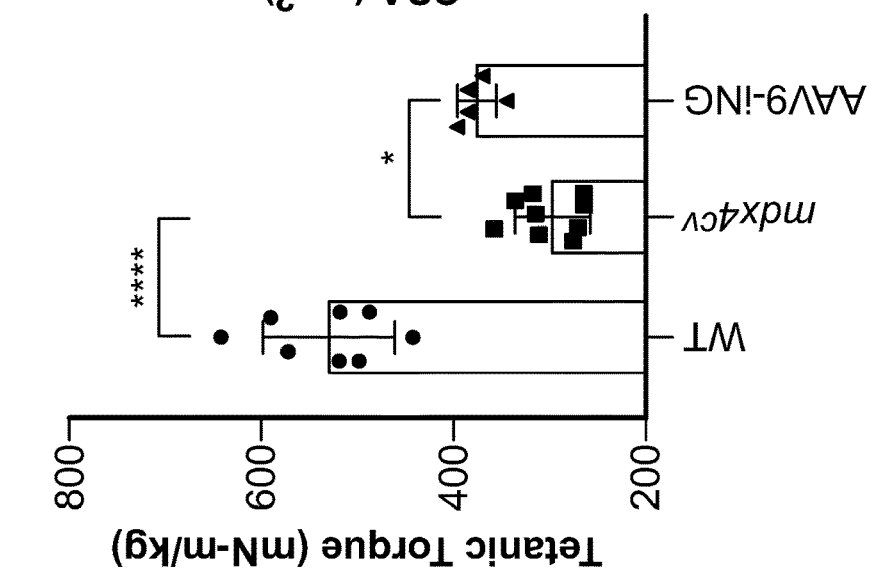
Figure 26C:
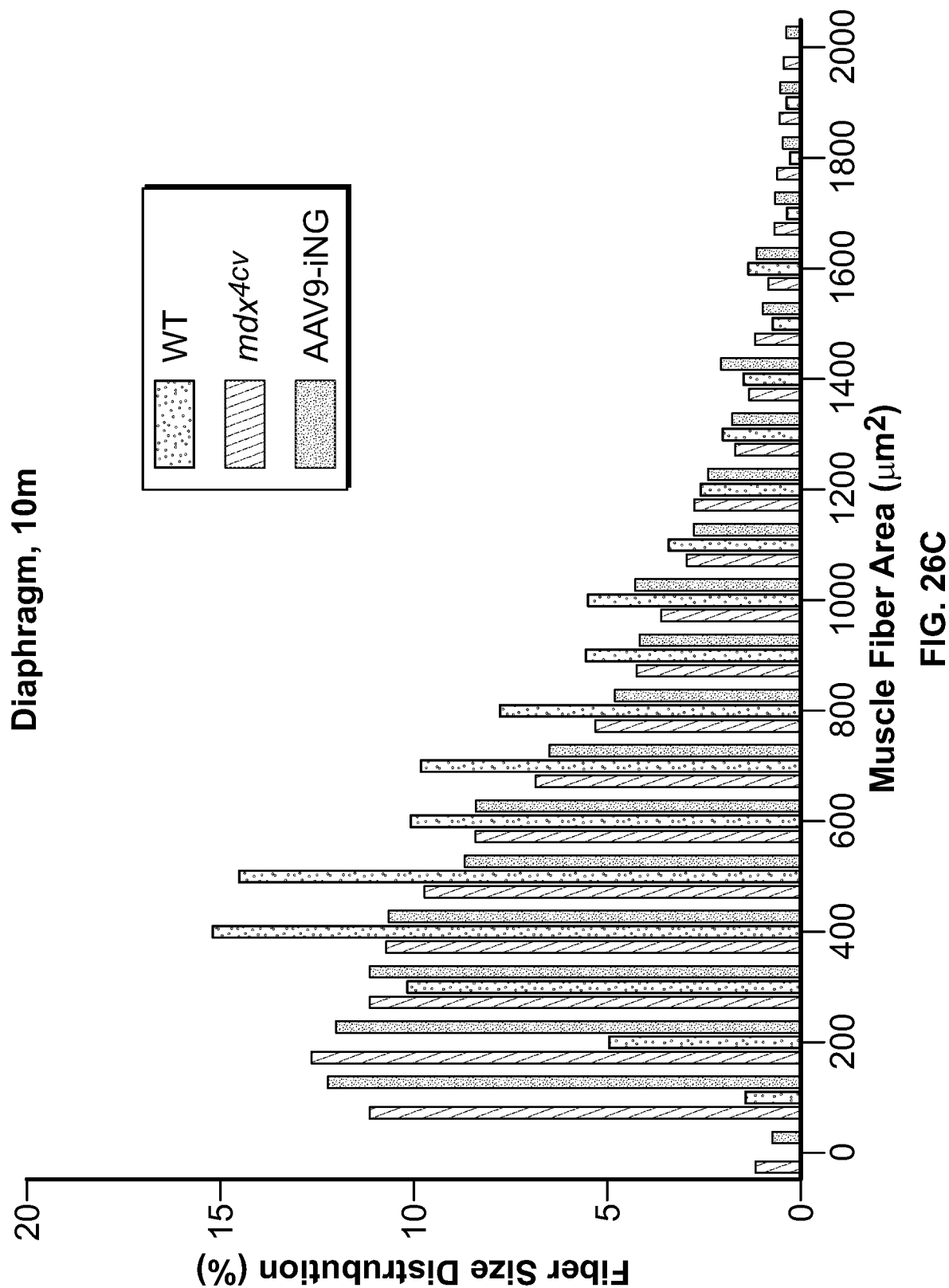
Figure 26D:
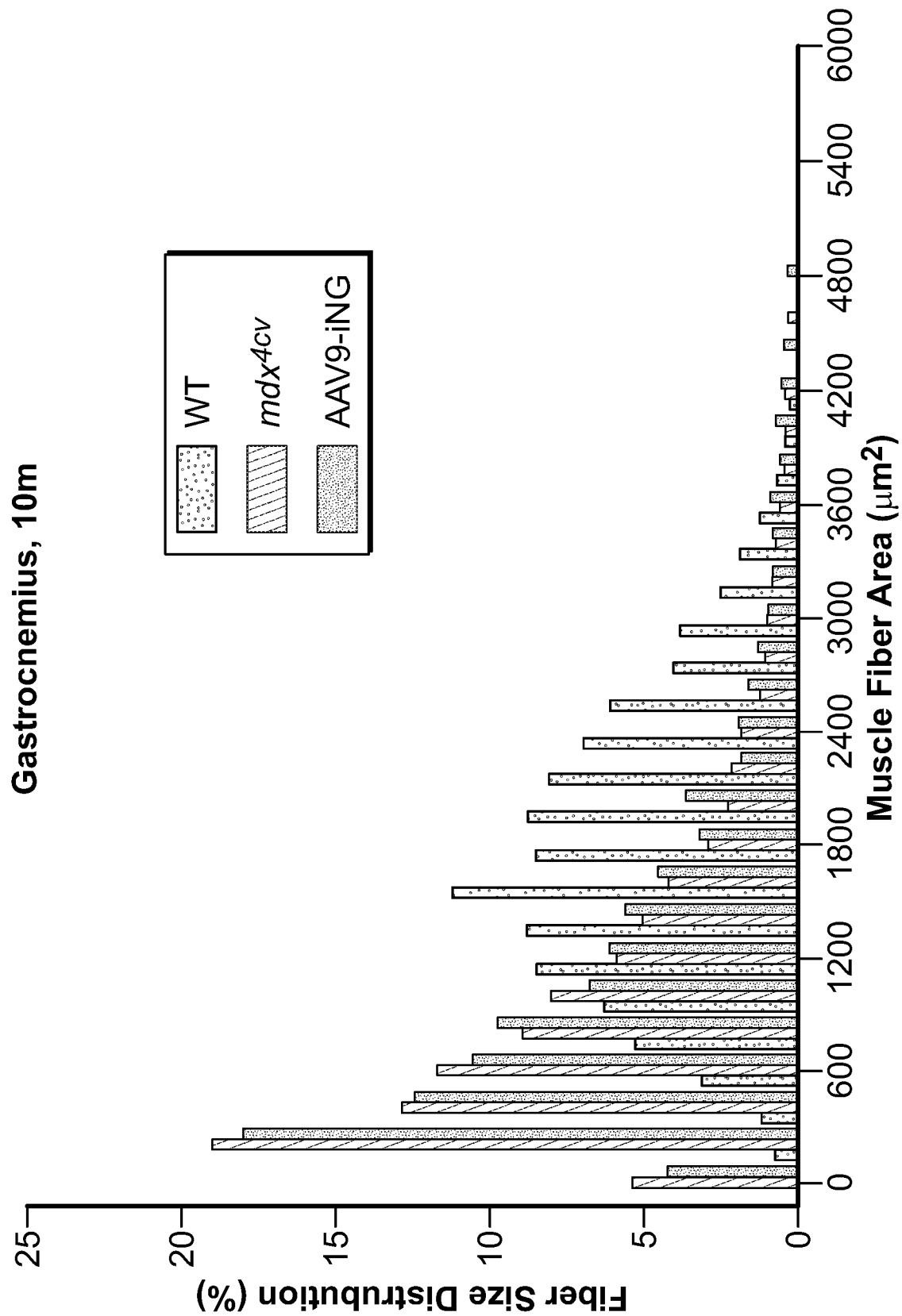

To test if systemic AAV9-iNG treatment can improve the muscle function, the muscle contractility was measured using an in vivo muscle test system. Maximum plantarflexion tetanic torque was measured during supramaximal electric stimulation of the tibial nerve at 150 Hz. While the $mdx^{4cv}$ mice produced significantly reduced torque as compared to the WT controls, systemic delivery of AAAV9-iNG significantly increased the tetanic torque in $mdx^{4cv}$ mice (FIG. 25m).

Example 5. The Safety Profile and Off-Target Activity of AAV9-iNG Treatment

Figure 27B:
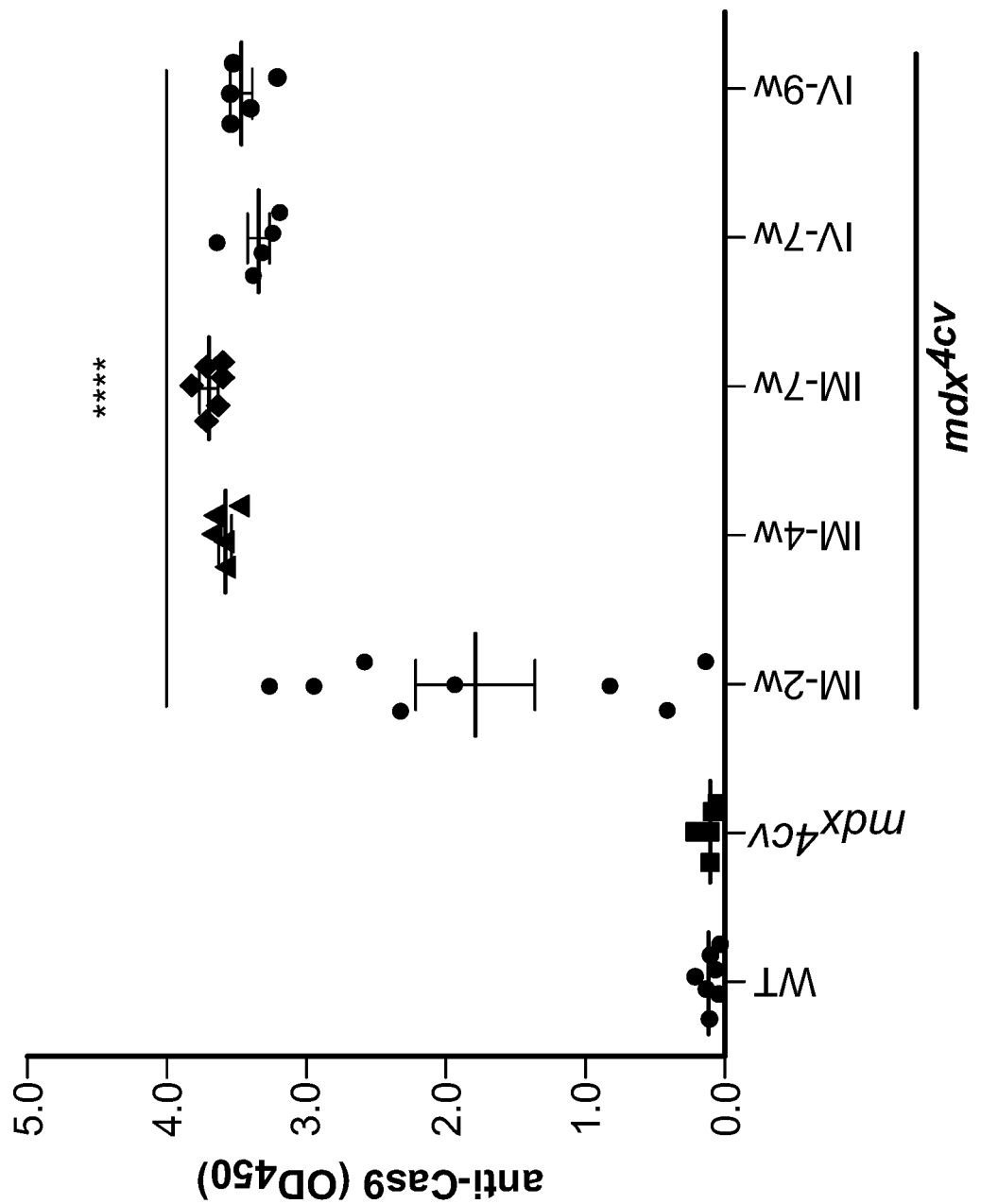

Previous studies showed that AAV-mediated delivery of CRISPR/Cas9 into neonatal mice resulted in humoral immune responses to AAV capsid but not Cas9. In contrast, AAV-mediated delivery of CRSPR/Cas9 into adult mice evoked robust anti-Cas9 immunity. Serum samples were collected to analyze the host immune responses to the AAV9 capsid and the base editor iABE-NGA. Intramuscular injection of AAV9-iNG into 5-6 weeks old $mdx^{4cv}$ mice produced robust anti-AAV9 capsid (FIG. 27a) and anti-Cas9 antibodies (FIG. 27b) at 2 weeks after injection. The anti-AAV9 titers were similar at different time points from 2 to 7 weeks post intramuscular injection and from 7 to 9 weeks post intravenous injection (FIG. 27a). The anti-Cas9 antibody titers showed a large variation among mice at 2 weeks after intramuscular injection, but all increased to peak by 4 weeks (FIG. 27b).

Figure 27C:
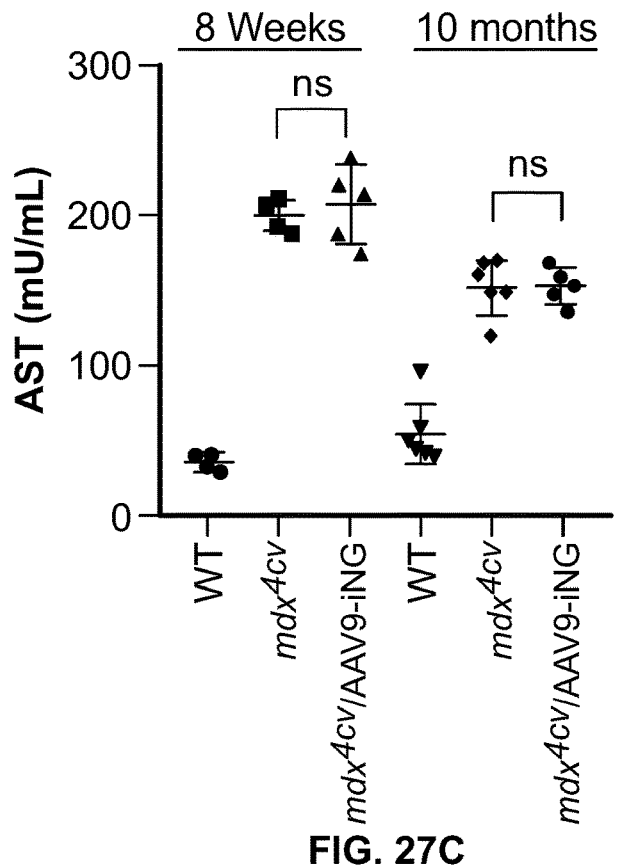
Figure 27D:
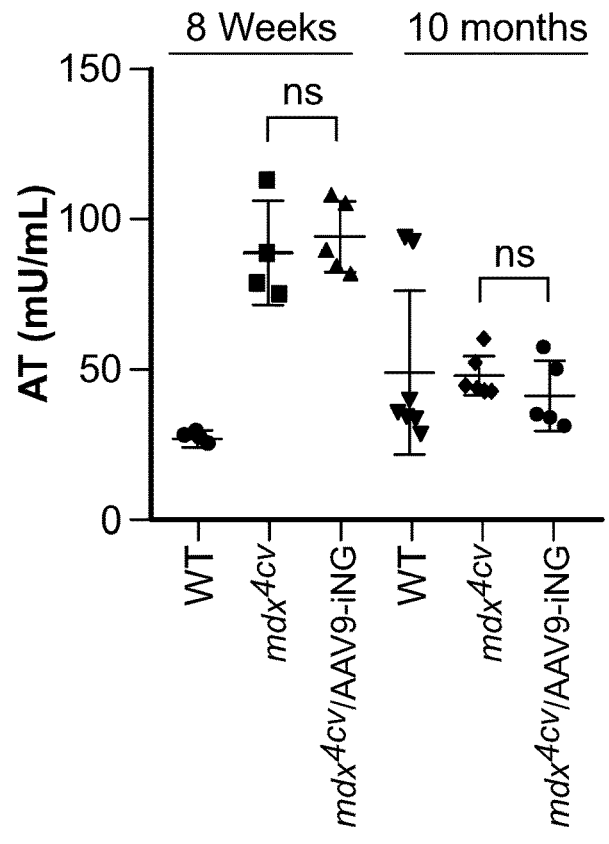
Figures 27E, 27F:
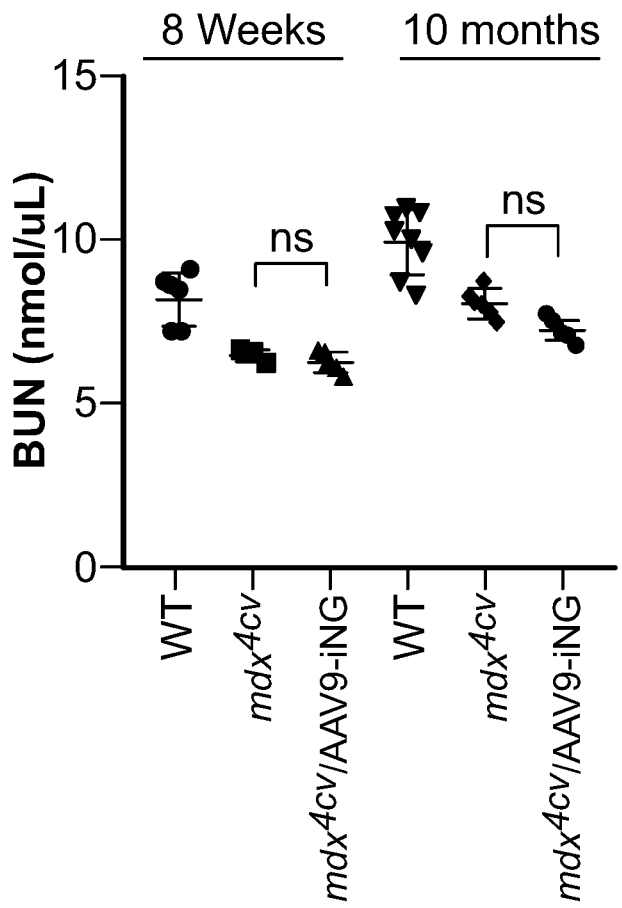

The liver toxicity of AAV9-iNG treatment was examined by measuring serum aspartate aminotransferase (AST) and alanine aminotransferase (ALT), and kidney toxicity by measuring blood urine nitrogen (BUN). As compared to WT mice, the $mdx^{4cv}$ mice showed elevated AST (FIG. 27c) and ALT (FIG. 27d). However, treatment of $mdx^{4cv}$ mice with AAV9-iNG did not further increase the serum levels of AST and ALT at either 8 weeks or 10 months of age. Measurement of BUN did not find significant changes in the treated or untreated $mdx^{4cv}$ mice (FIG. 27e).

Figure 27H:
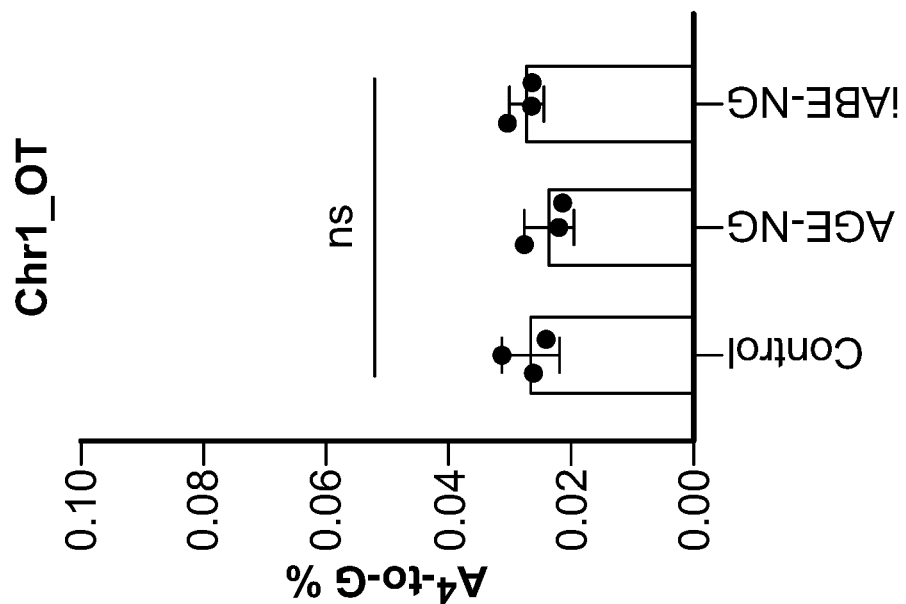
Figure 27G:
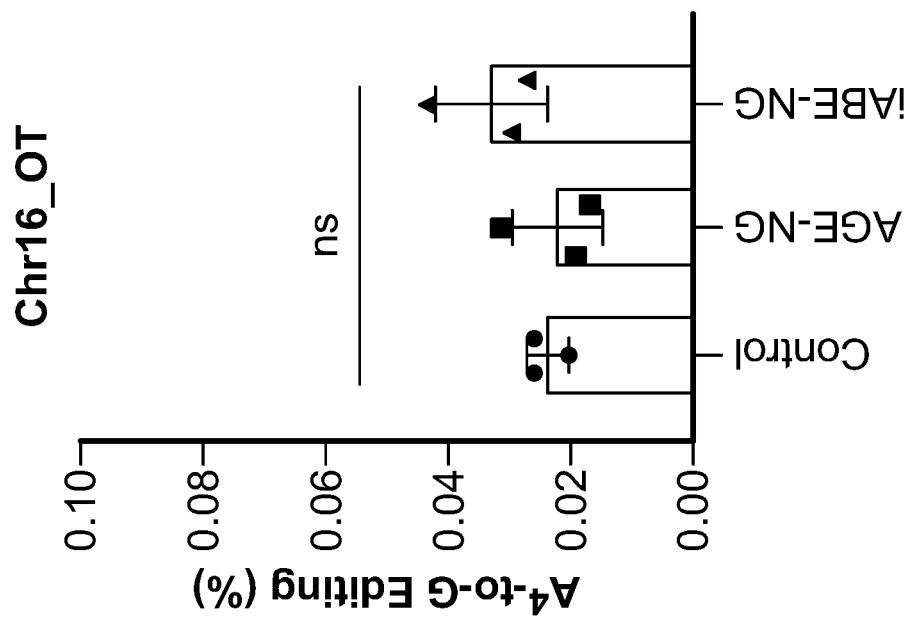

One concern with ABE-mediated gene correction is the off-target activities such as gRNA mismatch tolerance, bystander editing, and off-target RNA editing. Previous studies showed that ABE can tolerate 1-2 mismatches between the gRNA and its target sites. Prediction by Cas-OFFinder showed that one site on chromosome 16 (Chr16_OT) has only one mismatch, two other sites have two mismatches and 55 sites have three mismatches (FIG. 27f). The Chr16_OT differs from the $mdx^{4cv}$ target sequence by only one C at position 12. Neuro-2a cells were transfected with ABE-NG or iABE-NG plus the gRNA, amplified the Chr16_OT by PCR and subjected the amplicon to next generation sequencing (NGS). As shown in FIG. 27g, no significant editing of the A4 in either ABE-NG or iABE-NG transfected cells was observed. Similarly, the off-target site on chromosome 1 (Chr1_OT) was analyzed, which differs from the $mdx^{4cv}$ target sequence by an A at position 2 and a G at position 20. Again, it was found that ABE-NG or iABE-NG did not edit the A4 at Chr1_OT (FIG. 27h).

Figures 27I, 27J:
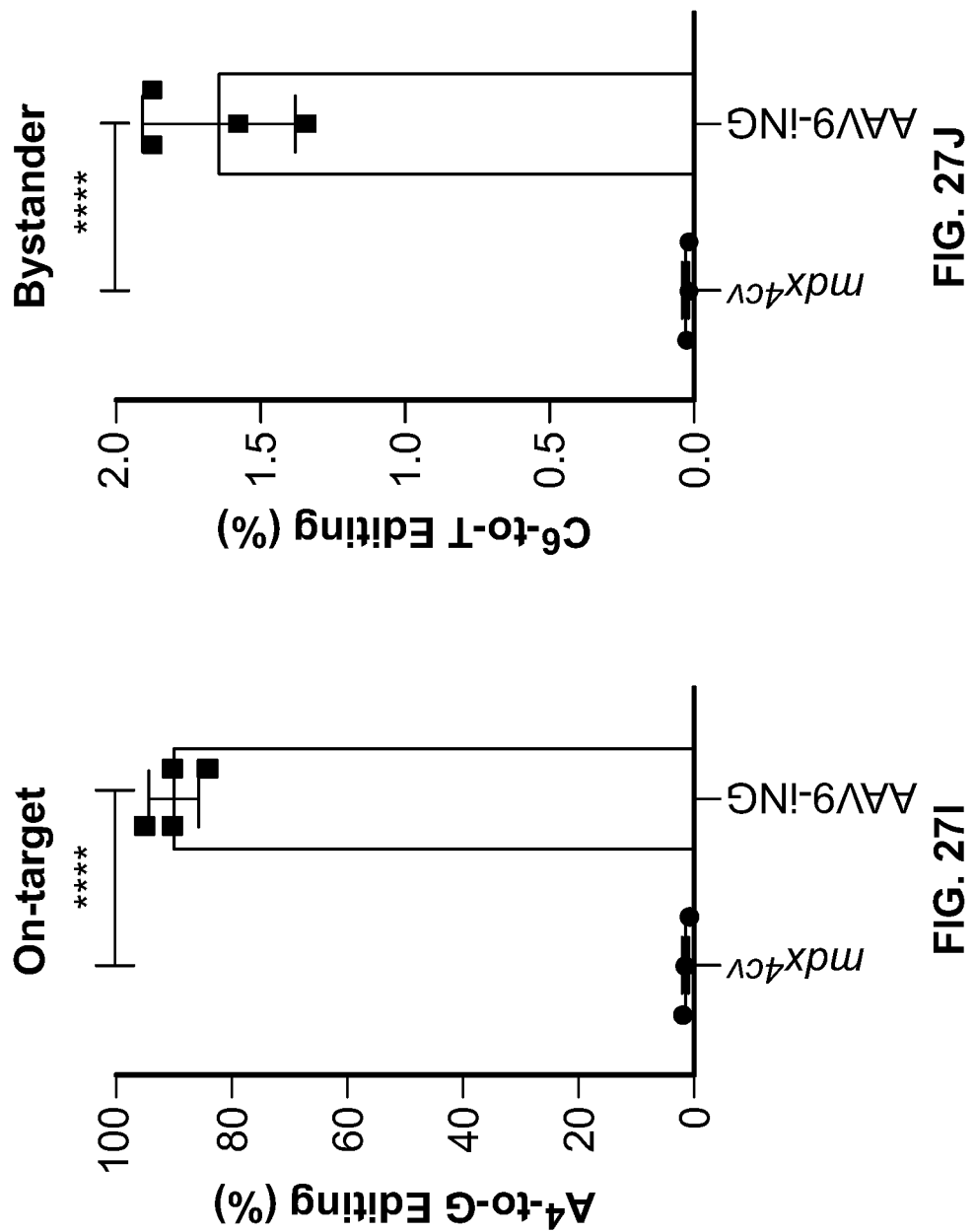

Next, the bystander editing at the on-target $mdx^{4cv}$ locus was analyzed in the mice treated with AAV9-iNG. Since the 10-month treated mouse hearts showed a high level of dystrophin rescue, the on-target editing efficiency was first determined in these mouse hearts by NGS. As mouse hearts contain multiple different cell types, analysis of the genomic DNA PCR products can significantly underestimate the editing efficiency. To verify this, NGS of the genomic DNA PCR products was performed from two mouse hearts receiving AAV9-iNG and exhibiting high dystrophin rescue, and an up to 11% edits at A4 was detected. Thus, the RT-PCR products were sequenced to estimate the editing efficiency at the on-target $mdx^{4cv}$ locus. The A at position 4 (corresponding to the T within the premature stop codon in the coding strand) was converted to G with high efficiency from all four mouse hearts (FIG. 28). On average, 86.2±2.4% A-to-G conversion was measured (FIG. 27i). At the $mdx^{4cv}$ target site, there was only one A within the editing window of 4-8, disallowing us to analyze the bystander A-to-G editing at this particular site. Another type of undesired ABE-mediated genome edits at an on-target locus is ABE-dependent cytosine-to-uracil conversion resulting in C·G to T·A mutation at that site. It was found that C6 at the $mdx^{4cv}$ target site was edited above background with an average efficiency of 1.6±0.1% (FIG. 27j).

Figure 29C:
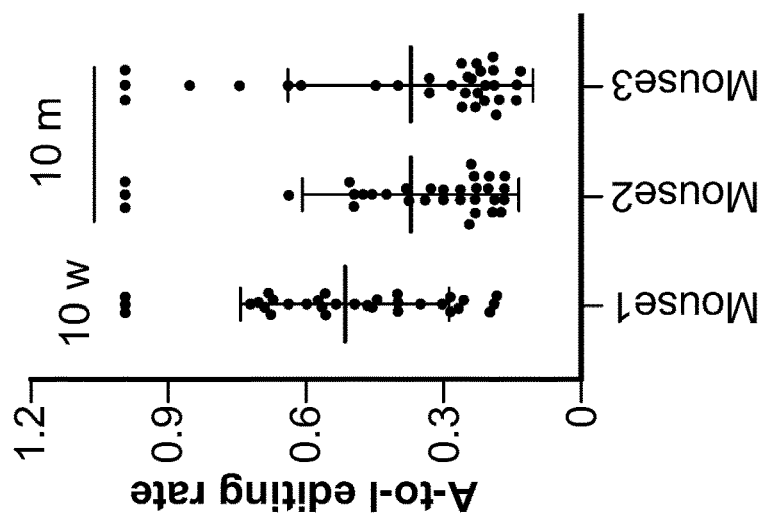
FIGS. 29a-29c show off-target RNA editing activities in the mdx$^{4cv}$ mouse hearts (10 weeks and 10 months of age) induced by systemic delivery of AAV9-iNG.
Figure 29B:
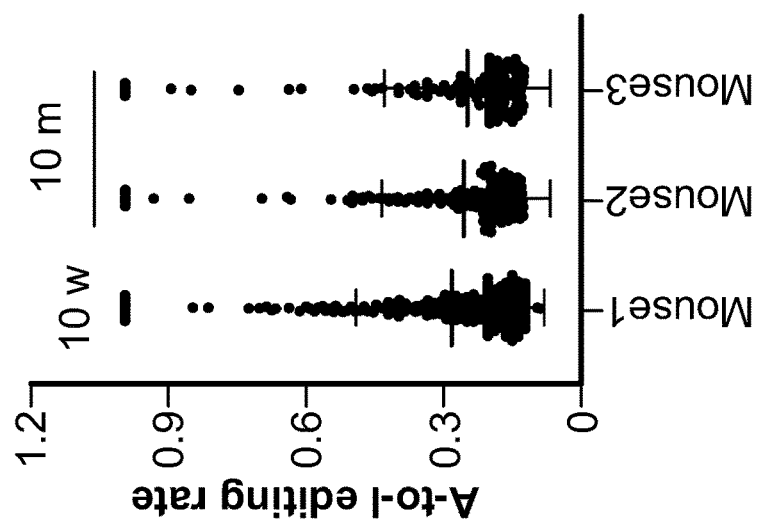
Figure 29A:
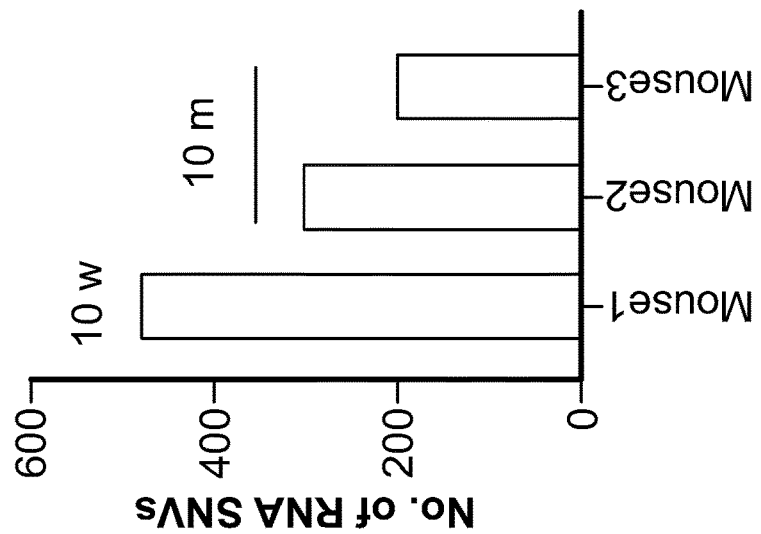

Finally, RNA-seq was performed to characterize the transcriptome-wide RNA off-target RNA editing induced by AAV9-iNG in the $mdx^{4cv}$ mouse heart samples. After filtering the confident variants from control $mdx^{4cv}$ heart samples, a few hundred RNA editing events were found in the three AAV9-iNG treated heart samples with only 32 shared by all of them (FIG. 29).

The present study has improved the split ABE-NG for AAV-mediated in vivo delivery by engineering a new NG PAM-interacting domain variant, a new adenine deaminase domain with higher on-target DNA editing efficiency without compromising the high fidelity of ABE-V82G, and a Gp41-1 intein split that mediates higher efficiency of protein splicing and editing. Together, these improvements allowed to achieve widespread dystrophin rescue and functional improvement in dystrophic mice. The editing efficiency in the heart was extraordinarily high in $mdx^{4cv}$ mice following systemic delivery of AAV9-iNG and over 90% of cardiomyocytes were corrected to express dystrophin in $mdx^{4cv}$ hearts at 10 months of age after a single intravenous administration of AAV9-iNG at 5 weeks old. There was no obvious toxicity detected following AAV9-iNG treatment, despite the host immune response to the AAV9 capsid and ABE. This has tremendous implication for base correction of genetic cardiomyopathies.

It was shown herein that the ecTadA* domain with the V82G mutation had significantly reduced on-target DNA editing activity as compared to the original ecTadA*. By adding the A56G mutation into the V82G variant of ecTadA*, the on-target DNA editing activity was dramatically improved without compromising the high fidelity of the V82G variant in terms of its low off-target RNA editing activity. Although the A56G_V82G variant was less efficient than the recently reported ABE8e, ABE8e had also significantly higher bystander editing activity than the A56G_V82G variant. It is essential to consider both the on-target DNA editing efficiency and the bystander DNA editing as well as off-target RNA editing activity for in vivo applications. The editors have high on-target DNA editing but induce minimal bystander DNA editing and off-target RNA editing events. The A56G_V82G variant offers a balance between the editing efficiency and the editing precision.

The iABE-NG and iABE-NGA can be broadly applied to correct DMD mutations and many other disease-causing mutations. Analysis of the ClinVar database showed that over 100 of the 174 total G>A or T>C point mutations for DMD can be targeted for repair by at least one of the ABEs (iABE-NGA). Describe all other cases including targeting the splicing sites for exon skipping and other diseases.

The recent advances in engineering Cas9 variants with non-G PAM further increases targeting capacity. Moreover, the ABE editing can be designed to induce skipping of mutant exons via targeting the canonical splicing donor or acceptor, thus further broadening the applicability of ABE editing therapy for a larger population of DMD.

The mice at ten months after AAV9-iNG delivery showed significantly higher dystrophin rescue than the mice at 10 weeks after the treatment. One explanation is that the DMD cardiomyocytes with restored dystrophin expression can gain advantage for selective survival and regeneration during the development stages after delivery of AAV9-iNG. Additionally, transduced cardiomyocyte-derived extracellular vesicles can deliver genetic materials such as transcripts encoding iABE-NG into proximal un-transduced cardiomyocytes and confer base editing in those cells.

This study has also shown that systemic delivery of AAV9-iNG resulted in dystrophin restoration in skeletal muscles and functional improvement. As compared to cardiomyocytes, the editing efficiency in skeletal muscles was substantially lower. This can be attributed to the observation that AAV9 has higher tropism towards cardiomyocytes than skeletal muscles. However, other mechanisms can also be responsible for the lower editing efficiency in skeletal muscles. For example, the dystrophic and inflammatory microenvironment in skeletal muscles can pose further constrains on AAV9 delivery and base editing. In addition, targeting muscle satellite cells can be required to improve the overall editing outcomes in skeletal muscle as they are constantly activated to replace injured skeletal muscle in DMD. Although AAV9 has been shown to transduce muscle satellite cells, the efficiency is relatively low. Moreover, the use of a muscle-specific promoter can further reduce the base editing in muscle satellite cells in the present study.

Improvements in these examples show exceptionally high editing efficiency in comparison to other approaches. First, the intein used in the current study (Gp41-1) has superfast kinetics, which allows more efficient assembly of full-length ABE (FIG. 6). Second, each half of the AAVs carries a gRNA-expressing cassette in the present study, while in the other study, gRNA is present in only the C-terminal half of the Npu intein split constructs. The data (FIG. 6h) showed that the gRNA dosage affects the editing efficiency. Third, the promoters used in these studies were also different, which can drive different expression levels of ABE in heart tissues. Finally, the intrinsic difference in the gRNAs and ABE variants can have impacts on the overall editing outcomes. Thus, the exceptionally high editing efficiency achieved in adult dystrophic mice indicates that the AAV9-iNG vectors disclosed herein are useful for clinical applications.

Example 6. Methods

Mice. Mice (C57BL/6J and B6Ros.Cg-Dmd$^{mdx-4Cv}$/J) were purchased from the Jackson Laboratory and maintained at The Ohio State University Laboratory Animal Resources in accordance with animal use guidelines. All the experimental procedures were approved by the Animal Care, Use, and Review Committee of the Ohio State University.

Plasmid construction. The pCMV-ABE7.10, pCMV-ABE-xCas9(3.7) and pCMV-ABEmax were obtained from Addgene. The NG mutations were introduced by fusion PCR of pCMV-ABEmax and subcloned into pCMV-ABEmax to make pCMV-ABEmaxNG. The A56G and V82G mutations were introduced into TadA* domain by fusion PCR and cloned into pCMV-ABEmaxNG to generate pCMV-iABE-maxNG. The CfaN minigene was synthesized by IDTdna and fused at the amino acid 573 of SpCas9-max through PCR amplification. The TadA-TadA*-SpCas9max(2-573)-CfaN fragment was PCR amplified and subcloned into pAAV under the control of meCMV promoter to generate pAAV-ABEmaxN-temp. The hU6 promoter with mdx$^{4cv}$-targeting gRNA was PCR amplified and cloned into pAAV-ABEmaxN-temp to make pAAV-ABEmaxN. The CfaC fused with SpCas9max(574-end) was generated by PCR and cloned into pAAV-ABEmaxN-temp to make pAAV-ABE-maxC. Similarly pAAV-ABEmaxN2 and pAAV-ABEmaxC2NG with the Gp41-1 intein, and pAAV-ABEmaxN3 and pAAV-ABEmaxC3NG with the Npu intein were constructed. The mdx$^{4cv}$ gRNA and other gRNA oligos (listed in Table 2) were annealed and ligated into pLenti-ogRNA. The mdx$^{4cv}$ reporter oligos were annealed and ligated into pLKO-puro-2A-mdx$^{4cv}$-EGFP. All plasmids used in this study are listed in Table 3.

Generation of AAV particles. AAV vectors were produced at the viral vector core of the Nationwide Children's Hospital as previously described. The Gp41-1 intein split of iABE-NGA and the gRNA targeting mdx4cv mutation (GT-TaTCTCCTGTTCTGCAGC TGT (SEQ ID NO: 621); note: the underlined PAM sequences were not included in the gRNA) or a non-targeting gRNA (GTTTaTGT-CACCAGAGTAAC (SEQ ID NO: 571), the different nucleotides are highlighted in blue) expression cassettes were packaged into AAV9 capsid using the standard triple transfection protocol. A quantitative PCR-based titration method was used to determine an encapsulated vector genome titer utilizing a Prism 7500 Fast Taqman detector system (PE Applied Biosystems Grand Island, NY USA). The following primers/probes were used: 5'-GGATTTC-CAAGTCTCCACCC-3' (SEQ ID NO: 630) and 5'-TCC-CACCGTACACGCCTAC-3' (SEQ ID NO: 631) for titering AAV9-NG, and AAV9-iNG was titered using digital droplet PCR. Titers are expressed as DNase resistant particles per ml (DRP/ml) and rAAV titers used for injection in mice were 8.9×10$^{12}$ DRP/ml (AAV9-NG) and 3.0×10$^{13}$ DRP/ml (AAV9-iNG).

Cell culture and transfection. HEK293 cells were cultured in Dulbecco's modified eagle's medium (DMEM) (Corning, Manassas, VA) containing 10% fetal bovine serum (FBS) and 1% 100× penicillin-streptomycin (10,000 U/ml, invitrogen). Cells were plated in 6-well plates and transfected with the 2 μg plasmids (0.5 μg reporter, 0.75 μg gRNA and 0.75 μg ABE) per well unless specified otherwise by polyethylenimine (PEI) as previously described.

Flow cytometry. At 72 hour post transfection, HEK293 cells transfected with ABE plasmids were collected from 6-well plate and analyzed on Becton Dickinson LSR II (BD Biosciences) to determine GFP-positive cells. A total of 100,000 cell events were collected and data analysis was performed using the FlowJo software (Tree Star, Ashland, OR, USA).

Intramuscular and intravenous administration of AAV/9 particles. AAV9-iNG viral particles (2×10$^{11}$ vg, 25 μl) were injected into the right gastrocnemius compartment of the male mdx$^{4cv}$ mice at 5-6 weeks of age or day 3. For systematic delivery, the male mdx$^{4cv}$ mice at 5-6 weeks of age were administered with AAV9-NG, AAV9-iNG or AAV9-GFP viral particles ($1\times10^{14}$ vg/kg) via tail vein injection.

Serological analysis. Blood samples were collected at various time points after intramuscular or intravenous injection. The blood samples were allowed to clot for 15 min to 30 min and centrifuged at 5000 rpm for 10 min in room temperature. The supernatant was collected as serum and stored at −80° C. for the biochemical assays. Measurement of ALT (BioVision Incorporated), AST (BioVision Incorporated), BUN (Arbor Assays, Michigan, USA) and cardiac Troponin I (Life Diagnostics, Inc) were performed according to the manufacturer's protocols.

Antibody ELISA. Antibodies against AAV9 and SpCas9 were detected by adapting previously published protocols. In brief, recombinant AAV9 ($2\times10^9$ vg/well) and SpCas9 protein (0.27 µg/well) were diluted in 1× Coating Buffer A (BioLegend) and used to coat a 96-well Nunc MaxiSorp plate. Proteins were incubated overnight at 4° C. to adsorb to the plate. Plates were washed four times 5 min each with PBS plus 0.05% Tween-20 and then blocked with 1× Assay Diluent A (BioLegend) for 1 h at room temperature. The anti-AAV2 (A20, cat. # 03-65155, American Research Products, Inc) and anti-SpCas9 antibody (Diagenode C15310258) was used as positive control for detection of anti-AAV9 and anti-SpCas9 antibodies, respectively. Serum samples were added in 1:50 dilution and plates were incubated for 2 h at room temperature with shaking. Plates were washed four times 5 min each and 100 µl of blocking solution containing goat anti-mouse IgG (Sigma 1:3,000) was added to each well and incubated at 1 h at room temperature. Plates were washed four times 5 min each, 100 µl of freshly mixed TMB Substrate Solution (BioLegend) was added to each well, and incubated in the dark for 20 min. The reaction was stopped by adding 100 µl 2N $H_2SO_4$ Stop Solution. Optical density at 450 nm was measured with a plate reader.

Muscle contractility measurements. At 5 weeks after intramuscular AAV9-NG or intravenous AAV9-iNG injection, muscle contractility was measured using an in vivo muscle test system (AuroraScientific Inc). Mice were anesthetized with 3% (w/v) isoflurane and anesthesia was maintained by 1.5% isoflurane (w/v) during muscle contractility measurement. Maximum plantarflexion tetanic torque was measured during a train of supramaximal electric stimulations of the tibial nerve (pulse frequency 150 Hz, pulse duration 0.2 ms).

Histopathological assessment of tissues. Mice were sacrificed at various time points, and tissues (heart, lung, diaphragm, spleen, kidney, liver, quadriceps and gastrocnemius) were harvested for histological, histochemical, biochemical and molecular analyses. For immunohistological examinations, tissues were embedded in optimal cutting temperature (OCT, Sakura Finetek, Netherlands) compound and snap-frozen in cold isopentane for cryosectioning. The tissues were stored at −80° C. and processed for biochemical analysis and histology assessment. Frozen cryosections (7 µm) were fixed with 4% paraformaldehyde for 15 minutes at room temperature. After washing with PBS, the slides were blocked with 3% BSA for 1 hour. The slides were incubated with primary antibodies against dystrophin (ab15277, 1:100, Abcam) and laminin-α2 (ALX-804-190-C100, 1:100, Enzo) at 4° C. for 1 hour. After that, the slides were washed extensively with PBS and incubated with secondary antibodies (Alexa Fluor 488 goat anti-rat IgG, Invitrogen, Carlsbad, CA or Alexa Fluor 568 donkey anti-rabbit IgG, Invitrogen) for 1 hour at room temperature. The slides were sealed with VECTASHIELD Antifade Mounting Medium with DAPI (Vector Laboratory, Burlingame, CA). All images were taken under a Nikon Ti-E fluorescence microscope (magnification 200×) (Nikon, Melville, NY). Laminin-α2-positive and dystrophin-positive muscle fibers were counted using NIS-Elements AR version 4.50 (Nikon, Melville, NY). The amount of dystrophin positive muscle fibers is represented as a percentage of total laminin-α2-positive muscle fibers.

For trichrome staining, Masson's 2000 Trichrome Kit was used (American MasterTech, Lodi, CA). The muscle and heart sections were fixed with 4% paraformaldehyde for 1 hour at room temperature. After washing with PBS, the tissue sections were stained with Masson's trichrome reagent following the manufacturer's instruction.

Western blot analysis. Mouse tissues from mdx$^{4cv}$ mice treated with or without AAV9-NG or AAV9-iNG were lysed with cold RIPA buffer supplemented with protease inhibitors and extracted protein samples were separated by SDS-PAGE (BioRad, 4-15%) and transferred onto Nitrocelluloase membranes (0.45 µm). The rabbit polyclonal anti-dystrophin (E2660, 1:500, Spring Bioscience, Pleasanton, CA), rabbit polyclonal anti-Cas9 (C15310258-100, 1:1000, Diagenode, Denville, NJ) and rabbit monoclonal anti-Gapdh (#2118, 1:2000, Cell Signaling Technology, Danvers, MA) antibodies were used for immunoblotting analysis. HRP conjugated goat anti-mouse (1:4000) and goat anti-rabbit (1:4000) secondary antibodies were obtained from Cell Signaling Technology, Danvers, MA The membranes were developed using ECL western blotting substrate (Pierce Biotechnology, Rockford, IL) and scanned by ChemiDoc XRS+ system (BioRad, Hercules, CA). Western blots were quantified using Image Lab 6.0.1 software (Bio-Rad Laboratories, Hercules, CA) according to the manufacturer's instruction.

Extraction of genomic DNA and total RNA, PCR and Sanger sequencing. Genomic DNA from mouse tissues and cultured HEK293 cells were extracted using DNeasy Blood & Tissue Kit (Qiagen, Germantown, MD). Total RNA was extracted from mouse tissues and HEK293 cells using Quick-RNA MiniPrep Kit (ZYMO Research, Irvine, CA). Five µg of treated RNA was used as template for first-strand cDNA synthesis by using RevertAid RT Reverse Transcription Kit (Life Technologies, Carlsbad, CA). Aliquots of the RT product were used for RT-PCR analysis of dystrophin editing. PCR reactions were carried out with 100 ng genomic DNA or cDNA in the GoTaq Master Mix (Promega) according to the manufacturer's instruction. The primers used for RT-PCR of the reporter genes and PCR of endogenous loci were listed in Table 2. The PCR products were purified using the Wizard SV Gel and PCR Clean-up System (Promega). Purified genomic DNA and RT PCR products (100 ng) were subjected to Sanger sequencing at the Genomics Shared Resource of the Ohio State University Comprehensive Cancer Center. The sequencing data were analyzed by BEAT program.

Targeted deep sequencing. The on-target and off-target loci were first amplified by genomic DNA PCR and/or RT-PCR using gene-specific primers with Illumina adapters (primers are provided in Table 4). The first PCR products were purified using a commercial purification kit (Promega, Madison, WI, USA), diluted, pooled, and subjected to a second round PCR with primers including the index sequences. The final PCR products were electrophoresed on an agarose gel, showing a single sharp peak. The quality and quantity were assayed using an Agilent Bioanalyzer 2100 (Genomics Shared Resource, Ohio State University Comprehensive Cancer Center). The purified amplicons were pooled and sent for sequencing using a MiSeq nano-scale flow cell (paired-end 300 base-pair reads) at The Genomics Services Laboratory of Nationwide Children's Hospital. The FASTQ files were analyzed using CRISPResso2 with default parameters.

RNA-seq experiments. RNA library preparation was performed using NEBNext® Ultra™ II Directional (stranded) RNA Kit for Illumina (NEB #E7760L New England Biolabs) with an initial input of 100 ng ng extracted RNA per sample, measured using Qubit RNA HS reagents (#Q32852 Invitrogen) for fragmentation, cDNA synthesis and amplification. Depletion of ribosomal RNA (rRNA) was carried out with NEBNext rRNA Depletion Kit (human, mouse, rat) from New England Biolabs (#E6310X). NEBNext Multiplex oligos indexes kits (E7335L, E7500L and E7710L) from New England Biolabs were used to barcode each library following the manufacturer protocol. RNA-seq libraries were examined using an Agilent 2100 Bioanalyzer and a High Sensitivity DNA kit (Agilent Technologies, Inc). RNA-seq libraries were sequenced on Novaseq SP Paired-End 150 bp format at The Genomics Services Laboratory of Nationwide Children's Hospital.

RNA sequence variant calling and variant filtering. Illumina paired-end fastq sequencing reads were processed according to GATK Best Practices for RNA-seq variant calling. In brief, reads were aligned to the mouse mm10 reference genome using STAR version 1.5.2 in two-pass mode with the parameters implemented by the ENCODE project. Picard tools (version 2.19.0) was then applied to sort and mark duplicates of the mapped BAM files. The refined BAM files were subject to split reads that spanned splice junctions, local realignment, base recalibration and variant calling with SplitNCigarReads, IndelRealigner, BaseRecalibrator and HaplotypeCaller tools from GATK (version 4.1.2.0), respectively. Known variants in dbSNP version 142 were used during base quality recalibration. From all called variants, downstream analyses focused solely on single-nucleotide variants (SNVs) on canonical (1-22, X, Y and M) chromosomes. To identify variants with high confidence, clusters of at least five SNVs were filtered that were within a window of 35 bases and variants with Fisher strand values >30.0, qual by depth values <2.0 and sequencing depth <10. Base edits labelled as A-to-I comprise A-to-I edits called on the positive strand as well as T-to-C edits sourced from the negative strand, since the RNAs were converted into cDNA before sequencing, both the nucleotide and its complementary base can be sequenced. Results obtained with this pipeline can underestimate the actual number of RNA edits occurring in cells because of the high stringency of the variant calling pipeline and potential under-representation of intronic and intergenic RNA in our experiments.

Any confident variants found in wild-type Neuro2a cells were considered to be SNPs and were filtered out from the base-editor-transfected groups for off-target analysis. Similarly, any confident variants found in control mdx$^{4cv}$ heart samples were filtered out from the AAV9-iNG group for off-target analysis. The editing rate was calculated as the number of mutated reads divided by the sequencing depth for each site.

ClinVar database analysis. The ClinVar data was converted into a tab-delimited flat file. A python script (clinvar.py) was written to process the tab-delimited flat file of ClinVar data.

Statistical analysis. The data were expressed as mean±S.E.M. and analyzed with GraphPad Prism 8.0.1 software (San Diego, USA). Statistical significance was determined using one-way ANOVA followed by Bonferroni post hoc-tests for multiple groups or student's t-test for two groups. A P value of less than 0.05 is regarded as significant.

Data availability. The sequencing data have been deposited in the NCBI SRA under project accession numbers (PRJNA673243).

Example 7. Use of the System for Treatment of Spinal Muscular Atrophy

Figure 30A:
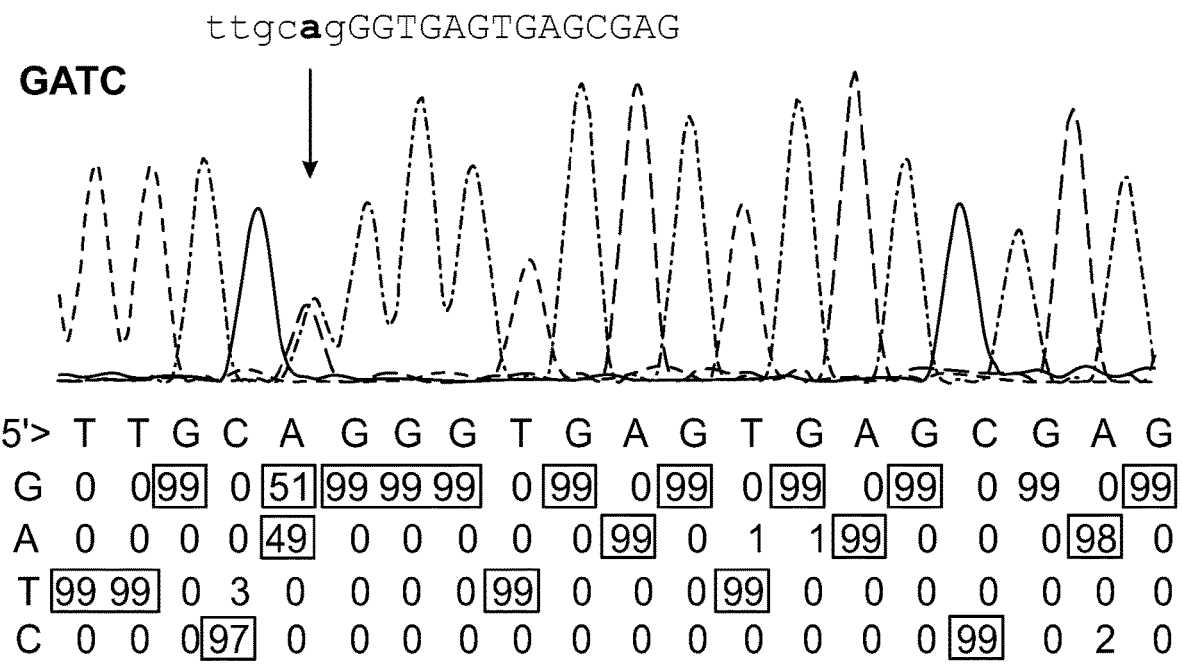
FIGS. 30a-30b show iABE-NGA editing-mediated exon skipping of human DMD exon 55 in DMD-hiPSC-derived cardiomyocytes.
Figure 30B:
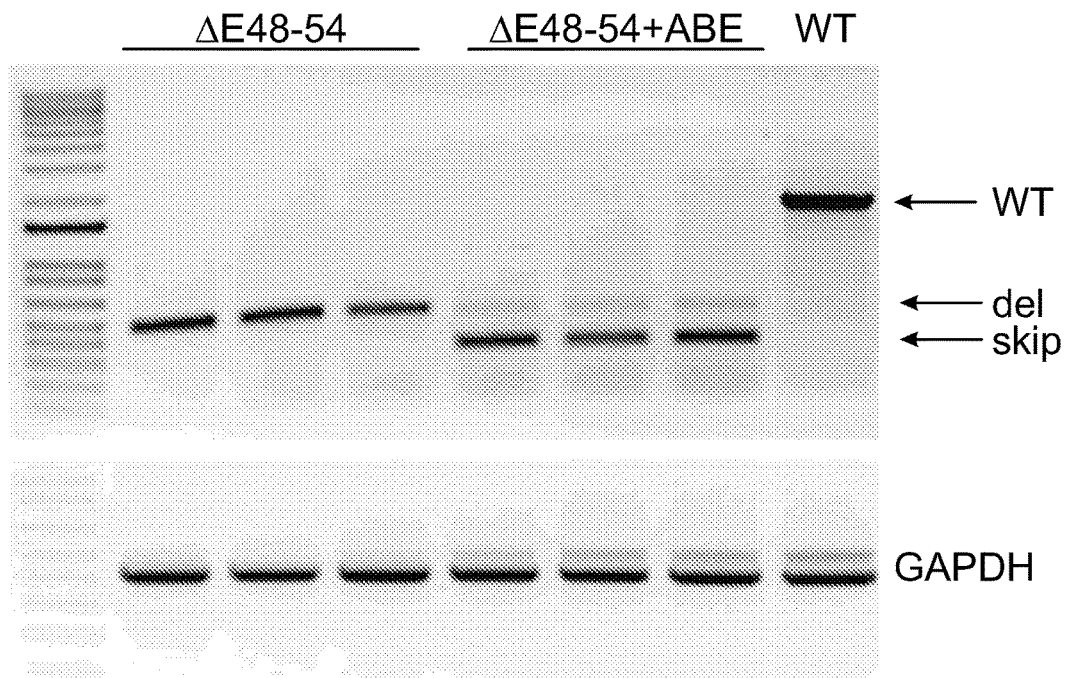

The iABE-NGA system can be broadly used to rescue dystrophin expression in DMD and treat other conditions, in addition to correcting point mutations in DMD and dysferlinopathy. For example, by targeting the splice sites, iABE-NGA can mediate exon skipping and rescue dystrophin expression in a human induced pluripotent stem cell-derived cardiomyocytes with a large deletion from exon 48 through 54 in DMD gene (FIG. 30).

Figures 31A, 31B:
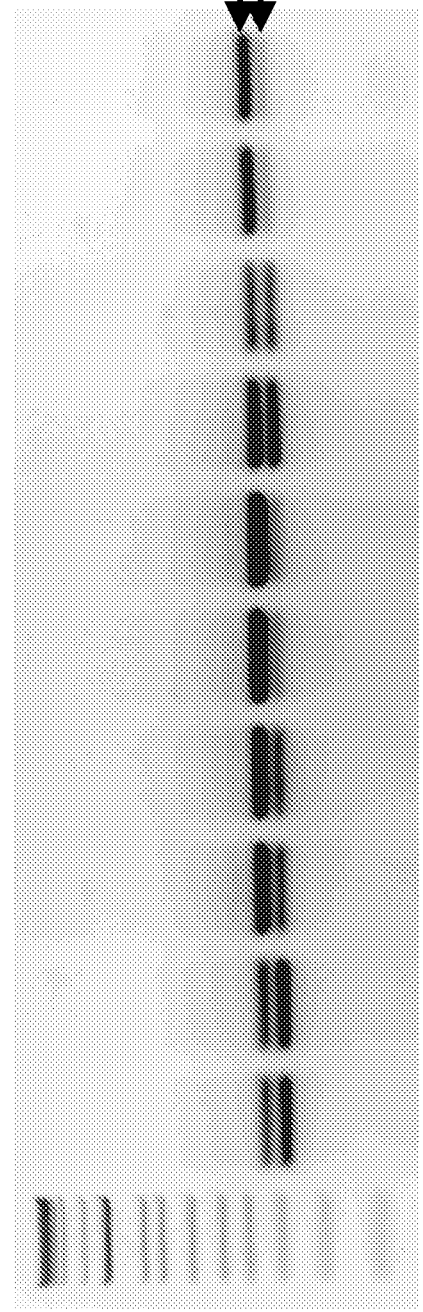
FIGS. 31a-31c show iABE-NGA editing-mediated exon 7 inclusion of human SMN2.
Figure 31C:
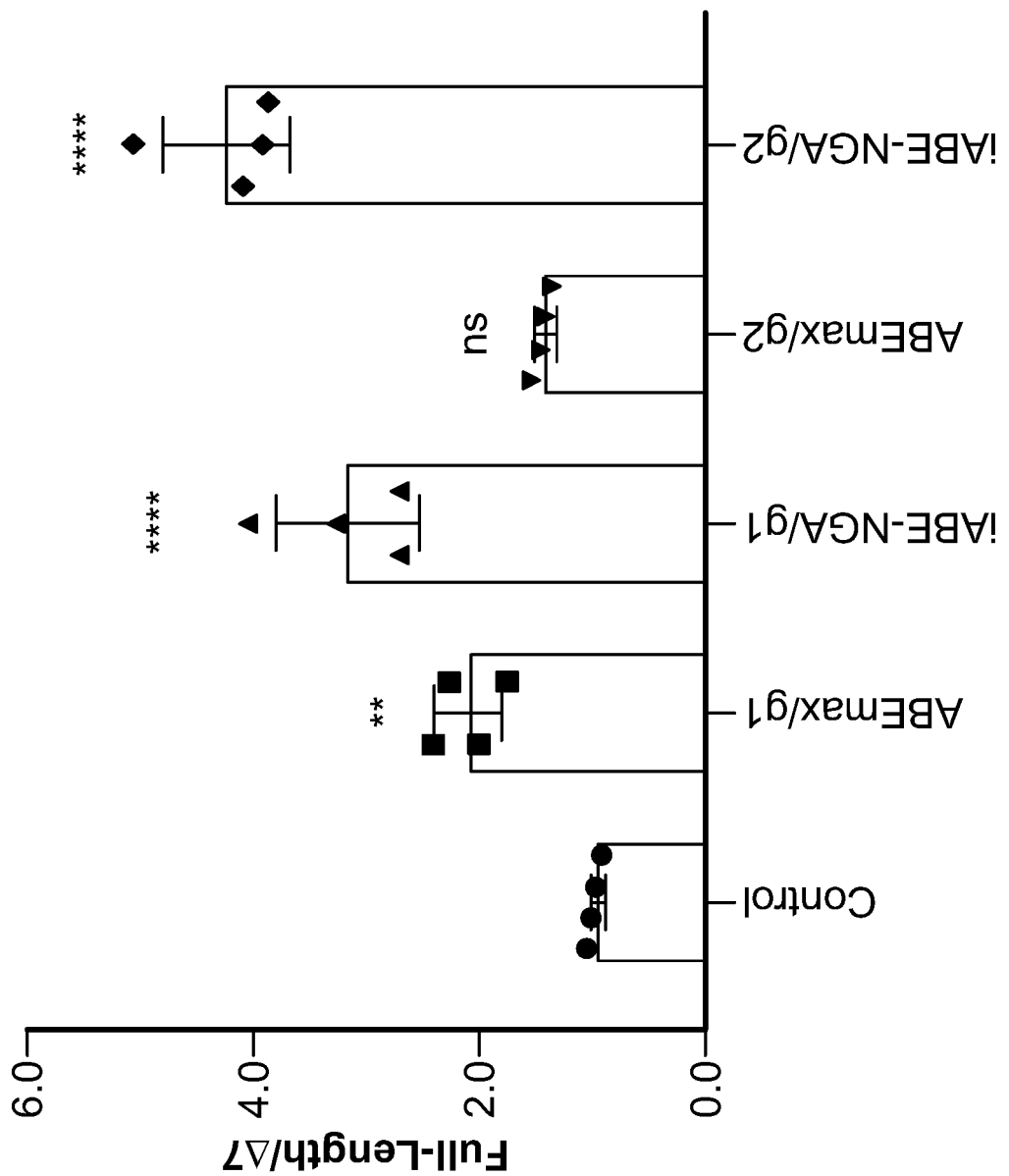

Mutations in the survival motor neuron 1 (SMN1) gene cause spinal muscular atrophy (SMA). There is a paralogous gene WM in human, present in almost all SMA patients. The SMN2 is different from SMN1 in exon 7, with position 6 converted from C to T in SMN2, which results in the skipping of exon 7 in SMN2 mRNA and non-functional SMN2 protein. Using iABE-NGA-mediated editing of A36 showed that the exon 7 of SMN2 was spliced in (FIG. 31), and thus this can be a therapy for SMA.

Figure 32C:
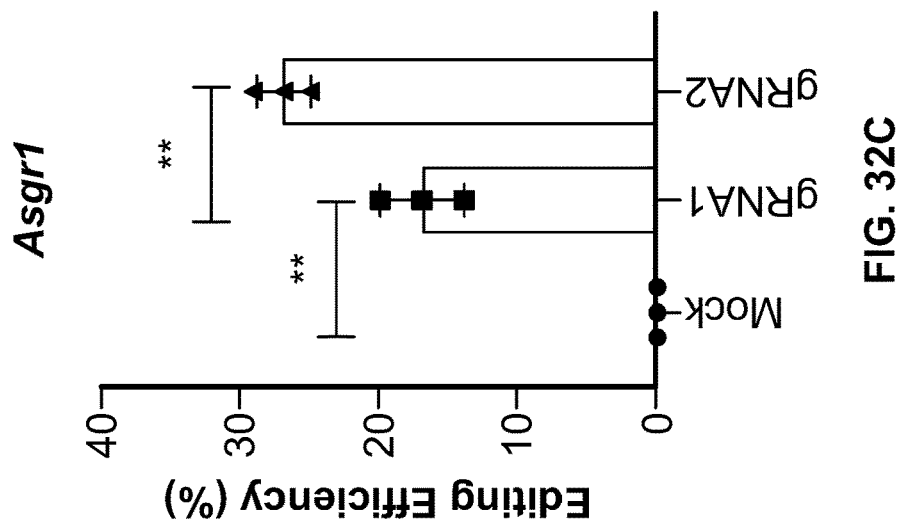
FIGS. 32a-32c show the iABE-MGA editing of mouse Angptl3 (FIG. 32a), Apoc3 (FIG. 32b) and Asgr1 (FIG. 32c) in Neuro-2a cells. p<0.01; *p<0.001; **p<0.0001
Figure 32B:
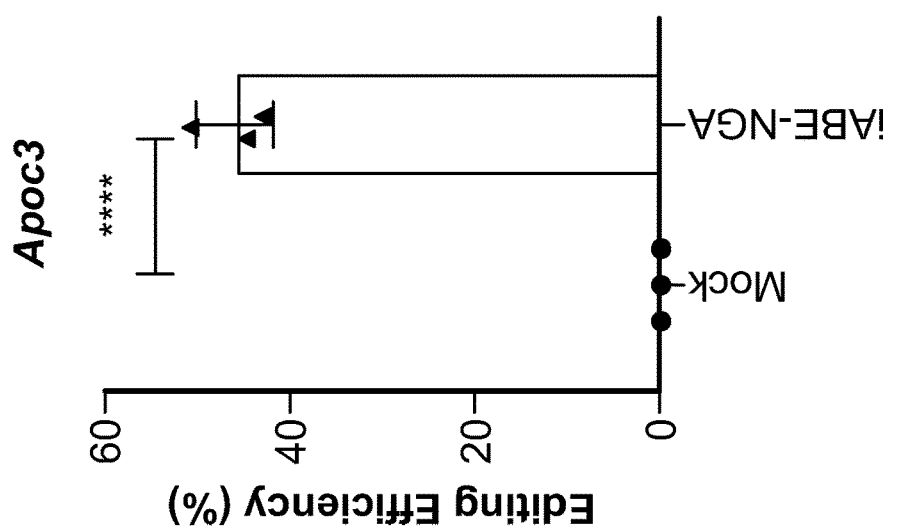
Figure 32A:
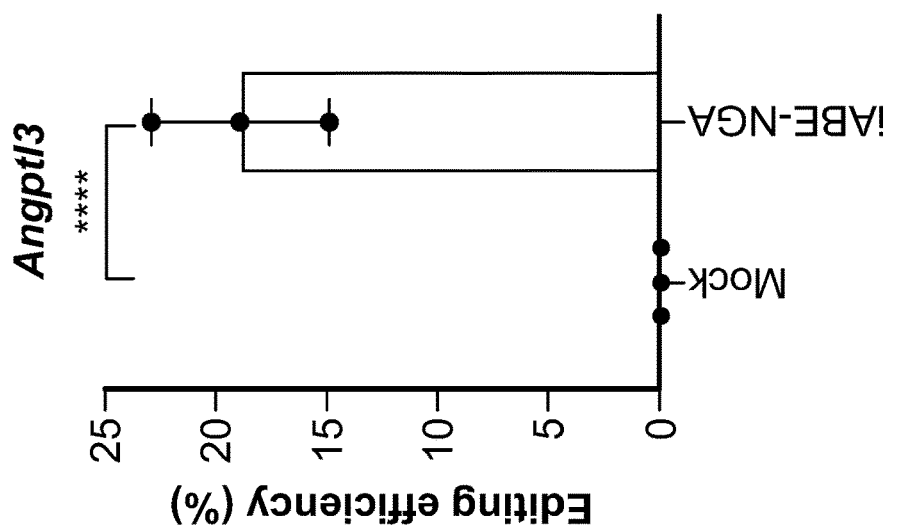

Moreover, by targeting the splice sites, one can generate loss-of-functions in the therapeutic targets such as those involved in the regulation of plasma cholesterol levels. Previous studies identified a number of protective loss-of-functions in genes such as ANGPTL3, APOC3 and ASGR1, which reduce the plasma low cholesterol levels and renders cardioprotection. iABE-NGA can install such loss-of-function mutations in the aforementioned genes, which can be used as a one-time cure for dyslipidemia (FIG. 32).

TABLE 1

List of ABE variants engineered in this study.

| Name | Description |
| --- | --- |
| ABE-NG | ABEmax with SpCas9-NG mutations R1335V/L1111R/D1135V/G1218R/E1219F/A1322R/T1337R |
| ABE-NGA | ABE-NG with R1335Q mutation |
| ABE-NGC | ABE-NG with R1335E mutation |
| ABE-NG-loop | ABE-NG with the loop sequence from ScCas9 (amino acids 367-376) inserted |
| ABE-NGX | ABE-NG with A262T/R324L/S409I/E480K/E543D/M694I mutations |
| ABE-NGX-NGA | ABE-NGX with R1335Q |
| ABE-NGX-NGC | ABE-NGX with R1335E |
| ABE-NGX-loop | ABE-NGX with the loop sequence from ScCas9 (amino acids 367-376) inserted |
| ABEmaxSc | ABEmax with SpCas9 nickase replaced with ScCas9 nickase |
| ABE-NGm | ABE-NG with the dimeric TadA-TadA* replaced with monomeric TadA* containing two additional mutations A56G and V82G |
| iABE-NGA | ABE-NGA with the dimeric TadA-TadA* replaced with monomeric TadA* containing two additional mutations A56G and V82G |

TABLE 2

List of gRNA target sequences and primers for PCR in this study.

| Name | Sequence | SEQ ID NOs |
|---|---|---|
| Mdx4cv-gRNA | GTTATCTCCTGTTCTGCAGC | SEQ ID NO: 570 |
| NT-gRNA | GTTTATGTCACCAGAGTAAC | SEQ ID NO: 571 |
| mDMD-i52-F | GAGGTAATAGAGCCAAGCCCT | SEQ ID NO: 572 |
| mDMD-i53-R | GCAAGAATTCCACTTTTCACTTCCT | SEQ ID NO: 573 |
| mDMD-E51-F | CTGTCATCTCCAAACTAGAAATGC | SEQ ID NO: 574 |
| mDMD-E55-R | GCAGCCTCTTGCTCACTTACTC | SEQ ID NO: 575 |
| S1-gRNA | GATGACAGGCAGGGGCACCG | SEQ ID NO: 576 |
| S1-F | TTCCAGTGGTTCAATGGTCA | SEQ ID NO: 577 |
| S1-R | CTTTCAACCCGAACGGAGAC | SEQ ID NO: 578 |
| VEGFA-S5-gRNA | GAGCGAGCAGCGTCTTCGAG | SEQ ID NO: 579 |
| VEGFA-S12-gRNA | GCAGACGGCAGTCACTAGGG | SEQ ID NO: 580 |
| VEGFA-S14-gRNA | GGGAAGCTGGGTGAATGGAG | SEQ ID NO: 581 |
| VEGFA-F | AGCTGTTTGGGAGGTCAGAA | SEQ ID NO: 582 |
| VEGFA-R | AGGGAGCAGGAAAGTGAGGT | SEQ ID NO: 583 |
| Site13-gRNA | GTCGCAGGACAGCTTTTCCT | SEQ ID NO: 584 |
| Site13-F | TGTAGCTACGCCTGTGATGG | SEQ ID NO: 585 |
| Site13-R | TGCCCTGAGATCTTTTCCTC | SEQ ID NO: 586 |
| FANCF-gRNA | GATCCAGGTGCTGCAGAAGG | SEQ ID NO: 587 |
| FANCF-F | CTCTTGCCTCCACTGGTTGT | SEQ ID NO: 588 |
| FANCF-R | TCGGTAGGATGCCCTACATC | SEQ ID NO: 589 |
| Q623X-gRNA | ATCCTACAGCATGGTGGCTG | SEQ ID NO: 590 |
| Puro-F | AGTGGTCTCCGGAAACCTCCGCGCCCCGCAAC | SEQ ID NO: 591 |
| GFP-R | TCCTTGAAGAAGATGGTGCG | SEQ ID NO: 592 |

TABLE 3

List of plasmids used in this study.

| ID | Name | Description |
|---|---|---|
| pXL-0570 | pCMV_ABEmax (Addgene # 112095) | Expressing ABEmax; used in FIG. 1c-e; FIG. 4b, d; Suppl. FIG. S2 |
| pXL-0550 | pCMV_xCas9_3.7_-ABE_7.10 (Addgene #108382) | Expressing ABE-x; used in FIG. 1c-e; FIG. 6b; FIG. 5. |
| pXL-0645 | pCMV_ABEmaxNG | Expressing ABE-NG; used in FIG. 1c-e; FIG. 2a-f; FIG. 3b; FIG. 6b-6d; |
| pXL-0752 | pLKO-puro-2A-mdx4cv-GFP | mdx$^{4cv}$ reporter; used in FIG. 1c-e; FIG. 6c, 6d, h; FIG. 4. |
| pXL-0631 | pLenti-puro-OgRNA_mdxE53 | gRNA targeting mdx$^{4cv}$ mutation; used in FIG. 1c-e; FIG. 3b-d; FIG. 6c-6h; FIG. 27g, 27h; FIG. 4. |
| pXL-0858 | pCMV_ABEmaxNG-NGA | Expressing ABE-NGA; used in FIG. 2a-f. |
| pXL-0869 | pCMV_ABE-NGC | Expressing ABE-NGC; used in FIG. 2a-f. |
| pXL-0872 | pCMV_ABE-NG-loop | Expression ABE-NG-loop; used in FIG. 2a-f. |

TABLE 3-continued

List of plasmids used in this study.

Figure 2A:
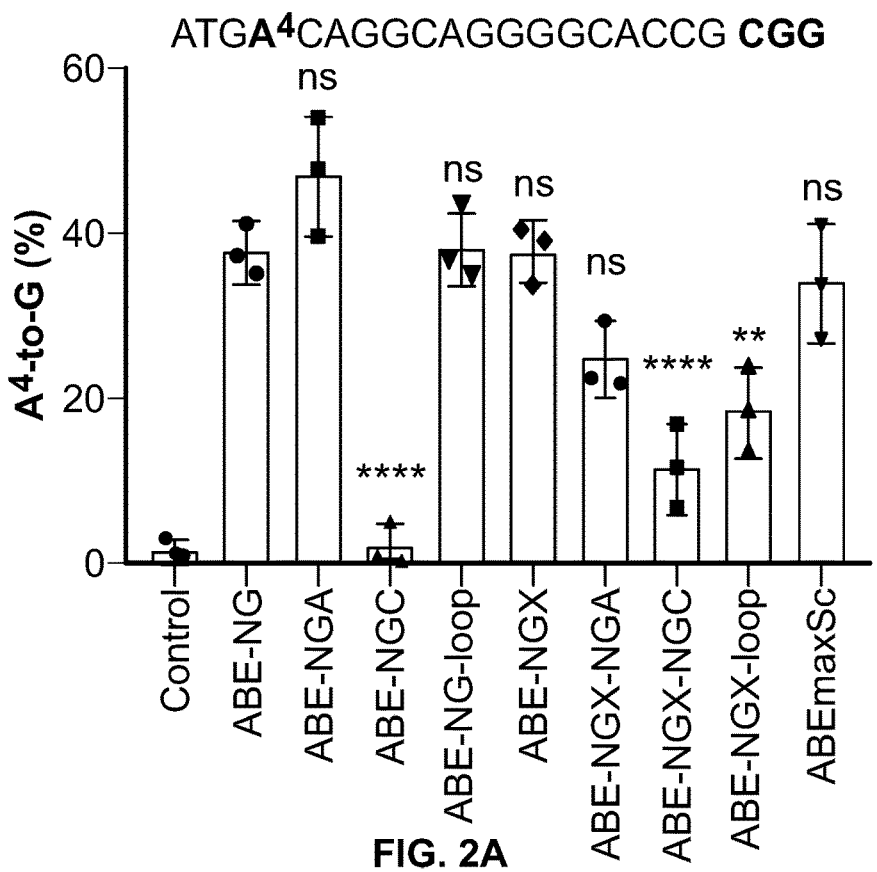
FIGS. 2a-2f show optimization of the PAM-interacting domain to improve the editing efficiency of ABE-NG at the NGN sites.
Figure 2B:
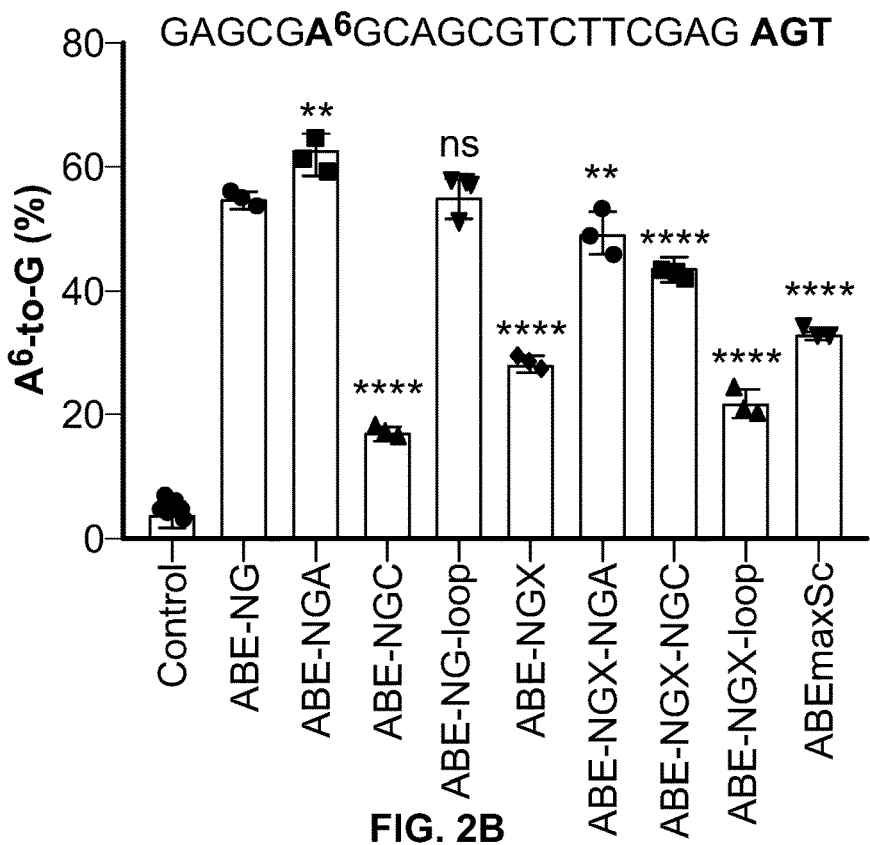
Figure 2C:
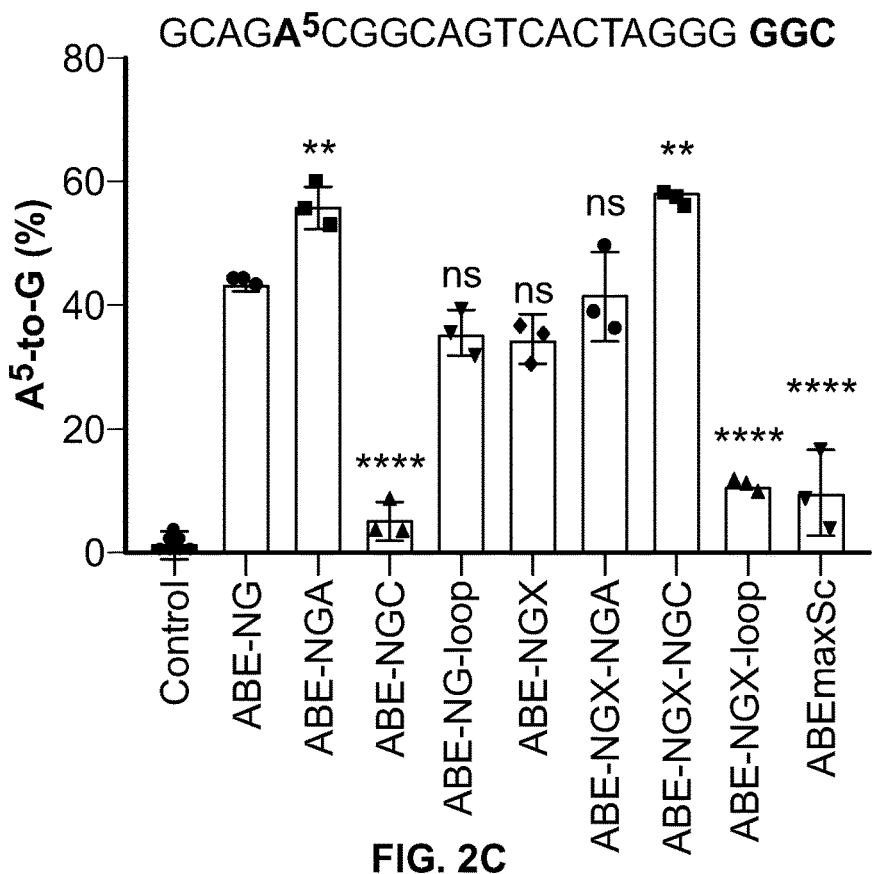
Figure 2D:
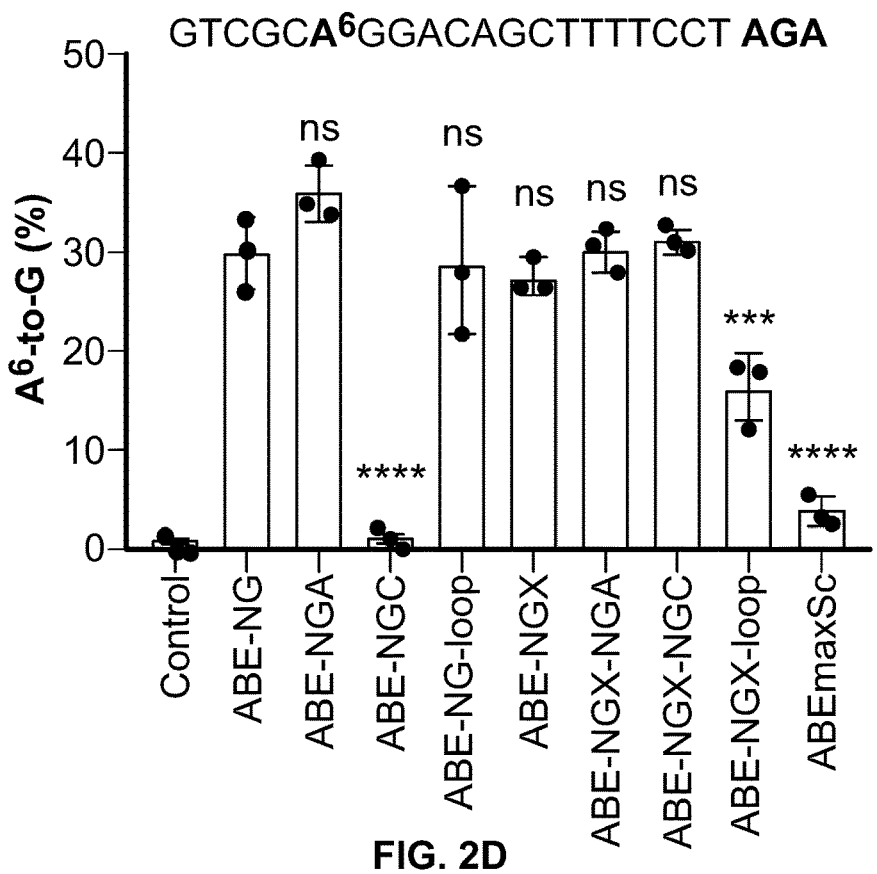
Figure 2E:
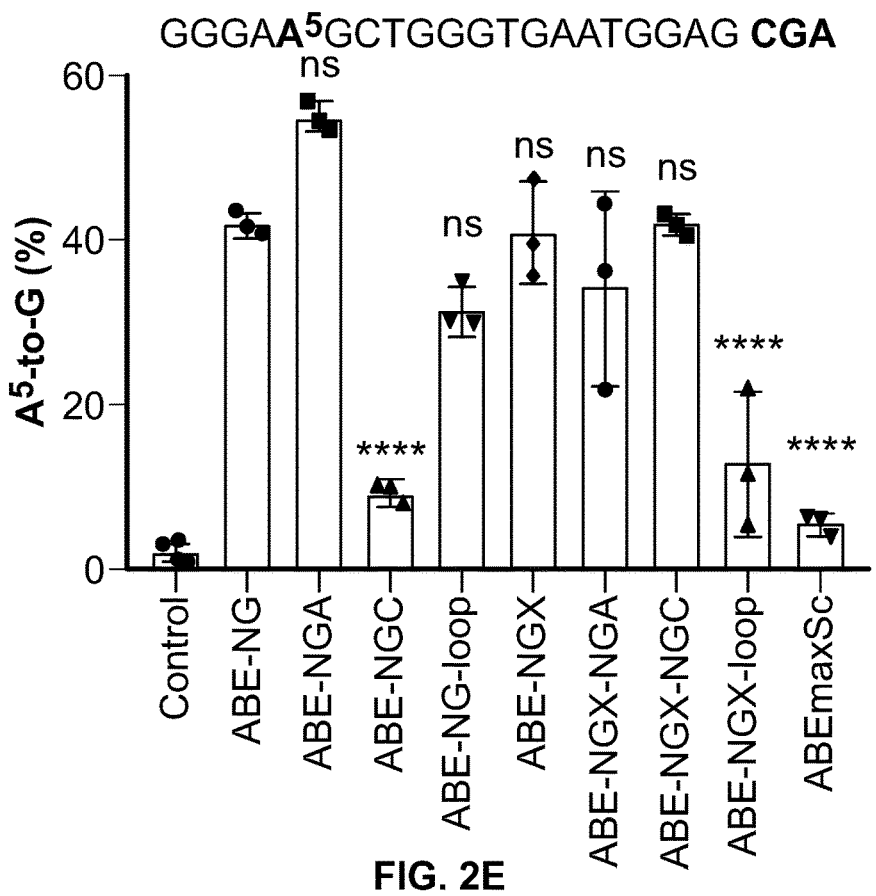
Figure 2F:
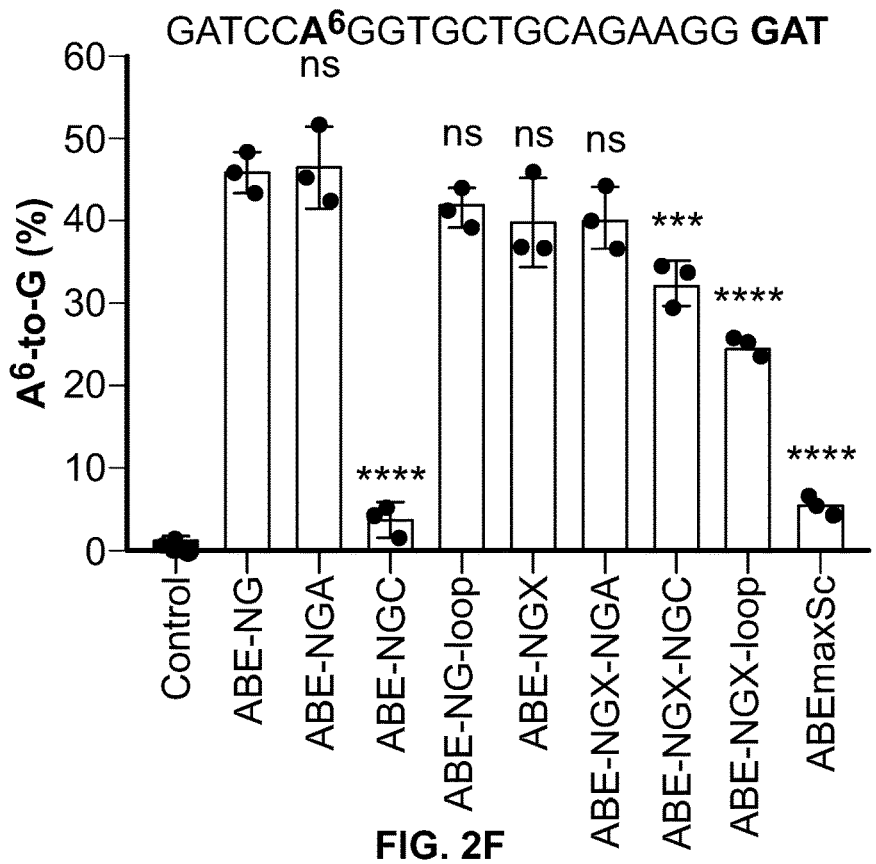

| ID | Name | Description |
| --- | --- | --- |
| pXL-0712 | pCMV-ABEmaxNGX | Expressing ABE-NGX; used in FIG. 2a-f. |
| pXL-0868 | pCMV-ABEmaxNGX-NGA | Expressing ABE-NGX-NGA; used in FIG. 2a-f. |
| pXL-0875 | pCMV-ABEmaxNGX-NGC | Expressing ABE-NGX-NGC; used in FIG. 2a-f. |
| pXL-0877 | pCMV-ABEmaxNGX-loop | Expressing ABE-NGX-loop; used in FIG. 2a-f. |
| pXL-0723 | pCMV-ABEmaxSC | Expressing ABEmaxSc; used in FIG. 2a-f. |
| pXL-0627 | pLenti-puro-S1OgRNA | S1 targeting gRNA; used in FIG. 2a. |
| pZC0009 | pLenti-Q2440X-ogRNA | Non-targeting gRNA; used in FIG. 7. |
| pXL-0796 | pLenti-VEGFA-S5 | gRNA targeting VEGFA Site5; used in FIG. 2b. |
| pXL-0797 | pLenti-VEGFA-S12 | gRNA targeting VEGFA Site 12; used in FIG. 2c. |
| pXL-0798 | pLenti-VEGFA-S14 | gRNA targeting VEGFA Site14; used in FIG. 2d. |
| pXL-0800 | pLenti-Site13 | gRNA targeting Site13; used in FIG. 2e. |
| pXL-0801 | pLenti-FANCF-ogRNA | gRNA targeting FANCF; used in FIG. 2f. |
| pZC0103 | pCMV_miniABE_NG(V82G) | Expressing miniABE(82G)-NG; used in FIG. 3b, 3c. |
| pZC0104 | pCMV_miniABE-NG | Expressing miniABE-NG; used in FIG. 3b-3d. |
| pXL-0853 | pCMV_miniABEmax-NG(A56G) | Expressing miniABE(A56G)-NG; used in FIG. 3b, 3c. |
| pXL-0854 | pCMV_miniABEmaxNG(GG) | Expressing miniABE(GG)-NG; used in FIG. 3b-3d, FIG. 4. |
| pXL-0420 | pCMV_ABE7.10 (Addgene #102919) | Expressing ABE7.10; used in FIG. 6b, FIG. 5 |
| pXL-0670 | pBac-rAAV-ABEmaxN-E53 OgRNA | Expressing Cfa Split_N of ABE and mdx4cv gRNA; used in FIG. 6b-6d. |
| pXL-0671 | pBac-rAAV-ABEmaxC-NG-E53 OgRNA | Expressing Cfa Split_C of ABE-NG and mdx4cv gRNA; used in FIG. 6b-6d. |
| pXL-0672 | pBac-rAAV-ABEmaxN2-E53 OgRNA | Expressing Gp41-1 Split_N of ABE and mdx4cv gRNA; used in FIG. 6b-6d. |
| pXL-0673 | pBac-rAAV-ABEmaxC2-NG-E53 OgRNA | Expressing Gp41-1 Split_C of ABE-NG and mdx4cv gRNA; used in FIG. 6b-6d. |
| pZC0117 | pX601-mhCMV-ABEmaxNGA-C3-E53ogRNA | Expressing Npu Split_C of iABE-NGA and mdx4cv gRNA; used in FIG. 6e-6h. |
| pZC0118 | pX601-mhCMV-miniABEmax-N3-E53ogRNA | Expressing Npu Split_N of iABE-NGA and mdx4cv gRNA; used in FIG. 6e-6h. |
| pZC0119 | pX601-mhCMV-miniABEmax-N3-zeo | Expressing Npu Split_N of iABE-NGA; used in FIG. 6e-6h. |
| pZC0031 | pX601-mhCMV-miniABEmax-N2-E53ogRNA | Expressing Gp41-1 Split_N of iABE-NGA and mdx4cv gRNA; used in FIG. 6e-6h. |
| pZC0033 | pX601-mhCMV-ABEmaxNGA-C2-E53ogRNA | Expressing Gp41-1 Split_C of iABE-NGA and mdx4cv gRNA; used in FIG. 6e-6h. |
| pXL-0855 | pX601-MHP1-miniABEmaxNG-N2-(GG) | Expressing Gp41-1 Split_N of iABE-NGA and mdx4cv gRNA, MHP1 promoter; used for AAV9 production in FIG. 8, 27. |
| pXL-0706 | pX601-MHP1-ABEmaxC2-NG-E53 ogRNA | Expressing Gp41-1 Split_C of iABE-NGA and mdx4cv gRNA, MHP1 promoter; used for AAV9 production in FIG. 8, 27. |
| pYZ1059 | pCMV_NG-ABE8e | Expressing ABE8e-NG; used in FIG. 4 |
| pZC0105 | pCMV_NG-ABE8.17 | Expressing ABE8.17-NG; used in FIG. 4 |
| pZC0106 | pCMV_NG-ABE8.20 | Expressing ABE8.20-NG; used in FIG. 4 |
| pZC0111 | pCMV_SpG-ABE8e(V106W) | Expressing ABE8e-SpG(V106W); used in FIG. 4 |

TABLE 3-continued

List of plasmids used in this study.

| ID | Name | Description |
|---|---|---|
| pPW-0007 | pLKO-puro-2A-Q623X-GFP | Q623X reporter; used in FIG. 4b. |
| pPW-0010 | pLenti-Q623X-ogRNA | Q623X targeting gRNA; used in FIG. 4b. |
| pXL-0419 | pCMV-ABE7.9 (Addgene #102918) | Expressing ABE7.9; used in FIG. 8. |
| pXL-0419 | pCMV-ABE7.9 (Addgene #102918) | Expressing ABE7.9; used in FIG. 8. |
| pYG9010 | pBac-rAAV-IntC-SpCas9n | Expressing Npu_N-SpCas9 nickase; used in FIG. 8. |
| pYG9011 | pBac-rAAV-ABE7.10v3 | Expressing GFP-TadA-TadA*-Npu_C; used in FIG. 8. |

TABLE 4

List of primers used for NGS in this study.

| Name | Sequence | |
|---|---|---|
| Mdx4cv-E52-F | ACACTCTTTCCCTACACGACGCTCTTCCGATCTGAACTCATTACTGCTGCCCAGA | SEQ ID NO: 593 |
| Mdx4cc-E53-R | GTGACTGGAGTTCAGACGTGTGCTCTTCCGATCGACCTGTTCGGCTTCTTCCTTA | SEQ ID NO: 594 |
| Mdx4cv-i52-F | ACACTCTTTCCCTACACGACGCTCTTCCGATCTAAATTTCCACTGTCTTCTCTTGAGT | SEQ ID NO: 595 |
| Mdx4cv-i53-R | GTGACTGGAGTTCAGACGTGTGGTCTTCCGATCGCTTGCCTCTGACCTGTCCTAT | SEQ ID NO: 596 |
| mChr16 OT-F | ACACTCTTTCCCTACACGACGCTCTTCCGATCTGTGACTAGGGGCAAAGCAAGAT | SEQ ID NO: 597 |
| mChr16 OT-R | GTGACTGGAGTTCAGACGTGTGCTCTTCCGATCCTTCCAAACTTTCTGCCCATTC | SEQ ID NO: 598 |
| mChr10 T-F | ACACTCTTTCCCTACACGACGCTCTTCCGATCTAACACAGCGTGCTCTTTCCTTAC | SEQ ID NO: 599 |
| mChr10 T-R | GTGACTGGAGTTCAGACGTGTGCTCTTCCGATCGTTCAGAAGAACATCCCGTTGAC | SEQ ID NO: 600 |
| NGS-final-F | AATGATACGGCGACCACCGAGATCTACACTCTTTCCCTACACGAC | SEQ ID NO: 601 |
| NGS-final-R1 | CAAGCAGAAGACGGCATACGAGATCTTGTAGTGACTGGAGTTCAGACGT | SEQ ID NO: 602 |
| NGS-final-R2 | CAAGCAGAAGACGGCATACGAGATCAGATCGTGACTGGAGTTCAGACGT | SEQ ID NO: 603 |
| NGS-final-R3 | CAAGCAGAAGACGGCATACGAGATCCGTCCGTGACTGGAGTTCAGACGT | SEQ ID NO: 604 |
| NGS-final-R4 | CAAGCAGAAGACGGCATACGAGATATGTCAGTGACTGGAGTTCAGACGT | SEQ ID NO: 605 |
| NGS-final-R5 | CAAGCAGAAGACGGCATACGAGAT GTCCGC GTGACTGGAGTTCAGACGT | SEQ ID NO: 606 |
| NGS-final-R6 | CAAGCAGAAGACGGCATACGAGAT TTAGGC GTGACTGGAGTTCAGACGT | SEQ ID NO: 607 |
| NGS-final-R7 | CAAGCAGAAGACGGCATACGAGAT CGATGT GTGACTGGAGTTCAGACGT | SEQ ID NO: 608 |
| NGS-final-R8 | CAAGCAGAAGACGGCATACGAGAT TGACCA GTGACTGGAGTTCAGACGT | SEQ ID NO: 609 |
| NGS-final-R9 | CAAGCAGAAGACGGCATACGAGAT AGTCAA GTGACTGGAGTTCAGACGT | SEQ ID NO: 610 |

TABLE 4-continued

List of primers used for NGS in this study.

| Name | Sequence | |
|---|---|---|
| NGS-final-R10 | CAAGCAGAAGACGGCATACGAGAT AGTTCC GTGACTGGAGTTCAGACGT | SEQ ID NO: 611 |
| NGS-final-R11 | CAAGCAGAAGACGGCATACGAGAT GATCAG GTGACTGGAGTTCAGACGT | SEQ ID NO: 612 |
| NGS-final-R12 | CAAGCAGAAGACGGCATACGAGAT ACAGTG GTGACTGGAGTTCAGACGT | SEQ ID NO: 613 |
| NGS-final-R13 | CAAGCAGAAGACGGCATACGAGAT TATACT GTGACTGGAGTTCAGACGT | SEQ ID NO: 614 |
| NGS-final-R14 | CAAGCAGAAGACGGCATACGAGAT CAACAA GTGACTGGAGTTCAGACGT | SEQ ID NO: 615 |
| NGS-final-R15 | CAAGCAGAAGACGGCATACGAGAT GTTGTT GTGACTGGAGTTCAGACGT | SEQ ID NO: 616 |
| NGS-final-R16 | CAAGCAGAAGACGGCATACGAGAT TCGGTT GTGACTGGAGTTCAGACGT | SEQ ID NO: 617 |
| NGS-final-R17 | CAAGCAGAAGACGGCATACGAGAT AGTATT GTGACTGGAGTTCAGACGT | SEQ ID NO: 618 |
| NGS-final-R18 | CAAGCAGAAGACGGCATACGAGAT TCTTGT GTGACTGGAGTTCAGACGT | SEQ ID NO: 619 |

TABLE 5

| chr | pos | hgvs_c | hgvs_p | all_traits | variants | variant type | repair editor | reference_seq | sgRNA_repair |
|---|---|---|---|---|---|---|---|---|---|
| X | 31173588 | NM_004020.3:c.2843+5081C>T | NP_003997.1:p.Gln3427Ter | Dilated cardiomyopathy 3B; Becker muscular dystrophy; Duchenne muscular dystrophy | G > A | intron variant | ABE | SEQ ID NO: 48 | SEQ ID NO: 222; SEQ ID NO: 223 |
| X | 32464674 | NM_004006.2:c.3188G>A | NP_003997.1:p.Trp1063Ter | Duchenne muscular dystrophy; DUCHENNE MUSCULAR DYSTROPHY | C > T | nonsense | ABE | SEQ ID NO: 49 | SEQ ID NO: 224; SEQ ID NO: 225; SEQ ID NO: 226; SEQ ID NO: 227 |
| X | 32217037 | NM_004006.2:c.6317G>A | NP_003997.1:p.Trp2106Ter | not provided; Not Provided | C > T | nonsense | ABE | SEQ ID NO: 50 | SEQ ID NO: 228; SEQ ID NO: 229 |
| X | 32362826 | NM_004006.2:c.5287C>T | NP_003997.1:p.Arg1763Ter | Dilated cardiomyopathy 3B; Becker muscular dystrophy; Duchenne muscular dystrophy | G > A | nonsense | ABE | SEQ ID NO: 51 | SEQ ID NO: 230; SEQ ID NO: 231; SEQ ID NO: 232 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31178668 | NM_004006.2:c.10223+1G>A | NP_004010.1:p.Thr340= | Dilated cardiomyopathy 3B; Becker muscular dystrophy; Duchenne muscular dystrophy | C>T | synonymous variant | ABE | SEQ ID NO: 52 | SEQ ID NO: 233; SEQ ID NO: 234; SEQ ID NO: 235; SEQ ID NO: 236 |
| X | 31180423 | NM_004006.2:c.10033C>T | NP_003997.1:p.Arg3345Ter | Dilated cardiomyopathy 3B; Becker muscular dystrophy; Duchenne muscular dystrophy; not provided; not specified | G>A | nonsense | ABE | SEQ ID NO: 53 | SEQ ID NO: 237; SEQ ID NO: 238 |
| X | 31478163 | NM_004006.2:c.8880G>A | NP_003997.1:p.Trp2960Ter |  | C>T | nonsense | ABE | SEQ ID NO: 54 | SEQ ID NO: 239 |
| X | 31479043 | NM_004006.2:c.8608C>T | NP_003997.1:p.Arg2870Ter | Dilated cardiomyopathy 3B; Becker muscular dystrophy; Duchenne muscular dystrophy | G>A | nonsense | ABE | SEQ ID NO: 55 | SEQ ID NO: 240 |
| X | 32697947 | NM_004006.2:c.883C>T | NP_003997.1:p.Arg295Ter | Becker muscular dystrophy; Duchenne muscular dystrophy; Dilated cardiomyopathy 3B | G>A | nonsense | ABE | SEQ ID NO: 56 | SEQ ID NO: 241; SEQ ID NO: 242; SEQ ID NO: 243; SEQ ID NO: 244; SEQ ID NO: 245 |
| X | 32573766 | NM_004006.2:c.1683G>A | NP_003997.1:p.Trp561Ter | Duchenne muscular dystrophy; Duchenne muscular dystrophy | C>T | nonsense | ABE | SEQ ID NO: 57 | SEQ ID NO: 246; SEQ ID NO: 247; SEQ ID NO: 248; SEQ ID NO: 249 |
| X | 32484918 | NM_004006.2:c.2803+1G>A |  | Dilated cardiomyopathy 3B; Dilated cardiomyopathy 3B | C>T | splice donor variant | ABE | SEQ ID NO: 58 | SEQ ID NO: 250 |
| X | 32573744 | NM_004006.2:c.1704+1G>A |  | Becker muscular dystrophy; Duchenne muscular dystrophy; not specified | C>T | splice donor variant | ABE | SEQ ID NO: 59 | SEQ ID NO: 251; SEQ ID NO: 252; SEQ ID NO: 253; SEQ ID NO: 254 |
| X | 32816541 | NM_004006.2:c.457C>T | NP_003997.1:p.Gln153Ter | Duchenne muscular dystrophy | G>A | nonsense | ABE | SEQ ID NO: 60 | SEQ ID NO: 255; SEQ ID NO: 256; SEQ ID NO: 257; SEQ ID NO: 258 |
| X | 32348501 | NM_004006.2:c.5353C>T | NP_003997.1:p.Gln1785Ter | Dilated cardiomyopathy 3B; Dilated cardiomyopathy 3B | G>A | nonsense | ABE | SEQ ID NO: 61 | SEQ ID NO: 259; SEQ ID NO: 260; SEQ ID NO: 261 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32411811 | NM_004006.2:c.4174C > T | NP_003997.1:p.Gln1392Ter | Duchenne muscular dystrophy; Becker muscular dystrophy | G > A | nonsense | ABE | SEQ ID NO: 62 | SEQ ID NO: 262; SEQ ID NO: 263; SEQ ID NO: 264; SEQ ID NO: 265; SEQ ID NO: 266 |
| X | 31182861 | NM_004006.2:c.9851G > A | NP_003997.1:p.Trp3284Ter | Dilated cardiomyopathy 3B; Dilated cardiomyopathy 3B | C > T | nonsense | ABE | SEQ ID NO: 63 | SEQ ID NO: 267; SEQ ID NO: 268 |
| X | 32809577 | NM_004006.2:c.565C > T | NP_003997.1:p.Gln189Ter | Duchenne muscular dystrophy; Becker muscular dystrophy | G > A | nonsense | ABE | SEQ ID NO: 64 | SEQ ID NO: 269 |
| X | 32216981 | NM_004006.2:c.6373C > T | NP_003997.1:p.Gln2125Ter | Duchenne muscular dystrophy; DUCHENNE MUSCULAR DYSTROPHY; Dilated cardiomyopathy 3B; Becker muscular dystrophy | G > A | nonsense | ABE | SEQ ID NO: 65 | SEQ ID NO: 270 |
| X | 32573812 | NM_004006.2:c.1637G > A | NP_003997.1:p.Trp546Ter | Motor delay; Muscle weakness; Muscle cramps; EMG abnormality; EMG; myopathic abnormalities; Calf muscle hypertrophy | C > T | nonsense | ABE | SEQ ID NO: 66 | SEQ ID NO: 271; SEQ ID NO: 272; SEQ ID NO: 273; SEQ ID NO: 274; SEQ ID NO: 275 |
| X | 31507314 | NM_004006.2:c.8357G > A | NP_003997.1:p.Trp2786Ter | Duchenne muscular dystrophy; Duchenne muscular dystrophy | C > T | nonsense | ABE | SEQ ID NO: 67 | SEQ ID NO: 276; SEQ ID NO: 277; SEQ ID NO: 278; SEQ ID NO: 279; SEQ ID NO: 280 |
| X | 32463458 | NM_004006.2:c.3413G > A | NP_003997.1:p.Trp1138Ter | Becker muscular dystrophy | C > T | nonsense | ABE | SEQ ID NO: 68 | SEQ ID NO: 281; SEQ ID NO: 282; SEQ ID NO: 283 |
| X | 31223071 | NM_004006.2:c.9337C > T | NP_003997.1:p.Arg3113Ter | Dilated cardiomyopathy 3B; Becker muscular dystrophy; Duchenne muscular dystrophy; not provided; Not Provided | G > A | nonsense | ABE | SEQ ID NO: 69 | SEQ ID NO: 284; SEQ ID NO: 285 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31929602 | NM_004006.2:c.6906G > A | NP_003997.1:p.Trp2302Ter | Dilated cardiomyopathy 3B; Becker muscular dystrophy; Duchenne muscular dystrophy | C > T | 5 prime UTR variant | ABE | SEQ ID NO: 70 | SEQ ID NO: 286 |
| X | 32595765 | NM_004006.2:c.1594C > T | NP_003997.1:p.Gln532Ter | Duchenne muscular dystrophy | G > A | nonsense | ABE | SEQ ID NO: 71 | SEQ ID NO: 287; SEQ ID NO: 288; SEQ ID NO: 289; SEQ ID NO: 290 |
| X | 32573834 | NM_004006.2:c.1615C > T | NP_003997.1:p.Arg539Ter | Dilated cardiomyopathy 3B; Becker muscular dystrophy; Duchenne muscular dystrophy | G > A | nonsense | ABE | SEQ ID NO: 72 | SEQ ID NO: 291; SEQ ID NO: 292; SEQ ID NO: 293; SEQ ID NO: 294; SEQ ID NO: 295 |
| X | 31679565 | NM_004006.2:c.7682G > A | NP_003997.1:p.Trp2561Ter | Dilated cardiomyopathy 3B; Becker muscular dystrophy; Duchenne muscular dystrophy | C > T | nonsense | ABE | SEQ ID NO: 73 | SEQ ID NO: 296; SEQ ID NO: 297 |
| X | 31679564 | NM_004006.2:c.7683G > A | NP_003997.1:p.Trp2561Ter | Dilated cardiomyopathy 3B; Becker muscular dystrophy; Duchenne muscular dystrophy | C > T | nonsense | ABE | SEQ ID NO: 74 | SEQ ID NO: 298 |
| X | 32485057 | NM_004006.2:c.2665C > T | NP_003997.1:p.Arg889Ter | Duchenne muscular dystrophy | G > A | nonsense | ABE | SEQ ID NO: 75 | SEQ ID NO: 299; SEQ ID NO: 300; SEQ ID NO: 301; SEQ ID NO: 302; SEQ ID NO: 303 |
| X | 32849781 | NM_004006.2:c.133C > T | NP_003997.1:p.Gln45Ter | Duchenne muscular dystrophy; Becker muscular dystrophy | G > A | 5 prime UTR variant | ABE | SEQ ID NO: 76 | SEQ ID NO: 304; SEQ ID NO: 305; SEQ ID NO: 306; SEQ ID NO: 307 |
| X | 32501767 | NM_004006.2:c.2368C > T | NP_003997.1:p.Gln790Ter | Duchenne muscular dystrophy; Duchenne muscular dystrophy | G > A | nonsense | ABE | SEQ ID NO: 77 | SEQ ID NO: 308; SEQ ID NO: 309; SEQ ID NO: 310 |
| X | 32545250 | NM_004006.2:c.2077C > T | NP_003997.1:p.Gln693Ter | Duchenne muscular dystrophy | G > A | nonsense | ABE | SEQ ID NO: 78 | SEQ ID NO: 311; SEQ ID NO: 312; SEQ ID NO: 313 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31679429 | NM_004006.2:c.7818G > A | NP_003997.1:p.Trp2606Ter | Dilated cardiomyopathy 3B; Dilated cardiomyopathy 3B | C > T | nonsense | ABE | SEQ ID NO: 79 | SEQ ID NO: 314; SEQ ID NO: 315 |
| X | 31679492 | NM_004006.2:c.7755G > A | NP_003997.1:p.Trp2585Ter | Duchenne muscular dystrophy; Duchenne muscular dystrophy | C > T | nonsense | ABE | SEQ ID NO: 80 | SEQ ID NO: 316; SEQ ID NO: 317; SEQ ID NO: 318; SEQ ID NO: 319; SEQ ID NO: 320 |
| X | 31875331 | NM_004006.2:c.6955C > T | NP_003997.1:p.Gln2319Ter | Duchenne muscular dystrophy; DUCHENNE MUSCULAR DYSTROPHY | G > A | 5 prime UTR variant | ABE | SEQ ID NO: 81 | SEQ ID NO: 321 |
| X | 32342105 | NM_004006.2:c.5917C > T | NP_003997.1:p.Gln1973Ter | Duchenne muscular dystrophy; Duchenne muscular dystrophy | G > A | nonsense | ABE | SEQ ID NO: 82 | SEQ ID NO: 322 |
| X | 31774193 | NM_004006.2:c.7310 − 1G > A | | Becker muscular dystrophy; Duchenne muscular dystrophy | C > T | splice acceptor variant | ABE | SEQ ID NO: 83 | SEQ ID NO: 323; SEQ ID NO: 324 |
| X | 31177932 | NM_004006.2:c.10262C > T | NP_003997.1:p.Ala3421Val | Becker muscular dystrophy; BECKER MUSCULAR DYSTROPHY; not specified | G > A | 500B downstream variant | ABE | SEQ ID NO: 84 | SEQ ID NO: 325; SEQ ID NO: 326 |
| X | 31658123 | NM_004006.2:c.7894C > T | NP_003997.1:p.Gln2632Ter | Dilated cardiomyopathy 3B; Becker muscular dystrophy; Duchenne muscular dystrophy | G > A | nonsense | ABE | SEQ ID NO: 85 | SEQ ID NO: 327 |
| X | 32468683 | NM_004006.2:c.2977C > T | NP_003997.1:p.Gln993Ter | Dilated cardiomyopathy 3B; Dilated cardiomyopathy 3B | G > A | nonsense | ABE | SEQ ID NO: 86 | SEQ ID NO: 328; SEQ ID NO: 329 |
| X | 32699111 | NM_004006.2:c.831 + 1G > A | | Duchenne muscular dystrophy | C > T | splice donor variant | ABE | SEQ ID NO: 87 | SEQ ID NO: 330; SEQ ID NO: 331; SEQ ID NO: 332 |
| X | 32411772 | NM_004006.2:c.4213C > T | NP_003997.1:p.Gln1405Ter | Duchenne muscular dystrophy; DUCHENNE MUSCULAR DYSTROPHY | G > A | nonsense | ABE | SEQ ID NO: 88 | SEQ ID NO: 333; SEQ ID NO: 334 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31178721 | NM_004006.2:c.10171C > T | NP_003997.1:p.Arg3391Ter | Dilated cardiomyopathy 3B; Becker muscular dystrophy; Duchenne muscular dystrophy; not provided; Not Provided | G > A | nonsense | ABE | SEQ ID NO: 89 | SEQ ID NO: 335; SEQ ID NO: 336 |
| X | 31478983 | NM_004006.2:c.8668G > A | NP_003997.1:p.Glu2890Lys | Dilated cardiomyopathy 3B; Dilated cardiomyopathy 3B | C > T | missense variant | ABE | SEQ ID NO: 90 | SEQ ID NO: 337; SEQ ID NO: 338 |
| X | 31180369 | NM_004006.2:c.10086 + 1G > A | | Dilated cardiomyopathy 3B; Becker muscular dystrophy; Duchenne muscular dystrophy | C > T | splice donor variant | ABE | SEQ ID NO: 91 | SEQ ID NO: 339; SEQ ID NO: 340; SEQ ID NO: 341 |
| X | 32364647 | NM_004006.2:c.5089C > T | NP_003997.1:p.Gln1697Ter | Duchenne muscular dystrophy; Becker muscular dystrophy | G > A | nonsense | ABE | SEQ ID NO: 92 | SEQ ID NO: 342 |
| X | 31496892 | NM_004006.2:c.8443C > T | NP_003997.1:p.Gln2815Ter | Dilated cardiomyopathy 3B; Duchenne muscular dystrophy | G > A | nonsense | ABE | SEQ ID NO: 93 | SEQ ID NO: 343; SEQ ID NO: 344; SEQ ID NO: 345; SEQ ID NO: 346 |
| X | 32411868 | NM_004006.2:c.4117C > T | NP_003997.1:p.Gln1373Ter | Dilated cardiomyopathy 3B; Becker muscular dystrophy; Duchenne muscular dystrophy | G > A | nonsense | ABE | SEQ ID NO: 94 | SEQ ID NO: 347; SEQ ID NO: 348 |
| X | 31819974 | NM_004006.2:c.7309 + 1G > A | | Dilated cardiomyopathy 3B; Becker muscular dystrophy; Duchenne muscular dystrophy | C > T | splice donor variant | ABE | SEQ ID NO: 95 | SEQ ID NO: 349 |
| X | 31444621 | NM_004006.2:c.8944C > T | NP_003997.1:p.Arg2982Ter | Duchenne muscular dystrophy; DUCHENNE MUSCULAR DYSTROPHY; Dilated cardiomyopathy 3B; Becker muscular dystrophy | G > A | nonsense | ABE | SEQ ID NO: 96 | SEQ ID NO: 350; SEQ ID NO: 351; SEQ ID NO: 352; SEQ ID NO: 353 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31627852 | NM_004006.2:c.8038C > T | NP_003997.1:p.Arg2680Ter | Duchenne muscular dystrophy; Becker muscular dystrophy | G > A | nonsense | ABE | SEQ ID NO: 97 | SEQ ID NO: 354; SEQ ID NO: 355; SEQ ID NO: 356; SEQ ID NO: 357 |
| X | 32501833 | NM_004006.2:c.2302C > T | NP_003997.1:p.Arg768Ter | Duchenne muscular dystrophy; DUCHENNE MUSCULAR DYSTROPHY; Dilated cardiomyopathy 3B | G > A | nonsense | ABE | SEQ ID NO: 98 | SEQ ID NO: 358; SEQ ID NO: 359; SEQ ID NO: 360 |
| X | 32365049 | NM_004006.2:c.4996C > T | NP_003997.1:p.Arg1666Ter | Dilated cardiomyopathy 3B; not provided; Duchenne muscular dystrophy | G > A | nonsense | ABE | SEQ ID NO: 99 | SEQ ID NO: 361; SEQ ID NO: 362 |
| X | 32345999 | NM_004006.2:c.5530C > T | NP_003997.1:p.Arg1844Ter | Dilated cardiomyopathy 3B; Becker muscular dystrophy; Duchenne muscular dystrophy | G > A | nonsense | ABE | SEQ ID NO: 100 | SEQ ID NO: 363; SEQ ID NO: 364; SEQ ID NO: 365; SEQ ID NO: 366 |
| X | 32468573 | NM_004006.2:c.3087G > A | NP_003997.1:p.Trp1029Ter | Dilated cardiomyopathy 3B; Dilated cardiomyopathy 3B | C > T | nonsense | ABE | SEQ ID NO: 101 | SEQ ID NO: 367; SEQ ID NO: 368 |
| X | 32518098 | NM_004006.2:c.2202G > A | NP_003997.1:p.Trp734Ter | Duchenne muscular dystrophy | C > T | nonsense | ABE | SEQ ID NO: 102 | SEQ ID NO: 369; SEQ ID NO: 370; SEQ ID NO: 371; SEQ ID NO: 372 |
| X | 31820055 | NM_004006.2:c.7229G > A | NP_003997.1:p.Trp2410Ter | Dilated cardiomyopathy 3B; Dilated cardiomyopathy 3B | C > T | 5 prime UTR variant | ABE | SEQ ID NO: 103 | SEQ ID NO: 373; SEQ ID NO: 374 |
| X | 32650983 | NM_004006.2:c.961 – 5831C > T | | Dilated cardiomyopathy 3B; Duchenne muscular dystrophy | G > A | intron variant | ABE | SEQ ID NO: 104 | SEQ ID NO: 375; SEQ ID NO: 376; SEQ ID NO: 377; SEQ ID NO: 378; SEQ ID NO: 379 |
| X | 31478129 | NM_004006.2:c.8914C > T | NP_003997.1:p.Gln2972Ter | Duchenne muscular dystrophy | G > A | nonsense | ABE | SEQ ID NO: 105 | SEQ ID NO: 380; SEQ ID NO: 381; SEQ ID NO: 382; SEQ ID NO: 383; SEQ ID NO: 384; SEQ ID NO: 385 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32389605 | NM_004006.2:c.4414C > T | NP_003997.1:p.Gln1472Ter | Duchenne muscular dystrophy; DUCHENNE MUSCULAR DYSTROPHY | G > A | nonsense | ABE | SEQ ID NO: 106 | SEQ ID NO: 386; SEQ ID NO: 387; SEQ ID NO: 388; SEQ ID NO: 389 |
| X | 32595855 | NM_004006.2:c.1504C > T | NP_003997.1:p.Gln502Ter | Duchenne muscular dystrophy | G > A | nonsense | ABE | SEQ ID NO: 107 | SEQ ID NO: 390 |
| X | 32699219 | NM_004006.2:c.724C > T | NP_003997.1:p.Gln242Ter | Duchenne muscular dystrophy; DUCHENNE MUSCULAR DYSTROPHY | G > A | nonsense | ABE | SEQ ID NO: 108 | SEQ ID NO: 391; SEQ ID NO: 392; SEQ ID NO: 393; SEQ ID NO: 394 |
| X | 33211304 | NM_004006.2:c.9G > A | NP_003997.1:p.Trp3Ter | Becker muscular dystrophy; BECKER MUSCULAR DYSTROPHY; Dilated cardiomyopathy 3B; Duchenne muscular dystrophy; not provided; Not Provided | C > T | nonsense | ABE | SEQ ID NO: 109 | SEQ ID NO: 395; SEQ ID NO: 396; SEQ ID NO: 397 |
| X | 32454833 | NM_004006.2:c.3433 − 1G > A | | Dilated cardiomyopathy 3B; Dilated cardiomyopathy 3B | C > T | splice acceptor variant | ABE | SEQ ID NO: 110 | SEQ ID NO: 398; SEQ ID NO: 399; SEQ ID NO: 400; SEQ ID NO: 401; SEQ ID NO: 402 |
| X | 32472252 | NM_004006.2:c.2861G > A | NP_003997.1:p.Trp954Ter | Duchenne muscular dystrophy | C > T | nonsense | ABE | SEQ ID NO: 111 | SEQ ID NO: 403; SEQ ID NO: 404; SEQ ID NO: 405 |
| X | 32389614 | NM_004006.2:c.4405C > T | NP_003997.1:p.Gln1469Ter | Dilated cardiomyopathy 3B; Dilated cardiomyopathy 3B | G > A | nonsense | ABE | SEQ ID NO: 112 | SEQ ID NO: 406; SEQ ID NO: 407; SEQ ID NO: 408 |
| X | 32438240 | NM_004006.2:c.4071 + 1G > A | | Duchenne muscular dystrophy | C > T | splice donor variant | ABE | SEQ ID NO: 113 | SEQ ID NO: 409; SEQ ID NO: 410; SEQ ID NO: 411; SEQ ID NO: 412; SEQ ID NO: 413; SEQ ID NO: 414 |
| X | 32491492 | NM_004006.2:c.2407C > T | NP_003997.1:p.Gln803Ter | Duchenne muscular dystrophy; Duchenne muscular dystrophy | G > A | nonsense | ABE | SEQ ID NO: 114 | SEQ ID NO: 415 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31206581 | NM_004006.2:c.9649 + 1G > A | | Duchenne muscular dystrophy | C > T | splice donor variant | ABE | SEQ ID NO: 115 | SEQ ID NO: 416; SEQ ID NO: 417; SEQ ID NO: 418 |
| X | 32390175 | NM_004006.2:c.4240C > T | NP_003997.1:p.Gln1414Ter | Duchenne muscular dystrophy; not specified | G > A | nonsense | ABE | SEQ ID NO: 116 | SEQ ID NO: 419; SEQ ID NO: 420; SEQ ID NO: 421; SEQ ID NO: 422; SEQ ID NO: 423 |
| X | 32491387 | NM_004006.2:c.2512C > T | NP_003997.1:p.Gln838Ter | Duchenne muscular dystrophy; Becker muscular dystrophy | G > A | nonsense | ABE | SEQ ID NO: 117 | SEQ ID NO: 424; SEQ ID NO: 425; SEQ ID NO: 426; SEQ ID NO: 427 |
| X | 32342154 | NM.004006.2:c.5868G > A | NP_003997.1:p.Trp1956Ter | Duchenne muscular dystrophy; Becker muscular dystrophy | C > T | nonsense | ABE | SEQ ID NO: 118 | SEQ ID NO: 428; SEQ ID NO: 429; SEQ ID NO: 430; SEQ ID NO: 431 |
| X | 32816509 | NM_004006.2:c.489G > A | NP_003997.1:p.Trp163Ter | Dilated cardiomyopathy 3B; Dilated cardiomyopathy 3B | C > T | nonsense | ABE | SEQ ID NO: 119 | SEQ ID NO: 432; SEQ ID NO: 433 |
| X | 32454685 | NM_004006.2:c.3580C > T | NP_003997.1:p.Gln1194Ter | Dilated cardiomyopathy 3B; Becker muscular dystrophy; Duchenne muscular dystrophy | G > A | nonsense | ABE | SEQ ID NO: 120 | SEQ ID NO: 434; SEQ ID NO: 435 |
| X | 32573529 | NM_004006.2:c.1812 + 1G > A | | Becker muscular dystrophy; Muscular dystrophy, Becker; Duchenne muscular dystrophy; not provided; Not Provided | C > T | splice donor variant | ABE | SEQ ID NO: 121 | SEQ ID NO: 436 |
| X | 31223046 | NM_004006.2:c.9361 + 1G > A | | Dilated cardiomyopathy 3B; Becker muscular dystrophy; Duchenne muscular dystrophy | C > T | splice donor variant | ABE | SEQ ID NO: 122 | SEQ ID NO: 437 |
| X | 32545310 | NM_004006.2:c.2017C > T | NP_003997.1:p.Gln673Ter | Duchenne muscular dystrophy; DUCHENNE MUSCULAR DYSTROPHY | G > A | nonsense | ABE | SEQ ID NO: 123 | SEQ ID NO: 438; SEQ ID NO: 439 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32343232 | NM_004006.2:c.5641C>T | NP_003997.1:p.Gln1881Ter | Duchenne muscular dystrophy; Duchenne muscular dystrophy | G > A | nonsense | ABE | SEQ ID NO: 124 | SEQ ID NO: 440; SEQ ID NO: 441; SEQ ID NO: 442; SEQ ID NO: 443 |
| X | 31679430 | NM_004006.2:c.7817G>A | NP_003997.1:p.Trp2606Ter | Duchenne muscular dystrophy; Duchenne muscular dystrophy | C > T | nonsense | ABE | SEQ ID NO: 125 | SEQ ID NO: 444 |
| X | 32809559 | NM_004006.2:c.583C>T | NP_003997.1:p.Arg195Ter | Dilated cardiomyopathy 3B; Becker muscular dystrophy; Duchenne muscular dystrophy; not provided; Not Provided | G > A | nonsense | ABE | SEQ ID NO: 126 | SEQ ID NO: 445; SEQ ID NO: 446; SEQ ID NO: 447; SEQ ID NO: 448 |
| X | 32573786 | NM_004006.2:c.1663C>T | NP 003997.1:p.Gln555Ter | Duchenne muscular dystrophy; Duchenne muscular dystrophy | G > A | nonsense | ABE | SEQ ID NO: 127 | SEQ ID NO: 449; SEQ ID NO: 450; SEQ ID NO: 451; SEQ ID NO: 452 |
| X | 31507313 | NM_004006.2:c.8358G>A | NP_003997.1:p.Trp2786Ter | Dilated cardiomyopathy 3B; Dilated cardiomyopathy 3B | C > T | nonsense | ABE | SEQ ID NO: 128 | SEQ ID NO: 453; SEQ ID NO: 454; SEQ ID NO: 455; SEQ ID NO: 456; SEQ ID NO: 457; SEQ ID NO: 458 |
| X | 32491463 | NM_004006.2:c.2436G>A | NP_003997.1:p.Trp812Ter | Dilated cardiomyopathy 3B; Dilated cardiomyopathy 3B | C > T | nonsense | ABE | SEQ ID NO: 129 | SEQ ID NO: 459; SEQ ID NO: 460; SEQ ID NO: 461 |
| X | 31658118 | NM_004006.2:c.7899G>A | NP_003997.1:p.Trp2633Ter | not specified | C > T | nonsense | ABE | SEQ ID NO: 130 | SEQ ID NO: 462; SEQ ID NO: 463; SEQ ID NO: 464; SEQ ID NO: 465; SEQ ID NO: 466 |
| X | 32448495 | NM_004006.2:c.3747G>A | NP_003997.1:p.Trp1249Ter | Duchenne muscular dystrophy | C > T | nonsense | ABE | SEQ ID NO: 131 | SEQ ID NO: 467; SEQ ID NO: 468; SEQ ID NO: 469; SEQ ID NO: 470; SEQ ID NO: 471 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31348571 | NM_004006.2:c.9148C>T | NP_003997.1:p.Gln3050Ter | not provided; Not Provided | G>A | nonsense | ABE | SEQ ID NO: 132 | SEQ ID NO: 472; SEQ ID NO: 473; SEQ ID NO: 474; SEQ ID NO: 475 |
| X | 32485072 | NM_004006.2:c.2650C>T | NP_003997.1:p.Gln884Ter | Dilated cardiomyopathy 3B; Becker muscular dystrophy; Duchenne muscular dystrophy; not provided | G>A | nonsense | ABE | SEQ ID NO: 133 | SEQ ID NO: 476; SEQ ID NO: 477; SEQ ID NO: 478; SEQ ID NO: 479 |
| X | 32463444 | NM_004006.2:c.3427C>T | NP_003997.1:p.Gln1143Ter | Duchenne muscular dystrophy; Duchenne muscular dystrophy | G>A | nonsense | ABE | SEQ ID NO: 134 | SEQ ID NO: 480; SEQ ID NO: 481; SEQ ID NO: 482 |
| X | 32565742 | NM_004006.2:c.1952G>A | NP 003997.1:p.Trp651Ter | Duchenne muscular dystrophy; DUCHENNE MUSCULAR DYSTROPHY; Dilated cardiomyopathy 3B | C>T | nonsense | ABE | SEQ ID NO: 135 | SEQ ID NO: 483; SEQ ID NO: 484; SEQ ID NO: 485; SEQ ID NO: 486 |
| X | 31147421 | NM_004006.2:c.10651C>T | NP_003997.1p.Gln3551Ter | not provided; Not Provided | G>A | nonsense | ABE | SEQ ID NO: 136 | |
| X | 31178700 | NM_004006.2:c.10192C>T | NP_003997.1:p.Gln3398Ter | Dilated cardiomyopathy 3B; Dilated cardiomyopathy 3B | G>A | nonsense | ABE | SEQ ID NO: 137 | |
| X | 31178751 | NM_004006.2:c.10141C>T | NP_003997.1:p.Arg3381Ter | Duchenne muscular dystrophy; DUCHENNE MUSCULAR DYSTROPHY; Dilated cardiomyopathy 3B; not provided; Not Provided | G>A | nonsense | ABE | SEQ ID NO: 138 | |
| X | 31180437 | NM_004006.2:c.10019G>A | NP_003997.1:p.Cys3340Tyr | Duchenne muscular dystrophy, mental retardation, and absence of erg b-wave; DUCHENNE MUSCULAR DYSTROPHY, MENTAL RETARDATION, AND ABSENCE OF ERG B-WAVE | C>T | missense variant | ABE | SEQ ID NO: 139 | |
| X | 31182784 | NM_004006.2:c.9928C>T | NP_003997.1:p.Gln3310Ter | Duchenne muscular dystrophy | G>A | nonsense | ABE | SEQ ID NO: 140 | |
| X | 31209497 | NM_004006.2:c.9563+1G>A | | Duchenne muscular dystrophy | C>T | splice donor variant | ABE | SEQ ID NO: 141 | |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31223062 | NM_004006.2:c.9346C>T | NP_003997.1:p.Gln3116Ter | Dilated cardiomyopathy 3B; Dilated cardiomyopathy 3B | G>A | nonsense | ABE | SEQ ID NO: 142 | |
| X | 31478330 | NM_004006.2:c.8713C>T | NP_003997.1:p.Arg2905Ter | Duchenne muscular dystrophy; DUCHENNE MUSCULAR DYSTROPHY; Dilated cardiomyopathy 3B; Becker muscular dystrophy | G>A | nonsense | ABE | SEQ ID NO: 143 | |
| X | 31478995 | NM_004006.2:c.8656C>T | NP_003997.1:p.Gln2886Ter | Dilated cardiomyopathy 3B; Becker muscular dystrophy; Duchenne muscular dystrophy | G>A | nonsense | ABE | SEQ ID NO: 144 | |
| X | 31627681 | NM_004006.2:c.82.09C>T | NP_003997.1:p.Gln2737Ter | Duchenne muscular dystrophy | G>A | nonsense | ABE | SEQ ID NO: 145 | |
| X | 31679575 | NM_004006.2:c.7672C>T | NP_003997.1:p.Gln2558Ter | not provided; Duchenne muscular dystrophy | G>A | nonsense | ABE | SEQ ID NO: 146 | |
| X | 31836729 | NM_004006.2:c.7189C>T | NP_003997.1:p.Gln2.397Ter | Dilated cardiomyopathy 3B; Becker muscular dystrophy; Duchenne muscular dystrophy | G>A | 5 prime UTR variant | ABE | SEQ ID NO: 147 | |
| X | 31929718 | NM_004006.2:c.6790C>T | NP_003997.1:p.Gln2264Ter | Duchenne muscular dystrophy; DUCHENNE MUSCULAR DYSTROPHY | G>A | 5 prime UTR variant | ABE | SEQ ID NO: 148 | |
| X | 32287536 | NM_004006.2:c.6283C>T | NP_003997.1:p.Arg2095Ter | Dilated cardiomyopathy 3B; Dilated cardiomyopathy 3B | G>A | nonsense | ABE | SEQ ID NO: 149 | |
| X | 32287596 | NM_004006.2:c.6223C>T | NP_003997.1:p.Gln2075Ter | Duchenne muscular dystrophy | G>A | nonsense | ABE | SEQ ID NO: 150 | |
| X | 32287680 | NM_004006.2:c.6139C>T | NP_003997.1:p.Gln2047Ter | Elevated serum creatine phosphokinase | G>A | nonsense | ABE | SEQ ID NO: 151 | |
| X | 32287702 | NM_004006.2:c.6118−1G>A | | Duchenne muscular dystrophy | C>T | splice acceptor variant | ABE | SEQ ID NO: 152 | |
| X | 32342171 | NM_004006.2:c.5851C>T | NP_003997.1:p.Gln1951Ter | not provided; not provided | G>A | nonsense | ABE | SEQ ID NO: 153 | |
| X | 32345975 | NM_004006.2:c.5554C>T | NP_003997.1:p.Gln1852Ter | Dilated cardiomyopathy 3B; Dilated cardiomyopathy 3B | G>A | nonsense | ABE | SEQ ID NO: 154 | |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32345978 | NM_004006.2:c.5551C > T | NP_003997.1:p.Gln1851Ter | Duchenne muscular dystrophy; DUCHENNE MUSCULAR DYSTROPHY; Duchenne muscular dystrophy | G > A | nonsense | ABE | SEQ ID NO: 155 | |
| X | 32346023 | NM_004006.2:c.5506C > T | NP_003997.1:p.Gln1836Ter | Duchenne muscular dystrophy | G > A | nonsense | ABE | SEQ ID NO: 156 | |
| X | 32364602 | NM_004006.2:c.5134C > T | NP_003997.1:p.Gln1712Ter | Dilated cardiomyopathy 3B; Dilated cardiomyopathy 3B | G > A | nonsense | ABE | SEQ ID NO: 157 | |
| X | 32364605 | NM_004006.2:c.5131C > T | XP_003997.1:p.Gln1711Ter | Duchenne muscular dystrophy; Duchenne muscular dystrophy | G > A | nonsense | ABE | SEQ ID NO: 158 | |
| X | 32365175 | NM_004006.2:c.4870C > T | NP_003997.1:p.Gln1624Ter | Duchenne muscular dystrophy | G > A | nonsense | ABE | SEQ ID NO: 159 | |
| X | 32389536 | NM_004006.2:c.4483C > T | NP_003997.1:p.Gln1495Ter | Duchenne muscular dystrophy | G > A | nonsense | ABE | SEQ ID NO: 160 | |
| X | 32389644 | NM_004006.2:c.4375C > T | NP_003997.1:p.Arg1459Ter | Dilated cardiomyopathy 3B; Duchenne muscular dystrophy | G > A | nonsense | ABE | SEQ ID NO: 161 | |
| X | 32454778 | NM_004006.2:c.3487C > T | NP_003997.1:p.Gln1163Ter | not provided; Not Provided | G > A | nonsense | ABE | SEQ ID NO: 162 | |
| X | 32463438 | NM_004006.2:c.3432 + 1G > A | | Dilated cardiomyopathy 3B; Becker muscular dystrophy; Duchenne muscular dystrophy | C > T | splice donor variant | ABE | SEQ ID NO: 163 | |
| X | 32464585 | NM_004006.2:c.3276 + 1G > A | | Dilated cardiomyopathy 3B; Becker muscular dystrophy; Duchenne muscular dystrophy | C > T | splice donor variant | ABE | SEQ ID NO: 164 | |
| X | 32464603 | NM_004006.2:c.3259C > T | XP_003997.1:p.Gln1087Ter | not provided; Not Provided | G > A | nonsense | ABE | SEQ ID NO: 165 | |
| X | 32468509 | NM_004006.2:c.3151C > T | NP_003997.1:p.Arg1051Ter | Dilated cardiomyopathy 3B; Duchenne muscular dystrophy; Becker muscular dystrophy | G > A | nonsense | ABE | SEQ ID NO: 166 | |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32468704 | NM_004006.2:c.2956C > T | XP_003997.1:p.Gln986Ter | Duchenne muscular dystrophy; Becker muscular dystrophy; Dilated cardiomyopathy 3B; not provided; Not Provided | G > A | nonsense | ABE | SEQ ID NO: 167 | |
| X | 32472310 | NM_004006.2:c.2804 − 1G > A | | Dilated cardiomyopathy 3B; Becker muscular dystrophy; Duchenne muscular dystrophy | C > T | splice acceptor variant | ABE | SEQ ID NO: 168 | |
| X | 32484925 | NM_004006.2:c.2797C > T | NP_003997.1:p.Gln933Ter | Duchenne muscular dystrophy; Duchenne muscular dystrophy | G > A | nonsense | ABE | SEQ ID NO: 169 | |
| X | 32484964 | NM_004006.2:c.2758C > T | NP_003997.1:p.Gln920Ter | Dilated cardiomyopathy 3B; Dilated cardiomyopathy 3B | G > A | nonsense | ABE | SEQ ID NO: 170 | |
| X | 32491276 | NM_004006.2:c.2622 + 1G > A | | Dilated cardiomyopathy 3B; Dilated cardiomyopathy 3B | C > T | splice donor variant | ABE | SEQ ID NO: 171 | |
| X | 32491344 | NM_004006.2:c.2555G > A | NP_003997.1:p.Trp852Ter | not provided; Not Provided | C > T | nonsense | ABE | SEQ ID NO: 172 | |
| X | 32491480 | NM_004006.2:c.2419C > T | NP_003997.1:p.Gln807Ter | Dilated cardiomyopathy 3B; Becker muscular dystrophy; Duchenne muscular dystrophy | G > A | nonsense | ABE | SEQ ID NO: 173 | |
| X | 32501803 | NM_004006.2:c.2332C > T | NP_003997.1:p.Gln778Ter | Dilated cardiomyopathy 3B; Becker muscular dystrophy; Duchenne muscular dystrophy | G > A | nonsense | ABE | SEQ ID NO: 174 | |
| X | 32545158 | NM_004006.2:c.2168 + 1G > A | | not provided; Not Provided; Duchenne muscular dystrophy | C > T | splice donor variant | ABE | SEQ ID NO: 175 | |
| X | 32545190 | NM_004006.2:c.2137C > T | NP_003997.1:p.Gln713Ter | Dilated cardiomyopathy 3B; Dilated cardiomyopathy 3B | G > A | nonsense | ABE | SEQ ID NO: 176 | |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32565704 | NM_004006.2:c.1990C > T | NP_003997.1:p.Gln664Ter | Dilated cardiomyopathy 3B; Becker muscular dystrophy; Duchenne muscular dystrophy | G > A | nonsense | ABE | SEQ ID NO: 177 | |
| X | 32565782 | NM_004006.2:c.1912C > T | NP_003997.1:p.Gln638Ter | Duchenne muscular dystrophy; Becker muscular dystrophy | G > A | nonsense | ABE | SEQ ID NO: 178 | |
| X | 32573796 | NM_004006.2:c.1653G > A | NP_003997.1:p.Trp551Ter | Duchenne muscular dystrophy; not provided | C > T | nonsense | ABE | SEQ ID NO: 179 | |
| X | 32595870 | NM_004006.2:c.1489C > T | NP_003997.1:p.Gln497Ter | Duchenne muscular dystrophy; DUCHENNE MUSCULAR DYSTROPHY; Duchenne muscular dystrophy | G > A | nonsense | ABE | SEQ ID NO: 180 | |
| X | 32614320 | NM_004006.2:c.1465C > T | NP_003997.1:p.Gln489Ter | Dilated cardiomyopathy 3B; Becker muscular dystrophy; Duchenne muscular dystrophy | G > A | nonsense | ABE | SEQ ID NO: 181 | |
| X | 32614397 | NM_004006.2:c.1388G > A | NP_003997.1:p.Trp463Ter | Duchenne muscular dystrophy; Duchenne muscular dystrophy | C > T | nonsense | ABE | SEQ ID NO: 182 | |
| X | 32644131 | NM_004006.2:c.1331 + 1G > A | | Duchenne muscular dystrophy; Duchenne muscular dystrophy | C > T | splice donor variant | ABE | SEQ ID NO: 183 | |
| X | 32644139 | NM_004006.2:c.1324C > T | NP_003997.1:p.Gln442Ter | Duchenne muscular dystrophy; Duchenne muscular dystrophy | G > A | nonsense | ABE | SEQ ID NO: 184 | |
| X | 32644202 | NM_004006.2:c.1261C > T | NP_003997.1:p.Gln421Ter | Dilated cardiomyopathy 3B; Becker muscular dystrophy; Duchenne muscular dystrophy | G > A | nonsense | ABE | SEQ ID NO: 185 | |
| X | 32645020 | NM_004006.2:c.1093C > T | NP_003997.1:p.Gln365Ter | Duchenne muscular dystrophy; Becker muscular dystrophy | G > A | nonsense | ABE | SEQ ID NO: 186 | |

TABLE 5-continued

| chr | pos | hgvs_c | hgvs_p | all_traits | variants | variant type | repair editor | reference_seq | sgRNA_repair |
|---|---|---|---|---|---|---|---|---|---|
|  | 32809492 | NM_004006.2:c.649 + 1G > A |  | Dilated cardiomyopathy 3B; Becker muscular dystrophy; Duchenne muscular dystrophy | C > T | splice donor variant | ABE | SEQ ID NO: 187 |  |
| X | 32816641 | NM.004006.2:c.358 − 1G > A |  | Becker muscular dystrophy | C > T | splice acceptor variant | ABE | SEQ ID NO: 188 |  |
| X | 32823297 | NM_004006.2:c.355C > T | NP_003997.1:p.Gln119Ter | Duchenne muscular dystrophy; Duchenne muscular dystrophy | G > A | 5 prime UTR variant | ABE | SEQ ID NO: 189 |  |
| X | 32849727 | NM_004006.2:c.186 + 1G > A |  | Duchenne muscular dystrophy | C > T | splice donor variant | ABE | SEQ ID NO: 190 |  |
| X | 32849736 | NM_004006.2:c.178C > T | NP_003997.1:p.Gln60Ter | Duchenne muscular dystrophy; DUCHENNE MUSCULAR DYSTROPHY; not provided | G > A | 5 prime UTR variant | ABE | SEQ ID NO: 191 |  |
| X | 33020138 | NM_004006.2:c.93 + 1G > A |  | Becker muscular dystrophy; Duchenne muscular dystrophy | C > T | splice donor variant | ABE | SEQ ID NO: 192 |  |
| X | 32595756 | NM_004006.2:c.1602 + 1G > A |  | not provided; Not Provided | C > T | splice donor variant | ABE | SEQ ID NO: 193 | SEQ ID NO: 487 |
| X | 31206668 | NM_004006.2:c.9564 − 1G > A |  | Dilated cardiomyopathy 3B; Becker muscular dystrophy; Duchenne muscular dystrophy | C > T | splice acceptor variant | ABE | SEQ ID NO: 194 | SEQ ID NO: 488; SEQ ID NO: 489; SEQ ID NO: 490; SEQ ID NO: 491 |
| X | 32217062 | NM_004006.2:c.6292C > T | NP_003997.1:p.Arg2098Ter | Duchenne muscular dystrophy; DUCHENNE MUSCULAR DYSTROPHY; Dilated cardiomyopathy 3B | G > A | nonsense | ABE | SEQ ID NO: 195 | SEQ ID NO: 492 |
| X | 32644314 | NM_004006.2:c.1150 − 1G > A |  | Duchenne muscular dystrophy; not provided; Not Provided | C > T | splice acceptor variant | ABE | SEQ ID NO: 196 | SEQ ID NO: 493; SEQ ID NO: 494; SEQ ID NO: 495 |
| X | 32849821 | NM_004006.2:c.94 − 1G > A |  | Duchenne muscular dystrophy; Duchenne muscular dystrophy | C > T | splice acceptor variant | ABE | SEQ ID NO: 197 | SEQ ID NO: 496 |
| X | 31496871 | NM_004006.2:c.8464C > T | NP_003997.1:p.Gln2822Ter | Dilated cardiomyopathy 3B; Dilated cardiomyopathy 3B | G > A | nonsense | ABE | SEQ ID NO: 198 | SEQ ID NO: 497; SEQ ID NO: 498; SEQ ID NO: 499 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32380626 | NM_004006.2:c.4729C>T | NP_003997.1:p.Arg1577Ter | Duchenne muscular dystrophy; not provided; Not Provided | G>A | nonsense | ABE | SEQ ID NO: 199 | SEQ ID NO: 500; SEQ ID NO: 501 |
| X | 32645052 | NM_004006.2:c.1061G>A | NP_003997.1:p.Trp354Ter | Duchenne muscular dystrophy | C>T | nonsense | ABE | SEQ ID NO: 200 | SEQ ID NO: 502; SEQ ID NO: 503; SEQ ID NO: 504; SEQ ID NO: 505 |
| X | 32491414 | NM_004006.2:c.2485C>T | NP_003997.1:p.Gln829Ter | not specified | G>A | nonsense | ABE | SEQ ID NO: 201 | SEQ ID NO: 506; SEQ ID NO: 507; SEQ ID NO: 508; SEQ ID NO: 509; SEQ ID NO: 510 |
| X | 31169519 | NM_004020.3:c.2843+9150C>T | NP_003997.1:p.Gln3493Ter | Duchenne muscular dystrophy; Becker muscular dystrophy | G>A | intron variant | ABE | SEQ ID NO: 202 | SEQ ID NO: 511; SEQ ID NO: 512; SEQ ID NO: 513; SEQ ID NO: 514 |
| X | 32364704 | NM_004006.2:c.5032C>T | NP_003997.1:p.Gln1678Ter | Duchenne muscular dystrophy | G>A | nonsense | ABE | SEQ ID NO: 203 | SEQ ID NO: 515; SEQ ID NO: 516 |
| X | 32545295 | NM_004006.2:c.2032C>T | NP_003997.1:p.Gln678Ter | Dilated cardiomyopathy 3B; Becker muscular dystrophy; Duchenne muscular dystrophy | G>A | nonsense | ABE | SEQ ID NO: 204 | SEQ ID NO: 517; SEQ ID NO: 518; SEQ ID NO: 519; SEQ ID NO: 520; SEQ ID NO: 521; SEQ ID NO: 522; SEQ ID NO: 523 |
| X | 31178784 | NM.004006.2:c.10108C>T | NP_003997.1:p.Arg3370Ter | Duchenne muscular dystrophy; DUCHENNE MUSCULAR DYSTROPHY; Dilated cardiomyopathy 3B; Becker muscular dystrophy | G>A | nonsense | ABE | SEQ ID NO: 205 | SEQ ID NO: 524; SEQ ID NO: 525; SEQ ID NO: 526; SEQ ID NO: 527 |
| X | 32342123 | NM_004006.2:c.5899C>T | NP_003997.1:p.Arg1967Ter | Duchenne muscular dystrophy; DUCHENNE MUSCULAR DYSTROPHY; Dilated cardiomyopathy 3B; Becker muscular dystrophy | G>A | nonsense | ABE | SEQ ID NO: 206 | SEQ ID NO: 528; SEQ ID NO: 529 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 31729736 | NM_004006.2:c.7555G > A | NP_003997.1:p.Asp2519Asn | not provided; Not Provided; Duchenne muscular dystrophy | C > T | missense variant | ABE | SEQ ID NO: 207 | SEQ ID NO: 530; SEQ ID NO: 531; SEQ ID NO: 532 |
| X | 33174335 | NM_004006.2:c.31 + 36947G > A | | Duchenne muscular dystrophy; Becker muscular dystrophy; Dilated cardiomyopathy 3B | C > T | intron variant | ABE | SEQ ID NO: 208 | SEQ ID NO: 533; SEQ ID NO: 534 |
| X | 32472247 | NM_004006.2:c.2866C > T | NP_003997.1:p.Gln956Ter | Dilated cardiomyopathy 3B; Dilated cardiomyopathy 3B | G > A | nonsense | ABE | SEQ ID NO: 209 | SEQ ID NO: 535; SEQ ID NO: 536; SEQ ID NO: 537; SEQ ID NO: 538 |
| X | 32389496 | NM_004006.2:c.4518 + 5G > A | | Dilated cardiomyopathy 3B; Duchenne muscular dystrophy | C > T | intron variant | ABE | SEQ ID NO: 210 | SEQ ID NO: 539; SEQ ID NO: 540; SEQ ID NO: 541 |
| X | 32438372 | NM_004006.2:c.3940C > T | NP_003997.1:p.Arg1314Ter | Becker muscular dystrophy; BECKER MUSCULAR DYSTROPHY; not provided; Not Provided; Duchenne muscular dystrophy | G > A | nonsense | ABE | SEQ ID NO: 211 | SEQ ID NO: 542; SEQ ID NO: 543 |
| X | 31206663 | NM_004006.2:c.9568C > T | NP_003997.1:p.Arg3190Ter | Duchenne muscular dystrophy; DUCHENNE MUSCULAR DYSTROPHY; Dilated cardiomyopathy 3B; Becker muscular dystrophy | G > A | nonsense | ABE | SEQ ID NO: 212 | SEQ ID NO: 544; SEQ ID NO: 545; SEQ ID NO: 546; SEQ ID NO: 547 |
| X | 31729634 | NM_004006.2:c.7657C > T | NP_003997.1:p.Arg2553Ter | Dilated cardiomyopathy 3B; Becker muscular dystrophy; Duchenne muscular dystrophy | G > A | nonsense | ABE | SEQ ID NO: 213 | SEQ ID NO: 548 |
| X | 31507280 | NM_004006.2:c.8390 + 1G > A | | not provided; Not Provided | C > T | splice donor variant | ABE | SEQ ID NO: 214 | SEQ ID NO: 549; SEQ ID NO: 550; SEQ ID NO: 551; SEQ ID NO: 552 |

TABLE 5-continued

| chr | pos | hgvs_c | hgvs_p | all_traits | variants | variant type | repair editor | reference_seq | sgRNA_repair |
|---|---|---|---|---|---|---|---|---|---|
| X | 32823316 | NM_004006.2:c.336G > A | NP_003997.1:p.Trp112Ter | Dilated cardiomyopathy 3B; Becker muscular dystrophy; Duchenne muscular dystrophy | C > T | 5 prime UTR variant | ABE | SEQ ID NO: 215 | SEQ ID NO: 553; SEQ ID NO: 554; SEQ ID NO: 555 |
| X | 32816565 | NM_004006.2:c.433C > T | NP_003997.1:p.Arg145Ter | Duchenne muscular dystrophy; DUCHENNE MUSCULAR DYSTROPHY; Dilated cardiomyopathy 3B; not provided; Not Provided; Becker muscular dystrophy | G > A | nonsense | ABE | SEQ ID NO: 216 | SEQ ID NO: 556; SEQ ID NO: 557; SEQ ID NO: 558; SEQ ID NO: 559 |
| X | 32463576 | NM_004006.2:c.3295C > T | NP_003997.1:p.Gln1099Ter | Dilated cardiomyopathy 3B; Becker muscular dystrophy; Duchenne muscular dystrophy | G > A | nonsense | ABE | SEQ ID NO: 217 | SEQ ID NO: 560; SEQ ID NO: 561 |
| X | 32844794 | NM_004006.2:c.253C > T | NP_003997.1:p.Gln85Ter | Duchenne muscular dystrophy; DUCHENNE MUSCULAR DYSTROPHY | G > A | 5 prime UTR variant | ABE | SEQ ID NO: 218 | SEQ ID NO: 562 |
| X | 32468539 | NM_004006.2:c.312C > T | NP_003997.1:p.Gln1041Ter | Duchenne muscular dystrophy; DUCHENNE MUSCULAR DYSTROPHY; Dilated cardiomyopathy 3B | G > A | nonsense | ABE | SEQ ID NO: 219 | SEQ ID NO: 563; SEQ ID NO: 564; SEQ ID NO: 565; SEQ ID NO: 566 |
| X | 32390103 | NM_004006.2:c.4312C > T | NP_003997.1:p.Gln1438Ter | Duchenne muscular dystrophy | G > A | nonsense | ABE | SEQ ID NO: 220 | SEQ ID NO: 567; SEQ ID NO: 568 |
| X | 32342264 | NM_004006.2:c.575C > T | NP_003997.1:p.Gln1920Ter | not provided; Not Provided | G > A | nonsense | ABE | SEQ ID NO: 221 | SEQ ID NO: 569 |

SEQUENCES

```
SEQ ID NO: 1 (pCMV-ABEmaxNG)
ATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGT
ATTAGTCATCGCTATTACCATGGTGATGCGGTTTTGGCAGTACATCAATGGGCGTGG
ATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCC
ATTGACGCAAATGGGCGGTAGGCGTGTACGGTGGGAGGTCTATATAAGCAGAGCTG
GTTTAGTGAACCGTCAGATCCGCTAGAGATCGCGGCCGCTAATACGACTCACTAT
AGGGAGAGCCGCCACCATGAAACGGACAGCCGACGGAAGCGAGTTCGAGTCACCA
AAGAAGAAGCGGAAAGTCTCTGAAGTCGAGTTTAGCCACGAGTATTGGATGAGGCA
CGCACTGACCCTGGCAAAGCGAGCATGGGATGAAAGAGAAGTCCCCGTGGGCGCC
GTGCTGGTGCACAACAATAGAGTGATCGGAGAGGGATGGAACAGGCCAATCGGCC
GCCACGACCCTACCGCACACGCAGAGATCATGGCACTGAGGCAGGGAGGCCTGGTC
ATGCAGAATTACCGCCTGATCGATGCCACCCTGTATGTGACACTGGAGCCATGCGT
GATGTGCGCAGGAGCAATGATCCACAGCAGGATCGGAAGAGTGGTGTTCGGAGCA
```

| SEQUENCES |
|---|
| CGGGACGCCAAGACCGGCGCAGCAGGCTCCCTGATGGATGTGCTGCACCACCCCGG |
| CATGAACCACCGGGTGGAGATCACAGAGGGAATCCTGGCAGACGAGTGCGCCGCC |
| CTGCTGAGCGATTTCTTTAGAATGCGGAGACAGGAGATCAAGGCCCAGAAGAAGGC |
| ACAGAGCTCCACCGACTCTGGAGGATCTAGCGGAGGATCCTCTGGAAGCGAGACAC |
| CAGGCACAAGCGAGTCCGCCACACCAGAGAGCTCCGGCGGCTCCTCCGGAGGATCC |
| TCTGAGGTGGAGTTTTCCCACGAGTACTGGATGAGACATGCCCTGACCCTGGCCAA |
| GAGGGCACGCGATGAGAGGGAGGTGCCTGTGGGAGCCGTGCTGGTGCTGAACAAT |
| AGAGTGATCGGCGAGGGCTGGAACAGAGCCATCGGCCTGCACGACCCAACAGCCC |
| ATGCCGAATTATGGCCCTGAGACAGGGCGGCCTGGTCATGCAGAACTACAGACTG |
| ATTGACGCCACCCTGTACGTGACATTCGAGCCTTGCGTGATGTGCGCCGGCGCCATG |
| ATCCACTCTAGGATCGGCCGCGTGGTGTTTGGCGTGAGGAACGCAAAAACCGGCGC |
| CGCAGGCTCCCTGATGGACGTGCTGCACTACCCCGGCATGAATCACCGCGTCGAAA |
| TTACCGAGGGAATCCTGGCAGATGAATGTGCCGCCCTGCTGTGCTATTTCTTTCGGA |
| TGCCTAGACAGGTGTTCAATGCTCAGAAGAAGGCCCAGAGCTCCACCGACTCCGGA |
| GGATCTAGCGGAGGCTCCTCTGGCTCTGAGACACCTGGCACAAGCGGAGGCGCAAC |
| ACCTGAAAGCAGCGGGGGCAGCAGCGGGGGGTCAGACAAGAAGTACAGCATCGGC |
| CTGGCCATCGGCACCAACTCTGTGGGCTGGGCCGTGATCACCGACGAGTACAAGGT |
| GCCCAGCAAGAAATTCAAGGTGCTGGGCAACACCGACCGGCACAGCATCAAGAAG |
| AACCTGATCGGAGCCCTGCTGTTCGACAGCGGCGAAACAGCCGAGGCCACCCGGCT |
| GAAGAGAACCGCCAGAAGAAGATACACCAGACGGAAGAACCGGATCTGCTATCTG |
| CAAGAGATCTTCAGCAACGAGATGGCCAAGGTGGACGACAGCTTCTTCCACAGACT |
| GGAAGAGTCCTTCCTGGTGGAAGAGGATAAGAAGCACGAGCGGCACCCCATCTTCG |
| GCAACATCGTGGACGAGGTGGCCTACCACGAGAAGTACCCCACCATCTACCACCTG |
| AGAAAGAAACTGGTGGACAGCACCGACAAGGCCGACCTGCGCCTGATCTATCTGGC |
| CCTGGCCCACATGATCAAGTTCCGGGGCCACTTCCTGATCGAGGGCGACCTGAACC |
| CCGACAACAGCGACGTGGACAAGCTGTTCATCCAGCTGGTGCAGACCTACAACCAG |
| CTGTTCGAGGAAAACCCCATCAACGCCAGCGGCGTGGACGCCAAGGCCATCCTGTC |
| TGCCAGACTGAGCAAGAGCAGACGGCTGGAAAATCTGATCGCCCAGCTGCCCGGCG |
| AGAAGAAGAATGGCCTGTTCGGAAACCTGATTGCCCTGAGCCTGGGCCTGACCCCC |
| AACTTCAAGAGCAACTTCGACCTGGCCGAGGATGCCAAACTGCAGCTGAGCAAGGA |
| CACCTACGACGACGACCTGGACAACCTGCTGGCCCAGATCGGCGACCAGTACGCCG |
| ACCTGTTTCTGGCCGCCAAGAACCTGTCCGACGCCATCCTGCTGAGCGACATCCTGA |
| GAGTGAACACCGAGATCACCAAGGCCCCCCTGAGCGCCTCTATGATCAAGAGATAC |
| GACGAGCACCACCAGGACCTGACCCTGCTGAAAGCTCTCGTGCGGCAGCAGCTGCC |
| TGAGAAGTACAAAGAGATTTTCTTCGACCAGAGCAAGAACGGCTACGCCGGCTACA |
| TTGACGGCGGAGCCAGCCAGGAAGAGTTCTACAAGTTCATCAAGCCCATCCTGGAA |
| AAGATGGACGGCACCGAGGAACTGCTCGTGAAGCTGAACAGAGAGGACCTGCTGC |
| GGAAGCAGCGGACCTTCGACAACGGCAGCATCCCCCACCAGATCCACCTGGGAGAG |
| CTGCACGCCATTCTGCGGCGGCAGGAAGATTTTTACCCATTCCTGAAGGACAACCG |
| GGAAAAGATCGAGAAGATCCTGACCTTCCGCATCCCCTACTACGTGGGGCCCTCTGG |
| CCAGGGGAAACAGCAGATTCGCCTGGATGACCAGAAAGAGCGAGGAAACCATCAC |
| CCCCTGGAACTTCGAGGAAGTGGTGGACAAGGGCGCTTCCGCCCAGAGCTTCATCG |
| AGCGGATGACCAACTTCGATAAGAACCTGCCCAACGAGAAGGTGCTGCCCAAGCAC |
| AGCCTGCTGTACAGTACTTCACCGTGTATAACGAGCTGACCAAAGTGAAATACGT |
| GACCGAGGGAATGAGAAAGCCCGCCTTCCTGAGCGGCGAGCAGAAAAAGGCCATC |
| GTGGACCTGCTGTTCAAGACCAACCGGAAAGTGACCGTGAAGCAGCTGAAAGAGG |
| ACTACTTCAAGAAAATCGAGTGCTTCGACTCCGTGGAAATCTCCGGCGTGGAAGAT |
| CGGTTCAACGCCTCCCTGGGCACATACCACGATCTGCTGAAAATTATCAAGGACAA |
| GGACTTCCTGGACAATGAGGAAAACGAGGACATTCTGGAAGATATCGTGCTGACCC |
| TGACACTGTTTGAGGACAGAGAGATGATCGAGGAACGGCTGAAAACCTATGCCCAC |
| CTGTTCGACGACAAAGTGATGAAGCAGCTGAAGCGGCGGAGATACACCGGCTGGG |
| GCAGGCTGAGCCGGAAGCTGATCAACGGCATCCGGGACAAGCAGTCCGGCAAGAC |
| AATCCTGGATTTCCTGAAGTCCGACGGCTTCGCCAACAGAAACTTCATGCAGCTGAT |
| CCACGACGACAGCCTGACCTTTAAAGAGGACATCCAGAAAGCCCAGGTGTCCGGCC |
| AGGGCGATAGCCTGCACGAGCACATTGCCAATCTGGCCGGCAGCCCCGCCATTAAG |
| AAGGGCATCCTGCAGACAGTGAAGGTGGTGGACGAGCTCGTGAAAGTGATGGGCC |
| GGCACAAGCCCGAGAACATCGTGATCGAAATGGCCAGAGAGAACCAGACCACCCA |
| GAAGGGACAGAAGAACAGCCGCGAGAGAATGAAGCGGATCGAAGAGGGCATCAA |
| AGAGCTGGGCAGCCAGATCCTGAAAGAACACCCCGTGGAAAACACCCAGCTGCAG |
| AACGAGAAGCTGTACCTGTACTACCTGCAGAATGGGCGGGATATGTACGTGGACCA |
| GGAACTGGACATCAACCGGCTGTCCGACTACGATGTGGACCATATCGTGCCTCAGA |
| GCTTTCTGAAGGACGACTCCATCGACAACAAGGTGCTGACCAGAAGCGACAAGAAC |
| CGGGGCAAGAGCGACAACGTGCCCTCCGAAGAGGTCGTGAAGAAGATGAAGAACT |
| ACTGGCGGCAGCTGCTGAACGCCAAGCTGATTACCCAGAGAAAGTTCGACAATCTG |
| ACCAAGGCCGAGAGAGGCGGCCTGAGCGAACTGGATAAGGCCGGCTTCATCAAGA |
| GACAGCTGGTGAAACCCGGCAGATCACAAAGCACGTGGCACAGATCCTGGACTCC |
| CGGATGAACACTAAGTACGACGAGAATGACAAGCTGATCCGGGAAGTGAAAGTGA |
| TCACCCTGAAGTCCAAGCTGGTGTCCGATTTCCGGAAGGATTTCCAGTTTTACAAAG |
| TGCGCGAGATCAACAACTACCACCACGCCCACGACGCCTACCTGAACGCCGTCGTG |
| GGAACCGCCCTGATCAAAAAGTACCCTAAGCTGGAAAGCGAGTTCGTGTACGGCGA |
| CTACAAGGTGTACGACGTGCGGAAGATGATCGCCAAGAGCGAGCAGGAAATCGGC |
| AAGGCTACCGCCAAGTACTTCTTCTACAGCAACATCATGAACTTTTTCAAGACCGAG |
| ATTACCCTGGCCAACGGCGAGATCCGGAAGCGGCCTCTGATCGAGACAAACGGCGA |
| AACCGGGGAGATCGTGTGGGATAAGGGCCGGGATTTTGCCACCGTGCGGAAAGTGC |
| TGAGCATGCCCCAAGTGAATATCGTGAAAAAGACCGAGGTGCAGACAGGCGGCTTC |
| AGCAAAGAGTCTATCCgGCCCAAGAGGAACAGCGATAAGCTGATCGCCAGAAAGA |
| AGGACTGGGACCCTAAGAAGTACGGCGGCTTCGLtCAGCCCCACCGTGGCCTATTCTG |

| SEQUENCES |
|---|
| TGCTGGTGGTGGCCAAAGTGGAAAAGGGCAAGTCCAAGAAACTGAAGAGTGTGAA
AGAGCTGCTGGGGATCACCATCATGGAAAGAAGCAGCTTCGAGAAGAATCCCATCG
ACTTTCTGGAAGCCAAGGGCTACAAAGAAGTGAAAAAGGACCTGATCATCAAGCTG
CCTAAGTACTCCCTGTTCGAGCTGGAAAACGGCCGGAAGAGAATGCTGGCCTCTGC
CcGCtttCTGCAGAAGGGAAACGAACTGGCCCTGCCCTCCAAATATGTGAACTTCCTG
TACCTGGCCAGCCACTATGAGAAGCTGAAGGGCTCCCCCGAGGATAATGAGCAGAA
ACAGCTGTTTGTGGAACAGCACAAGCACTACCTGGACGAGATCATCGAGCAGATCA
GCGAGTTCTCCAAGAGAGTGATCCTGGCCGACGCTAATCTGGACAAAGTGCTGTCC
GCCTACAACAAGCACCGGGATAAGCCCATCAGAGAGCAGGCCGAGAATATCATCC
ACCTGTTTACCCTGACCAATCTGGGAGCCCCTCggGCCTTCAAGTACTTTGACACCAC
CATCGACCGGAAGgtGTACcggAGCACCAAAGAGGTGCTGGACGCCACCCTGATCCA
CCAGAGCATCACCGGCCTGTACGAGACACGGATCGACCTGTCTCAGCTGGGAGGTG
ACTCTGGCGGCTCAAAAAGAACCGCCGACGGCAGCGAATTCGAGCCCAAGAAGAA
GAGGAAAGTCTAACCGGTCATCATCACCATCACCATTGAGTTTAAACCCGCTGATC
AGCCTCGACTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGA
CAGCAAGGGGGAGGATTGGGAAGACAATAGCAGGCATGCTGGGGATGCGGTGGGC
TCTATGGCTTCTGAGGCGGAAAGAACCAGCTGGGGCTCGATACCGTCGACCTCTAG
CTAGAGCTTGGCGTAATCATGGTCATAGCTGTTTCCTGTGTGAAATTGTTATCCGCT
CACAATTCCACACAACATACGAGCCGGAAGCATAAAGTGTAAAGCCTAGGGTGCCT
AATGAGTGAGCTAACTCACATTAATTGCGTTGCGCTCACTGCCCGCTTTCCAGTCGG
GAAACCTGTCGTGCCAGCTGCATTAATGAATCGGCCAACGCGCGGGGAGAGGCGGT
TTGCGTATTGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCCACAGAA
TCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAGC
ATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGA
GTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAAC
TACGGCTACACTAGAAGAACAGTATTTGGTATCTGCGCTCTGCTGAAGCCAGTTACC
TTCGGAAAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTCAAGAAG
ATCCTTTGATCTTTTCTACGGGGTCTGACACTCAGTGGAACGAAAACTCACGTTAAG
GGATTTTGGTCATGAGATTATCAAAAAGGATCTTCACCTAGATCCTTTTAAATTAAA
AATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAA
GTTGGCCGCAGTGTTATCACTCATGGTTATGGCAGCACTGCATAATTCTCTTACTGT
CATGCCATCCGTAAGATGCTTTTCTGTGACTGGTGAGTACTCAACCAAGTCATTCTG
AGAATAGTGTATGCGGCGACCGAGTTGCTCTTGCCCGGCGTCAATACGGGATAATA
CCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAA
TACTCATACTCTTCCTTTTTCAATATTATTGAAGCATTTATCAGGGTTATTGTCTCAT
GAGCGGATACATATTTGAATGTATTTAGAAAAATAAACAAATAGGGGTTCCGCGCA
CATTTCCCCGAAAAGTGCCACCTGACGTCGACGGATCGGGAGATCGATCTCCCGAT
CCCCTAGGGTCGACTCTCAGTACAATCTGCTCTGATGCCGCATAGTTAAGCCAGTAT
CTGCTCCCTGCTTGTGTGTTGGAGGTCGCTGAGTAGTGCGCGAGCAAAATTTAAGCT
ACAACAAGGCAAGGCTTGACCGACAATTGCATGAAGAATCTGCTTAGGGTTAGGCG
TTTTGCGCTGCTTCGCGATGTACGGGCCAGATATACGCGTTGACATTGATTATTGAC
TAGTTATTAATAGTAATCAATTACGGGGTCATTAGTTCATAGCCCATATATGGAGTT
CCGCGTTACATAACTTACGGTAAATGGCCCGCCTGGCTGACCGCCCAACGACCCCC
GCCCATTGACGTCAATAATGACGTATGTTCCCATAGTAACGCCAATAGGGACTTTCC
ATTGACGTCAATGGGTGGAGTATTTACGGTAAACTGCCCACTTGGCAGTACATCAA
GTGTATC |

SEQ ID NO: 2 (pCMV-ABEmaxNG)
ATATGCCAAGTACGCCCCCTATTGACGTCAATGACGGTAAATGGCCCGCCTG
GCATTATGCCCAGTACATGACCTTATGGGACTTTCCTACTTGGCAGTACATCTACGT
ATTAGTCATCGCTATTACCATGGTGATGCGGTTTTGGCAGTACATCAATGGGCGTGG
ATAGCGGTTTGACTCACGGGGATTTCCAAGTCTCCACCCCATTGACGTCAATGGGAG
TTTGTTTTGGCACCAAAATCAACGGGACTTTCCAAAATGTCGTAACAACTCCGCCCC
ATTGACGCAAATGGGCGGTAGGCGTGTACGGTGGGAGGTCTATATAAGCAGAGCTG
GTTTAGTGAACCGTCAGATCCGCTAGAGATCCGCGGCCGCTAATACGACTCACTAT
AGGGAGAGCCGccaccatggctagcATGAAACGGACAGCCGACGGAAGCGAGTTCGAGTC

| SEQUENCES |
|---|
| ACCAAAGAAGAAGCGGAAAGTCGGATCCTCTGAGGTGGAGTTTTCCCACGAGTACT |
| GGATGAGACATGCCCTGACCCTGGCCAAGAGGGCACGCGATGAGAGGGAGGTGCC |
| TGTGGGAGCCGTGCTGGTGCTGAACAATAGAGTGATCGGCGAGGGCTGGAACAGA |
| GCCATCGGCCTGCACGACCCAACAGgCCATGCCGAAATTATGGCCCTGAGgCAGGG |
| CGGCCTGGTCATGCAGAACTACAGACTGATTGACGCCACCCTGTACGgACATTCGA |
| GCCTTGCGTGATGTGCGCCGGCGCCATGATCCACTCTAGGATCGGCCGCGTGGTGTT |
| TGGCGTGAGGAACGCAAAAACCGGCGCCGCAGGCTCCCTGATGGACGTGCTGCACT |
| ACCCCGGCATGAATCACCGCGTCGAAATTACCGAGGGAATCCTGGCAGATGAATGT |
| GCCGCCCTGCTGTGCTATTTCTTTCGGATGCCTAGACAGGTGTTCAATGCTCAGAAG |
| AAGGGCCCAGAGCTCCACCGACTCCGGAGGATCTAGCGGAGGCTCCTCTGGCTCTGA |
| GACACCTGGCACAAGCGAGAGCGCAACACCTGAAAGCAGCGGGGGCAGCAGCGGG |
| GGGTCAGACAAGAAGTACAGCATCGGCCTGGCCATCGGCACCAACTCTGTGGGCTG |
| GGCCGTGATCACCGACGAGTACAAGGTGCCCAGCAAGAAATTCAAGGTGCTGGGCA |
| ACACCGACCGGCACAGCATCAAGAAGAACCTGATCGGAGCCCTGCTGTTCGACAGC |
| GGCGAAACAGCCGAGGCCACCCGGCTGAAGAGAACCGCCAGAAGAAGATACACCA |
| GACGGAAGAACCGGATCTGCTATCTGCAAGAGATCTTCAGCAACGAGATGGCCAAG |
| GTGGACGACAGCTTCTTCCACAGACTGGAAGAGTCCTTCCTGGTGGAAGAGGATAA |
| GAAGCACGAGCGGCACCCCATCTTCGGCAACATCGTGGACGAGGTGGCCTACCACG |
| AGAAGTACCCCACCATCTACCACCTGAGAAAGAAACTGGTGGACAGCACCGACAA |
| GGCCGACCTGCGGCTGATCTATCTGGCCCTGGCCCACATGATCAAGTTCCGGGGCC |
| ACTTCCTGATCGAGGGCGACCTGAACCCCGACAACAGCGACGTGGACAAGCTGTTC |
| ATCCAGCTGGTGCAGACCTACAACCAGCTGTTCGAGGAAAACCCCATCAACGCCAG |
| CGGCGTGGACGCCAAGGCCATCCTGTCTGCCAGACTGAGCAAGAGCAGACGGCTGG |
| AAAATCTGATCGCCCAGCTGCCCGGCGAGAAGAAGAATGGCCTGTTCGGAAACCTG |
| ATTGCCCTGAGCCTGGGCCTGACCCCCAACTTCAAGAGCAACTTCGACCTGGCCGA |
| GGATGCCAAACTGCAGCTGAGCAAGGACACCTACGACGACGACCTGGACAACCTGC |
| TGGCCCAGATCGGCGACCAGTACGCCGACCTGTTTCTGGCCGCCAAGAACCTGTCC |
| GACGCCATCCTGCTGAGCGACATCCTGAGAGTGAACACCGAGATCACCAAGGCCCC |
| CCTGAGCGCCTCTATGATCAAGAGATACGACGAGCACCACCAGGACCTGACCCTGC |
| TGAAAGCTCTCGTGCGGCAGCAGCTGCCTGAGAAGTACAAAGAGATTTTCTTCGAC |
| CAGAGCAAGAACGGCTACGCCGGCTACATTGACGGCGGAGCCAGCCAGGAAGAGT |
| TCTACAAGTTCATCAAGCCCATCCTGGAAAAGATGGACGGCACCGAGGAACTGCTC |
| GTGAAGCTGAACAGAGAGGACCTGCTGCGGAAGCAGCGGACCTTCGACAACGGCA |
| GCATCCCCCACCAGATCCACCTGGGAGAGCTGCACGCCATTCTGCGGCGGCAGGAA |
| GATTTTTACCCATTCCTGAAGGACAACCGGGAAAAGATCGAGAAGATCCTGACCTT |
| CCGCATCCCCTACTACGTGGGCCCTCTGGCCAGGGGAAACAGCAGATTCGCCTGGA |
| TGACCAGAAAGAGCGAGGAAACCATCACCCCCTGGAACTTCGAGGAAGTGGTGGA |
| CAAGGGCGCTTCCGCCCAGAGCTTCATCGAGCGGATGACCAACTTCGATAAGAACC |
| TGCCCAACGAGAAGGTGCTGCCCAAGCACAGCCTGCTGTACGAGTACTTCACCGTG |
| TATAACGAGCTGACCAAAGTGAAATACGTGACCGAGGGAATGAGAAAGCCCGCCTT |
| CCTGAGCGGCGAGCAGAAAAAGGCCATCGTGGACCTGCTGTTCAAGACCAACCGGA |
| AAGTGACCGTGAAGCAGCTGAAAGAGGACTACTTCAAGAAAATCGAGTGCTTCGAC |
| TCCGTGGAAATCTCCGGCGTGGAAGATCGGTTCAACGCCTCCCTGGGCACATACCA |
| CGATCTGCTGAAAATTATCAAGGACAAGGACTTCCTGGACAATGAGGAAAACGAGG |
| ACATTCTGGAAGATATCGTGCTGACCCTGACACTGTTTGAGGACAGAGAGATGATC |
| GAGGAACGGCTGAAAACCTATGCCCACCTGTTCGACGACAAAGTGATGAAGCAGCT |
| GAAGCGGCGGAGATACACCGGCTGGGGCAGGCTGAGCCGGAAGCTGATCAACGGC |
| ATCCGGGACAAGCAGTCCGGCAAGACAATCCTGGATTTCCTGAAGTCCGACGGCTT |
| CGCCAACAGAAACTTCATGCAGCTGATCCACGACGACAGCCTGACCTTTAAAGAGG |
| ACATCCAGAAAGCCCAGGTGTCCGGCCAGGGCGATAGCCTGCACGAGCACATTGCC |
| AATCTGGCCGGCAGCCCCGCCATTAAGAAGGGCATCCTGCAGACAGTGAAGGTGGT |
| GGACGAGCTCGTGAAAGTGATGGGCCGGCACAAGCCCGAGAACATCGTGATCGAA |
| ATGGCCAGAGAGAACCAGACCACCCAGAAGGGACAGAAGAACAGCCGCGAGAGA |
| ATGAAGCGGATCGAAGAGGGCATCAAAGAGCTGGGCAGCCAGATCCTGAAAGAAC |
| ACCCCGTGGAAAACACCCAGCTGCAGAACGAGAAGCTGTACCTGTACTACCTGCAG |
| AATGGGCGGGATATGTACGTGGACCAGGAACTGGACATCAACCGGCTGTCCGACTA |
| CGATGTGGACCATATCGTGCCTCAGAGCTTTCTGAAGGACGACTCCATCGACAACA |
| AGGTGCTGACCAGAAGCGACAAGAACCGGGGCAAGAGCGACAACGTGCCCTCCGA |
| AGAGGTCGTGAAGAAGATGAAGAACTACTGGCGGCAGCTGCTGAACGCCAAGCTG |
| ATTACCCAGAGAAAGTTCGACAATCTGACCAAGGCCGAGAGAGGCGGCCTGAGCG |
| AACTGGATAAGGCCGGCTTCATCAAGAGACAGCTGGTGGAAACCCGGCAGATCACA |
| AAGCACGTGGCACAGATCCTGGACTCCCGGATGAACACTAAGTACGACGAGAATGA |
| CAAGCTGATCCGGGAAGTGAAAGTGATCACCCTGAAGTCCAAGCTGGTGTCCGATT |
| TCCGGAAGGATTTCCAGTTTTACAAAGTGCGCGAGATCAACAACTACCACCACGCC |
| CACGACGCCTACCTGAACGCCGTCGTGGGAACCGCCCTGATCAAAAAGTACCCTAA |
| GCTGGAAAGCGAGTTCGTGTACGGCGACTACAAGGTGTACGACGTGCGGAAGATGA |
| TCGCCAAGAGCGAGCAGGAAATCGGCAAGGCTACCGCCAAGTACTTCTTCTACAGC |
| AACATCATGAACTTTTTCAAGACCGAGATTACCCTGGCCAACGGCGAGATCCGGAA |
| GCGGCCTCTGATCGAGACAAACGGCGAAACCGGGGAGATCGTGTGGGATAAGGGC |
| CGGGATTTTGCCACCGTGCGGAAAGTGCTGAGCATGCCCCAAGTGAATATCGTGAA |
| AAAGACCGAGGTGCAGACAGGCGGCTTCAGCAAAGAGTCTATCCgCCCAAGAGGA |
| ACAGCGATAAGCTGATCGCACGAAAGAAGGACTGGGACCCTAAGAAGTACGGCGG |
| CTTCGtCAGCCCCACCGTGGCCTATTCTGTGCTGGTGGTGGCCAAAGTGGAAAAGGG |
| CAAGTCCAAGAAACTGAAGAGTGTGAAAGAGCTGCTGGGGATCACCATCATGGAA |
| AGAAGCAGCTTCGAAGAATCCCATCGACTTTCTGGAAGCCAAGGGCTACAAAGA |
| AGTGAAAAAGGACCTGATCATCAAGCTGCCTAAGTACTCCCTGTTCGAGCTGGAAA |
| ACGGCCGGAAGAGAATGCTGGCCTCTGCCcGCtttCTGCAGAAGGGAAACGAACTGGC |

| SEQUENCES |
|---|
| CCTGCCCTCCAAATATGTGAACTTCCTGTACCTGGCCAGCCACTATGAAGAAGCTGAA |
| GGGCTCCCCCGAGGATAATGAGCAGAAACAGCTGTTTGTGGAACAGCACAAGCACT |
| ACCTGGACGAGATCATCGAGCAGATCAGCGAGTTCTCCAAGAGAGTGATCCTGGCC |
| GACGCTAATCTGGACAAAGTGCTGTCCGCCTACAACAAGCACCGGGATAAGCCCAT |
| CAGAGAGCAGGCCGAGAATATCATCCACCTGTTTACCCTGACCAATCTGGGAGCCC |
| CTcggGCCTTCAAGTACTTTGACACCACCATCGACCGGAAGgtGTACcggAGCACCAAA |
| GAGGTGCTGGACGCCACCCTGATCCACCAGAGCATCACCGGCCTGTACGAGACACG |
| GATCGACCTGTCTCAGCTGGGAGGTGACTCTGGCGGCTCAAAAAGAACCGCCGACG |
| GCAGCGAATTCGAGCCCAAGAAGAAGAGGAAAGTCTAACCGGTCATCATCACCATC |
| ACCATTGAGTTTAAACCCGCTGATCAGCCTCGACTGTGCCTTCTAGTTGCCAGCCAT |
| CTGTTGTTTGCCCCTCCCCCGTGCCTTCCTTGACCCTGGAAGGTGCCACTCCCACTGT |
| CCTTTCCTAATAAAATGAGGAAATTGCATCGCATTGTCTGAGTAGGTGTCATTCTAT |
| TCTGGGGGGTGGGGTGGGGCAGGACAGCAAGGGGGAGGATTGGGAAGACAATAGC |
| AGGCATGCTGGGGATGCGGTGGGCTCTATGGCTTCTGAGGCGGAAAGAACCAGCTG |
| GGGCTCGATACCGTCGACCTCTAGCTAGAGCTTGGCGTAATCATGGTCATAGCTGTT |
| TCCTGTGTGAAATTGTTATCCGCTCACAATTCCACACAACATACGAGCCGGAAGCAT |
| AAAGTGTAAAGCCTAGGGTGCCTAATGAGTGAGCTAACTCACATTAATTGCGTTGC |
| GCTCACTGCCCGCTTTCCAGTCGGGAAACCTGTCGTGCCAGCTGCATTAATGAATCG |
| GCCAACGCGCGGGGAGAGGCGGTTTGCGTATTGGGCGCTCTTCCGCTTCCTCGCTCA |
| CTGACTCGCTGCGCTCGGTCGTTCGGCTGCGGCGAGCGGTATCAGCTCACTCAAAG |
| GCGGTAATACGGTTATCCACAGAATCAGGGGATAACGCAGGAAAGAACATGTGAG |
| CAAAAGGCCAGCAAAAGGCCAGGAACCGTAAAAAGGCCGCGTTGCTGGCGTTTTTC |
| CATAGGCTCCGCCCCCCTGACGAGCATCACAAAAATCGACGCTCAAGTCAGAGGTG |
| GCGAAACCCGACAGGACTATAAAGATACCAGGCGTTTCCCCCTGGAAGCTCCCTCG |
| TGCGCTCTCCTGTTCCGACCCTGCCGCTTACCGGATACCTGTCCGCCTTTCTCCCTTC |
| GGGAAGCGTGGCGCTTTCTCATAGCTCACGCTGTAGGTATCTCAGTTCGGTGTAGGT |
| CGTTCGCTCCAAGCTGGGCTGTGTGCACGAACCCCCCGTTCAGCCCGACCGCTGCGC |
| CTTATCCGGTAACTATCGTCTTGAGTCCAACCCGGTAAGACACGACTTATCGCCACT |
| GGCAGCAGCCACTGGTAACAGGATTAGCAGAGCGAGGTATGTAGGCGGTGCTACA |
| GAGTTCTTGAAGTGGTGGCCTAACTACGGCTACACTAGAAGAACAGTATTTGGTAT |
| CTGCGCTCTGCTGAAGCCAGTTACCTTCGGAAAAAGAGTTGGTAGCTCTTGATCCGG |
| CAAACAAACCACCGCTGGTAGCGGTGGTTTTTTTGTTTGCAAGCAGCAGATTACGCG |
| CAGAAAAAAAGGATCTCAAGAAGATCCTTTGATCTTTTCTACGGGGTCTGACACTC |
| AGTGGAACGAAAACTCACGTTAAGGGATTTTGGTCATGAGATTATCAAAAAGGATC |
| TTCACCTAGATCCTTTTAAATTAAAAATGAAGTTTTAAATCAATCTAAAGTATATAT |
| GAGTAAACTTGGTCTGACAGTTACCAATGCTTAATCAGTGAGGCACCTATCTCAGCG |
| ATCTGTCTATTTCGTTCATCCATAGTTGCCTGACTCCCCGTCGTGTAGATAACTACGA |
| TACGGGAGGGCTTACCATCTGGCCCCAGTGCTGCAATGATACCGCGAGACCCACGC |
| TCACCGGCTCCAGATTTATCAGCAATAAACCAGCCAGCCGGAAGGGCCGAGCGCAG |
| AAGTGGTCCTGCAACTTTATCCGCCTCCATCCAGTCTATTAATTGTTGCCGGGAAGC |
| TAGAGTAAGTAGTTCGCCAGTTAATAGTTTGCGCAACGTTGTTGCCATTGCTACAGG |
| CATCGTGGTGTCACGCTCGTCGTTTGGTATGGCTTCATTCAGCTCCGGTTCCCAACG |
| ATCAAGGCGAGTTACATGATCCCCCATGTTGTGCAAAAAAGCGGTTAGCTCCTTCG |
| GTCCTCCGATCGTTGTCAGAAGTAAGTTGGCCGCAGTGTTATCACTCATGGTTATGG |
| CAGCACTGCATAATTCTCTTACTGTCATGCCATCCGTAAGATGCTTTTCTGTGACTG |
| GTGAGTACTCAACCAAGTCATTCTGAGAATAGTGTATGCGGCGACCGAGTTGCTCTT |
| GCCCGGCGTCAATACGGGATAATACCGCGCCACATAGCAGAACTTTAAAGTGCTC |
| ATCATTGGAAAACGTTCTTCGGGGCGAAAACTCTCAAGGATCTTACCGCTGTTGAG |
| ATCCAGTTCGATGTAACCCACTCGTGCACCCAACTGATCTTCAGCATCTTTTACTTTC |
| ACCAGCGTTTCTGGGTGAGCAAAAACAGGAAGGCAAAATGCCGCAAAAAAGGGAA |
| TAAGGGCGACACGGAAATGTTGAATACTCATACTCTTCCTTTTTCAATATTATTGAA |
| GCATTTATCAGGGTTATTGTCTCATGAGCGGATACATATTTGAATGTATTTAGAAAA |
| ATAAACAAATAGGGGTTCCGCGCACATTTCCCCGAAAAGTGCCACCTGACGTCGAC |
| GGATCGGGAGATCGATCTCCCGATCCCCTAGGGTCGACTCTCAGTACAATCTGCTCT |
| GATGCCGCATAGTTAAGCCAGTATCTGCTCCCTGCTTGTGTGTTGGAGGTCGCTGAG |
| TAGTGCGCGAGCAAAATTTAAGCTACAACAAGGCAAGGCTTGACCGACAATTGCAT |
| GAAGAATCTGCTTAGGGTTAGGCGTTTTGCGCTGCTTCGCGATGTACGGGCCAGATA |
| TACGCGTTGACATTGATTATTGACTAGTTATTAATAGTAATCAATTACGGGGTCATT |
| AGTTCATAGCCCATATATGGAGTTCCGCGTTACATAACTTACGGTAAATGGCCCGCC |
| TGGCTGACCGCCOAACGACCCCCGCCCATTGACGTCAATAATGACGTATGTTCCCAT |
| AGTAACGCCAATAGGGACTTTCCATTGACGTCAATGGGTGGAGTATTTACGGTAAA |
| CTGCCCACTTGGCAGTACATCAAGTGTATC |

SEQ ID NO: 3 (pAAV-meCMV-ABEmax-N)
aaagtagccgaagatgacggtttgtcacatggagttggcaggatgtttgattaaaaacataacaggaagaaaaatgccccgctg
tgggcggacaaaatagttgggaactgggaggggtggaaatggagttttttaaggattatttagggaagagtgacaaaatagatgggaactg
ggtgtagcgtcgtaagctaatacgaaaattaaaaatgacaaaatagtttggaactagatttcacttatctggttcggatctcctaggctcaagca
gtgatcagatccagacatgataagatacattgatgagtttggacaaaccacaactgaatgcagtgaaaaaaatgctttatttgtgaaatttgtg
atgctattgctttatttgtaaccattataagctgcaataaacaagttaacaacaacaattccatgtcctgcaggcagctgcgcgctcgctcgctc
actgaggccgcccgggcgtcgggcgacctttggtcgcccggcctcagtgagcgagcgagcgcgcagagagggagtggccaactccat
cactagggggttcctgcggcctctagactcgagCGCGTGATGAGAGCAGCCACTACGGGTCTAGGCTGC
CCATGTAAGGAGGCAAGGCCTGGGACACCCGAGATGCCTGGTTATAATTAACCCA
GACATGTGGCTGCCCCCCCCCCCCAACACCTGCTGCCTGCTAAAAATAACCCTGTC
CCTGGTGGCCctgcatgcccACTCACGGGGATTTCCAAGTCTCCACCCCATTGACGTCAAT
GGGAGTTTGTTTTGGCACCAAAATCAACGGGACTTTCCAAAATGTCGTAACAACTCC
GCCCCATTGACGCAAATGGGCGGTAGGCGTGTACGGTGGGAGGTCTATATAAGCAG
AGCTGGTTTAGTGAACCGTCAGATCcgccaccATGgctagcATGAAACGGACAGCCGACG

| SEQUENCES |
|---|
| GAAGCGAGTTCGAGTCACCAAAGAAGAAGCGGAAAGTCTCTGAAGTCGAGTTTAGC |
| CACGAGTATTGGATGAGGCACGCACTGACCCTGGCAAAGCGAGCATGGGATGAAA |
| GAGAAGTCCCCGTGGGCGCCGTGCTGGTGCACAACAATAGAGTGATCGGAGAGGG |
| ATGGAACAGGCCAATCGGCCGCCACGACCCTACCGCACACGCAGAGATCATGGCAC |
| TGAGGCAGGGAGGCCTGGTCATGCAGAATTACCGCCTGATCGATGCCACCCTGTAT |
| GTGACACTGGAGCCATGCGTGATGTGCGCAGGAGCAATGATCCACAGCAGGATCGG |
| AAGAGTGGTGTTCGGAGCACGGGACGCCAAGACCGGCGCAGCAGGCTCCCTGATG |
| GATGTGCTGCACCACCCCGGCATGAACCACCGGGTGGAGATCACAGAGGGAATCCT |
| GGCAGAGAGTGCGCCGCCCTGCTGAGCGATTTCTTTAGAATGCGGAGACAGGAGA |
| TCAAGGCCCAGAAGAAGGCACAGAGCTCCACCGACTCTGGAGGATCTAGCGGAGG |
| ATCCTCTGGAAGCGAGACACCAGGCACAAGCGAGTCCGCCACACCAGAGAGCTCCG |
| GCGGCTCCTCCGGAGGATCCTCTGAGGTGGAGTTTTCCCACGAGTACTGGATGAGA |
| CATGCCCTGACCCTGGCCAAGAGGGCACGCGATGAGAGGGAGGTGCCTGTGGGAG |
| CCGTGCTGGTGCTGAACAATAGAGTGATCGGCGAGGGCTGGAACAGAGCCATCGGC |
| CTGCACGACCCAACAGCCCATGCCGAAATTATGGCCCTGAGCACAGGGCGGCCTGGT |
| CATGCAGAACTACAGACTGATTGACGCCACCCTGTACGTGACATTCGAGCCTTGCGT |
| GATGTGCGCCGGCGCCATGATCCACTCTAGGATCGGCCGCGTGGTGTTTGGCGTGA |
| GGAACGCAAAAACCGGCGCCGCAGGCTCCCTGATGGACGTGCTGCACTACCCCGGC |
| ATGAATCACCGCGTCGAAATTACCGAGGGAATCCTGGCAGATGAATGTGCCGCCCT |
| GCTGTGCTATTTCTTTCGGATGCCTAGACAGGTGTTCAATGCTCAGAAGAAGGCCCA |
| GAGCTCCACCGACTCCGGAGGATCTAGCGGAGGCTCCTCTGGCTCTGAGACACCTG |
| GCACAAGCGAGAGCGCAACACCTGAAAGCAGCGGGGGCAGCAGCGGGGGTCAGA |
| CAAGAAGTACAGCATCGGCCTGGCCATCGGCACCAACTCTGTGGGCTGGGCCGTGA |
| TCACCGACGAGTACAAGGTGCCCAGCAAGAAATTCAAGGTGCTGGGCAACACCGAC |
| CGGCACAGCATCAAGAAGAACCTGATCGGAGCCCTGCTGTTCGACAGCGGCGAAAC |
| AGCCGAGGCCACCCGGCTGAAGAGAACCGCCAGAAGAAGATACACCAGACGGAAG |
| AACCGGATCTGCTATCTGCAAGAGATCTTCAGCAACGAGATGGCCAAGGTGGACGA |
| CAGCTTCTTCCACAGACTGGAAGAGTCCTTCCTGGTGGAAGAGGATAAGAAGCACG |
| AGCGGCACCCCATCTTCGGCAACATCGTGGACGAGGTGGCCTACCACGAGAAGTAC |
| CCCACCATCTACCACCTGAGAAAGAAACTGGTGGACAGCACCGACAAGGCCGACCT |
| GCGGCTGATCTATCTGGCCCTGGCCCACATGATCAAGTTCCGGGGCCACTTCCTGAT |
| CGAGGGCGACCTGAACCCCGACAACAGCGACGTGGACAAGCTGTTCATCCAGCTGG |
| TGCAGACCTACAACCAGCTGTTCGAGGAAAACCCCATCAACGCCAGCGGCGTGGAC |
| GCCAAGGCCATCCTGTCTGCCAGACTGAGCAAGAGCAGACGGCTGGAAAATCTGAT |
| CGCCCAGCTGCCCGGCGAGAAGAAGAATGGCCTGTTCGGAAACCTGATTGCCCTGA |
| GCCTGGGCCTGACCCCCAACTTCAAGAGCAACTTCGACCTGGCCGAGGATGCCAAA |
| CTGCAGCTGAGCAAGGACACCTACGACGACGACCTGGACAACCTGCTGGCCCAGAT |
| CGGCGACCAGTACGCCGACCTGTTTCTGGCCGCCAAGAACCTGTCCGACGCCATCCT |
| GCTGAGCGACATCCTGAGAGTGAACACCGAGATCACCAAGGCCCCCCTGAGCGCCT |
| CTATGATCAAGAGATACGACGAGCACCACCAGGACCTGACCCTGCTGAAAGCTCTC |
| GTGCGGCAGCAGCTGCCTGAGAAGTACAAAGAGATTTTCTTCGACCAGAGCAAGAA |
| CGGCTACGCCGGCTACATTGACGGCGGAGCCAGCCAGGAAGAGTTCTACAAGTTCA |
| TCAAGCCCATCCTGGAAAAGATGGACGGCACCGAGGAACTGCTCGTGAAGCTGAAC |
| AGAGAGGACCTGCTGCGGAAGCAGCGGACCTTCGACAACGGCAGCATCCCCCACCA |
| GATCCACCTGGGAGAGCTGCACGCCATTCTGCGGCGGCAGGAAGATTTTTACCCAT |
| TCCTGAAGGACAACCGGGAAAAGATCGAGAAGATCCTGACCTTCCGCATCCCCTAC |
| TACGTGGGCCCTCTGGCCAGGGGAAACAGCAGATTCGCCTGGATGACCAGAAAGAG |
| CGAGGAAACCATCACCCCCTGGAACTTCGAGGAAGTGGTGGACAAGGGCGCTTCCG |
| CCCAGAGCTTCATCGAGCGGATGACCAACTTCGATAAGAACCTGCCCAACGAGAAG |
| GTGCTGCCCAAGCACAGCCTGCTGTACGAGTACTTCACCGTGTATAACGAGCTGAC |
| CAAAGTGAAATACGTGACCGAGGGAATGAGAAAGCCCGCCTTCCTGAGCGGCGAG |
| CAGAAAAAGGCCATCGTGGACCTGCTGTTCAAGACCAACCGGAAAGTGACCGTGAA |
| GCAGCTGAAAGAGGACTACTTCAAGAAAATCGAGTGTCTCAGTTATGACACCGAAA |
| TCCTGACAGTCGAGTATGGATTCTGCCGATCGGCAAGATTGTGGAGgAGAGAATTG |
| AATGTACGGTCTATAcgGTCGACAAgAATGGTtCgTCTACACCCAACCAaTTGCTCAA |
| TGGCATaATCGAGGGGAGCAGGAGGTGTTTGAGTATTGCCTGGAGGACGGGTCAATC |
| ATTAGAGCTACAAAGGACCATAAGTTTATGACAacCGATGGTCAAATGCTGCCGATA |
| GATGAAATATTCGAAAGGGgACTGGATCTTAAGCaAGTCGATggCCTTCCAaacTAgtAg |
| aattcctagagctcgctgatcagcctcgactgtgccttctagttgccagccatctgttgtttgcccctccccgtgccttccttgaccctggaag |
| gtgccactcccactgtcctttcctaataaaatgaggaaattgcatcgcattgtctgagtaggtgtcattctattctgggggtggggtgggca |
| ggacagcaaggggggaggattgggaagagaatagcaggcatgctggggaggtaccgagggcctatttcccatgattccttcatatttgcat |
| atacgatacaaggctgttagagagataattggaattaattttgactgtaaacacaaagatattagtacaaaatacgtgacgtagaaagtaataat |
| ttcttgggtagtttgcagttttaaaattatgttttaaaatggactatcatatgcttaccgtaacttgaaagtatttcgatttcttggctttatatatc |
| ttGTGGAAAGGACGAAACACCGGTTATCTCCTGTTCTGCAGCGTTTcAGAGCTAtgctgGAA |
| AcagcaTAGCAAGTTgAAATAAGGCTAGTCCGTTATCAACTTGAAAAAGTGGCACCGA |
| GTCGGTGCTTTTTTgcggccgcaggaaccctagtgatggagttggccactccctctctgcgcgctcgctcgctcactgaggc |
| cgggcgaccaaaggtcgcccgacgcccgggctttgcccgggcgtcctcagtgagcgagcgagcgcgcagctgcctgcagggggcgcc |
| tgtaccgggagatgggggaggctaactgaaacacggaaggagacaataccggaaggaacccgcgctatgacggcaataaaaagacag |
| aataaaacgcacgggtgtttgggtcgtttgttcataaacgcggggttcggtcccagggctggcactctgtcgataccccaccgagacccatt |
| gggaccaatacgcccgcgtttcttccttttccccaccccaaccccaagttcgggtgaaggcccagggctcgcagccaacgtcggggcg |
| gcaagccctgccatagccactacgggtacgtaggccaaccactagaactatagctagagtcctgggcgaacaaacgatgctcgccttcca |
| gaaaaccgaggatgcgaaccacttcatccgggggtcagcaccaccggcaagggcgacggccgaggtctaccgatctcctgaagcca |
| gggcagatccgtgcacagcacccttgccgtagaagaacagcaaggccgccaatgcctgacgatgcgtggagaccgaaaccttgcgctcg |
| ttcgccagccaggacagaaatgcctcgacttcgctgctgcccaaggttgccgggtgacgcacaccgtggaaacggatgaaggcacgaa |
| cccagttgacataagcctgttcggttcgtaaactgtaatgcaagtagcgtatgcgctcacgcaactggtccagaaccttgaccgaacgcagc |
| ggtggtaacggcgcagtggcggttttcatggcttgttatgactgtttttttgtacagtctatgcctcgggcatccaagcagcaagcgcgttacg |
| ccgtgggtcgatgtttgatgttatggagcagcaacgatgttacgcagcagcaacgatgttacgcagcagggcagtcgccctaaaacaaagt |

| SEQUENCES |
|---|
| taggtggctcaagtatgggcatcattcgcacatgtaggctcggccctgaccaagtcaaatccatgcgggctgctcttgatcttttcggtcgtg
agttcggagacgtagccacctactcccaacatcagccggactccgattacctcgggaacttgctccgtagtaagacattcatcgcgcttgct
gccttcgaccaagaagcggttgttggcgctctcgcggcttacgttctgccaggtttgagcagccgcgtagtgagatctatatctatgatctc
gcagtctccggcgagcaccggaggcagggcattgccaccgcgctcatcaatctcctcaagcatgaggcaacgcgcttggtgcttatgtg
atctacgtgcaagcagattacggtgacgatcccgcagtggctctctatacaaagttgggcatacgggaagaagtgatgcactttgatatcga
cccaagtaccgccacctaacaattcgttcaagccgagatcggcttcccggccgcggagttgttcggtaaattgtcacaacgccgcgaatat
agtctttaccatgcccttggccacgcccctctttaatacgacgggcaatttgcacttcagaaaatgaagagtttgctttagccataacaaaagtc
cagtatgcttttcacagcataactggactgatttcagtttacaactattctgtctagtttaagactttattgtcatagtttagatctattttgttca
gtttaagactttattgtccgcccacaccgcttacgcagggcatccatttattactcaaccgtaaccgattttgccaggttacgcggctggtctgcgg
tgtgaaataccgcacagatgcgtaaggagaaaataccgcatcaggcgctcttccgcttcctcgctcactgactcgctgcgctcggtcgttcg
gctgcggcgagcggtatcagctcactcaaaggcggtaatacggttatccacagaatcaggggataacgcaggaaagaacatgtgagcaa
aaggccagcaaaaggccaggaaccgtaaaaaggccgcgttgctggcgtttttccataggctccgcccccctgacgagcatcacaaaaat
cgacgctcaagtcagaggtggcgaaacccgacaggactataaagataccaggcgtttccccctggaagctccctcgtgcgctctcctgttc
cgaccctgccgcttaccggatacctgtccgcctttctcccttcgggaagcgtggcgctttctcaatgctcacgctgtaggtatctcagttcggt
gtaggtcgttcgctccaagctgggctgtgtgcacgaaccccccgttcagcccgaccgctgcgccttatccggtaactatcgtcttgagtcca
acccggtaagacacgacttatcgccactggcagcagccactggtaacaggattagcagagcgaggtatgtaggcggtgctacagagttct
tgaagtggtggcctaactacggctacactagaaggacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaaggatctcaagaa
gatcctttgatcttttctacggggtctgacgctcagtggaacgaaaactcacgttaagggattttggtcatgagattatcaaaaaggatcttcac
ctagatccttttaaattaaaaatgaagttttaaatcaatctaaagtatatatgagtaaacttggtctgacagttaccaatgcttaatcagtgaggca
cctatctcagcgatctgtctatttcgttcatccatagttgcctgactccccgtcgtgtagataactacgatacgggagggcttaccatctggccc
cagtgctgcaatgataccgcgagacccacgctcaccggctccagatttatcagcaataaaccagccagccggaagggccgagcgcaga
agtggtcctgcaactttatccgcctccatccagtctattaattgttgccgggaagctagagtaagtagttcgccagttaatagtttgcgcaacgt
tgttgccattgctacaggcatcgtggtgtcacgctcgtcgtttggtatggcttcattcagctccggttcccaacgatcaaggcgagttacatgat
ccccatgttgtgcaaaaaagcggttagctccttcggtcctccgatcgttgtcagaagtaagttggccgcagtgttatcactcatggttatggc
agcactgcataattctcttactgtcatgccatccgtaagatgcttttctgtgactggtgagtactcaaccaagtcattctgagaatagtgtatgcg
gcgaccgagttgctcttgcccggcgtcaatacgggataataccgcgccacatagcagaactttaaaagtgctcatcattggaaaacgttcttc
ggggcgaaaactctcaaggatcttaccgctgttgagatccagttcgatgtaacccactcgtgcacccaactgatcttcagcatcttttactttca
ccagcgtttctgggtgagcaaaaacaggaaggcaaaatgccgcaaaaaagggaataagggcgacacggaaatgttgaatactcatactct
tcctttttcaatattattgaagcatttatcagggttattgtctcatgagcggatacatatttgaatgtatttagaaaaataaacaaataggggttccg
cgcacatttccccgaaaagtgccacctgaaattgtaaacgttaatattttgttaaaattcgcgttaaattttttgttaaatcagctcattttttaaccaa
taggccgaaatcggcaaaatcccttataaatcaaaagaatagaccgagatagggttgagtgttgttccagtttggaacaagagtccactatta
aagaacgtggactccaacgtcaaagggcgaaaaaccgtctatcagggcgatggcccactacgtgaaccatcacccctaatcaagttttttgg
ggtcgaggtgccgtaaagcactaaatcggaacccctaaagggagcccccgatttagagctttgacgggaaaccggcgaacgtggcgag
aaaggaagggaagaaagcgaaaggagcgggcgctagggcgctggcaagtgtagcggtcacgctgcgcgtaaccaccacacccgccg
cgcttaatgcgccgctacagggcgcgtcccattcgccattcaggctgcaaataagcgttgatattcagtcaattacaaacattaataacgaag
agatgacagaaaattttcattctgtgacagagaa |

SEQ ID NO: 4 (pAAV-ABEmaxNG-C)
aaagtagccgaagatgacggtttgtcacatggagttggcaggatgtttgattaaaaacataacaggaagaaaaatgccccgctg
tgggcggacaaatagttgggaactggggaggggtggaaatggagttttaaggattatttagggaagagtgacaaaatagatgggaactg
ggtgtagcgtcgtaagctaatacgaaaattaaaaatgacaaaatagtttggaactagatttcacttatctggttcggatctcctaggctcaagca
gtgatcagatccagacatgataagatacattgatgagtttggacaaaccacaactagaatgcagtgaaaaaaatgctttatttgtgaaatttgtg
atgctattgctttatttgtaaccattataagctgcaataaacaagttaacaacaacaattccatgtcctgcaggcagctgcgcgctcgctcgctc
actgaggccgcccgggcgtcgggcgacctttggtcgcccggcctcagtgagcgagcgagcgcgcagagagggagtggccaactccat
cactaggggttcctgcggcctctagactcgagCGCGTGATGAGAGCAGCCACTACGGGTCTAGGCTGC
CCATGTAAGGAGGCAAGGCCTGGGGACACCCGAGATGCCTGGTTATAATTAACCCA
GACATGTGGCTGCCCCCCCCCCCCAACACCTGCTGCCTGCTAAAAATAACCCTGTC
CCTGGTGGCcctgcatgcccACTCACGGGGATTTCCAAGTCTCCACCCCATTGACGTCAAT
GGGAGTTTGTTTTGGCACCAAAATCAACGGGACTTTCCAAAATGTCGTAACAACTCC
GCCCCATTGACGCAAATGGGCGGTAGGCGTGTACGGTGGGAGGTCTATATAAGCAG
AGCTGGTTTAGTGAACCGTCAGATCCgccaccATGgTcAAgATTatCAgcCGCAAATcCTTG
GGGAcACAGAATGTATATGACATCGGCGTGGAaaGGATCACAATTTTctgCTGAAGA
ATGGTcTTgTTGCTtccAAtTGCTTCGACTCCGTGGAAATCTCCGGCGTGGAAGATCGG
TTCAACGCCTCCCTGGGACATATACCACGATCTGCTGAAAATTATCAAGGACAAGGA
CTTCCTGGACAATGAGGAAAACGAGGACATTCTGGAAGATATCGTGCTGACCCTGA
CACTGTTTGAGGACAGAGAGATGATCGAGGAACGGCTGAAAACCTATGCCCACCTG
TTCGACGACAAAGTGATGAAGCAGCTGAAGCGGCGGAGATACACCGGCTGGGGCA
GGCTGAGCCGGAAGCTGATCAACGGCATCCGGGACAAGCAGTCCGGCAAGACAAT
CCTGGATTTCCTGAAGTCCGACGGCTTCGCCAACAGAAACTTCATGCAGCTGATCCA
CGACGACAGCCTGACCTTTAAAGAGGACATCCAGAAAGCCCAGGTGTCCGGCCAGG
GCGATAGCCTGCACGAGCACATTGCCAATCTGGCCGGCAGCCCCGCCATTAAGAAG
GGCATCCTGCAGACAGTGAAGGTGGTGGACGAGCTCGTGAAAGTGATGGGCCGGC
ACAAGCCCGAGAACATCGTGATCGAAATGGCCAGAGAGAACCAGACCACCCAGAA
GGGACAGAAGAACAGCCGCGAGAGAATGAAGCGGATCGAAGAGGGCATCAAAGA
GCTGGGCAGCCAGATCCTGAAAGAACACCCCGTGGAAAACACCCAGCTGCAGAAC
GAGAAGCTGTACCTGTACTACCTGCAGAATGGGCGGGATATGTACGTGGACCAGGA
ACTGGACATCAACCGGCTGTCCGACTACGATGTGGACCATATCGTGCCTCAGAGCTT
TCTGAAGGACGACTCCATCGACAACAAGGTGCTGACCAGAAGCGACAAGAACCGG
GGCAAGAGCGACAACGTGCCCTCCGAAGAGGTCGTGAAGAAGATGAAGAACTACT
GGCGGCAGCTGCTGAACGCCAAGCTGATTACCCAGAGAAAGTTCGACAATCTGACC
AAGGCCGAGAGAGGCGGCCTGAGCGAACTGGATAAGGCCGGCTTCATCAAGAGAC
AGCTGGTGGAAACCCGGCAGATCACAAAGCACGTGGCACAGATCCTGGACTCCCGG
ATGAACACTAAGTACGACGAGAATGACAAGCTGATCCGGGAAGTGAAAGTGATCA
CCCTGAAGTCCAAGCTGGTGTCCGATTTCCGGAAGGATTTCCAGTTTTACAAAGTGC
GCGAGATCAACAACTACCACCACGCCCACGACGCCTACCTGAACGCCGTCGTGGGA
ACCGCCCTGATCAAAAAGTACCCTAAGCTGGAAAGCGAGTTCGTGTACGGCGACTA -continued

| SEQUENCES |
|---|
| CAAGGTGTACGACGTGCGGAAGATGATCGCCAAGAGCGAGCAGGAAATCGGCAAG |
| GCTACCGCCAAGTACTTCTTCTACAGCAACATCATGAACTTTTTCAAGACCGAGATT |
| ACCCTGGCCAACGGCGAGATCCGGAAGCGGCCTCTGATCGAGACAAACGGCGAAA |
| CCGGGGAGATCGTGTGGGATAAGGGCCGGGATTTTGCCACCGTGCGGAAAGTGCTG |
| AGCATGCCCCAAGTGAATATCGTGAAAAAGACCGAGGTGCAGACAGGCGGCTTCA |
| GCAAAGAGTCTATCCgGCCCAAGAGGAACAGCGATAAGCTGATCGCCAGAAAGAA |
| GGACTGGGACCCTAAGAAGTACGGCGGCTTCGtCAGCCCCACCGTGGCCTATTCTGT |
| GCTGGTGGTGGCCAAAGTGGAAAAGGGCAAGTCCAAGAAACTGAAGAGTGTGAAA |
| GAGCTGCTGGGGATCACCATCATGGAAAGAAGCAGCTTCGAGAAGAATCCCATCGA |
| CTTTCTGGAAGCCAAGGGCTACAAAGAAGTGAAAAAGGACCTGATCATCAAGCTGC |
| CTAAGTACTCCCTGTTCGAGCTGGAAAACGGCCGGAAGAGAATGCTGGCCTCTGCCC |
| GCttCTGCAGAAGGGAAACGAACTGGCCCTGCCCTCCAAATATGTGAACTTCCTGTA |
| CCTGGCCAGCCACTATGAGAAGCTGAAGGGCTCCCCGAGGATAATGAGCAGAAAC |
| AGCTGTTTGTGGAACAGCACAAGCACTACCTGGACGAGATCATCGAGCAGATCAGC |
| GAGTTCTCCAAGAGAGTGATCCTGGCCGACGCTAATCTGGACAAAGTGCTGTCCGC |
| CTACAACAAGCACCGGGATAAGCCCATCAGAGAGCAGGCCGAGAATATCATCCACC |
| TGTTTACCCTGACCAATCTGGGAGCCCCTCggGCCTTCAAGTACTTTGACACCACCAT |
| CGACCGGAAGgtGTACcggAGCACCAAAGAGGTGCTGGACGCCACCCTGATCCACCA |
| GAGCATOACCGGCCTGTACGAGACACGGATCGACCTGTCTCAGCTGGGAGGTGACT |
| CTGGCGGCTCAAAAAGAACCGCCGACGGCAGCGAATTCGAGCCCAAGAAGAAGAG |
| GAAAGTCtaacTAgtAgaattcctagagctcgctgatcagcctcgactgtgccttctagttgccagccatctgttgtttgccctccc |
| ccgtgccttccttgaccctggaaggtgccactcccactgt.cctttcctaataaaatgaggaaattgcatcgcattgtctgagtaggtgtcattct |
| attctgggggtggggtggggcaggacagcaaggggaggattgggaagagaatagcaggcatgctgggaggtaccgagggccta |
| tttcccatgattccttcatatttgcatatacgatacaaggctgttagagagataattggaattaatttgactgtaaacaaagatattagtacaaa |
| atacgtgacgtagaaagtaataattcttgggtagtttgcagttttaaaattatgttttaaaatggactatcatatgcttaccgtaacttgaaagtatt |
| tcgatttcttggctttatatatcttGTGGAAAGGACGAAACACCGGTTATCTCCTGTTCTGCAGCGTT |
| TcAGAGCTAtgctgGAAAcagcaTAGCAAGTTgAAATAAGGCTAGTCCGTTATCAACTTGA |
| AAAAGTGGCACCGAGTCGGTGCTTTTTTgcggccgcaggaaccccctagtgatggagttggccactccctctctg |
| cgcgctcgctcgctcactgaggccgggcgaccaaaggtcgcccgacgcccgggctttgcccgggcggcctcagtgagcgagcgagcg |
| cgcagctgcctgcaggggcgcctgtaccgggagatggggggaggctaactgaaacacggaaggagacaataccggaaggaacccgcg |
| ctatgacggcaataaaaagacagaataaaacgcacgggtgttgggtcgtttgttcataaacgcggggttcggtcccagggctggcactctg |
| tcgataccccaccgagacccattgggaccaataccgcccgcgctttcttccttttccccaccccaaccccccaagttcgggtgaaggcccagg |
| gctcgcagccaacgtcggggcggcaagccctgccatagcccactacgggtacgtaggccaaccactagaactatagctagagtcctgggc |
| gaacaaacgatgctcgccttccagaaaaaccgaggatgcgaaccacttcatccggggtcagcaccaccggcaagcgccgcgacggccg |
| aggtctaccgatctcctgaagccagggcagatccgtgcacagcacctttgccgtagaagaacagcaaggccgccaatgcctgacgatgcg |
| tggagaccgaaaccttgcgctcgttcgccagccaggacagaaatgcctcgacttcgctgctgcccaaggttgccgggtgacgcacaccgt |
| ggaaacggatgaaggcacgaaccagttgacataagcctgttcggtctcgtaaactgtaatgcaagtagcgtatgcgctcacgcaactggtc |
| cagaaccttgaccgaacgcagcggtggtaacggcgcagtggcggttcatggcttgttatgactgttttttttgtacagtctatgcctcgggca |
| tccaagcagcaagcgcgttacgccgtgggtcgatgtttgatgttatggagcagcaacgatgttacgcagcagcaacgatgttacgcagcag |
| ggcagtcgccctaaaacaaagttaggtggctcaagtatgggcatcattcgcacatgtaggctcggccctgaccaagtcaaatccatgcggg |
| ctgctcttgatctttcggtcgtgagttcggagacgtagccaacctactcccaacatcagccggactccgattacctcgggaacttgctcgtag |
| taagacattcatcgcgcttgctgccttcgaccaagaagcggttgttggcgctctcgcggcttacgttctgcccaggtttgagcagcgcgta |
| gtgagatctatatctatgatctcgcagtctccggcgagcaccggaggcagggcattgccaccgcgctcatcaatctcctcaagcatgaggc |
| caacgcgcttggtgcttatgtgatctacgtgcaagcagattacggtgacgatcccgcagtggctctctatacaaagttgggcatacgggaag |
| aagtgatgcacttttgatatcgacccaagtaccgccacctaacaattcgttcaagccgagatcggcttcccggccgcggagttgttcggtaaa |
| ttgtcacaacgccgcgaatatagtctttaccatgcccttggccacgcccctctttaatacgcgggcaatttgcacttcagaaaatgaagagtt |
| tgctttagccataacaaaagtccagtatgcttttttcacagcataactggactgatttcagtttacaactattctgtcagtttaagactttattgtcat |
| agtttagatctatttttgttcagtttaagacttttattgtccgcccacacccgcttacgcagggcatccatttattactcaaccgtaaccgattttgcca |
| ggttacgcggctggtctgcggtgtgaaataccgcacagatgcgtaaggagaaaataccgcatcaggcgctcttccgcttcctcgctcactg |
| actcgctgcgctcggtcgttcggctgcggcgagcggtatcagctcactcaaaggcggtaatacggttatccacagaatcaggggataacg |
| caggaaagaacatgtgagcaaaaggccagcaaaaggccaggaaccgtaaaaaggccgcgttgctggcgtttttccataggctccgcccc |
| cctgacgagcatcacaaaaatcgacgctcaagtcagaggtggcgaaacccgacaggactataaagataccaggcgtttccccctggaag |
| ctccctcgtgcgctctcctgttccgaccctgccgcttaccggatacctgtccgcctttctcccttcgggaagcgtggcgctttctcaatgctcac |
| gctgtaggtatctcagttcggtgtaggtcgttcgctccaagctgggctgtgtgcacgaaccccccgttcagcccgaccgctgcgccttatcc |
| ggtaactatcgtcttgagtccaacccggtaagacacgacttatcgccactggcagcagccactggtaacaggattagcagagcgaggtatg |
| taggcggtgctacagagttcttgaagtggtggcctaactacggctacactagaaggacagtatttggtatctgcgctctgctgaagccagtta |
| ccttcggaaaaagagttggtagctcttgatccggcaaacaaaccaccgctggtagcggtggtttttttgttgcaagcagcagattacgcgca |
| gaaaaaaaggatctcaagaagatccttgatctttctacggggtctgacgctcagtggaacgaaaactcacgttaagggattttggtcatga |
| gattatcaaaaaggatcttcacctagatccttttaaattaaaaatgaagttttaaatcaatctaaagtatatatgagtaaacttggtctgacagttac |
| caatgcttaatcagtgaggcacctatctcagcgatctgtctatttcgttcatccatagttgcctgactccccgtcgtgtagataactacgatacg |
| ggagggcttaccatctggccccagtgctgcaatgataccgcgagacccacgctcaccggctccagatttatcagcaataaaccagccagc |
| cggaagggccgagccgcagaagtggtcctgcaactttatccgcctccatccagtctattaattgttgccgggaagctagagtaagtagttcgc |
| cagttaatagtttgcgcaacgttgttgccattgctacaggcatcgtggtgtcacgctcgtcgtttggtatggcttcattcagctccggttcccaa |
| cgatcaaggcgagttacatgatccccatgttgtgcaaaaaagcggttagctccttcggtcctccgatcgttgtcagaagtaagttggccgca |
| gtgttatcactcatggttatggcagcactgcataattctcttactgtcatgccatccgtaagatgcttttctgtgactggtgagtactcaaccaagt |
| cattctgagaatagtgtatgcggcgaccgagttgctcttgcccggcgtcaatacgggataataccgcgccacatagcagaactttaaaagtg |
| ctcatcattggaaaacgttcttcggggcgaaaactctcaaggatcttaccgctgttgagatccagttcgatgtaacccactcgtgcacccaact |
| gatcttcagcatcttttactttcaccagcgtttctgggtgagcaaaaacaggaaggcaaaatgccgcaaaaaagggaataagggcgacacg |
| gaaatgttgaatactcatactcttcctttttcaatattattgaagcatttatcagggttattgtctcatgagcggatacatatttgaatgtatttaga |
| aaaataaacaaataggggttccgcgcacatttccccgaaaagtgccacctgaaattgtaaacgttaatattttgttaaaattcgcgttaaattttgt |
| taaatcagctcatttttaaccaataggccgaaatcggcaaaatcccttataaatcaaaagaatagaccgagatagggttgagtgttgttccagt |
| ttggaacaagagtccactattaaagaacgtggactccaacgtcaaagggcgaaaaaccgtctatcagggcgatggcccactacgtgaacc |
| atcaccctaatcaagttttttggggtcgaggtgccgtaaagcactaaatcggaacccctaaagggagcccccgatttagagcttgacgggga |
| aagccggcgaacgtggcgagaaaggaagggaagaaagcgaaaggagcgggcgctagggcgctggcaagtgtagcggtcacgctgc |
| gcgtaaccaccacacccgccgcgcttaatgcgccgctacagggcgcgtcccattcgccattcaggctgcaaataagcgttgatattcagtc |
| aattacaaacattaataacgaagagatgacagaaaaattttcattctgtgacagagaa |

SEQUENCES

SEQ ID NO: 5 (pX601-meCMV-ABEmax-N2)
cctgcaggcagctgcgcgctcgctcgctcactgaggccgcccgggcgtcgggcgacctttggtcgcccggcctcagtgagc
gagcgagcgcgcagagagggagtggccaactccatcactaggggttcctgcggcctctagactcgagCGCGTGATGAGAG
CAGCCACTACGGGTCTAGGCTGCCCATGTAAGGAGGCAAGGCTGGGGACACCCGA
GATGCCTGGTTATAATTAACCCAGACATGTGGCTGCCCCCCCCCCCCAACACCTGC
TGCCTGCTAAAAATAACCCTGTCCCTGGTGGccCtgcatgcccACTCACGGGGATTTCCAA
GTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTA
CGGTGGGAGGTCTATATAAGCAGAGCTGGTTTAGTGAACCGTCAGATCcgcAcCATGg
ctagcATGAAACGGACAGCCGACGGAAGCGAGTTCGAGTCACCAAAGAAGAAGCGGA
AAGTCTCTGAAGTCGAGTTTAGCCACGAGTATTGGATGAGGCACGCACTGACCCTG
GCAAAGCGAGCATGGGATGAAAGAGAAGTCCCCGTGGGCGCCGTGCTGGTGCACA
ACAATAGAGTGATCGGAGAGGGATGGAACAGGCCAATCGGCCGCCACGACCCTAC
CGCACACGCAGAGATCATGGCACTGAGGCAGGGAGGCCTGGTCATGCAGAATTACC
GCCTGATCGATGCCACCCTGTATGTGACACTGGAGCCATGCGTGATGTGCGCAGGA
GCAATGATCCACAGCAGGATCGGAAGAGTGGTGTTCGGAGCACGGGACGCCAAGA
CCGGCGCAGCAGGCTCCCTGATGGATGTGCTGCACCACCCCGGCATGAACCACCGG
GTGGAGATCACAGAGGGAATCCTGGCAGACGAGTGCGCCGCCCTGCTGAGCGATTT
CTTTAGAATGCGGAGACAGGAGATCAAGGCCCAGAAGAAGGCACAGAGCTCCACC
GACTCTGGAGGATCTAGCGGAGGATCCTCTGGAAGCGAGACCACCAGGCACAAGCG
AGTCCGCCACACCAGAGAGCTCCGGCGGCTCCTCCGGAGGATCCTCTGAGGTGGAG
TTTTCCCACGAGTACTGGATGAGACATGCCCTGACCCTGGCCAAGAGGGCACGCGA
TGAGAGGGAGGTGCCTGTGGGAGCCGTGCTGGTGCTGAACAATAGAGTGATCGGCG
AGGGCTGGAACAGAGCCATCGGCCTGCACGACCCAACAGCCCATGCCGAAATTATG
GCCCTGAGACAGGGCGGCCTGGTCATGCAGAACTACAGACTGATTGACGCCACCCT
GTACGTGACATTCGAGCCTTGCGTGATGTGCGCCGGCGCCATGATCCACTCTAGGAT
CGGCCGCGTGGTGTTTGGCGTGAGGAACGCAAAAACCGGCGCCGCAGGCTCCCTGA
TGGACGTGCTGCACTACCCCGGCATGAATCACCGCGTCGAAATTACCGAGGGAATC
CTGGCAGATGAATGTGCCGCCCTGCTGTGCTATTTCTTTCGGATGCCTAGACAGGTG
TTCAATGCTCAGAAGAAGGCCCAGAGCTCCACCGACTCCGGAGGATCTAGCGGAGG
CTCCTCTGGCTCTGAGACACCTGGCACAAGCGAGAGCGCAACACCTGAAAGCAGCG
GGGGCAGCAGCGGGGGTCAGACAAGAAGTACAGCATCGGCCTGGCCATCGGCAC
CAACTCTGTGGGCTGGGCCGTGATCACCGACGAGTACAAGGTGCCCAGCAAGAAAT
TCAAGGTGCTGGGCAACACCGACCGGCACAGCATCAAGAAGAACCTGATCGGAGC
CCTGCTGTTCGACAGCGGCGAAACAGCCGAGGCCACCCGGCTGAAGAGAACCGCCA
GAAGAAGATACACCAGACGGAAGAACCGGATCTGCTATCTGCAAGAGATCTTCAGC
AACGAGATGGCCAAGGTGGACGACAGCTTCTTCCACAGACTGGAAGAGTCCTTCCT
GGTGGAAGAGGATAAGAAGCACGAGCGGCACCCCATCTTCGGCAACATCGTGGAC
GAGGTGGCCTACCACGAGAAGTACCCCACCATCTACCACCTGAGAAAGAAACTGGT
GGACAGCACCGACAAGGCCGACCTGCGGCTGATCTATCTGGCCCTGGCCCACATGA
TCAAGTTCCGGGGCCACTTCCTGATCGAGGGCGACCTGAACCCCGACAACAGCGAC
GTGGACAAGCTGTTCATCCAGCTGGTGCAGACCTACAACCAGCTGTTCGAGGAAAA
CCCCATCAACGCCAGCGGCGTGGACGCCAAGGCCATCCTGTCTGCCAGACTGAGCA
AGAGCAGACGGCTGGAAAATCTGATCGCCCAGCTGCCCGGCGAGAAGAAGAATGG
CCTGTTCGGAAACCTGATTGCCCTGAGCCTGGGCCTGACCCCCAACTTCAAGAGCA
ACTTCGACCTGGCCGAGGATGCCAAACTGCAGCTGAGCAAGGACACCTACGACGAC
GACCTGGACAACCTGCTGGCCCAGATCGGCGACCAGTACGCCGACCTGTTTCTGGC
CGCCAAGAACCTGTCCGACGCCATCCTGCTGAGCGACATCCTGAGAGTGAACACCG
AGATCACCAAGGCCCCCCTGAGCGCCTCTATGATCAAGAGATACGACGAGCACCAC
CAGGACCTGACCCTGCTGAAAGCTCTCGTGCGGCAGCAGCTGCCTGAGAAGTACAA
AGAGATTTTCTTCGACCAGAGCAAGAACGGCTACGCCGGCTACATTGACGGCGGAG
CCAGCCAGGAAGAGTTCTACAAGTTCATCAAGCCCATCCTGGAAAAGATGGACGGC
ACCGAGGAACTGCTCGTGAAGCTGAACAGAGAGGACCTGCTGCGGAAGCAGCGGA
CCTTCGACAACGGCAGCATCCCCCACCAGATCCACCTGGGAGAGCTGCACGCCATT
CTGCGGCGGCAGGAAGATTTTTACCCATTCCTGAAGGACAACCGGGAAAAGATCGA
GAAGATCCTGACCTTCCGCATCCCCTACTACGTGGGCCCTCTGGCCAGGGGAAACA
GCAGATTCGCCTGGATGACCAGAAAGAGCGAGGAAACCATCACCCCCTGGAACTTC
GAGGAAGTGGTGGACAAGGGCGCTTCCGCCCAGAGCTTCATCGAGCGGATGACCAA
CTTCGATAAGAACCTGCCCAACGAGAAGGTGCTGCCCAAGCACAGCCTGCTGTACG
AGTACTTCACCGTGTATAACGAGCTGACCAAAGTGAAATACGTGACCGAGGGAATG
AGAAAGCCCGCCTTCCTGAGCGGCGAGCAGAAAAAGGCCATCGTGGACCTGCTGTT
CAAGACCAACCGGAAAGTGACCGTGAAGCAGCTGAAAGAGGACTACTTCAAGAAA
ATCGAGTGTTTGGATCTGAAAACGCAAGTTCAAACGCCACAGGGTATGAAAGAAAT
ATCCAATATACAGGTCGGCGATCTCGTCTTGTCTAACACTGGCTATAACGAGGTGCT
GAATGTATTTCCAAAAAGCAAGAAAAAAGTTACAAGATAACTCTGGAAGATGGA
AAAGAAATTATCTGTTCTGAGGAGCATCTGTTTCCGACCCAAACAGGGGAGATGAA
TATCAGTGGCGGTCTCAAAGAGGGTATGTGTTTGTATGTCAAGGaataactagtagaattcctag
agctcgctgatcagcctcgactgtgccttctagttgccagccatctgttgtttgcccctcccccgtgccttccttgaccctggaaggtgccact
cccactgtccttttcctaataaaatgaggaaattgcatcgcattgtctgagtaggtgtcattctattctggggggtggggtggggcaggacagc
aagggggaggattgggaagagaatagcaggcatgctggggaggtaccgagggcctatttcccatgattccttcatatttgcatatacgata
caaggctgttagagagataattggaattaatttgactgtaaacacaaagatattagtacaaaatacgtgacgtagaaagtaataatttcttgggt
agtttgcagttttaaaattatgttttaaaatggactatcatatgcttaccgtaacttgaaagtatttcgatttcttggctttatatatcttGTGGAA
AGGACGAAACACCGGTTATCTCCTGTTCTGCAGCGTTTcAGAGCTAtgctgAAAcagcaT
AGCAAGTTgAAATAAGGCTAGTCCGTTATCAACTTGAAAAGTGGCACCGAGTCGG
TGCTTTTTTgcggccgcaggaaccccctagtgatggagttggccactccctctctgcgcgctcgctcgctcactgaggccgggcga
ccaaaggtcgcccgacgcccgggctttgcccgggcggcctcagtgagcgagcgagcgcgcagctgcctgcaggggcgcctgatgcg
gtattttctccttacgcatctgtgcggtatttcacaccgcatacgtcaaagcaaccatagtacgcgcccgtagcggcgcattaagcgcggcg -continued

SEQUENCES ggtgtggtggttacgcgcagcgtgaccgctacacttgccagcgccctagcgcccgctcctttcgctttcttccttccttttctcgccacgttcg
ccggctttccccgtcaagctctaaatcggggctccctttagggttccgatttagtgctttacggcacctcgaccccaaaaaacttgatttggg
tgatggttcacgtagtgggccatcgccctgatagacggttttttcgccctttgacgttggagtccacgttctttaatagtggactcttgttccaaac
tggaacaacactcaaccctatctcgggctattcttttgatttataagggattttgccgatttcggcctattggttaaaaaatgagctgatttaacaa
aaatttaacgcgaattttaacaaaatattaacgtttacaattttatggtgcactctcagtacaatctgctctgatgccgcatagttaagccagccc
cgacacccgccaacacccgctgacgcgccctgacgggcttgtctgctcccggcatccgcttacagacaagctgtgaccgtctccgggag
ctgcatgtgtcagaggttttcaccgtcatcaccgaaacgcgcgagacgaaagggcctcgtgatacgcctatttttataggttaatgtcatgata
ataatggtttcttagacgtcaggtggcacttttcgggaaatgtgcgcggaacccctatttgttttatttttctaaatacattcaaatatgtatccgct
catgagacaataaccctgataaatgcttcaataatattgaaaaaggaagagtatgagtattcaacatttccgtgtcgcccttattccctttttgcg
gcattttgccttcctgtttttgctcacccagaaacgctggtgaaagtaaaagatgctgaagatcagttgggtgcacgagtgggttacatcgaa
ctggatctcaacagcggtaagatccttgagagttttcgccccgaagaacgttttccaatgatgagcacttttaaagttctgctatgtggcgcgg
tattatcccgtattgacgccgggcaagagcaactcggtcgccgcatacactattctcagaatgacttggttgagtactcaccagtcacagaaa
agcatcttacggatggcatgacagtaagagaattatgcagtgctgccataaccatgagtgataacactgcggccaacttacttctgacaacg
atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagc
ttcccggcaacaattaatagactggatggaggcggataaagttgcaggaccacttctgcgctcggcccttccggctggctggtttattgctg
ataaatctggagccggtgagcgtggaagccgcggtatcattgcagcactggggccagatggtaagccctcccgtatcgtagtctatcacac
gacggggagtcaggcaactatggatgaacgaaatagacagatcgctgagataggtgcctcactgattaagcattggtaactgtcagacca
agtttactcatatactctttagattgatttaaaacttcattttaatttaaaaggatctaggtgaagatcctttttgataatctcatgaccaaaatcc
cttaacgtgagttttcgttccactgagcgtcagaccccgtagaaaagatcaaaggatcttcttgagatccttttttttctgcgcgtaatctgctgcttgc
aaacaaaaaaaccaccgctaccagcggtggtttgtttgccggatcaagagctaccaactctttttccgaaggtaactggcttcagcagagcg
cagataccaaatactgtccttctagtgtagccgtagttaggccaccacttcaagaactctgtagcaccgcctacatacctcgctctgctaatcc
tgttaccagtggctgctgccagtggcgataagtcgtgtcttaccgggttggactcaagacgatagttaccggataaggcgcagcggtcggg
ctgaacggggggttcgtgcacacagcccagcttggagcgaacgacctacaccgaactgagatacctacagcgtgagctatgagaaagc
gccacgcttcccgaagggagaaaggcggacaggtatccggtaagcggcagggtcggaacaggagagcgcacgagggagcttccagg
gggaaacgcctggtatctttatagtcctgtcgggtttcgccacctctgacttgagcgtcgatttttgtgatgctcgtcaggggggcggagccta
tggaaaaacgccagcaacgcggcctttttacggttcctggccttttgctggccttttgctcacatgt SEQ ID NO: 6 (pX601-meCMV-ABEmaxC2NG)
cctgcaggcagctgcgcgctcgctcgctcactgaggccgcccgggcgtcgggcgacctttggtcgcccggcctcagtgagc
gagcgagcgcgcagagagggagtggccaactccatcactaggggttcctgcggcctctagactcgagCGCGTGATGAGAG
CAGCCACTACGGGTCTAGGCTGCCCATGTAAGGAGGCAAGGCCTGGGGACACCCGA
GATGCCTGGTTATAATTAACCCAGACATGTGGCTGCCCCCCCCCCCCAACACCTGC
TGCCTGCTAAAAATAACCCTGTCCCTGGTGGCcctgcatgcccACTCACGGGGATTTCCAA
GTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTA
CGGTGGGAGGTCTATATAAGCAGAGCTGGTTTAGTGAACCGTCAGATCgctagcaccAT
GATGCTCAAGAAGATCCTCAAGATTGAAGAGTTGGACGAGCGCGAGCTTATAGACA
TAGAAGTCAGTGGTAATCACCTTTTCTACGCAAATGACATTTTGACTCACAACTCCT
CTTCAGACGTTTGCTTCGACTCCGTGGAAATCTCCGGCGTGGAAGATCGGTTCAACG
CCTCCCTGGGCACATACCACGATCTGCTGAAAATTATCAAGGACAAGGACTTCCTG
GACAATGAGGAAAACGAGGACATTCTGGAAGATATCGTGCTGACCCTGACACTGTT
TGAGGACAGAGAGATGATCGAGGAACGGCTGAAAACCTATGCCCACCTGTTCGACG
ACAAAGTGATGAAGCAGCTGAAGCGGCGGAGATACACCGGCTGGGGCAGGCTGAG
CCGGAAGCTGATCAACGGCATCCGGGACAAGCAGTCCGGCAAGACAATCCTGGATT
TCCTGAAGTCCGACGGCTTCGCCAACAGAAACTTCATGCAGCTGATCCACGACGAC
AGCCTGACCTTTAAAGAGGACATCCAGAAAGCCCAGGTGTCCGGCCAGGGCGATAG
CCTGCACGAGCACATTGCCAATCTGGCCGGCAGCCCCGCCATTAAGAAGGGCATCC
TGCAGACAGTGAAGGTGGTGGACGAGCTCGTGAAAGTGATGGGCCGGCACAAGCC
CGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCA
GCCAGATCCTGAAAGAACACCCCGTGGAAAACACCCAGCTGCAGAACGAGAAGCT
GTACCTGTACTACCTGCAGAATGGGCGGGATATGTACGGGACCAGGAACTGGACA
TCAACCGGCTGTCCGACTACGATGTGGACCATATCGTGCCTCAGAGCTTTCTGAAGG
ACGACTCCATCGACAACAAGGTGCTGACCAGAAGCGACAAGAACCGGGGCAAGAG
CGACAACGTGCCCTCCGAAGAGGTCGTGAAGAAGATGAAGAACTACTGGCGGCAG
CTGCTGAACGCCAAGCTGATTACCCAGAGAAAGTTCGACAATCTGACCAAGGCCGA
GAGAGGCGGCCTGAGCGAACTGGATAAGGCCGGCTTCATCAAGAGACAGCTGGTG
GAAACCCGGCAGATCACAAAGCACGTGGCACAGATCCTGGACTCCCGGATGAACAC
TAAGTACGACGAGAATGACAAGCTGATCCGGGAAGTGAAAGTGATCACCCTGAAGT
CCAAGCTGGTGTCCGATTTCCGGAAGGATTTCCAGTTTTACAAAGTGCGCGAGATCA
ACAACTACCACCACGCCCACGACGCCTACCTGAACGCCGTCGTGGGAACCGCCCTG
ATCAAAAAGTACCCTAAGCTGGAAAGCGAGTTCGTGTACGGCGACTACAAGGTGTA
CGACGTGCGGAAGATGATCGCCAAGAGCGAGCAGGAAATCGGCAAGGCTACCGCC
AAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGA
TCGTGTGGGATAAGGGCCGGGATTTTGCCACCGTGCGGAAAGTGCTGAGCATGCCC
CAAGTGAATATCGTGAAAAAGACCGAGGTGCAGACAGGCGGCTTCAGCAAAGAGT
CTATCCgGCCCAAGAGGAACAGCGATAAGCTGATCGCCAGAAAGAAGGACTGGGAC
CCTAAGAAGTACGGCGGCTTCGtCAGCCCCACCGTGGCCTATTCTGTGCTGGTGGTG
GCCAAAGTGGAAAAGGGCAAGTCCAAGAAACTGAAGAGTGTGAAAGAGCTGCTGG
GGATCACCATCATGGAAAGAAGCAGCTTCGAGAAGAATCCCATCGACTTTCTGGAA
GCCAAGGGCTACAAAGAAGTGAAAAAGGACCTGATCATCAAGCTGCCTAAGTACTC
CCTGTTCGAGCTGGAAAACGGCCGAAAGAGAATGCTGGCCTCTGCCcGCtttCTGCAG
AAGGGAAACGAACTGGCCCTGCCCTCCAAATATGTGAACTTCCTGTACCTGGCCAG
CCACTATGAGAAGCTGAAGGGCTCCCCCGAGGATAATGAGCAGAAACAGCTGTTTG
TGGAACAGCACAAGCACTACCTGGACGAGATCATCGAGCAGATCAGCGAGTTCTCC

| SEQUENCES |
|---|
| AAGAGAGTGATCCTGGCCGACGCTAATCTGGACAAAGTGCTGTCCGCCTACAACAA |
| GCACCGGGATAAGCCCATCAGAGAGCAGGCCGAGAATATCATCCACCTGTTTACCC |
| TGACCAATCTGGGAGCCCCTcggGCCTTCAAGTACTTTGACACCACCATCGACCGGA |
| AGgtGTACcggAGCACCAAAGAGGTGCTGGACGCCACCCTGATCCACCAGAGCATCA |
| CCGGCCTGTACGAGACACGGATCGACCTGTCTCAGCTGGGAGGTGACTCTGGCGGC |
| TCAAAAAGAACCGCCGACGGCAGCGAATTCGAGCCCAAGAAGAAGAGGAAAGTCta |
| acTAgtAgaattcctagagctcgctgatcagcctcgactgtgccttctagttgccagcccatctgttgtttgccctccccgtgccttccttg |
| accctggaaggtgccactcccactgtccttcctaataaaatgaggaaattgcatcgcattgtctgagtaggtgtcattctattctgggggtg |
| gggtggggcaggacagcaaggggaggattgggaagagaatagcaggcatgctggggaggtaccgagggcctatttcccatgattcct |
| tcatatttgcatatacgatacaaggctgttagagagataattggaattaatttgactgtaaacacaaagatattagtacaaaatacgtgacgtag |
| aaagtaataaatttcttgggtagtttgcagttttaaaattatgttttaaaatggactatcatatgcttaccgtaacttgaaagtatttcgatttcttgg |
| ctttatatatcttGTGGAAAGGACGAAACACCGGTTATCTCCTGTTCTGCAGCGTTTcAGAGCTA |
| tgctgGAAAcagcatAGCAAGTTgAAATAAGGCTAGTCCGTTATCAACTTGAAAAAGTGG |
| CACCGAGTCGGTGCTTTTTTgcggccgcaggaaccccctagtgatggagttggccactccctctgcgcgctcgctcgc |
| tcactgaggccgggcgaccaaaggtcgcccgacgcccgggctttgcccgggcggcctcagtgagcgagcgagcgcgcagctgcctgc |
| aggggcgcctgatgcggtattttctccttacgcatctgtgcggtatttcacaccgcatacgtcaaagcaaccatagtacgcgccctgtagcgg |
| cgcattaagcgcggcgggtgtggtggttacgcgcagcgtgaccgctacacttgccagcgccctagcgcccgctccttctcgctttcttcccctt |
| cctttctcgccacgttcgccggctttccccgtcaagctctaaatcggggggctcccctttagggttccgatttagtgctttacggcacctcgaccc |
| caaaaaacttgatttgggtgatggttcacgtagtgggccatcgccctgatagacggtttttcgccctttgacgttggagtccacgttctttaata |
| gtggactcttgttccaaactggaacaacactcaaccctatctcgggctattctttttgatttataagggattttgccgatttcggcctattggttaaa |
| aaatgagctgatttaacaaaaatttaacgcgaattttaacaaaatattaacgtttacaattttatggtgcactctcagtacaatctgctctgatgcc |
| gcatagttaagccagccccgacacccgccaacacccgctgacgcgccctgacgggcttgtctgctcccggcatccgcttacagacaagct |
| gtgaccgtctccgggagctgcatgtgtcagaggttttcaccgtcatcaccgaaacgcgcgagacgaaagggcctcgtgatacgcctatttt |
| ataggttaatgtcatgataataatggtttcttagacgtcaggtggcacttttcggggaaatgtgcgcggaacccctatttgtttatttttctaaatac |
| attcaaatatgtatccgctcatgagacaataaccctgataaatgcttcaataatattgaaaaaggaagagtatgagtattcaacatttccgtgtc |
| gcccttattcccttttttgcggcattttgccttcctgtttttgctcacccagaaacgctggtgaaagtaaaagatgctgaagatcagttgggtgca |
| cgagtgggttacatcgaactggatctcaacagcggtaagatccttgagagttttcgccccgaagaacgttttccaatgatgagcacttttaaa |
| gttctgctatgtggcgcggtattatcccgtattgacgccgggcaagagcaactcggtcgccgcatacactattctcagaatgacttggttgag |
| tactcaccagtcacagaaaagcatcttacggatggcatgacagtaagagaattatgcagtgctgccataaccatgagtgataacactgcgg |
| ccaacttacttctgacaacgatcggaggaccgaaggagctaaccgcttttttgcacaacatgggggatcatgtaactcgccttgatcgttggg |
| aaccggagctgaatgaagccataccaaacgacgagcgtgacaccacgatgcctgtagcaatggcaacaacgttgcgcaaactattaactg |
| gcgaactacttactctagcttcccggcaacaattaatagactggatggaggcggataaagttgcaggaccacttctgcgctcggcccttccg |
| gctggctggtttattgctgataaatctggagccggtgagcgtggaagccgcggtatcattgcagcactggggccagatggtaagccctccc |
| gtatcgtagttatctacacgacggggagtcaggcaactatggatgaacgaaatagacagatcgctgagataggtgcctcactgattaagcat |
| tggtaactgtcagaccaagtttactcatatatactttagattgatttaaaacttcatttttaatttaaaaggatctaggtgaagatcctttttgataa |
| tctcatgaccaaaatcccttaacgtgagttttcgttccactgagcgtcagacccgtagaaaagatcaaaggatcttcttgagatccttttttctgcg |
| cgtaatctgctgcttgcaaacaaaaaaaccaccgctaccagcggtggtttgtttgccggatcaagagctaccaactctttttccgaaggtaact |
| ggcttcagcagagcgcagataccaaatactgtccttctagtgtagccgtagttaggccaccacttcaagaactctgtagcaccgcctacata |
| cctcgctctgctaatcctgttaccagtggctgctgccagtggcgataagtcgtgtcttaccgggttggactcaagacgatagttaccggataa |
| ggcgcagcggtcgggctgaacggggggttcgtgcacacagcccagcttggagcgaacgacctacaccgaactgagatacctacagcgt |
| gagctatgagaaagcgccacgcttcccgaagggagaaaggcggacaggtatccggtaagcggcagggtcggaacaggagagcgcac |
| gagggagcttccagggggaaacgcctggtatctttatagtcctgtcgggtttcgccacctctgacttgagcgtcgatttttgtgatgctcgtca |
| ggggggcggagcctatggaaaaacgccagcaacgcggcctttttacggttcctggccttttgctggccttttgctcacatgt |

SEQ ID NO: 7 (pX601-MHP1-ABEmaxN2)
cctgcaggcagctgcgcgctcgctcgctcactgaggccgcccggcgtcgggcgacctttggtcgcccggcctcagtgagc
gagcgagcgcgcagagagggagtggccaactccatcactaggggttcctgcggcctctagactcgaggCCCTTCAGATTAA
AAATAACTGAGGTAAGGGCCTGGGTAGGGGAGGTGGTGTGAGACGCTCCTGTCTCT
CCTCTATCTGCCCATCGGCCCTTTGGGGAGGAGGAATGTGCCCAAGGACTAAAAAA
AGGCCATGGAGCCAGAGGGGCGAGGGCAACAGACCTTTCATGGGCAAACCTTGGG
GCCcTGCTGactgtaGATGAGAGCAGCCACTACGGGTCTAGGCTGCCCATGTAAGGAG
GCAAGGCCTGGGGACACCCGAGATGCCTGGTTATAATTAACCCAGACATGTGGCTG
CCCCCCCCCCCCCAACACCTGCTGCCTGCTAAAAATAACCCTGTCCTGGTGGccCtgc
atgCCCTCCCTGGGGACAGCCCCTCCTGGCTAGTCACACCCTGTAGGGTCCTCTATAT
AACCCAGGGGCACAGGGGCTGCCCtcatttACCACCACCTCCACAGCACAGACAGACA
CTCAGGAGCCAGCccaccatggctagcATGAAACGGACAGCCGACGGAAGCGAGTTCGAGT
CACCAAAGAAGAAGCGGAAAGTCGGATCCTCTGAGGTGGAGTTTTCCCACGAGTAC
TGGATGAGACATGCCCTGACCCTGGCCAAGAGGGCACGCGATGAGAGGGAGGTGC
CTGTGGGAGCCGTGCTGGTGCTGAACAATAGAGTGATCGGCGAGGGCTGGAACAGA
GCCATCGGCCTGCACGACCCAACAGgCCATGCCGAAATTATGGCCCTGAGgCAGGG
CGGCCTGGTCATGCAGAACTACAGACTGATTGACGCCACCCTGTACGgGACATTCGA
GCCTTGCGTGATGTGCGCCGGCGCCATGATCCACTOTAGGATCGGCCGCGTGGTGTT
TGGCGTGAGGAACGCAAAAACCGGCGCCGCAGGCTCCCTGATGGACGTGCTGCACT
ACCCCGGCATGAATCACCGCGTCGAAATTACCGAGGGAATCCTGGCAGATGAATGT
GCCGCCCTGCTGTGCTATTTCTTTCGGATGCCTAGACAGGTGTTCAATGCTCAGAAG
AAGGCCCAGAGCTCCACCGACTCCGGAGGATCTAGCGGAGGCTCCTCTGGCTCTGA
GACACCTGGCACAAGCGAGAGCGCAACACCTGAAAGCAGCGGGGGCAGCAGCGGG
GGGTCAGACAAGAAGTACAGCATCGGCCTGGCCATCGGCACCAACTCTGTGGGCTG
GGCCGTGATCACCGACGAGTACAAGGTGCCCAGCAAGAAATTCAAGGTGCTGGGCA
ACACCGACCGGCACAGCATCAAGAAGAACCTGATCGGAGCCCTGCTGTTCGACAGC
GGCGAAACAGCCGAGGCCACCCGGCTGAAGAGAACCGCCAGAAGAAGATACACCA
GACGGAAGAACCGGATCTGCTATCTGCAAGAGATCTTCAGCAACGAGATGGCCAAG
GTGGACGACAGCTTCTTCCACAGACTGGAAGAGTCCTTCCTGGTGGAAGAGGATAA
GAAGCACGAGCGGCACCCCATCTTCGGCAACATCGTGGACGAGGTGGCCTACCACG
AGAAGTACCCCACCATCTACCACCTGAGAAAGAAACTGGTGGACAGCACCGACAA
GGCCGACCTGCGGCTGATCTATCTGGCCCTGGCCCACATGATCAAGTTCCGGGGCC
ACTTCCTGATCGAGGGCGACCTGAACCCCGACAACAGCGACGTGGACAAGCTGTTC

| SEQUENCES |
|---|
| ATCCAGCTGGTGCAGACCTACAACCAGCTGTTCGAGGAAAACCCCATCAACGCCAG |
| CGGCGTGGACGCCAAGGCCATCCTGTCTGCCAGACTGAGCAAGAGCAGACGGCTGG |
| AAAATCTGATCGCCCAGCTGCCCGGCGAGAAGAAGAATGGCCTGTTCGGAAACCTG |
| ATTGCCCTGAGCCTGGGCCTGACCCCCAACTTCAAGAGCAACTTCGACCTGGCCGA |
| GGATGCCAAACTGCAGCTGAGCAAGGACACCTACGACGACGACCTGGACAACCTGC |
| TGGCCCAGATCGGCGACCAGTACGCCGACCTGTTTCTGGCCGCCAAGAACCTGTCC |
| GACGCCATCCTGCTGAGCGACATCCTGAGAGTGAACACCGAGATCACCAAGGCCCC |
| CCTGAGCGCCTCTATGATCAAGAGATACGACGAGCACCACCAGGACCTGACCCTGC |
| TGAAAGCTCTCGTGCGGCAGCAGCTGCCTGAGAAGTACAAAGAGATTTTCTTCGAC |
| CAGAGCAAGAACGGCTACGCCGGCTACATTGACGGCGGAGCCAGCCAGGAAGAGT |
| TCTACAAGTTCATCAAGCCCATCCTGGAAAAGATGGACGGCACCGAGGAACTGCTC |
| GTGAAGCTGAACAGAGAGGACCTGCTGCGGAAGCAGCGGACCTTCGACAACGGCA |
| GCATCCCCCACCAGATCCACCTGGGAGAGCTGCACGCCATTCTGCGGCGGCAGGAA |
| GATTTTTACCCATTCCTGAAGGACAACCGGGAAAAGATCGAGAAGATCCTGACCTT |
| CCGCATCCCCTACTACGTGGGCCCTCTGGCCAGGGGAAACAGCAGATTCGCCTGGA |
| TGACCAGAAAGAGCGAGGAAACCATCACCCCCTGGAACTTCGAGGAAGTGGTGGA |
| CAAGGGCGCTTCCGCCCAGAGCTTCATCGAGCGGATGACCAACTTCGATAAGAACC |
| TGCCCAACGAGAAGGTGCTGCCCAAGCACAGCCTGCTGTACGAGTACTTCACCGTG |
| TATAACGAGCTGACCAAAGTGAAATACGTGACCGAGGGAATGAGAAAGCCCGCCTT |
| CCTGAGCGGCGAGCAGAAAAAGGCCATCGTGGACCTGCTGTTCAAGACCAACCGGA |
| AAGTGACCGTGAAGCAGCTGAAAGAGGACTACTTCAAGAAAATCGAGTGTTTGGAT |
| CTGAAAACGCAAGTTCAAACGCCACAGGGTATGAAAGAAATATCCAATATACAGGT |
| CGGCGATCTCGTCTTGTCTAACACTGGCTATAACGAGGTGCTGAATGTATTTCCAA |
| AAGCAAGAAAAAAGTTACAAGATAACTCTGGAAGATGGAAAAGAAATTATCTGT |
| TCTGAGGAGCATCTGTTTCCGACCCAAACAGGGGAGATGAATATCAGTGGCGGTCT |
| CAAAGAGGGTATGTGTTTGTATGTCAAGGaataactagtagaattcctagagctcgctgatcagcctcgactgt |
| gccttctagttgccagccatctgttgtttgcccctcccccgtgccttccttgaccctggaaggtgccactcccactgtcctttcctaataaaatga |
| ggaaattgcatcgcattgtctgagtaggtgtcattgtattctgggggggtggggtgggcaggacagcaaggggaggattgggaagaga |
| atagcaggcatgctggggaggtaccgagggcctatttcccatgattccttcatatttgcatatacgatacaaggctgttagagagataattgg |
| aattaatttgactgtaaacacaaagatattagtacaaaatacgtgacgtagaaagtaataatttcttgggtagtttgcagttttaaaattatgttttta |
| aaatggactatcatatgcttaccgtaacttgaaagtatttcgatttcttggctttatatatcttGTGGAAAGGACGAAACACCG |
| GTTATCTCCTGTTCTGCAGCGTTTcAGAGCTAtgctgGAAAcagcaTAGCAAGTTgAAATA |
| AGGCTAGTCCGTTATCAACTTGAAAAAGTGGCACCGAGTCGGTGCTTTTTTgcggccgca |
| ggaaccctagtgatggagttggccactccctctctgcgcgctcgctcgctcactgaggccgggcgaccaaaggtcgcccgacgcccgg |
| gctttgcccgggcggcctcagtgagcgagcgagcgcgcagctgcctgcaggggcgcctgatgcggtattttctccttacgcatctgtgcg |
| gtatttcacaccgcatacgtcaaagcaaccatagtacgcgccctgtagcggcgcattaagcgcggcgggtgtggtggttacgcgcagcgt |
| gaccgctacacttgccagcgccctagcgcccgctccttcgctttcttcccttcctttctcgccacgttcgccggctttccccgtcaagctctaa |
| atcgggggctccctttagggttccgatttagtgctttacggcacctcgaccccaaaaaacttgatttgggtgatggttcacgtagtgggccatc |
| gccctgatagacggtttttcgccctttgacgttggagtccacgttctttaatagtggactcttgttccaaactggaacaacactcaaccctatctc |
| gggctattcttttgatttataaggattttgccgatttcggcctattggttaaaaaatgagctgatttaacaaaaatttaacgcgaattttaacaaaa |
| tattaacgtttacaattttatggtgcactctcagtacaatctgctctgatgccgcatagttaagccagccccgacacccgccaacacccgctga |
| cgcgccctgacgggcttgtctgctcccggcatccgcttacagacaagctgtgaccgtctccgggagctgcatgtgtcagaggttttcaccgt |
| catcaccgaaacgcgcgagacgaaagggcctcgtgatacgcctatttttataggttaatgtcatgataataatggtttcttagacgtcaggtgg |
| cacttttcggggaaatgtgcgcggaacccctatttgtttatttttctaaatacattcaaatatgtatccgctcatgagacaataaccctgataaatg |
| cttcaataatattgaaaaaggaagagtatgagtattcaacatttccgtgt.cgcccttattccctttttgcggcattttgccttcctgtttttgctc |
| acccagaaacgctggtgaaagtaaaagatgctgaagatcagttgggtgcacgagtgggttacatcgaactggatctcaacagcggtaagatc |
| cttgagagttttcgccccgaagaacgttttccaatgatgagcacttttaaagttctgctatgtggcgcggtattatcccgtattgacgccgggca |
| agagcaactcggtcgccgcatacactattctcagaatgacttggttgagtactcaccagtcacagaaaagcatcttacggatggcatgacag |
| taagagaattatgcagtgctgccataaccatgagtgataacactgcggccaacttacttctgacaacgatcggaggaccgaaggagctaac |
| cgcttttttgcacaacatgggggatcatgtaactcgccttgatcgttgggaaccggagctgaatgaagccataccaaacgacgagcgtgac |
| accacgatgcctgtagcaatggcaacaacgttgcgcaaactattaactggcgaactacttactctagcttcccggcaacaattaatagactgg |
| atggaggcggataaagttgcaggaccacttctgcgctcggcccttccggctggctggtttattgctgataaatctggagccggtgagcgtg |
| gaagccgcggtatcattgcagcactggggccagatggtaagccctcccgtatcgtagttatctacacgacggggagtcaggcaactatgg |
| atgaacgaaatagacagatcgctgagataggtgcctcactgattaagcattggtaactgtcagaccaagtttactcatatatactttagattgat |
| ttaaaacttcatttttaatttaaaaggatctaggtgaagatcctttttgataatctcatgaccaaaatcccttaacgtgagttttcgttccactgagcg |
| tcagaccccgtagaaaagatcaaaggatcttcttgagatccttttttttctgcgcgtaatctgctgcttgcaaacaaaaaaaccaccgctaccag |
| cggtggtttgtttgccggatcaagagctaccaactctttttccgaaggtaactggcttcagcagagcgcagataccaaatactgtccttctagt |
| gtagccgtagttaggccaccacttcaagaactctgtagcaccgcctacatacctcgctctgctaatcctgttaccagtggctgctgccagtgg |
| cgataagtcgtgtcttaccgggttggactcaagacgatagttaccggataaggcgcagcggtcgggctgaacggggggttcgtgcacaca |
| gcccagcttggagcgaacgacctacaccgaactgagatacctacagcgtgagctatgagaaagcgccacgcttcccgaagggagaaag |
| gcggacaggtatccggtaagcggcagggtcggaacaggagagcgcacgagggagcttccagggggaaacgcctggtatctttatagtc |
| ctgtcgggtttcgccacctctgacttgagcgtcgatttttgtgatgctcgtcaggggggcggagcctatggaaaaacgccagcaacgcggc |
| cttttacggttcctggccttttgctggccttttgctcacatgt |

SEQ ID NO: 8 (pX601-MHP1-iABEmaxC2NG: ITR-MHP1-Gp41-1 inteinC-
Cas9NG574-1368-NLS-bGHpA-hU6-mdx4cv_spacer-ogRNA_scaffold-ITR)
cctgcaggcagctgcgcgctcgctcgctcactgaggccgcccgggcgtcgggcgacctttggtcgcccggcctcagtgagc
gagcgagcgcgcagagagggagtggccaactccatcactaggggttcctgcggcctctagactcgaggCCCTTCAGATTAA
AAATAACTGAGGTAAGGGCCTGGGTAGGGGAGGTGGTGTGAGACGCTCCTGTCTCT
CCTCTATCTGCCCATCGGCCCTTTGGGGAGGAGGAATGTGCCCAAGGACTAAAAAA
AGGCCATGGAGCCAGAGGGGCGAGGGCAACAGACCTTTCATGGGCAAACCTTGGG
GCCCTGCTGactgtaGATGAGAGCAGCCACTACGGGTCTAGGCTGCCCATGTAAGGAG
GCAAGGCCTGGGACACCCGAGATGCCTGGTTATAATTAACCCAGACATGTGGCTG
CCCCCCCCCCCCAACACCTGCTGCCTGCTAAAAATAACCCTGTCCCTGGTGGCCCTGC
atgCcCTCCCTGGGGACAGCCCCTCCTGGCTAGTCACACCCTGTAGGCTCCTCTATAT
AACCCAGGGGCACAGGGGCTGCCCtcatttACCACCACCTCCACAGCACAGACAGACA
CTCAGGAGCCAGCtagccaccATGATGCTCAAGAAGATCCTCAAGATTGAAGAGTTGGA

| SEQUENCES |
|---|
| CGAGCGCGAGCTTATAGACATAGAAGTCAGTGGTAATCACCTTTTCTACGCAAATG |
| ACATTTTGACTCACAACTCCTCTTCAGACGTTTGCTTCGACTCCGTGGAAATCTCCG |
| GCGTGGAAGATCGGTTCAACGCCTCCCTGGGCACATACCACGATCTGCTGAAAATT |
| ATCAAGGACAAGGACTTCCTGGACAATGAGGAAAACGAGGACATTCTGGAAGATA |
| TCGTGCTGACCCTGACACTGTTTGAGGACAGAGAGATGATCGAGGAACGGCTGAAA |
| ACCTATGCCCACCTGTTCGACGACAAAGTGATGAAGCAGCTGAAGCGGCGGAGATA |
| CACCGGCTGGGGCAGGCTGAGCCGGAAGCTGATCAACGGCATCCGGGACAAGCAG |
| TCCGGCAAGACAATCCTGGATTTCCTGAAGTCCGACGGCTTCGCCAACAGAAACTT |
| CATGCAGCTGATCCACGACGACAGCCTGACCTTTAAAGAGGACATCCAGAAAGCCC |
| AGGTGTCCGGCCAGGGCGATAGCCTGCACGAGCACATTGCCAATCTGGCCGGCAGC |
| CCCGCCATTAAGAAGGGCATCCTGCAGACAGTGAAGGTGGTGGACGAGCTCGTGAA |
| AGTGATGGGCCGGCACAAGCCCGAGAACATCGTGATCGAAATGGCCAGAGAGAAC |
| CAGACCACCCAGAAGGGACAGAAGAACAGCCGCGAGAGAATGAAGCGGATCGAAG |
| AGGGCATCAAAGAGCTGGGCAGCCAGATCCTGAAAGAACACCCCGTGGAAAACAC |
| CCAGCTGCAGAACGAGAAGCTGTACCTGTACTACCTGCAGAATGGGCGGGATATGT |
| ACGTGGACCAGGAACTGGACATCAACCGGCTGTCCGACTACGATGTGGACCATATC |
| GTGCCTCAGAGCTTTCTGAAGGACGACTCCATCGACAACAAGGTGCTGACCAGAAG |
| CGACAAGAACCGGGGCAAGAGCGACAACGTGCCCTCCGAAGAGGTCGTGAAGAAG |
| ATGAAGAACTACTGGCGGCAGCTGCTGAACGCCAAGCTGATTACCCAGAGAAAGTT |
| CGACAATCTGACCAAGGCCGAGAGAGGCGGCCTGAGCGAACTGGATAAGGCCGGC |
| TTCATCAAGAGACAGCTGGTGGAAACCCGGCAGATCACAAAGCACGTGGCACAGAT |
| CCTGGACTCCCGGATGAACACTAAGTACGACGAGAATGACAAGCTGATCCGGGAAG |
| TGAAAGTGATCACCCTGAAGTCCAAGCTGGTGTCCGATTTCCGGAAGGATTTCCAGT |
| TTTACAAAGTGCGCGAGATCAACAACTACCACCACGCCCACGACGCCTACCTGAAC |
| GCCGTCGTGGGAACCGCCCTGATCAAAAAGTACCCTAAGCTGGAAAGCGAGTTCGT |
| GTACGGCGACTACAAGGTGTACGACGTGCGGAAGATGATCGCCAAGAGCGAGCAG |
| GAAATCGGCAAGGCTACCGCCAAGTACTTCTTCTACAGCAACATCATGAACTTTTTC |
| AAGACCGAGATTACCCTGGCCAACGGCGAGATCCGGAAGCGGCCTCTGATCGAGAC |
| AAACGGCGAAACCGGGGAGATCGTGTGGGATAAGGGCCGGGATTTTGCCACCGTGC |
| GGAAAGTGCTGAGCATGCCCCAAGTGAATATCGTGAAAAAGACCGAGGTGCAGAC |
| AGGCGGCTTCAGCAAGAGTCTATCCgGCCCAAGAGGAACAGCGATAAGCTGATCG |
| CCAGAAAGAAGGACTGGGACCCTAAGAAGTACGGCGGCTTCGtCAGCCCCACCGTG |
| GCCTATTCTGTGCTGGTGGTGGCCAAAGTGGAAAAGGGCAAGTCCAAGAAACTGAA |
| GAGTGTGAAAGAGCTGCTGGGGATCACCATCATGGAAAGAAGCAGCTTCGAGAAG |
| AATCCCATCGACTTTCTGGAAGCCAAGGGCTACAAAGAAGTGAAAAAGGACCTGAT |
| CATCAAGCTGCCTAAGTACTCCCTGTTCGAGCTGGAAAACGGCCGGAAGAGAATGC |
| TGGCCTCTGCCcGCtttCTGCAGAAGGGAAACGAACTGGCCCTGCCCTCCAAATATGT |
| GAACTTCCTGTACCTGGCCAGCCACTATGAGAAGCTGAAGGGCTCCCCCGAGGATA |
| ATGAGCAGAAACAGCTGTTTGTGGAACAGCACAAGCACTACCTGGACGAGATCATC |
| GAGCAGATCAGCGAGTTCTCCAAGAGAGTGATCCTGGCCGACGCTAATCTGGACAA |
| AGTGCTGTCCGCCTACAACAAGCACCGGGATAAGCCCATCAGAGAGCAGGCCGAG |
| AATATCATCCACCTGTTTACCCTGACCAATCTGGGAGCCCCTCgGGCCTTCAAGTACT |
| TTGACACCACCATCGACCGGAAGgtGTACggAGCACCAAAGAGGTGCTGGACGCCA |
| CCCTGATCCACCAGAGCATCACCGGCCTGTACGAGACACGGATCGACCTGTCTCAG |
| CTGGGAGGTGACTCTGGCGGCTCAAAAAGAACCGCCGACGGCAGCGAATTCGAGCC |
| CAAGAAGAAGAGGAAAGTCtaacTAgtAgaattcctagagctcgctgatcagcctcgactgtgccttctagttgccag |
| ccatctgttgtttgcccctcccccgtgccttccttgaccctggaaggtgccactcccactgtcctttcctaataaaatgaggaaattgcatcgca |
| ttgtctgagtaggtgtcattctattctggggggtggggtggggcaggacagcaaggggaggattgggaagagaatagcaggcatgctg |
| gggaggtaccgagggcctatttcccatgattccttcatatttgcatatacgatacaaggctgttagagagataattggaattaatttgactgtaa |
| acacaaagatattagtacaaaatacgtgacgtagaaagtaataatttcttgggtagtttgcagtttttaaaattatgtttttaaaatggactatcatatg |
| cttaccgtaacttgaaagtatttcgatttcttggctttatatatcttGTGGAAAGGACGAAACACCGGTTATCTCCT |
| GTTCTGCAGCGTTTcAGAGCTAtgctgAAAcagcaTAGCAAGTTgAAATAAGGCTAGTCC |
| GTTATCAACTTGAAAAAGTGGCACCGAGTCGGTGCTTTTTTgccggccgcaggaaccccctagtgatg |
| gagttggccactccctctctgcgcgctcgctcgctcactgaggccgggcgaccaaaggtcgcccgacgcccgggctttgccggggcgg |
| cctcagtgagcgagcgagcgcgcagctgcctgcaggggcgcctgatgcggtattttctccttacgcatctgtgcggtatttcacaccgcata |
| cgtcaaagcaaccatagtacgcgccctgtagcggcgcattaagcgcggcgggtgtggtggttacgcgcagcgtgaccgctacacttgcc |
| agcgccctagcgcccgctccttcgctttcttcccttcctttctcgccacgttcgccggctttccccgtcaagctctaaatcgggggctccctttta |
| gggttccgatttagtgctttacggcacctcgaccccaaaaaacttgatttgggtgatggttcacgtagtgggccatcgccctgatagacggttt |
| ttcgccctttgacgttggagtccacgttctttaatagtggactcttgttccaaactggaacaacactcaaccctatctcgggctattcttttgattta |
| taagggattttgccgatttcggcctattggttaaaaaatgagctgatttaacaaaaatttaacgcgaattttaacaaaatattaacgtttacaattttt |
| atggtgcactctcagtacaatctgctctgatgccgcatagttaagccagccccgacacccgccaacacccgctgacgcgccctgacgggc |
| ttgtctgctcccggcatccgcttacagacaagctgtgaccgtctccgggagctgcatgtgtcagaggttttcaccgtcatcaccgaaacgcg |
| cgagacgaaagggcctcgtgatacgcctatttttataggttaatgtcatgataataatggtttcttagacgtcaggtggcacttttcggggaaat |
| gtgcgcggaaccccatttgtttatttttctaaatacattcaaatatgtatccgctcatgagacaataaccctgataaatgcttcaataatattgaaa |
| aaggaagagtatgagtattcaactttccgtgtcgcccttattcccttttttgcggcattttgccttcctgttttgctcacccagaaacgctggtg |
| aaagtaaaagatgctgaagatcagttgggtgcacgagtgggttacatcgaactggatctcaacagcggtaagatccttgagagttttcgccc |
| cgaagaacgttttccaatgatgagcactttaaagttctgctatgtggcgcggtattatcccgtattgacgccgggcaagagcaactcggtcg |
| ccgcatacactattctcagaatgacttggttgagtactcaccagtcacagaaaagcatcttacggatggcatgacagtaagagaattatgcag |
| tgctgccataaccatgagtgataacactgcggccaacttacttctgacaacgatcggaggaccgaaggagctaaccgcttttttgcacaaca |
| tgggggatcatgtaactcgccttgatcgttgggaaccggagctgaatgaagccataccaaacgacgagcgtgacaccacgatgcctgtag |
| caatggcaacaacgttgcgcaaactattaactggcgaactacttactctagcttcccggcaacaattaatagactggatggaggcggataaa |
| gttgcaggaccacttctgcgctcggcccttccggctggctggtttattgctgataaatctggagccggtgagcgtggaagccgcggtatcat |
| tgcagcactggggccagatggtaagccctcccgtatcgtagttatctacacgacggggagtcaggcaactatggatgaacgaaatagaca |
| gatcgctgagataggtgcctcactgattaagcattggtaactgtcagaccaagtttactcatatatactttagattgatttaaaacttcattttttaat |
| ttaaaaggatctaggtgaagatcctttttgataatctcatgaccaaaatcccttaacgtgagttttcgttccactgagcgtcagaccccgtagaaa |
| agatcaaaggatcttcttgagatcctttttttctgcgcgtaatctgctgcttgcaaacaaaaaaaccaccgctaccagcggtggtttgtttgccg |
| gatcaagagctaccaactctttttccgaaggtaactggcttcagcagagcgcagataccaaatactgtccttctagtgtagccgtagttaggc |

-continued

| SEQUENCES |
|---|
| caccacttcaagaactctgtagcaccgcctacatacctcgctctgctaatcctgttaccagtggctgctgccagtggcgataagtcgtgtctta |
| ccgggttggactcaagacgatagttaccggataaggcgcagcggtcgggctgaacgggggttcgtgcacacagcccagcttggagcg |
| aacgacctacaccgaactgagatacctacagcgtgagctatgagaaagcgccacgcttcccgaagggagaaaggcggacaggtatccg |
| gtaagcggcagggtcggaacaggagagcgcacgagggagcttccagggggaaacgcctggtatctttatagtcctgtcgggtttcgcca |
| cctctgacttgagcgtcgattttgtgatgctcgtcagggggcggagcctatggaaaaacgccagcaacgcggccttttacggttcctgg |
| cctttgctggccttttgctcacatgt |

SEQ ID NO: 9 (pLenti-mdx$^{4cv}$-ogRNA: U6 promoter, mdx4cv spacer, optimized gRNA scaffold)
gtcgacggatcgggagatctcccgatcccctatggtgcactctcagtacaatctgctctgatgccgcatagttaagccagtatctg
ctccctgcttgtgtgttggaggtcgctgagtagtgcgcgagcaaaatttaagctacaacaaggcaaggcttgaccgacaattgcatgaagaa
tctgcttagggttaggcgttttgcgctgcttcgcgatgtacgggccagatatacgcgttgacattgattattgactagttattaatagtaatcaatt
acggggtcattagttcatagcccatatatggagttccgcgttacataacttacggtaaatggcccgcctggctgaccgcccaacgacccccg
cccattgacgtcaataatgacgtatgttcccatagtaacgccaatagggactttccattgacgtcaatgggtggagtatttacggtaaactgcc
cacttggcagtacatcaagtgtatcatatgccaagtacgccccctattgacgtcaatgacggtaaatggcccgcctggcattatgcccagtac
atgaccttatggacttcctacttggcagtacatctacgtattagtcatcgctattaccatggtgatgcggttttggcagtacatcaatgggcgt
ggatagcggttttgactcacggggatttccaagtctccaccccattgacgtcaatggggagtttgttttggcaccaaaatcaacgggactttcca
aaatgtcgtaacaactccgccccattgacgcaaatgggcggtaggcgtgtacggtgggaggtctatataagcagcgcgttttgcctgtactg
ggtctctctggttagaccagatctgagcctgggagctctctggctaactagggaacccactgcttaagcctcaataaagcttgccttgagtgc
ttcaagtagtgtgtgcccgtctgttgtgtgactctggtaactagagatccctcagacccttttagtcagtgtggaaaatctctagcagtggcgcc
cgaacagggacttgaaagcgaaagggaaaccagaggagctctctcgacgcaggactcggcttgctgaagcgcgcacggcaagaggc
gaggggcggcgactggtgagtacgccaaaaattttgactagcggaggctagaaggagagagatgggtgcgagagcgtcagtattaagc
gggggagaattagatcgcgatgggaaaaaattcggttaaggccagggggaaagaaaaaatataaattaaaacatatagtatgggcaagca
gggagctagaacgattcgcagttaatcctggcctgttagaaacatcagaaggctgtagacaaaatactgggacagctacaaccatcccttca
gacaggatcagaagaacttagatcattatataatacagtagcaaccctctattgtgtgcatcaaaggatagagatcaaaagacaccaaggaag
ctttagacaagatagaggaagagcaaaacaaaagtaagaccaccgcacagcaagcggccgctgatcttcagacctggaggaggagata
tgagggacaattggagaagtgaattatataaatataaagtagtaaaaattgaaccattaggagtagcacccaccaaggcaaagaagagt
ggtgcagagaaaaaagacagtgggaataggagctttgttccttgggttcttgggagcagcaggaagcactatgggcgcagcgtcaa
tgacgctgacggtacaggccagacaattattgtctggtatagtgcagcagcagaacaattgctgagggctattgaggcgcaacagcatct
gttgcaactcacagtctggggcatcaagcagctccaggcaagaatcctggctgtggaaagataccctaaaggatcaacagctcctgggatt
tggggttgctctggaaaactcatttgcaccactgctgtgccttggaatgctagttggagtaataaatctctggaacagatttggaatcacacga
cctgatggagtgggacagagaaattaacaattacacaagcttaatacactccttaattgaagaatcgcaaaaccagcaagaaaagaatga
acaagaattattggaattagataaatgggcaagtttgtggaattggttttaacataacaaattggctgtgtatataaaattattcataatgatagta
ggaggcttggtaggtttaagaatagtttttgctgtactttctatagtgaatagagttaggcagggatattcaccattatcgtttcagacccacctc
ccaacccgaggggacccgacaggcccgaaggaatagaagaagaaggtggagagagaacagagacagatccattcgattagtgaa
cggatcggcactgcgtgcgccaattctgcagacaaatggcagtattcatccacaattttaaaagaaaaggggggattgggggtacagtgc
aggggaaagaatagtagacataataagcaacagacatacaaaactaaagaattacaaaaacaaattacaaaaattcaaaattttcgggtttatta
cagggacagcagagatccagtttggttaattagctagcaggtacctgagggcctatttcccatgattccttcatatttgcatatacgatacaag
gctgttagagagataattggaattaatttgactgtaaacacaaagatattagtacaaaatacgtgacgtagaaagtaataatttcttgggtagttt
gcagtttaaaattatgttttaaaatggactatcatatgcttaccgtaacttgaaagtatttcgatttcttggctttatatatcttgtggaaaggacga
aacaccgGTTATCTCCTGTTCTGCAGCGTTTcAGAGCTAtgctgGAAAcagcaTAGCAAGTTgA
AATAAGGCTAGTCCGTTATCAACTTGAAAAAGTGGCACCGAGTCGGTGCTTTTTTgcg
gccgcggatcctgcaaagatggataaagttttaaacagagaggaatctttgcagctaatggaccttctaggtcttgaaaggagtgggaattg
gctccggtgcccgtcagtgggcagagcgcacatcgcccacagtccccgagaagttgggggagggtcggcaattgatccggtgccta
gagaaggtggcgcggggtaaactgggaaagtgatgtcgtgtactggctcgcctttttcccgagggtgggggagaaccgtatataagtgc
agtagtcgccgtgaacgttcttttttcgcaacgggtttgccgccagaacacaggtaagtgccgtgtgtggttcccgcgggcctggcctctttac
gggttatggcccttgcgtgccttgaattacttccactggctgcagtacgtgattcttgatcccgagcttcgggttggaagtgggtgggagagtt
cgaggccttgcgcttaaggagccccttcgcctcgtgcttgagttgaggcctggcctgggcgctggggccgccgcgtgcgaatctggtggc
accttcgcgcctgtctcgctgcttcgataagtctctagccatttaaaattttttgatgacctgctgcgacgctttttttctggcaagatagtcttgta
aatgcgggccaagatctgcacactggtatttcggtttttggggccgcggccggcgacggggcccgtgcgtcccagcgcacatgttcggc
gaggcgggcctgcgagcgcggccaccgagaatcggacggggtagtctcaagctggccggcctgctctggtgcctggcctcgcgcc
gccgtgtatcgccccgccctgggcggcaaggctgcccggtcggcaccagttgcgtgagcggaaagatggccgcttcccggccctgct
gcagggagctcaaaatggaggacgcggcgctcgggagagcgggcgggtgagtcacccacacaaaggaaaagggcctttccgtcctca
gccgtcgcttcatgtgactccacgagtaccgggcgccgtccaggcacctcgattagttctccgagctttggagtacgtcgtctttaggttgg
ggggaggggttttatgcgatggagtttccccacactgagtgggtggagactgaagttaggccagcttggcacttgatgtaattctccttggaa
tttgccctttttgagtttggatcttggttcattctcaagcctcagacagtggttcaaagtttttttcttccatttcaggtgtcgtgatgtacaatggcc
aagttgaccagtgccgttccggtgctcaccgcgcgcgacgtcgccggagcggtcgagttctggaccgaccggctcgggttcccgggac
ttcgtggaggacgacttcgcccggtgtggtccggacgacgtgaccctgttcatcagcgcggtccaggcaggtggtgccggcaacac
cctgcctggtgggtgcgcggcctggacgagctgtacgccgagtggtcggagtcgtgtccacgaactccggacgcctccgg
ccggccatgaccgagatcggcgagcagccgtggggcgggagttcgcctcgcgaccccggcggcaactcgtgcacttcgtgcc
gaggagcaggactgagaattcgatatcaagcttatcggtaatcaacctctggattacaaaatttgtgaaagattgactggtattcttaactatgtt
gctccttttacgctatgtggatacgctgctttaatgcctttgtatcatgctattgcttcccgtatggctttcattttctcctccttgtataaatcctg
gttgctgtctctttatgaggagttgtgcccgttgtcaggcaactggtggtgttgcactgtgtttgctgacgcaaccccactggttggggcat
tgccaccacctgtcagctcctttccgggactttcgctttccccctccctattgccacggcggaactcatcgccgcctgccttgcccgctgctg
gacagggctcggctgttgggcactgacaattccgtggtgttgtcggggaaatcatcgtcctttccttggctgctcgcctgtgttgccacctg
gattctgcgcgggacgtccttctgctacgtcccttcggccctcaatccagcggaccttccttcccgcggcctgctgccggctctgcggcctct
tccgcgtcttcgccttcgccctcagacgagtcggatctcccttttgggccgcctccccgcatcgataccgtcgacctcgagacctagaaaaac
atggagcaatcacaagtagcaatacagcagctaccaatgctgattgtgcctggctagaagcacaagaggaggaggagggtggtttttccag
tcacacctcaggtacctttaagaccaatgacttacaaggcagctgtagatcttagccacttttttaaaagaaaaggggggactggaagggcta
attcactcccaacgaagacaagatatccttgatctgtggatctaccacacacaaggctacttccctgattggcagaactacacaccagggcc
agggatcagatatccactgacctttggatggtgctacaagctagtaccagttgagcaagagaaggtagaagaagccaatgaaggagaa
caccgcttgttacaccctgtgagcctgcatgggatggatgacccggagagagaagtattagagtggaggtttgacagccgcctagcatttt
catcacatggcccgagagctgcatccggactgtactgggtctctctggttagaccagatctgagcctgggagctctctggctaactaggga
acccactgcttaagcctcaataaagcttgccttgagtgcttcaagtagtgtgtgcccgtctgttgtgtgactctggtaactagagatccctcaga
cccttttagtcagtgtggaaaatctctagcagggcccgtttaaacccgctgatcagcctcgactgtgccttctagttgccagccatctgttgttt
gcccctcccccgtgccttccttgaccctggaaggtgccactcccactgtcctttcctaataaaatgaggaaattgcatcgcattgtctgagtag
gtgtcattctattctggggggtggggtggggcaggacagcaagggggaggattgggaagacaatagcaggcatgctggggatgcggtg

```
ggctctatggcttctgaggcggaaagaaccagctggggctctaggggggtatccccacgcgccctgtagcggcgcattaagcgcggcgg
gtgtggtggttacgcgcagcgtgaccgctacacttgccagcgccctagcgcccgctcctttcgctttcttcccttcctttctcgccacgttcgc
cggctttccccgtcaagctctaaatcgggggctcccttagggttccgatttagtgctttacggcacctcgaccccaaaaaacttgattagggt
gatggttcacgtagtgggccatcgccctgatagacggttttttcgccctttgacgttggagtccacgttctttaatagtggactcttgttccaaact
ggaacaacactcaaccctatctcggtctattcttttgatttataagggattttgccgattcggcctattggttaaaaaatgagctgatttaacaaa
aatttaacgcgaattaattctgtggaatgtgtgtcagttagggtgtggaaagtccccaggctccccagcaggcagaagtatgcaaagcatgc
atctcaattagtcagcaaccaggtgtggaaagtccccaggctccccagcaggcagaagtatgcaaagcatgcatctcaattagtcagcaac
catagtcccgcccctaactccgcccatcccgcccctaactccgcccagttccgcccattctccgccccatggctgactaatttttttttatttatgc
agaggccgaggccgcctctgcctctgagctattccagaagtagtgaggaggcttttttggaggcctaggcttttgcaaaaagctcccggga
gcttgtatatccattttcggatctgatcagcacgtgttgacaattaatcatcggcatagtatatcggcatagtataatacgacaaggtgaggaac
taaaccatggccaagttgaccagtgccgttccggtgctcaccgcgcgcgacgtcgccggagcggtcgagttctggaccgaccggctcgg
gttctcccggggacttcgtggaggacgacttcgccggtgtggtccgggacgacgtgaccgttcatcagcgcggtccaggaccaggtggt
gccggacaacacctggcctgggtgtgggtgcgcggcctggacgagctgtacgcgagtggtcggaggtcgtgtccacgaacttccgg
gacgcctccgggccggccatgaccgagatcggcgagcagccgtgggggcgggagttcgccctgcgcgacccggccggcaactgcgt
gcacttcgtggccgaggagcaggactgacacgtgctacgagatttcgattccaccgccgcctctatgaaaggtttgggcttcggaatcgttt
tccgggacgccggctggatgatcctccagcgcggggatctcatgctggagtttcttcgcccacccccaacttgttttattgcagcttataatggtt
acaaataaagcaatagcatcacaaatttcacaaataaagcattttttttcactgcattctagttgtggtttgtccaaactcatcaatgtatcttatcat
gtctgtataccgtcgacctctagctagagcttggcgtaatcatggtcatagctgtttcctgtgtgaaattgttatccgctcacaattccacacaac
atacgagccggaagcataaagtgtaaagcctggggtgcctaatgagtgagctaactcacattaattgcgttgcgctcactgcccgctttcca
gtcgggaaacctgtcgtgccagctgcattaatgaatcggccaacgcgcggggagaggcggtttgcgtattgggcgctcttccgcttcctcg
ctcactgactcgctgcgctcggtcgttcggctgcggcgagcggtatcagctcactcaaaggcggtaatacggttatccacagaatcagggg
ataacgcaggaaagaacatgtgagcaaaaggccagcaaaaggccaggaaccgtaaaaaggccgcgttgctggcgtttttccataggctc
cgcccccctgacgagcatcacaaaaatcgacgctcaagtcagaggtggcgaaacccgacaggactataaagataccaggcgtttcccc
tggaagctccctcgtgcgctctcctgttccgaccctgccgcttaccggatacctgtccgcctttctcccttcgggaagcgtggcgctttctcat
agctcacgctgtaggtatctcagttcggtgtaggtcgttcgctccaagctgggctgtgtgcacgaacccccgttcagcccgaccgctgcg
ccttatccggtaactatcgtcttgagtccaacccggtaagacacgacttatcgccactggcagcagccactggtaacaggattagcagagc
gaggtatgtaggcggtgctacagagttcttgaagtggtggcctaactacggctacactagaagaacagtatttggtatctgcgctctgctgaa
gccagttaccttcggaaaaagagttggtagctcttgatccggcaaacaaaccaccgctggtagcggtggtttttttgtttgcaagcagcagat
tacgcgcagaaaaaaggatctcaagaagatcctttgatcttttctacggggtctgacgctcagtggaacgaaaactcacgttaagggatttt
ggtcatgagattatcaaaaaggatcttcacctagatccttttaaattaaaaatgaagttttaaatcaatctaaagtatatatgagtaaacttggtct
gacagttaccaatgcttaatcagtgaggcacctatctcagcgatctgtctatttcgttcatccatagttgcctgactccccgtcgtgtagataact
acgatacgggagggcttaccatctggccccagtgctgcaatgataccgcgagacccacgctcaccggctccagatttatcagcaataaac
cagccagccgaagggccgagccgagcagaagtggtcctgcaactttatccgcctccatccagtctattaattgttgccgggaagctagagtaa
gtagttcgccagttaatagtttgcgcaacgttgttgccattgctacaggcatcgtggtgtcacgctcgtcgtttggtatggcttcattcagctccg
gttcccaacgatcaaggcgagttacatgatccccatgttgtgcaaaaaagcggttagctccttcggtcctccgatcgttgtcagaagtaagtt
ggccgcagtgttatcactcatggttatggcagcactgcataattctcttactgtcatgccatccgtaagatgcttttctgtgactggtgagtactc
aaccaagtcattctgagaatagtgtatgcggcgaccgagttgctcttgcccggcgtcaatacgggataataccgcgccacatagcagaactt
taaaagtgctcatcattggaaaacgttcttcggggcgaaaactctcaaggatcttaccgctgttgagatccagttcgatgtaacccactcgtgc
acccaactgatcttcagcatcttttactttcaccagcgtttctgggtgagcaaaaacaggaaggcaaaatgccgcaaaaaagggaataagg
gcgacacggaaatgttgaatactcatactcttcctttttcaatattattgaagcatttatcagggttattgtctcatgagcggatacatatttgaatg
tatttagaaaaataaacaaatagggggttccgcgcacatttccccgaaaagtgccacctgac
```

SEQ ID NO: 10 (pLKO-puro-2A-mdx<sup>4cv</sup>-EGFP)
```
gggtctctctggttagaccagatctgagcctgggagctctctggctaactagggaacccactgcttaagcctcaataaagcttgc
cttgagtgcttcaagtagtgtgtgcccgtctgttgtgtgactctggtaactagagatccctcagacccttttagtcagtgtggaaaatctctagc
agtggcgcccgaacagggacttgaaagcgaaagggaaaccagaggagctctctcgacgcaggactcggcttgctgaagcgcgcacgg
caagaggcgaggggcggcgactggtgagtacgccaaaaattttgactagcggaggctagaaggagagagatgggtgcgagagcgtca
gtattaagcgggggagaattagatcgcgatgggaaaaaattcggttaaggccagggggaaagaaaaaatataaattaaaacatatagtatg
ggcaagcagggagctagaacgattcgcagttaatcctggcctgttagaaacatcagaaggctgtagacaaatactgggacagctacaacc
atcccttcagacaggatcagaagaacttagatcattatataatacagtagcaaccctctattgtgtgcatcaaaggatagagataaaagacac
caaggaagctttagacaagatagaggaagagcaaaacaaaagtaagaccaccgcacagcaagcggccgctgatcttcagacctggagg
aggagatatgagggacaattggagaagtgaattatataaatataaagtagtaaaaattgaaccattaggagtagcacccaccaaggcaaag
agaagagtggtgcagagagaaaaaagagcagtggaataggagctttgttccttgggttcttgggagcagcaggaagcactatgggcgc
agcgtcaatgacgctgacggtacaggccagacaattattgtctggtatagtgcagcagcagaacaatttgctgagggctattgaggcgcaa
cagcatctgttgcaactcacagtctggggcatcaagcagctccaggcaagaatcctggctgtggaaagatacctaaaggatcaacagctcc
tggggatttggggttgctctggaaaactcatttgcaccactgctgtgccttggaatgctagttggagtaataaatctctggaacagatttggaat
cacacgacctggatggagtgggacagagaaattaacaattacacaagcttaatacactccttaattgaagaatcgcaaaaccagcaagaaa
agaatgaacaagaattattggaattagataaatgggcaagtttgtggaattggtttaacataacaaattggctgtggtatataaaattattcataa
tgatagtaggaggcttggtaggtttaagaatagtttttgctgtactttctatagtgaatagagttaggcagggatattcaccattatcgtttcagac
ccacctcccaaccccgaggggacccgacaggcccgaaggaatagaagaagaaggtggagagagagacagagacagatccattcgatt
agtgaacggatctcgacggtatcgatcacgagactagcctcgagacaaatggcagtattcatccacaattttaaaagaaaaggggggattg
gggggtacagtgcagggggaagaataatagcagacataatagcaacagacatacaaactaaagaattacaaaaacaaattacaaaaattcaa
aattttcgggtttattacagggacagcagagatccactttggccgcggTAGTTATTAATAGTAATCAATTACGGGG
TCATTAGTTCATAGCCCATATATGGAGTTCCGCGTTACATAACTTACGGTAAATGGC
CCGCCTGGCTGACCGCCCAACGACCCCCGCCCATTGACGTCAATAATGACGTATGTT
CCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTAT
TGACGTCAATGACGGTAAATGGCCCGCCTGGCATTATGCCCAGTACATGACCTTATG
GGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCC
AAGTCTCCACCCCATTGACGTCAATGGGAGTTTGTTTTGGCACCAAAATCAACGGG
ACTTTCCAAAATGTCGTAACAACTCCGCCCCATTGACGCAAATGGGCGGTAGGCGT
GTACGGTGGGAGGTCTATATAAGCAGAGCTGGTTTAGTGAACCGTCAGATCCGCTA
GCCACCATGACCGAGTACAAGCCCACGGTGCGCCTCGCCACCCGCGACGACGTCCC
CAGGGCCGTACGCACCCTCGCCGCCGCGTTCGCCGACTACCCCGCCACGCGCCACA
CCGTCGATCCGGACCGCCACATCGAGCGGGTCACCGAGCTGCAAGAACTCTTCCTC
ACGCGCGTCGGGCTCGACATCGGCAAGGTGTGGGTCGCGGACGACGGCGCCGCGGT
```

SEQUENCES

```
GGCGGTCTGGACCACGCCGGAGAGCGTCGAAGCGGGGCGGTGTTCGCCGAGATC
GGCCCGCGCATGGCCGAGTTGAGCGGTTCCCGGCTGGCCGCGCAGCAACAGATGGA
AGGCCTCCTGGCGCCGCCACCGGCCCAAGGAGCCCGCGTGGTTCCTGGCCACCGTCG
GCGTgTCGCCCGACCACCAGGGCAAGGGTCTGGGCAGCGCCGTCGTGCTCCCCGGA
GTGGAGGCGGCCGAGCGCGCCGGGGTGCCCGCCTTCCTGGAaACCTCCGCGCCCCG
CAACCTCCCCTTCTACGAGCGGCTCGGCTTCACCGTCACCGCCGACGTCGAGGTGCC
CGAAGGACCGCGCACCTGGTGCATGACCCGCAAGCCCGGTGCCCTGTACAAGCAAT
GTACTAACTACGCTTTGTTGAAACTCGCTGGCGATGTTGAAAGTAACCCCGGTCCTg
aattcCAAGAACAGCTGCAGAACAGGAGATAACAGTTGggatccGTGAGCAAGGGCGAG
GAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGA
CCACCCTGACCTACGGCGTGCAGTGCTTCAGCCGCTACCCCGACCACATGAAGCAG
CACGACTTCTTCAAGTCCGCCATGCCCGAAGGCTACGTCCAGGAGCGCACCATCTTC
TTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATC
CTGGGGCACAAGCTGGAGTACAACTACAACAGCCACAACGTCTATATCATGGCCGA
CAAGCAGAAGAACGGCATCAAGGTGAACTTCAAGATCCGCCACAACATCGAGGAC
GGCAGCGTGCAGCTCGCCGACCACTACCAGCAGAACACCCCCATCGGCGACGGCCC
CGTGCTGCTGCCCGACAACCACTACCTGAGCACCCAGTCCGCTCTGAGCAAGACC
CCAACGAGAAGCGCGATCACATGGTCCTGCTGGAGTTCGTGACCGCCGCCGGGATC
ACTCTCGGCATGGACGAGCTGTACAAGtaaGgtacctttaagaccaatgacttacaaggcagctgtagatcttag
ccactttttaaaagaaaagggggggactggaagggctaattcactcccaacgaagacaagatctgcttttttgcttgtactgggtctctctggtta
gaccagatctgagcctgggagctctctggctaactagggaaccactgcttaagcctcaactaaaagcttgccttgagtgcttcaagtagtgtgt
gcccgtctgttgtgtgactctggtaactagagatccctcagacccttttagtcagtgtggaaaatctctagcagtagtagttcatgtcatcttatta
ttcagtatttataacttgcaaagaaatgaatatcagagagtgagaggaacttgtttattgcagcttataatggttacaaataaagcaatagcatca
caaatttcacaaataaagcatttttttcactgcattctagtigiggttigtccaaactcatcaatgtatccttatcatgtctggctctagctatccgcc
cctaactccgcccatccgcccctaactccgcccagttccgcccattctccgccatcctccggctgactaatttttttttattatgcagaggccgag
gccgcctcggcctctgagctattccgaagtagtgaggaggcttttttggaggccctagggacgtacccaattcgccctatagtgagtcgtatt
acgcgcgctcactggccgtcgttttacaacgtcgtgactgggaaaacctggcgttacccaacttaatcgccttgcagcacatccccctttcg
ccagctggcgtaatagcgaagaggcccgcaccgatcgcccttcccaacagttgcgcagcctgaatggcgaatgggacgcgccctgtag
cggcgcattaagcgcggcgggtgtggtggttacgcgcagcgtgaccgctacacttgccagcgccctagcgcccgctcctttcgctttcttc
ccttcctttctcgccacgttcgccggctttccccgtcaagctctaaatcgggggctccctttagggttccgatttagtgctttacggcacctcga
ccccaaaaaacttgattagggtgatggttcacgtagtgggccatcgccctgatagacggtttttcgccctttgacgttggagtccacgttctta
atagtggactcttgttccaaactggaacaacactcaaccctatctcggtctatcttttgatttataagggatttgccgatttcggcctattggtta
aaaaatgagctgatttaacaaaaatttaacgcgaattttaacaaaatattaacgcttacaattaggtggcacttttcggggaaatgtgcgcgga
acccctatttgtttatttttctaaatacattcaaatatgtatccgctcatgagacaataaccctgataaatgcttcaataatattgaaaaaggaaga
gtatgagtattcaacatttccgtgtcgcccttattcccttttttgcggcattttgccttcctgtttttgctcacccagaaacgctggtgaaagtaaaa
gatgctgaagatcagttgggtgcacgagtgggttacatcgaactggatctcaacagcggtaagatccttgagagttttcgccccgaagaac
gttttccaatgatgagcacttttaaagttctgctatgtggcgcggtattatcccgtattgacgccgggcaagagcaactcggtcgccgcataca
ctattctcagaatgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaacatgggggat
catgtaactcgccttgatcgttgggaaccggagctgaatgaagccataccaaacgacgagcgtgacaccacgatgcctgtagcaatggca
acaacgttgcgcaaactattaactggcgaactacttactctagcttcccggcaacaattaatagactggatggaggcggataaagttgcagg
accacttctgcgctcggcccttccggctggctggtttattgctgataaatctggagccggtgagcgtgggtctcgcggtatcattgcagcact
ggggccagatggtaagccctcccgtatcgtagttatctacacgacggggagtcaggcaactcggatgaacgaaatagacagatcgctga
gataggtgcctcactgattaagcattggtaactgtcagaccaagtttactcatatatactttagattgatttaaaacttcattttaatttaaaaggat
ctaggtgaagatcctttttgataatctcatgaccaaaatcccttaacgtgagttttcgttccactgagcgtcagaccccgtagaaaagatcaaa
ggatcttcttgagatccttttttctgcgcgtaatctgctgcttgcaaacaaaaaaaccaccgctaccagcggtggtttgtttgccggatcaaga
gctaccaactctttttccgaaggtaactggcttcagcagagcgcagataccaaatactgttcttctagtgtagccgtagttaggccaccacttc
aagaactctgtagcaccgcctacatacctcgctctgctaatcctgttaccagtggctgctgccagtggcgataagtcgtgtcttaccgggttg
gactcaagacgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatccggtaagcgg
cagggtcggaacaggagagcgcacgagggagcttccaggggaaagcgcctggtatctttatagtcctgtcgggtttcgccacctctgactt
gagcgtcgatttttgtgatgctcgtcaggggggcggagcctatgaaaaacgccagcaacgcggcctttttacggttcctggccttttgctg
gccttttgctcacatgttctttcctgcgttatcccctgattctgtggataaccgtattaccgcctttgagtgagctgataccgctcgccgcagccg
aacgaccgagcgcagcgagtcagtgagcgaggaagcggaagagcgcccaatacgcaaaccgcctctccccgcgcgttggccgattca
ttaatgcagctggcacgacaggtttcccgactggaaagcgggcagtgagcgcaacgcaattaatgtgagttagctcactcattaggcaccc
caggctttacacttatgcttccggctcgtatgttgtgtggaattgtgagcggataacaatttcacacaggaaacagctatgaccatgattacgc
caagcgcgcaattaaccctcactaaagggaacaaaagctggagctcaagcttaatgtagtcttatgcaatactcttgtagtcttgcaacatg
gtaacgatgagttagcaacatgccttacaaggagagaaaaagcaccgtgcatgccgattggtggaagtaaggtggtacgatcgtgcctttat
taggaaggcaacagacgggtctgacatggattggacgaaccactgaattgccgcattgcagagatattgtatttaagtgcctagctcgatac
ataaac
```

SEQ ID NO: 11, Wild Type SpCas9(D10A): Protein sequence:
MDKKYSIGLAIGTNSVGWAVITDEYKVPSKKFKVLGNTDRHSIKKNLIGALLFDS
GETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGDQYADLFLAA
KNLSDAILLSDILRVNTEITKAPLSASMIKRYDEHHQDLTLLKALVRQQLPEKYKEIFFD
QSKNGYAGYIDGGASQEEFYKFIKPILEKMDGTEELLVKLNREDLLRKQRTFDNGSIPH
QIHLGELHAILRRQEDFYPFLKDNREKIEKILTFRIPYYVGPLARGNSRFAWMTRKSEETI
TPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEERLKTYAHLFDDKVMKQ
LKRRRYTGWGRLSRKLINGIRDKQSGKTILDFLKSDGFANRNFMQLIHDDSLTFKEDIQ

| SEQUENCES |
|---|
| KAQVSGQGDSLHEHIANLAGSPAIKKGILQTVKVVDELVKVMGRHKPENIVIEMAREN
QTTQKGQKNSRERMKRIEEGIKELGSQILKEHPVENTQLQNEKLYLYYLQNGRDMYVD
QELDINRLSDYDVDHIVPQSFLKDDSIDNKVLTRSDKNRGKSDNVPSEEVVKKMKNYW
RQLLNAKLITQRKFDNLTKAERGGLSELDKAGFIKRQLVETRQITKHVAQILDSRMNTK
YDENDKLIREVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEITLANGEIRK
RPLIETNGETGEIVWDKGRDFATVRKVLSMPQVNIVKKTEVQTGGFSKESILPKRNSDK
LIARKKDWDPKKYGGFDSPTVAYSVLVVAKVEGKSKKLKSVKELLGITIMERSSFEK
NPIDFLEAKGYKEVKKDLIIKLPKYSLFELENGRKRMLASAGELQKGNELALPSKYVNF
LYLASHYEKLKGSPEDNEQKQLFVEQHKHYLDEIIEQISEFSKRVILADANLDKVLSAYN
KHRDKPIREQAENIIHLFTLTNLGAPAAFKYFDTTIDRKRYTSTKEVLDATLIHQSITGLY
ETRIDLSQLGGD

SEQ ID NO: 12, SpCas9(D10A)-NG: Protein sequence:
MDKKYSIGLAIGTNSVGWAVITDEYKVPSKKFKVLGNTDRHSIKKNLIGALLFDS
GETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDAKLQLSKDTYDDDLDNLLAQIGDQYADLFLAA
KNLSDAILLSDILRVNTEITKAPLSASMIKRYDEHHQDLTLLKALVRQQLPEKYKEIFFD
QSKNGYAGYIDGGASQEEFYKFIKPILEKMDGTEELLVKLNREDLLRKQRTFDNGSIPH
QIHLGELHAILRRQEDFYPFLKDNREKIEKILTFRIPYYVGPLARGNSRFAWMTRKSEETI
TPWNFEEVVDKGASAQSFIERMTNFDKNLPNEKVLPKHSLLYEYFTVYNELTKVKYVT
EGMRKPAFLSGEQKKAIVDLLFKTNRKVTVKQLKEDYFKKIECFDSVEISGVEDRFNAS
LGTYHDLLKIIKDKDFLDNEENEDILEDIVLTLTLFEDREMIEEERLKTYAHLFDDKVMKQ
LKRRRYTGWGRLSRKLINGIRDKQSGKTILDFLKSDGFANRNFMQLIHDDSLTFKEDIQ
KAQVSGQGDSLHEHIANLAGSPAIKKGILQTVKVVDELVKVMGRHKPENIVIEMAREN
QTTQKGQKNSRERMKRIEEGIKELGSQILKEHPVENTQLQNEKLYLYYLQNGRDMYVD
QELDINRLSDYDVDHIVPQSFLKDDSIDNKVLTRSDKNRGKSDNVPSEEVVKKMKNYW
RQLLNAKLITQRKFDNLTKAERGGLSELDKAGFIKRQLVETRQITKHVAQILDSRMNTK
YDENDKLIREVKVITLKSKLVSDFRKDFQFYKVREINNYHHAHDAYLNAVVGTALIKK
YPKLESEFVYGDYKVYDVRKMIAKSEQEIGKATAKYFFYSNIMNFFKTEITLANGEIRK
RPLIETNGETGEIVWDKGRDFATVRKVLSMPQVNIVKKTEVQTGGFSKESIRPKRNSDK
LIARKKDWDPKKYGGFVSPTVAYSVLVVAKVEGKSKKLKSVKELLGITIMERSSFEK
NPIDFLEAKGYKEVKKDLIIKLPKYSLFELENGRKRMLASARFLQKGNELALPSKYVNF
LYLASHYEKLKGSPEDNEQKQLFVEQHKHYLDEIIEQISEFSKRVILADANLDKVLSAYN
KHRDKPIREQAENIIHLFTLTNLGAPRAFKYFDTTIDRKVYRSTKEVLDATLIHQSITGLY
ETRIDLSQLGGD SEQ ID NO: 13, xCas9(3.7)-D10A: Protein sequence:
MDKKYSIGLAIGTNSVGWAVITDEYKVPSKKFKVLGNTDRHSIKKNLIGALLFDS
GETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKFRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDTKLQLSKDTYDDDLDNLLAQIGDQYADLFLAA
KNLSDAILLSDILRVNTEITKAPLSASMIKLYDEHHQDLTLLKALVRQQLPEKYKEIFFD
QSKNGYAGYIDGGASQEEFYKFIKPILEKMDGTEELLVKLNREDLLRKQRTFDNGIIPHQ
IHLGELHAILRRQEDFYPFLKDNREKIEKILTFRIPYYVGPLARGNSRFAWMTRKSEETIT
PWNFEKVVDKGASAQSFIERMTNFDKNLPNEKVLPKHSLLYEYFTVYNELTKVKYVTE
GMRKPAFLSGDQKKAIVDLLFKTNRKVTVKQLKEDYFKKIECFDSVEISGVEDRFNASL
GTYHDLLKIIKDKDFLDNEENEDILEDIVLTLTLFEDREMIEERLKTYAHLFDDKVMKQL
KRRRYTGWGRLSRKLINGIRDKQSGKTILDFLKSDGFANRNFIQLIHDDSLTFKEDIQKA
QVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQEL
DINRLSDYDVDHIVPQSFLKDDSIDNKVLTRSDKNRGKSDNVPSEEVVKKMKNYWRQL
LNAKLITQRKFDNLTKAERGGLSELDKAGFIKRQLVETRQITKHVAQILDSRMNTKYDE
NDKLIREVKVITLKSKLVSDFRKDFQFYKVREINNYHHAHDAYLNAVVGTALIKKYPKL
ESEFVYGDYKVYDVRKMIAKSEQEIGKATAKYFFYSNIMNFFKTEITLANGEIRKRPLIE
TNGETGEIVWDKGRDFATVRKVLSMPQVNIVKKTEVQTGGFSKESILPKRNSDKLIARK
KDWDPKKYGGFDSPTVAYSVLVVAKVEGKSKKLKSVKELLGITIMERSSFEKNPIDFL
EAKGYKEVKKDLIIKLPKYSLFELENGRKRMLASAGVLQKGNELALPSKYVNFLYLAS
HYEKLKGSPEDNEQKQLFVEQHKHYLDEIIEQISEFSKRVILADANLDKVLSAYNKHRD
KPIREQAENIIHLFTLTNLGAPAAFKYFDTTIDRKRYTSTKEVLDATLIHQSITGLYETRID
LSQLGGD SEQ ID NO: 14, SpCas9(D10A)-NGX: Protein sequence:
MDKKYSIGLAIGTNSVGWAVITDEYKVPSKKFKVLGNTDRHSIKKNLIGALLFDS
GETAEATRLKRTARRRYTRRKNRICYLQEIFSNEMAKVDDSFFHRLEESFLVEEDKKHE
RHPIFGNIVDEVAYHEKYPTIYHLRKKLVDSTDKADLRLIYLALAHMIKIRGHFLIEGDL
NPDNSDVDKLFIQLVQTYNQLFEENPINASGVDAKAILSARLSKSRRLENLIAQLPGEKK
NGLFGNLIALSLGLTPNFKSNFDLAEDTKLQLSKDTYDDDLDNLLAQIGDQYADLFLAA
KNLSDAILLSDILRVNTEITKAPLSASMIKLYDEHHQDLTLLKALVRQQLPEKYKEIFFD
QSKNGYAGYIDGGASQEEFYKFIKPILEKMDGTEELLVKLNREDLLRKQRTFDNGIIPHQ
IHLGELHAILRRQEDFYPFLKDNREKIEKILTFRIPYYVGPLARGNSRFAWMTRKSEETIT
PWNFEKVVDKGASAQSFIERMTNFDKNLPNEKVLPKHSLLYEYFTVYNELTKVKYVTE
GMRKPAFLSGDQKKAIVDLLFKTNRKVTVKQLKEDYFKKIECFDSVEISGVEDRFNASL
GTYHDLLKIIKDKDFLDNEENEDILEDIVLTLTLFEDREMIEERLKYAHLFDDKVMKQL |

| SEQUENCES |
|---|
| KRRRYTGWGRLSRKLINGIRDKQSGKTILDFLKSDGFANRNFIQLIHDDSLTFKEDIQKA<br>QVSGQGDSLHEHIANLAGSPAIKKGILQTVKVVDELVKVMGRHKPENIVIEMARENQTT<br>QKGQKNSRERMKRIEEGIKELGSQILKEHPVENTQLQNEKLYLYYLQNGRDMYVDQEL<br>DINRLSDYDVDHIVPQSFLKDDSIDNKVLTRSDKNRGKSDNVPSEEVVKKMKNYWRQL<br>LNAKLITQRKFDNLTKAERGGLSELDKAGFIKRQLVETRQITKHVAQILDSRMNTKYDE<br>NDKLIREVKVITLKSKLVSDFRKDFQFYKVREINNYHHAHDAYLNAVVGTALIKKYPKL<br>ESEFVYGDYKVYDVRKMIAKSEQEIGKATAKYFFYSNIMNFFKTEITLANGEIRKRPLIE<br>TNGETGEIVWDKGRDFATVRKVLSMPQVNIVKKTEVQTGGFSKESIRPKRNSDKLIARK<br>KDWDPKKYGGFVSPTVAYSVLVVAKVEKGKSKKLKSVKELLGITIMERSSFEKNPIDFL<br>EAKGYKEVKKDLIIKLPKYSLFELENGRKRMLASARFLQKGNELALPSKYVNFLYLASH<br>YEKLKGSPEDNEQKQLFVEQHKYLDEIIEQISEFSKRVILADANLDKVLSAYNKHRDK<br>PIREQAENIIHLFTLTNLGAPRAFKYFDTTIDRKVYRSTKEVLDATLIHQSITGLYETRIDL<br>SQLGGD<br><br>SEQ ID NO: 15, SpCas9(D10A)-NGA: Protein sequence:<br>MDKKYSIGLAIGTNSVGWAVITDEYKVPSKKFKVLGNTDRHSIKKNLIGALLFDS<br>GETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDAKLQLSKDTYDDDLDNLLAQIGDQYADLFLAA<br>KNLSDAILLSDILRVNTEITKAPLSASMIKRYDEHHQDLTLLKALVRQQLPEKYKEIEFD<br>QSKNGYAGYIDGGASQEEFYKFIKPILEKMDGTEELLVKLNREDLLRKQRTFDNGSIPH<br>QIHLGELHAILRRQEDFYPFLKDNREKIEKILTFRIPYYVGPLARGNSRFAWMTRKSEETI<br>TPWNFEEVVDKGASAQSFIERMTNFDKNLPNEKVLPKHSLLYEYFTVYNELTKVKYVI<br>EGMRKPAFLSGEQKKAIVDLLFKTNRKVTVKQLKEDYFKKIECFDSVEISGVEDRFNAS<br>LGTYHDLLKIIKDKDFLDNEENEDILEDIVLTLTLFEDREMIEERLKTYAHLFDDKVMKQ<br>LKRRRYTGWGRLSRKLINGIRDKQSGKTILDFLKSDGFANRNFMQLIHDDSLTFKEDIQ<br>KAQVSGQGDSLHEHIANLAGSPAIKKGILQTVKVVDELVKVMGRHKPENIVIEMAREN<br>QTTQKGQKNSRERMKRIEEGIKELGSQILKEHPVENTQLQNEKLYLYYLQNGRDMYVD<br>QELDINRLSDYDVDHIVPQSFLKDDSIDNKVLTRSDKNRGKSDNVPSEEVVKKMKNYW<br>RQLLNAKLITQRKFDNLTKAERGGLSELDKAGFIKRQLVETRQITKHVAQILDSRMNTK<br>YDENDKLIREVKVITLKSKLVSDFRKDFQFYKVREINNYHHAHDAYLNAVVGTALIKK<br>YPKLESEFVYGDYKVYDVRKMIAKSEQEIGKATAKYFFYSNIMNFFKTEITLANGEIRK<br>RPLIETNGETGEIVWDKGRDFATVRKVLSMPQVNIVKKTEVQTGGFSKESIRPKRNSDK<br>LIARKKDWDPKKYGGFVSPTVAYSVLVVAKVEKGKSKKLKSVKELLGITIMERSSFEK<br>NPIDFLEAKGYKEVKKDLIIKLPKYSLFELENGRKRMLASARFLQKGNELALPSKYVNF<br>LYLASHYEKLKGSPEDNEQKQLFVEQHKYLDEIIEQISEFSKRVILADANLDKVLSAYN<br>KHRDKPIREQAENIIHLFTLTNLGAPRAFKYFDTTIDRKQYRSTKEVLDATLIHQSITGLY<br>ETRIDLSQLGGD<br><br>SEQ ID NO: 16, SpCas9(D10A)-NGC: Protein sequence:<br>MDKKYSIGLAIGTNSVGWAVITDEYKVPSKKFKVLGNTDRHSIKKNLIGALLFDS<br>GETAEATRLKRIARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDAKLQLSKDTYDDDLDNLLAQIGDQYADLFLAA<br>KNLSDAILLSDILRVNTEITKAPLSASMIKRYDEHHQDLTLLKALVRQQLPEKYKEIFFD<br>QSKNGYAGYIDGGASQEEFYKFIKPILEKMDGTEELLVKLNREDLLRKQRTFDNGSIPH<br>QIHLGELHAILRRQEDFYPFLKDNREKIEKILTFRIPYYVGPLARGNSRFAWMTRKSEETI<br>TPWNFEEVVDKGASAQSFIERMTNFDKNLPNEKVLPKHSLLYEYFTVYNELTKVKYVT<br>EGMRKPAFLSGEQKKAIVDLLFKTNRKVTVKQLKEDYFKKIECFDSVEISGVEDRFNAS<br>LGTYHDLLKIIKDKDFLDNEENEDILEDIVLTLTLFEDREMIEERLKTYAHLFDDKVMKQ<br>LKRRRYTGWGRLSRKLINGIRDKQSGKTILDFLKSDGFANRNFMQLIHDDSLTFKEDIQ<br>KAQVSGQGDSLHEHIANLAGSPAIKKGILQTVKVVDELVKVMGRHKPENIVIEMAREN<br>QTTQKGQKNSRERMKRIEEGIKELGSQILKEHPVENTQLQNEKLYLYYLQNGRDMYVD<br>QELDINRLSDYDVDHTVPQSFLKDDSIDNKVLTRSDKNRGKSDNVPSEEVVKKMKNYW<br>RQLLNAKIITQRKFDNLTKAERGGLSELDKAGFIKRQLVETRQITKHVAQILDSRMNTK<br>YDENDKLIREVKVITLKSKLVSDFRKDFQFYKVREINNYHHAHDAYLNAVVGTALIKK<br>YPKLESEFVYGDYKVYDVRKMIAKSEQEIGKATAKYFFYSNIMNFFKTEITLANGEIRK<br>RPLIETNGETGEIVWDKGRDFATVRKVLSMPQVNIVKKTEVQTGGFSKESIRPKRNSDK<br>LIARKKDWDPKKYGGFVSPTVAYSVLVVAKVEKGKSKKLKSVKELLGITIMERSSFEK<br>NPIDFLEAKGYKEVKKDLIIKLPKYSLFELENGRKRMLASARFLQKGNELALPSKYVNF<br>LYLASHYEKLKGSPEDNEQKQLFVEQHKYLDEIIEQISEFSKRVILADANLDKVLSAYN<br>KHRDKPIREQAENIIHLFTLTNLGAPRAFKYFDTTIDRKEYRSTKEVLDATLIHQSITGLY<br>ETRIDLSQLGGD<br><br>SEQ ID NO: 17, SpCas9(D10A)-NGX-NGA: Protein sequence:<br>MDKKYSIGLAIGTNSVGWAVITDEYKVPSKKFKVLGNTDRHSIKKNLIGALLFDS<br>GETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDTKLQLSKDTYDDDLDNLLAQIGDQYADLFLAA<br>KNLSDAILLSDILRVNTEITKAPLSASMIKLYDEHHQDLTLLKALVRQQLPEKYKEIFFD<br>QSKNGYAGYIDGGASQEEFYKFIKPILEKMDGTEELLVKLNREDLLRKQRTFDNGIIPHQ<br>IHLGELHAILRRQEDFYPFLKDNREKIEKILTFRIPYYVGPLARGNSRFAWMTRKSEETIT<br>PWNFEKVVDKGASQSFIERMTNFDKNLPNEKVLPKHSLLYEYFTVYNELTKVKYVTE<br>GMRKPAFLSGDQKKAIVDLLFKTNRKVTVKQLKEDYFKKIECFDSVEISGVEDRFNASL |

| SEQUENCES |
|---|
| GTYHDLLKIIKDKDFLDNEENEDILEDIVLTLTLFEDREMIEERLKTYAHLFDDKVMKQL<br>KRRRYTGWGRLSRKLINGIRDKQSGKTILDFLKSDGFANRNFIQLIHDDSLTFKEDIQKA<br>QVSGQGDSLHEHIANLAGSPAIKKGILQTVKVVDELVKVMGRHKPENIVIEMARENQTT<br>QKGQKNSRERMKRIEEGIKELGSQILKEHPVENTQLQNEKLYLYYLQNGRDMYVDQEL<br>DINRLSDYDVDHIVPQSFLKDDSIDNKVLTRSDKNRGKSDNVPSEEVVKKMKNYWRQL<br>LNAKLITQRKFDNLTKAERGGLSELDKAGFIKRQLVETRQITKHVAQILDSRMNTKYDE<br>NDKLIREVKVITLKSKLVSDFRKDFQFYKVREINNYHHAHDAYLNAVVGTALIKKYPKL<br>ESESEFVYGDYKVYDVRKMIAKSEQEIGKATAKYFFYSNIMNFFKTEITLANGEIRKRPLIE<br>TNGETGEIVWDKGRDFATVRKVLSMPQVNIVKKTEVQTGGFSKESIRPKRNSDKLIARK<br>KDWDPKKYGGFVSPTVAYSVLVVAKVEKGKSKKLKSVKELLGITIMERSSFEKNPIDFL<br>EAKGYKEVKKDLIIKLPKYSLFELENGRKRMLASARFLQKGNELALPSKYVNFLYLASH<br>YEKLKGSPEDNEQKQLFVEQHKHYLDEIIEQISEFSKRVILADANLDKVLSAYNKHRDK<br>PIREQAENIIHLFTLTNLGAPRAFKYFDTTIDRKQYRSTKEVLDATLIHQSITGLYETRIDL<br>SQLGGD |
| SEQ ID NO: 18, SpCas9(D10A)-NGX-NGC: Protein sequence:<br>MDKKYSIGLAIGTNSVGWAVITDEYKVPSKKFKVLGNTDRHSIKKNLIGALLFDS<br>GETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDTKLQLSKDTYDDDLDNLLAQIGDQYADLFLAA<br>KNLSDAILLSDILRVNTEITKAPLSASMIKLYDEHHQDLTLLKALVRQQLPEKYKEIFFD<br>QSKNGYAGYIDGGASQEEFYKFIKPILEKMDGTEELLVKLNREDLLRKQRTFDNGIIPHQ<br>IHLGELHAILRRQEDFYPFLKDNREKIEKILTFRIPYYVGPLARGNSRFAWMTRKSEETIT<br>PWNFEKVVDKGASAQSFIERMTNFDKNLPNEKVLPKHSLLYEYFTVYNELTKVKYVTE<br>GMRKPAFLSGDQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAHLFDDKVMKQL<br>KRRRYTGWGRLSRKLINGIRDKQSGKTILDFLKSDGFANRNFIQLIHDDSLTFKEDIQKA<br>QVSGQGDSLHEHIANLAGSPAIKKGILQTVKVVDELVKVMGRHKPENIVIEMARENQTT<br>QKGQKNSRERMKRIEEGIKELGSQILKEHPVENTQLQNEKLYLYYLQNGRDMYVDQEL<br>DINRLSDYDVDHIVPQSFLKDDSIDNKVLTRSDKNRGKSDNVPSEEVVKKMKNYWRQL<br>LNAKLITQRKFDNLTKAERGGLSELDKAGFIKRQLVETRQITKHVAQILDSRMNTKYDE<br>NDKLIREVKVITLKSKLVSDFRKDFQFYKVREINNYHHAHDAYLNAVVGTALIKKYPKL<br>ESESEFVYGDYKVYDVRKMIAKSEQEIGKATAKYFFYSNIMNFFKTEITLANGEIRKRPLIE<br>TNGETGEIVWDKGRDFATVRKVLSMPQVNIVKKTEVQTGGFSKESIRPKRNSDKLIARK<br>KDWDPKKYGGFVSPTVAYSVLVV'AKVEKGKSKKLKSVKELLGITIMERSSFEKNPIDFL<br>EAKGYKEVKKDLIIKLPKYSLFELENGRKRMLASARFLQKGNELALPSKYVNFLYLASH<br>YEKLKGSPEDNEQKQLFVEQHKHYLDEIEQISEFSKRVILADANLDKVLSAYNKHRDK<br>PIREQAENIIHLFTLTNLGAPRAFKYFDTTIDRKEYRSTKEVLDATLIHQSITGLYETRIDL<br>SQLGGD |
| SEQ ID: 19, SpCas9(D10A)-NG-loop: Protein sequence:<br>MDKKYSIGLAIGTNSVGWAVITDEYKVPSKKFKVLGNTDRHSIKKNLIGALLFDS<br>GETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDAKLQLSKDTYDDDLDNLLAQIGDQYADLFLAA<br>KNLSDAILLSDILRVNTEITKAPLSASMIKRYDEHHQDLTLLKALVRQQLPEKYKEIFFD<br>QSKNGYAGYVGADKKLRKRSSKLATEEEFYKFIKPILEKMDGTEELLVKLNREDLLRK<br>QRTFDNGSIPHQIHLGELHAILRRQEDFYPFLKDNREKIEKILTFRIPYYVGPLARGNSRF<br>AWMTRKSEETITPWNFEEVVDKGASAQSFIERMTNFDKNLPNEKVLPKHSLLYEYFTV<br>YNELTKVKYVTEGMRKPAFLSGEQKKAIVDLLFKTNRKVTVKQLKEDYFKKIECFDSV<br>EISGVEDRFNASLGTYHDLLKIIKDKDFLDNEENEDILEDIVLTLTLFEDREMIEERLKTY<br>AHLFDDKVMKQLKRRRYTGWGRLSRKLINGIRDKQSGKTILDFLKSDGFANRNFMQLI<br>HDDSLTFKEDIQKAQVSGQGDSLHEHIANLAGSPAIKKGILQTVKVVDELVKVMGRHK<br>PENIVIEMARENQTTQKGQKNSRERMKRIEEGIKELGSQILKEHPVENTQLQNEKLYLY<br>YLQNGRDMYVDQELDINRLSDYDVDHIVPQSFLKDDSIDNKVLTRSDKNRGKSDNVPS<br>EEVVKKMKNYWRQLLNAKLITQRKFDNLTKAERGGLSELDKAGFIKRQLVETRQITKH<br>VAQILDSRMNTKYDENDKLIREVKVITLKSKLVSDFRKDFQFYKVREINNYHHAHDAY<br>LNAVVGTALIKKYPKLESEFVYGDYKVYDVRKMIAKSEQEIGKATAKYFFYSNIMNFF<br>KTEITLANGEIRKRPLIETNGETGEIVWDKGRDFATVRKVLSMPQVNIVKKTEVQTGGFS<br>KESIRPKRNSDKLIARKKDWDPKKYGGFVSPTVAYSVLVVAKVEKGKSKKLKSVKELL<br>GITIMERSSFEKNPIDFLEAKGYKEVKKDLIIKLPKYSLFELENGRKRMLASARFLQKGN<br>ELALPSKYVNFLYLASHYEKLKGSPEDNEQKQLFVEQHKHYLDHIEQISEFSKRVILAD<br>ANLDKVLSAYNKHRDKPIREQAENIIHLFTLTNLGAPRAFKYFDTTIDRKVYRSTKEVLD<br>ATLIHQSITGLYETRIDLSQLGGD |
| SEQ ID NO: 20, SpCas9(D10A)-NGX-loop: Protein sequence:<br>MDKKYSIGLAIGTNSVGWAVITDEYKVPSKKFKVLGNTDRHSIKKNLIGALLFDS<br>GETAEATRLKRTARRRYTRRKNRICYLQEIFSNEMAKVDDSFFHRLEESFLVEEDKKHE<br>RHPIFGNIVDEVAYHEKYPTIYHLRKKLVDSTDKADLRLIYLALAHMIKFRGHFLIEGDL<br>NPDNSDVDKLFIQLVQTYNQLFEENPINASGVDAKAILSARLSKSRRLENLIAQLPGEKK<br>NGLFGNLIALSLGLTPNFKSNFDLAEDTKLQLSKDTYDDDLDNLLAQIGDQYADLFLAA<br>KNLSDAILLSDILRVNTEITKAPLSASMIKLYDEHHQDLTLLKALVRQQLPEKYKEIFFD<br>QSKNGYAGYVGADKKLRKRSSKLATEEEFYKFIKPILEKMDGTEELLVKLNREDLLRK<br>QRTFDNGIIPHQIHLGELHAILRRQEDFYPFLKDNREKIEKILTFRIPYYVGPLARGNSRFA<br>WMTRKSEETITPWNFEKVVDKGASAQSFIERMTNFDKNLPNEKVLPKHSLLYEYFTVY |

| SEQUENCES |
|---|
| NELTKVKYVTEGMRKPAFLSGDQKKAIVDLLFKTNRKVTVKQLKEDYFKKIECFDSVEI<br>SGVEDRFNASLGTYHDLLKIIKDKDFLDNEENEDILEDIVLTLTLFEDREMIEERLKTYA<br>HLFDDKVMKQLKRRRYTGWGRLSRKLINGIRDKQSGKTILDFLKSDGFANRNFIQLIHD<br>DSLTFKEDIQKAQVSGQGDSLHEHIANLAGSPAIKKGILQTVKVVDELVKVMGRHKPEN<br>IVIEMARENQTTQKGQKNSRERMKRIEEGIKELGSQILKEHPVENTQLQNEKLYLYYLQ<br>NGRDMYVDQELDINRLSDYDVDHIVPQSFLKDDSIDNKVLTRSDKNRGKSDNVPSEEV<br>VKKMKNYWRQLLNAKLITQRKFDNLTKAERGGLSELDKAGFIKRQLVETRQITKHVAQ<br>ILDSRMNTKYDENDKLIREVKVITLKSKLVSDFRKDFQFYKVREINNYHHAHDAYLNA<br>VVGTALIKKYPKLESEFVYGDYKVYDVRKMIAKSEQEIGKATAKYFFYSNIMNFFKTEI<br>TLANGEIRKRPLIETNGETGEIVWDKGRDFATVRKVLSMPQVNIVKKTEVQTGGFSKESI<br>RPKRNSDKLIARKKDWDPKKYGGFVSPTVAYSVLVVAKVEKGKSKKLKSVKELLGITI<br>MERSSFEKNPIDFLEAKGYKEVKKDLIIKLPKYSLFELENGRKRMLASARFLQKGNELA<br>LPSKYVNFLYLASHYEKLKGSPEDNEQKQLFVEQHKHYLDEIIEQISEFSKRVILADANL<br>DKVLSAYNKHRDKPIREQAENIIHLFTLTNLGAPRAFKYFDTTIDRKVYRSTKEVLDATL<br>IHQSITGLYETRIDLSQLGGD |
| SEQ ID NO: 21, ScCas9(D10A): Protein sequence:<br>MEKKYSIGLAIGTNSVGWAVITDDYKVPSKKFKVLGNTNRKSIKKNLMGALLFD<br>SGETAEATRLKRTARRRYTRRKNRIRYLQEIFANEMAKLDDSFFQRLEESFLVEEDKKN<br>ERHPIFGNLADEVAYHRNYPTIYHLRKKLADSPEKADLRLIYLALAHIIKFRGHFLIEGKL<br>NAENSDVAKLFYQLIQTYNQLFEESPLDEIEVDAKGILSARLSKSKRLEKLIAVFPNEKK<br>NGLFGNIIALALGLTPNFKSNFDLTEDAKLQLSKDTYDDDLDELLGQIGDQYADLFSAA<br>KNLSDAILLSDILRSNSEVTKAPLSASMVKRYDEHHQDLALLKTLVRQQFPEKYAEIFK<br>DDTKNGYAGYVGIGIKHRKRTTKLATQEEFYKFIKPILEKMDGAEELLAKLNRDDLLRK<br>QRTFDNGSIPHQIHLKELHAILRRQEEFYPPLFKENREKIEKILTFRIPYYVGPLARGNSRFA<br>WLTRKSEEAITPWNFEEVVDKGASAQSFIERMTNFDEQLPNKKVLPKHSLLYEYFTVYN<br>ELTKVKYVTERMRKPEFLSGEQKKAIVDLLFKTNRKVTVKQLKEDYFKKIECFDSVEIIG<br>VEDRFNASLGTYHDLLKIIKDKDFLDNEENEDILEDIVLTLTLFEDREMIEERLKTYAHLF<br>DDKVMKQLKRRHYTGWGRLSRKMINGIRDKQSGKTILDFLKSDGFSNRNFMQLIHDDS<br>LTFKEEIEKAQVSGQGDSLHEQIADLAGSPAIKKGILQTVKIVDELVKVMGHKPENIVIE<br>MARENQTTTKGLQQSRERKKRIEEGIKELESQILKENPVENTQLQNEKLYLYYLQNGRD<br>MYVDQELDINRLSDYDVDHIVPQSFIKDDSIDNKVLTRSVENRGKSDNVPSEEVVKKM<br>KNYWRQLLNAKLITQRKFDNLTKAERGGLSEADKAGFIKRQLVETRQITKHVARILDSR<br>MNTKRDKNDKPIREVKVITLKSKLVSDFRKDFQLYKVRDINNYHHAHDAYLNAVVGT<br>ALIKKYPKLESEFVYGDYKVYDVRKMIAKSEQEIGKATAKRFFYSNIMNFFKTEVKLAN<br>GEIRKRPLIETNGETGEVVWNKEKDFATVRKVLAMPQVNIVKKTEVQTGGFSKESILSK<br>RESAKLIPRKKGWDTRKYGGFGSPTVAYSILVVAKVEKGKAKKLKSVKVLVGITIMEK<br>GSYEKDPIGFLEAKGYKDIKKELIFKLPKYSLFELENGRRRMLASATELQKANELVLPQH<br>LVRLLYYTQNISATTGSNNLGYIEQHREEFKEIFEKIIDFSEKYILKNKVSNLKSSFDEQF<br>AVSDSILLSNSFVSLLKYTSFGASGGFTFLDLDVKQGRLRYQTVTEVLDATLIYQSITGL<br>YETRTDLSQLGGD |
| SEQ ID NO: 22, TadA-TadA*: Protein sequence:<br>SEVEFSHEYWMRHALTLAKRAWDEREVPVGAVLVHNNRVIGEGWNRPIGRHD<br>PTAHAEIMALRQGGLVMQNYRLIDATLYVTLEPCVMCAGAMIHSRIGRVVFGARDAKT<br>GAAGSLMDVLHHPGMNHRVEITEGILADECAALLSDFFRMRRQEIKAQKKAQSSTDSG<br>GSSGGSSGSETPGTSESATPESSGGSSGGSSEVEFSHEYWMRHALTLAKRARDEREVPV<br>GAVLVLNNRVIGEGWNRAIGLHDPTAHAEIMALRQGGLVMQNYRLIDATLYVTFEPCV<br>MCAGAMIHSRIGRVVFGVRNAKTGAAGSLMDVLHYPGMNHRVEITEGILADECAALL<br>CYFFRMPRQVFNAQKKAQSSTD |
| SEQ ID: 23, TadA*(A56G_V82G): Protein sequence:<br>SEVEFSHEYWMRHALTLAKRARDEREVPVGAVLVLNNRVIGEGWNRAIGLHDP<br>TGHAEIMALRQGGLVMQNYRLIDATLYGTFEPCVMCAGAMIHSRIGRVVFGVRNAKT<br>GAAGSLMDVLHYPGMNHRVEITEGILADECAALLCYFFRMPRQVFNAQKKAQSSTD |
| SEQ ID NO: 24, Gp41-1-N: Protein sequence:<br>CLDLK TQVQTPQGMKEISNIQVGDLVLSNTGYNEVLNVEPKSKKKSYKITLEDG<br>KEIICSEEHLFPTQTGEMNISGGLKEGMCLYVKE |
| SEQ ID NO: 25, Gp41-1-C: Protein sequence:<br>MMLKKILKIEELDERELIDIEVSGNHLFYANDILTHNS |
| SEQ ID NO: 26, Cfa-N: Protein sequence:<br>CLSYDTEILTVEYGFLPIGKIVEERIECTVYTVDKNGFVYTQPIAQWHNRGEQEV<br>FEYCLEDGSIIRATKDHKFMTTDGQMLPIDEIFERGLDLKQVDGLPN |
| SEQ ID NO: 27, Cfa-C: Protein sequence:<br>MVKIISRKSLGTQNVYDIGVEKDHNFLLKNGLVASN |
| SEQ ID NO: 28, meCMV:<br>tegagCGCGTGATGAGAGCAGCCACTACGGGTCTAGGCTGCCCATGTAAGGAG<br>GCAAGGCCTGGGGACACCCGAGATGCCTGGTTATAATTAACCCAGACATGTGGCTG<br>CCCCCCCCCCCCAACACCTGCTGCCTGCTAAAAATAACCCTGTCCCTGGTGGccCtgc<br>atgcccACTCACGGGGATTTCCAAGTCTCCACCCCATTGACGTCAATGGGAGTTTGTTT |

| SEQUENCES |
|---|
| TGGCACCAAAATCAACGGGACTTTCCAAAATGTCGTAACAACTCCGCCCCATTGAC<br>GCAAATGGGCGGTAGGCGTGTACGGTGGGAGGTCTATATAAGCAGAGCTGGTTTAG<br>TGAACCGTCAGATC<br><br>SEQ ID NO: 29, SEMHP1:<br>CCCTTCAGATTAAAAATAACTGAGGTAAGGGCCTGGGTAGGGGAGGTGGTG<br>TGAGACGCTCCTGTCTCTCCTCTATCTGCCCATCGGCCCTTTGGGGAGGAGGAATGT<br>GCCCAAGGACTAAAAAAAGGCCATGGAGCCAGAGGGGCGAGGGCAACAGACCTTT<br>CATGGGCAAACCTTGGGGCCCTGCTGactgtaGATGAGAGCAGCCACTACGGGTCTAG<br>GCTGCCCATGTAAGGAGGCAAGGCCTGGGGACACCCGAGATGCCTGGTTATAATTA<br>ACCCAGACATGTGGCTGCCCCCCCCCCCCCAACACCTGCTGCCTGCTAAAAATAACC<br>CTGTCCCTGGTGGccctgcatgCCCTCCCTGGGGACAGCCCCTCCTGGCTAGTCACACCC<br>TGTAGGCTCCTCTATATAACCCAGGGGCACAGGGGCTGCCCtcattctACCACCACCTCC<br>ACAGCACAGACAGACACTCAGGAGCCAGC<br><br>SEQ ID NO: 30, Wild Type SpCas9(D10A): Nucleotide sequence:<br>ATGGACAAGAAGTACAGCATCGGCCTGGCCATCGGCACCAACTCTGTGGGCT<br>GGGCCGTGATCACCGACGAGTACAAGGTGCCCAGCAAGAAATTCAAGGTGCTGGGC<br>AACACCGACCGGCACAGCATCAAGAAGAACCTGATCGGAGCCCTGCTGTTCGACAG<br>CGGCGAAACAGCCGAGGCCACCCGGCTGAAGAGAACCGCCAGAAGAAGATACACC<br>AGACGGAAGAACCGGATCTGCTATCTGCAAGAGATCTTCAGCAACGAGATGGCCAA<br>GGTGGACGACAGCTTCTTCCACAGACTGGAAGAGTCCTTCCTGGTGGAAGAGGATA<br>AGAAGCACGAGCGGCACCCCATCTTCGGCAACATCGTGGACGAGGTGGCCTACCAC<br>GAGAAGTACCCCACCATCTACCACCTGAGAAAGAAACTGGTGGACAGCACCGACA<br>AGGCCGACCTGCGGCTGATCTATCTGGCCCTGGCCCACATGATCAAGTTCCGGGGC<br>CACTTCCTGATCGAGGGCGACCTGAACCCCGACAACAGCGACGTGGACAAGCTGTT<br>CATCCAGCTGGTGCAGACCTACAACCAGCTGTTCGAGGAAAACCCCATCAACGCCA<br>GCGGCGTGGACGCCAAGGCCATCCTGTCTGCCAGACTGAGCAAGAGCAGACGGCTG<br>GAAAATCTGATCGCCCAGCTGCCCGGCGAGAAGAAGAATGGCCTGTTCGGAAACCT<br>GATTGCCCTGAGCCTGGGCCTGACCCCCAACTTCAAGAGCAACTTCGACCTGGCCG<br>AGGATGCCAAACTGCAGCTGAGCAAGGACACCTACGACGACGACCTGGACAACCT<br>GCTGGCCCAGATCGGCGACCAGTACGCCGACCTGTTTCTGGCCGCCAAGAACCTGT<br>CCGACGCCATCCTGCTGAGCGACATCCTGAGAGTGAACACCGAGATCACCAAGGCC<br>CCCCTGAGCGCCTCTATGATCAAGAGATACGACGAGCACCACCAGGACCTGACCCT<br>GCTGAAAGCTCTCGTGCGGCAGCAGCTGCCTGAGAAGTACAAAGAGATTTTCTTCG<br>ACCAGAGCAAGAACGGCTACGCCGGCTACATTGACGGCGGAGCCAGCCAGGAAGA<br>GTTCTACAAGTTCATCAAGCCCATCCTGGAAAAGATGGACGGCACCGAGGAACTGC<br>TCGTGAAGCTGAACAGAGAGGACCTGCTGCGGAAGCAGCGGACCTTCGACAACGG<br>CAGCATCCCCCACCAGATCCACCTGGGAGAGCTGCACGCCATTCTGCGGCGGCAGG<br>AAGATTTTTACCCATTCCTGAAGGACAACCGGGAAAAGATCGAGAAGATCCTGACC<br>TTCCGCATCCCCTACTACGTGGGCCCTCTGGCCAGGGGAAACAGCAGATTCGCCTG<br>GATGACCAGAAAGAGCGAGGAAACCATCACCCCCTGGAACTTCGAGGAAGTGGTG<br>GACAAGGGCGCTTCCGCCCAGAGCTTCATCGAGCGGATGACCAACTTCGATAAGAA<br>CCTGCCCAACGAGAAGGTGCTGCCCAAGCACAGCCTGCTGTACGAGTACTTCACCG<br>TGTATAACGAGCTGACCAAAGTGAAATACGTGACCGAGGGAATGAGAAAGCCCGC<br>CTTCCTGAGCGGCGAGCAGAAAAAGGCCATCGTGGACCTGCTGTTCAAGACCAACC<br>GGAAAGTGACCGTGAAGCAGCTGAAGGAGGACTACTTCAAGAAAATCGAGTGCTTC<br>GACTCCGTGGAAATCTCCGGCGTGGAAGATCGGTTCAACGCCTCCCTGGGCACATA<br>CCACGATCTGCTGAAAATTATCAAGGACAAGGACTTCCTGGACAATGAGGAAAACG<br>AGGACATTCTGGAAGATATCGTGCTGACCCTGACACTGTTTGAGGACAGAGAGATG<br>ATCGAGGAACGGCTGAAAACCTATGCCCACCTGTTCGACGACAAAGTGATGAAGCA<br>GCTGAAGCGGCGGAGATACACCGGCTGGGGCAGGCTGAGCCGGAAGCTGATCAAC<br>GGCATCCGGGACAAGCAGTCCGGCAAGACAATCCTGGATTTCCTGAAGTCCGACGG<br>CTTCGCCAACAGAAACTTCATGCAGCTGATCCACGACGACAGCCTGACCTTTAAAG<br>AGGACATCCAGAAAGCCCAGGTGTCCGGCCAGGGCGATAGCCTGCACGAGCACATT<br>GCCAATCTGGCCGGCAGCCCCGCCATTAAGAAGGGCATCCTGCAGACAGTGAAGGT<br>GGTGGACGAGCTCGTGAAAGTGATGGGCCGGCACAAGCCCGAGAACATCGTGATC<br>GAAATGGCCAGAGAGAACCAGACCACCCAGAAGGGACAGAAGAACAGCCGCGAG<br>AGAATGAAGCGGATCGAAGAGGGCATCAAAGAGCTGGGCAGCCAGATCCTGAAAG<br>AACACCCCGTGGAAAACACCCAGCTGCAGAACGAGAAGCTGTACCTGTACTACCTG<br>CAGAATGGGCGGGATATGTACGTGGACCAGGAACTGGACATCAACCGGCTGTCCGA<br>CTACGATGTGGACCATATCGTGCCTCAGAGCTTTCTGAAGGACGACTCCATCGACA<br>ACAAGGTGCTGACCAGAAGCGACAAGAACCGGGGCAAGAGCGACAACGTGCCCTC<br>CGAAGAGGTCGTGAAGAAGATGAAGAACTACTGGCGGCAGCTGCTGAACGCCAAG<br>CTGATTACCCAGAGAAAGTTCGACAATCTGACCAAGGCCGAGAGAGGCGGCCTGAG<br>CGAACTGGATAAGGCCGGCTTCATCAAGAGACAGCTGGTGGAAACCCGGCAGATCA<br>CAAAGCACGTGGCACAGATCCTGGACTCCCGGATGAACACTAAGTACGACGAGAAT<br>GACAAGCTGATCCGGGAAGTGAAAGTGATCACCCTGAAGTCCAAGCTGGTGTCCGA<br>TTTCCGGAAGGATTTCCAGTTTTACAAAGTGCGCGAGATCAACAACTACCACCACG<br>CCCACGACGCCTACCTGAACGCCGTCGTGGGAACCGCCCTGATCAAAAAGTACCCT<br>AAGCTGGAAAGCGAGTTCGTGTACGGCGACTACAAGGTGTACGACGTGCGGAAGAT<br>GATCGCCAAGAGCGAGCAGGAAATCGGCAAGGCTACCGCCAAGTACTTCTTCTACA<br>GCAACATCATGAACTTTTTCAAGACCGAGATTACCCTGGCCAACGGCGAGATCCGG<br>AAGCGGCCTCTGATCGAGACAAACGGCGAAACCGGGGAGATCGTGTGGGATAAGG<br>GCCGGGATTTTGCCACCGTGCGGAAAGTGCTGAGCATGCCCCAAGTGAATATCGTG<br>AAAAAGACCGAGGTGCAGACAGGCGGCTTCAGCAAAGAGTCTATCCTGCCCAAGA<br>GGAACAGCGATAAGCTGATCGCCAGAAAGAAGGACTGGGACCCTAAGAAGTACGG |

```
CGGCTTCGACAGCCCCACCGTGGCCTATTCTGTGCTGGTGGTGGCCAAAGTGGAAA
AGGGCAAGTCCAAGAAACTGAAGAGTGTGAAAGAGCTGCTGGGGATCACCATCAT
GGAAAGAAGCAGCTTCGAGAAGAATCCCATCGACTTTCTGGAAGCCAAGGGCTACA
AAGAAGTGAAAAAGGACCTGATCATCAAGCTGCCTAAGTACTCCCTGTTCGAGCTG
GAAAACGGCCGGAAGAGAATGCTGGCCTCTGCCGGCGAACTGCAGAAGGGAAACG
AACTGGCCCTGCCCTCCAAATATGTGAACTTCCTGTACCTGGCCAGCCACTATGAGA
AGCTGAAGGGCTCCCCCGAGGATAATGAGCAGAAACAGCTGTTTGTGGAACAGCAC
AAGCACTACCTGGACGAGATCATCGAGCAGATCAGCGAGTTCTCCAAGAGAGTGAT
CCTGGCCGACGCTAATCTGGACAAAGTGCTGTCCGCCTACAACAAGCACCGGGATA
AGCCCATCAGAGAGCAGGCCGAGAATATCATCCACCTGTTTACCCTGACCAATCTG
GGAGCCCCTGCCGCCTTCAAGTACTTTGACACCACCATCGACCGGAAGAGGTACAC
CAGCACCAAAGAGGTGCTGGACGCCACCCTGATCCACCAGAGCATCACCGGCCTGT
ACGAGACACGGATCGACCTGTCTCAGCTGGGAGGTGAC

SEQ ID NO: 31, SpCas9(D10A)-NG: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATGCCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGAGATACGACGAGCACCACCAGGACCTGACCCT
GCTGAAAGCTCTCGTCCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CAGCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCTGACC
TTCCGCATCCCCTACTACGTGGGCCCTCTGGCCAGGGGAAACAGCAGATTCGCCTG
GATGACCAGAAAGAGCGAGGAAACCATCACCCCCTGGAACTTCGAGGAAGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATGCAGCTGATCCACGACGACAGCCTGACCTTTAAAG
AGGACATCCAGAAAGCCCAGGTGTCCGGCCAGGGCGATAGCCTGCACGAGCACATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCCGGATGAACACTAAGTACGACGAGAAT
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGAT
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAAGAGTCTATCCgGCCCAAGAG
GAACAGCGATAAGCTGATCGCCAGAAAGAAGGACTGGGACCCTAAGAAGTACGGC
GGCTTCGtCAGCCCCACCGTGGCCTATTCTGTGCTGGTGGTGGCCAAAGTGGAAAAG
```

| SEQUENCES |
|---|
| GGCAAGTCCAAGAAACTGAAGAGTGTGAAAGAGCTGCTGGGGATCACCATCATGG<br>AAAGAAGCAGCTTCGAGAAGAATCCCATCGACTTTCTGGAAGCCAAGGGCTACAAA<br>GAAGTGAAAAAGGACCTGATCATCAAGCTGCCTAAGTACTACCCTGTTCGAGCTGGA<br>AAACGGCCGGAAGAGAATGCTGGCCTCTGCCCGCttCTGCAGAAGGGAAACGAACT<br>GGCCCTGCCCTCCAAATATGTGAACTTCCTGTACCTGGCCAGCCACTATGAGAAGCT<br>GAAGGGCTCCCCCGAGGATAATGAGCAGAAACAGCTGTTTGTGGAACAGCACAAG<br>CACTACCTGGACGAGATCATCGAGCAGATCAGCGAGTTCTCCAAGAGAGTGATCCT<br>GGCCGACGCTAATCTGGACAAAGTGCTGTCCGCCTACAACAAGCACCGGGATAAGC<br>CCATCAGAGAGCAGGCCGAGAATATCATCCACCTGTTTACCCTGACCAATCTGGGA<br>GCCCCTcggGCCTTCAAGTACTTTGACACCACCATCGACCGGAAGgtGTACcggAGCAC<br>CAAAGAGGTGCTGGACGCCACCCTGATCCACCAGAGCATCACCGGCCTGTACGAGA<br>CACGGATCGACCTGTCTCAGCTGGGAGGTGAC |

SEQ ID NO: 32, xCas9(3.7)-D10A, Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATACCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGCGTACGACGAGCACCACCAGGACCTGACCCT
GCTGAAAGCTCTCGTGCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CATCATCCCCCACCAGATCCACCTGGGAGAGCTGCACGCCATTCTGCGGCGGCAGG
AAGATTTnACCCATTCCTGAAGGACAACGGGAAAGATCGAGAAGATCCTGACC
TTCCGCATCCCCTACTACGTGGGCCCTCTGGCCAGGGGAAACAGCAGATTCGCCTG
GATGACCAGAAAGAGCGAGGAAACCATCACCCCCTGGAACTTCGAGGAAGGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGACCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAACG
AGGACATTCTGGAAGATATCGTGCTGACCCTGACACTGTTiTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATCCAGCTGATCCACGACGACAGCCTGACCTTTAAAG
AGGACATCCAGAAAGCCCAGGTGTCCGGCCAGGGCGATAGCCTGCACGAGCAATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCGGATGAACACTAAGTACGACGAGAAr
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGAT
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAAGAGTCTATCCTGCCCAAGA
GGAACAGCGATAAGCTGATCGCCAGAAAGAAGGACTGGGACCCTAAGAAGTACGG
CGGCTTCGACAGCCCCACCGTGGCCTATTCTGTGCTGGTGGTGGCCAAAGTGGAAA
AGGGCAAGTCCAAGAAACTGAAGAGTGTGAAAGAGCTGCTGGGGATCACCATCAT

| SEQUENCES |
|---|
| GGAAAGAAGCAGCTTCGAGAAGAATCCCATCGACTTTCTGGAAGCCAAGGGCTACA<br>AAGAAGTGAAAAAGGACCTGATCATCAAGCTGCCTAAGTACTCCCTGTTCGAGCTG<br>GAAAACGGCCGGAAGAATGCTGGCCTCTGCCGGCGTGCTGCAGAAGGGAAACG<br>AACTGGCCCTGCCCTCCAAATATGTGAACTTCCTGTACCTGGCCAGCCACTATGAGA<br>AGCTGAAGGGCTCCCCCGAGGATAATGAGCAGAAACAGCTGTTTGTGGAACAGCAC<br>AAGCACTACCTGGACGAGATCATCGAGCAGATCAGCGAGTTCTCCAAGAGAGTGAT<br>CCTGGCCGACGCTAATCTGGACAAAGTGCTGTCCGCCTACAACAAGCACCGGGATA<br>AGCCCATCAGAGAGCAGGCCGAGAATATCATCCACCTGTTTACCCTGACCAATCTG<br>GGAGCCCCTGCCGCCTTCAAGTACTTTGACACCACCATCGACCGGAAGAGGTACAC<br>CAGCACCAAAGAGGTGCTGGACGCCACCCTGATCCACCAGAGCATCACCGGCCTGT<br>ACGAGACACGGATCGACCTGTCTCAGCTGGGAGGCGAC |
| SEQ ID NO: 33, SpCas9(D10A)-NGX: Nucleotide sequence:<br>ATGGACAAGAAGTACAGCATCGGCCTGGCCATCGGCACCAACTCTGTGGGCT<br>GGGCCGTGATCACCGACGAGTACAAGGTGCCCAGCAAGAAATTCAAGGTGCTGGGC<br>AACACCGACCGGCACAGCATCAAGAAGAACCTGATCGGAGCCCTGCTGTTCGACAG<br>CGGCGAAACAGCCGAGGCCACCCGGCTGAAGAGAACCGCCAGAAGAAGATACACC<br>AGACGGAAGAACCGGATCTGCTATCTGCAAGAGATCTTCAGCAACGAGATGGCCAA<br>GGTGGACGACAGCTTCTTCCACAGACTGGAAGAGTCCTTCCTGGTGGAAGAGGATA<br>AGAAGCACGAGCGGCACCCCATCTTCGGCAACATCGTGGACGAGGTGGCCTACCAC<br>GAGAAGTACCCCACCATCTACCACCTGAGAAAGAAACTGGTGGACAGCACCGACA<br>AGGCCGACCTGCGGCTGATCTATCTGGCCCTGGCCCACATGATCAAGTTCCGGGGC<br>CACTTCCTGATCGAGGGCGACCTGAACCCCGACAACAGCGACGTGGACAAGCTGTT<br>CATCCAGCTGGTGCAGACCTACAACCAGCTGTTCGAGGAAAACCCCATCAACGCCA<br>GCGGCGTGGACGCCAAGGCCATCCTGTCTGCCAGACTGAGCAAGAGCAGACGGCTG<br>GAAAATCTGATCGCCCAGCTGCCCGGCGAGAAGAAGAATGGCCTGTTCGGAAACCT<br>GATTGCCCTGAGCCTGGGCCTGACCCCCAACTTCAAGAGCAACTTCGACCTGGCCG<br>AGGATACCAAACTGCAGCTGAGCAAGGACACCTACGACGACGACCTGGACAACCT<br>GCTGGCCCAGATCGGCGACCAGTACGCCGACCTGTTTCTGGCCGCCAAGAACCTGT<br>CCGACGCCATCCTGCTGAGCGACATCCTGAGAGTGAACACCGAGATCACCAAGGCC<br>CCCCTGAGCGCCTCTATGATCAAGCGTATACGACGAGCACCACCAGGACCTGACCCT<br>GCTGAAAGCTCTCGTGCGGCAGCAGCTGCCTGAGAAGTACAAAGAGATTTTCTTCG<br>ACCAGAGCAAGAACGGCTACGCCGGCTACATTGACGGCGGAGCCAGCCAGGAAGA<br>GTTCTACAAGTTCATCAAGCCCATCCTGGAAAAGATGGACGGCACCGAGGAACTGC<br>TCGTGAAGCTGAACAGAGAGGACCTGCTGCGGAAGCAGCGGACCTTCGACAACGG<br>CATCATCCCCCACCAGATCCACCTGGGAGAGCTGCACGCCATTCTGCGGCGGCAGG<br>AAGATTTTTACCCATTCCTGAAGGACAACCGGGAAAAGATCGAGAAGATCCTGACC<br>TTCCGCATCCCCTACTACGTGGGCCCTCTGGCCAGGGGAAACAGCAGATTCGCCTG<br>GATGACCAGAAGAGCGAGGAAACCATCACCCCCTGGAACTTCGAGAAGGTGGTG<br>GACAAGGGCGCTTCCGCCCAGAGCTTCATCGAGCGGATGACCAACTTCGATAAGAA<br>CCTGCCCAACGAGAAGGTGCTGCCCAAGCACAGCCTGCTGTACGAGTACTTCACCG<br>TGTATAACGAGCTGACCAAAGTGAAATACGTGACCGAGGGAATGAGAAAGCCCGC<br>CTTCCTGAGCGGCGACCAGAAAAAGGCCATCGTGGACCTGCTGTTCAAGACCAACC<br>GGAAAGTGACCGTGAAGCAGCTGAAGGAGGACTACTTCAAGAAAATCGAGTGCTTC<br>GACTCCGTGGAAATCTCCGGCGTGGAAGATCGGTTCAACGCCTCCCTGGGCACATA<br>CCACGATCTGCTGAAAATTATCAAGGACAAGGACTTCCTGGACAATGAGGAAAACG<br>AGGACATTCTGGAAGATATCGTGCTGACCCTGACACTGTTTGAGGACAGAGAGATG<br>ATCGAGGAACGGCTGAAAACCTATGCCCACCTGTTCGACGACAAAGTGATGAAGCA<br>GCTGAAGCGGCGGAGATACACCGGCTGGGGCAGGCTGAGCCGGAAGCTGATCAAC<br>GGCATCCGGGACAAGCAGTCCGGCAAGACAATCCTGGATTTCCTGAAGTCCGACGG<br>CTTCGCCAACAGAAACTTCATCCAGCTGATCCACGACGACAGCCTGACCTTTAAAG<br>AGGACATCCAGAAAGCCCAGGTGTCCGGCCAGGGCGATAGCCTGCACGAGCACATT<br>GCCAATCTGGCCGGCAGCCCCGCCATTAAGAAGGGCATCCTGCAGACAGTGAAGGT<br>GGTGGACGAGCTCGTGAAAGTGATGGGCCGGCACAAGCCCGAGAACATCGTGATC<br>GAAATGGCCAGAGAGAACCAGACCACCCAGAAGGGACAGAAGAACAGCCGCGAG<br>AGAATGAAGCGGATCGAAGAGGGCATCAAAGAGCTGGGCAGCCAGATCCTGAAAG<br>AACACCCCGTGGAAAACACCCAGCTGCAGAACGAGAAGCTGTACCTGTACTACCTG<br>CAGAATGGGCGGGATATGTACGTGGACCAGGAACTGGACATCAACCGGCTGTCCGA<br>CTACGATGTGGACCATATCGTGCCTCAGAGCTTTCTGAAGGACGACTCCATCGACA<br>ACAAGGTGCTGACCAGAAGCGACAAGAACCGGGGCAAGAGCGACAACGTGCCCTC<br>CGAAGAGGTCGTGAAGAAGATGAAGAACTACTGGCGGCAGCTGCTGAACGCCAAG<br>CTGATTACCCAGAGAAAGTTCGACAATCTGACCAAGGCCGAGAGAGGCGGCCTGAG<br>CGAACTGGATAAGGCCGGCTTCATCAAGAGACAGCTGGTGGAAACCCGGCAGATCA<br>CAAAGCACGTGGCACAGATCCTGGACTCCGGATGAACACTAAGTACGACGAGAAT<br>GACAAGCTGATCCGGGAAGTGAAAGTGATCACCCTGAAGTCCAAGCTGGTGTCCGA<br>TTTCCGGAAGGATTTCCAGTTTTACAAAGTGCGCGAGATCAACAACTACCACCACG<br>CCCACGACGCCTACCTGAACGCCGTCGTGGGAACCGCCCTGATCAAAAAGTACCCT<br>AAGCTGGAAAGCGAGTTCGTGTACGGCGACTACAAGGTGTACGACGTGCGGAAGAT<br>GATCGCCAAGAGCGAGCAGGAAATCGGCAAGGCTACCGCCAAGTACTTCTTCTACA<br>GCAACATCATGAACTTTTTCAAGACCGAGATTACCCTGGCCAACGGCGAGATCCGG<br>AAGCGGCCTCTGATCGAGACAAACGGCGAAACCGGGGAGATCGTGTGGGATAAGG<br>GCCGGGATTTTGCCACCGTGCGGAAAGTGCTGAGCATGCCCCAAGTGAATATCGTG<br>AAAAAGACCGAGGTGCAGACAGGCGGCTTCAGCAAAGAGTCTATCCgGCCCAAGAG<br>GAACAGCGATAAGCTGATCGCCAGAAAGAAGGACTGGGACCCTAAGAAGTACGGC<br>GGCTTCGtCAGCCCCACCGTGGCCTATTCTGTGCTGGTGGTGGCCAAAGTGGAAAAG<br>GGCAAGTCCAAGAAACTGAAGAGTGTGAAAGAGCTGCTGGGGATCACCATCATGG<br>AAAGAAGCAGCTTCGAGAAGAATCCCATCGACTTTCTGGAAGCCAAGGGCTACAAA |

| SEQUENCES |
|---|
| GAAGTGAAAAAGGACCTGATCATCAAGCTGCCTAAGTACTCCCTGTTCGAGCTGGA |
| AAACGGCCGGAAGAGAATGCTGGCCTCTGCCcGCtttCTGCAGAAGGGAAACGAACT |
| GGCCCTGCCCTCCAAATATGTGAACTTCCTGTACCTGGCCAGCCACTATGAGAAGCT |
| GAAGGGCTCCCCCGAGGATAATGAGCAGAAACAGCTGTTTGTGGAACAGCACAAG |
| CACTACCTGGACGAGATCATCGAGCAGATCAGCGAGTTCTCCAAGAGAGTGATCCT |
| GGCCGACGCTAATCTGGACAAAGTGCTGTCCGCCTACAACAAGCACCGGGATAAGC |
| CCATCAGAGAGCAGGCCGAGAATATCATCCACCTGTTTACCCTGACCAATCTGGGA |
| GCCCCTcggGCCTTCAAGTACTTTGACACCACCATCGACCGGAAGgtGTACcggAGCAC |
| CAAAGAGGTGCTGGACGCCACCCTGATCCACCAGAGCATCACCGGCCTGTACGAGA |
| CACGGATCGACCTGTCTCAGCTGGGAGGTGAC |

SEQ ID NO: 34, SpCas9(D10A)-NGA: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATGCCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGAGATACGACGAGCACCACCAGGACCTGACCCT
GCTGAAAGCTCTCGTCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CAGCATCCCCCACCAGATCCACCTGGGAGAGCTGCACGCCATTCTGCGGCGGCAGG
AAGATTTTTACCCATTCCTGAAGGACAACCGGGAAAAGATCGAAAAGATCCTGACC
TTCCGCATCCCCTACTACGTGGGCCCTCTGGCCAGGGGAAACAGCAGATTCGCCTG
GATGACCAGAAAGAGCGAGGAAACCATCACCCCCTGGAACTTCGAGGAAGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATGCAGCTGATCCACGACGACAGCCTGACCTTTAAAG
AGGACATCCAGAAGCCCAGGTGTCCGGCCAGGGCGATAGCCTGCACGAGCACATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGCCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCCGGATGAACACTAAGTACGACGAGAAT
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGA1
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAAGAGTCTATCCggCCCAAGAG
GAACAGCGATAAGCTGATCGCCAGAAAGAAGGACTGGGACCCTAAGAAGTACGGC
GGCTTCGtCAGCCCCACCGTGGCCTATTCTGTGCTGGTGGTGGCCAAAGTGGAAAAG
GGCAAGTCCAAGAAACTGAAGAGTGTGAAAGAGCTGCTGGGGATCACCATCATGG
AAAGAAGCAGCTTCGAGAAGAATCCCATCGACTTTCTGGAAGCCAAGGGCTACAAA
GAAGTGAAAAAGGACCTGATCATCAAGCTGCCTAAGTACTCCCTGTTCGAGCTGGA

```
AAACGGCCGGAAGAGAATGCTGGCCTCTGCCCGCtCTGCAGAAGGGAAACGAACT
GGCCCTGCCCTCCAAATATGTGAACTTCCTGTACCTGGCCAGCCACTATGAGAAGCT
GAAGGGCTCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCT
GGCCGACGCTAATCTGGACAAAGTGCTGTCCGCCTACAACAAGCACGGGATAAGC
CCATCAGAGAGCAGGCCGAGAATATCATCCACCTGTTTACCCTGACCAATCTGGGA
GCCCCTcggGCCTTCAAGTACTTTGACACCACCATCGACCGGAAGcaGTACcggAGCAC
CAAAGAGGTGCTGGACGCCACCCTGATCCACCAGAGCATCACCGGCCTGTACGAGA
CACGGATCGACCTGTCTCAGCTGGAGGTGAC SEQ ID NO: 35, SpCas9(D10A)-NGC: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATGCCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGAGATACGACGAGCACCACCAGGACCTGACCCT
GCTGAAAGCTCTCGTCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CAGCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCCGACC
TTCCGCATCCCCTACTACGTGGGCCCTCTGGCCAGGGGAAACAGCAGATTCGCCTG
GATGACCAGAAAGAGCGAGGAAACCATCACCCCCTGGAACTTCGAGGAAGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCTGGGCACATA
CCACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATGCAGCTGATCCACGACGACAGCCTGACCTTTAAAG
AGGACATCCAGAAAGCCCAGGTGTCCGGCCAGGGCGATAGCCTGCACGAGCACATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCCGGATGAACACTAAGTACGACGAGAAT
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGAT
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAAGAGTCTATCcgGCCCAAGAG
GAACAGCGATAAGCTGATCGCCAGAAAGAAGGACTGGGACCCTAAGAAGTACGGC
GGCTTCGtCAGCCCCACCGTGGCCTATTCTGTGCTGGTGGTGGCCAAAGTGGAAAAG
GGCAAGTCCAAGAAACTGAAGAGTGTGAAAGAGCTGCTGGGGATCACCATCATGG
AAAGAAGCAGCTTCGAGAAGAATCCCATCGACTTTCTGGAAGCCAAGGGCTACAAA
GAAGTGAAAAAGGACCTGATCATCAAGCTGCCTAAGTACTCCCTGTTCGAGCTGGA
AAACGGCCGGAAGAGAATGCTGGCCTCTGCCcGCtttCTGCAGAAGGGAAACGAACT
```

| SEQUENCES |
|---|
| GGCCCTGCCCTCCAAATATGTGAACTTCCTGTACCTGGCCAGCCACTATGAGAAGCT
GAAGGGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCT
GGCCGACGCTAATCTGGACAAAGTGCTGTCCGCCTACAACAAGCACCGGGATAAGC
CCATCAGAGAGCAGGCCGAGAATATCATCCACCTGTTTACCCTGACCAATCTGGGA
GCCCCTcggGCCTTCAAGTACTTTGACACCACCATCGACCGGAAGgaGTACcggAGCAC
CAAAGAGGTGCTGGACGCCACCCTGATCCACCAGAGCATCACCGGCCTGTACGAGA
CACGGATCGACCTGTCTCAGCTGGGAGGTGAC SEQ ID NO: 36, SpCas9(D10A)-NGX-NGA: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATACCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGCTGTACGACGAGCACCACCAGGACCTGACCCT
GCTGAAAGCTCTCGTGCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CATCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCTGACC
TTCCGCATCCCCTACTACGTGGGCCCTCTGGCCAGGGGAAACAGCAGATTCGCCTG
GATGACCAGAAAGAGCGAGGAAACCATCACCCCCTGGAACTTCGAGGAGGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGAACCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATCCAGCTGATCCACGACGACAGCCTGACCTTTAAAG
AGGACATCCAGAAAGCCCAGGTGTCCGGCCAGGGCGATAGCCTGCACGAGCACATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCCGGATGAACACTAAGTACGACGAGAAT
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGAT
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAGGAGTCTATCCgGCCCAAGAG
GAACAGCGATAAGCTGATCGCCAGAAAGAAGGACTGGGACCCTAAGAAGTACGGC
GGCTTCGTCAGCCCCACCGTGGCCTATTCTGTGCTGGTGGTGGCCAAAGTGGAAAAG
GGCAAGTCCAAGAAACTGAAGAGTGTGAAAGAGCTGCTGGGGATCACCATCATGG
AAAGAAGCAGCTTCGAAGAAGAATCCCATCGACTTTCTGGAAGCCAAGGGCTACAAA
GAAGTGAAAAAGGACCTGATCATCAAGCTGCCTAAGTACTCCCTGTTCGAGCTGGA
AAACGGCCGGAAGAGAATGCTGGCCTCTGCCcGCtttCTGCAGAAGGGAAACGAACT
GGCCCTGCCCTCCAAATATGTGAACTTCCTGTACCTGGCCAGCCACTATGAGAAGCT |

```
GAAGGGCTCCCCCGAGGATAATGAGCAGAAACAGCTGTTTGTGGAACAGCACAAG
CACTACCTGGACGAGATCATCGAGCAGATCAGCGAGTTCTCCAAGAGAGTGATCCT
GGCCGACGCTAATCTGGACAAAGTGCTGTCCGCCTACAACAAGCACCGGGATAAGC
CCATCAGAGAGCAGGCCGAGAATATCATCCACCTGTTTACCCTGACCAATCTGGGA
GCCCCTcggGCCTTCAAGTACTTTGACACCACCATCGACCGGAAGcaGTACcggAGCAC
CAAAGAGGTGCTGGACGCCACCCTGATCCACCAGAGCATCACCGGCCTGTACGAGA
CACGGATCGACCTGTCTCAGCTGGAGGTGAC
```

SEQ ID NO: 37, SpCas9(D10A)-NGX-NGC, Nucleotide sequence:
```
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATACCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGCGTATACGACGAGCACCACCAGGACCTGACCCT
GCTGAAAGCTCTCGTGCGGCAGCAGCTGCCTGAGAAGTACAAAGAGATTTTCTTCG
ACCAGAGCAAGAACGGCTACGCCGGCTACATTGACGGCGGAGCCAGCCAGGAAGA
GTTCTACAAGTTCATCAAGCCCATCCTGGAAAAGATGGACGGCACCGAGGAACTGC
TCGTGAAGCTGAACAGAGAGGACCTGCTGCGGAAGCAGCGGACCTTCGACAACGG
CATCATCCCCCACCAGATCCACCTGGGAGAGCTGCACGCCATTCTGCGGCGGCAGG
AAGATTTTTACCCATTCCTGAAGGACAACCGGGAAAAGATCGAGAAGATCCTGACC
TTCCGCATCCCCTACTACGTGGGCCCTCTGGCCAGGGGAAACAGCAGATTCGCCTG
GATGACCAGAAGAGCGAGGAAAACCATCACCCCCTGGAACTTCGAGAAGGTGGTG
GACAAGGGCGCTTCCGCCCAGAGCTTCATCGAGCGGATGACCAACTTCGATAAGAA
CCTGCCCAACGAGAAGGTGCTGCCCAAGCACAGCCTGCTGTACGAGTACTTCACCG
TGTATAACGAGCTGACCAAAGTGAAATACGTGACCGAGGGAATGAGAAAGCCCGC
CTTCCTGAGCGGCGAGCAGAAAAAGGCCATCGTGGACCTGCTGTTCAAGACCAACC
GGAAAGTGACCGTGAAGCAGCTGAAAGAGGACTACTTCAAGAAAATCGAGTGCTTC
GACTCCGTGGAAATCTCCGGCGTGGAAGATCGGTTCAACGCCTCCCTGGGCACATA
CCACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGATG
ATCGAGGAACGGCTGAAAACCTATGCCCACCTGTTCGACGACAAAGTGATGAAGCA
GCTGAAGCGGCGGAGATACACCGGCTGGGGCAGGCTGAGCCGGAAGCTGATCAAC
GGCATCCGGGACAAGCAGTCCGGCAAGACAATCCTGGATTTCCTGAAGTCCGACGG
CTTCGCCAACAGAAACTTCATCCAGCTGATCCACGACGACAGCCTGACCTTTAAAG
AGGACATCCAGAAGCCCAGGTGTCCGGCCAGGGCGATAGCCTGCACGAGCACATT
GCCAATCTGGCCGGCAGCCCCGCCATTAAGAAGGGCATCCTGCAGACAGTGAAGGT
GGTGGACGAGCTCGTGAAAGTGATGGGCCGGCACAAGCCCGAGAACATCGTGATC
GAAATGGCCAGAGAGAACCAGACCACCCAGAAGGGACAGAAGAACAGCCGCGAG
AGAATGAAGCGGATCGAAGAGGGCATCAAAGAGCTGGGCAGCCAGATCCTGAAAG
AACACCCCGTGGAAAACACCCAGCTGCAGAACGAGAAGCTGTACCTGTACTACCTG
CAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACA
ACAAGGTGCTGACCAGAAGCGACAAGAACCGGGGCAAGAGCGACAACGTGCCCTC
CGAAGAGGTCGTGAAGAAGATGAAGAACTACTGGCGGCAGCTGCTGAACGCCAAG
CTGATTACCCAGAGAAAGTTCGACAATCTGACCAAGGCCGAGAGAGGCGGCCTGAG
CGAACTGGATAAGGCCGGCTTCATCAAGAGACAGCTGGTGGAAACCCGGCAGATCA
CAAAGCACGTGGCACAGATCCTGGACTCCGGATGAACACTAAGTACGACGAGAAT
GACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACG
CCCACGACGCCTACCTGAACGCCGTCGTGGGAACCGCCCTGATCAAAAAGTACCCT
AAGCTGGAAAGCGAGTTCGTGTACGGCGACTACAAGGTGTACGACGTGCGGAAGAT
GATCGCCAAGAGCGAGCAGGAAATCGGCAAGGCTACCGCCAAGTACTTCTTCTACA
GCAACATCATGAACTTTTTCAAGACCGAGATTACCCTGGCCAACGGCGAGATCCGG
AAGCGGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATATCGTG
AAAAAGACCGAGGTGCAGACAGGCGGCTTCAGCAAAGAGTCTATCCgGCCCAAGAG
GAACAGCGATAAGCTGATCGCCAGAAAGAAGGACTGGGACCCTAAGAAGTACGGC
GGCTTCGtCAGCCCCACCGTGGCCTATTCTGTGCTGGTGGTGGCCAAAGTGGAAAAG
GGCAAGTCCAAGAAACTGAAGAGTGTGAAAGAGCTGCTGGGGATCACCATCATGG
AAAGAAGCAGCTTCGAAGAGAATCCCATCGACTTTCTGGAAGCCAAGGGCTACAAA
GAAGTGAAAAAGGACCTGATCATCAAGCTGCCTAAGTACTCCCTGTTCGAGCTGGA
AAACGGCCGGAAGAGAATGCTGGCCTCTGCCcGCtttCTGCAGAAGGGAAACGAACT
GGCCCTGCCCTCCAAATATGTGAACTTCCTGTACCTGGCCAGCCACTATGAAGCT
GAAGGGCTCCCCCGAGGATAATGAGCAGAAACAGCTGTTTGTGGAACAGCACAAG
```

```
CACTACCTGGACGAGATCATCGAGCAGATCAGCGAGTTCTCCAAGAGAGTGATCCT
GGCCGACGCTAATCTGGACAAAGTGCTGTCCGCCTACAACAAGCACCGGGATAAGC
CCATCAGAGAGCAGGCCGAGAATATCATCCACCTGTTTACCCTGACCAATCTGGGA
GCCCCTcggGCCTTCAAGTACTTTGACACCACCATCGACCGGAAGgaGTACcggAGCAC
CAAAGAGGTGCTGGACGCCACCCTGATCCACCAGAGCATCACCGGCCTGTACGAGA
CACGGATCGACCTGTCTCAGCTGGGAGGTGAC SEQ ID: 38, SpCas9(D10A)-NG-loop: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGrACCCCACCATCrACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATGCCAAACTGCAGCTGAGCAAGGACACCTACGACGACGACCTGGACAACCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGAGATACGACGAGCACCACCAGGACCTGACCCT
GCTGAAAGCTCTCGTCGGCAGCAGCTGCCTGAGAAGTACAAAGAGATTTTCTTCG
ACCAGAGCAAGAACGGCTACGCCGGCTACgtgggcgccgacaagaagctgcgcaagcgcagctctaaactg
gccacagagGAAGAGTTCTACAAGTTCATCAAGCCCATCCTGGAAAAGATGGACGGCAC
CGAGGAACTGCTCGTGAAGCTGAACAGAGAGGACCTGCTGCGGAAGCAGCGGACC
TTCGACAACGGCAGCATCCCCCACCAGATCCACCTGGGAGAGCTGCACGCCATTCT
GCGGCGGCAGGAAGATTTTTACCCATTCCTGAAGGACAACCGGGAAAAGATCGAGA
AGATCCTGACCTTCCGCATCCCCTACTACGTGGGCCCTCTGGCCAGGGGAAACAGC
AGATTCGCCTGGATGACCAGAAAGAGCGAGGAAACCATCACCCCCTGGAACTTCGA
GGAAGTGGTGGACAAGGGCGCTTCCGCCCAGAGCTTCATCGAGCGGATGACCAACT
TCGATAAGAACCTGCCCAACGAGAAGGTGCTGCCCAAGCACAGCCTGCTGTACGAG
TACTTCACCGTGTATAACGAGCTGACCAAAGTGAAATACGTGACCGAGGGAATGAG
AAAGCCCGCCTTCCTGAGCGGCGAGCAGAAAAAGGCCATCGTGGACCTGCTGTTCA
AGACCAACCGGAAAGTGACCGTGAAGCAGCTGAAAGAGGACTACTTCAAGAAAAT
CGAGTGCTTCGACTCCGTGGAAATCTCCGGCGTGGAAGATCGGTTCAACGCCTCCCT
GGGCACATACCACGATCTGCTGAAAATTATCAAGGACAAGGACTTCCTGGACAATG
AGGAAAACGAGGACATTCTGGAAGATATCGTGCTGACCCTGACACTGTTTGAGGAC
AGAGAGATGATCGAGGAACGGCTGAAAACCTATGCCCACCTGTTCGACGACAAAGT
GATGAAGCAGCTGAAGCGGCGGAGATACACCGGCTGGGGCAGGCTGAGCCGGAAG
CTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGA
CCTTTAAAGAGGACATCCAGAAAGCCCAGGTGTCCGGCCAGGGCGATAGCCTGCAC
GAGCACATTGCCAATCTGGCCGGCAGCCCCGCCATTAAGAAGGGCATCCTGCAGAC
AGTGAAGGTGGTGGACGAGCTCGTGAAAGTGATGGGCCGGCACAAGCCCGAGAAC
ATCGTGATCGAAATGGCCAGAGAGAACCAGACCACCCAGAAGGGACAGAAGAACA
GCCGCGAGAGAATGAAGCGGATCGAAGAGGGCATCAAAGAGCTGGGOAGCCAGAr
CCTGAAAGAACACCCCGTGGAAAACACCCAGCTGCAGAACGAGAAGCTGTACCTGT
ACTACCTGCAGAATGGGCGGGATATGTACGTGGACCAGGAACTGGACATCAACCGG
CTGTCCGACTACGATGTGGACCATATCGTGCCTCAGAGCTTTCTGAAGGACGACTCC
ATCGACAACAAGGTGCTGACCAGAAGCGACAAGAACCGGGGCAAGAGCGACAACG
TGCCCTCCGAAGAGGTCGTGAAGAAGATGAAGAACTACTGGCGGCAGCTGCTGAAC
GCCAAGCTGATTACCCAGAGAAAGTTCGACAATCTGACCAAGGCCGAGAGAGGCG
GCCTGAGCGAACTGGATAAGGCCGGCTTCATCAAGAGACAGCTGGTGGAAACCCGG
CAGATCACAAAGCACGTGGCACAGATCCTGGACTCCGGATGAACACTAAGTACGA
CGAGAATGACAAGCTGATCCGGGAAGTGAAAGTGATCACCCTGAAGTCCAAGCTGG
TGTCCGATTTCCGGAAGGATTTCCAGTTTTACAAAGTGCGCGAGATCAACAACTACC
ACCACGCCCACGACGCCTACCTGAACGCCGTCGTGGGAACCGCCCTGATCAAAAAG
TACCCTAAGCTGGAAAGCGAGTTCGTGTACGGCGACTACAAGGTGTACGACGTGCG
GAAGATGATCGCCAAGAGCGAGCAGGAAATCGGCAAGGCTACCGCCAAGTACTTCT
TCTACAGCAACATCATGAACTTTTTCAAGACCGAGATTACCCTGGCCAACGGCGAG
ATCCGGAAGCGGCCTCTGATCGAGACAAACGGCGAAACCGGGGAGATCGTGTGGG
ATAAGGGCCGGGATTTTGCCACCGTGCGGAAAGTGCTGAGCATGCCCCAAGTGAAT
ATCGTGAAAAAGACCGAGGTGCAGACAGGCGGCTTCAGCAAAGAGTCTATCCgGCC
CAAGAGGAACAGCGATAAGCTGATCGCCAGAAAGAAGGACTGGGACCCCTAAGAAG
TACGGCGGCTTCGtCAGCCCCACCGTGGCCTATTCTGTGCTGGTGGTGGCCAAAGTG
GAAAAGGGCAAGTCCAAGAAACTGAAGAGTGTGAAAGAGCTGCTGGGGATCACCA
TCATGGAAAGAAGCAGCTTCGAGAAGAATCCCATCGACTTTCTGGAAGCCAAGGGC
TACAAGAAGTGAAAAAGGACCTGATCATCAAGCTGCCTAAGTACTCCCTGTTCGA
GCTGGAAAACGGCCGGAAGAGAATGCTGGCCTCTGCCgCtttCTGCAGAAGGGAAA
CGAACTGGCCCTGCCCTCCAAATATGTGAACTTCCTGTACCTGGCCAGCCACTATGA
GAAGCTGAAGGGCTCCCCCGAGGATAATGAGCAGAAACAGCTGTTTGTGAACAGC
ACAAGCACTACCTGGACGAGATCATCGAGCAGATCAGCGAGTTCTCCAAGAGAGTG
```

| SEQUENCES |
|---|
| ATCCTGGCCGACGCTAATCTGGACAAAGTGCTGTCCGCCTACAACAAGCACCGGGA<br>TAAGCCCATCAGAGAGCAGGCCGAGAATATCATCCACCTGTTTACCCTGACCAATC<br>TGGGAGCCCCTcggGCCTTCAAGTACTTTGACACCACCATCGACCGGAAGgtGTACcgg<br>AGCACCAAAGAGGTGCTGGACGCCACCCTGATCCACCAGAGCATCACCGGCCTGTA<br>CGAGACACGGATCGACCTGTCTCAGCTGGAGGTGAC |

SEQ ID NO: 39, SpCas9(D10A)-NGX-loop: Nucleotide sequence:
ATGGACAAGAAGTACAGCATCGGCCTGGCCATCGGCACCAACTCTGTGGGCT
GGGCCGTGATCACCGACGAGTACAAGGTGCCCAGCAAGAAATTCAAGGTGCTGGGC
AACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACC
AGACGGAAGAACCGGATCTGCTATCTGCAAGAGATCTTCAGCAACGAGATGGCCAA
GGTGGACGACAGCTTCTTCCACAGACTGGAAGAGTCCTTCCTGGTGGAAGAGGATA
AGAAGCACGAGCGGCACCCCATCTTCGGCAACATCGTGGACGAGGTGGCCTACCAC
GAGAAGTACCCCACCATCTACCACCTGAGAAAGAAACTGGTGGACAGCACCGACA
AGGCCGACCTGCGGCTGATCTATCTGGCCCTGGCCCACATGATCAAGTTCCGGGGC
CACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCA
GCGGCGTGGACGCCAAGGCCATCCTGTCTGCCAGACTGAGCAAGAGCAGACGGCTG
GAAAATCTGATCGCCCAGCTGCCCGGCGAGAAGAAGAATGGCCTGTTCGGAAACCT
GATTGCCCTGAGCCTGGGCCTGACCCCCAACTTCAAGAGCAACTTCGACCTGGCCG
AGGATACCAAACTGCAGCTGAGCAAGGACACCTACGACGACGACCTGGACAACCCT
GCTGGCCCAGATCGGCGACCAGTACGCCGACCTGTTTCTGGCCGCCAAGAACCTGT
CCGACGCCATCCTGCTGAGCGACATCCTGAGAGTGAACACCGAGATCACCAAGGCC
CCCCTGAGCGCCTCTATGATCAAGCTGTACGACGAGCACCACCAGGACCTGACCCT
GCTGAAAGCTCTCGTGCGGCAGCAGCTGCCTGAGAAGTACAAAGAGATTTTCTTCG
ACCAGAGCAAGAACGGCTACGCCGGCTACgtgggcgccgacaagaagctgcgcaagcgcagctctaaactg
gccacagagGAAGAGTTCTACAAGTTCATCAAGCCCATCCTGGAAAAGATGGACGGCAC
CGAGGAACTGCTCGTGAAGCTGAACAGAGAGGACCTGCTGCGGAAGCAGCGGACC
TTCGACAACGGCATCATCCCCCACCAGATCCACCTGGGAGAGCTGCACGCCATTCT
GCGGCGGCAGGAAGATTTTTACCCATTCCTGAAGGACAACCGGGAAAAGATCGAGA
AGATCCTGACCTTCCGCATCCCCTACTACGTGGGCCCTCTGGCCAGGGGAAACAGC
AGATTCGCCTGGATGACCAGAAAGAGCGAGGAAACCATCACCCCCTGGAACTTCGA
GGAGGTGGTGGACAAGGGCGCTTCCGCCCAGAGCTTCATCGAGCGGATGACCAACT
TCGATAAGAACCTGCCCAACGAGAAGGTGCTGCCCAAGCACAGCCTGCTGTACGAG
TACTTCACCGTGTATAACGAGCTGACCAAAGTGAAATACGTGACCGAGGGAATGAG
AAAGCCCGCCTTCCTGAGCGGCGAGCAGAAAAAGGCCATCGTGGACCTGCTGTTCA
AGACCAACCGGAAAGTGACCGTGAAGCAGCTGAAAGAGGACTACTTCAAGAAAAr
CGAGTGCTTCGACTCCGTGGAAATCTCCGGCGTGGAAGATCGGTTCAACGCCTCCCT
GGGCACATACCACGATCTGCTGAAAATTATCAAGGACAAGGACTTCCTGGACAATG
AGGAAAACGAGGACATTCTGGAAGATATCGTGCTGACCCTGACACTGTTTGAGGAC
AGAGAGATGATCGAGGAACGGCTGAAAACCTATGCCCACCTGTTCGACGACAAAGT
GATGAAGCAGCTGAAGCGGCGGAGATACACCGGCTGGGGCAGGCTGAGCCGGAAG
CTGATCAACGGCATCCGGGACAAGCAGTCCGGCAAGACAATCCTGGATTTCCTGAA
GTCCGACGGCTTCGCCAACAGAAACTTCATCCAGCTGATCCACGACGACAGCCTGA
CCTTTAAAGAGGACATCCAGAAAGCCCAGGTGTCCGGCCAGGGCGATAGCCTGCAC
GAGCACATTGCCAATCTGGCCGGCAGCCCCGCCATTAAGAAGGGCATCCTGCAGAC
AGTGAAGGTGGTGGACGAGCTCGTGAAAGTGATGGGCCGGCACAAGCCCGAGAAC
ATCGTGATCGAAATGGCCAGAGAGAACCAGACCACCCAGAAGGGACAGAAGAACA
GCCGCGAGAGAATGAAGCGGATCGAAGAGGGCATCAAAGAGCTGGGCAGCCAGAT
CCTGAAAGAACACCCCGTGGAAAACACCCAGCTGCAGAACGAGAAGCTGTACCTGT
ACTACCTGCAGAATGGGCGGGATATGTACGTGGACCAGGAACTGGACATCAACCGG
CTGTCCGACTACGATGTGGACCATATCGTGCCTCAGAGCTTTCTGAAGGACGACTCC
ATCGACAACAAGGTGCTGACCAGAAGCGACAAGAACCGGGGCAAGAGCGACAACG
TGCCCTCCGAAGAGGTCGTGAAGAAGATGAAGAACTACTGGCGGCAGCTGCTGAAC
GCCAAGCTGATTACCCAGAGAAAGTTCGACAATCTGACCAAGGCCGAGAGAGGCG
GCCTGAGCGAACTGGATAAGGCCGGCTTCATCAAGAGACAGCTGGTGGAAACCCGG
CAGATCACAAAGCACGTGGCACAGATCCTGGACTCCCGGATGAACACTAAGTACGA
CGAGAATGACAAGCTGATCCGGGAAGTGAAAGTGATCACCCTGAAGTCCAAGCTGG
TGTCCGATTTCCGGAAGGATTTCCAGTTTTACAAAGTGCGCGAGATCAACAACTACC
ACCACGCCCACGACGCCTACCTGAACGCCGTCGTGGGAACCGCCCTGATCAAAAAG
TACCCTAAGCTGGAAAGCGAGTTCGTGTACGGCGACTACAAGGTGTACGACGTGCG
GAAGATGATCGCCAAGAGCGAGCAGGAAATCGGCAAGGCTACCGCCAAGTACTTCT
TCTACAGCAACATCATGAACTTTTTTCAAGACCGAGATTACCCTGGCCAACGGCGAG
ATCCGGAAGCGGCCTCTGATCGAGACAAACGGCGAAACCGGGGAGATCGTGTGGG
ATAAGGGCCGGGATTTTGCCACCGTGCGGAAAGTGCTGAGCATGCCCCAAGTGAAT
ATCGTGAAAAAGACCGAGGTGCAGACAGGCGGCTTCAGCAAAGAGTCTATCCgGCC
CAAGAGGAACAGCGATAAGCTGATCGCCAGAAAGAAGGACTGGGACCCTAAGAAG
TACGGCGGCTTCgtCAGCCCCACCGTGGCCTATTCTGTGCTGGTGGTGGCCAAAGTG
GAAAAGGGCAAGTCCAAGAAACTGAAGAGTGTGAAAGAGCTGCTGGGGATCACCA
TCATGGAAAGAAGCAGCTTCGAGAAGAATCCCATCGACTTTCTGGAAGCCAAGGGC
TACAAAGAAGTGAAAAAGGACCTGATCATCAAGCTGCCTAAGTACTCCCTGTTCGA
GCTGGAAAACGGCCGGAAGAGAATGCTGGCCTCTGCCcGCtttCTGCAGAAGGGAAA
CGAACTGGCCCTGCCCTCCAAATATGTGAACTTCCTGTACCTGGCCAGCCACTATGA
GAAGCTGAAGGGCTCCCCCGAGGATAATGAGCAGAAACAGCTGTTTGTGGAACAGC
ACAAGCACTACCTGGACGAGATCATCGAGCAGATCAGCGAGTTCTCCAAGAGAGTG
ATCCTGGCCGACGCTAATCTGGACAAAGTGCTGTCCGCCTACAACAAGCACCGGGA

| SEQUENCES |
|---|
| TAAGCCCATCAGAGAGCAGGCCGAGAATATCATCCACCTGTTTACCCTGACCAATC<br>TGGGAGCCCCTcggGCCTTCAAGTACTTTGACACCACCATCGACCGGAAGgtGTACcgg<br>AGCACCAAAGAGGTGCTGGACGCCACCCTGATCCACCAGAGCATCACCGGCCTGTA<br>CGAGACACGGATCGACCTGTCTCAGCTGGGAGGTGAC<br><br>SEQ ID NO: 40, ScCas9(D10A): Nucleotide sequence:<br>ATGGAGAAGAAGTACAGCATCGGCCTGGCCATCGGCACCAACAGCGTGGGC<br>TGGGCCGTGATCACCGACGACTACAAGGTGCCCAGCAAGAAGTTCAAGGTGCTGGG<br>CAACACCAACCGCAAGAGCATCAAGAAGAACCTGATGGGCGCCCTGCTGTTCGACA<br>GCGGCGAGACCGCCGAGGCCACCCGCCTGAAGCGCACCGCCCGCCGCCGCTACACC<br>CGCCGCAAGAACCGCATCCGCTACCTGCAGGAGATATTCGCCAACGAGATGGCCAA<br>GCTGGACGACAGCTTCTTCCAGCGCCTGGAGGAGAGCTTCCTGGTGGAGGAGGACA<br>AGAAGAACGAGCGCCACCCCATCTTCGGCAACCTGGCCGACGAGGTGGCCTACCAC<br>CGCAACTACCCCACCATCTACCACCTGCGCAAGAAGCTGGCCGACAGCCCCGAGAA<br>GGCCGACCTGCGCCTGATCTACCTGGCCCTGGCCCACATCATCAAGTTCCGCGGCCA<br>CTTCCTGATCGAGGGCAAGCTGAACGCCGAGAACAGCGACGTGGCCAAGCTGTTCT<br>ACCAGCTGATCCAGACCTACAACCAGCTGTTCGAGGAGAGCCCCCTGGACGAGATC<br>GAGGTGGACGCCAAGGGCATCCTGAGCGCCCGCCTGAGCAAGAGCAAGCGCCTGG<br>AGAAGCTGATCGCCGTGTTCCCCAACGAGAAGAAGAACGGCCTGTTCGGCAACATC<br>ATCGCCCTGGCCCTGGGCCTGACCCCCAACTTCAAGAGCAACTTCGACCTGACCGA<br>GGACGCCAAGCTGCAGCTGAGCAAGGACACCTACGACGACGACCTGGACGAGCTG<br>CTGGGCCAGATCGGCGACCAGTACGCCGACCTGTTCAGCGCCGCCAAGAACCTGAG<br>CGACGCCATCCTGCTGAGCGACATCCTGCGCAGCAACAGCGAGGTGACCAAGGCCC<br>CCCTGAGCGCCAGCATGGTGAAGCGCTACGACGAGCACCACCAGGACCTGGCCCTG<br>CTGAAGACCCTGGTGCGCCAGCAGTTCCCCGAGAAGTACGCCGAGATATTCAAGGA<br>CGACACCAAGAACGGCTACGCCGGCTACGTGGGCATCGGCATCAAGCACCGCAAGC<br>GCACCACCAAGCTGGCCACCCAGGAGGAGTTCTACAAGTTCATCAAGCCCATCCTG<br>GAGAAGATGGACGGCGCCGAGGAGCTGCTGGCCAAGCTGAACCGCGACGACCTGC<br>TGCGCAAGCAGCGCACCTTCGACAACGGCAGCATCCCCCACCAGATCCACCTGAAG<br>GAGCTGCACGCCATCCTGCGCCGCCAGGAGGAGTTCTACCCCTTCCTGAAGGAGAA<br>CCGCGAGAAGATCGAGAAGATCCTGACCTTCCGCATCCCCTACTACGTGGGCCCCC<br>TGGCCCGCGGCAACAGCCGCTTCGCCTGGCTGACCCGCAAGAGCGAGGAGGCCATC<br>ACCCCCTGGAACTTCGAGGAGGTGGTGGACAAGGGCGCCAGCGCCCAGAGCTTCAT<br>CGAGCGCATGACCAACTTCGACGAGCAGCTGCCCAACAAGAAGGTGCTGCCCAAGC<br>ACAGCCTGCTGTACGAGTACTTCACCGTGTACAACGAGCTGACCAAGGTGAAGTAC<br>GTGACCGAGCGCATGCGCAAGCCCGAGTTCCTGAGCGGCGAGCAGAAGAAGGCCA<br>TCGTGGACCTGCTGTTCAAGACCAACCGCAAGGTGACCGTGAAGCAGCTGAAGGAG<br>GACTACTTCAAGAAGATCGAGTGCTTCGACAGCGTGGAGATCATCGGCGTGGAGGA<br>CCGCTTCAACGCCAGCCTGGGCACCTACCACGACCTGCTGAAGATCATCAAGGACA<br>AGGACTTCCTGGACAACGAGGAGAACGAGGACATCCTGGAGGACATCGTGCTGACC<br>CTGACCCTGTTCGAGGACCGCGAGATGATCGAGGAGCGCCTGAAGACCTACGCCCA<br>CCTGTTCGACGACAAGGTGATGAAGCAGCTGAAGCGCCGCCACTACACCGGCTGGG<br>GCCGCCTGAGCCGCAAGATGATCAACGGCATCCGCGACAAGCAGAGCGGCAAGAC<br>CATCCTGGACTTCCTGAAGAGCGACGGCTTCAGCAACCGCAACTTCATGCAGCTGA<br>TCCACGACGACAGCCTGACCTTCAAGGAGGATCGAGAAGGCCCAGGTGAGCGG<br>CCAGGGCGACAGCCTGCACGAGCAGATCGCCGACCTGGCCGGCAGCCCCGCCATCA<br>AGAAGGGCATCCTGCAGACCGTGAAGATCGTGGACGAGCTGGTGAAGGTGATGGG<br>CCACAAGCCCGAGAACATCGTGATCGAGATGGCCCGCGAGAACCAGACCACCACC<br>AAGGGCCTGCAGCAGAGCCGCGAGCGCAAGAAGCGCATCGAGGAGGGCATCAAGG<br>AGCTGGAGAGCCAGATCCTGAAGGAGAACCCCGTGGAGAACACCCAGCTGCAGAA<br>CGAGAAGCTGTACCTGTACTACCTGCAGAACGGCCGCGACATGTACGTGGACCAGG<br>AGCTGGACATCAACCGCCTGAGCGACTACGACGTGGACCACATCGTGCCCCAGAGC<br>TTCATCAAGGACGACAGCATCGACAACAAGGTGCTGACCCGCAGCGACAAGAACCG<br>CGGCAAGAGCGACAACGTGCCAGCGAGGAGGTGGTGAAGAAGATGAAGAACTAC<br>TGGCGCCAGCTGCTGAACGCCAAGCTGATCACCCAGCGCAAGTTCGACAACCTGAC<br>CAAGGCCGAGCGCGGCGGCCTGAGCGAGGCCGACAAGGCCGGCTTCATCAAGCGC<br>CAGCTGGTGGAGACCCGCCAGATCACCAAGCACGTGGCCCGCATCCTGGACAGCCG<br>CATGAACACCAAGCGCGACAAGAACGACAAGCCCATCCGCGAGGTGAAGGTGATC<br>ACCCTGAAGAGCAAGCTGGTGAGCGACTTCCGCAAGGACTTCCAGCTGTACAAGGT<br>GCGCGACATCAACAACTACCACCACGCCCACGACGCCTACCTGAACGCCGTGGTGG<br>GCACCGCCCTGATCAAGAAGTACCCCAAGCTGGAGAGCGAGTTCGTGTACGGCGAC<br>TACAAGGTGTACGACGTGCGCAAGATGATCGCCAAGAGCGAGCAGGAGATCGGCA<br>AGGCCACCGCCAAGCGCTTCTTCTACAGCAACATCATGAACTTCTTCAAGACCGAG<br>GTGAAGCTGGCCAACGGCGAGATCCGCAAGCGCCCCCTGATCGAGACCAACGGCG<br>AGACCGGCGAGGTGGTGTGGAACAAGGAGAAGGACTTCGCCACCGTGCGCAAGGT<br>GCTGGCCATGCCCCAGGTGAACATCGTGAAGAAGACCGAGGTGCAGACCGGCGGCT<br>TCAGCAAGGAGAGCATCCTGAGCAAGCGCGAGAGCGCCAAGCTGATCCCCGCAA<br>GAAGGGCTGGGACACCCGCAAGTACGGCGGCTTCGGCAGCCCCACCGTGGCCTACA<br>GCATCCTGGTGGTGGCCAAGGTGGAGAAGGGCAAGGCCAAGAAGCTGAAGAGCGT<br>GAAGGTGCTGGTGGGCATCACCATCATGGAGAAGGGCAGCTACGAGAAGGACCCC<br>ATCGGCTTCCTGGAGGCCAAGGGCTACAAGGACATCAAGAAGGAGCTGATCTTCAA<br>GCTGCCCAAGTACAGCCTGTTCGAGCTGGAGAACGGCCGCCGCCGCATGCTGGCCA<br>GCGCCACCGAGCTGCAGAAGGCCAACGAGCTGGTGCTGCCCCAGCACCTGGTGCGC<br>CTGCTGTACTACACCCAGAACATCAGCGCCACCACCGGCAGCAACAACCTGGGCTA<br>CATCGAGCAGCACCGCGAGGAGTTCAAGGAGATATTCGAAGATCATCGACTTCA<br>GCGAGAAGTACATCCTGAAGAACAAGGTGAACAGCAACCTGAAGAGCAGCTTCGA<br>CGAGCAGTTCGCCGTGAGCGACAGCATCCTGCTGAGCAACAGCTTCGTGAGCCTGC |

| SEQUENCES |
|---|
| TGAAGTACACCAGCTTCGGCGCCAGCGGCGGCTTCACCTTCCTGGACCTGGACGTG<br>AAGCAGGGCCGCCTGCGCTACCAGACCGTGACCGAGGTGCTGGACGCCACCCTGAT<br>CTACCAGAGCATCACCGGCCTGTACGAGACCCGCACCGACCTGAGCCAGCTGGGCG<br>GCGAC<br><br>SEQ ID NO: 41, TadA-TadA* Nucleotide sequence:<br>TCTGAAGTCGAGTTTAGCCACGAGTATTGGATGAGGCACGCACTGACCCTGG<br>CAAAGCGAGCATGGGATGAAAGAGAAGTCCCCGTGGGCGCCGTGCTGGTGCACAA<br>CAATAGAGTGATCGGAGAGGGATGGAACAGGCCAATCGGCCGCCACGACCCTACC<br>GCACACGCAGAGATCATGGCACTGAGGCAGGGAGGCCTGGTCATGCAGAATTACCG<br>CCTGATCGATGCCACCCTGTATGTGACACTGGAGCCATGCGTGATGTGCGCAGGAG<br>CAATGATCCACAGCAGGATCGGAAGAGTGGTGTTCGGAGCACGGGACGCCAAGAC<br>CGGCGCAGCAGGCTCCCTGATGGATGTGCTGCACCACCCCGGCATGAACCACCGGG<br>TGGAGATCACAGAGGGAATCCTGGCAGACGAGTGCGCCGCCCTGCTGAGCGATTTC<br>TTTAGAATGCGGAGACAGGAGATCAAGGCCCAGAAGAAGGCACAGAGCTCCACCG<br>ACTCTCTGGAGGATCTAGCGGAGGATCCTCTGGAAGCGAGACACCAGGCACAAGCGA<br>GTCCGCCACACCAGAGAGCTCCGGCGGCTCCTCCGGAGGATCCTCTGAGGTGGAGT<br>TTTCCCACGAGTACTGGATGAGACATGCCCTGACCCTGGCCAAGAGGGCACGCGAT<br>GAGAGGGAGGTGCCTGTGGGAGCCGTGCTGGTGCTGAACAATAGAGTGATCGGCG<br>AGGGCTGGAACAGAGCCATCGGCCTGCACGACCCAACAGCCCATGCCGAAATTATG<br>GCCCTGAGACAGGGCGGCCTGGTCATGCAGAACTACAGACTGATTGACGCCACCCT<br>GTACGTGACATTCGAGCCTTGCGTGATGTGCGCCGGCGCCATGATCCACTCTAGGAT<br>CGGCCGCGTGGTGTTTGGCGTGAGGAACGCAAAAACCGGCGCCGCAGGCTCCCTGA<br>TGGACGTGCTGCACTACCCCGGCATGAATCACCGCGTCGAAATTACCGAGGGAATC<br>CTGGCAGATGAATGTGCCGCCCTGCTGTGCTATTTCTTTCGGATGCCTAGACAGGTG<br>TTCAATGCTCAGAAGAAGGCCCAGAGCTCCACCGAC<br><br>SEQ ID: 42, TadA*(A56G_V82G) Nucleotide sequence:<br>TCTGAGGTGGAGTTTTCCCACGAGTACTGGATGAGACATGCCCTGACCCTGG<br>CCAAGAGGGCACGCGATGAGAGGGAGGTGCCTGTGGGAGCCGTGCTGGTGCTGAA<br>CAATAGAGTGATCGGCGAGGGCTGGAACAGAGCCATCGGCCTGCACGACCCAACA<br>GgCCATGCCGAAATTATGGCCCTGAGgCAGGGCGGCCTGGTCATGCAGAACTACAG<br>ACTGATTGACGCCACCCTGTACGgACATTCGAGCCTTGCGTGATGTGCGCCGGCGC<br>CATGATCCACTCTAGGATCGGCCGCGTGGTGTTTGGCGTGAGGAACGCAAAAACCG<br>GCGCCGCAGGCTCCCTGATGGACGTGCTGCACTACCCCGGCATGAATCACCGCGTC<br>GAAATTACCGAGGGAATCCTGGCAGATGAATGTGCCGCCCTGCTGTGCTATTTCTTT<br>CGGATGCCTAGACAGGTGTTCAATGCTCAGAAGAAGGCCCAGAGCTCCACCGAC<br><br>SEQ ID NO: 43, Gp41-1-N: Nucleotide sequence:<br>TGTTTGGATCTGAAAACGCAAGTTCAAACGCCACAGGGTATGAAAGAAATAT<br>CCAATATACAGGTCGGCGATCTCGTCTTGTCTAACACTGGCTATAACGAGGTGCTGA<br>ATGTATTTCCAAAAAGCAAGAAAAAAAGTTACAAGATAACTCTGGAAGATGGAAA<br>AGAAATTATCTGTTCTGAGGAGCATCTGTTTCCGACCCAAACAGGGGAGATGAATA<br>TCAGTGGCGGTCTCAAAGAGGGTATGTGTTTGTATGTCAAGGaataa<br><br>SEQ ID NO: 44, Gp41-1-C: Nucleotide sequence:<br>ATGATGCTCAAGAAGATCCTCAAGATTGAAGAGTTGGACGAGCGCGAGCTT<br>ATAGACATAGAAGTCAGTGGTAATCACCTTTTCTACGCAAATGACATTTTGACTCAC<br>AACTCC<br><br>SEQ ID NO: 45, Cfa-N: Nucleotide sequence:<br>TGTCTCAGTTATGAcACCGAAATCCTGACAGTCGAGTATGGAtTtCTGCCGATCC<br>GGCAAGATTGTGGAGgAGAGAATTGAATGTACGGTCTATAcgGTCGACAAgAATGGTt<br>tCgTCTACACCCAACCAaTTGCTCAATGGCATaATCGAGGGGAGCAGGAGGTGTTTGA<br>GTATTGCCTGGAGGACGGGTCAaTCATTAGAGCTACAAAGGACCATAAGTTTATGAC<br>AacCGATGGTCAAATGCTGCCGATAGATGAAATATTCGAAAGGGgACTGGATCTTAa<br>GCaAGTCGATggCCTTCCAaac<br><br>SEQ ID NO: 46, Cfa-C, Nucleotide sequence:<br>ATGgTcAAgATTatCAgcCGCAAAtcCTTGGGGAcACAGAATGTATATGACATCG<br>GCGTGGAAaaGGATCACAATTTTctgCTGAAGAATGGTcTTgTTGCTtccAAt<br><br>SEQ ID NO: 47, Tad A,<br>SEVEFSHEYWMRHALTLAKRARDEREVPVGAVLVLNNRVIGEGWNRAIGLHDP<br>TAHAEIMALRQGGLVMQNYRLIDATLYVTFEPCVMCAGAMIHSRIGRVVFGVRNAKT<br>GAAGSLMDVLHYPGMNHRVEITEGILADECAALLCYFFRMPRQVFNAQKKAQSSTD<br><br>SEQ ID NO: 48<br>TGAGTATCATCGTGTGAAAGCTgAGGGGACGAGGCAGGCCTATAA<br><br>SEQ ID NO: 49<br>AAAAACATCAACTTCAGCCATCCATTTCTTCAGGGTTTGTATGTG<br><br>SEQ ID NO: 50<br>TATATCATAATGAAAACGCCGCCATTTCTCAACAGATCTGTCAAA |

| SEQUENCES |
|---|
| SEQ ID NO: 51<br>CTGTGTGAAATGGCTGCAAATCgATGGTTGAGCTCTGAGATTTGG |
| SEQ ID NO: 52<br>GTTCTGCTTTTGCTACTACTCACGTTTCCATGTTGTCCCCCTCTA |
| SEQ ID NO: 53<br>ATTTTATGGCCTTTTGCAACTCgACCAGAAAAAAAGCAGCTTTGG |
| SEQ ID NO: 54<br>TGAGGAGATCGCCCACGGGCTGCCAGGATCCCTTGATCACCTCAG |
| SEQ ID NO: 55<br>GGCTGCTCTGTCAGAAATATTCgTACAGTCTCAAGAGTACTCATG |
| SEQ ID NO: 56<br>GTGTAGGCATAGCTCTTGAATCgAGGCTTAGGGGAAGAAGTTCTC |
| SEQ ID NO: 57<br>CCTGTTCTTCAGTAAGACGTTGCCATTTGAGAAGGATGTCTTGTA |
| SEQ ID NO: 58<br>GCCATTTTAGGCTTTTTACTTACTTGTCTGTAGCTCTTTCTCTCT |
| SEQ ID NO: 59<br>CTAGTTTCTCACACATGACACACCTGTTCTTCAGTAAGACGTTGC |
| SEQ ID NO: 60<br>GTGAAGTTGATTACATTAACCTgTGGATAATTACGAGTTGATTGT |
| SEQ ID NO: 61<br>ttttgtatATCTGAGTTAAACTgCTCCAATTCCTTCAAAGGAATG |
| SEQ ID NO: 62<br>TCTGCAATATAAGCTGCCAACTgCTTGTCAATGAATGTGAGGGAC |
| SEQ ID NO: 63<br>GGACTGGGGTTCCAGTCTCATCCAGTCTAGGAAGAGGGCCGCTTC |
| SEQ ID NO: 64<br>AGTCGTTGTGTGGCTGACTGCTgGCAAACCACACTATTCCAGTCA |
| SEQ ID NO: 65<br>ATTTGtgtctttctgagaaactgttcaGCTTCTGTTAGCCACTGA |
| SEQ ID NO: 66<br>AAGAACCCAGCGGTCTTCTGTCCATCTACAGATGTTTGCCCATCG |
| SEQ ID NO: 67<br>AGACTTTTTCCGAAGTTCACTCCACTTGAAGTTCATGTTATCCAA |
| SEQ ID NO: 68<br>TACCTGTTGGCACATGTGATCCCACTGAGTGTTAAGTTCTTTGAG |
| SEQ ID NO: 69<br>CAAAGGGCCTTCTGCAGTCTTCgGAGTTTCATGGCAGTCCTATAA |
| SEQ ID NO: 70<br>ATGGTTAATGTCTAACCTTTATCCACTGGAGATTTGTCTGCTTGA |
| SEQ ID NO: 71<br>CAAAATAATCTGACCTTAAGTTgTTCTTCCAAAGCAGCAGTTGCG |
| SEQ ID NO: 72<br>CATCTACAGATGTTTGCCCATCgATCTCCCAATACCTGGAGAAGA |
| SEQ ID NO: 73<br>AAGGTGTTCTTGTACTTCATCCCACTGATTCTGAATTCTTTCAac |
| SEQ ID NO: 74<br>GAAGGTGTTCTTGTACTTCATCCCACTGATTCTGAATTCTTTCAa |
| SEQ ID NO: 75<br>GCTATGCTTTGAATTTTTAATCgTTCAATTTGAGGTTGAAGATCT |

-continued

| SEQUENCES |
|---|

SEQ ID NO: 76
TCTAGGAGGCGCCTCCCATCCTgTAGGTCACTGAAGAGGTTCTCA

SEQ ID NO: 77
GTGTAATTACCATTCACCATCTgTTCCACCAGGGCCTGAGCTGAT

SEQ ID NO: 78
TGAGCATGCTTTACCAGGATCTgTTCCCTTGTGGTCACCGTAGTT

SEQ ID NO: 79
CTACTGTATAGGGACCCTCCTTCCATGACTCAAGCTTGGCTCTGG

SEQ ID NO: 80
CAGCTTCTTCCTTAGCTTCCAGCCATTGTGTTGAATCCTTTAACA

SEQ ID NO: 81
AGCTGCCCAAGGTCTTTTATTTgAGCTTCAATTTCTCCTTGTTTC

SEQ ID NO: 82
TGCCAGTAACAACTCACAATTTgTGCAAAGTTGAGTCTTCGAAAC

SEQ ID NO: 83
AGAGTAACAGTCTGAGTAGGAGctaaaatattttgggttttttgca

SEQ ID NO: 84
CTTCAGCAAAAAAGTACTCACgCAGAATCTACTGGCCAGAAGTT

SEQ ID NO: 85
ACATCTACATTTGTCTGCCACTGgCGGAGGTCTTTGGCCAACTGC

SEQ ID NO: 86
CTGAGATAGTATAGGCCACTTTgTTGCTCTTGCAGAGAACTTTGT

SEQ ID NO: 87
TAGCTGTCCTTTACACACTTTACCTGTTGAGAATAGTGCATTTGA

SEQ ID NO: 88
GCCTGGGCTTCCTGAGGCATTTgAGCTGCGTCCACCTTGTCTGCA

SEQ ID NO: 89
TGCACTGGCAGGTAGCCCATTCgGGGATGCTTCGCAAAATACCTT

SEQ ID NO: 90
TTATAGTTCCACATTCAATTACcTCTGGGCTCCTGGTAGAGTTTC

SEQ ID NO: 91
CGTCAGGCTGGCGTCAAACTTAcCGGAGTGCAATATTCCACCATG

SEQ ID NO: 92
taTCCAAAAGTGTGTCAGCCTgAATGATCCACTTTGTGATGTGG

SEQ ID NO: 93
TGTAGCCACACCAGAAGTTCCTgCAGAGAAAGGTGCAGACGCTTC

SEQ ID NO: 94
TGTAAGGATTTTTCAGTCTCCTgGGCAGACTGGATGCTCTGTTCA

SEQ ID NO: 95
AGAATGGGATCCAGTATACTTAcAGGCTCCAATAGTGGTCAGTCC

SEQ ID NO: 96
TTCAGAGGCGCAATTTCTCCTCgAAGTGCCTGTGTGCAATAGTCA

SEQ ID NO: 97
GTTTCTTCCAAAGCAGCCTCTCgCTCACTCACCCTGCAAAGGACC

SEQ ID NO: 98
CTGAACTTCTCAGCTTTTTCTCgCTCTATGGCCTGCAGCATGAGA

SEQ ID NO: 99
AGATTTAACCACTCTTCTGCTCgGGAGGTGACAGCTATCCAGTTA

SEQ ID NO: 100
tgttttatctttatttcctctCgCTTTCTCTCATCTGTGATTCTT

| SEQUENCES |
|---|
| SEQ ID NO: 101<br>CCAGCTGGGAGGAGAGCTTCTTcCAGCGTCCCTCAATTTCTTCAA |
| SEQ ID NO: 102<br>ACACAGCTTCTGAGCGAGTAATcCAGCTGTGAAGTTCAGTTATAT |
| SEQ ID NO: 103<br>AAGTAAACGGTTTACCGCCTTCcACTCAGAGCTCAGATCTTCTAA |
| SEQ ID NO: 104<br>aaatagaaaaattagatgacttgccaaaggtcacaaaGGTAACTG |
| SEQ ID NO: 105<br>TTGACTTTCTCGAGGTGATCTTgGAGAGAGTCAATGAGGAGATCG |
| SEQ ID NO: 106<br>TCTAAAATCATCTTACTTTCTTgTAGACGCTGCTCAAAATTGGCT |
| SEQ ID NO: 107<br>GAATTGACCCTGACTTGTTCTTgTTCTAGATCTTCTTGAAGCACc |
| SEQ ID NO: 108<br>TGGATGGCTTCAATGCTCACTTgTTGAGGCAAAACTTGGAAGAGT |
| SEQ ID NO: 109<br>AACAGTCCTCTACTTCTTCCCAcCAAAGCATTTTGAAAAGTGTAT |
| SEQ ID NO: 110<br>AGGCCTCCTTTCTGGCATAGACcttccacaaaacaaacaaacaaa |
| SEQ ID NO: 111<br>TTTGGTTTCTGACTGCTGGACCcATGTCCTGATGGCACTCATGGT |
| SEQ ID NO: 112<br>ATCTTACTTTCTTGTAGACGCTgCTCAAAATTGGCTGGTTTCTGG |
| SEQ ID NO: 113<br>AGATTTTTCACTTATCTTCATAcCTCTTCATGTAGTTCCCTCCAA |
| SEQ ID NO: 114<br>CTGTTCAGTTGTTCTGAGGCTTgTTTGATGCTATCTGCATTAACA |
| SEQ ID NO: 115<br>CAGCATTAATATACACGACTTAcATCTGTACTTGTCTTCCAAATG |
| SEQ ID NO: 116<br>TCATGACTTGTCAAATCAGATTgGATTTTCTGTTGGGAGGATAGC |
| SEQ ID NO: 117<br>ATCTGCTCCAATTGTTGTAGCTgATTATAGAAAGCGATGATGTTG |
| SEQ ID NO : 118<br>CAAATTTGCTCTCAATTTCCCGcCAGCGCTTGCTGAGCTGGATCT |
| SEQ ID NO: 119<br>CATTCAAAGCCAGGCCATCAGAcCAGCTGGTGGTGAAGTTGATTA |
| SEQ ID NO: 120<br>ttcatcTCTTCAACTGCTTTCTgTAATTCATCTGGAGTTTTATAT |
| SEQ ID NO: 121<br>ATTGAAAGCTAGAAAGTACATAcGGCCAGTTTTTGAAGACTTGAT |
| SEQ ID NO: 122<br>TTCAAATACTGGCCAATACTTAcAGCAAAGGGCCTTCTGCAGTCT |
| SEQ ID NO: 123<br>GTTGTCTGTGTTAGTGATGGCTgAGTGGTGGTGACAGCCTGTGAA |
| SEQ ID NO: 124<br>TCATCAGCCTGCCTCTTGTACTgATACCACTGATGAGAAATTTCT |
| SEQ ID NO: 125<br>TACTGTATAGGGACCCTCCTTCcATGACTCAAGCTTGGCTCTGGC |
| SEQ ID NO: 126<br>ATGTTGAATGCATGTTCCAGTCgTTGTGTGGCTGACTGCTGGCAA |

| SEQUENCES |
| --- |

SEQ ID NO: 127
TGCCATTTGAGAAGGATGTCTTgTAAAAGAACCCAGCGGTCTTCT

SEQ ID NO: 128
GAGACTTTTTCCGAAGTTCACTcCACTTGAAGTTCATGTTATCCA

SEQ ID NO: 129
TTAGCAACTGGCAGAATTCGATcCACCGGCTGTTCAGTTGTTCTG

SEQ ID NO: 130
TTGCCACATCTACATTTGTCTGcCACTGGCGGAGGTCTTTGGCCA

SEQ ID NO: 131
TCCCATTCAGCCTAGTGCAGAGcCACTGGTAGTTGGTGGTTAGAG

SEQ ID NO: 132
GACTTACTGGAAAGAAAGTGCTgAGATGCTGGACCAAAGTCCCTG

SEQ ID NO: 133
TTTAATCGTTCAATTTGAGGTTgAAGATCTGATAGCCGGTTGACT

SEQ ID NO: 134
AAAGAGATTGTCTATACCTGTTgGCACATGTGATCCCACTGAGTG

SEQ ID NO: 135
AAGTTTTTGGACTAAATTATCCcAACACCGGGCAAAGTTATCCAG

SEQ ID NO: 136
AGCTCAGCATCCCGGGGACTCTgGGGAGAGGTGGGCATCATTTCA

SEQ ID NO: 137
TTGTCCCCCTCTAAGACAGTCTgCACTGGCAGGTAGCCCATTCGG

SEQ ID NO: 138
TTCGCAAAATACCTTTTGGTTCgAAATTTGTTTTTTAGTACCTTG

SEQ ID NO: 139
TGCAACTCGACCAGAAAAAAAGcAGCTTTGGCAGATGTCATAATT

SEQ ID NO: 140
TTGCAGATGTTACATTTGGCCTgATGCTTGGCAGTTTCTGCAGCA

SEQ ID NO: 141
AAATAAAAACATGCCATACGTAcGTATCATAAACATTCAGCAGCC

SEQ ID NO: 142
TACTTACAGCAAAGGGCCTTCTgCAGTCTTCGGAGTTTCATGGCA

SEQ ID NO: 143
TTGACCTCCTCAGCCTGCTTTCgTAGAAGCCGAGTGACATTCTGG

SEQ ID NO: 144
ATTCAATTACCTCTGGGCTCCTgGTAGAGTTTCTCTAGTCCTTCC

SEQ ID NO: 145
AATGCCTGACTTACTTGCCATTgTTTCATCAGCTCTTTTACTCCC

SEQ ID NO: 146
TGTACTTCATCCCACTGATTCTgAATTCTTTCAactagaataaaa

SEQ ID NO: 147
TGCTTCATTACCTTCACTGGCTgAGTGGCTGGTTTTTCCTTGTAC

SEQ ID NO: 148
TTTAATTGTTTGAGAATTCCCTgGCGCAGGGGCAACTCTTCCACC

SEQ ID NO: 149
atatgtgttaCCTACCCTTGTCgGTCCTTGTacatttttgttaact

SEQ ID NO: 150
TCAAGCTGGGAGAGAGCTTCCTgTAGCTTCACCCTTTCCACAGGC

SEQ ID NO: 151
ATGTCAATCCGACCTGAGCTTTgTTGTAGACTATCTTTTATATTc

| SEQUENCES |
|---|
| SEQ ID NO: 152<br>GTTGTAGACTATCTTTTATATTctgtaatataaaaattttaaaac |
| SEQ ID NO: 153<br>TCCCGCCAGCGCTTGCTGAGCTgGATCTGAGTTGGCTCCACTGCC |
| SEQ ID NO: 154<br>TTATGTTTTGTCTGTAACAGCTgctgttttatctttatttcctct |
| SEQ ID NO: 155<br>TGTTTTGTCTGTAACAGCTgctgttttatctttatttcctctCGC |
| SEQ ID NO: 156<br>TTTCTCTCATCTGTGATTCTTTgTTGTAAGTTGTCTCCTCTTTGC |
| SEQ ID NO: 157<br>aCCTTAAGCACGTCTTCTTTTTgCtggggtttcttttctctgat |
| SEQ ID NO: 158<br>TTAAGCACGTCTTCTTTTTGCtggggtttcttttctctgattca |
| SEQ ID NO: 159<br>ATACTCTTCAGGTGCACCTTCTgTTTCTCAATCTCTTTTTGAGTA |
| SEQ ID NO: 160<br>AGCTGTGACTGTACTACTTCCTgTTCCACACTCTTTGTTTCCAAT |
| SEQ ID NO: 161<br>TTGGCTGGTTTCTGGAATAATCgAAACTTCATGGAGACATCTTGT |
| SEQ ID NO: 162<br>TGCATCTCTGATAGATCTTTCTgGAGGCTTACAGTTTTCTCCAAA |
| SEQ ID NO: 163<br>ACAGTGAAAGAGATTGTCTATAcCTGTTGGCACATGTGATCCCAC |
| SEQ ID NO: 164<br>AAGGCATCATATAAAAATCTTAcTCTGCACTGTTTCAGCTGCTTT |
| SEQ ID NO: 165<br>CTTACTCTGCACTGTTTCAGCTgCTTTTTTAGAATTTCTGAATCC |
| SEQ ID NO: 166<br>TCTTGAATTACCTGAATTTTTCgGAGTTTATTCATTTGCTCCTCT |
| SEQ ID NO: 167<br>TGTTGCTCTTGCAGAGAACTTTgTAAAgcctaaaaaacaattttt |
| SEQ ID NO: 168<br>ATTGGTGGCAAAGTGTCAAAAAcTTtatcaaaagggaaaaaagaa |
| SEQ ID NO: 169<br>TAGGCTTTTTACTTACTTGTCTgTAGCTCTTTCTCTCTGGCCTGC |
| SEQ ID NO: 170<br>GCCTGCACATCAGAAAAGACTTgCTTAAAATGATTTGTAAAGGCC |
| SEQ ID NO: 171<br>ATGGAAGGAGAAGAGATTCTTAcCTTACAAATTTTTAACTGACTT |
| SEQ ID NO: 172<br>GGTGGTGGGTTGGATTTTCAACcAGTTTTCAGCAGTAGTTGTCAT |
| SEQ ID NO: 173<br>TCGATCCACCGGCTGTTCAGTTgTTCTGAGGCTTGTTTGATGCTA |
| SEQ ID NO: 174<br>TGAGCTGATCTGCTGGCATCTTgCAGTTTTCTGAACTTCTCAGCT |
| SEQ ID NO: 175<br>ATAAAAGCTTAAGATGCTCTCAcCTTTTCCTAATTTCAGAATCCA |
| SEQ ID NO: 176<br>ATTTCAGAATCCACAGTAATCTgCCTCTTCTTttggggaggtggt |
| SEQ ID NO: 177<br>TGATAATTGGTATCACTAACCTgTGCTGTACTCTTTTCAAGTTTT |

SEQUENCES

SEQ ID NO: 178
TCCAGCCATGCTTCCGTCTTCTgGGTCACTGACTTATTCTTCAGT

SEQ ID NO: 179
GAAGGATGTCTTGTAAAAGAACcCAGCGGTCTTCTGTCCATCTAC

SEQ ID NO: 180
TGTTCTTGTTCTAGATCTTCTTgAAGCACctgaaagataaaatgt

SEQ ID NO: 181
CCTACCTTATGTTGTTGTACTTgGCGTTTTAGGTCTTCAAGATCA

SEQ ID NO: 182
tctttcttctgttttgttagCcAGTCATTCAACTCTTTCAGTTT

SEQ ID NO: 183
attaaaaacaaataaggacTTAcTTGCTTTGTTTTTCCATGCTAG

SEQ ID NO: 184
caaataaggacTTACTTGCTTTgTTTTTCCATGCTAGCTACCCTG

SEQ ID NO: 185
TTTAGGAGATTCATCTGCTCTtgtacttcagtttcttcatcttct

SEQ ID NO: 186
ACATCATTAGAAATCTCTCCTTgTGCTTGCAATGTGTCCTCAGCA

SEQ ID NO: 187
TGGTAGTCCAGAAATTTACCAAcCTTCAGGATCGAGTAGTTTCTC

SEQ ID NO: 188
tattttttcattacattttttgaCcTACATGtggaaataaattttca

SEQ ID NO: 189
CCATTCATCAGGATTCTTACCTgCCAGTGGAGGATTATATTCCAA

SEQ ID NO: 190
tttcttaaaaataagtcaCATAcCAGTTTTTGCCCTGTCAGGCCT

SEQ ID NO: 191
aataagtcaCATACCAGTTTTTgCCCTGTCAGGCCTTCGAGGAGG

SEQ ID NO: 192
GTAAAGTAACAAACCATTCTTAcCTTAGAAAATTGTGCATTTACC

SEQ ID NO: 193
TTTACTAAGCAAAATAATCTGAcCTTAAGTTGTTCTTCCAAAGCA

SEQ ID NO: 194
ACGGATCCTCCCTGTTCGTCCCcTATTATGAAGAATCAAAGCAGA

SEQ ID NO: 195
TTCTCAACAGATCTGTCAAATCgCCTGCAGGTAAAAGCATATGGA

SEQ ID NO: 196
CTGTCAAATCCATCATGTACCCcTGACAAAGAAGGAAGTTAACAA

SEQ ID NO: 197
TCTCAATATGCtgcttcccaaactgaaattaaaaaaaatacactc

SEQ ID NO: 198
CTTAATTCATCATCTTTCAGCTgTAGCCACACCAGAAGTTCCTGC

SEQ ID NO: 199
GTCAAGACATTCATTTCCTTTCgCATCTTACGGGACAATTTCAAG

SEQ ID NO: 200
TGTGTCCTCAGCAGAAAGAAGCcACGATAATACTTCTTCTAAAGC

SEQ ID NO: 201
TAGAAAGCGATGATGTTGTTCTgATACTCCAGCCAGTTAAGTCTC

SEQ ID NO: 202
CTCTCTAAGGAAATCAAGATCTgGGCAGGACTACGAGGCTGGCTC

| SEQUENCES |
|---|
| SEQ ID NO: 203<br>TCAAAAGTTTCCATGTGTTTCTgGTATTCCTTAATTGTACAGAGA |
| SEQ ID NO: 204<br>ACTGTTTCCATTACAGTTGTCTgTGTTAGTGATGGCTGAGTGGTG |
| SEQ ID NO: 205<br>TTTAGTACCTTGGCAAAGTCTCgAACATCTTCTCCTGATGTAGTC |
| SEQ ID NO: 206<br>ATTTGTGCAAAGTTGAGTCTTCgAAACTGAGCAAATTTGCTCTCA |
| SEQ ID NO: 207<br>TGGGGACGCCTCTGTTCCAAATcCTGCATTGTTGCCTGTAAGAAC |
| SEQ ID NO: 208<br>GTCTCCTATGAACTCGAGAAGCcGCAAAaccaaggaagagaaaga |
| SEQ ID NO: 209<br>GAGAGTTTGGTTTCTGACTGCTgGACCCATGTCCTGATGGCACTC |
| SEQ ID NO: 210<br>TGCGTATTTGCCACCAGAAATAcATACCACACAATGATTTAGCTG |
| SEQ ID NO: 211<br>TTTGGGTTATCCTCTGAATGTCgCATCAAATTTTCAAGTGACTGA |
| SEQ ID NO: 212<br>AGGACACGGATCCTCCCTGTTCgTCCCCTATTATGAAGAATCAAA |
| SEQ ID NO: 213<br>TGCTTGTTAAAAAACTTACTTCgATCCGTAATGATTGTTCTAGCC |
| SEQ ID NO: 214<br>TTTTGCTCCACATCTTTTCCTAcCTAATGTTGAGAGACTTTTTCC |
| SEQ ID NO: 215<br>CCTGCCAGTGGAGGATTATATTcCAAATCAAACCAAGAGTCAGTT |
| SEQ ID NO: 216<br>GGATAATTACGAGTTGATTGTCgGACCCAGCTCAGGAGAATCTTT |
| SEQ ID NO: 217<br>TTTAGACTGGGCTGAATTGTCTgAATATCACTGACTAAAagctaa |
| SEQ ID NO: 218<br>GTACTACTTACATTATTGTTCTgCAAAACCCGCAGTGCCTTGTTG |
| SEQ ID NO: 219<br>TTCATTTGCTCCTCTAGCTTTTgACAATGCTCAACCAGCTGGGAG |
| SEQ ID NO: 220<br>TCAATCTGAGACAGGACTCTTTgGGCAGCCTCCTTCCCCTGAtta |
| SEQ ID NO: 221 TTCagctcctctttcttcttctgcaaTTCCCGATCAATTTCCTAT |
| SEQ ID NO: 222 AAAGCTaAGGGGACGAGGCAGGC |
| SEQ ID NO: 223 GAAAGCTaAGGGGACGAGGCAGG |
| SEQ ID NO: 224 AAATaGATGGCTGAAGTTGATGT |
| SEQ ID NO: 225 GAAATaGATGGCTGAAGTTGATG |
| SEQ ID NO: 226 AAGAAATaGATGGCTGAAGTTGA |
| SEQ ID NO: 227 CTGAAGAAATaGATGGCTGAAGTTGAT |
| SEQ ID NO: 228 AAATaGCGGCGTTTTCATTATGA |
| SEQ ID NO: 229 GAGAAATaGCGGCGTTTTCATTATGAT |
| SEQ ID NO: 230 AAATCaATGGTTGAGCTCTGAGA |
| SEQ ID NO: 231 GCAAATCaATGGTTGAGCTCTGA |
| SEQ ID NO: 232 TGCAAATCaATGGTTGAGCTCTGAGAT |

| SEQUENCES |
|---|
| SEQ ID NO: 233 AACaTGAGTAGTAGCAAAAGCAG |
| SEQ ID NO: 234 GAAACaTGAGTAGTAGCAAAAGC |
| SEQ ID NO: 235 GGAAACaTGAGTAGTAGCAAAAG |
| SEQ ID NO: 236 TGGAAACaTGAGTAGTAGCAAAA |
| SEQ ID NO: 237 AACTCaACCAGAAAAAAAGCAGC |
| SEQ ID NO: 238 CAACTCaACCAGAAAAAAAGCAG |
| SEQ ID NO: 239 AAGGGATCCTGaCAGCCCGTGGGCGAT |
| SEQ ID NO: 240 AATATTCaTACAGTCTCAAGAGT |
| SEQ ID NO: 241 AATCaAGGCTTAGGGGAAGAAGT |
| SEQ ID NO: 242 GAATCaAGGCTTAGGGGAAGAAG |
| SEQ ID NO: 243 TGAATCaAGGCTTAGGGGAAGAA |
| SEQ ID NO: 244 TTGAATCaAGGCTTAGGGGAAGA |
| SEQ ID NO: 245 CTTGAATCaAGGCTTAGGGGAAGAAGT |
| SEQ ID NO: 246 AATGaCAACGTCTTACTGAA GAA |
| SEQ ID NO: 247 AAATGaCAACGTCTTACTGA AGA |
| SEQ ID NO: 248 CAAATGaCAACGTCTTACTG AAG |
| SEQ ID NO: 249 TCAAATGaCAACGTCTTACT GAA |
| SEQ ID NO: 250 ACAAaTAAGTAAAAAGCCTA AAA |
| SEQ ID NO: 251 ACAGaTGTGTCATGTGTGAG AAA |
| SEQ ID NO: 252 AACAGaTGTGTCATGTGTGA GAA |
| SEQ ID NO: 253 GAACAGaTGTGTCATGTGTG AGA |
| SEQ ID NO: 254 AGAACAGaTGTGTCATGTGT GAG |
| SEQ ID NO: 255 ACCTaTGGATAATTACGAGT TGA |
| SEQ ID NO: 256 AACCTaTGGATAATTACGAG TTG |
| SEQ ID NO: 257 TTAACCTaTGGATAATTACG AGT |
| SEQ ID NO: 258 TTAACCTaTGGATAATTACGA GTTGAT |
| SEQ ID NO: 259 ACTaCTCCAATTCCTTCAAA GGA |
| SEQ ID NO: 260 AACTaCTCCAATTCCTTCAA AGG |
| SEQ ID NO: 261 AAACTaCTCCAATTCCTTCAA AGGAAT |
| SEQ ID NO: 262 ACTaCTTGTCAATGAATGTG AGG |
| SEQ ID NO: 263 AACTaCTTGTCAATGAATGT GAG |
| SEQ ID NO: 264 CAACTaCTTGTCAATGAATG TGA |
| SEQ ID NO: 265 CCAACTaCTTGTCAATGAAT GTG |
| SEQ ID NO: 266 GCCAACTaCTTGTCAATGAA TGT |
| SEQ ID NO: 267 ACTaGATGAGACTGGAACCC CAG |
| SEQ ID NO: 268 TAGACTaGATGAGACTGGAAC CCCAGT |
| SEQ ID NO: 269 ACTGCTaGCAAACCACACTAT TCCAGT |
| SEQ ID NO: 270 agaaactattcaGCTTCTGT TAG |

| SEQUENCES |
|---|
| SEQ ID NO: 271 AGATaGACAGAAGACCGCTG GGT |
| SEQ ID NO: 272 TAGATaGACAGAAGACCGCT GGG |
| SEQ ID NO: 273 GTAGATaGACAGAAGACCGC TGG |
| SEQ ID NO: 274 TGTAGATaGACAGAAGACCG CTG |
| SEQ ID NO: 275 CTGTAGATaGACAGAAGACCG CTGGGT |
| SEQ ID NO: 276 AGTaGAGTGAACTTCGGAAA AAG |
| SEQ ID NO: 277 AAGTaGAGTGAACTTCGGAA AAA |
| SEQ ID NO: 278 CAAGTaGAGTGAACTTCGGA AAA |
| SEQ ID NO: 279 TCAAGTaGAGTGAACTTCGG AAA |
| SEQ ID NO: 280 TCAAGTaGAGTGAACTTCGGA AAAAGT |
| SEQ ID NO: 281 AGTaGGATCACATGTGCCAA CAG |
| SEQ ID NO: 282 CTCAGTaGGATCACATGTGC CAA |
| SEQ ID NO: 283 TCAGTaGGATCACATGTGCCA ACAGGT |
| SEQ ID NO: 284 AGTCTTCaGAGTTTCATGGC AGT |
| SEQ ID NO: 285 CTGCAGTCTTCaGAGTTTCAT GGCAGT |
| SEQ ID NO: 286 AGTGaATAAAGGTTAGACAT TAA |
| SEQ ID NO: 287 AGTTaTTCTTCCAAAGCAGC AGT |
| SEQ ID NO: 288 AAGTTaTTCTTCCAAAGCAG CAG |
| SEQ ID NO: 289 TTAAGTTaTTCTTCCAAAGC AGC |
| SEQ ID NO: 290 CTTAAGTTaTTCTTCCAAAGC AGCAGT |
| SEQ ID NO: 291 ATCaATCTCCCAATACCTGG AGA |
| SEQ ID NO: 292 CATCaATCTCCCAATACCTG GAG |
| SEQ ID NO: 293 CCATCaATCTCCCAATACCT GGA |
| SEQ ID NO: 294 CCCATCaATCTCCCAATACC TGG |
| SEQ ID NO: 295 GCCCATCaATCTCCCAATAC CTG |
| SEQ ID NO: 296 ATCAGTaGGATGAAGTACAA GAA |
| SEQ ID NO: 297 AATCAGTaGGATGAAGTACA AGA |
| SEQ ID NO: 298 ATCAGTGaGATGAAGTACAA GAA |
| SEQ ID NO: 299 ATCaTTCAATTTGAGGTTGA AGA |
| SEQ ID NO: 300 AATCaTTCAATTTGAGGTTG AAG |
| SEQ ID NO: 301 TAATCaTTCAATTTGAGGTT GAA |
| SEQ ID NO: 302 TTAATCaTTCAATTTGAGGT TGA |
| SEQ ID NO: 303 TTTAATCaTTCAATTTGAGG TTG |
| SEQ ID NO: 304 ATCCTaTAGGTCACTGAAGA GGT |
| SEQ ID NO: 305 CATCCTaTAGGTCACTGAAG AGG |
| SEQ ID NO: 306 CCATCCTaTAGGTCACTGAA GAG |
| SEQ ID NO: 307 TCCCATCCTaTAGGTCACTGA AGAGGT |
| SEQ ID NO: 308 ATCTaTTCCACCAGGGCCTG AGC |
| SEQ ID NO: 309 ACCATCTaTTCCACCAGGGC CTG |

| SEQUENCES |
|---|
| SEQ ID NO: 310 ATCTaTTCCACCAGGGCCTGA GCTGAT |
| SEQ ID NO: 311 ATCTaTTCCCTTGTGGTCAC CGT |
| SEQ ID NO: 312 GATCTaTTCCCTTGTGGTCA CCG |
| SEQ ID NO: 313 GATCTaTTCCCTTGTGGTCAC CGTAGT |
| SEQ ID NO: 314 ATGaAAGGAGGGTCCCTATA CAG |
| SEQ ID NO: 315 GTCATGaAAGGAGGGTCCCTA TACAGT |
| SEQ ID NO: 316 ATGaCTGGAAGCTAAGGAAG AAG |
| SEQ ID NO: 317 AATGaCTGGAAGCTAAGGAA GAA |
| SEQ ID NO: 318 CAATGaCTGGAAGCTAAGGA AGA |
| SEQ ID NO: 319 ACAATGaCTGGAAGCTAAGG AAG |
| SEQ ID NO: 320 CACAATGaCTGGAAGCTAAG GAA |
| SEQ ID NO: 321 ATTTaAGCTTCAATTTCTCC TTG |
| SEQ ID NO: 322 ATTTaTGCAAAGTTGAGTCT TCG |
| SEQ ID NO: 323 attttaaCTCCTACTCAGAC TGT |
| SEQ ID NO: 324 tattttaaCTCCTACTCAGA CTG |
| SEQ ID NO: 325 CACaCAGAATCTACTGGCCA GAA |
| SEQ ID NO: 326 CTCACaCAGAATCTACTGGC CAG |
| SEQ ID NO: 327 CACTaGCGGAGGTCTTTGGC CAA |
| SEQ ID NO: 328 CACTTTaTTGCTCTTGCAGA GAA |
| SEQ ID NO: 329 CCACTTTaTTGCTCTTGCAG AGA |
| SEQ ID NO: 330 CAGaTAAAGTGTGTAAAGGA CAG |
| SEQ ID NO: 331 CAACAGaTAAAGTGTGTAAA GGA |
| SEQ ID NO: 332 TCAACAGaTAAAGTGTGTAA AGG |
| SEQ ID NO: 333 CATTTaAGCTGCGTCCACCT TGT |
| SEQ ID NO: 334 GCATTTaAGCTGCGTCCACC TTG |
| SEQ ID NO: 335 CCATTCaGGGATGCTTCGCA AAA |
| SEQ ID NO: 336 CCCATTCaGGGATGCTTCGC AAA |
| SEQ ID NO: 337 CCCAGAaGTAATTGAATGTG GAA |
| SEQ ID NO: 338 GCCCAGAaGTAATTGAATGT GGA |
| SEQ ID NO: 339 CCGaTAAGTTTGACGCCAGC CTG |
| SEQ ID NO: 340 ACTCCGaTAAGTTTGACGCC AGC |
| SEQ ID NO: 341 CACTCCGaTAAGTTTGACGC CAG |
| SEQ ID NO: 342 CCTaAATGATCCACTTTGTG ATG |
| SEQ ID NO: 343 CCTaCAGAGAAAGGTGCAGA CGC |
| SEQ ID NO: 344 TCCTaCAGAGAAAGGTGCAG ACG |
| SEQ ID NO: 345 GTTCCTaCAGAGAAAGGTGC AGA |
| SEQ ID NO: 346 AGTTCCTaCAGAGAAAGGTG CAG |
| SEQ ID NO: 347 CCTaGGCAGACTGGATGCTC TGT |

| SEQUENCES |
|---|
| SEQ ID NO: 348 TCCTaGGCAGACTGGATGCT CTG |
| SEQ ID NO: 349 CTATTGGAGCCTaTAAGTATA CTGGAT |
| SEQ ID NO: 350 CTCaAAGTGCCTGTGTGCAA TAG |
| SEQ ID NO: 351 CTCCTCaAAGTGCCTGTGTG CAA |
| SEQ ID NO: 352 CTCCTCaAAGTGCCTGTGTGC AATAGT |
| SEQ ID NO: 353 TTTCTCCTCaAAGTGCCTGTG TGCAAT |
| SEQ ID NO: 354 CTCaCTCACTCACCCTGCAA AGG |
| SEQ ID NO: 355 TCTCaCTCACTCACCCTGCA AAG |
| SEQ ID NO: 356 CTCTCaCTCACTCACCCTGC AAA |
| SEQ ID NO: 357 CCTCTCaCTCACTCACCCTG CAA |
| SEQ ID NO: 358 CTCaCTCTATGGCCTGCAGC ATG |
| SEQ ID NO: 359 TTTCTCaCTCTATGGCCTGC AGC |
| SEQ ID NO: 360 TTTTCTCaCTCTATGGCCTGCAG |
| SEQ ID NO: 361 CTCaGGAGGTGACAGCTATC CAG |
| SEQ ID NO: 362 CTGCTCaGGAGGTGACAGCTA TCCAGT |
| SEQ ID NO: 363 ctctCaCTTTCTCTCATCTG TGA |
| SEQ ID NO: 364 cctctCaCTTTCTCTCATCT GTG |
| SEQ ID NO: 365 tcctctCaCTTTCTCTCATC TGT |
| SEQ ID NO: 366 ttcctCtCaCTTTCTCTCATC TGTGAT |
| SEQ ID NO: 367 CTGaAAGAAGCTCTCCTCCC AGC |
| SEQ ID NO: 368 GCTGaAAGAAGCTCTCCTCC CAG |
| SEQ ID NO: 369 CTGaATTACTCGCTCAGAAG CTG |
| SEQ ID NO: 370 AGCTGaATTACTCGCTCAGA AGC |
| SEQ ID NO: 371 CAGCTGaATTACTCGCTC AG AAG |
| SEQ ID NO: 372 ACAGCTGaATTACTCGCTCA GAA |
| SEQ ID NO: 373 CTGAGTaGAAGGCGGTAAAC CGT |
| SEQ ID NO: 374 TCTGAGTaGAAGGCGGTAAA CCG |
| SEQ ID NO: 375 cttaccaaaggtcacaaaGG TAA |
| SEQ ID NO: 376 gacttaccaaaggtcacaaa GGT |
| SEQ ID NO: 377 tgacttaccaaaggtcacaa aGG |
| SEQ ID NO: 378 atgacttaccaaaggtcaca aaG |
| SEQ ID NO: 379 agatgacttaccaaaggtcac aaaGGT |
| SEQ ID NO: 380 CTTaGAGAGAGTCAATGAGG AGA |
| SEQ ID NO: 381 TCTTaGAGAGAGTCAATGAG GAG |
| SEQ ID NO: 382 ATCTTaGAGAGAGTCAATGA GGA |
| SEQ ID NO: 383 GATCTTaGAGAGAGTCAATG AGG |
| SEQ ID NO: 384 TGATCTTaGAGAGAGTCAAT GAG |
| SEQ ID NO: 385 GATCTTaGAGAGAGTCAATGA GGAGAT |
| SEQ ID NO: 386 CTTaTAGACGCTGCTCAAAA TTG |

| SEQUENCES |
|---|
| SEQ ID NO: 387 TTTCTTaTAGACGCTGCTCA AAA |
| SEQ ID NO: 388 CTTTCTTaTAGACGCTGCTC AAA |
| SEQ ID NO: 389 TACTTTCTTaTAGACGCTGCT CAAAAT |
| SEQ ID NO: 390 CTTaTTCTAGATCTTCTTGA AGC |
| SEQ ID NO: 391 CTTaTTGAGGCAAAACTTGG AAG |
| SEQ ID NO: 392 TCACTTaTTGAGGCAAAACT TGG |
| SEQ ID NO: 393 CTCACTTaTTGAGGCAAAAC TTG |
| SEQ ID NO: 394 ACTTaTTGAGGCAAAACTTGG AAGAGT |
| SEQ ID NO: 395 CTTTGaTGGGAAGAAGTAGA GGA |
| SEQ ID NO: 396 GCTTTGaTGGGAAGAAGTAG AGG |
| SEQ ID NO: 397 TGCTTTGaTGGGAAGAAGTA GAG |
| SEQ ID NO: 398 gaaaGTCTATGCCAGAAAGG AGG |
| SEQ ID NO: 399 ggaaaGTCTATGCCAGAAAG GAG |
| SEQ ID NO: 400 tggaaaGTCTATGCCAGAAA GGA |
| SEQ ID NO: 401 gtggaaaGTCTATGCCAGAA AGG |
| SEQ ID NO: 402 tgtggaaaGTCTATGCCAGA AAG |
| SEQ ID NO: 403 GACATaGGTCCAGCAGTCAG AAA |
| SEQ ID NO: 404 GGACATaGGTCCAGCAGTCA GAA |
| SEQ ID NO: 405 AGGACATaGGTCCAGCAGTC AGA |
| SEQ ID NO: 406 GACGCTaCTCAAAATTGGCT GGT |
| SEQ ID NO: 407 AGACGCTaCTCAAAATTGGC TGG |
| SEQ ID NO: 408 TGTAGACGCTaCTCAAAATTG GCTGGT |
| SEQ ID NO: 409 GAGaTATGAAGATAAGTGAA AAA |
| SEQ ID NO: 410 AGAGaTATGAAGATAAGTGA AAA |
| SEQ ID NO: 411 AAGAGaTATGAAGATAAGTG AAA |
| SEQ ID NO: 412 GAAGAGaTATGAAGATAAGT GAA |
| SEQ ID NO: 413 TGAAGAGaTATGAAGATAAG TGA |
| SEQ ID NO: 414 GAAGAGaTATGAAGATAAGTG AAAAT |
| SEQ ID NO: 415 GAGGCTTaTTTGATGCTATC TGC |
| SEQ ID NO: 416 GATaTAAGTCGTGTATATTA ATG |
| SEQ ID NO: 417 CAGATaTAAGTCGTGTATAT TAA |
| SEQ ID NO: 418 GTACAGATaTAAGTCGTGTAT ATTAAT |
| SEQ ID NO: 419 GATTaGATTTTCTGTTGGGA GGA |
| SEQ ID NO: 420 AGATTaGATTTTCTGTTGGG AGG |
| SEQ ID NO: 421 CAGATTaGATTTTCTGTTGG GAG |
| SEQ ID NO: 422 TCAGATTaGATTTTCTGTTG GGA |
| SEQ ID NO: 423 TCAGATTaGATTTTCTGTTGG GAGGAT |
| SEQ ID NO: 424 GCTaATTATAGAAAGCGATG ATG |

| SEQUENCES |
|---|
| SEQ ID NO: 425 TAGCTaATTATAGAAAGCCGA TGA |
| SEQ ID NO: 426 GTAGCTaATTATAGAAAGCG ATG |
| SEQ ID NO: 427 TTGTAGCTaATTATAGAAAGC GATGAT |
| SEQ ID NO: 428 GCTGaCGGGAAATTGAGAGC AAA |
| SEQ ID NO: 429 CGCTGaCGGGAAATTGAGAG CAA |
| SEQ ID NO: 430 AGCGCTGaCGGGAAATTGAG AGC |
| SEQ ID NO: 431 AGCGCTGaCGGGAAATTGAGA GCAAAT |
| SEQ ID NO: 432 GCTGaTCTGATGGCCTGGCT TTG |
| SEQ ID NO: 433 AGCTGaTCTGATGGCCTGGCT TTGAAT |
| SEQ ID NO: 434 GCTTTCTaTAATTCATCTGG AGT |
| SEQ ID NO: 435 AACTGCTTTCTaTAATTCATC TGGAGT |
| SEQ ID NO: 436 GGCCaTATGTACTTTCTAGCT TTCAAT |
| SEQ ID NO: 437 GGCCCTTTGCTaTAAGTATTG GCCAGT |
| SEQ ID NO: 438 GGCTaAGTGGTGGTGACAGC CTG |
| SEQ ID NO: 439 GATGGCTaAGTGGTGGTGAC AGC |
| SEQ ID NO: 440 GTACTaATACCACTGATGAG AAA |
| SEQ ID NO: 441 TGTACTaATACCACTGATGA GAA |
| SEQ ID NO: 442 TTGTACTaATACCACTGATG AGA |
| SEQ ID NO: 443 CTTGTACTaATACCACTGATG AGAAAT |
| SEQ ID NO: 444 GTCATaGAAGGAGGGTCCCTA TACAGT |
| SEQ ID NO: 445 GTCaTTGTGTGGCTGACTGC TGG |
| SEQ ID NO: 446 AGTCaTTGTGTGGCTGACTG CTG |
| SEQ ID NO: 447 CCAGTCaTTGTGTGGCTGAC TGC |
| SEQ ID NO: 448 TCCAGTCaTTGTGTGGCTGA CTG |
| SEQ ID NO: 449 GTCTTaTAAAAGAACCCAGC GGT |
| SEQ ID NO: 450 TGTCTTaTAAAAGAACCCAG CGG |
| SEQ ID NO: 451 ATGTCTTaTAAAAGAACCCA GCG |
| SEQ ID NO: 452 GGATGTCTTaTAAAAGAACCC AGCGGT |
| SEQ ID NO: 453 GTGaAGTGAACTTCGGAAAA AGT |
| SEQ ID NO: 454 AGTGaAGTGAACTTCGGAAA AAG |
| SEQ ID NO: 455 AAGTGaAGTGAACTTCGGAA AAA |
| SEQ ID NO: 456 CAAGTGaAGTGAACTTCGGA AAA |
| SEQ ID NO: 457 TCAAGTGaAGTGAACTTCGG AAA |
| SEQ ID NO: 458 TCAAGTGaAGTGAACTTCGGA AAAGT |
| SEQ ID NO: 459 GTGaATCGAATTCTGCCAGT TGC |
| SEQ ID NO: 460 GGTGaATCGAATTCTGCCAG TTG |
| SEQ ID NO: 461 GCCGGTGaATCGAATTCTGC CAG |
| SEQ ID NO: 462 GTGaCAGACAAATGTAGATG TGG |
| SEQ ID NO: 463 AGTGaCAGACAAATGTAGAT GTG |

| SEQUENCES |
| --- |
| SEQ ID NO: 464 CAGTGaCAGACAAATGTAGA TGT |
| SEQ ID NO: 465 CCAGTGaCAGACAAATGTAG ATG |
| SEQ ID NO: 466 CTCCGCCAGTGaCAGACAAAT GTAGAT |
| SEQ ID NO: 467 GTGaCTCTGCACTAGGCTGA ATG |
| SEQ ID NO: 468 CAGTGaCTCTGCACTAGGCT GAA |
| SEQ ID NO: 469 CCAGTGaCTCTGCACTAGGC TGA |
| SEQ ID NO: 470 ACCAGTGaCTCTGCACTAGG CTG |
| SEQ ID NO: 471 TACCAGTGaCTCTGCACTAGG CTGAAT |
| SEQ ID NO: 472 GTGCTaAGATGCTGGACCAA AGT |
| SEQ ID NO: 473 AGTGCTaAGATGCTGGACCA AAG |
| SEQ ID NO: 474 AAGTGCTaAGATGCTGGACC AAA |
| SEQ ID NO: 475 GAAAGTGCTaAGATGCTGGAC CAAAGT |
| SEQ ID NO: 476 GTTaAAGATCTGATAGCCGG TTG |
| SEQ ID NO: 477 GAGGTTaAAGATCTGATAGC CGG |
| SEQ ID NO: 478 TGAGGTTaAAGATCTGATAG CCG |
| SEQ ID NO: 479 TTTGAGGTTaAAGATCTGATA GCCGGT |
| SEQ ID NO: 480 GTTaGCACATGTGATCCCAC TGA |
| SEQ ID NO: 481 TGTTaGCACATGTGATCCCA CTG |
| SEQ ID NO: 482 CTGTTaGCACATGTGATCCCA CTGAGT |
| SEQ ID NO: 483 GTTaGGATAATTTAGTCCAA AAA |
| SEQ ID NO: 484 TGTTaGGATAATTTAGTCCA AAA |
| SEQ ID NO: 485 GTGTTaGGATAATTTAGTCC AAA |
| SEQ ID NO: 486 GGTGTTaGGATAATTTAGTC CAA |
| SEQ ID NO: 487 TAAGaTCAGATTATTTTGCT TAG |
| SEQ ID NO: 488 TAATAaGGGACGAACAGGGA GGA |
| SEQ ID NO: 489 ATAATAaGGGACGAACAGGG AGG |
| SEQ ID NO: 490 CATAATAaGGGACGAACAGG GAG |
| SEQ ID NO: 491 TCATAATAAGGGACGAACAGG GAGGAT |
| SEQ ID NO: 492 TCAAATCaCCTGCAGGTAAA AGC |
| SEQ ID NO: 493 TCAaGGGTACATGATGGATT TGA |
| SEQ ID NO: 494 GTCAaGGGTACATGATGGAT TTG |
| SEQ ID NO: 495 CTTCTTTGTCAaGGGTACATG ATGGAT |
| SEQ ID NO: 496 tcaatttgggaagcaGCATA TTG |
| SEQ ID NO: 497 TCAGCTaTAGCCACACCAGA AGT |
| SEQ ID NO: 498 TTCAGCTaTAGCCACACCAG AAG |
| SEQ ID NO: 499 TCTTTCAGCTaTAGCCACACC AGAAGT |
| SEQ ID NO: 500 TCCTTTCaCATCTTACGGGA CAA |
| SEQ ID NO: 501 ATTTCCTTTCaCATCTTACGG GACAAT |

| SEQUENCES |
|---|
| SEQ ID NO: 502 TCGTaGCTTCTTTCTGCTGA GGA |
| SEQ ID NO: 503 ATCGTaGCTTCTTTCTGCTG AGG |
| SEQ ID NO: 504 TATCGTaGCTTCTTTCTGCT GAG |
| SEQ ID NO: 505 TTATCGTaGCTTCTTTCTGC TGA |
| SEQ ID NO: 506 TCTaATACTCCAGCCAGTTA AGT |
| SEQ ID NO: 507 TTCTaATACTCCAGCCAGTT AAG |
| SEQ ID NO: 508 GTTCTaATACTCCAGCCAGT TAA |
| SEQ ID NO: 509 TTGTTCTaATACTCCAGCCAG TTAAGT |
| SEQ ID NO: 510 TGATGTTGTTCTaATACTCCA GCCAGT |
| SEQ ID NO: 511 TCTaGGCAGGACTACGAGGC TGG |
| SEQ ID NO: 512 ATCTaGGCAGGACTACGAGG CTG |
| SEQ ID NO: 513 AGATCTaGGCAGGACTACGA GGC |
| SEQ ID NO: 514 AAGATCTaGGCAGGACTACG AGG |
| SEQ ID NO: 515 TCTaGTATTCCTTAATTGTA CAG |
| SEQ ID NO: 516 TGTTTCTaGTATTCCTTAAT TGT |
| SEQ ID NO: 517 TCTaTGTTAGTGATGGCTGA GTG |
| SEQ ID NO: 518 GTCTaTGTTAGTGATGGCTG AGT |
| SEQ ID NO: 519 TGTCTaTGTTAGTGATGGCT GAG |
| SEQ ID NO: 520 TTGTCTaTGTTAGTGATGGC TGA |
| SEQ ID NO: 521 GTTGTCTaTGTTAGTGATGG CTG |
| SEQ ID NO: 522 TGTCTaTGTTAGTGATGGCTG AGTGGT |
| SEQ ID NO: 523 AGTTGTCTaTGTTAGTGATGG CTGAGT |
| SEQ ID NO: 524 TCTCaAACATCTTCTCCTGA TGT |
| SEQ ID NO: 525 GTCTCaAACATCTTCTCCTG ATG |
| SEQ ID NO: 526 AAGTCTCaAACATCTTCTCC TGA |
| SEQ ID NO: 527 GTCTCaAACATCTTCTCCTGA TGTAGT |
| SEQ ID NO: 528 TCTTCaAAACTGAGCAAATT TGC |
| SEQ ID NO: 529 GTCTTCaAAACTGAGCAAAT TTG |
| SEQ ID NO: 530 TGCAGaATTTGGAACAGAGG CGT |
| SEQ ID NO: 531 ATGCAGaATTTGGAACAGAG GCG |
| SEQ ID NO: 532 AATGCAGaATTTGGAACAGA GGC |
| SEQ ID NO: 533 TGCaGCTTCTCGAGTTCATA GGA |
| SEQ ID NO: 534 TTGCaGCTTCTCGAGTTCAT AGG |
| SEQ ID NO: 535 TGCTaGACCCATGTCCTGAT GGC |
| SEQ ID NO: 536 CTGCCTaGACCCATGTCCTGA TGG |
| SEQ ID NO: 537 ACTGCTaGACCCATGTCCTG ATG |
| SEQ ID NO: 538 TTCTGACTGCTaGACCCATGT CCTGAT |
| SEQ ID NO: 539 TGGTATaTATTTCTGGTGGC AAA |
| SEQ ID NO: 540 GTGGTATaTATTTCTGGTGG CAA |

-continued

| SEQUENCES |
|---|
| SEQ ID NO: 541 GTGTGGTATaTATTTCTGGTG GCAAAT |
| SEQ ID NO: 542 TGTCaCATCAAATTTTCAAG TGA |
| SEQ ID NO: 543 ATGTCaCATCAAATTTTCAA GTG |
| SEQ ID NO: 544 TGTTCaTCCCCTATTATGAA GAA |
| SEQ ID NO: 545 CTGTTCaTCCCCTATTATGA AGA |
| SEQ ID NO: 546 CCTGTTCaTCCCCTATTATG AAG |
| SEQ ID NO: 547 CCCTGTTCaTCCCCTATTATG AAGAAT |
| SEQ ID NO: 548 TTACTTCaATCCGTAATGAT TGT |
| SEQ ID NO: 549 TTAGaTAGGAAAAGATGTGG AGC |
| SEQ ID NO: 550 ATTAGaTAGGAAAAGATGTG GAG |
| SEQ ID NO: 551 CATTAGaTAGGAAAAGATGT GGA |
| SEQ ID NO: 552 ACATTAGaTAGGAAAAGATG TGG |
| SEQ ID NO: 553 TTGaAATATAATCCTCCACT GGC |
| SEQ ID NO: 554 TTTGaAATATAATCCTCCAC TGG |
| SEQ ID NO: 555 ATTTGaAATATAATCCTCCA CTG |
| SEQ ID NO: 556 TTGTCaGACCCAGCTCAGGA GAA |
| SEQ ID NO: 557 ATTGTCaGACCCAGCTCAGG AGA |
| SEQ ID NO: 558 GATTGTCaGACCCAGCTCAG GAG |
| SEQ ID NO: 559 TGATTGTCaGACCCAGCTCAG GAGAAT |
| SEQ ID NO: 560 TTGTCTaAATATCACTGACT AAA |
| SEQ ID NO: 561 ATTGTCTaAATATCACTGAC TAA |
| SEQ ID NO: 562 TTGTTCTaCAAAACCCGCAG TGC |
| SEQ ID NO: 563 TTTaACAATGCTCAACCAGC TGG |
| SEQ ID NO: 564 TTTTaACAATGCTCAACCAG CTG |
| SEQ ID NO: 565 GCTTTTaACAATGCTCAACC AGC |
| SEQ ID NO: 566 AGCTTTTaACAATGCTCAAC CAG |
| SEQ ID NO: 567 TTTaGGCAGCCTCCTTCCCC TGA |
| SEQ ID NO: 568 CTTTaGGCAGCCTCCTTCCC CTG |
| SEQ ID NO: 569 tttcttcttctacaaTTCCCG ATCAAT |
| SEQ ID NO: 570 GTTATCTCCTGTTCTGCAGC |
| SEQ ID NO: 571 GTTTATGTCACCAGAGTAAC |
| SEQ ID NO: 572 GAGGTAATAGAGCCAAGCCCT |
| SEQ ID NO: 573 GCAAGAATTCCACTTTTCACTTCCT |
| SEQ ID NO: 574 CTGTCATCTCCAAACTAGAAATGC |
| SEQ ID NO: 575 GCAGCCTCTTGCTCACTTACTC |
| SEQ ID NO: 576 GATGACAGGCAGGGGCACCG |
| SEQ ID NO: 577 TTCCAGTGGTTCAATGGTCA |
| SEQ ID NO: 578 CTTTCAACCCGAACGGAGAC |

| SEQUENCES |
|---|
| SEQ ID NO: 579 GAGCGAGCAGCGTCTTCGAG |
| SEQ ID NO: 580 GCAGACGGCAGTCACTAGGG |
| SEQ ID NO: 581 GGGAAGCTGGGTGAATGGAG |
| SEQ ID NO: 582 AGCTGTTTGGGAGGTCAGAA |
| SEQ ID NO: 583 AGGGAGCAGGAAAGTGAGGT |
| SEQ ID NO: 584 GTCGCAGGACAGCTTTTCCT |
| SEQ ID NO: 585 TGTAGCTACGCCTGTGATGG |
| SEQ ID NO: 586 TGCCCTGAGATCTTTTCCTC |
| SEQ ID NO: 587 GATCCAGGTGCTGCAGAAGG |
| SEQ ID NO: 588 CTCTTGCCTCCACTGGTTGT |
| SEQ ID NO: 589 TCGGTAGGATGCCCTACATC |
| SEQ ID NO: 590 ATCCTACAGCATGGTGGCTG |
| SEQ ID NO: 591 AGTGGTCTCCGGAAACCTCCGCGCCCCGCAAC |
| SEQ ID NO: 592 TCCTTGAAGAAGATGGTGCG |
| SEQ ID NO: 593<br>ACACTCTTTCCCTACACGACGCTCTTCCGATCTGAACTCATTACTGCTGCCCAGA |
| SEQ ID NO: 594<br>GTGACTGGAGTTCAGACGTGTGCTCTTCCGATCGACCTGTTCGGCTTCTTCCTTA |
| SEQ ID NO: 595<br>ACACTCTTTCCCTACACGACGCTCTTCCGATCTAAATTTCCACTGTCTTCTCTTGAGT |
| SEQ ID NO: 596<br>GTGACTGGAGTTCAGACGTGTGCTCTTCCGATCGCTTGCCTCTGACCTGTCCTAT |
| SEQ ID NO: 597<br>ACACTCTTTCCCTACACGACGCTCTTCCGATCTGTGACTAGGGGCAAAGCAAGAT |
| SEQ ID NO: 598<br>GTGACTGGAGTTCAGACGTGTGCTCTTCCGATCCTTCCAAACTTTCTGCCCATTC |
| SEQ ID NO: 599<br>ACACTCTTTCCCTACACGACGCTCTTCCGATCTAACACAGCGTGCTCTTTCCTTAG |
| SEQ ID NO: 600<br>GTGACTGGAGTTCAGACGTGTGCTCTTCCGATCGTTCAGAAGAACATCCCGTTGAC |
| SEQ ID NO: 601<br>AATGATACGGCGACCACCGAGATCTACACTCTTTCCCTACACGAC |
| SEQ ID NO: 602<br>CAAGCAGAAGACGGCATACGAGATCTTGTAGTGACTGGAGTTCAGACGT |
| SEQ ID NO: 603<br>CAAGCAGAAGACGGCATACGAGATCAGATCGTGACTGGAGTTCAGACGT |
| SEQ ID NO: 604<br>CAAGCAGAAGACGGCATACGAGATCCGTCCGTGACTGGAGTTCAGACGT |
| SEQ ID NO: 605<br>CAAGCAGAAGACGGCATACGAGATATGTCAGTGACTGGAGTTCAGACGT |
| SEQ ID NO: 606<br>CAAGCAGAAGACGGCATACGAGAT GTCCGC GTGACTGGAGTTCAGACGT |

| SEQUENCES |
|---|
| SEQ ID NO: 607<br>CAAGCAGAAGACGGCATACGAGAT TTAGGC GTGACTGGAGTTCAGACGT |
| SEQ ID NO: 608<br>CAAGCAGAAGACGGCATACGAGAT CGATGT GlGACIGGAGTTCAGACGT |
| SEQ ID NO: 609<br>CAAGCAGAAGACGGCATACGAGAT TGACCA GTGACTGGAGTTCAGACGT |
| SEQ ID NO: 610<br>CAAGCAGAAGACGGCATACGAGAT AGTCAA GTGACTGGAGTTCAGACGT |
| SEQ ID NO: 611 CAAGCAGAAGACGGCATACGAGAT AGTTCC<br>GTGACTGGAGTTCAGACGT |
| SEQ ID NO: 612<br>CAAGCAGAAGACGGCATACGAGAT GATCAG GTGACTGGAGTTCAGACGT |
| SEQ ID NO: 613<br>CAAGCAGAAGACGGCATACGAGAT ACAGTG GTGACTGGAGTTCAGACGT |
| SEQ ID NO: 614<br>CAAGCAGAAGACGGCATACGAGAT TATACT GTGACTGGAGTTCAGACGT |
| SEQ ID NO: 615<br>CAAGCAGAAGACGGCATACGAGAT CAACAA GTGACTGGAGTTCAGACGT |
| SEQ ID NO: 616<br>CAAGCAGAAGACGGCATACGAGAT GTTGTT GTGACTGGAGTTCAGACGT |
| SEQ ID NO: 617<br>CAAGCAGAAGACGGCATACGAGAT TCGGTT GTGACTGGAGTTCAGACGT |
| SEQ ID NO: 618<br>CAAGCAGAAGACGGCATACGAGAT AGTATT GTGACTGGAGTTCAGACGT |
| SEQ ID NO: 619<br>CAAGCAGAAGACGGCATACGAGAT TCTTGT GTGACTGGAGTTCAGACGT |
| SEQ ID NO: 620 GAACAGCTGCAGAACAGGAGATAACAG |
| SEQ ID NO: 621 GTTaTCTCCTGTTCTGCAGCTGT |
| SEQ ID NO: 622 ATGACAGGCAGGGGCACCGCGG |
| SEQ ID NO: 623 GAGCGAGCAGCGTCTTCGAGAGT |
| SEQ ID NO: 624 GCAGACGGCAGTCACTAGGGGGC |
| SEQ ID NO: 625 GTCGCAGGACAGCTTTTCCTAGA |
| SEQ ID NO: 626 GGGAAGCTGGGTGAATGGAGCGA |
| SEQ ID NO: 627 GATCCAGGTGCIGCAGAAGGGAT |
| SEQ ID NO: 628 GTTATCTCCTGCTCTGCAGCAGA |
| SEQ ID NO: 629 GATATCTCCTGTTCTGCAGGAGA |
| SEQ ID NO: 630 GGATTTCCAAGTCTCCACCC |
| SEQ ID NO: 631 TCCCACCGTACACGCCTAC |
| SEQ ID NO: 632<br>GGTTTCAGACAAAATCAAAAGAAGGAAGGTGCTCACATTCCTTAAATTAAG<br>GA |
| SEQ ID NO: 633<br>GGTTTTAGACAAAATCAAAAGAAGGAAGGTGCTCACATTCCTTAAATTAAG<br>GA |
| SEQ ID NO: 634 GTGCTCACATTCCTTAAATTAAGG |
| SEQ ID NO: 635 GGCTCACATTCCTTAAATTAAGGA |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A fusion protein comprising a Cas9 nickase and a monomeric adenine deaminase,
   wherein the Cas9 nickase comprises amino acid substitutions L1111R, D1135V, G1218R, E1219F, A1322R, and T1337R, and at least one additional mutation selected from R1335V, R1335Q or R1335E when compared to SEQ ID NO: 11, and
   wherein the monomeric adenine deaminase comprises amino acid substitutions A56G and V82G when compared to SEQ ID NO: 47.

2. The fusion protein of claim 1, wherein the Cas9 nickase comprises the amino acid sequence of SEQ ID NO: 15.

3. The fusion protein of claim 1, wherein the Cas9 nickase when in conjunction with a bound guide RNA (gRNA) specifically binds to a target nucleic acid sequence.

4. The fusion protein of claim 1, wherein the Cas9 nickase recognizes a NG protospacer adjacent motif (PAM) sequence.

5. The fusion protein of claim 1, wherein the adenine deaminase comprises the amino acid sequence set forth in SEQ ID NO: 23.

6. A system for base editing comprising:
   a first nucleotide sequence encoding a N-terminal portion of a Cas9 nickase fused at its C-terminus to an intein-N; and
   a second nucleotide sequence encoding an intein-C fused to the N-terminus of a C-terminal portion of the Cas9 nickase;
   wherein the first nucleotide sequence further comprises a nucleotide sequence encoding a monomeric adenine deaminase fused to the N-terminus of the N-terminal portion of the Cas9 nickase,
   wherein the Cas9 nickase comprises amino acid substitutions L1111R, D1135V, G1218R, E1219F, A1322R, and T1337R, and at least one additional mutation selected from R1335V, R1335Q or R1335E when compared to SEQ ID NO: 11, and
   wherein the monomeric adenine deaminase comprises amino acid substitutions A56G and V82G when compared to SEQ ID NO: 47.

7. The system of claim 6, wherein the N-terminal portion of the Cas9 nickase comprises the amino acid positions 2-573 of the amino acid sequence of SEQ ID NO: 15 and the C-terminal portion of the Cas9 nickase comprises the amino acid positions 574-1368 of the amino acid sequence of SEQ ID NO: 15.

8. The system of claim 6, wherein the intein-N is a Cfa intein-N or a gp41-1 intein-N.

9. The system of claim 6, wherein the intein-C is a Cfa intein-C or a gp41-1 intein-C.

10. The system of claim 6, wherein the first nucleotide sequence or the second nucleotide sequence further comprises a nucleotide encoding a guide RNA (gRNA).

11. A composition comprising:
   a first recombinant adeno-associated virus (AAV) particle comprising a first nucleotide sequence encoding a N-terminal portion of a Cas9 nickase fused at its C-terminus to an intein-N; and
   a second recombinant AAV particle comprising a second nucleotide sequence encoding an intein-C fused to the N-terminus of a C-terminal portion of the Cas9 nickase;
   wherein first nucleotide sequence further comprises a nucleotide sequence encoding a monomeric adenine deaminase fused to the N-terminus of the N-terminal portion of the Cas9 nickase,
   wherein the Cas9 nickase comprises amino acid substitutions L1111R, D1135V, G1218R, E1219F, A1322R, and T1337R, and at least one additional mutation selected from R1335V, R1335Q or R1335E when compared to SEQ ID NO: 11, and
   wherein the monomeric adenine deaminase comprises amino acid substitutions A56G and V82G when compared to SEQ ID NO: 47.

12. A method of treating a genetic disease in a subject, comprising administering a therapeutically effective amount of the composition of claim 11.

13. The method of claim 12, wherein the genetic disease is a muscular dystrophy or spinal muscular atrophy.

14. The method of claim 13, wherein the muscular dystrophy is Duchenne muscular dystrophy.

15. The method of claim 13, wherein the muscular dystrophy is dysferlinopathy.

\* \* \* \* \*

SEQUENCE LISTING

<160> NUMBER OF SEQ ID NOS: 635

<210> SEQ ID NO 1
<211> LENGTH: 8811
<212> TYPE: DNA
<213> ORGANISM: Artificial Sequence
<220> FEATURE:
<223> OTHER INFORMATION: Synthetic Construct

<400> SEQUENCE: 1

| | | | | | |
|---|---|---|---|---|---|
| atatgccaag | tacgcccct | attgacgtca | atgacggtaa | atggcccgcc | tggcattatg | 60 |
| cccagtacat | gaccttatgg | gactttccta | cttggcagta | catctacgta | ttagtcatcg | 120 |
| ctattaccat | ggtgatgcgg | ttttggcagt | acatcaatgg | gcgtggatag | cggtttgact | 180 |
| cacggggatt | tccaagtctc | caccccattg | acgtcaatgg | gagtttgttt | tggcaccaaa | 240 |
| atcaacggga | ctttccaaaa | tgtcgtaaca | actccgcccc | attgacgcaa | atgggcggta | 300 |
| ggcgtgtacg | gtgggaggtc | tatataagca | gagctggttt | agtgaaccgt | cagatccgct | 360 |
| agagatccgc | ggccgctaat | acgactcact | ataggagag | ccgccaccat | gaaacggaca | 420 |
| gccgacggaa | gcgagttcga | gtcaccaaag | aagaagcgga | agtctctga | agtcgagttt | 480 |
| agccacgagt | attggatgag | gcacgcactg | accctggcaa | agcgagcatg | ggatgaaaga | 540 |
| gaagtccccg | tgggcgccgt | gctggtgcac | aacaatagag | tgatcggaga | gggatggaac | 600 |
| aggccaatcg | gccgccacga | ccctaccgca | cacgcagaga | tcatggcact | gaggcaggga | 660 |
| ggcctggtca | tgcagaatta | ccgcctgatc | gatgccaccc | tgtatgtgac | actggagcca | 720 |
| tgcgtgatgt | gcgcaggagc | aatgatccac | agcaggatcg | gaagagtggt | gttcggagca | 780 |
| cgggacgcca | agaccggcgc | agcaggctcc | ctgatggatg | tgctgcacca | ccccggcatg | 840 |
| aaccaccggg | tggagatcac | agagggaatc | ctggcagacg | agtgcgccgc | cctgctgagc | 900 |
| gatttcttta | gaatgcggag | acaggagatc | aaggcccaga | agaaggcaca | gagctccacc | 960 |
| gactctggag | gatctagcgg | aggatcctct | ggaagcgaga | caccaggcac | aagcgagtcc | 1020 |
| gccacaccag | agagctccgg | cggctcctcc | ggaggatcct | ctgaggtgga | gtttcccac | 1080 |
| gagtactgga | tgagacatgc | cctgaccctg | gccaagaggg | cacgcgatga | gagggaggtg | 1140 |
| cctgtgggag | ccgtgctggt | gctgaacaat | agagtgatcg | gcgagggctg | gaacagagcc | 1200 |
| atcggcctgc | acgacccaac | agcccatgcc | gaaattatgg | ccctgagaca | gggcggcctg | 1260 |
| gtcatgcaga | actacagact | gattgacgcc | accctgtacg | tgacattcga | gccttgcgtg | 1320 |
| atgtgcgccg | gcgccatgat | ccactctagg | atcggccgcg | tggtgtttgg | cgtgaggaac | 1380 |
| gcaaaaaccg | gcgccgcagg | ctccctgatg | gacgtgctgc | actaccccgg | catgaatcac | 1440 |
| cgcgtcgaaa | ttaccgaggg | aatcctggca | gatgaatgtg | ccgccctgct | gtgctatttc | 1500 |
| tttcggatgc | ctagacaggt | gttcaatgct | cagaagaagg | cccagagctc | caccgactcc | 1560 |
| ggaggatcta | gcgaggctc | ctctggctct | gagacacctg | gcacaagcga | gagcgcaaca | 1620 |
| cctgaaagca | gcgggggcag | cagcgggggg | tcagacaaga | agtacagcat | cggcctggcc | 1680 |

```
atcggcacca actctgtggg ctgggccgtg atcaccgacg agtacaaggt gcccagcaag    1740
aaattcaagg tgctgggcaa caccgaccgg cacagcatca agaagaacct gatcggagcc    1800
ctgctgttcg acagcggcga aacagccgag gccacccggc tgaagagaac cgccagaaga    1860
agatacacca gacggaagaa ccggatctgc tatctgcaag atcttcag caacgagatg    1920
gccaaggtgg acgacagctt cttccacaga ctggaagagt ccttcctggt ggaagaggat    1980
aagaagcacg agcggcaccc catcttcggc aacatcgtgg acgaggtggc ctaccacgag    2040
aagtacccca ccatctacca cctgagaaag aaactggtgg acagcaccga aaggccgac    2100
ctgcggctga tctatctggc cctggccac atgatcaagt ccggggcca cttcctgatc    2160
gagggcgacc tgaaccccga caacagcgac gtggacaagc tgttcatcca gctggtgcag    2220
acctacaacc agctgttcga ggaaaacccc atcaacgcca gcggcgtgga cgccaaggcc    2280
atcctgtctg ccagactgag caagagcaga cggctggaaa atctgatcgc ccagctgccc    2340
ggcgagaaga agaatggcct gttcggaaac ctgattgccc tgagcctggg cctgaccccc    2400
aacttcaaga gcaacttcga cctggccgag gatgccaaac tgcagctgag caaggacacc    2460
tacgacgacg acctggacaa cctgctggcc cagatcggcg accagtacgc cgacctgttt    2520
ctggccgcca gaacctgtc cgacgccatc ctgctgagcg acatcctgag agtgaacacc    2580
gagatcacca aggcccccct gagcgcctct atgatcaaga gatacgacga gcaccaccag    2640
gacctgaccc tgctgaaagc tctcgtgcgg cagcagctgc ctgagaagta caaagagatt    2700
ttcttcgacc agagcaagaa cggctacgcc ggctacattg acggcggagc cagccaggaa    2760
gagttctaca gttcatcaa gcccatcctg gaaaagatgg acggcaccga ggaactgctc    2820
gtgaagctga acagagagga cctgctgcgg aagcagcgga ccttcgacaa cggcagcatc    2880
ccccaccaga tccacctggg agagctgcac gccattctgc ggcggcagga agattttta    2940
ccattcctga aggacaaccg ggaaaagatc gagaagatcc tgaccttccg catcccctac    3000
tacgtgggcc ctctggccag ggaaacagc agattcgcct ggatgaccag aaagagcgag    3060
gaaaccatca ccccctggaa cttcgaggaa gtggtggaca agggcgcttc cgcccagagc    3120
ttcatcgagc ggatgaccaa cttcgataag aacctgccca cgagaaggt gctgcccaag    3180
cacagcctgc tgtacgagta cttcaccgtg tataacgagc tgaccaaagt gaaatacgtg    3240
accgagggaa tgagaaagcc cgccttcctg agcggcgagc agaaaaaggc catcgtggac    3300
ctgctgttca gaccaaccg gaaagtgacc gtgaagcagc tgaaagagga ctacttcaag    3360
aaaatcgagt gcttcgactc cgtggaaatc tccggcgtgg aagatcggtt caacgcctcc    3420
ctgggcacat accacgatct gctgaaaatt atcaaggaca aggacttcct ggacaatgag    3480
gaaaacgagg acattctgga agatatcgtg ctgacccga cactgtttga ggacagagag    3540
atgatcgagg aacggctgaa aacctatgcc cacctgttcg acgacaaagt gatgaagcag    3600
ctgaagcggc ggagatacac cggctgggc aggctgagcc ggaagctgat caacggcatc    3660
cgggacaagc agtccggcaa gacaatcctg gatttcctga gtccgacgg cttcgccaac    3720
agaaacttca tgcagctgat ccacgacgac agcctgacct ttaaagagga catccagaaa    3780
gcccaggtgt ccggccaggg cgatagcctg cacgagcaca ttgccaatct ggccggcagc    3840
cccgccatta gaagggcat cctgcagaca gtgaaggtgg tggacgagct cgtgaaagtg    3900
atgggccggc acaagcccga gaacatcgtg atcgaaatgg ccagagagaa ccagaccacc    3960
cagaagggac agaagaacag ccgcgagaga atgaagcgga tcgagagggg catcaaagag    4020
ctgggcagcc agatcctgaa agaacacccc gtggaaaaca cccagctgca gaacgagaag    4080
```

```
ctgtacctgt actacctgca gaatgggcgg gatatgtacg tggaccagga actggacatc    4140
aaccggctgt ccgactacga tgtggaccat atcgtgcctc agagctttct gaaggacgac    4200
tccatcgaca acaaggtgct gaccagaagc gacaagaacc ggggcaagag cgacaacgtg    4260
ccctccgaag aggtcgtgaa gaagatgaag aactactggc ggcagctgct gaacgccaag    4320
ctgattaccc agagaaagtt cgacaatctg accaaggccg agagaggcgg cctgagcgaa    4380
ctggataagg ccggcttcat caagagacag ctggtggaaa cccggcagat cacaaagcac    4440
gtggcacaga tcctggactc ccggatgaac actaagtacg acgagaatga caagctgatc    4500
cgggaagtga aagtgatcac cctgaagtcc aagctggtgt ccgatttccg gaaggatttc    4560
cagttttaca agtgcgcga gatcaacaac taccaccacg cccacgacgc ctacctgaac    4620
gccgtcgtgg aaccgccct gatcaaaaag taccctaagc tggaaagcga gttcgtgtac    4680
ggcgactaca aggtgtacga cgtgcggaag atgatcgcca agagcgagca ggaaatcggc    4740
aaggctaccg ccaagtactt cttctacagc aacatcatga actttttcaa gaccgagatt    4800
accctggcca acggcgagat ccggaagcgg cctctgatcg agacaaacgg cgaaaccggg    4860
gagatcgtgt gggataaggg ccgggatttt gccaccgtgc ggaaagtgct gagcatgccc    4920
caagtgaata tcgtgaaaaa gaccgaggtg cagacaggcg gcttcagcaa agagtctatc    4980
cggcccaaga ggaacagcga taagctgatc gccagaaaga aggactggga ccctaagaag    5040
tacggcggct tcgtcagccc caccgtggcc tattctgtgc tggtggtggc caaagtggaa    5100
aagggcaagt ccaagaaact gaagagtgtg aaagagctgc tggggatcac catcatggaa    5160
agaagcagct tcgagaagaa tcccatcgac tttctggaag ccaagggcta caaggaagtg    5220
aaaaaggacc tgatcatcaa gctgcctaag tactccctgt tcgagctgga aaacggccgg    5280
aagagaatgc tggcctctgc cgcctttctg cagaagggaa acgaactggc cctgccctcc    5340
aaatatgtga acttcctgta cctggccagc cactatgaga agctgaaggg ctcccccgag    5400
gataatgagc agaaacagct gtttgtggaa cagcacaagc actacctgga cgagatcatc    5460
gagcagatca gcgagttctc caagagagtg atcctggccg acgctaatct ggacaaagtg    5520
ctgtccgcct acaacaagca ccgggataag cccatcagag caggccga gaatatcatc    5580 cacctgtttta ccctgaccaa tctgggagcc ctcgggcct tcaagtactt tgacaccacc    5640
atcgaccgga aggtgtaccg gagcaccaaa gaggtgctgg acgccaccct gatccaccag    5700
agcatcaccg gcctgtacga gacacggatc gacctgtctc agctgggagg tgactctggc    5760
ggctcaaaaa gaaccgccga cggcagcgaa ttcgagccca agaagaagag gaaagtctaa    5820
ccggtcatca tcaccatcac cattgagttt aaacccgctg atcagcctcg actgtgcctt    5880
ctagttgcca gccatctgtt gtttgcccct cccccgtgcc ttccttgacc ctggaaggtg    5940
ccactcccac tgtcctttcc taataaaatg aggaaattgc atcgcattgt ctgagtaggt    6000
gtcattctat tctggggggt ggggtggggc aggacagcaa ggggaggat tgggaagaca    6060 atagcaggca tgctggggat gcggtgggct ctatggcttc tgaggcggaa agaaccagct    6120
ggggctcgat accgtcgacc tctagctaga gcttggcgta atcatggtca tagctgtttc    6180
ctgtgtgaaa ttgttatccg ctcacaattc cacacaacat acgagccgga agcataaagt    6240
gtaaagccta gggtgcctaa tgagtgagct aactcacatt aattgcgttg cgctcactgc    6300
ccgctttcca gtcgggaaac ctgtcgtgcc agctgcatta tgaatcggc caacgcgcgg    6360 ggagaggcgg tttgcgtatt gggcgctctt ccgcttcctc gctcactgac tcgctgcgct    6420
```

```
cggtcgttcg gctgcggcga gcggtatcag ctcactcaaa ggcggtaata cggttatcca    6480
cagaatcagg ggataacgca ggaaagaaca tgtgagcaaa aggccagcaa aaggccagga    6540
accgtaaaaa ggccgcgttg ctggcgtttt tccataggct ccgcccccct gacgagcatc    6600
acaaaaatcg acgctcaagt cagaggtggc gaaacccgac aggactataa agataccagg    6660
cgtttccccc tggaagctcc ctcgtgcgct ctcctgttcc gaccctgccg cttaccggat    6720
acctgtccgc ctttctccct tcgggaagcg tggcgctttc tcatagctca cgctgtaggt    6780
atctcagttc ggtgtaggtc gttcgctcca agctgggctg tgtgcacgaa ccccccgttc    6840
agcccgaccg ctgcgcctta tccggtaact atcgtcttga gtccaacccg gtaagcacg     6900
acttatcgcc actggcagca gccactggta acaggattag cagagcgagg tatgtaggcg    6960
gtgctacaga gttcttgaag tggtggccta actacggcta cactagaaga acagtatttg    7020
gtatctgcgc tctgctgaag ccagttacct tcggaaaaag agttggtagc tcttgatccg    7080
gcaaacaaac caccgctggt agcggtggtt tttttgtttg caagcagcag attacgcgca    7140
gaaaaaaagg atctcaagaa gatcctttga tcttttctac ggggtctgac actcagtgga    7200
acgaaaactc acgttaaggg attttggtca tgagattatc aaaaaggatc ttcacctaga    7260
tccttttaaa ttaaaaatga agttttaaat caatctaaag tatatatgag taaacttggt    7320
ctgacagtta ccaatgctta atcagtgagg cacctatctc agcgatctgt ctatttcgtt    7380
catccatagt tgcctgactc cccgtcgtgt agataactac gatacgggag ggcttaccat    7440
ctggccccag tgctgcaatg ataccgcgag acccacgctc accggctcca gatttatcag    7500
caataaacca gccagccgga agggccgagc gcagaagtgg tcctgcaact ttatccgcct    7560
ccatccagtc tattaattgt tgccgggaag ctagagtaag tagttcgcca gttaatagtt    7620
tgcgcaacgt tgttgccatt gctacaggca tcgtggtgtc acgctcgtcg tttggtatgg    7680
cttcattcag ctccggttcc caacgatcaa ggcgagttac atgatccccc atgttgtgca    7740
aaaaagcggt tagctccttc ggtcctccga tcgttgtcag aagtaagttg gccgcagtgt    7800
tatcactcat ggttatggca gcactgcata attctcttac tgtcatgcca tccgtaagat    7860
gcttttctgt gactggtgag tactcaacca agtcattctg agaatagtgt atgcggcgac    7920
cgagttgctc ttgcccggcg tcaatacggg ataataccgc gccacatagc agaactttaa    7980
aagtgctcat cattggaaaa cgttcttcgg ggcgaaaact ctcaaggatc ttaccgctgt    8040
tgagatccag ttcgatgtaa cccactcgtg cacccaactg atcttcagca tcttttactt    8100
tcaccagcgt ttctgggtga gcaaaaacag gaaggcaaaa tgccgcaaaa aagggaataa    8160
gggcgacacg gaaatgttga atactcatac tcttcctttt tcaatattat tgaagcattt    8220
atcagggtta ttgtctcatg agcggataca tatttgaatg tatttagaaa aataaacaaa    8280
taggggttcc gcgcacattt ccccgaaaag tgccacctga cgtcgacgga tcgggagatc    8340
gatctcccga tccccctaggg tcgactctca gtacaatctg ctctgatgcc gcatagttaa    8400
gccagtatct gctccctgct tgtgtgttgg aggtcgctga gtagtgcgcg agcaaaattt    8460
aagctacaac aaggcaaggc ttgaccgaca attgcatgaa gaatctgctt agggttaggc    8520
gttttgcgct gcttcgcgat gtacgggcca gatatacgcg ttgacattga ttattgacta    8580
gttattaata gtaatcaatt acgggtcat tagttcatag cccatatatg gagttccgcg    8640
ttacataact tacggtaaat ggcccgcctg gctgaccgcc caacgacccc cgcccattga    8700
cgtcaataat gacgtatgtt cccatagtaa cgccaatagg gactttccat tgacgtcaat    8760
gggtggagta tttacggtaa actgcccact tggcagtaca tcaagtgtat c             8811
```

<210> SEQ ID NO 2
<211> LENGTH: 8232
<212> TYPE: DNA
<213> ORGANISM: Artificial Sequence
<220> FEATURE:
<223> OTHER INFORMATION: Synthetic Construct

<400> SEQUENCE: 2

| | | | | | |
|---|---|---|---|---|---|
| atatgccaag | tacgccccct | attgacgtca | atgacggtaa | atggcccgcc | tggcattatg | 60 |
| cccagtacat | gaccttatgg | gactttccta | cttggcagta | catctacgta | ttagtcatcg | 120 |
| ctattaccat | ggtgatgcgg | ttttggcagt | acatcaatgg | gcgtggatag | cggtttgact | 180 |
| cacggggatt | tccaagtctc | caccccattg | acgtcaatgg | gagtttgttt | tggcaccaaa | 240 |
| atcaacggga | ctttccaaaa | tgtcgtaaca | actccgcccc | attgacgcaa | atgggcggta | 300 |
| ggcgtgtacg | gtgggaggtc | tatataagca | gagctggttt | agtgaaccgt | cagatccgct | 360 |
| agagatccgc | ggccgctaat | acgactcact | atagggagag | ccgccaccat | ggctagcatg | 420 |
| aaacggacag | ccgacggaag | cgagttcgag | tcaccaaaga | gaagcggaa | agtcggatcc | 480 |
| tctgaggtgg | agttttccca | cgagtactgg | atgagacatg | ccctgaccct | ggccaagagg | 540 |
| gcacgcgatg | agagggaggt | gcctgtggga | gccgtgctgg | tgctgaacaa | tagagtgatc | 600 |
| ggcgagggct | ggaacagagc | catcggcctg | cacgacccaa | caggccatgc | cgaaattatg | 660 |
| gccctgaggc | agggcggcct | ggtcatgcag | aactacagac | tgattgacgc | caccctgtac | 720 |
| gggacattcg | agccttgcgt | gatgtgcgcc | ggcgccatga | tccactctag | gatcggccgc | 780 |
| gtggtgtttg | gcgtgaggaa | cgcaaaaacc | ggcgccgcag | gctccctgat | ggacgtgctg | 840 |
| cactaccccg | gcatgaatca | ccgcgtcgaa | attaccgagg | gaatcctggc | agatgaatgt | 900 |
| gccgccctgc | tgtgctattt | ctttcggatg | cctagacagg | tgttcaatgc | tcagaagaag | 960 |
| gcccagagct | ccaccgactc | cggaggatct | agcggaggct | cctctggctc | tgagacacct | 1020 |
| ggcacaagcg | agagcgcaac | acctgaaagc | agcgggggca | gcgggggg | gtcagacaag | 1080 |
| aagtacagca | tcggcctggc | catcggcacc | aactctgtgg | gctgggccgt | gatcaccgac | 1140 |
| gagtacaagg | tgcccagcaa | gaaattcaag | gtgctgggca | caccgaccg | gcacagcatc | 1200 |
| aagaagaacc | tgatcggagc | cctgctgttc | gacagcggcg | aaacagccga | ggccacccgg | 1260 |
| ctgaagagaa | ccgccagaag | aagatacacc | agacggaaga | accggatctg | ctatctgcaa | 1320 |
| gagatcttca | gcaacgagat | ggccaaggtg | gacgacagct | tcttccacag | actggaagag | 1380 |
| tccttcctgg | tggaagagga | taagaagcac | gagcggcacc | ccatcttcgg | caacatcgtg | 1440 |
| gacgaggtgg | cctaccacga | gaagtacccc | accatctacc | acctgagaaa | gaaactggtg | 1500 |
| gacagcaccg | acaaggccga | cctgcggctg | atctatctgg | ccctggccca | catgatcaag | 1560 |
| ttccggggcc | acttcctgat | cgagggcgac | ctgaaccccg | acaacagcga | cgtggacaag | 1620 |
| ctgttcatcc | agctggtgca | gacctacaac | cagctgttcg | aggaaaaccc | catcaacgcc | 1680 |
| agcggcgtgg | acgccaaggc | catcctgtct | gccagactga | gcaagagcag | acggctggaa | 1740 |
| aatctgatcg | cccagctgcc | cggcgagaag | aagaatggcc | tgttcggaaa | cctgattgcc | 1800 |
| ctgagcctgg | gcctgacccc | caacttcaag | agcaacttcg | acctggccga | ggatgccaaa | 1860 |
| ctgcagctga | gcaaggacac | ctacgacgac | gacctggaca | acctgctggc | ccagatcggc | 1920 |
| gaccagtacg | ccgacctgtt | tctggccgcc | aagaacctgt | ccgacgccat | cctgctgagc | 1980 |
| gacatcctga | gagtgaacac | cgagatcacc | aaggcccccc | tgagcgcctc | tatgatcaag | 2040 |

```
agatacgacg agcaccacca ggacctgacc ctgctgaaag ctctcgtgcg gcagcagctg    2100
cctgagaagt acaaagagat tttcttcgac cagagcaaga acggctacgc cggctacatt    2160
gacggcggag ccagccagga agagttctac aagttcatca agcccatcct ggaaaagatg    2220
gacggcaccg aggaactgct cgtgaagctg aacagagagg acctgctgcg gaagcagcgg    2280
accttcgaca acggcagcat ccccccaccag atccacctgg agagctgca cgccattctg    2340 cggcggcagg aagatttttta cccattcctg aaggacaacc gggaaaagat cgagaagatc    2400
ctgaccttcc gcatccccta ctacgtgggc cctctggcca ggggaaacag cagattcgcc    2460
tggatgacca aaagagcga ggaaaccatc accccctgga acttcgagga agtggtggac    2520
aagggcgctt ccgcccagag cttcatcgag cggatgacca acttcgataa gaacctgccc    2580
aacgagaagt gctgcccaa gcacagcctg ctgtacgagt acttcaccgt gtataacgag    2640
ctgaccaaag tgaaatacgt gaccgaggga atgagaaagc ccgccttcct gagcggcgag    2700
cagaaaaagg ccatcgtgga cctgctgttc aagaccaacc ggaaagtgac cgtgaagcag    2760
ctgaaagagg actacttcaa gaaaatcgag tgcttcgact ccgtggaaat ctccggcgtg    2820
gaagatcggt tcaacgcctc cctgggcaca taccacgatc tgctgaaaat tatcaaggac    2880
aaggacttcc tggacaatga ggaaaacgag gacattctgg aagatatcgt gctgaccctg    2940
acactgtttg aggacagaga gatgatcgag aacggctga aaacctatgc ccacctgttc    3000
gacgacaaag tgatgaagca gctgaagcgg cggagataca ccggctgggg caggctgagc    3060
cggaagctga tcaacggcat ccgggacaag cagtccggca agacaatcct ggatttcctg    3120
aagtccgacg gcttcgccaa cagaaacttc atgcagctga tccacgacga cagcctgacc    3180
tttaaagagg acatccagaa agcccaggtg tccggccagg gcgatagcct gcacgagcac    3240
attgccaatc tggccggcag ccccgccatt aagaagggca tcctgcagac agtgaaggtg    3300
gtggacgagc tcgtgaaagt gatgggccgg cacaagcccg agaacatcgt gatcgaaatg    3360
gccagagaga accagaccac ccagaaggga cagaagaaca gccgcgagag aatgaagcgg    3420
atcgaagagg gcatcaaaga gctgggcagc cagatcctga aagaaacccc cgtggaaaac    3480
acccagctgc agaacgagaa gctgtacctg tactacctgc agaatgggcg ggatatgtac    3540
gtggaccagg aactggacat caaccggctg tccgactacg atgtggacca tatcgtgcct    3600
cagagctttc tgaaggacga ctccatcgac aacaaggtgc tgaccagaag cgacaagaac    3660
cggggcaaga gcgacaacgt gcccctccgaa gaggtcgtga agaagatgaa gaactactgg    3720
cggcagctgc tgaacgccaa gctgattacc cagagaaagt tcgacaatct gaccaaggcc    3780
gagagaggcg gcctgagcga actggataag gccggcttca tcaagagaca gctggtggaa    3840
acccggcaga tcacaaagca cgtggcacag atcctggact cccggatgaa cactaagtac    3900
gacgagaatg acaagctgat ccgggaagtg aaagtgatca ccctgaagtc caagctggtg    3960
tccgatttcc ggaaggattt ccagttttac aaagtgcgcg agatcaacaa ctaccaccac    4020
gcccacgacg cctacctgaa cgccgtcgtg ggaaccgccc tgatcaaaaa gtaccctaag    4080
ctggaaagcg agttcgtgta cggcgactac aaggtgtacg acgtgcggaa gatgatcgcc    4140
aagagcgagc aggaaatcgg caaggctacc gccaagtact tcttctacag caacatcatg    4200 aacttttttca agaccgagat taccctggcc aacggcgaga tccggaagcg gcctctgatc    4260
gagacaaacg gcgaaaccgg ggagatcgtg tgggataagg gccgggattt tgccaccgtg    4320
cggaaagtgc tgagcatgcc ccaagtgaat atcgtgaaaa agaccgaggt gcagacaggc    4380
ggcttcagca aagagtctat ccggcccaag aggaacagcg ataagctgat cgccagaaag    4440
```

```
aaggactggg accctaagaa gtacggcggc ttcgtcagcc ccaccgtggc ctattctgtg    4500
ctggtggtgg ccaaagtgga aagggcaag tccaagaaac tgaagagtgt gaagagctg     4560 ctggggatca ccatcatgga aagaagcagc ttcgagaaga atcccatcga ctttctggaa    4620
gccaagggct acaagaagt gaaaaaggac ctgatcatca agctgcctaa gtactccctg    4680
ttcgagctgg aaaacggccg gaagagaatg ctggcctctg cccgctttct gcagaaggga    4740
aacgaactgg ccctgccctc caaatatgtg aacttcctgt acctggccag ccactatgag    4800
aagctgaagg gctcccccga ggataatgag cagaaacagc tgtttgtgga acagcacaag    4860
cactacctgg acgagatcat cgagcagatc agcgagttct ccaagagagt gatcctggcc    4920
gacgctaatc tggacaaagt gctgtccgcc tacaacaagc accgggataa gcccatcaga    4980
gagcaggccg agaatatcat ccacctgttt accctgacca atctgggagc ccctcgggcc    5040
ttcaagtact ttgacaccac catcgaccgg aaggtgtacc ggagcaccaa agaggtgctg    5100
gacgccaccc tgatccacca gagcatcacc ggcctgtacg agacacggat cgacctgtct    5160
cagctgggag gtgactctgg cggctcaaaa agaaccgccg acggcagcga attcgagccc    5220
aagaagaaga ggaaagtcta accggtcatc atcaccatca ccattgagtt taaacccgct    5280
gatcagcctc gactgtgcct tctagttgcc agccatctgt tgtttgcccc tccccgtgc    5340 cttccttgac cctggaaggt gccactccca ctgtcctttc ctaataaaat gaggaaattg    5400
catcgcattg tctgagtagg tgtcattcta ttctgggggg tggggtgggg caggacagca    5460
agggggagga ttgggaagac aatagcaggc atgctgggga tgcggtgggc tctatggctt    5520
ctgaggcgga aagaaccagc tggggctcga taccgtcgac ctctagctag agcttggcgt    5580
aatcatggtc atagctgttt cctgtgtgaa attgttatcc gctcacaatt ccacacaaca    5640
tacgagccgg aagcataaag tgtaaagcct agggtgccta atgagtgagc taactcacat    5700
taattgcgtt gcgctcactg cccgctttcc agtcggaaaa cctgtcgtgc cagctgcatt    5760
aatgaatcgg ccaacgcgcg gggagaggcg gtttgcgtat tgggcgctct tccgcttcct    5820
cgctcactga ctcgctgcgc tcggtcgttc ggctgcggcg agcggtatca gctcactcaa    5880
aggcggtaat acggttatcc acagaatcag gggataacgc aggaaagaac atgtgagcaa    5940
aaggccagca aaaggccagg aaccgtaaaa aggccgcgtt gctggcgttt ttccataggc    6000
tccgcccccc tgacgagcat cacaaaaatc gacgctcaag tcagaggtgg cgaaacccga    6060
caggactata agataccagg cgtttccccc tggaagctcc ctcgtgcgc tctcctgttc     6120 cgaccctgcc gcttaccgga tacctgtccg cctttctccc ttcgggaagc gtggcgcttt    6180
ctcatagctc acgctgtagg tatctcagtt cggtgtaggt cgttcgctcc aagctgggct    6240
gtgtgcacga accccccgtt cagcccgacc gctgcgcctt atccggtaac tatcgtcttg    6300
agtccaaccc ggtaagacac gacttatcgc cactggcagc agccactggt aacaggatta    6360
gcagagcgag gtatgtaggc ggtgctacag agttcttgaa gtggtggcct aactacggct    6420
acactagaag aacagtattt ggtatctgcg ctctgctgaa gccagttacc ttcggaaaaa    6480
gagttggtag ctcttgatcc ggcaaacaaa ccaccgctgg tagcggtggt ttttttgttt    6540
gcaagcagca gattacgcgc agaaaaaaag gatctcaaga agatcctttg atcttttcta    6600
cggggtctga cactcagtgg aacgaaaact cacgttaagg gattttggtc atgagattat    6660
caaaaaggat cttcacctag atccttttaa attaaaaatg aagttttaaa tcaatctaaa    6720
gtatatatga gtaaacttgg tctgacagtt accaatgctt aatcagtgag gcacctatct    6780
```

| | |
|---|---|
| cagcgatctg tctatttcgt tcatccatag ttgcctgact ccccgtcgtg tagataacta | 6840 |
| cgatacggga gggcttacca tctggcccca gtgctgcaat gataccgcga gacccacgct | 6900 |
| caccggctcc agatttatca gcaataaacc agccagccgg aagggccgag cgcagaagtg | 6960 |
| gtcctgcaac tttatccgcc tccatccagt ctattaattg ttgccgggaa gctagagtaa | 7020 |
| gtagttcgcc agttaatagt ttgcgcaacg ttgttgccat tgctacaggc atcgtggtgt | 7080 |
| cacgctcgtc gtttggtatg gcttcattca gctccggttc ccaacgatca aggcgagtta | 7140 |
| catgatcccc catgttgtgc aaaaaagcgg ttagctcctt cggtcctccg atcgttgtca | 7200 |
| gaagtaagtt ggccgcagtg ttatcactca tggttatggc agcactgcat aattctctta | 7260 |
| ctgtcatgcc atccgtaaga tgcttttctg tgactggtga gtactcaacc aagtcattct | 7320 |
| gagaatagtg tatgcggcga ccgagttgct cttgcccggc gtcaatacgg ataataccg | 7380 |
| cgccacatag cagaacttta aaagtgctca tcattggaaa acgttcttcg gggcgaaaac | 7440 |
| tctcaaggat cttaccgctg ttgagatcca gttcgatgta acccactcgt gcacccaact | 7500 |
| gatcttcagc atctttact ttcaccagcg tttctgggtg agcaaaaaca ggaaggcaaa | 7560 |
| atgccgcaaa aaagggaata agggcgacac ggaaatgttg aatactcata ctcttccttt | 7620 |
| ttcaatatta ttgaagcatt tatcagggtt attgtctcat gagcggatac atatttgaat | 7680 |
| gtatttagaa aaataaacaa ataggggttc cgcgcacatt tccccgaaaa gtgccacctg | 7740 |
| acgtcgacga tcgggagat cgatctcccg atccctagg gtcgactctc agtacaatct | 7800 |
| gctctgatgc cgcatagtta agccagtatc tgctccctgc ttgtgtgttg gaggtcgctg | 7860 |
| agtagtgcgc gagcaaaatt taagctacaa caaggcaagg cttgaccgac aattgcatga | 7920 |
| agaatctgct tagggttagg cgttttgcgc tgcttcgcga tgtacgggcc agatatacgc | 7980 |
| gttgacattg attattgact agttattaat agtaatcaat tacggggtca ttagttcata | 8040 |
| gcccatatat ggagttccgc gttacataac ttacggtaaa tggcccgcct ggctgaccgc | 8100 |
| ccaacgaccc ccgcccattg acgtcaataa tgacgtatgt tcccatagta acgccaatag | 8160 |
| ggactttcca ttgacgtcaa tgggtggagt atttacggta aactgcccac ttggcagtac | 8220 |
| atcaagtgta tc | 8232 |

<210> SEQ ID NO 3
<211> LENGTH: 9254
<212> TYPE: DNA
<213> ORGANISM: Artificial Sequence
<220> FEATURE:
<223> OTHER INFORMATION: Synthetic Construct

<400> SEQUENCE: 3

| | |
|---|---|
| aaagtagccg aagatgacgg tttgtcacat ggagttggca ggatgtttga ttaaaaacat | 60 |
| aacaggaaga aaaatgcccc gctgtgggcg acaaaatag ttgggaactg ggaggggtgg | 120 |
| aaatggagtt tttaaggatt atttagggaa gagtgacaaa atagatggga actgggtgta | 180 |
| gcgtcgtaag ctaatacgaa aattaaaaat gacaaaatag tttggaacta gatttcactt | 240 |
| atctggttcg gatctcctag gctcaagcag tgatcagatc cagacatgat aagatacatt | 300 |
| gatgagtttg gacaaaccac aactagaatg cagtgaaaaa aatgctttat ttgtgaaatt | 360 |
| tgtgatgcta ttgctttatt tgtaaccatt ataagctgca ataaacaagt taacaacaac | 420 |
| aattccatgt cctgcaggca gctgcgcgct cgctcgctca ctgaggccgc ccgggcgtcg | 480 |
| ggcgaccttt ggtcgcccgg cctcagtgag cgagcgagcg cgcagagagg gagtggccaa | 540 |
| ctccatcact aggggttcct gcggcctcta gactcgagcg cgtgatgaga gcagccacta | 600 |

```
cgggtctagg ctgcccatgt aaggaggcaa ggcctgggga cacccgagat gcctggttat    660
aattaaccca gacatgtggc tgccccccccc cccccaacac ctgctgcctg ctaaaaataa    720
ccctgtccct ggtggccctg catgcccact cacggggatt ccaagtctc cacccattg      780 acgtcaatgg gagtttgttt tggcaccaaa atcaacggga cttttccaaaa tgtcgtaaca   840 actccgcccc attgacgcaa atgggcggta ggcgtgtacg gtgggaggtc tatataagca    900
gagctggttt agtgaaccgt cagatccgcc accatggcta gcatgaaacg gacagccgac    960
ggaagcgagt tcgagtcacc aaagaagaag cggaaagtct ctgaagtcga gtttagccac   1020
gagtattgga tgaggcacgc actgaccctg gcaaagcgag catgggatga agagaagtc    1080 cccgtgggcg ccgtgctggt gcacaacaat agagtgatcg agagggatg gaacaggcca    1140 atcggccgcc acgaccctac cgcacacgca gagatcatgg cactgaggca gggaggcctg    1200
gtcatgcaga attaccgcct gatcgatgcc accctgtatg tgacactgga gccatgcgtg    1260
atgtgcgcag gagcaatgat ccacagcagg atcggaagag tggtgttcgg agcacgggac    1320
gccaagaccg gcgcagcagg ctccctgatg gatgtgctgc accacccgg catgaaccac     1380 cgggtggaga tcacagaggg aatcctggca gacgagtgcg ccgccctgct gagcgatttc    1440
tttagaatgc ggagacagga gatcaaggcc cagaagaagg cacagagctc caccgactct    1500
ggaggatcta gcgaggatc ctctggaagc gagacaccag gcacaagcga gtccgccaca     1560
ccagagagct ccggcggctc ctccggagga tcctctgagg tggagttttc ccacgagtac    1620
tggatgagac atgccctgac cctggccaag agggcacgcg atgagaggga ggtgcctgtg    1680
ggagccgtgc tggtgctgaa caatagagtg atcggcgagg gctggaacag agccatcggc    1740
ctgcacgacc caacagccca tgccgaaatt atggccctga cagggcgg cctggtcatg      1800 cagaactaca gactgattga cgccaccctg tacgtgacat cgagccttg cgtgatgtgc    1860 gccggcgcca tgatccactc taggatcggc gcgtggtgt ttggcgtgag gaacgcaaaa    1920
accggcgccg caggctccct gatggacgtg ctgcactacc ccggcatgaa tcaccgcgtc   1980
gaaattaccg agggaatcct ggcagatgaa tgtgccgccc tgctgtgcta tttcttcgg    2040 atgcctagac aggtgttcaa tgctcagaag aaggcccaga gctccaccga ctccggagga   2100
tctagcggag ctcctctgg ctctgagaca cctggcacaa gcgagagcgc aacacctgaa    2160
agcagcgggg gcagcagcgg ggggtcgac aagaagtaca gcatcggcct ggccatcggc    2220
accaactctg tgggctgggc cgtgatcacc gacgagtaca aggtgcccag caagaaattc   2280
aaggtgctgg gcaacaccga ccggcacagc atcaagaaga acctgatcgg agccctgctg   2340
ttcgacagcg gcgaaacagc cgaggccacc cggctgaaga gaaccgccag aagaagatac   2400
accagacgga gaaccggat ctgctatctg caagagatct tcagcaacga gatggccaag    2460
gtggacgaca gcttcttcca cagactggaa gagtccttcc tggtggaaga ggataagaag   2520
cacgagcggc accccatctt cggcaacatc gtggacgagg tggcctacca cgagaagtac   2580
cccaccatct accacctgag aaagaaactg gtggacagca ccgacaaggc cgacctgcgg   2640
ctgatctatc tggccctggc ccacatgatc aagttccggg gccacttcct gatcgagggc    2700
gacctgaacc ccgacaacag cgacgtggac aagctgttca tccagctggt gcagacctac    2760
aaccagctgt tcgaggaaaa ccccatcaac gccagcggcg tggacgccaa ggccatcctg   2820
tctgccagac tgagcaagag cagacggctg gaaaatctga tcgcccagct gccccggcgag  2880 aagaagaatg gcctgttcgg aaacctgatt gccctgagcc tgggcctgac ccccaacttc   2940
```

```
aagagcaact tcgacctggc cgaggatgcc aaactgcagc tgagcaagga cacctacgac    3000
gacgacctgg acaacctgct ggcccagatc ggcgaccagt acgccgacct gtttctggcc    3060
gccaagaacc tgtccgacgc catcctgctg agcgacatcc tgagagtgaa caccgagatc    3120
accaaggccc ccctgagcgc ctctatgatc aagagatacg acgagcacca ccaggacctg    3180
accctgctga agctctcgt gcggcagcag ctgcctgaga agtacaaaga gattttcttc    3240
gaccagagca agaacggcta cgccggctac attgacggcg agccagcca ggaagagttc    3300 tacaagttca tcaagcccat cctggaaaag atggacggca ccgaggaact gctcgtgaag    3360
ctgaacagag aggacctgct gcggaagcag cggaccttcg acaacggcag catccccac    3420 cagatccacc tgggagagct gcacgccatt ctgcggcggc aggaagattt ttacccattc    3480
ctgaaggaca accgggaaaa gatcgagaag atcctgacct tccgcatccc ctactacgtg    3540
ggccctctgg ccaggggaaa cagcagattc gcctggatga ccagaaagag cgaggaaacc    3600
atcaccccct ggaacttcga ggaagtggtg gacaagggcg cttccgccca gagcttcatc    3660
gagcggatga ccaacttcga taagaacctg cccaacgaga aggtgctgcc caagcacagc    3720
ctgctgtacg agtacttcac cgtgtataac gagctgacca agtgaaata cgtgaccgag    3780 ggaatgagaa agcccgcctt cctgagcggc agcagaaaa aggccatcgt ggacctgctg    3840
ttcaagacca accggaaagt gaccgtgaag cagctgaaag aggactactt caagaaaatc    3900
gagtgtctca gttatgacac cgaaatcctg acagtcgagt atggatttct gccgatcggc    3960
aagattgtgg aggagagaat tgaatgtacg gtctatacgg tcgacaagaa tggtttcgtc    4020
tacacccaac caattgctca atggcataat cgaggggagc aggaggtgtt tgagtattgc    4080
ctggaggacg ggtcaatcat tagagctaca aaggaccata agtttatgac aaccgatggt    4140
caaatgctgc cgatagatga aatattcgaa aggggactgg atcttaagca agtcgatggc    4200
cttccaaact agtagaattc ctagagctcg ctgatcagcc tcgactgtgc cttctagttg    4260
ccagccatct gttgtttgcc cctccccgt gccttccttg accctggaag gtgccactcc    4320
cactgtcctt tcctaataaa atgaggaaat tgcatcgcat tgtctgagta ggtgtcattc    4380
tattctgggg gtgggtgg ggcaggacag caaggggag gattgggaag agaatagcag    4440
gcatgctggg gaggtaccga gggcctattt cccatgattc cttcatattt gcatatacga    4500
tacaaggctg ttagagagat aattggaatt aatttgactg taaacacaaa gatattagta    4560
caaaatacgt gacgtagaaa gtaataattt cttgggtagt ttgcagttt aaaattatgt    4620 tttaaaatgg actatcatat gcttaccgta acttgaaagt atttcgattt cttggcttta    4680
tatatcttgt ggaaaggacg aaacaccggt tatctcctgt tctgcagcgt ttcagagcta    4740
tgctggaaac agcatagcaa gttgaaataa ggctagtccg ttatcaactt gaaaaagtgg    4800
caccgagtcg gtgctttttt gcggccgcag gaacccctag tgatggagtt ggccactccc    4860
tctctgcgcg ctcgctcgct cactgaggcc gggcgaccaa aggtcgcccg acgcccgggc    4920
tttgcccggg cggcctcagt gagcgagcga gcgcgcagct gcctgcaggg gcgcctgtac    4980
cgggagatgg gggaggctaa ctgaaacacg gaaggagaca ataccggaag gaacccgcgc    5040
tatgacggca ataaaaagac agaataaaac gcacgggtgt tgggtcgttt gttcataaac    5100
gcggggttcg gtcccagggc tggcactctg tcgataccc accgagaccc cattgggacc    5160
aatacgcccg cgtttcttcc ttttccccac cccaaccccc aagttcgggt gaaggcccag    5220
ggctcgcagc caacgtcggg gcggcaagcc ctgccatagc cactacgggt acgtaggcca    5280
accactagaa ctatagctag agtcctgggc gaacaaacga tgctcgcctt ccagaaaacc    5340
```

```
gaggatgcga accacttcat ccggggtcag caccaccggc aagcgccgcg acggccgagg    5400
tctaccgatc tcctgaagcc agggcagatc cgtgcacagc accttgccgt agaagaacag    5460
caaggccgcc aatgcctgac gatgcgtgga gaccgaaacc ttgcgctcgt tcgccagcca    5520
ggacagaaat gcctcgactt cgctgctgcc caaggttgcc gggtgacgca caccgtggaa    5580
acggatgaag gcacgaaccc agttgacata agcctgttcg gttcgtaaac tgtaatgcaa    5640
gtagcgtatg cgctcacgca actggtccag aaccttgacc gaacgcagcg gtggtaacgg    5700
cgcagtggcg gttttcatgg cttgttatga ctgtttttt gtacagtcta tgcctcgggc     5760
atccaagcag caagcgcgtt acgccgtggg tcgatgtttg atgttatgga gcagcaacga    5820
tgttacgcag cagcaacgat gttacgcagc agggcagtcg ccctaaaaca aagttaggtg    5880
gctcaagtat gggcatcatt cgcacatgta ggctcggccc tgaccaagtc aaatccatgc    5940
gggctgctct tgatcttttc ggtcgtgagt tcggagacgt agccacctac tcccaacatc    6000
agccggactc cgattacctc gggaacttgc tccgtagtaa gacattcatc gcgcttgctg    6060
ccttcgacca agaagcggtt gttggcgctc tcgcggctta cgttctgccc aggtttgagc    6120
agccgcgtag tgagatctat atctatgatc tcgcagtctc cggcgagcac cggaggcagg    6180
gcattgccac cgcgctcatc aatctcctca agcatgaggc caacgcgctt ggtgcttatg    6240
tgatctacgt gcaagcagat tacggtgacg atcccgcagt ggctctctat acaaagttgg    6300
gcatacggga agaagtgatg cactttgata tcgacccaag taccgccacc taacaattcg    6360
ttcaagccga gatcggcttc ccggccgcgg agttgttcgg taaattgtca caacgccgcg    6420
aatatagtct ttaccatgcc cttggccacg cccctcttta atacgacggg caatttgcac    6480
ttcagaaaat gaagagtttg ctttagccat aacaaaagtc cagtatgctt tttcacagca    6540
taactggact gatttcagtt tacaactatt ctgtctagtt taagacttta ttgtcatagt    6600
ttagatctat tttgttcagt ttaagacttt attgtccgcc cacacccgct tacgcagggc    6660
atccatttat tactcaaccg taaccgattt tgccaggtta cgcggctggt ctgcggtgtg    6720
aaataccgca cagatgcgta aggagaaaat accgcatcag gcgctcttcc gcttcctcgc    6780
tcactgactc gctgcgctcg gtcgttcggc tgcggcgagc ggtatcagct cactcaaagg    6840
cggtaatacg gttatccaca gaatcagggg ataacgcagg aaagaacatg tgagcaaaag    6900
gccagcaaaa ggccaggaac cgtaaaaagg ccgcgttgct ggcgtttttc cataggctcc    6960
gcccccctga cgagcatcac aaaaatcgac gctcaagtca gaggtggcga aacccgacag    7020
gactataaag ataccaggcg tttccccctg gaagctccct cgtgcgctct cctgttccga    7080
ccctgccgct taccggatac ctgtccgcct ttctcccttc gggaagcgtg gcgctttctc    7140
aatgctcacg ctgtaggtat ctcagttcgg tgtaggtcgt tcgctccaag ctgggctgtg    7200
tgcacgaacc ccccgttcag cccgaccgct gcgccttatc cggtaactat cgtcttgagt    7260
ccaacccggt aagacacgac ttatcgccac tggcagcagc cactggtaac aggattagca    7320
gagcgaggta tgtaggcggt gctacagagt tcttgaagtg gtggcctaac tacggctaca    7380
ctagaaggac agtatttggt atctgcgctc tgctgaagcc agttaccttc ggaaaaagag    7440
ttggtagctc ttgatccggc aaacaaacca ccgctggtag cggtggtttt tttgtttgca    7500
agcagcagat tacgcgcaga aaaaaggat ctcaagaaga tcctttgatc ttttctacgg     7560
ggtctgacgc tcagtggaac gaaaactcac gttaagggat tttggtcatg agattatcaa    7620
aaaggatctt cacctagatc cttttaaatt aaaaatgaag ttttaaatca atctaaagta    7680
```

```
tatatgagta aacttggtct gacagttacc aatgcttaat cagtgaggca cctatctcag    7740
cgatctgtct atttcgttca tccatagttg cctgactccc cgtcgtgtag ataactacga    7800
tacgggaggg cttaccatct ggccccagtg ctgcaatgat accgcgagac ccacgctcac    7860
cggctccaga tttatcagca ataaaccagc cagccggaag ggccgagcgc agaagtggtc    7920
ctgcaacttt atccgcctcc atccagtcta ttaattgttg ccgggaagct agagtaagta    7980
gttcgccagt taatagtttg cgcaacgttg ttgccattgc tacaggcatc gtggtgtcac    8040
gctcgtcgtt tggtatggct tcattcagct ccggttccca acgatcaagg cgagttacat    8100
gatccccat gttgtgcaaa aaagcggtta gctccttcgg tcctccgatc gttgtcagaa    8160
gtaagttggc cgcagtgtta tcactcatgg ttatggcagc actgcataat tctcttactg    8220
tcatgccatc cgtaagatgc ttttctgtga ctggtgagta ctcaaccaag tcattctgag    8280
aatagtgtat gcggcgaccg agttgctctt gcccggcgtc aatacgggat aataccgcgc    8340
cacatagcag aactttaaaa gtgctcatca ttggaaaacg ttcttcgggg cgaaaactct    8400
caaggatctt accgctgttg agatccagtt cgatgtaacc cactcgtgca cccaactgat    8460
cttcagcatc ttttactttc accagcgttt ctgggtgagc aaaaacagga aggcaaaatg    8520
ccgcaaaaaa gggaataagg gcgacacgga aatgttgaat actcatactc ttccttttc    8580
aatattattg aagcatttat cagggttatt gtctcatgag cggatacata tttgaatgta    8640
tttagaaaaa taaacaaata ggggttccgc gcacatttcc ccgaaaagtg ccacctgaaa    8700
ttgtaaacgt taatattttg ttaaaattcg cgttaaattt ttgttaaatc agctcatttt    8760
ttaaccaata ggccgaaatc ggcaaaatcc cttataaatc aaaagaatag accgagatag    8820
ggttgagtgt tgttccagtt tggaacaaga gtccactatt aaagaacgtg gactccaacg    8880
tcaaagggcg aaaaaccgtc tatcagggcg atggcccact acgtgaacca tcaccctaat    8940
caagttttt ggggtcgagg tgccgtaaag cactaaatcg gaaccctaaa gggagccccc    9000
gatttagagc ttgacgggga aagccggcga acgtggcgag aaaggaaggg aagaaagcga    9060
aaggagcggg cgctagggcg ctggcaagtg tagcggtcac gctgcgcgta accaccacac    9120
ccgccgcgct taatgcgccg ctacagggcg cgtcccattc gccattcagg ctgcaaataa    9180
gcgttgatat tcagtcaatt acaaacatta ataacgaaga gatgacagaa aaattttcat    9240
tctgtgacag agaa                                                      9254

<210> SEQ ID NO 4
<211> LENGTH: 8538
<212> TYPE: DNA
<213> ORGANISM: Artificial Sequence
<220> FEATURE:
<223> OTHER INFORMATION: Synthetic Construct

<400> SEQUENCE: 4
aaagtagccg aagatgacgg tttgtcacat ggagttggca ggatgtttga ttaaaaacat      60
aacaggaaga aaaatgcccc gctgtgggcg gacaaaatag ttgggaactg ggaggggtgg     120
aaatggagtt tttaaggatt atttagggaa gagtgacaaa atagatggga actgggtgta     180
gcgtcgtaag ctaatacgaa aattaaaaat gacaaaatag tttggaacta gatttcactt     240
atctggttcg gatctcctag gctcaagcag tgatcagatc cagacatgat aagatacatt     300
gatgagtttg gacaaaccac aactagaatg cagtgaaaaa aatgctttat ttgtgaaatt     360
tgtgatgcta ttgcttttat tgtaaccatt ataagctgca ataaacaagt taacaacaac     420
aattccatgt cctgcaggca gctgcgcgct cgctcgctca ctgaggccgc ccgggcgtcg     480
```

```
ggcgaccttt ggtcgcccgg cctcagtgag cgagcgagcg cgcagagagg gagtggccaa      540
ctccatcact aggggttcct gcggcctcta gactcgagcg cgtgatgaga gcagccacta      600
cgggtctagg ctgcccatgt aaggaggcaa ggcctgggga cacccgagat gcctggttat      660
aattaaccca gacatgtggc tgcccccccc ccccaacac ctgctgcctg ctaaaaataa       720
ccctgtccct ggtggccctg catgcccact cacggggatt tccaagtctc caccccattg      780
acgtcaatgg gagtttgttt tggcaccaaa atcaacggga cttTccaaaa tgtcgtaaca      840
actccgcccc attgacgcaa atgggcggta ggcgtgtacg gtgggaggtc tatataagca      900
gagctggttt agtgaaccgt cagatccgcc accatggtca agattatcag ccgcaaatcc      960
ttggggacac agaatgtata tgacatcggc gtggaaaagg atcacaattt tctgctgaag     1020
aatggtcttt tgcttccaa ttgcttcgac tccgtgaaaa tctccggcgt ggaagatcgg      1080
ttcaacgcct ccctgggcac ataccacgat ctgctgaaaa ttatcaagga caaggacttc     1140
ctggacaatg aggaaaacga ggacattctg gaagatatcg tgctgacccT gacactgttt     1200
gaggacagag agatgatcga ggaacggctg aaaacctatg cccacctgtt cgacgacaaa     1260
gtgatgaagc agctgaagcg gcggagatac accggctggg gcaggctgag ccggaagctg     1320
atcaacggca tccgggacaa gcagtccggc aagacaatcc tggatttcct gaagtccgac     1380
ggcttcgcca acagaaactt catgcagctg atccacgacg acagcctgac ctttaaagag     1440
gacatccaga agcccaggt gtccggccag ggcgatagcc tgcacgagca cattgccaat      1500
ctggccggca gccccgccat taagaagggc atcctgcaga cagtgaaggt ggtggacgag     1560
ctcgtgaaag tgatgggccg gcacaagccc gagaacatcg tgatcgaaat ggccagagag     1620
aaccagacca cccagaaggg acagaagaac agccgcgaga gaatgaagcg gatcgaagag     1680
ggcatcaaag agctgggcag ccagatcctg aaagaacacc ccgtggaaaa cacccagctg     1740
cagaacgaga gctgtacct gtactacctg cagaatgggc gggatatgta cgtggaccag     1800
gaactggaca tcaaccggct gtccgactac gatgtggacc atatcgtgcc tcagagcttT     1860
ctgaaggacg actccatcga caacaaggtg ctgaccagaa gcgacaagaa ccggggcaag     1920
agcgacaacg tgccctccga gaggtcgtg aagaagatga gaactactg gcggcagctg      1980 ctgaacgcca agctgattac ccagagaaag ttcgacaatc tgaccaaggc cgagagaggc     2040
ggcctgagcg aactggataa ggccggcttc atcaagagac agctggtgga aacccggcag     2100
atcacaaagc acgtggcaca gatcctggac tcccggatga acactaagta cgacgagaat     2160
gacaagctga tccgggaagt gaaagtgatc accctgaagt ccaagctggt gtccgatttc     2220
cggaaggatt tccagttta caaagtgcgc gagatcaaca actaccacca cgcccacgac     2280
gcctacctga acgccgtcgt gggaaccgcc ctgatcaaaa agtaccctaa gctggaaagc     2340
gagttcgtgt acggcgacta caaggtgtac gacgtgcgga agatgatcgc caagagcgag     2400
caggaaatcg gcaaggctac cgccaagtac ttcttctaca gcaacatcat gaacttTttc     2460
aagaccgaga ttaccctggc caacggcgag atccggaagc ggcctctgat cgagacaaac     2520
ggcgaaaccg gggagatcgt gtgggataag ggccgggatt ttgccaccgt gcggaaagtg     2580
ctgagcatgc cccaagtgaa tatcgtgaaa aagaccgagg tgcagacagg cggcttcagc     2640
aaagagtcta tccggcccaa gaggaacagc gataagctga tcgccagaaa gaaggactgg     2700 gacccctaaga agtacggcgg cttcgtcagc cccaccgtgg cctattctgt gctggtggtg     2760
gccaaagtgg aaaagggcaa gtccaagaaa ctgaagagtg tgaaagagct gctggggatc     2820
```

| | |
|---|---|
| accatcatgg aaagaagcag cttcgagaag aatcccatcg actttctgga agccaagggc | 2880 |
| tacaaagaag tgaaaaagga cctgatcatc aagctgccta agtactccct gttcgagctg | 2940 |
| gaaaacggcc ggaagagaat gctggcctct gcccgctttc tgcagaaggg aaacgaactg | 3000 |
| gccctgccct ccaaatatgt gaacttcctg tacctggcca gccactatga aagctgaag | 3060 |
| ggctccccg aggataatga gcagaaacag ctgtttgtgg aacagcacaa gcactacctg | 3120 |
| gacgagatca tcgagcagat cagcgagttc tccaagagag tgatcctggc cgacgctaat | 3180 |
| ctggacaaag tgctgtccgc ctacaacaag caccgggata gcccatcag agagcaggcc | 3240 |
| gagaatatca tccacctgtt taccctgacc aatctgggag cccctcgggc cttcaagtac | 3300 |
| tttgacacca ccatcgaccg gaaggtgtac cggagcacca agaggtgct ggacgccacc | 3360 |
| ctgatccacc agagcatcac cggcctgtac gagacacgga tcgacctgtc tcagctggga | 3420 |
| ggtgactctg gcggctcaaa aagaaccgcc gacggcagcg aattcgagcc caagaagaag | 3480 |
| aggaaagtct aactagtaga attcctagag ctcgctgatc agcctcgact gtgccttcta | 3540 |
| gttgccagcc atctgttgtt tgcccctccc ccgtgccttc cttgaccctg gaaggtgcca | 3600 |
| ctcccactgt cctttcctaa taaaatgagg aaattgcatc gcattgtctg agtaggtgtc | 3660 |
| attctattct ggggggtggg gtggggcagg acagcaaggg ggaggattgg gaagagaata | 3720 |
| gcaggcatgc tggggaggta ccgagggcct atttcccatg attccttcat atttgcatat | 3780 |
| acgatacaag gctgttagag agataattgg aattaatttg actgtaaaca caaagatatt | 3840 |
| agtacaaaat acgtgacgta gaaagtaata atttcttggg tagtttgcag ttttaaaatt | 3900 |
| atgtttaaa atggactatc atatgcttac cgtaacttga agtatttcg atttcttggc | 3960 |
| tttatatatc ttgtggaaag gacgaaacac cggttatctc ctgttctgca gcgtttcaga | 4020 |
| gctatgctgg aaacagcata gcaagttgaa ataaggctag tccgttatca acttgaaaaa | 4080 |
| gtggcaccga gtcggtgctt ttttgcggcc gcaggaaccc ctagtgatgg agttggccac | 4140 |
| tccctctctg cgcgctcgct cgctcactga ggccgggcga ccaaaggtcg cccgacgccc | 4200 |
| gggctttgcc cgggcggcct cagtgagcga gcgagcgcgc agctgcctgc aggggcgcct | 4260 |
| gtaccgggag atgggggagg ctaactgaaa cacggaagga caataccg gaaggaaccc | 4320 |
| gcgctatgac ggcaataaaa agacagaata aaacgcacgg gtgttgggtc gtttgttcat | 4380 |
| aaacgcgggg ttcggtccca gggctggcac tctgtcgata ccccaccgag accccattgg | 4440 |
| gaccaatacg cccgcgtttc ttccttttcc caccccaac cccaagttc gggtgaaggc | 4500 |
| ccagggctcg cagccaacgt cggggcggca agccctgcca tagccactac gggtacgtag | 4560 |
| gccaaccact agaactatag ctagagtcct gggcgaacaa acgatgctcg ccttccagaa | 4620 |
| aaccgaggat gcgaaccact tcatccgggg tcagcaccac cggcaagcgc cgcgacggcc | 4680 |
| gaggtctacc gatctcctga agccagggca gatccgtgca cagcaccttg ccgtagaaga | 4740 |
| acagcaaggc cgccaatgcc tgacgatgcg tggagaccga aaccttgcgc tcgttcgcca | 4800 |
| gccaggacag aaatgcctcg acttcgctgc tgcccaaggt tgccgggtga cgcacaccgt | 4860 |
| ggaaacggat gaaggcacga acccagttga cataagcctg ttcggttcgt aaactgtaat | 4920 |
| gcaagtagcg tatgcgctca cgcaactggt ccagaacctt gaccgaacgc agcggtggta | 4980 |
| acggcgcagt ggcggttttc atggcttgtt atgactgttt ttttgtacag tctatgcctc | 5040 |
| gggcatccaa gcagcaagcg cgttacgccg tgggtcgatg tttgatgtta tggagcagca | 5100 |
| acgatgttac gcagcagcaa cgatgttacg cagcagggca gtcgccctaa aacaaagtta | 5160 |
| ggtggctcaa gtatgggcat cattcgcaca tgtaggctcg gccctgacca agtcaaatcc | 5220 |

```
atgcgggctg ctcttgatct tttcggtcgt gagttcggag acgtagccac ctactcccaa    5280
catcagccgg actccgatta cctcgggaac ttgctccgta gtaagacatt catcgcgctt    5340
gctgccttcg accaagaagc ggttgttggc gctctcgcgg cttacgttct gcccaggttt    5400
gagcagccgc gtagtgagat ctatatctat gatctcgcag tctccggcga gcaccggagg    5460
cagggcattg ccaccgcgct catcaatctc ctcaagcatg aggccaacgc gcttggtgct    5520
tatgtgatct acgtgcaagc agattacggt gacgatcccg cagtggctct ctatacaaag    5580
ttgggcatac gggaagaagt gatgcacttt gatatcgacc caagtaccgc cacctaacaa    5640
ttcgttcaag ccgagatcgg cttcccggcc gcggagttgt tcggtaaatt gtcacaacgc    5700
cgcgaatata gtctttacca tgcccttggc cacgcccctc tttaatacga cgggcaattt    5760
gcacttcaga aaatgaagag tttgctttag ccataacaaa agtccagtat gcttttcac     5820 agcataactg gactgatttc agtttacaac tattctgtct agtttaagac tttattgtca    5880
tagtttagat ctattttgtt cagtttaaga ctttattgtc cgcccacacc cgcttacgca    5940
gggcatccat ttattactca accgtaaccg attttgccag gttacgcggc tggtctgcgg    6000
tgtgaaatac cgcacagatg cgtaaggaga aataccgca tcaggcgctc ttccgcttcc     6060
tcgctcactg actcgctgcg ctcggtcgtt cggctgcggc gagcggtatc agctcactca    6120
aaggcggtaa tacggttatc cacagaatca ggggataacg caggaaagaa catgtgagca    6180
aaaggccagc aaaaggccag gaaccgtaaa aaggccgcgt tgctggcgtt tttccatagg    6240
ctccgccccc ctgacgagca tcacaaaaat cgacgctcaa gtcagaggtg gcgaaacccg    6300
acaggactat aaagatacca ggcgtttccc cctggaagct ccctcgtgcg ctctcctgtt    6360
ccgaccctgc cgcttaccgg atacctgtcc gcctttctcc cttcgggaag cgtggcgctt    6420
tctcaatgct cacgctgtag gtatctcagt tcggtgtagg tcgttcgctc caagctgggc    6480
tgtgtgcacg aaccccccgt tcagcccgac cgctgcgcct tatccggtaa ctatcgtctt    6540
gagtccaacc cggtaagaca cgacttatcg ccactggcag cagccactgg taacaggatt    6600
agcagagcga ggtatgtagg cggtgctaca gagttcttga agtggtggcc taactacggc    6660
tacactagaa ggacagtatt tggtatctgc gctctgctga gccagttac cttcggaaaa     6720 agagttggta gctcttgatc cggcaaacaa accaccgctg gtagcggtgg ttttttgtt     6780 tgcaagcagc agattacgcg cagaaaaaaa ggatctcaag aagatccttt gatcttttct    6840
acggggtctg acgctcagtg gaacgaaaac tcacgttaag ggattttggt catgagatta    6900
tcaaaaagga tcttcaccta gatccttttta aattaaaaat gaagttttaa atcaatctaa    6960
agtatatatg agtaaacttg gtctgacagt taccaatgct taatcagtga ggcacctatc    7020
tcagcgatct gtctatttcg ttcatccata gttgcctgac tccccgtcgt gtagataact    7080
acgatacggg agggcttacc atctggcccc agtgctgcaa tgataccgcg agacccacgc    7140
tcaccggctc cagatttatc agcaataaac cagccagccg aagggccga gcgcagaagt    7200 ggtcctgcaa ctttatccgc ctccatccag tctattaatt gttgccggga agctagagta    7260
agtagttcgc cagttaatag tttgcgcaac gttgttgcca ttgctacagg catcgtggtg    7320
tcacgctcgt cgtttggtat ggcttcattc agctccggtt cccaacgatc aaggcgagtt    7380
acatgatccc ccatgttgtg caaaaaagcg gttagctcct tcggtcctcc gatcgttgtc    7440
agaagtaagt tggccgcagt gttatcactc atggttatgg cagcactgca taattctctt    7500
actgtcatgc catccgtaag atgcttttct gtgactggtg agtactcaac caagtcattc    7560
```

| | |
|---|---|
| tgagaatagt gtatgcggcg accgagttgc tcttgcccgg cgtcaatacg ggataatacc | 7620 |
| gcgccacata gcagaacttt aaaagtgctc atcattggaa aacgttcttc ggggcgaaaa | 7680 |
| ctctcaagga tcttaccgct gttgagatcc agttcgatgt aacccactcg tgcacccaac | 7740 |
| tgatcttcag catcttttac tttcaccagc gtttctgggt gagcaaaaac aggaaggcaa | 7800 |
| aatgccgcaa aaagggaat aagggcgaca cggaaatgtt gaatactcat actcttcctt | 7860 |
| tttcaatatt attgaagcat ttatcagggt tattgtctca tgagcggata catatttgaa | 7920 |
| tgtatttaga aaaataaaca aataggggtt ccgcgcacat ttccccgaaa agtgccacct | 7980 |
| gaaattgtaa acgttaatat tttgttaaaa ttcgcgttaa attttgtta aatcagctca | 8040 |
| ttttttaacc aataggccga atcggcaaa atcccttata aatcaaaaga atagaccgag | 8100 |
| atagggttga gtgttgttcc agtttggaac aagagtccac tattaaagaa cgtggactcc | 8160 |
| aacgtcaaag ggcgaaaaac cgtctatcag ggcgatggcc cactacgtga accatcaccc | 8220 |
| taatcaagtt ttttggggtc gaggtgccgt aaagcactaa atcggaaccc taaagggagc | 8280 |
| ccccgattta gagcttgacg gggaaagccg gcgaacgtgg cgagaaagga agggaagaaa | 8340 |
| gcgaaaggag cgggcgctag ggcgctggca agtgtagcgg tcacgctgcg cgtaaccacc | 8400 |
| acacccgccg cgcttaatgc gccgctacag ggcgcgtccc attcgccatt caggctgcaa | 8460 |
| ataagcgttg atattcagtc aattacaaac attaataacg aagagatgac agaaaaattt | 8520 |
| tcattctgtg acagagaa | 8538 |

<210> SEQ ID NO 5
<211> LENGTH: 7098
<212> TYPE: DNA
<213> ORGANISM: Artificial Sequence
<220> FEATURE:
<223> OTHER INFORMATION: Synthetic Construct

<400> SEQUENCE: 5

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggcctcta gactcgagcg cgtgatgaga gcagccacta cgggtctagg | 180 |
| ctgcccatgt aaggaggcaa ggcctgggga cacccgagat gcctggttat aattaaccca | 240 |
| gacatgtggc tgcccccccc ccccaacac ctgctgcctg ctaaaaataa ccctgtccct | 300 |
| ggtggccctg catgcccact cacggggatt tccaagtctc caccccattg acgtcaatgg | 360 |
| gagtttgttt tggcaccaaa atcaacggga ctttccaaaa tgtcgtaaca actccgcccc | 420 |
| attgacgcaa atgggcggta ggcgtgtacg gtgggaggtc tatataagca gagctggttt | 480 |
| agtgaaccgt cagatccgcc accatggcta gcatgaaacg gacagccgac ggaagcgagt | 540 |
| tcgagtcacc aaagaagaag cggaaagtct ctgaagtcga gtttagccac gagtattgga | 600 |
| tgaggcacgc actgacccctg gcaaagcgag catgggatga agagaagtc cccgtgggcg | 660 |
| ccgtgctggt gcacaacaat agagtgatcg gagagggatg gaacaggcca atcggccgcc | 720 |
| acgaccctac cgcacacgca gagatcatgg cactgaggca gggaggcctg gtcatgcaga | 780 |
| attaccgcct gatcgatgcc accctgtatg tgacactgga gccatgcgtg atgtgcgcag | 840 |
| gagcaatgat ccacagcagg atcggaagag tggtgttcgg agcacgggac gccaagaccg | 900 |
| gcgcagcagg ctccctgatg gatgtgctgc accaccccgg catgaaccac cgggtggaga | 960 |
| tcacagaggg aatcctggca gacgagtgcg ccgccctgct gagcgatttc tttagaatgc | 1020 |
| ggagacagga gatcaaggcc cagaagaagg cacagagctc caccgactct ggaggatcta | 1080 |

-continued

```
gcggaggatc ctctggaagc gagacaccag gcacaagcga gtccgccaca ccagagagct    1140
ccggcggctc ctccggagga tcctctgagg tggagttttc ccacgagtac tggatgagac    1200
atgccctgac cctggccaag agggcacgcg atgagaggga ggtgcctgtg ggagccgtgc    1260
tggtgctgaa caatagagtg atcggcgagg gctggaacag agccatcggc ctgcacgacc    1320
caacagccca tgccgaaatt atggccctga cagggcgg cctggtcatg cagaactaca    1380
gactgattga cgccacccctg tacgtgacat tcgagccttg cgtgatgtgc gccggcgcca    1440
tgatccactc taggatcggc cgcgtggtgt ttggcgtgag gaacgcaaaa accggcgccg    1500
caggctccct gatggacgtg ctgcactacc ccggcatgaa tcaccgcgtc gaaattaccg    1560
agggaatcct ggcagatgaa tgtgccgccc tgctgtgcta tttctttcgg atgcctagac    1620
aggtgttcaa tgctcagaag aaggcccaga gctccaccga ctccggagga tctagcggag    1680
gctcctctgg ctctgagaca cctggcacaa gcgagagcgc aacacctgaa agcagcgggg    1740
gcagcagcgg ggggtcagac aagaagtaca gcatcggcct ggccatcggc accaactctg    1800
tgggctgggc cgtgatcacc gacgagtaca aggtgcccag caagaaattc aaggtgctgg    1860
gcaacaccga ccggcacagc atcaagaaga acctgatcgg agccctgctg ttcgacagcg    1920
gcgaaacagc cgaggccacc cggctgaaga gaaccgccag aagaagatac accagacgga    1980
agaaccggat ctgctatctg caagagatct tcagcaacga gatggccaag gtggacgaca    2040
gcttcttcca cagactggaa gagtccttcc tggtggaaga ggataagaag cacgagcggc    2100
accccatctt cggcaacatc gtggacgagg tggcctacca cgagaagtac cccaccatct    2160
accacctgag aaagaaactg gtggacagca ccgacaaggc cgacctgcgg ctgatctatc    2220
tggccctggc ccacatgatc aagttccggg gccacttcct gatcgagggc gacctgaacc    2280
ccgacaacag cgacgtggac aagctgttca tccagctggt gcagacctac aaccagctgt    2340
tcgaggaaaa ccccatcaac gccagcggcg tggacgccaa ggccatcctg tctgccagac    2400
tgagcaagag cagacggctg gaaaatctga tcgcccagct gcccggcgag aagaagaatg    2460
gcctgttcgg aaacctgatt gccctgagcc tgggcctgac ccccaacttc aagagcaact    2520
tcgacctggc cgaggatgcc aaactgcagc tgagcaagga cacctacgac gacgacctgg    2580
acaacctgct ggcccagatc ggcgaccagt acgccgacct gtttctggcc gccaagaacc    2640
tgtccgacgc catcctgctg agcgacatcc tgagagtgaa caccgagatc accaaggccc    2700
ccctgagcgc ctctatgatc aagagatacg acgagcacca ccaggacctg accctgctga    2760
aagctctcgt gcggcagcag ctgcctgaga agtacaaaga gatttttctt gaccagagca    2820
agaacggcta cgccggctac attgacggcg gagccagcca ggaagagttc tacaagttca    2880
tcaagcccat cctggaaaag atggacggca ccgaggaact gctcgtgaag ctgaacagag    2940
aggacctgct gcggaagcag cggaccttcg acaacggcag catcccccac cagatccacc    3000
tgggagagct gcacgccatt ctgcggcggc aggaagattt ttacccattc ctgaaggaca    3060
accgggaaaa gatcgagaag atcctgacct tccgcatccc ctactacgtg ggccctctgg    3120
ccaggggaaa cagcagattc gcctggatga ccagaaagag cgaggaaacc atcacccct    3180 ggaacttcga ggaagtggtg gacaagggcg cttccgccca gagcttcatc gagcggatga    3240
ccaacttcga taagaacctg cccaacgaga aggtgctgcc caagcacagc ctgctgtacg    3300
agtacttcac cgtgtataac gagctgacca aagtgaaata cgtgaccgag ggaatgagaa    3360
agcccgcctt cctgagcggc gagcagaaaa aggccatcgt ggacctgctg ttcaagacca    3420
```

```
accggaaagt gaccgtgaag cagctgaaag aggactactt caagaaaatc gagtgtttgg   3480
atctgaaaac gcaagttcaa acgccacagg gtatgaaaga aatatccaat atacaggtcg   3540
gcgatctcgt cttgtctaac actggctata acgaggtgct gaatgtattt ccaaaaagca   3600
agaaaaaaag ttacaagata actctggaag atggaaaaga aattatctgt tctgaggagc   3660
atctgtttcc gacccaaaca ggggagatga atatcagtgg cggtctcaaa gagggtatgt   3720
gtttgtatgt caaggaataa ctagtagaat tcctagagct cgctgatcag cctcgactgt   3780
gccttctagt tgccagccat ctgttgtttg cccctccccc gtgccttcct tgaccctgga   3840
aggtgccact cccactgtcc tttcctaata aaatgaggaa attgcatcgc attgtctgag   3900
taggtgtcat tctattctgg ggggtggggt ggggcaggac agcaaggggg aggattggga   3960
agagaatagc aggcatgctg gggaggtacc gagggcctat ttcccatgat tccttcatat   4020
ttgcatatac gatacaaggc tgttagagag ataattggaa ttaatttgac tgtaaacaca   4080
aagatattag tacaaaatac gtgacgtaga agtaataat ttcttgggta gtttgcagtt    4140
ttaaaattat gttttaaaat ggactatcat atgcttaccg taacttgaaa gtatttcgat   4200
ttcttggctt tatatatctt gtggaaagga cgaaacaccg ttatctcct gttctgcagc    4260
gtttcagagc tatgctggaa acagcatagc aagttgaaat aaggctagtc cgttatcaac   4320
ttgaaaagt ggcaccgagt cggtgctttt tgcggccgc aggaacccct agtgatggag     4380
ttggccactc cctctctgcg cgctcgctcg ctcactgagg ccgggcgacc aaaggtcgcc   4440
cgacgcccgg gctttgcccg gcgcctca gtgagcgagc gagcgcgcag ctgcctgcag      4500
gggcgcctga tgcggtattt tctccttacg catctgtgcg gtatttcaca ccgcatacgt   4560
caaagcaacc atagtacgcg ccctgtagcg gcgcattaag cgcggcgggt gtggtggtta   4620
cgcgcagcgt gaccgctaca cttgccagcg ccctagcgcc cgctcctttc gctttcttcc   4680
cttcctttct cgccacgttc gccggctttc cccgtcaagc tctaaatcgg gggctccctt   4740
tagggttccg atttagtgct ttacggcacc tcgaccccaa aaaacttgat ttgggtgatg   4800
gttcacgtag tgggccatcg ccctgataga cggtttttcg ccctttgacg ttggagtcca   4860
cgttctttaa tagtggactc ttgttccaaa ctggaacaac actcaaccct atctcgggct   4920
attcttttga tttataaggg attttgccga tttcggccta ttggttaaaa atgagctga    4980
tttaacaaaa atttaacgcg aattttaaca aaatattaac gtttacaatt ttatggtgca   5040
ctctcagtac aatctgctct gatgccgcat agttaagcca gccccgacac ccgccaacac   5100
ccgctgacgc gccctgacgg gcttgtctgc tcccggcatc cgcttacaga caagctgtga   5160
ccgtctccgg gagctgcatg tgtcagaggt tttcaccgtc atcaccgaaa cgcgcgagac   5220
gaaagggcct cgtgatacgc ctatttttat aggttaatgt catgataata atggtttctt   5280
agacgtcagg tggcacttt cggggaaatg tgcgcggaac ccctatttgt ttatttttct    5340
aaatacattc aaatatgtat ccgctcatga caataaacc ctgataaatg cttcaataat    5400
attgaaaaag gaagagtatg agtattcaac atttccgtgt cgcccttatt ccctttttttg   5460
cggcattttg ccttcctgtt tttgctcacc cagaaacgct ggtgaaagta aaagatgctg   5520
aagatcagtt gggtgcacga gtgggttaca tcgaactgga tctcaacagc ggtaagatcc   5580
ttgagagttt tcgccccgaa gaacgttttc caatgatgag cacttttaaa gttctgctat   5640
gtggcgcggt attatcccgt attgacgccg ggcaagagca actcggtcgc cgcatacact   5700
attctcagaa tgacttggtt gagtactcac cagtcacaga aaagcatctt acggatggca   5760
tgacagtaag agaattatgc agtgctgcca taaccatgag tgataacact gcggccaact   5820
```

```
tacttctgac aacgatcgga ggaccgaagg agctaaccgc ttttttgcac aacatggggg    5880
atcatgtaac tcgccttgat cgttgggaac cggagctgaa tgaagccata ccaaacgacg    5940
agcgtgacac cacgatgcct gtagcaatgg caacaacgtt gcgcaaacta ttaactggcg    6000
aactacttac tctagcttcc cggcaacaat taatagactg gatggaggcg ataaagttg     6060 caggaccact tctgcgctcg gcccttccgg ctggctggtt tattgctgat aaatctggag    6120
ccggtgagcg tggaagccgc ggtatcattg cagcactggg gccagatggt aagccctccc    6180
gtatcgtagt tatctacacg acggggagtc aggcaactat ggatgaacga aatagacaga    6240
tcgctgagat aggtgcctca ctgattaagc attggtaact gtcagaccaa gtttactcat    6300
atatacttta gattgattta aaacttcatt tttaatttaa aaggatctag gtgaagatcc    6360
tttttgataa tctcatgacc aaaatccctt aacgtgagtt ttcgttccac tgagcgtcag    6420
accccgtaga aagatcaaa ggatcttctt gagatccttt tttctgcgc gtaatctgct      6480 gcttgcaaac aaaaaaacca ccgctaccag cggtggtttg tttgccggat caagagctac    6540
caactctttt tccgaaggta actggcttca gcagagcgca gataccaaat actgtccttc    6600
tagtgtagcc gtagttaggc caccacttca agaactctgt agcaccgcct acatacctcg    6660
ctctgctaat cctgttacca gtggctgctg ccagtggcga taagtcgtgt cttaccgggt    6720
tggactcaag acgatagtta ccggataagg cgcagcggtc gggctgaacg ggggttcgt     6780 gcacacagcc cagcttggag cgaacgacct acaccgaact gagatacctá cagcgtgagc    6840 tatgagaaag cgccacgctt cccgaaggga gaaaggcgga caggtatccg gtaagcggca    6900
gggtcggaac aggagagcgc acgagggagc ttccaggggg aaacgcctgg tatctttata    6960
gtcctgtcgg gtttcgccac ctctgacttg agcgtcgatt tttgtgatgc tcgtcagggg    7020
ggcggagcct atggaaaaac gccagcaacg cggccttttt acggttcctg gccttttgct    7080
ggccttttgc tcacatgt                                                  7098
```

<210> SEQ ID NO 6
<211> LENGTH: 6441
<212> TYPE: DNA
<213> ORGANISM: Artificial Sequence
<220> FEATURE:
<223> OTHER INFORMATION: Synthetic Construct

<400> SEQUENCE: 6

```
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact    120
aggggttcct gcggcctcta gactcgagcg cgtgatgaga gcagccacta cgggtctagg    180
ctgcccatgt aaggaggcaa ggcctgggga caccgagat gctggttat aattaaccca      240 gacatgtggc tgcccccccc ccccaacac ctgctgcctg ctaaaaataa ccctgtccct     300 ggtgccctg catgcccact cacggggatt ccaagtctc cacccattg acgtcaatgg       360 gagtttgttt tggcaccaaa atcaacggga cttttccaaaa tgtcgtaaca actccgcccc  420
attgacgcaa atgggcggta ggcgtgtacg gtgggaggtc tatataagca gagctggttt   480
agtgaaccgt cagatcgcta gccaccatga tgctcaagaa gatcctcaag attgaagagt  540
tggacgagcg cgagcttata gacatagaag tcagtggtaa tcacctttttc tacgcaaatg 600 acattttgac tcacaactcc tcttcagacg tttgcttcga ctccgtggaa atctccggcg 660
tggaagatcg gttcaacgcc tccctgggca cataccacga tctgctgaaa attatcaagg 720
```

```
acaaggactt cctggacaat gaggaaaacg aggacattct ggaagatatc gtgctgaccc    780
tgacactgtt tgaggacaga gagatgatcg aggaacggct gaaaacctat gcccacctgt    840
tcgacgacaa agtgatgaag cagctgaagc ggcggagata caccggctgg ggcaggctga    900
gccggaagct gatcaacggc atccgggaca agcagtccgg caagacaatc ctggatttcc    960
tgaagtccga cggcttcgcc aacagaaact tcatgcagct gatccacgac gacagcctga   1020
cctttaaaga ggacatccag aaagcccagg tgtccggcca gggcgatagc ctgcacgagc   1080
acattgccaa tctggccggc agccccgcca ttaagaaggg catcctgcag acagtgaagg   1140
tggtggacga gctcgtgaaa gtgatgggcc ggcacaagcc cgagaacatc gtgatcgaaa   1200
tggccagaga gaaccagacc acccagaagg acagaagaa cagccgcgag agaatgaagc    1260
ggatcgaaga gggcatcaaa gagctgggca gccagatcct gaaagaacac cccgtggaaa   1320
acacccagct gcagaacgag aagctgtacc tgtactacct gcagaatggg cgggatatgt   1380
acgtggacca ggaactggac atcaaccggc tgtccgacta cgatgtggac catatcgtgc   1440
ctcagagctt tctgaaggac gactccatcg acaacaaggt gctgaccaga gcgacaaga   1500 accggggcaa gagcgacaac gtgccctccg aagaggtcgt gaagaagatg aagaactact   1560
ggcggcagct gctgaacgcc aagctgatta cccagagaaa gttcgacaat ctgaccaagg   1620
ccgagagagg cggcctgagc gaactggata aggccggctt catcaagaga cagctggtgg   1680
aaacccggca gatcacaaag cacgtggcac agatcctgga ctcccggatg aacactaagt   1740
acgacgagaa tgacaagctg atccgggaag tgaaagtgat caccctgaag tccaagctgg   1800
tgtccgattt ccgaaggat ttccagtttt acaaagtgcg cgagatcaac aactaccacc    1860
acgcccacga cgcctacctg aacgccgtcg tgggaaccgc cctgatcaaa agtaccccta   1920
agctggaaag cgagttcgtg tacggcgact acaaggtgta cgacgtgcgg aagatgatcg   1980
ccaagagcga gcaggaaatc ggcaaggcta ccgccaagta cttcttctac agcaacatca   2040 tgaactttt caagaccgag attaccctgg ccaacggcga gatccggaag cggcctctga   2100
tcgagacaaa cggcgaaacc ggggagatcg tgtgggataa gggccgggat tttgccaccg   2160
tgcggaaagt gctgagcatg ccccaagtga atatcgtgaa aaagaccgag gtgcagacag   2220
gcggcttcag caaagagtct atccggccca agaggaacag cgataagctg atcgccagaa   2280
agaaggactg ggaccctaag aagtacggcg gcttcgtcag ccccaccgtg gcctattctg   2340
tgctggtggt ggccaaagtg gaaaagggca gtccaagaa actgaagagt gtgaaagagc    2400
tgctggggat caccatcatg gaaagaagca gcttcgagaa gaatcccatc gactttctgg   2460
aagccaaggg ctacaaagaa gtgaaaaagg acctgatcat caagctgcct aagtactccc   2520
tgttcgagct ggaaaacggc cggaagagaa tgctggcctc tgcccgcttt ctgcagaagg   2580
gaaacgaact ggccctgccc tccaaatatg tgaacttcct gtacctggcc agccactatg   2640
agaagctgaa gggctccccc gaggataatg agcagaaaca gctgtttgtg gaacagcaca   2700
agcactacct ggacgagatc atcgagcaga tcagcgagtt ctccaagaga gtgatcctgg   2760
ccgacgctaa tctggacaaa gtgctgtccg cctacaacaa gcaccgggat aagcccatca   2820
gagagcaggc cgagaatatc atccacctgt ttacccctga caatctggga gcccctcggg   2880
ccttcaagta ctttgacacc accatcgacc ggaaggtgta ccggagcacc aaagaggtgc   2940
tggacgccac cctgatccac cagagcatca ccggcctgta cgagacacgg atcgacctgt   3000
ctcagctggg aggtgactct ggcggctcaa aaagaaccgc cgacgcagc gaattcgagc    3060 ccaagaagaa gaggaaagtc taactagtag aattcctaga gctcgctgat cagcctcgac   3120
```

```
tgtgccttct agttgccagc catctgttgt ttgcccctcc cccgtgcctt ccttgaccct    3180
ggaaggtgcc actcccactg tcctttccta ataaaatgag gaaattgcat cgcattgtct    3240
gagtaggtgt cattctattc tggggggtgg ggtggggcag gacagcaagg gggaggattg    3300
ggaagagaat agcaggcatg ctggggaggt accgagggcc tatttcccat gattccttca    3360
tatttgcata tacgatacaa ggctgttaga gagataattg gaattaattt gactgtaaac    3420
acaaagatat tagtacaaaa tacgtgacgt agaaagtaat aatttcttgg gtagtttgca    3480
gttttaaaat tatgttttaa aatggactat catatgctta ccgtaacttg aaagtatttc    3540
gatttcttgg ctttatatat cttgtggaaa ggacgaaaca ccggttatct cctgttctgc    3600
agcgtttcag agctatgctg gaaacagcat agcaagttga ataaggcta gtccgttatc    3660 aacttgaaaa agtggcaccg agtcggtgct tttttgcggc cgcaggaacc cctagtgatg    3720
gagttggcca ctccctctct gcgcgctcgc tcgctcactg aggccgggcg accaaaggtc    3780
gcccgacgcc cgggctttgc ccgggcggcc tcagtgagcg agcgagcgcg cagctgcctg    3840
caggggcgcc tgatgcggta ttttctcctt acgcatctgt gcggtatttc acaccgcata    3900
cgtcaaagca accatagtac gcgccctgta gcggcgcatt aagcgcggcg ggtgtggtgg    3960
ttacgcgcag cgtgaccgct acacttgcca gcgccctagc gcccgctcct ttcgctttct    4020
tcccttcctt tctcgccacg ttcgccggct ttccccgtca gctctaaat cggggctcc    4080 ctttagggtt ccgatttagt gctttacggc acctcgaccc caaaaaactt gatttgggtg    4140
atggttcacg tagtgggcca tcgccctgat agacggtttt tcgccctttg acgttggagt    4200
ccacgttctt taatagtgga ctcttgttcc aaactggaac aacactcaac cctatctcgg    4260
gctattcttt tgatttataa gggattttgc cgatttcggc ctattggtta aaaaatgagc    4320
tgatttaaca aaaatttaac gcgaatttta acaaaatatt aacgtttaca attttatggt    4380
gcactctcag tacaatctgc tctgatgccg catagttaag ccagcccga cacccgccaa    4440 cacccgctga cgcgccctga cgggcttgtc tgctcccggc atccgcttac agacaagctg    4500
tgaccgtctc cgggagctgc atgtgtcaga ggttttcacc gtcatcaccg aaacgcgcga    4560
gacgaaaggg cctcgtgata cgcctatttt tataggttaa tgtcatgata ataatggttt    4620
cttagacgtc aggtggcact tttcggggaa atgtgcgcgg aacccctatt tgtttatttt    4680
tctaaataca ttcaaatatg tatccgctca tgagacaata accctgataa atgcttcaat    4740
aatattgaaa aaggaagagt atgagtattc aacatttccg tgtcgccctt attcccttt    4800 ttgcggcatt ttgccttcct gtttttgctc acccagaaac gctggtgaaa gtaaagatg    4860 ctgaagatca gttgggtgca cgagtgggtt acatcgaact ggatctcaac agcggtaaga    4920
tccttgagag ttttcgcccc gaagaacgtt ttccaatgat gagcactttt aaagttctgc    4980
tatgtggcgc ggtattatcc cgtattgacg ccgggcaaga gcaactcggt cgccgcatac    5040
actattctca gaatgacttg gttgagtact caccagtcac agaaaagcat cttacgatg    5100 gcatgacagt aagagaatta tgcagtgctg ccataaccat gagtgataac actgcggcca    5160
acttacttct gacaacgatc ggaggaccga aggagctaac cgcttttttg cacaacatgg    5220
gggatcatgt aactcgcctt gatcgttggg aaccggagct gaatgaagcc ataccaaacg    5280
acgagcgtga caccacgatg cctgtagcaa tggcaacaac gttgcgcaaa ctattaactg    5340
gcgaactact tactctagct tcccggcaac aattaataga ctggatggag gcggataaag    5400
ttgcaggacc acttctgcgc tcggcccttc cggctggctg gtttattgct gataaatctg    5460
```

| | |
|---|---|
| gagccggtga gcgtggaagc cgcggtatca ttgcagcact ggggccagat ggtaagccct | 5520 |
| cccgtatcgt agttatctac acgacgggga gtcaggcaac tatggatgaa cgaaatagac | 5580 |
| agatcgctga gataggtgcc tcactgatta agcattggta actgtcagac caagtttact | 5640 |
| catatatact ttagattgat ttaaaacttc attttttaatt taaaaggatc taggtgaaga | 5700 |
| tcctttttga taatctcatg accaaaatcc cttaacgtga gttttcgttc cactgagcgt | 5760 |
| cagaccccgt agaaaagatc aaaggatctt cttgagatcc ttttttttctg cgcgtaatct | 5820 |
| gctgcttgca acaaaaaaa ccaccgctac cagcggtggt ttgtttgccg gatcaagagc | 5880 |
| taccaactct ttttccgaag gtaactggct tcagcagagc gcagatacca atactgtcc | 5940 |
| ttctagtgta gccgtagtta ggccaccact tcaagaactc tgtagcaccg cctacatacc | 6000 |
| tcgctctgct aatcctgtta ccagtggctg ctgccagtgg cgataagtcg tgtcttaccg | 6060 |
| ggttggactc aagacgatag ttaccggata aggcgcagcg gtcgggctga acggggggtt | 6120 |
| cgtgcacaca gcccagcttg gagcgaacga cctacaccga actgagatac ctacagcgtg | 6180 |
| agctatgaga aagcgccacg cttcccgaag ggagaaaggc ggacaggtat ccggtaagcg | 6240 |
| gcagggtcgg aacaggagag cgcacgaggg agcttccagg gggaaacgcc tggtatcttt | 6300 |
| atagtcctgt cgggtttcgc cacctctgac ttgagcgtcg atttttgtga tgctcgtcag | 6360 |
| ggggggcggag cctatggaaa aacgccagca acgcggcctt tttacggttc ctggccttt | 6420 |
| gctggccttt tgctcacatg t | 6441 |

<210> SEQ ID NO 7
<211> LENGTH: 6644
<212> TYPE: DNA
<213> ORGANISM: Artificial Sequence
<220> FEATURE:
<223> OTHER INFORMATION: Synthetic Construct

<400> SEQUENCE: 7

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggcctcta gactcgaggc ccttcagatt aaaaataact gaggtaaggg | 180 |
| cctgggtagg ggaggtggtg tgagacgctc ctgtctctcc tctatctgcc catcggccct | 240 |
| ttggggagga ggaatgtgcc caaggactaa aaaaaggcca tggagccaga ggggcgaggg | 300 |
| caacagacct ttcatgggca aaccttgggg ccctgctgac tgtagatgag agcagccact | 360 |
| acgggtctag gctgcccatg taaggaggca aggcctgggg acacccgaga tgcctggtta | 420 |
| taattaaccc agacatgtgg ctgcccccccc ccccccaaca cctgctgcct gctaaaaata | 480 |
| accctgtccc tggtggccct gcatgccctc cctggggaca gccctcctg gctagtcaca | 540 |
| ccctgtaggc tcctctatat aacccagggg cacaggggct gccctcattc taccaccacc | 600 |
| tccacagcac agacagacac tcaggagcca gcccaccatg gctagcatga acgacagc | 660 |
| cgacggaagc gagttcgagt caccaaagaa gaagcggaaa gtcggatcct ctgaggtgga | 720 |
| gttttcccac gagtactgga tgagacatgc cctgaccctg gccaagaggg cacgcgatga | 780 |
| gagggaggtg cctgtgggag ccgtgctggt gctgaacaat agagtgatcg gcgagggctg | 840 |
| gaacagagcc atcggcctgc acgacccaac aggccatgcc gaattatgg ccctgaggca | 900 |
| gggcggcctg gtcatgcaga actacagact gattgacgcc accctgtacg ggacattcga | 960 |
| gccttgcgta atgtgcgccg cgccatgat ccactctagg atcggccgcg tggtgtttgg | 1020 |
| cgtgaggaac gcaaaaaccg cgccgcagg ctccctgatg gacgtgctgc actaccccgg | 1080 |

```
catgaatcac cgcgtcgaaa ttaccgaggg aatcctggca gatgaatgtg ccgccctgct    1140
gtgctatttc tttcggatgc ctagacaggt gttcaatgct cagaagaagg cccagagctc    1200
caccgactcc ggaggatcta gcggaggctc ctctggctct gagacacctg cacaagcga     1260 gagcgcaaca cctgaaagca gcgggggcag cagcggggg tcagacaaga agtacagcat    1320
cggcctggcc atcggcacca actctgtggg ctgggccgtg atcaccgacg agtacaaggt    1380
gcccagcaag aaattcaagg tgctgggcaa caccgaccgg cacagcatca agaagaacct    1440
gatcggagcc ctgctgttcg acagcggcga acagccgag gccacccggc tgaagagaac    1500
cgccagaaga agatacacca gacgaagaa ccggatctgc tatctgcaag agatcttcag    1560
caacgagatg gccaaggtgg acgacagctt cttccacaga ctggaagagt ccttcctggt    1620
ggaagaggat aagaagcacg agcggcaccc catcttcggc aacatcgtgg acgaggtggc    1680
ctaccacgag aagtacccca ccatctacca cctgagaaag aaactggtgg acagcaccga    1740
caaggccgac ctgcggctga tctatctggc cctggcccac atgatcaagt ccggggcca    1800 cttcctgatc gagggcgacc tgaaccccga caacagcgac gtggacaagc tgttcatcca    1860
gctggtgcag acctcaaacc agctgttcga ggaaaacccc atcaacgcca gcggcgtgga    1920
cgccaaggcc atcctgtctg ccagactgag caagagcaga cggctggaaa tctgatcgc    1980 ccagctgccc ggcgagaaga gaatggcct gttcggaaac ctgattgccc tgagcctggg    2040
cctgaccccc aacttcaaga gcaacttcga cctggccgag gatgccaaac tgcagctgag    2100
caaggacacc tacgacgacg acctggacaa cctgctggcc cagatcggcg accagtacgc    2160
cgacctgttt ctggccgcca agaacctgtc cgacgccatc ctgctgagcg acatcctgag    2220
agtgaacacc gagatcacca aggcccccct gagcgcctct atgatcaaga gatacgacga    2280
gcaccaccag gacctgaccc tgctgaaagc tctcgtgcgg cagcagctgc ctgagaagta    2340
caaagagatt ttcttcgacc agagcaagaa cggctacgcc ggctacattg acggcggagc    2400
cagccaggaa gagttctaca gttcatcaa gcccatcctg gaaaagatgg acggcaccga    2460
ggaactgctc gtgaagctga acagagagga cctgctgcgg aagcagcgga ccttcgacaa    2520
cggcagcatc ccccaccaga tccacctggg agagctgcac gccattctgc ggcggcagga    2580 agattttttac ccattcctga aggacaaccg ggaaaagatc gagaagatcc tgaccttccg    2640
catcccctac tacgtgggcc ctctggccag gggaaacagc agattcgcct ggatgaccag    2700
aaagagcgag gaaccatca ccccctggaa cttcgaggaa gtggtggaca agggcgcttc    2760
cgcccagagc ttcatcgagc ggatgaccaa cttcgataag aacctgccca cgagaaggt    2820 gctgccaag cacagcctgc tgtacgagta cttcaccgtg tataacgagc tgaccaaagt    2880
gaaatacgtg accgagggaa tgagaaagcc cgccttcctg agcggcgagc agaaaaaggc    2940
catcgtggac ctgctgttca gaccaaccg gaaagtgacc gtgaagcagc tgaaagagga    3000
ctacttcaag aaaatcgagt gtttggatct gaaaacgcaa gttcaaacgc acagggtat    3060 gaaagaaata tccaatatac aggtcggcga tctcgtcttg tctaacactg ctataacga    3120 ggtgctgaat gtatttccaa aaagcaagaa aaaaagttac aagataactc tggaagatgg    3180
aaaagaaatt atctgttctg aggagcatct gtttccgacc caaacagggg agatgaatat    3240
cagtggcggt ctcaaagagg gtatgtgttt gtatgtcaag aataactag tagaattcct    3300 agagctcgct gatcagcctc gactgtgcct tctagttgcc agccatctgt tgtttgcccc    3360 tccccgtgc cttccttgac cctggaaggt gccactccca ctgtcctttc ctaataaaat    3420
```

-continued

| | | | | |
|---|---|---|---|---|
| gaggaaattg | catcgcattg | tctgagtagg | tgtcattcta | ttctggggggg tggggtgggg | 3480 |
| caggacagca | agggggagga | ttgggaagag | aatagcaggc | atgctgggga ggtaccgagg | 3540 |
| gcctatttcc | catgattcct | tcatatttgc | atatacgata | caaggctgtt agagagataa | 3600 |
| ttggaattaa | tttgactgta | aacacaaaga | tattagtaca | aaatacgtga cgtagaaagt | 3660 |
| aataatttct | tgggtagttt | gcagttttaa | aattatgttt | taaaatggac tatcatatgc | 3720 |
| ttaccgtaac | ttgaaagtat | ttcgatttct | tggctttata | tatcttgtgg aaaggacgaa | 3780 |
| acaccggtta | tctcctgttc | tgcagcgttt | cagagctatg | ctggaaacag catagcaagt | 3840 |
| tgaaataagg | ctagtccgtt | atcaacttga | aaaagtggca | ccgagtcggt gcttttttgc | 3900 |
| ggccgcagga | acccctagtg | atggagttgg | ccactccctc | tctgcgcgct cgctcgctca | 3960 |
| ctgaggccgg | cgaccaaag | gtcgcccgac | gcccgggctt | tgcccgggcg gcctcagtga | 4020 |
| gcgagcgagc | gcgcagctgc | ctgcaggggc | gcctgatgcg | gtattttctc cttacgcatc | 4080 |
| tgtgcggtat | ttcacaccgc | atacgtcaaa | gcaaccatag | tacgcgccct gtagcggcgc | 4140 |
| attaagcgcg | gcgggtgtgg | tggttacgcg | cagcgtgacc | gctacacttg ccagcgccct | 4200 |
| agcgcccgct | cctttcgctt | tcttcccttc | ctttctcgcc | acgttcgccg gctttccccg | 4260 |
| tcaagctcta | aatcgggggc | tccctttagg | gttccgattt | agtgctttac ggcacctcga | 4320 |
| ccccaaaaaa | cttgatttgg | gtgatggttc | acgtagtggg | ccatcgccct gatagacggt | 4380 |
| ttttcgccct | ttgacgttgg | agtccacgtt | ctttaatagt | ggactcttgt tccaaactgg | 4440 |
| aacaacactc | aaccctatct | cgggctattc | ttttgattta | taagggattt tgccgatttc | 4500 |
| ggcctattgg | ttaaaaaatg | agctgattta | acaaaaattt | aacgcgaatt ttaacaaaat | 4560 |
| attaacgttt | acaattttat | ggtgcactct | cagtacaatc | tgctctgatg ccgcatagtt | 4620 |
| aagccagccc | cgacacccgc | caacacccgc | tgacgcgccc | tgacgggctt gtctgctccc | 4680 |
| ggcatccgct | tacagacaag | ctgtgaccgt | ctccgggagc | tgcatgtgtc agaggttttc | 4740 |
| accgtcatca | ccgaaacgcg | cgagacgaaa | gggcctcgtg | atacgcctat ttttataggt | 4800 |
| taatgtcatg | ataataatgg | tttcttagac | gtcaggtggc | acttttcggg gaaatgtgcg | 4860 |
| cggaaccccct | atttgtttat | ttttctaaat | acattcaaat | atgtatccgc tcatgagaca | 4920 |
| ataaccctga | taaatgcttc | aataatattg | aaaaaggaag | agtatgagta ttcaacattt | 4980 |
| ccgtgtcgcc | cttattccct | ttttttgcggc | attttgcctt | cctgttttg ctcacccaga | 5040 |
| aacgctggtg | aaagtaaaag | atgctgaaga | tcagttgggt | gcacgagtgg gttacatcga | 5100 |
| actggatctc | aacagcggta | agatccttga | gagttttcgc | cccgaagaac gttttccaat | 5160 |
| gatgagcact | tttaaagttc | tgctatgtgg | cgcggtatta | tcccgtattg acgccgggca | 5220 |
| agagcaactc | ggtcgccgca | tacactattc | tcagaatgac | ttggttgagt actcaccagt | 5280 |
| cacagaaaag | catcttacgg | atggcatgac | agtaagagaa | ttatgcagtg ctgccataac | 5340 |
| catgagtgat | aacactgcgg | ccaacttact | tctgacaacg | atcggaggac cgaaggagct | 5400 |
| aaccgctttt | ttgcacaaca | tgggggatca | tgtaactcgc | cttgatcgtt gggaaccgga | 5460 |
| gctgaatgaa | gccataccaa | acgacgagcg | tgacaccacg | atgcctgtag caatggcaac | 5520 |
| aacgttgcgc | aaactattaa | ctggcgaact | acttactcta | gcttcccggc aacaattaat | 5580 |
| agactggatg | gaggcggata | aagttgcagg | accacttctg | cgctcggccc ttccggctgg | 5640 |
| ctggtttatt | gctgataaat | ctggagccgg | tgagcgtgga | agccgcggta tcattgcagc | 5700 |
| actggggcca | gatggtaagc | cctcccgtat | cgtagttatc | tacacgacgg ggagtcaggc | 5760 |
| aactatggat | gaacgaaata | gacagatcgc | tgagataggt | gcctcactga ttaagcattg | 5820 |

| | |
|---|---|
| gtaactgtca gaccaagttt actcatatat actttagatt gatttaaaac ttcatttta | 5880 |
| atttaaaagg atctaggtga agatccttt tgataatctc atgaccaaaa tcccttaacg | 5940 |
| tgagttttcg ttccactgag cgtcagaccc cgtagaaaag atcaaaggat cttcttgaga | 6000 |
| tccttttttt ctgcgcgtaa tctgctgctt gcaaacaaaa aaaccaccgc taccagcggt | 6060 |
| ggtttgtttg ccggatcaag agctaccaac tcttttccg aaggtaactg gcttcagcag | 6120 |
| agcgcagata ccaaatactg tccttctagt gtagccgtag ttaggccacc acttcaagaa | 6180 |
| ctctgtagca ccgcctacat acctcgctct gctaatcctg ttaccagtgg ctgctgccag | 6240 |
| tggcgataag tcgtgtctta ccgggttgga ctcaagacga tagttaccgg ataaggcgca | 6300 |
| gcggtcgggc tgaacggggg gttcgtgcac acagcccagc ttggagcgaa cgacctacac | 6360 |
| cgaactgaga tacctacagc gtgagctatg agaaagcgcc acgcttcccg aagggagaaa | 6420 |
| ggcggacagg tatccggtaa gcggcagggt cggaacagga gagcgcacga gggagcttcc | 6480 |
| agggggaaac gcctggtatc tttatagtcc tgtcgggttt cgccacctct gacttgagcg | 6540 |
| tcgatttttg tgatgctcgt caggggggcg gagcctatgg aaaaacgcca gcaacgcggc | 6600 |
| cttttacgg ttcctggcct tttgctggcc ttttgctcac atgt | 6644 |

<210> SEQ ID NO 8
<211> LENGTH: 6575
<212> TYPE: DNA
<213> ORGANISM: Artificial Sequence
<220> FEATURE:
<223> OTHER INFORMATION: Synthetic Construct

<400> SEQUENCE: 8

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggcctcta gactcgaggc ccttcagatt aaaaataact gaggtaaggg | 180 |
| cctgggtagg ggaggtggtg tgagacgctc ctgtctctcc tctatctgcc catcggccct | 240 |
| ttggggagga ggaatgtgcc caaggactaa aaaaaggcca tggagccaga ggggcgaggg | 300 |
| caacagacct tcatgggca aaccttgggg ccctgctgac tgtagatgag agcagccact | 360 |
| acgggtctag gctgcccatg taaggaggca aggcctgggg acacccgaga tgcctggtta | 420 |
| taattaaccc agacatgtgg ctgcccccc cccccaaca cctgctgcct gctaaaaata | 480 |
| accctgtccc tggtggccct gcatgccctc cctgggaca gccctcctg gctagtcaca | 540 |
| ccctgtaggc tcctctatat aacccagggg cacaggggct gccctcattc taccaccacc | 600 |
| tccacagcac agacagacac tcaggagcca gctagccacc atgatgctca agaagatcct | 660 |
| caagattgaa gagttggacg agcgcgagct tatagacata gaagtcagtg gtaatcacct | 720 |
| tttctacgca aatgacattt tgactcacaa ctcctcttca gacgtttgct tcgactccgt | 780 |
| ggaaatctcc ggcgtggaag atcggttcaa cgcctccctg gcacatacc acgatctgct | 840 |
| gaaaattatc aaggacaagg acttcctgga caatgaggaa aacgaggaca ttctggaaga | 900 |
| tatcgtgctg accctgacac tgtttgagga cagagagatg atcgaggaac ggctgaaaac | 960 |
| ctatgcccac ctgttcgacg acaaagtgat gaagcagctg aagcggcgga gatacaccgg | 1020 |
| ctggggcagg ctgagccgga agctgatcaa cggcatccgg gacaagcagt ccggcaagac | 1080 |
| aatcctggat ttcctgaagt ccgacggctt cgccaacaga aacttcatgc agctgatcca | 1140 |
| cgacgacagc ctgaccttta aagaggacat ccagaaagcc caggtgtccg gccagggcga | 1200 |

```
tagcctgcac gagcacattg ccaatctggc cggcagcccc gccattaaga agggcatcct   1260
gcagacagtg aaggtggtgg acgagctcgt gaaagtgatg ggccggcaca agcccgagaa   1320
catcgtgatc gaaatggcca gagagaacca gaccacccag aagggacaga gaacagccg    1380
cgagagaatg aagcggatcg aagagggcat caaagagctg ggcagccaga tcctgaaaga   1440
acaccccgtg gaaaacaccc agctgcagaa cgagaagctg tacctgtact acctgcagaa   1500
tgggcgggat atgtacgtgg accaggaact ggacatcaac cggctgtccg actacgatgt   1560
ggaccatatc gtgcctcaga gctttctgaa ggacgactcc atcgacaaca aggtgctgac   1620
cagaagcgac aagaaccggg gcaagagcga acgtgcccc ccgaagagg tcgtgaagaa     1680
gatgaagaac tactggcggc agctgctgaa cgccaagctg attcccaga gaaagttcga     1740
caatctgacc aaggccgaga gaggcggcct gagcgaactg gataaggccg gcttcatcaa    1800
gagacagctg gtggaaaccc ggcagatcac aaagcacgtg gcacagatcc tggactcccg    1860
gatgaacact aagtacgacg agaatgacaa gctgatccgg gaagtgaaag tgatcaccct    1920
gaagtccaag ctggtgtccg atttccggaa ggatttccag ttttacaaag tgcgcgagat    1980
caacaactac caccacgccc acgacgccta cctgaacgcc gtcgtgggaa ccgccctgat    2040
caaaaagtac cctaagctgg aaagcgagtt cgtgtacggc gactacaagg tgtacgacgt    2100
gcggaagatg atcgccaaga gcgagcagga atcggcaag gctaccgcca agtacttctt     2160
ctacagcaac atcatgaact ttttcaagac cgagattacc ctggccaacg cgagatccg     2220
gaagcggcct ctgatcgaga caaacggcga accggggag atcgtgtggg ataagggccg     2280
ggattttgcc accgtgcgga aagtgctgag catgccccaa gtgaatatcg tgaaaaagac    2340
cgaggtgcag acaggcggct tcagcaaaga gtctatccgg cccaagagga acagcgataa    2400
gctgatcgcc agaaagaagg actgggaccc taagaagtac ggcggcttcg tcagccccac    2460
cgtggcctat tctgtgctgg tggtggccaa agtggaaaag ggcaagtcca gaaaactgaa    2520
gagtgtgaaa gagctgctgg ggatcaccat catggaaaga agcagcttcg agaagaatcc    2580
catcgacttt ctggaagcca agggctacaa agaagtgaaa aaggacctga tcatcaagct    2640
gcctaagtac tccctgttcg agctggaaaa cggccggaag agaatgctgg cctctgcccg    2700
cttttctgcag aagggaaacg aactggccct gccctccaaa tatgtgaact tcctgtacct    2760
ggccagccac tatgagaagc tgaagggctc ccccgaggat aatgagcaga acagctgtt     2820
tgtggaacag cacaagcact acctggacga gatcatcgag cagatcagcg agttctccaa    2880
gagagtgatc ctggccgacg ctaatctgga caaagtgctg tccgcctaca acaagcaccg    2940
ggataagccc atcagagagc aggccgagaa tatcatccac ctgtttaccc tgaccaatct    3000
gggagcccct cgggccttca gtactttga caccaccatc gaccggaagg tgtaccggag    3060
caccaaagag gtgctggacg ccaccctgat ccaccagagc atcaccggcc tgtacgagac   3120
acggatcgac ctgtctcagc tgggaggtga ctctggcggc tcaaaaagaa ccgccgacgg   3180
cagcgaattc gagcccaaga agaagaggaa agtctaacta gtagaattcc tagagctcgc   3240
tgatcagcct cgactgtgcc ttctagttgc cagccatctg ttgtttgccc ctcccccgtg   3300
ccttccttga ccctggaagg tgccactccc actgtccttt cctaataaaa tgaggaaatt   3360
gcatcgcatt gtctgagtag gtgtcattct attctggggg gtggggtggg gcaggacagc   3420
aagggggagg attgggaaga gaatagcagg catgctgggg aggtaccgag ggcctatttc    3480
ccatgattcc ttcatatttg catatacgat acaaggctgt tagagagata attggaatta   3540
atttgactgt aaacacaaag atattagtac aaaatacgtg acgtagaaag taataatttc   3600
```

```
ttgggtagtt tgcagtttta aaattatgtt ttaaaatgga ctatcatatg cttaccgtaa    3660
cttgaaagta tttcgatttc ttggctttat atatcttgtg gaaaggacga aacaccggtt    3720
atctcctgtt ctgcagcgtt tcagagctat gctggaaaca gcatagcaag ttgaaataag    3780
gctagtccgt tatcaacttg aaaaagtggc accgagtcgg tgcttttttg cggccgcagg    3840 aaccccctagt gatggagttg gccactccct ctctgcgcgc tcgctcgctc actgaggccg    3900
ggcgaccaaa ggtcgcccga cgcccgggct tgcccgggc ggcctcagtg agcgagcgag    3960
cgcgcagctg cctgcagggg cgcctgatgc ggtattttct ccttacgcat ctgtgcggta    4020
tttcacaccg catacgtcaa agcaaccata gtacgcgccc tgtagcggcg cattaagcgc    4080
ggcgggtgtg gtggttacgc gcagcgtgac cgctacactt gccagcgccc tagcgcccgc    4140
tcctttcgct ttcttccctt cctttctcgc cacgttcgcc ggctttcccc gtcaagctct    4200
aaatcggggg ctccctttag ggttccgatt tagtgcttta cggcacctcg accccaaaaa    4260
acttgatttg ggtgatggtt cacgtagtgg gccatcgccc tgatagacgg ttttcgccc    4320 tttgacgttg gagtccacgt tctttaatag tggactcttg ttccaaactg gaacaacact    4380
caaccctatc tcgggctatt cttttgattt ataagggatt ttgccgattt cggcctattg    4440
gttaaaaaat gagctgattt aacaaaaatt taacgcgaat tttaacaaaa tattaacgtt    4500
tacaatttta tggtgcactc tcagtacaat ctgctctgat gccgcatagt taagccagcc    4560
ccgacacccg ccaacacccg ctgacgcgcc ctgacgggct tgtctgctcc cggcatccgc    4620
ttacagacaa gctgtgaccg tctccgggag ctgcatgtgt cagaggtttt caccgtcatc    4680
accgaaacgc gcgagacgaa agggcctcgt gatacgccta ttttataagg ttaatgtcat    4740
gataataatg gtttcttaga cgtcaggtgg cacttttcgg ggaaatgtgc gcggaacccc    4800
tatttgttta ttttttctaaa tacattcaaa tatgtatccg ctcatgagac aataaccctg    4860
ataaatgctt caataatatt gaaaaaggaa gagtatgagt attcaacatt tccgtgtcgc    4920
ccttattccc ttttttgcgg cattttgcct tcctgttttt gctcacccag aaacgctggt    4980
gaaagtaaaa gatgctgaag atcagttggg tgcacgagtg ggttacatcg aactggatct    5040
caacagcggt aagatccttg agagttttcg ccccgaagaa cgttttccaa tgatgagcac    5100
ttttaaagtt ctgctatgtg gcgcggtatt atcccgtatt gacgccgggc aagagcaact    5160
cggtcgccgc atacactatt ctcagaatga cttggttgag tactcaccag tcacagaaaa    5220
gcatcttacg gatggcatga cagtaagaga attatgcagt gctgccataa ccatgagtga    5280
taacactgcg gccaacttac ttctgacaac gatcggagga ccgaaggagc taaccgcttt    5340
tttgcacaac atgggggatc atgtaactcg ccttgatcgt tgggaaccgg agctgaatga    5400
agccatacca aacgacgagc gtgacaccac gatgcctgta gcaatggcaa caacgttgcg    5460
caaactatta actggcgaac tacttactct agcttcccgg caacaattaa tagactggat    5520
ggaggcggat aaagttgcag gaccacttct gcgctcggcc cttccggctg gctggtttat    5580
tgctgataaa tctggagccg gtgagcgtgg aagccgcggt atcattgcag cactggggcc    5640
agatggtaag ccctcccgta tcgtagttat ctacacgacg gggagtcagg caactatgga    5700
tgaacgaaat agacagatcg ctgagatagg tgcctcactg attaagcatt ggtaactgtc    5760
agaccaagtt tactcatata ctttagat tgatttaaaa cttcattttt aatttaaaag    5820
gatctaggtg aagatccttt ttgataatct catgaccaaa atcccttaac gtgagttttc    5880
gttccactga gcgtcagacc ccgtagaaaa gatcaaagga tcttcttgag atccttttt    5940
```

-continued

| | |
|---|---|
| tctgcgcgta atctgctgct tgcaaacaaa aaaaccaccg ctaccagcgg tggtttgttt | 6000 |
| gccggatcaa gagctaccaa ctcttttttcc gaaggtaact ggcttcagca gagcgcagat | 6060 |
| accaaatact gtccttctag tgtagccgta gttaggccac cacttcaaga actctgtagc | 6120 |
| accgcctaca tacctcgctc tgctaatcct gttaccagtg gctgctgcca gtggcgataa | 6180 |
| gtcgtgtctt accgggttgg actcaagacg atagttaccg gataaggcgc agcggtcggg | 6240 |
| ctgaacgggg ggttcgtgca cacagcccag cttggagcga acgacctaca ccgaactgag | 6300 |
| atacctacag cgtgagctat gagaaagcgc cacgcttccc gaagggagaa aggcggacag | 6360 |
| gtatccggta agcggcaggg tcggaacagg agagcgcacg agggagcttc caggggggaaa | 6420 |
| cgcctggtat ctttatagtc ctgtcgggtt tcgccacctc tgacttgagc gtcgattttt | 6480 |
| gtgatgctcg tcagggggc ggagcctatg gaaaaacgcc agcaacgcgg cctttttacg | 6540 |
| gttcctggcc ttttgctggc cttttgctca catgt | 6575 |

<210> SEQ ID NO 9
<211> LENGTH: 9962
<212> TYPE: DNA
<213> ORGANISM: Artificial Sequence
<220> FEATURE:
<223> OTHER INFORMATION: Synthetic Construct
<400> SEQUENCE: 9

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt gcgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagaccctt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc aggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |

```
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtgaaaga tacctaaagg atcaacagct cctgggatt      1920 tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta gctagcaggt acctgagggc ctatttccca tgattccttc    2640
atatttgcat atacgataca aggctgttag agagataatt ggaattaatt tgactgtaaa    2700
cacaaagata ttagtacaaa atacgtgacg tagaaagtaa taatttcttg ggtagtttgc    2760
agttttaaaa ttatgttta aaatggacta tcatatgctt accgtaactt gaaagtattt    2820
cgatttcttg gctttatata tcttgtggaa aggacgaaac accggttatc tcctgttctg    2880
cagcgtttca gagctatgct ggaaacagca tagcaagttg aaataaggct agtccgttat    2940
caacttgaaa aagtggcacc gagtcggtgc ttttttgcgg ccgcggatcc tgcaaagatg    3000
gataaagttt taaacagaga ggaatctttg cagctaatgg accttctagg tcttgaaagg    3060
agtgggaatt ggctccggtg cccgtcagtg ggcagagcgc acatcgccca cagtccccga    3120
gaagttgggg ggaggggtcg gcaattgatc cggtgcctag agaaggtggc gcggggtaaa    3180
ctgggaaagt gatgtcgtgt actggctccg cctttttccc gagggtgggg gagaaccgta    3240
tataagtgca gtagtcgccg tgaacgttct ttttcgcaac gggtttgccg ccagaacaca    3300
ggtaagtgcc gtgtgtggtt cccgcgggcc tggcctcttt acgggttatg gcccttgcgt    3360
gccttgaatt acttccactg gctgcagtac gtgattcttg atcccgagct tcgggttgga    3420
agtgggtggg agagttcgag gccttgcgct taaggagccc cttcgcctcg tgcttgagtt    3480
gaggcctggc ctgggcgctg gggccgccgc gtgcgaatct ggtggcacct tcgcgcctgt    3540
ctcgctgctt tcgataagtc tctagccatt taaaattttt gatgacctgc tgcgacgctt    3600
tttttctggc aagatagtct tgtaaatgcg ggccaagatc tgcacactgg tatttcggtt    3660
tttggggccg cggcggcga cggggcccgt cgtcccagc gcacatgttc ggcgaggcgg    3720
ggcctgcgag cgcggccacc gagaatcgga cgggggtagt ctcaagctgg ccggcctgct    3780
```

```
ctggtgcctg gcctcgcgcc gccgtgtatc gccccgccct gggcggcaag gctggcccgg    3840
tcggcaccag ttgcgtgagc ggaaagatgg ccgcttccog gccctgctgc agggagctca    3900
aaatggagga cgcggcgctc gggagagcgg gcgggtgagt cacccacaca aaggaaaagg    3960
gcctttccgt cctcagccgt cgcttcatgt gactccacgg agtaccgggc gccgtccagg    4020
cacctcgatt agttctcgag cttttggagt acgtcgtctt taggttgggg ggaggggttt    4080
tatgcgatgg agtttcccca cactgagtgg gtggagactg aagttaggcc agcttggcac    4140
ttgatgtaat tctccttgga atttgccctt tttgagtttg gatcttggtt cattctcaag    4200
cctcagacag tggttcaaag ttttttttctt ccatttcagg tgtcgtgatg tacaatggcc    4260
aagttgacca gtgccgttcc ggtgctcacc gcgcgcgacg tcgccggagc ggtcgagttc    4320
tggaccgacc ggctcgggtt ctcccgggac ttcgtggagg acgacttcgc cggtgtggtc    4380
cgggacgacg tgaccctgtt catcagcgcg gtccaggacc aggtggtgcc ggacaacacc    4440
ctggcctggg tgtgggtgcg cggcctggac gagctgtacg ccgagtggtc ggaggtcgtg    4500
tccacgaact tccgggacgc ctccgggccg gccatgaccg agatcggcga gcagccgtgg    4560
gggcgggagt tcgccctgcg cgacccggcc ggcaactgcg tgcacttcgt ggccgaggag    4620
caggactgag aattcgatat caagcttatc ggtaatcaac ctctggatta caaaatttgt    4680
gaaagattga ctggtattct taactatgtt gctccttttta cgctatgtgg atacgctgct    4740
ttaatgcctt tgtatcatgc tattgcttcc cgtatggctt tcattttctc ctccttgtat    4800
aaatcctggt tgctgtctct ttatgaggag ttgtggcccg ttgtcaggca acgtggcgtg    4860
gtgtgcactg tgtttgctga cgcaaccccc actggttggg gcattgccac cacctgtcag    4920
ctcctttccg ggactttcgc tttccccctc cctattgcca cggcggaact catcgccgcc    4980
tgccttgccc gctgctggac aggggctcgg ctgttgggca ctgacaattc cgtggtgttg    5040
tcggggaaat catcgtcctt tccttggctg ctcgcctgtg ttgccacctg gattctgcgc    5100
gggacgtcct tctgctacgt cccttcggcc ctcaatccag cggaccttcc ttcccgcggc    5160
ctgctgccgg ctctgcggcc tcttccgcgt cttcgccttc gccctcagac gagtcggatc    5220
tccctttggg ccgcctcccc gcatcgatac cgtcgacctc gagacctaga aaaacatgga    5280
gcaatcacaa gtagcaatac agcagctacc aatgctgatt gtgcctggct agaagcacaa    5340
gaggaggagg aggtgggttt tccagtcaca cctcaggtac cttttaagacc aatgacttac    5400 aaggcagctg tagatcttag ccacttttta aaagaaaagg ggggactgga agggctaatt    5460
cactcccaac gaagacaaga tatccttgat ctgtggatct accacacaca aggctacttc    5520
cctgattggc agaactacac accagggcca gggatcagat atccactgac ctttggatgg    5580
tgctacaagc tagtaccagt tgagcaagag aaggtagaag aagccaatga aggagagaac    5640
acccgcttgt tacaccctgt gagcctgcat gggatggatg acccggagag agaagtatta    5700
gagtggaggt ttgacagccg cctagcattt catcacatgg cccgagagct gcatccggac    5760
tgtactgggt ctctctggtt agaccagatc tgagcctggg agctctctgg ctaactaggg    5820
aacccactgc ttaagcctca ataaagcttg ccttgagtgc ttcaagtagt gtgtgcccgt    5880
ctgttgtgtg actctggtaa ctagagatcc ctcagaccct tttagtcagt gtggaaaatc    5940
tctagcaggg cccgtttaaa cccgctgatc agcctcgact gtgccttcta gttgccagcc    6000
atctgttgtt tgcccctccc ccgtgccttc cttgaccctg gaaggtgcca ctcccactgt    6060
cctttcctaa taaaatgagg aaattgcatc gcattgtctg agtaggtgtc attctattct    6120
ggggggtggg gtggggcagg acagcaaggg ggaggattgg gaagacaata gcaggcatgc    6180
```

```
tggggatgcg gtgggctcta tggcttctga ggcggaaaga accagctggg gctctagggg    6240
gtatccccac gcgccctgta gcggcgcatt aagcgcggcg ggtgtggtgg ttacgcgcag    6300
cgtgaccgct acacttgcca gcgccctagc gcccgctcct ttcgctttct tcccttcctt    6360
tctcgccacg ttcgccggct ttccccgtca agctctaaat cggggggctcc ctttagggtt    6420
ccgatttagt gctttacggc acctcgaccc caaaaaactt gattagggtg atggttcacg    6480
tagtgggcca tcgccctgat agacggtttt tcgccctttg acgttggagt ccacgttctt    6540
taatagtgga ctcttgttcc aaactggaac aacactcaac cctatctcgg tctattcttt    6600
tgatttataa gggattttgc cgatttcggc ctattggtta aaaaatgagc tgatttaaca    6660
aaaatttaac gcgaattaat tctgtggaat gtgtgtcagt tagggtgtgg aaagtcccca    6720
ggctccccag caggcagaag tatgcaaagc atgcatctca attagtcagc aaccaggtgt    6780
ggaaagtccc caggctcccc agcaggcaga agtatgcaaa gcatgcatct caattagtca    6840
gcaaccatag tcccgcccct aactccgccc atcccgcccc taactccgcc cagttccgcc    6900
cattctccgc cccatggctg actaattttt tttatttatg cagaggccga ggccgcctct    6960
gcctctgagc tattccagaa gtagtgagga ggcttttttg gaggcctagg cttttgcaaa    7020
aagctcccgg gagcttgtat atccattttc ggatctgatc agcacgtgtt gacaattaat    7080
catcggcata gtatatcggc atagtataat acgacaaggt gaggaactaa accatggcca    7140
agttgaccag tgccgttccg gtgctcaccg cgcgcgacgt cgccggagcg tcgagttct    7200
ggaccgaccg gctcgggttc tcccgggact cgtggagga cgacttcgcc ggtgtggtcc    7260
gggacgacgt gaccctgttc atcagcgcgg tccaggacca ggtggtgccg gacaacaccc    7320
tggcctgggt gtgggtgcgc ggcctggacg agctgtacgc cgagtggtcg gaggtcgtgt    7380
ccacgaactt ccgggacgcc tccggccgg ccatgaccga gatcggcgag cagccgtggg    7440
ggcgggagtt cgccctgcgc gacccggccg gcaactgcgt gcacttcgtg gccgaggagc    7500
aggactgaca cgtgctacga gatttcgatt ccaccgccgc cttctatgaa aggttgggct    7560
tcggaatcgt tttccgggac gccggctgga tgatcctcca gcgcggggat ctcatgctgg    7620
agttcttcgc ccacccccaac ttgtttattg cagcttataa tggttacaaa taaagcaata    7680
gcatcacaaa tttcacaaat aaagcatttt tttcactgca ttctagttgt ggtttgtcca    7740
aactcatcaa tgtatcttat catgtctgta taccgtcgac ctctagctag agcttggcgt    7800
aatcatggtc atagctgttt cctgtgtgaa attgttatcc gctcacaatt ccacacaaca    7860
tacgagccgg aagcataaag tgtaaagcct ggggtgccta atgagtgagc taactcacat    7920
taattgcgtt gcgctcactg cccgctttcc agtcgggaaa cctgtcgtgc cagctgcatt    7980
aatgaatcgg ccaacgcgcg gggagaggcg gtttgcgtat tgggcgctct tccgcttcct    8040
cgctcactga ctcgctgcgc tcggtcgttc ggctgcggcg agcggtatca gctcactcaa    8100
aggcggtaat acggttatcc acagaatcag gggataacgc aggaaagaac atgtgagcaa    8160
aaggccagca aaaggccagg aaccgtaaaa aggccgcgtt gctggcgttt ttccataggc    8220
tccgccccc tgacgagcat cacaaaaatc gacgctcaag tcagaggtgg cgaaacccga    8280
caggactata aagataccag gcgtttcccc ctggaagctc cctcgtgcgc tctcctgttc    8340
cgaccctgcc gcttaccgga tacctgtccg cctttctccc ttcgggaagc gtggcgcttt    8400
ctcatagctc acgctgtagg tatctcagtt cggtgtaggt cgttcgctcc aagctgggct    8460
gtgtgcacga accccccgtt cagcccgacc gctgcgcctt atccggtaac tatcgtcttg    8520
```

| | | | | | |
|---|---|---|---|---|---|
| agtccaaccc | ggtaagacac | gacttatcgc | cactggcagc | agccactggt | aacaggatta | 8580 |
| gcagagcgag | gtatgtaggc | ggtgctacag | agttcttgaa | gtggtggcct | aactacggct | 8640 |
| acactagaag | aacagtattt | ggtatctgcg | ctctgctgaa | gccagttacc | ttcggaaaaa | 8700 |
| gagttggtag | ctcttgatcc | ggcaaacaaa | ccaccgctgg | tagcggtggt | ttttttgttt | 8760 |
| gcaagcagca | gattacgcgc | agaaaaaaag | gatctcaaga | agatcctttg | atcttttcta | 8820 |
| cggggtctga | cgctcagtgg | aacgaaaact | cacgttaagg | gattttggtc | atgagattat | 8880 |
| caaaaaggat | cttcacctag | atccttttaa | attaaaaatg | aagttttaaa | tcaatctaaa | 8940 |
| gtatatatga | gtaaacttgg | tctgacagtt | accaatgctt | aatcagtgag | gcacctatct | 9000 |
| cagcgatctg | tctatttcgt | tcatccatag | ttgcctgact | ccccgtcgtg | tagataacta | 9060 |
| cgatacggga | gggcttacca | tctggcccca | gtgctgcaat | gataccgcga | gacccacgct | 9120 |
| caccggctcc | agatttatca | gcaataaacc | agccagccgg | aagggccgag | cgcagaagtg | 9180 |
| gtcctgcaac | tttatccgcc | tccatccagt | ctattaattg | ttgccgggaa | gctagagtaa | 9240 |
| gtagttcgcc | agttaatagt | ttgcgcaacg | ttgttgccat | tgctacaggc | atcgtggtgt | 9300 |
| cacgctcgtc | gtttggtatg | gcttcattca | gctccggttc | ccaacgatca | aggcgagtta | 9360 |
| catgatcccc | catgttgtgc | aaaaaagcgg | ttagctcctt | cggtcctccg | atcgttgtca | 9420 |
| gaagtaagtt | ggccgcagtg | ttatcactca | tggttatggc | agcactgcat | aattctctta | 9480 |
| ctgtcatgcc | atccgtaaga | tgcttttctg | tgactggtga | gtactcaacc | aagtcattct | 9540 |
| gagaatagtg | tatgcggcga | ccgagttgct | cttgcccggc | gtcaatacgg | gataataccg | 9600 |
| cgccacatag | cagaacttta | aaagtgctca | tcattggaaa | acgttcttcg | gggcgaaaac | 9660 |
| tctcaaggat | cttaccgctg | ttgagatcca | gttcgatgta | acccactcgt | gcacccaact | 9720 |
| gatcttcagc | atcttttact | ttcaccagcg | tttctgggtg | agcaaaaaca | ggaaggcaaa | 9780 |
| atgccgcaaa | aaagggaata | agggcgacac | ggaaatgttg | aatactcata | ctcttccttt | 9840 |
| ttcaatatta | ttgaagcatt | tatcagggtt | attgtctcat | gagcggatac | atatttgaat | 9900 |
| gtatttagaa | aaataaacaa | ataggggttc | cgcgcacatt | tccccgaaaa | gtgccacctg | 9960 |
| ac | | | | | | 9962 |

<210> SEQ ID NO 10
<211> LENGTH: 7580
<212> TYPE: DNA
<213> ORGANISM: Artificial Sequence
<220> FEATURE:
<223> OTHER INFORMATION: Synthetic Construct

<400> SEQUENCE: 10

| | | | | | |
|---|---|---|---|---|---|
| gggtctctct | ggttagacca | gatctgagcc | tgggagctct | ctggctaact | agggaaccca | 60 |
| ctgcttaagc | ctcaataaag | cttgccttga | gtgcttcaag | tagtgtgtgc | ccgtctgttg | 120 |
| tgtgactctg | gtaactagag | atccctcaga | cccttttagt | cagtgtggaa | aatctctagc | 180 |
| agtggcgccc | gaacagggac | ttgaaagcga | aagggaaacc | agaggagctc | tctcgacgca | 240 |
| ggactcggct | tgctgaagcg | cgcacggcaa | gaggcgaggg | gcggcgactg | gtgagtacgc | 300 |
| caaaatttt | gactagcgga | ggctagaagg | agagagatgg | gtgcgagagc | gtcagtatta | 360 |
| agcgggggag | aattagatcg | cgatgggaaa | aaattcggtt | aaggccaggg | ggaaagaaaa | 420 |
| aatataaatt | aaaacatata | gtatgggcaa | gcagggagct | agaacgattc | gcagttaatc | 480 |
| ctggcctgtt | agaaacatca | gaaggctgta | gacaaatact | gggacagcta | caaccatccc | 540 |
| ttcagacagg | atcagaagaa | cttagatcat | tatataatac | agtagcaacc | ctctattgtg | 600 |

```
tgcatcaaag gatagagata aaagacacca aggaagcttt agacaagata gaggaagagc      660
aaaacaaaag taagaccacc gcacagcaag cggccgctga tcttcagacc tggaggagga      720
gatatgaggg acaattggag aagtgaatta tataaatata aagtagtaaa aattgaacca      780
ttaggagtag cacccaccaa ggcaaagaga agagtggtgc agagagaaaa aagagcagtg      840
ggaataggag ctttgttcct tgggttcttg ggagcagcag gaagcactat gggcgcagcg      900
tcaatgacgc tgacggtaca ggccagacaa ttattgtctg gtatagtgca gcagcagaac      960
aatttgctga gggctattga ggcgcaacag catctgttgc aactcacagt ctggggcatc     1020
aagcagctcc aggcaagaat cctggctgtg gaaagatacc taaaggatca acagctcctg     1080
gggatttggg gttgctctgg aaaactcatt tgcaccactg ctgtgccttg gaatgctagt     1140
tggagtaata atctctggaa acagatttgg aatcacacga cctggatgga gtgggacaga     1200
gaaattaaca attacacaag cttaatacac tccttaattg aagaatcgca aaaccagcaa     1260
gaaaagaatg aacaagaatt attggaatta gataaatggg caagtttgtg gaattggttt     1320
aacataacaa attggctgtg gtatataaaa ttattcataa tgatagtagg aggcttggta     1380
ggtttaagaa tagttttgc tgtactttct atagtgaata gagttaggca gggatattca     1440
ccattatcgt ttcagaccca cctcccaacc ccgaggggac ccgacaggcc cgaaggaata     1500
gaagaagaag gtggagagag agacagagac agatccattc gattagtgaa cggatctcga     1560
cggtatcgat cacgagacta gcctcgagac aaatggcagt attcatccac aattttaaaa     1620
gaaaaggggg gattggggg tacagtgcag gggaaagaat agtagacata atagcaacag     1680
acatacaaac taaagaatta caaaaacaaa ttacaaaaat tcaaaatttt cgggtttatt     1740
acagggacag cagagatcca ctttggccgc ggtagttatt aatagtaatc aattacgggg     1800
tcattagttc atagcccata tatggagttc cgcgttacat aacttacggt aaatggcccg     1860
cctggctgac cgcccaacga ccccgcccca ttgacgtcaa taatgacgta tgttcccata     1920
gtaacgccaa tagggacttt ccattgacgt caatgggtgg agtatttacg gtaaactgcc     1980
cacttggcag tacatcaagt gtatcatatg ccaagtacgc ccctattga cgtcaatgac     2040 ggtaaatggc ccgcctggca ttatgcccag tacatgacct tatgggactt tcctacttgg     2100
cagtacatct acgtattagt catcgctatt accatggtga tgcggttttg gcagtacatc     2160
aatgggcgtg gatagcggtt tgactcacgg ggatttccaa gtctccaccc cattgacgtc     2220
aatgggagtt tgttttggca ccaaaatcaa cgggactttc caaaatgtcg taacaactcc     2280
gccccattga cgcaaatggg cggtaggcgt gtacggtggg aggtctatat aagcagagct     2340
ggtttagtga accgtcagat ccgctagcca ccatgaccga gtacaagccc acggtgcgcc     2400
tcgccacccg cgacgacgtc cccagggccg tacgcaccct cgccgccgcg ttcgccgact     2460
accccgccac gcgccacacc gtcgatccgg accgccacat cgagcgggtc accgagctgc     2520
aagaactctt cctcacgcgc gtcgggctcg acatcggcaa ggtgtgggtc gcggacgacg     2580
gcgccgcggt ggcggtctgg accacgccgg agagcgtcga agcggggcg gtgttcgccg     2640 agatcggccc cgcgatggcc gagttgagcg gttcccggct ggccgcgcag caacagatgg     2700
aaggcctcct ggcgccgcac cggcccaagg agccgcgtg gttcctggcc accgtcggcg     2760
tgtcgcccga ccaccagggc aagggtctgg gcagcgccgt cgtgctcccc ggagtggagg     2820
cggccgagcg cgccggggtg cccgccttcc tggaaacctc cgcgcccgc aacctccct     2880 tctacgagcg gctcggcttc accgtcaccg ccgacgtcga ggtgcccgaa ggaccgcgca     2940
```

```
cctggtgcat gacccgcaag cccggtgccc tgtacaagca atgtactaac tacgctttgt    3000
tgaaactcgc tggcgatgtt gaaagtaacc ccggtcctga attccaagaa cagctgcaga    3060
acaggagata acagttggga tccgtgagca agggcgagga gctgttcacc ggggtggtgc    3120
ccatcctggt cgagctggac ggcgacgtaa acggccacaa gttcagcgtg tccggcgagg    3180
gcgagggcga tgccacctac ggcaagctga ccctgaagtt catctgcacc accggcaagc    3240
tgcccgtgcc ctggcccacc ctcgtgacca ccctgaccta cggcgtgcag tgcttcagcc    3300 gctacccega ccacatgaag cagcacgact tcttcaagtc cgccatgccc gaaggctacg    3360
tccaggagcg caccatcttc ttcaaggacg acggcaacta caagacccgc gccgaggtga    3420
agttcgaggg cgacaccctg gtgaaccgca tcgagctgaa gggcatcgac ttcaaggagg    3480
acggcaacat cctggggcac aagctggagt acaactacaa cagccacaac gtctatatca    3540
tggccgacaa gcagaagaac ggcatcaagg tgaacttcaa gatccgccac aacatcgagg    3600
acggcagcgt gcagctcgcc gaccactacc agcagaacac ccccatcggc gacggccccg    3660
tgctgctgcc cgacaaccac tacctgagca cccagtccgc cctgagcaaa gaccccaacg    3720
agaagcgcga tcacatggtc ctgctggagt tcgtgaccgc cgccgggatc actctcggca    3780
tggacgagct gtacaagtaa ggtacccttt agaccaatga cttacaaggc agctgtagat    3840
cttagccact ttttaaaaga aagggggga ctggaagggc taattcactc ccaacgaaga    3900
caagatctgc ttttgcttg tactgggtct ctctggttag accagatctg agcctgggag    3960
ctctctggct aactagggaa cccactgctt aagcctcaat aaagcttgcc ttgagtgctt    4020
caagtagtgt gtgcccgtct gttgtgtgac tctggtaact agagatccct cagacccttt    4080
tagtcagtgt ggaaaatctc tagcagtagt agttcatgtc atcttattat tcagtattta    4140
taacttgcaa agaaatgaat atcagagagt gagaggaact tgtttattgc agcttataat    4200
ggttacaaat aaagcaatag catcacaaat ttcacaaata aagcattttt ttcactgcat    4260
tctagttgtg gtttgtccaa actcatcaat gtatcttatc atgtctggct ctagctatcc    4320
cgcccctaac tccgcccatc ccgcccctaa ctccgcccag ttccgcccat tctccgcccc    4380
atggctgact aattttttt atttatgcag aggccgaggc cgcctcggcc tctgagctat    4440
tccagaagta gtgaggaggc ttttttggag gcctaggac gtacccaatt cgccctatag    4500
tgagtcgtat tacgcgcgct cactggccgt cgttttacaa cgtcgtgact gggaaaaccc    4560
tggcgttacc caacttaatc gccttgcagc acatccccct ttcgccagct ggcgtaatag    4620
cgaagaggcc cgcaccgatc gcccttccca acagttgcgc agcctgaatg gcgaatggga    4680
cgcgccctgt agcggcgcat taagcgcggc gggtgtggtg gttacgcgca gcgtgaccgc    4740
tacacttgcc agcgccctag cgcccgctcc tttcgctttc ttcccttcct ttctcgccac    4800
gttcgccggc tttccccgtc aagctctaaa tcggggctc cctttagggt tccgatttag    4860
tgctttacgg cacctcgacc ccaaaaaact tgattaggt gatggttcac gtagtgggcc    4920
atcgccctga tagacggttt ttcgcccttt gacgttggag tccacgttct ttaatagtgg    4980
actcttgttc caaactggaa caacactcaa ccctatctcg gtctattctt ttgatttata    5040 agggatttg ccgatttcgg cctattggtt aaaaaatgag ctgatttaac aaaaatttaa    5100
cgcgaatttt aacaaaatat taacgcttac aatttaggtg cacttttcg gggaaatgtg    5160 cgcggaaccc ctatttgttt atttttctaa atacattcaa atatgtatcc gctcatgaga    5220 caataacccct gataaatgct tcaataatat tgaaaaagga agagtatgag tattcaacat    5280
ttccgtgtcg cccttattcc cttttttgcg gcattttgcc ttcctgtttt tgctcaccca    5340
```

```
gaaacgctgg tgaaagtaaa agatgctgaa gatcagttgg gtgcacgagt gggttacatc    5400
gaactggatc tcaacagcgg taagatcctt gagagttttc gccccgaaga acgttttcca    5460
atgatgagca cttttaaagt tctgctatgt ggcgcggtat tatcccgtat tgacgccggg    5520
caagagcaac tcggtcgccg catacactat tctcagaatg acttggttga gtactcacca    5580
gtcacagaaa agcatcttac ggatggcatg acagtaagag aattatgcag tgctgccata    5640
accatgagtg ataacactgc ggccaactta cttctgacaa cgatcggagg accgaaggag    5700
ctaaccgctt ttttgcacaa catgggggat catgtaactc gccttgatcg ttgggaaccg    5760
gagctgaatg aagccatacc aaacgacgag cgtgacacca cgatgcctgt agcaatggca    5820
acaacgttgc gcaaactatt aactggcgaa ctacttactc tagcttcccg gcaacaatta    5880
atagactgga tggaggcgga taaagttgca ggaccacttc tgcgctcggc ccttccggct    5940
ggctggttta ttgctgataa atctggagcc ggtgagcgtg ggtctcgcgg tatcattgca    6000
gcactggggc cagatggtaa gccctcccgt atcgtagtta tctacacgac ggggagtcag    6060
gcaactatgg atgaacgaaa tagacagatc gctgagatag gtgcctcact gattaagcat    6120
tggtaactgt cagaccaagt ttactcatat atactttaga ttgatttaaa acttcatttt    6180
taatttaaaa ggatctaggt gaagatcctt tttgataatc tcatgaccaa aatcccttaa    6240
cgtgagtttt cgttccactg agcgtcagac cccgtagaaa agatcaaagg atcttcttga    6300
gatccttttt ttctgcgcgt aatctgctgc ttgcaaacaa aaaaaccacc gctaccagcg    6360
gtggtttgtt tgccggatca agagctacca actctttttc cgaaggtaac tggcttcagc    6420
agagcgcaga taccaaatac tgttcttcta gtgtagccgt agttaggcca ccacttcaag    6480
aactctgtag caccgcctac atacctcgct ctgctaatcc tgttaccagt ggctgctgcc    6540
agtggcgata agtcgtgtct taccgggttg gactcaagac gatagttacc ggataaggcg    6600
cagcggtcgg gctgaacggg gggttcgtgc acacagccca gcttggagcg aacgacctac    6660
accgaactga gatacctaca gcgtgagcta tgagaaagcg ccacgcttcc cgaagggaga    6720
aaggcggaca ggtatccggt aagcggcagg gtcggaacag gagagcgcac gagggagctt    6780
ccagggggaa acgcctggta tctttatagt cctgtcgggt ttcgccacct ctgacttgag    6840
cgtcgatttt tgtgatgctc gtcaggggggg cggagcctat ggaaaaacgc cagcaacgcg    6900
gcctttttac ggttcctggc cttttgctgg ccttttgctc acatgttctt tcctgcgtta    6960
tcccctgatt ctgtggataa ccgtattacc gcctttgagt gagctgatac cgctcgccgc    7020
agccgaacga ccgagcgcag cgagtcagtg agcgaggaag cggaagagcg cccaatacgc    7080
aaaccgcctc tccccgcgcg ttggccgatt cattaatgca gctggcacga caggtttccc    7140
gactggaaag cgggcagtga gcgcaacgca attaatgtga gttagctcac tcattaggca    7200
ccccaggctt tacactttat gcttccggct cgtatgttgt gtggaattgt gagcggataa    7260
caatttcaca caggaaacag ctatgaccat gattacgcca agcgcgcaat taaccctcac    7320
taaagggaac aaaagctgga gctgcaagct taatgtagtc ttatgcaata ctcttgtagt    7380
cttgcaacat ggtaacgatg agttagcaac atgccttaca aggagagaaa aagcaccgtg    7440
catgccgatt ggtggaagta aggtggtacg atcgtgcctt attaggaagg caacagacgg    7500
gtctgacatg gattggacga accactgaat tgccgcattg cagagatatt gtatttaagt    7560
gcctagctcg atacataaac                                                7580
```

<210> SEQ ID NO 11

<211> LENGTH: 1368
<212> TYPE: PRT
<213> ORGANISM: Artificial Sequence
<220> FEATURE:
<223> OTHER INFORMATION: Synthetic Construct

<400> SEQUENCE: 11

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                    85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
        210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380
```

```
Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800
```

```
Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
```

```
                1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 12
<211> LENGTH: 1309
<212> TYPE: PRT
<213> ORGANISM: Artificial Sequence
<220> FEATURE:
<223> OTHER INFORMATION: Synthetic Construct

<400> SEQUENCE: 12

Glu Ala Thr Arg Leu Lys Arg Thr Ala Arg Arg Tyr Thr Arg Arg
1               5                   10                  15

Lys Asn Arg Ile Cys Tyr Leu Gln Glu Ile Phe Ser Asn Glu Met Ala
            20                  25                  30

Lys Val Asp Asp Ser Phe Phe His Arg Leu Glu Glu Ser Phe Leu Val
        35                  40                  45

Glu Glu Asp Lys Lys His Glu Arg His Pro Ile Phe Gly Asn Ile Val
    50                  55                  60

Asp Glu Val Ala Tyr His Glu Lys Tyr Pro Thr Ile Tyr His Leu Arg
65                  70                  75                  80

Lys Lys Leu Val Asp Ser Thr Asp Lys Ala Asp Leu Arg Leu Ile Tyr
                85                  90                  95

Leu Ala Leu Ala His Met Ile Lys Phe Arg Gly His Phe Leu Ile Glu
            100                 105                 110

Gly Asp Leu Asn Pro Asp Asn Ser Asp Val Asp Lys Leu Phe Ile Gln
        115                 120                 125

Leu Val Gln Thr Tyr Asn Gln Leu Phe Glu Glu Asn Pro Ile Asn Ala
    130                 135                 140

Ser Gly Val Asp Ala Lys Ala Ile Leu Ser Ala Arg Leu Ser Lys Ser
145                 150                 155                 160

Arg Arg Leu Glu Asn Leu Ile Ala Gln Leu Pro Gly Glu Lys Lys Asn
                165                 170                 175

Gly Leu Phe Gly Asn Leu Ile Ala Leu Ser Leu Gly Leu Thr Pro Asn
            180                 185                 190

Phe Lys Ser Asn Phe Asp Leu Ala Glu Asp Ala Lys Leu Gln Leu Ser
```

```
                195                 200                 205
Lys Asp Thr Tyr Asp Asp Leu Asp Asn Leu Leu Ala Gln Ile Gly
    210                 215                 220

Asp Gln Tyr Ala Asp Leu Phe Leu Ala Ala Lys Asn Leu Ser Asp Ala
225                 230                 235                 240

Ile Leu Leu Ser Asp Ile Leu Arg Val Asn Thr Glu Ile Thr Lys Ala
                245                 250                 255

Pro Leu Ser Ala Ser Met Ile Lys Arg Tyr Asp Glu His His Gln Asp
                260                 265                 270

Leu Thr Leu Leu Lys Ala Leu Val Arg Gln Gln Leu Pro Glu Lys Tyr
    275                 280                 285

Lys Glu Ile Phe Phe Asp Gln Ser Lys Asn Gly Tyr Ala Gly Tyr Ile
    290                 295                 300

Asp Gly Gly Ala Ser Gln Glu Glu Phe Tyr Lys Phe Ile Lys Pro Ile
305                 310                 315                 320

Leu Glu Lys Met Asp Gly Thr Glu Glu Leu Leu Val Lys Leu Asn Arg
                325                 330                 335

Glu Asp Leu Leu Arg Lys Gln Arg Thr Phe Asp Asn Gly Ser Ile Pro
                340                 345                 350

His Gln Ile His Leu Gly Glu Leu His Ala Ile Leu Arg Arg Gln Glu
            355                 360                 365

Asp Phe Tyr Pro Phe Leu Lys Asp Asn Arg Glu Lys Ile Glu Lys Ile
    370                 375                 380

Leu Thr Phe Arg Ile Pro Tyr Tyr Val Gly Pro Leu Ala Arg Gly Asn
385                 390                 395                 400

Ser Arg Phe Ala Trp Met Thr Arg Lys Ser Glu Glu Thr Ile Thr Pro
                405                 410                 415

Trp Asn Phe Glu Glu Val Val Asp Lys Gly Ala Ser Ala Gln Ser Phe
                420                 425                 430

Ile Glu Arg Met Thr Asn Phe Asp Lys Asn Leu Pro Asn Glu Lys Val
            435                 440                 445

Leu Pro Lys His Ser Leu Leu Tyr Glu Tyr Phe Thr Val Tyr Asn Glu
    450                 455                 460

Leu Thr Lys Val Lys Tyr Val Thr Glu Gly Met Arg Lys Pro Ala Phe
465                 470                 475                 480

Leu Ser Gly Glu Gln Lys Lys Ala Ile Val Asp Leu Leu Phe Lys Thr
                485                 490                 495

Asn Arg Lys Val Thr Val Lys Gln Leu Lys Glu Asp Tyr Phe Lys Lys
                500                 505                 510

Ile Glu Cys Phe Asp Ser Val Glu Ile Ser Gly Val Glu Asp Arg Phe
            515                 520                 525

Asn Ala Ser Leu Gly Thr Tyr His Asp Leu Leu Lys Ile Ile Lys Asp
    530                 535                 540

Lys Asp Phe Leu Asp Asn Glu Glu Asn Glu Asp Ile Leu Glu Asp Ile
545                 550                 555                 560

Val Leu Thr Leu Thr Leu Phe Glu Asp Arg Glu Met Ile Glu Glu Arg
                565                 570                 575

Leu Lys Thr Tyr Ala His Leu Phe Asp Asp Lys Val Met Lys Gln Leu
            580                 585                 590

Lys Arg Arg Arg Tyr Thr Gly Trp Gly Arg Leu Ser Arg Lys Leu Ile
    595                 600                 605

Asn Gly Ile Arg Asp Lys Gln Ser Gly Lys Thr Ile Leu Asp Phe Leu
    610                 615                 620
```

```
Lys Ser Asp Gly Phe Ala Asn Arg Asn Phe Met Gln Leu Ile His Asp
625                 630                 635                 640

Asp Ser Leu Thr Phe Lys Glu Asp Ile Gln Lys Ala Gln Val Ser Gly
                645                 650                 655

Gln Gly Asp Ser Leu His Glu His Ile Ala Asn Leu Ala Gly Ser Pro
                660                 665                 670

Ala Ile Lys Lys Gly Ile Leu Gln Thr Val Lys Val Val Asp Glu Leu
            675                 680                 685

Val Lys Val Met Gly Arg His Lys Pro Glu Asn Ile Val Ile Glu Met
690                 695                 700

Ala Arg Glu Asn Gln Thr Thr Gln Lys Gly Gln Lys Asn Ser Arg Glu
705                 710                 715                 720

Arg Met Lys Arg Ile Glu Glu Gly Ile Lys Glu Leu Gly Ser Gln Ile
                725                 730                 735

Leu Lys Glu His Pro Val Glu Asn Thr Gln Leu Gln Asn Glu Lys Leu
            740                 745                 750

Tyr Leu Tyr Tyr Leu Gln Asn Gly Arg Asp Met Tyr Val Asp Gln Glu
            755                 760                 765

Leu Asp Ile Asn Arg Leu Ser Asp Tyr Asp Val Asp His Ile Val Pro
        770                 775                 780

Gln Ser Phe Leu Lys Asp Asp Ser Ile Asp Asn Lys Val Leu Thr Arg
785                 790                 795                 800

Ser Asp Lys Asn Arg Gly Lys Ser Asp Asn Val Pro Ser Glu Glu Val
                805                 810                 815

Val Lys Lys Met Lys Asn Tyr Trp Arg Gln Leu Leu Asn Ala Lys Leu
                820                 825                 830

Ile Thr Gln Arg Lys Phe Asp Asn Leu Thr Lys Ala Glu Arg Gly Gly
            835                 840                 845

Leu Ser Glu Leu Asp Lys Ala Gly Phe Ile Lys Arg Gln Leu Val Glu
850                 855                 860

Thr Arg Gln Ile Thr Lys His Val Ala Gln Ile Leu Asp Ser Arg Met
865                 870                 875                 880

Asn Thr Lys Tyr Asp Glu Asn Asp Lys Leu Ile Arg Glu Val Lys Val
                885                 890                 895

Ile Thr Leu Lys Ser Lys Leu Val Ser Asp Phe Arg Lys Asp Phe Gln
            900                 905                 910

Phe Tyr Lys Val Arg Glu Ile Asn Asn Tyr His His Ala His Asp Ala
            915                 920                 925

Tyr Leu Asn Ala Val Val Gly Thr Ala Leu Ile Lys Lys Tyr Pro Lys
            930                 935                 940

Leu Glu Ser Glu Phe Val Tyr Gly Asp Tyr Lys Val Tyr Asp Val Arg
945                 950                 955                 960

Lys Met Ile Ala Lys Ser Glu Gln Glu Ile Gly Lys Ala Thr Ala Lys
                965                 970                 975

Tyr Phe Phe Tyr Ser Asn Ile Met Asn Phe Phe Lys Thr Glu Ile Thr
            980                 985                 990

Leu Ala Asn Gly Glu Ile Arg Lys Arg Pro Leu Ile Glu Thr Asn Gly
            995                 1000                1005

Glu Thr Gly Glu Ile Val Trp Asp Lys Gly Arg Asp Phe Ala Thr
    1010                1015                1020

Val Arg Lys Val Leu Ser Met Pro Gln Val Asn Ile Val Lys Lys
    1025                1030                1035
```

Thr Glu Val Gln Thr Gly Gly Phe Ser Lys Glu Ser Ile Arg Pro
    1040                1045                1050

Lys Arg Asn Ser Asp Lys Leu Ile Ala Arg Lys Lys Asp Trp Asp
    1055                1060                1065

Pro Lys Lys Tyr Gly Gly Phe Val Ser Pro Thr Val Ala Tyr Ser
    1070                1075                1080

Val Leu Val Val Ala Lys Val Glu Lys Gly Lys Ser Lys Lys Leu
    1085                1090                1095

Lys Ser Val Lys Glu Leu Leu Gly Ile Thr Ile Met Glu Arg Ser
    1100                1105                1110

Ser Phe Glu Lys Asn Pro Ile Asp Phe Leu Glu Ala Lys Gly Tyr
    1115                1120                1125

Lys Glu Val Lys Lys Asp Leu Ile Ile Lys Leu Pro Lys Tyr Ser
    1130                1135                1140

Leu Phe Glu Leu Glu Asn Gly Arg Lys Arg Met Leu Ala Ser Ala
    1145                1150                1155

Arg Phe Leu Gln Lys Gly Asn Glu Leu Ala Leu Pro Ser Lys Tyr
    1160                1165                1170

Val Asn Phe Leu Tyr Leu Ala Ser His Tyr Glu Lys Leu Lys Gly
    1175                1180                1185

Ser Pro Glu Asp Asn Glu Gln Lys Gln Leu Phe Val Glu Gln His
    1190                1195                1200

Lys His Tyr Leu Asp Glu Ile Ile Glu Gln Ile Ser Glu Phe Ser
    1205                1210                1215

Lys Arg Val Ile Leu Ala Asp Ala Asn Leu Asp Lys Val Leu Ser
    1220                1225                1230

Ala Tyr Asn Lys His Arg Asp Lys Pro Ile Arg Glu Gln Ala Glu
    1235                1240                1245

Asn Ile Ile His Leu Phe Thr Leu Thr Asn Leu Gly Ala Pro Arg
    1250                1255                1260

Ala Phe Lys Tyr Phe Asp Thr Thr Ile Asp Arg Lys Val Tyr Arg
    1265                1270                1275

Ser Thr Lys Glu Val Leu Asp Ala Thr Leu Ile His Gln Ser Ile
    1280                1285                1290

Thr Gly Leu Tyr Glu Thr Arg Ile Asp Leu Ser Gln Leu Gly Gly
    1295                1300                1305

Asp

<210> SEQ ID NO 13
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 13

Met Asp Lys Lys Tyr Ser Ile Gly Leu Ala Ile Gly Thr Asn Ser Val
  1               5                  10                  15

Gly Trp Ala Val Ile Thr Asp Glu Tyr Lys Val Pro Ser Lys Lys Phe
             20                  25                  30

Lys Val Leu Gly Asn Thr Asp Arg His Ser Ile Lys Lys Asn Leu Ile
         35                  40                  45

Gly Ala Leu Leu Phe Asp Ser Gly Glu Thr Ala Glu Ala Thr Arg Leu
     50                  55                  60

Lys Arg Thr Ala Arg Arg Arg Tyr Thr Arg Arg Lys Asn Arg Ile Cys

-continued

```
                65                  70                  75                  80
Tyr Leu Gln Glu Ile Phe Ser Asn Glu Met Ala Lys Val Asp Asp Ser
                    85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Thr Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Leu Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ile Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
                450                 455                 460
Met Thr Arg Lys Ser Glu Glu Thr Ile Thr Pro Trp Asn Phe Glu Lys
465                 470                 475                 480
Val Val Asp Lys Gly Ala Ser Ala Gln Ser Phe Ile Glu Arg Met Thr
                485                 490                 495
```

```
Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Asp Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
            645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Ile Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
            850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910
```

```
Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Val Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
```

```
            1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 14
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 14

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Thr Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

-continued

```
                305                 310                 315                 320
            Met Ile Lys Leu Tyr Asp Glu His His Gln Asp Leu Thr Leu Leu Lys
                                325                 330                 335

Ala Leu Val Arg Gln Gln Leu Pro Glu Lys Tyr Lys Glu Ile Phe Phe
                            340                 345                 350

Asp Gln Ser Lys Asn Gly Tyr Ala Gly Tyr Ile Asp Gly Gly Ala Ser
                        355                 360                 365

Gln Glu Glu Phe Tyr Lys Phe Ile Lys Pro Ile Leu Glu Lys Met Asp
                    370                 375                 380

Gly Thr Glu Glu Leu Leu Val Lys Leu Asn Arg Glu Asp Leu Leu Arg
            385                 390                 395                 400

Lys Gln Arg Thr Phe Asp Asn Gly Ile Ile Pro His Gln Ile His Leu
                            405                 410                 415

Gly Glu Leu His Ala Ile Leu Arg Arg Gln Glu Asp Phe Tyr Pro Phe
                        420                 425                 430

Leu Lys Asp Asn Arg Glu Lys Ile Glu Lys Ile Leu Thr Phe Arg Ile
                    435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Lys
            465                 470                 475                 480

Val Val Asp Lys Gly Ala Ser Ala Gln Ser Phe Ile Glu Arg Met Thr
                            485                 490                 495

Asn Phe Asp Lys Asn Leu Pro Asn Glu Lys Val Leu Pro Lys His Ser
                        500                 505                 510

Leu Leu Tyr Glu Tyr Phe Thr Val Tyr Asn Glu Leu Thr Lys Val Lys
                    515                 520                 525

Tyr Val Thr Glu Gly Met Arg Lys Pro Ala Phe Leu Ser Gly Asp Gln
                530                 535                 540

Lys Lys Ala Ile Val Asp Leu Leu Phe Lys Thr Asn Arg Lys Val Thr
            545                 550                 555                 560

Val Lys Gln Leu Lys Glu Asp Tyr Phe Lys Lys Ile Glu Cys Phe Asp
                            565                 570                 575

Ser Val Glu Ile Ser Gly Val Glu Asp Arg Phe Asn Ala Ser Leu Gly
                        580                 585                 590

Thr Tyr His Asp Leu Leu Lys Ile Ile Lys Asp Lys Asp Phe Leu Asp
                    595                 600                 605

Asn Glu Glu Asn Glu Asp Ile Leu Glu Asp Ile Val Leu Thr Leu Thr
                610                 615                 620

Leu Phe Glu Asp Arg Glu Met Ile Glu Glu Arg Leu Lys Thr Tyr Ala
            625                 630                 635                 640

His Leu Phe Asp Asp Lys Val Met Lys Gln Leu Lys Arg Arg Arg Tyr
                            645                 650                 655

Thr Gly Trp Gly Arg Leu Ser Arg Lys Leu Ile Asn Gly Ile Arg Asp
                        660                 665                 670

Lys Gln Ser Gly Lys Thr Ile Leu Asp Phe Leu Lys Ser Asp Gly Phe
                    675                 680                 685

Ala Asn Arg Asn Phe Ile Gln Leu Ile His Asp Asp Ser Leu Thr Phe
                690                 695                 700

Lys Glu Asp Ile Gln Lys Ala Gln Val Ser Gly Gln Gly Asp Ser Leu
            705                 710                 715                 720

His Glu His Ile Ala Asn Leu Ala Gly Ser Pro Ala Ile Lys Lys Gly
                            725                 730                 735
```

-continued

```
Ile Leu Gln Thr Val Lys Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
     1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Arg Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Val Ser Pro Thr Val Ala Tyr Ser Val
    1130                1135                1140
```

-continued

```
Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Arg
    1205                1210                1215

Phe Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Arg Ala
    1310                1315                1320

Phe Lys Tyr Phe Asp Thr Thr Ile Asp Arg Lys Val Tyr Arg Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 15
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 15

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

```
His Glu Lys Tyr Pro Thr Ile Tyr His Leu Arg Lys Leu Val Asp
130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
```

```
               545                 550                 555                 560
     Val Lys Gln Leu Lys Glu Asp Tyr Phe Lys Ile Glu Cys Phe Asp
                         565                 570                 575

Ser Val Glu Ile Ser Gly Val Glu Asp Arg Phe Asn Ala Ser Leu Gly
                         580                 585                 590

Thr Tyr His Asp Leu Leu Lys Ile Ile Lys Asp Lys Asp Phe Leu Asp
                         595                 600                 605

Asn Glu Glu Asn Glu Asp Ile Leu Glu Asp Ile Val Leu Thr Leu Thr
                 610                 615                 620

Leu Phe Glu Asp Arg Glu Met Ile Glu Glu Arg Leu Lys Thr Tyr Ala
     625                 630                 635                 640

His Leu Phe Asp Asp Lys Val Met Lys Gln Leu Lys Arg Arg Arg Tyr
                         645                 650                 655

Thr Gly Trp Gly Arg Leu Ser Arg Lys Leu Ile Asn Gly Ile Arg Asp
                         660                 665                 670

Lys Gln Ser Gly Lys Thr Ile Leu Asp Phe Leu Lys Ser Asp Gly Phe
                         675                 680                 685

Ala Asn Arg Asn Phe Met Gln Leu Ile His Asp Asp Ser Leu Thr Phe
                 690                 695                 700

Lys Glu Asp Ile Gln Lys Ala Gln Val Ser Gly Gln Gly Asp Ser Leu
     705                 710                 715                 720

His Glu His Ile Ala Asn Leu Ala Gly Ser Pro Ala Ile Lys Lys Gly
                         725                 730                 735

Ile Leu Gln Thr Val Lys Val Val Asp Glu Leu Val Lys Val Met Gly
                         740                 745                 750

Arg His Lys Pro Glu Asn Ile Val Ile Glu Met Ala Arg Glu Asn Gln
                         755                 760                 765

Thr Thr Gln Lys Gly Gln Lys Asn Ser Arg Glu Arg Met Lys Arg Ile
                 770                 775                 780

Glu Glu Gly Ile Lys Glu Leu Gly Ser Gln Ile Leu Lys Glu His Pro
     785                 790                 795                 800

Val Glu Asn Thr Gln Leu Gln Asn Glu Lys Leu Tyr Leu Tyr Tyr Leu
                         805                 810                 815

Gln Asn Gly Arg Asp Met Tyr Val Asp Gln Glu Leu Asp Ile Asn Arg
                         820                 825                 830

Leu Ser Asp Tyr Asp Val Asp His Ile Val Pro Gln Ser Phe Leu Lys
                 835                 840                 845

Asp Asp Ser Ile Asp Asn Lys Val Leu Thr Arg Ser Asp Lys Asn Arg
     850                 855                 860

Gly Lys Ser Asp Asn Val Pro Ser Glu Glu Val Val Lys Lys Met Lys
     865                 870                 875                 880

Asn Tyr Trp Arg Gln Leu Leu Asn Ala Lys Leu Ile Thr Gln Arg Lys
                         885                 890                 895

Phe Asp Asn Leu Thr Lys Ala Glu Arg Gly Gly Leu Ser Glu Leu Asp
                         900                 905                 910

Lys Ala Gly Phe Ile Lys Arg Gln Leu Val Glu Thr Arg Gln Ile Thr
                         915                 920                 925

Lys His Val Ala Gln Ile Leu Asp Ser Arg Met Asn Thr Lys Tyr Asp
                 930                 935                 940

Glu Asn Asp Lys Leu Ile Arg Glu Val Lys Val Ile Thr Leu Lys Ser
     945                 950                 955                 960

Lys Leu Val Ser Asp Phe Arg Lys Asp Phe Gln Phe Tyr Lys Val Arg
                         965                 970                 975
```

```
Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Arg Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Val Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Arg
        1205                1210                1215

Phe Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Arg Ala
        1310                1315                1320

Phe Lys Tyr Phe Asp Thr Thr Ile Asp Arg Lys Gln Tyr Arg Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365
```

```
<210> SEQ ID NO 16
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 16

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
```

```
            785                 790                 795                 800
Val Glu Asn Thr Gln Leu Gln Asn Glu Lys Leu Tyr Leu Tyr Tyr Leu
                    805                 810                 815
Gln Asn Gly Arg Asp Met Tyr Val Asp Gln Glu Leu Asp Ile Asn Arg
                    820                 825                 830
Leu Ser Asp Tyr Asp Val Asp His Ile Val Pro Gln Ser Phe Leu Lys
                    835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                    885                 890                 895
Phe Asp Asn Leu Thr Lys Ala Glu Arg Gly Gly Leu Ser Glu Leu Asp
                    900                 905                 910
Lys Ala Gly Phe Ile Lys Arg Gln Leu Val Glu Thr Arg Gln Ile Thr
                    915                 920                 925
Lys His Val Ala Gln Ile Leu Asp Ser Arg Met Asn Thr Lys Tyr Asp
                    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                    965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                    995                 1000                1005
Val Tyr Gly Asp Tyr Lys Val Tyr Asp Val Arg Lys Met Ile Ala
                    1010                1015                1020
Lys Ser Glu Gln Glu Ile Gly Lys Ala Thr Ala Lys Tyr Phe Phe
                    1025                1030                1035
Tyr Ser Asn Ile Met Asn Phe Phe Lys Thr Glu Ile Thr Leu Ala
                    1040                1045                1050
Asn Gly Glu Ile Arg Lys Arg Pro Leu Ile Glu Thr Asn Gly Glu
                    1055                1060                1065
Thr Gly Glu Ile Val Trp Asp Lys Gly Arg Asp Phe Ala Thr Val
                    1070                1075                1080
Arg Lys Val Leu Ser Met Pro Gln Val Asn Ile Val Lys Lys Thr
                    1085                1090                1095
Glu Val Gln Thr Gly Gly Phe Ser Lys Glu Ser Ile Arg Pro Lys
                    1100                1105                1110
Arg Asn Ser Asp Lys Leu Ile Ala Arg Lys Lys Asp Trp Asp Pro
                    1115                1120                1125
Lys Lys Tyr Gly Gly Phe Val Ser Pro Thr Val Ala Tyr Ser Val
                    1130                1135                1140
Leu Val Val Ala Lys Val Glu Lys Gly Lys Ser Lys Lys Leu Lys
                    1145                1150                1155
Ser Val Lys Glu Leu Leu Gly Ile Thr Ile Met Glu Arg Ser Ser
                    1160                1165                1170
Phe Glu Lys Asn Pro Ile Asp Phe Leu Glu Ala Lys Gly Tyr Lys
                    1175                1180                1185
Glu Val Lys Lys Asp Leu Ile Ile Lys Leu Pro Lys Tyr Ser Leu
                    1190                1195                1200
```

```
Phe Glu Leu Glu Asn Gly Arg Lys Arg Met Leu Ala Ser Ala Arg
    1205                1210                1215

Phe Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Arg Ala
    1310                1315                1320

Phe Lys Tyr Phe Asp Thr Thr Ile Asp Arg Lys Glu Tyr Arg Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 17
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 17

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190
```

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Thr Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Leu Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ile Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Lys
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Asp Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605
```

```
Asn Glu Glu Asn Glu Asp Ile Leu Glu Asp Ile Val Leu Thr Leu Thr
            610             615             620

Leu Phe Glu Asp Arg Glu Met Ile Glu Arg Leu Lys Thr Tyr Ala
625             630             635             640

His Leu Phe Asp Asp Lys Val Met Lys Gln Leu Lys Arg Arg Arg Tyr
                645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
        675             680             685

Ala Asn Arg Asn Phe Ile Gln Leu Ile His Asp Ser Leu Thr Phe
690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
        755             760             765

Thr Thr Gln Lys Gly Gln Lys Asn Ser Arg Glu Arg Met Lys Arg Ile
770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp His Ile Val Pro Gln Ser Phe Leu Lys
        835             840             845

Asp Asp Ser Ile Asp Asn Lys Val Leu Thr Arg Ser Asp Lys Asn Arg
        850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
        915             920             925

Lys His Val Ala Gln Ile Leu Asp Ser Arg Met Asn Thr Lys Tyr Asp
        930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys Tyr Pro Lys Leu Glu Ser Glu Phe
            995             1000            1005

Val Tyr Gly Asp Tyr Lys Val Tyr Asp Val Arg Lys Met Ile Ala
        1010            1015            1020

Lys Ser Glu Gln Glu Ile Gly Lys Ala Thr Ala Lys Tyr Phe Phe
```

```
            1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Arg Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Val Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Arg
        1205                1210                1215

Phe Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Arg Ala
        1310                1315                1320

Phe Lys Tyr Phe Asp Thr Thr Ile Asp Arg Lys Gln Tyr Arg Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
        1355                1360                1365

<210> SEQ ID NO 18
<211> LENGTH: 1368
<212> TYPE: PRT
<213> ORGANISM: Artificial Sequence
<220> FEATURE:
<223> OTHER INFORMATION: Synthetic Construct

<400> SEQUENCE: 18

Met Asp Lys Lys Tyr Ser Ile Gly Leu Ala Ile Gly Thr Asn Ser Val
```

-continued

```
1               5                   10                  15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
                35                  40                  45
Gly Ala Leu Leu Phe Asp Ser Gly Glu Thr Ala Glu Ala Thr Arg Leu
                50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
                115                 120                 125
His Glu Lys Tyr Pro Thr Ile Tyr His Leu Arg Lys Lys Leu Val Asp
                130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
                180                 185                 190
Asn Gln Leu Phe Glu Glu Asn Pro Ile Asn Ala Ser Gly Val Asp Ala
                195                 200                 205
Lys Ala Ile Leu Ser Ala Arg Leu Ser Lys Ser Arg Arg Leu Glu Asn
                210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Thr Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
                275                 280                 285
Leu Phe Leu Ala Ala Lys Asn Leu Ser Asp Ala Ile Leu Leu Ser Asp
                290                 295                 300
Ile Leu Arg Val Asn Thr Glu Ile Thr Lys Ala Pro Leu Ser Ala Ser
305                 310                 315                 320
Met Ile Lys Leu Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
                340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
                370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ile Ile Pro His Gln Ile His Leu
                405                 410                 415
Gly Glu Leu His Ala Ile Leu Arg Arg Gln Glu Asp Phe Tyr Pro Phe
                420                 425                 430
```

```
Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Lys
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Asp Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Ile Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845
```

-continued

```
Asp Asp Ser Ile Asp Asn Lys Val Leu Thr Arg Ser Asp Lys Asn Arg
            850                 855                 860
Gly Lys Ser Asp Asn Val Pro Ser Glu Val Val Lys Lys Met Lys
865                 870                 875                 880
Asn Tyr Trp Arg Gln Leu Leu Asn Ala Lys Leu Ile Thr Gln Arg Lys
            885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
            930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
            965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
            995                1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Arg Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Val Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Arg
    1205                1210                1215
Phe Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
```

-continued

```
               1250                1255                1260

His Tyr Leu Asp Glu Ile Ile Glu Gln Ile Ser Glu Phe Ser Lys
               1265                1270                1275

Arg Val Ile Leu Ala Asp Ala Asn Leu Asp Lys Val Leu Ser Ala
               1280                1285                1290

Tyr Asn Lys His Arg Asp Lys Pro Ile Arg Glu Gln Ala Glu Asn
               1295                1300                1305

Ile Ile His Leu Phe Thr Leu Thr Asn Leu Gly Ala Pro Arg Ala
               1310                1315                1320

Phe Lys Tyr Phe Asp Thr Thr Ile Asp Arg Lys Glu Tyr Arg Ser
               1325                1330                1335

Thr Lys Glu Val Leu Asp Ala Thr Leu Ile His Gln Ser Ile Thr
               1340                1345                1350

Gly Leu Tyr Glu Thr Arg Ile Asp Leu Ser Gln Leu Gly Gly Asp
               1355                1360                1365

<210> SEQ ID NO 19
<211> LENGTH: 1378
<212> TYPE: PRT
<213> ORGANISM: Artificial Sequence
<220> FEATURE:
<223> OTHER INFORMATION: Synthetic Construct

<400> SEQUENCE: 19

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
                20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
```

```
                         245                 250                 255
Asp Leu Ala Glu Asp Ala Lys Leu Gln Leu Ser Lys Asp Thr Tyr Asp
                 260                 265                 270

Asp Asp Leu Asp Asn Leu Leu Ala Gln Ile Gly Asp Gln Tyr Ala Asp
             275                 280                 285

Leu Phe Leu Ala Ala Lys Asn Leu Ser Asp Ala Ile Leu Leu Ser Asp
         290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                 325                 330                 335

Ala Leu Val Arg Gln Gln Leu Pro Glu Lys Tyr Lys Glu Ile Phe Phe
             340                 345                 350

Asp Gln Ser Lys Asn Gly Tyr Ala Gly Tyr Val Gly Ala Asp Lys Lys
         355                 360                 365

Leu Arg Lys Arg Ser Ser Lys Leu Ala Thr Glu Glu Phe Tyr Lys
    370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp
                 405                 410                 415

Asn Gly Ser Ile Pro His Gln Ile His Leu Gly Glu Leu His Ala Ile
             420                 425                 430

Leu Arg Arg Gln Glu Asp Phe Tyr Pro Phe Leu Lys Asp Asn Arg Glu
         435                 440                 445

Lys Ile Glu Lys Ile Leu Thr Phe Arg Ile Pro Tyr Tyr Val Gly Pro
    450                 455                 460

Leu Ala Arg Gly Asn Ser Arg Phe Ala Trp Met Thr Arg Lys Ser Glu
465                 470                 475                 480

Glu Thr Ile Thr Pro Trp Asn Phe Glu Glu Val Val Asp Lys Gly Ala
                 485                 490                 495

Ser Ala Gln Ser Phe Ile Glu Arg Met Thr Asn Phe Asp Lys Asn Leu
             500                 505                 510

Pro Asn Glu Lys Val Leu Pro Lys His Ser Leu Leu Tyr Glu Tyr Phe
         515                 520                 525

Thr Val Tyr Asn Glu Leu Thr Lys Val Lys Tyr Val Thr Glu Gly Met
    530                 535                 540

Arg Lys Pro Ala Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                 565                 570                 575

Asp Tyr Phe Lys Lys Ile Glu Cys Phe Asp Ser Val Glu Ile Ser Gly
             580                 585                 590

Val Glu Asp Arg Phe Asn Ala Ser Leu Gly Thr Tyr His Asp Leu Leu
         595                 600                 605

Lys Ile Ile Lys Asp Lys Asp Phe Leu Asp Asn Glu Glu Asn Glu Asp
    610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
                 645                 650                 655

Val Met Lys Gln Leu Lys Arg Arg Arg Tyr Thr Gly Trp Gly Arg Leu
             660                 665                 670
```

-continued

Ser Arg Lys Leu Ile Asn Gly Ile Arg Asp Lys Gln Ser Gly Lys Thr
        675                 680                 685

Ile Leu Asp Phe Leu Lys Ser Asp Gly Phe Ala Asn Arg Asn Phe Met
690                 695                 700

Gln Leu Ile His Asp Asp Ser Leu Thr Phe Lys Glu Asp Ile Gln Lys
705                 710                 715                 720

Ala Gln Val Ser Gly Gln Gly Asp Ser Leu His Glu His Ile Ala Asn
                725                 730                 735

Leu Ala Gly Ser Pro Ala Ile Lys Lys Gly Ile Leu Gln Thr Val Lys
                740                 745                 750

Val Val Asp Glu Leu Val Lys Val Met Gly Arg His Lys Pro Glu Asn
                755                 760                 765

Ile Val Ile Glu Met Ala Arg Glu Asn Gln Thr Thr Gln Lys Gly Gln
770                 775                 780

Lys Asn Ser Arg Glu Arg Met Lys Arg Ile Glu Glu Gly Ile Lys Glu
785                 790                 795                 800

Leu Gly Ser Gln Ile Leu Lys Glu His Pro Val Glu Asn Thr Gln Leu
                805                 810                 815

Gln Asn Glu Lys Leu Tyr Leu Tyr Tyr Leu Gln Asn Gly Arg Asp Met
                820                 825                 830

Tyr Val Asp Gln Glu Leu Asp Ile Asn Arg Leu Ser Asp Tyr Asp Val
                835                 840                 845

Asp His Ile Val Pro Gln Ser Phe Leu Lys Asp Asp Ser Ile Asp Asn
850                 855                 860

Lys Val Leu Thr Arg Ser Asp Lys Asn Arg Gly Lys Ser Asp Asn Val
865                 870                 875                 880

Pro Ser Glu Glu Val Val Lys Lys Met Lys Asn Tyr Trp Arg Gln Leu
                885                 890                 895

Leu Asn Ala Lys Leu Ile Thr Gln Arg Lys Phe Asp Asn Leu Thr Lys
                900                 905                 910

Ala Glu Arg Gly Gly Leu Ser Glu Leu Asp Lys Ala Gly Phe Ile Lys
                915                 920                 925

Arg Gln Leu Val Glu Thr Arg Gln Ile Thr Lys His Val Ala Gln Ile
        930                 935                 940

Leu Asp Ser Arg Met Asn Thr Lys Tyr Asp Glu Asn Asp Lys Leu Ile
945                 950                 955                 960

Arg Glu Val Lys Val Ile Thr Leu Lys Ser Lys Leu Val Ser Asp Phe
                965                 970                 975

Arg Lys Asp Phe Gln Phe Tyr Lys Val Arg Glu Ile Asn Asn Tyr His
                980                 985                 990

His Ala His Asp Ala Tyr Leu Asn Ala Val Val Gly Thr Ala Leu Ile
        995                 1000                1005

Lys Lys Tyr Pro Lys Leu Glu Ser Glu Phe Val Tyr Gly Asp Tyr
        1010                1015                1020

Lys Val Tyr Asp Val Arg Lys Met Ile Ala Lys Ser Glu Gln Glu
        1025                1030                1035

Ile Gly Lys Ala Thr Ala Lys Tyr Phe Phe Tyr Ser Asn Ile Met
        1040                1045                1050

Asn Phe Phe Lys Thr Glu Ile Thr Leu Ala Asn Gly Glu Ile Arg
        1055                1060                1065

Lys Arg Pro Leu Ile Glu Thr Asn Gly Glu Thr Gly Glu Ile Val
        1070                1075                1080

Trp Asp Lys Gly Arg Asp Phe Ala Thr Val Arg Lys Val Leu Ser
    1085            1090                1095

Met Pro Gln Val Asn Ile Val Lys Lys Thr Glu Val Gln Thr Gly
    1100            1105                1110

Gly Phe Ser Lys Glu Ser Ile Arg Pro Lys Arg Asn Ser Asp Lys
    1115            1120                1125

Leu Ile Ala Arg Lys Lys Asp Trp Asp Pro Lys Lys Tyr Gly Gly
    1130            1135                1140

Phe Val Ser Pro Thr Val Ala Tyr Ser Val Leu Val Val Ala Lys
    1145            1150                1155

Val Glu Lys Gly Lys Ser Lys Lys Leu Lys Ser Val Lys Glu Leu
    1160            1165                1170

Leu Gly Ile Thr Ile Met Glu Arg Ser Ser Phe Glu Lys Asn Pro
    1175            1180                1185

Ile Asp Phe Leu Glu Ala Lys Gly Tyr Lys Glu Val Lys Lys Asp
    1190            1195                1200

Leu Ile Ile Lys Leu Pro Lys Tyr Ser Leu Phe Glu Leu Glu Asn
    1205            1210                1215

Gly Arg Lys Arg Met Leu Ala Ser Ala Arg Phe Leu Gln Lys Gly
    1220            1225                1230

Asn Glu Leu Ala Leu Pro Ser Lys Tyr Val Asn Phe Leu Tyr Leu
    1235            1240                1245

Ala Ser His Tyr Glu Lys Leu Lys Gly Ser Pro Glu Asp Asn Glu
    1250            1255                1260

Gln Lys Gln Leu Phe Val Glu Gln His Lys His Tyr Leu Asp Glu
    1265            1270                1275

Ile Ile Glu Gln Ile Ser Glu Phe Ser Lys Arg Val Ile Leu Ala
    1280            1285                1290

Asp Ala Asn Leu Asp Lys Val Leu Ser Ala Tyr Asn Lys His Arg
    1295            1300                1305

Asp Lys Pro Ile Arg Glu Gln Ala Glu Asn Ile Ile His Leu Phe
    1310            1315                1320

Thr Leu Thr Asn Leu Gly Ala Pro Arg Ala Phe Lys Tyr Phe Asp
    1325            1330                1335

Thr Thr Ile Asp Arg Lys Val Tyr Arg Ser Thr Lys Glu Val Leu
    1340            1345                1350

Asp Ala Thr Leu Ile His Gln Ser Ile Thr Gly Leu Tyr Glu Thr
    1355            1360                1365

Arg Ile Asp Leu Ser Gln Leu Gly Gly Asp
    1370            1375

<210> SEQ ID NO 20
<211> LENGTH: 1378
<212> TYPE: PRT
<213> ORGANISM: Artificial Sequence
<220> FEATURE:
<223> OTHER INFORMATION: Synthetic Construct

<400> SEQUENCE: 20

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

```
Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
 65                  70                  75                  80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Thr Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Leu Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Val Gly Ala Asp Lys Lys
        355                 360                 365

Leu Arg Lys Arg Ser Ser Lys Leu Ala Thr Glu Glu Phe Tyr Lys
        370                 375                 380

Phe Ile Lys Pro Ile Leu Glu Lys Met Asp Gly Thr Glu Glu Leu Leu
385                 390                 395                 400

Val Lys Leu Asn Arg Glu Asp Leu Leu Arg Lys Gln Arg Thr Phe Asp
                405                 410                 415

Asn Gly Ile Ile Pro His Gln Ile His Leu Gly Glu Leu His Ala Ile
            420                 425                 430

Leu Arg Arg Gln Glu Asp Phe Tyr Pro Phe Leu Lys Asp Asn Arg Glu
        435                 440                 445

Lys Ile Glu Lys Ile Leu Thr Phe Arg Ile Pro Tyr Tyr Val Gly Pro
450                 455                 460

Leu Ala Arg Gly Asn Ser Arg Phe Ala Trp Met Thr Arg Lys Ser Glu
```

-continued

```
            465                 470                 475                 480
        Glu Thr Ile Thr Pro Trp Asn Phe Glu Lys Val Val Asp Lys Gly Ala
                            485                 490                 495
        Ser Ala Gln Ser Phe Ile Glu Arg Met Thr Asn Phe Asp Lys Asn Leu
                            500                 505                 510
        Pro Asn Glu Lys Val Leu Pro Lys His Ser Leu Leu Tyr Glu Tyr Phe
                            515                 520                 525
        Thr Val Tyr Asn Glu Leu Thr Lys Val Lys Tyr Val Thr Glu Gly Met
                            530                 535                 540
        Arg Lys Pro Ala Phe Leu Ser Gly Asp Gln Lys Lys Ala Ile Val Asp
        545                 550                 555                 560
        Leu Leu Phe Lys Thr Asn Arg Lys Val Thr Val Lys Gln Leu Lys Glu
                            565                 570                 575
        Asp Tyr Phe Lys Lys Ile Glu Cys Phe Asp Ser Val Glu Ile Ser Gly
                            580                 585                 590
        Val Glu Asp Arg Phe Asn Ala Ser Leu Gly Thr Tyr His Asp Leu Leu
                            595                 600                 605
        Lys Ile Ile Lys Asp Lys Asp Phe Leu Asp Asn Glu Glu Asn Glu Asp
        610                 615                 620
        Ile Leu Glu Asp Ile Val Leu Thr Leu Thr Leu Phe Glu Asp Arg Glu
        625                 630                 635                 640
        Met Ile Glu Glu Arg Leu Lys Thr Tyr Ala His Leu Phe Asp Asp Lys
                            645                 650                 655
        Val Met Lys Gln Leu Lys Arg Arg Arg Tyr Thr Gly Trp Gly Arg Leu
                            660                 665                 670
        Ser Arg Lys Leu Ile Asn Gly Ile Arg Asp Lys Gln Ser Gly Lys Thr
                            675                 680                 685
        Ile Leu Asp Phe Leu Lys Ser Asp Gly Phe Ala Asn Arg Asn Phe Ile
                            690                 695                 700
        Gln Leu Ile His Asp Asp Ser Leu Thr Phe Lys Glu Asp Ile Gln Lys
        705                 710                 715                 720
        Ala Gln Val Ser Gly Gln Gly Asp Ser Leu His Glu His Ile Ala Asn
                            725                 730                 735
        Leu Ala Gly Ser Pro Ala Ile Lys Lys Gly Ile Leu Gln Thr Val Lys
                            740                 745                 750
        Val Val Asp Glu Leu Val Lys Val Met Gly Arg His Lys Pro Glu Asn
                            755                 760                 765
        Ile Val Ile Glu Met Ala Arg Glu Asn Gln Thr Thr Gln Lys Gly Gln
                            770                 775                 780
        Lys Asn Ser Arg Glu Arg Met Lys Arg Ile Glu Gly Ile Lys Glu
        785                 790                 795                 800
        Leu Gly Ser Gln Ile Leu Lys Glu His Pro Val Glu Asn Thr Gln Leu
                            805                 810                 815
        Gln Asn Glu Lys Leu Tyr Leu Tyr Tyr Leu Gln Asn Gly Arg Asp Met
                            820                 825                 830
        Tyr Val Asp Gln Glu Leu Asp Ile Asn Arg Leu Ser Asp Tyr Asp Val
                            835                 840                 845
        Asp His Ile Val Pro Gln Ser Phe Leu Lys Asp Ser Ile Asp Asn
                            850                 855                 860
        Lys Val Leu Thr Arg Ser Asp Lys Asn Arg Gly Lys Ser Asp Asn Val
        865                 870                 875                 880
        Pro Ser Glu Glu Val Val Lys Lys Met Lys Asn Tyr Trp Arg Gln Leu
                            885                 890                 895
```

-continued

```
Leu Asn Ala Lys Leu Ile Thr Gln Arg Lys Phe Asp Asn Leu Thr Lys
            900                 905                 910
Ala Glu Arg Gly Gly Leu Ser Glu Leu Asp Lys Ala Gly Phe Ile Lys
            915                 920                 925
Arg Gln Leu Val Glu Thr Arg Gln Ile Thr Lys His Val Ala Gln Ile
            930                 935                 940
Leu Asp Ser Arg Met Asn Thr Lys Tyr Asp Glu Asn Asp Lys Leu Ile
945                 950                 955                 960
Arg Glu Val Lys Val Ile Thr Leu Lys Ser Lys Leu Val Ser Asp Phe
                965                 970                 975
Arg Lys Asp Phe Gln Phe Tyr Lys Val Arg Glu Ile Asn Asn Tyr His
            980                 985                 990
His Ala His Asp Ala Tyr Leu Asn Ala Val Val Gly Thr Ala Leu Ile
            995                 1000                1005
Lys Lys Tyr Pro Lys Leu Glu Ser Glu Phe Val Tyr Gly Asp Tyr
            1010                1015                1020
Lys Val Tyr Asp Val Arg Lys Met Ile Ala Lys Ser Glu Gln Glu
            1025                1030                1035
Ile Gly Lys Ala Thr Ala Lys Tyr Phe Phe Tyr Ser Asn Ile Met
            1040                1045                1050
Asn Phe Phe Lys Thr Glu Ile Thr Leu Ala Asn Gly Glu Ile Arg
            1055                1060                1065
Lys Arg Pro Leu Ile Glu Thr Asn Gly Glu Thr Gly Glu Ile Val
            1070                1075                1080
Trp Asp Lys Gly Arg Asp Phe Ala Thr Val Arg Lys Val Leu Ser
            1085                1090                1095
Met Pro Gln Val Asn Ile Val Lys Lys Thr Glu Val Gln Thr Gly
            1100                1105                1110
Gly Phe Ser Lys Glu Ser Ile Arg Pro Lys Arg Asn Ser Asp Lys
            1115                1120                1125
Leu Ile Ala Arg Lys Lys Asp Trp Asp Pro Lys Lys Tyr Gly Gly
            1130                1135                1140
Phe Val Ser Pro Thr Val Ala Tyr Ser Val Leu Val Val Ala Lys
            1145                1150                1155
Val Glu Lys Gly Lys Ser Lys Lys Leu Lys Ser Val Lys Glu Leu
            1160                1165                1170
Leu Gly Ile Thr Ile Met Glu Arg Ser Ser Phe Glu Lys Asn Pro
            1175                1180                1185
Ile Asp Phe Leu Glu Ala Lys Gly Tyr Lys Glu Val Lys Lys Asp
            1190                1195                1200
Leu Ile Ile Lys Leu Pro Lys Tyr Ser Leu Phe Glu Leu Glu Asn
            1205                1210                1215
Gly Arg Lys Arg Met Leu Ala Ser Ala Arg Phe Leu Gln Lys Gly
            1220                1225                1230
Asn Glu Leu Ala Leu Pro Ser Lys Tyr Val Asn Phe Leu Tyr Leu
            1235                1240                1245
Ala Ser His Tyr Glu Lys Leu Lys Gly Ser Pro Glu Asp Asn Glu
            1250                1255                1260
Gln Lys Gln Leu Phe Val Glu Gln His Lys His Tyr Leu Asp Glu
            1265                1270                1275
Ile Ile Glu Gln Ile Ser Glu Phe Ser Lys Arg Val Ile Leu Ala
            1280                1285                1290
```

Asp Ala Asn Leu Asp Lys Val Leu Ser Ala Tyr Asn Lys His Arg
    1295            1300                1305

Asp Lys Pro Ile Arg Glu Gln Ala Glu Asn Ile Ile His Leu Phe
    1310            1315                1320

Thr Leu Thr Asn Leu Gly Ala Pro Arg Ala Phe Lys Tyr Phe Asp
    1325            1330                1335

Thr Thr Ile Asp Arg Lys Val Tyr Arg Ser Thr Lys Glu Val Leu
    1340            1345                1350

Asp Ala Thr Leu Ile His Gln Ser Ile Thr Gly Leu Tyr Glu Thr
    1355            1360                1365

Arg Ile Asp Leu Ser Gln Leu Gly Gly Asp
    1370            1375

<210> SEQ ID NO 21
<211> LENGTH: 1375
<212> TYPE: PRT
<213> ORGANISM: Artificial Sequence
<220> FEATURE:
<223> OTHER INFORMATION: Synthetic Construct

<400> SEQUENCE: 21

Met Glu Lys Lys Tyr Ser Ile Gly Leu Ala Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asn Arg Lys Ser Ile Lys Lys Asn Leu Met
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Arg
65                  70                  75                  80

Tyr Leu Gln Glu Ile Phe Ala Asn Glu Met Ala Lys Leu Asp Asp Ser
                85                  90                  95

Phe Phe Gln Arg Leu Glu Glu Ser Phe Leu Val Glu Glu Asp Lys Lys
            100                 105                 110

Asn Glu Arg His Pro Ile Phe Gly Asn Leu Ala Asp Glu Val Ala Tyr
        115                 120                 125

His Arg Asn Tyr Pro Thr Ile Tyr His Leu Arg Lys Lys Leu Ala Asp
    130                 135                 140

Ser Pro Glu Lys Ala Asp Leu Arg Leu Ile Tyr Leu Ala Leu Ala His
145                 150                 155                 160

Ile Ile Lys Phe Arg Gly His Phe Leu Ile Glu Gly Lys Leu Asn Ala
                165                 170                 175

Glu Asn Ser Asp Val Ala Lys Leu Phe Tyr Gln Leu Ile Gln Thr Tyr
            180                 185                 190

Asn Gln Leu Phe Glu Glu Ser Pro Leu Asp Glu Ile Glu Val Asp Ala
        195                 200                 205

Lys Gly Ile Leu Ser Ala Arg Leu Ser Lys Ser Arg Leu Glu Lys
    210                 215                 220

Leu Ile Ala Val Phe Pro Asn Glu Lys Lys Asn Gly Leu Phe Gly Asn
225                 230                 235                 240

Ile Ile Ala Leu Ala Leu Gly Leu Thr Pro Asn Phe Lys Ser Asn Phe
                245                 250                 255

Asp Leu Thr Glu Asp Ala Lys Leu Gln Leu Ser Lys Asp Thr Tyr Asp
            260                 265                 270

```
Asp Asp Leu Asp Glu Leu Leu Gly Gln Ile Gly Asp Gln Tyr Ala Asp
            275                 280                 285

Leu Phe Ser Ala Ala Lys Asn Leu Ser Asp Ala Ile Leu Leu Ser Asp
    290                 295                 300

Ile Leu Arg Ser Asn Ser Glu Val Thr Lys Ala Pro Leu Ser Ala Ser
305                 310                 315                 320

Met Val Lys Arg Tyr Asp Glu His His Gln Asp Leu Ala Leu Leu Lys
                325                 330                 335

Thr Leu Val Arg Gln Gln Phe Pro Glu Lys Tyr Ala Glu Ile Phe Lys
            340                 345                 350

Asp Asp Thr Lys Asn Gly Tyr Ala Gly Tyr Val Gly Ile Gly Ile Lys
        355                 360                 365

His Arg Lys Arg Thr Thr Lys Leu Ala Thr Gln Glu Glu Phe Tyr Lys
    370                 375                 380

Phe Ile Lys Pro Ile Leu Glu Lys Met Asp Gly Ala Glu Glu Leu Leu
385                 390                 395                 400

Ala Lys Leu Asn Arg Asp Asp Leu Leu Arg Lys Gln Arg Thr Phe Asp
                405                 410                 415

Asn Gly Ser Ile Pro His Gln Ile His Leu Lys Glu Leu His Ala Ile
            420                 425                 430

Leu Arg Arg Gln Glu Glu Phe Tyr Pro Phe Leu Lys Glu Asn Arg Glu
        435                 440                 445

Lys Ile Glu Lys Ile Leu Thr Phe Arg Ile Pro Tyr Tyr Val Gly Pro
    450                 455                 460

Leu Ala Arg Gly Asn Ser Arg Phe Ala Trp Leu Thr Arg Lys Ser Glu
465                 470                 475                 480

Glu Ala Ile Thr Pro Trp Asn Phe Glu Glu Val Val Asp Lys Gly Ala
                485                 490                 495

Ser Ala Gln Ser Phe Ile Glu Arg Met Thr Asn Phe Asp Glu Gln Leu
            500                 505                 510

Pro Asn Lys Lys Val Leu Pro Lys His Ser Leu Leu Tyr Glu Tyr Phe
        515                 520                 525

Thr Val Tyr Asn Glu Leu Thr Lys Val Lys Tyr Val Thr Glu Arg Met
    530                 535                 540

Arg Lys Pro Glu Phe Leu Ser Gly Glu Gln Lys Lys Ala Ile Val Asp
545                 550                 555                 560

Leu Leu Phe Lys Thr Asn Arg Lys Val Thr Val Lys Gln Leu Lys Glu
                565                 570                 575

Asp Tyr Phe Lys Lys Ile Glu Cys Phe Asp Ser Val Glu Ile Ile Gly
            580                 585                 590

Val Glu Asp Arg Phe Asn Ala Ser Leu Gly Thr Tyr His Asp Leu Leu
        595                 600                 605

Lys Ile Ile Lys Asp Lys Asp Phe Leu Asp Asn Glu Glu Asn Glu Asp
    610                 615                 620

Ile Leu Glu Asp Ile Val Leu Thr Leu Thr Leu Phe Glu Asp Arg Glu
625                 630                 635                 640

Met Ile Glu Glu Arg Leu Lys Thr Tyr Ala His Leu Phe Asp Asp Lys
                645                 650                 655

Val Met Lys Gln Leu Lys Arg Arg His Tyr Thr Gly Trp Gly Arg Leu
            660                 665                 670

Ser Arg Lys Met Ile Asn Gly Ile Arg Asp Lys Gln Ser Gly Lys Thr
        675                 680                 685

Ile Leu Asp Phe Leu Lys Ser Asp Gly Phe Ser Asn Arg Asn Phe Met
```

-continued

```
            690                 695                 700
Gln Leu Ile His Asp Asp Ser Leu Thr Phe Lys Glu Ile Glu Lys
705                 710                 715                 720

Ala Gln Val Ser Gly Gln Gly Asp Ser Leu His Glu Gln Ile Ala Asp
                725                 730                 735

Leu Ala Gly Ser Pro Ala Ile Lys Lys Gly Ile Leu Gln Thr Val Lys
                740                 745                 750

Ile Val Asp Glu Leu Val Lys Val Met Gly His Lys Pro Glu Asn Ile
            755                 760                 765

Val Ile Glu Met Ala Arg Glu Asn Gln Thr Thr Lys Gly Leu Gln
770                 775                 780

Gln Ser Arg Glu Arg Lys Lys Arg Ile Glu Glu Gly Ile Lys Glu Leu
785                 790                 795                 800

Glu Ser Gln Ile Leu Lys Glu Asn Pro Val Glu Asn Thr Gln Leu Gln
                805                 810                 815

Asn Glu Lys Leu Tyr Leu Tyr Tyr Leu Gln Asn Gly Arg Asp Met Tyr
                820                 825                 830

Val Asp Gln Glu Leu Asp Ile Asn Arg Leu Ser Asp Tyr Asp Val Asp
                835                 840                 845

His Ile Val Pro Gln Ser Phe Ile Lys Asp Asp Ser Ile Asp Asn Lys
850                 855                 860

Val Leu Thr Arg Ser Val Glu Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
                900                 905                 910

Glu Arg Gly Gly Leu Ser Glu Ala Asp Lys Ala Gly Phe Ile Lys Arg
                915                 920                 925

Gln Leu Val Glu Thr Arg Gln Ile Thr Lys His Val Ala Arg Ile Leu
                930                 935                 940

Asp Ser Arg Met Asn Thr Lys Arg Asp Lys Asn Asp Lys Pro Ile Arg
945                 950                 955                 960

Glu Val Lys Val Ile Thr Leu Lys Ser Lys Leu Val Ser Asp Phe Arg
                965                 970                 975

Lys Asp Phe Gln Leu Tyr Lys Val Arg Asp Ile Asn Asn Tyr His His
                980                 985                 990

Ala His Asp Ala Tyr Leu Asn Ala  Val Val Gly Thr Ala  Leu Ile Lys
                995                 1000                1005

Lys Tyr  Pro Lys Leu Glu Ser  Glu Phe Val Tyr Gly  Asp Tyr Lys
1010                 1015                 1020

Val Tyr  Asp Val Arg Lys Met  Ile Ala Lys Ser Glu  Gln Glu Ile
                1025                 1030                 1035

Gly Lys  Ala Thr Ala Lys Arg  Phe Phe Tyr Ser Asn  Ile Met Asn
                1040                 1045                 1050

Phe Phe  Lys Thr Glu Val Lys  Leu Ala Asn Gly Glu  Ile Arg Lys
                1055                 1060                 1065

Arg Pro  Leu Ile Glu Thr Asn  Gly Glu Thr Gly Glu  Val Val Trp
                1070                 1075                 1080

Asn Lys  Glu Lys Asp Phe Ala  Thr Val Arg Lys Val  Leu Ala Met
                1085                 1090                 1095

Pro Gln  Val Asn Ile Val Lys  Lys Thr Glu Val Gln  Thr Gly Gly
                1100                 1105                 1110
```

```
Phe Ser Lys Glu Ser Ile Leu Ser Lys Arg Glu Ser Ala Lys Leu
    1115                1120                1125

Ile Pro Arg Lys Lys Gly Trp Asp Thr Arg Lys Tyr Gly Gly Phe
    1130                1135                1140

Gly Ser Pro Thr Val Ala Tyr Ser Ile Leu Val Val Ala Lys Val
    1145                1150                1155

Glu Lys Gly Lys Ala Lys Lys Leu Lys Ser Val Lys Val Leu Val
    1160                1165                1170

Gly Ile Thr Ile Met Glu Lys Gly Ser Tyr Glu Lys Asp Pro Ile
    1175                1180                1185

Gly Phe Leu Glu Ala Lys Gly Tyr Lys Asp Ile Lys Lys Glu Leu
    1190                1195                1200

Ile Phe Lys Leu Pro Lys Tyr Ser Leu Phe Glu Leu Glu Asn Gly
    1205                1210                1215

Arg Arg Arg Met Leu Ala Ser Ala Thr Glu Leu Gln Lys Ala Asn
    1220                1225                1230

Glu Leu Val Leu Pro Gln His Leu Val Arg Leu Leu Tyr Tyr Thr
    1235                1240                1245

Gln Asn Ile Ser Ala Thr Thr Gly Ser Asn Asn Leu Gly Tyr Ile
    1250                1255                1260

Glu Gln His Arg Glu Glu Phe Lys Glu Ile Phe Glu Lys Ile Ile
    1265                1270                1275

Asp Phe Ser Glu Lys Tyr Ile Leu Lys Asn Lys Val Asn Ser Asn
    1280                1285                1290

Leu Lys Ser Ser Phe Asp Glu Gln Phe Ala Val Ser Asp Ser Ile
    1295                1300                1305

Leu Leu Ser Asn Ser Phe Val Ser Leu Leu Lys Tyr Thr Ser Phe
    1310                1315                1320

Gly Ala Ser Gly Gly Phe Thr Phe Leu Asp Leu Asp Val Lys Gln
    1325                1330                1335

Gly Arg Leu Arg Tyr Gln Thr Val Thr Glu Val Leu Asp Ala Thr
    1340                1345                1350

Leu Ile Tyr Gln Ser Ile Thr Gly Leu Tyr Glu Thr Arg Thr Asp
    1355                1360                1365

Leu Ser Gln Leu Gly Gly Asp
    1370                1375

<210> SEQ ID NO 22
<211> LENGTH: 364
<212> TYPE: PRT
<213> ORGANISM: Artificial Sequence
<220> FEATURE:
<223> OTHER INFORMATION: Synthetic Construct

<400> SEQUENCE: 22

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
            35                  40                  45

Gly Arg His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80
```

```
Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
        115                 120                 125

Val Glu Ile Thr Glu Gly Ile Leu Ala Asp Glu Cys Ala Ala Leu Leu
    130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Gly Gly Ser Ser Gly
                165                 170                 175

Ser Glu Thr Pro Gly Thr Ser Glu Ser Ala Thr Pro Glu Ser Ser Gly
                180                 185                 190

Gly Ser Ser Gly Gly Ser Ser Glu Val Glu Phe Ser His Glu Tyr Trp
            195                 200                 205

Met Arg His Ala Leu Thr Leu Ala Lys Arg Ala Arg Asp Glu Arg Glu
        210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
            260                 265                 270

Ile Asp Ala Thr Leu Tyr Val Thr Phe Glu Pro Cys Val Met Cys Ala
        275                 280                 285

Gly Ala Met Ile His Ser Arg Ile Gly Arg Val Val Phe Gly Val Arg
    290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
            340                 345                 350

Phe Asn Ala Gln Lys Lys Ala Gln Ser Ser Thr Asp
        355                 360

<210> SEQ ID NO 23
<211> LENGTH: 166
<212> TYPE: PRT
<213> ORGANISM: Artificial Sequence
<220> FEATURE:
<223> OTHER INFORMATION: Synthetic Construct

<400> SEQUENCE: 23

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Gly His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80
```

```
Gly Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 24
<211> LENGTH: 88
<212> TYPE: PRT
<213> ORGANISM: Artificial Sequence
<220> FEATURE:
<223> OTHER INFORMATION: Synthetic Construct

<400> SEQUENCE: 24

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Leu Lys Glu
65                  70                  75                  80

Gly Met Cys Leu Tyr Val Lys Glu
                85

<210> SEQ ID NO 25
<211> LENGTH: 38
<212> TYPE: PRT
<213> ORGANISM: Artificial Sequence
<220> FEATURE:
<223> OTHER INFORMATION: Synthetic Construct

<400> SEQUENCE: 25

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn Ser
        35

<210> SEQ ID NO 26
<211> LENGTH: 102
<212> TYPE: PRT
<213> ORGANISM: Artificial Sequence
<220> FEATURE:
<223> OTHER INFORMATION: Synthetic Construct

<400> SEQUENCE: 26

Cys Leu Ser Tyr Asp Thr Glu Ile Leu Thr Val Glu Tyr Gly Phe Leu
1               5                   10                  15
```

```
Pro Ile Gly Lys Ile Val Glu Glu Arg Ile Glu Cys Thr Val Tyr Thr
            20                  25                  30

Val Asp Lys Asn Gly Phe Val Tyr Thr Gln Pro Ile Ala Gln Trp His
        35                  40                  45

Asn Arg Gly Glu Gln Glu Val Phe Glu Tyr Cys Leu Glu Asp Gly Ser
    50                  55                  60

Ile Ile Arg Ala Thr Lys Asp His Lys Phe Met Thr Thr Asp Gly Gln
65                  70                  75                  80

Met Leu Pro Ile Asp Glu Ile Phe Glu Arg Gly Leu Asp Leu Lys Gln
                85                  90                  95

Val Asp Gly Leu Pro Asn
            100

<210> SEQ ID NO 27
<211> LENGTH: 36
<212> TYPE: PRT
<213> ORGANISM: Artificial Sequence
<220> FEATURE:
<223> OTHER INFORMATION: Synthetic Construct

<400> SEQUENCE: 27

Met Val Lys Ile Ile Ser Arg Lys Ser Leu Gly Thr Gln Asn Val Tyr
1               5                   10                  15

Asp Ile Gly Val Glu Lys Asp His Asn Phe Leu Leu Lys Asn Gly Leu
            20                  25                  30

Val Ala Ser Asn
        35

<210> SEQ ID NO 28
<211> LENGTH: 353
<212> TYPE: DNA
<213> ORGANISM: Artificial Sequence
<220> FEATURE:
<223> OTHER INFORMATION: Synthetic Construct

<400> SEQUENCE: 28
tcgagcgcgt gatgagagca gccactacgg gtctaggctg cccatgtaag gaggcaaggc      60
ctggggacac ccgagatgcc tggttataat taacccagac atgtggctgc ccccccccc     120 ccaacacctg ctgcctgcta aaaataaccc tgtccctggt ggccctgcat gcccactcac    180
ggggatttcc aagtctccac cccattgacg tcaatgggag tttgttttgg caccaaaatc    240
aacgggactt tccaaaatgt cgtaacaact ccgccccatt gacgcaaatg ggcggtaggc    300
gtgtacggtg ggaggtctat ataagcagag ctggtttagt gaaccgtcag atc           353

<210> SEQ ID NO 29
<211> LENGTH: 483
<212> TYPE: DNA
<213> ORGANISM: Artificial Sequence
<220> FEATURE:
<223> OTHER INFORMATION: Synthetic Construct

<400> SEQUENCE: 29
cccttcagat taaaaataac tgaggtaagg gcctgggtag gggaggtggt gtgagacgct      60
cctgtctctc ctctatctgc ccatcggccc tttggggagg aggaatgtgc ccaaggacta    120
aaaaaaggcc atggagccag aggggcgagg gcaacagacc tttcatgggc aaaccttggg    180
gccctgctga ctgtagatga gagcagccac tacgggtcta ggctgcccat gtaaggaggc    240
aaggcctggg gacacccgag atgcctggtt ataattaacc cagacatgtg gctgcccccc    300
```

-continued

| | |
|---|---|
| cccccccaac acctgctgcc tgctaaaaat aaccctgtcc ctggtggccc tgcatgccct | 360 |
| ccctggggac agcccctcct ggctagtcac accctgtagg ctcctctata taacccaggg | 420 |
| gcacagggc tgccctcatt ctaccaccac ctccacagca cagacagaca ctcaggagcc | 480 |
| agc | 483 |

<210> SEQ ID NO 30
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 30

| | |
|---|---|
| atggacaaga agtacagcat cggcctggcc atcggcacca actctgtggg ctgggccgtg | 60 |
| atcaccgacg agtacaaggt gcccagcaag aaattcaagg tgctgggcaa caccgaccgg | 120 |
| cacagcatca agaagaacct gatcggagcc ctgctgttcg acagcggcga aacagccgag | 180 |
| gccacccggc tgaagagaac cgccagaaga agatacacca gacggaagaa ccggatctgc | 240 |
| tatctgcaag agatcttcag caacgagatg gccaaggtgg acgacagctt cttccacaga | 300 |
| ctggaagagt ccttcctggt ggaagaggat aagaagcacg agcggcaccc catcttcggc | 360 |
| aacatcgtgg acgaggtggc ctaccacgag aagtacccca ccatctacca cctgagaaag | 420 |
| aaactggtgg acagcaccga caaggccgac ctgcggctga tctatctggc cctggcccac | 480 |
| atgatcaagt tccggggcca cttcctgatc gagggcgacc tgaaccccga caacagcgac | 540 |
| gtggacaagc tgttcatcca gctggtgcag acctacaacc agctgttcga ggaaaacccc | 600 |
| atcaacgcca gcggcgtgga cgccaaggcc atcctgtctg ccagactgag caagagcaga | 660 |
| cggctggaaa atctgatcgc ccagctgccc ggcgagaaga gaatggcct gttcggaaac | 720 |
| ctgattgccc tgagcctggg cctgaccccc aacttcaaga gcaacttcga cctggccgag | 780 |
| gatgccaaac tgcagctgag caaggacacc tacgacgacg acctggacaa cctgctggcc | 840 |
| cagatcggcg accagtacgc cgacctgttt ctggccgcca gaacctgtc cgacgccatc | 900 |
| ctgctgagcg acatcctgag agtgaacacc gagatcacca aggcccccct gagcgcctct | 960 |
| atgatcaaga gatacgacga gcaccaccag gacctgaccc tgctgaaagc tctcgtgcgg | 1020 |
| cagcagctgc ctgagaagta caaagagatt ttcttcgacc agagcaagaa cggctacgcc | 1080 |
| ggctacattg acggcggagc cagccaggaa gagttctaca agttcatcaa gcccatcctg | 1140 |
| gaaaagatgg acggcaccga ggaactgctc gtgaagctga acagagagga cctgctgcgg | 1200 |
| aagcagcgga ccttcgacaa cggcagcatc ccccaccaga tccacctggg agagctgcac | 1260 |
| gccattctgc ggcggcagga agatttttac ccattcctga aggacaaccg ggaaaagatc | 1320 |
| gagaagatcc tgaccttccg catcccctac tacgtgggcc ctctggccag ggaaacagc | 1380 |
| agattcgcct ggatgaccag aaagagcgag gaaaccatca cccctggaa cttcgaggaa | 1440 |
| gtggtggaca agggcgcttc cgcccagagc ttcatcgagc ggatgaccaa cttcgataag | 1500 |
| aacctgccca acgagaaggt gctgcccaag cacagcctgc tgtacgagta cttcaccgtg | 1560 |
| tataacgagc tgaccaaagt gaaatacgtg accgaggaa tgagaaagcc cgccttcctg | 1620 |
| agcggcgagc agaaaaaggc catcgtggac ctgctgttca gaccaaccg gaaagtgacc | 1680 |
| gtgaagcagc tgaaagagga ctacttcaag aaaatcgagt gcttcgactc cgtggaaatc | 1740 |
| tccggcgtgg aagatcggtt caacgcctcc ctgggcacat accacgatct gctgaaaatt | 1800 |
| atcaaggaca aggacttcct ggacaatgag gaaaacgagg acattctgga agatatcgtg | 1860 |

```
ctgaccctga cactgtttga ggacagagag atgatcgagg aacggctgaa aacctatgcc      1920
cacctgttcg acgacaaagt gatgaagcag ctgaagcggc ggagatacac cggctggggc      1980
aggctgagcc ggaagctgat caacggcatc cgggacaagc agtccggcaa gacaatcctg      2040
gatttcctga agtccgacgg cttcgccaac agaaacttca tgcagctgat ccacgacgac      2100
agcctgacct ttaaagagga catccagaaa gcccaggtgt ccggccaggg cgatagcctg      2160
cacgagcaca ttgccaatct ggccggcagc cccgccatta agaagggcat cctgcagaca      2220
gtgaaggtgg tggacgagct cgtgaaagtg atgggccggc acaagcccga gaacatcgtg      2280
atcgaaatgg ccagagagaa ccagaccacc cagaagggac agaagaacag ccgcgagaga      2340
atgaagcgga tcgaagaggg catcaaagag ctgggcagcc agatcctgaa agaacacccc      2400
gtggaaaaca cccagctgca gaacgagaag ctgtacctgt actacctgca gaatgggcgg      2460
gatatgtacg tggaccagga actggacatc aaccggctgt ccgactacga tgtggaccat      2520
atcgtgcctc agagctttct gaaggacgac tccatcgaca caaggtgct gaccagaagc      2580 gacaagaacc ggggcaagag cgacaacgtg ccctccgaag aggtcgtgaa aagatgaag      2640 aactactggc ggcagctgct gaacgccaag ctgattaccc agagaaagtt cgacaatctg      2700
accaaggccg agagaggcgg cctgagcgaa ctggataagg ccggcttcat caagagacag      2760
ctggtggaaa cccggcagat cacaaagcac gtggcacaga tcctggactc ccggatgaac      2820
actaagtacg acgagaatga caagctgatc cgggaagtga aagtgatcac cctgaagtcc      2880
aagctggtgt ccgatttccg gaaggatttc cagttttaca agtgcgcga gatcaacaac      2940 taccaccacg cccacgacgc ctacctgaac gccgtcgtgg aaccgccct gatcaaaaag      3000 taccctaagc tggaaagcga gttcgtgtac ggcgactaca aggtgtacga cgtgcggaag      3060
atgatcgcca agagcgagca ggaaatcggc aaggctaccg ccaagtactt cttctacagc      3120
aacatcatga ctttttcaa gaccgagatt accctggcca acggcgagat ccggaagcgg      3180
cctctgatcg agacaaacgg cgaaaccggg gagatcgtgt gggataaggg ccgggatttt      3240
gccaccgtgc ggaaagtgct gagcatgccc caagtgaata tcgtgaaaaa gaccgaggtg      3300
cagacaggcg gcttcagcaa agagtctatc ctgcccaaga ggaacagcga taagctgatc      3360
gccagaaaga aggactggga ccctaagaag tacggcggct tcgacagccc caccgtggcc      3420
tattctgtgc tggtggtggc caaagtggaa aagggcaagt ccaagaaact gaagagtgtg      3480
aaagagctgc tggggatcac catcatggaa agaagcagct tcgagaagaa tcccatcgac      3540
tttctggaag ccaagggcta caaagaagtg aaaaaggacc tgatcatcaa gctgcctaag      3600
tactccctgt tcgagctgga aaacggccgg aagagaatgc tggcctctgc cggcgaactg      3660
cagaagggaa acgaactggc cctgccctcc aaatatgtga acttcctgta cctggccagc      3720
cactatgaga agctgaaggg ctcccccgag gataatgagc agaaacagct gtttgtggaa      3780
cagcacaagc actacctgga cgagatcatc gagcagatca gcgagttctc caagagagtg      3840
atcctggccg acgctaatct ggacaaagtg ctgtccgcct acaacaagca ccgggataag      3900
cccatcagag agcaggccga gaatatcatc cacctgttta ccctgaccaa tctgggagcc      3960
cctgccgcct tcaagtactt tgacaccacc atcgaccgga agaggtacac cagcaccaaa      4020
gaggtgctgg acgccacccct gatccaccag agcatcaccg gcctgtacga gacacggatc      4080
gacctgtctc agctgggagg tgac                                            4104
```

<210> SEQ ID NO 31

<211> LENGTH: 4104
<212> TYPE: DNA
<213> ORGANISM: Artificial Sequence
<220> FEATURE:
<223> OTHER INFORMATION: Synthetic Construct

<400> SEQUENCE: 31

| | |
|---|---|
| atggacaaga agtacagcat cggcctggcc atcggcacca actctgtggg ctgggccgtg | 60 |
| atcaccgacg agtacaaggt gcccagcaag aaattcaagg tgctgggcaa caccgaccgg | 120 |
| cacagcatca agaagaacct gatcggagcc ctgctgttcg acagcggcga acagccgag | 180 |
| gccacccggc tgaagagaac cgccagaaga agatacacca gacggaagaa ccggatctgc | 240 |
| tatctgcaag agatcttcag caacgagatg gccaaggtgg acgacagctt cttccacaga | 300 |
| ctggaagagt ccttcctggt ggaagaggat aagaagcacg agcggcaccc catcttcggc | 360 |
| aacatcgtgg acgaggtggc ctaccacgag aagtacccca ccatctacca cctgagaaag | 420 |
| aaactggtgg acagcaccga caaggccgac ctgcggctga tctatctggc cctggcccac | 480 |
| atgatcaagt tccggggcca cttcctgatc gagggcgacc tgaaccccga caacagcgac | 540 |
| gtggacaagc tgttcatcca gctggtgcag acctacaacc agctgttcga ggaaaacccc | 600 |
| atcaacgcca gcggcgtgga cgccaaggcc atcctgtctg ccagactgag caagagcaga | 660 |
| cggctggaaa atctgatcgc ccagctgccc ggcgagaaga gaatggcct gttcggaaac | 720 |
| ctgattgccc tgagcctggg cctgacccc aacttcaaga gcaacttcga cctggccgag | 780 |
| gatgccaaac tgcagctgag caaggacacc tacgacgacg acctggacaa cctgctggcc | 840 |
| cagatcggcg accagtacgc cgacctgttt ctggccgcca gaaacctgtc cgacgccatc | 900 |
| ctgctgagcg acatcctgag agtgaacacc gagatcacca aggcccccct gagcgcctct | 960 |
| atgatcaaga gatacgacga gcaccaccag gacctgaccc tgctgaaagc tctcgtgcgg | 1020 |
| cagcagctgc ctgagaagta caaagagatt ttcttcgacc agagcaagaa cggctacgcc | 1080 |
| ggctacattg acggcggagc cagccaggaa gagttctaca agttcatcaa gcccatcctg | 1140 |
| gaaaagatgg acggcaccga ggaactgctc gtgaagctga acagagagga cctgctgcgg | 1200 |
| aagcagcgga ccttcgacaa cggcagcatc ccccaccaga tccacctggg agagctgcac | 1260 |
| gccattctgc ggcggcagga agatttttac ccattcctga aggacaaccg ggaaaagatc | 1320 |
| gagaagatcc tgaccttccg catcccctac tacgtgggcc ctctggccag ggaaacagc | 1380 |
| agattcgcct ggatgaccag aaagagcgag gaaaccatca cccctggaa cttcgaggaa | 1440 |
| gtggtggaca gggcgcttc cgcccagagc ttcatcgagc ggatgaccaa cttcgataag | 1500 |
| aacctgccca cgagaaggt gctgccaag cacagcctgc tgtacgagta cttcaccgtg | 1560 |
| tataacgagc tgaccaaagt gaaatacgtg accgagggaa tgagaaagcc cgccttcctg | 1620 |
| agcggcgagc agaaaaaggc catcgtggac ctgctgttca gaccaaccg gaaagtgacc | 1680 |
| gtgaagcagc tgaaagagga ctacttcaag aaaatcgagt gcttcgactc cgtggaaatc | 1740 |
| tccggcgtgg aagatcggtt caacgcctcc ctgggcacat accacgatct gctgaaaatt | 1800 |
| atcaaggaca aggacttcct ggacaatgag gaaaacgagg acattctgga agatatcgtg | 1860 |
| ctgaccctga cactgtttga ggacagagag atgatcgaga acggctgaa acctatgcc | 1920 |
| cacctgttcg acgacaaagt gatgaagcag ctgaagcggc ggagatacac cggctgggc | 1980 |
| aggctgagcc ggaagctgat caacggcatc cgggacaagc agtccggcaa gacaatcctg | 2040 |
| gatttcctga agtccgacgg cttcgccaac agaaacttca tgcagctgat ccacgacgac | 2100 |
| agcctgacct ttaaagagga catccagaaa gcccaggtgt ccggccaggg cgatagcctg | 2160 |

```
cacgagcaca ttgccaatct ggccggcagc cccgccatta agaagggcat cctgcagaca    2220
gtgaaggtgg tggacgagct cgtgaaagtg atgggccggc acaagcccga gaacatcgtg    2280
atcgaaatgg ccagagagaa ccagaccacc cagaagggac agaagaacag ccgcgagaga    2340
atgaagcgga tcgaagaggg catcaaagag ctgggcagcc agatcctgaa agaacacccc    2400
gtggaaaaca cccagctgca gaacgagaag ctgtacctgt actacctgca gaatgggcgg    2460
gatatgtacg tggaccagga actggacatc aaccggctgt ccgactacga tgtggaccat    2520
atcgtgcctc agagctttct gaaggacgac tccatcgaca caaggtgct gaccagaagc    2580 gacaagaacc ggggcaagag cgacaacgtg ccctccgaag aggtcgtgaa aagatgaag    2640 aactactggc ggcagctgct gaacgccaag ctgattaccc agagaaagtt cgacaatctg    2700
accaaggccg agagaggcgg cctgagcgaa ctggataagg ccggcttcat caagagacag    2760
ctggtggaaa cccggcagat cacaaagcac gtggcacaga tcctggactc ccggatgaac    2820
actaagtacg acgagaatga caagctgatc cgggaagtga agtgatcac cctgaagtcc    2880 aagctggtgt ccgatttccg gaaggatttc cagttttaca agtgcgcga tcaacaac    2940 taccaccacg cccacgacgc ctacctgaac gccgtcgtgg aaccgcccct gatcaaaaag    3000
tacccctaag ctggaaagcga gttcgtgtac ggcgactaca aggtgtacga cgtgcggaag    3060
atgatcgcca gagcgagca ggaaatcggc aaggctaccg ccaagtactt cttctacagc    3120
aacatcatga cttttttcaa gaccgagatt accctggcca acgcgagat ccggaagcgg    3180 cctctgatcg agacaaacgg cgaaaccggg gagatcgtgt gggataaggg ccgggatttt    3240
gccaccgtgc ggaaagtgct gagcatgccc caagtgaata tcgtgaaaaa gaccgaggtg    3300
cagacaggcg gcttcagcaa agagtctatc cggcccaaga ggaacagcga taagctgatc    3360
gccagaaaga aggactggga ccctaagaag tacgcggct cgtcagccc caccgtggcc    3420 tattctgtgc tggtggtggc caaagtggaa aagggcaagt ccaagaaact gaagagtgtg    3480
aaagagctgc tggggatcac catcatggaa agaagcagct cgagaagaa tcccatcgac    3540 tttctggaag ccaagggcta caaagaagtg aaaaaggacc tgatcatcaa gctgcctaag    3600 tactcctgt tcgagctgga aaacggccgg aagagaatgc tggcctctgc ccgctttctg    3660
cagaagggaa acgaactggc cctgccctcc aaatatgtga acttcctgta cctggccagc    3720
cactatgaga agctgaaggg ctccccgag gataatgagc agaaacagct gtttgtggaa    3780
cagcacaagc actacctgga cgagatcatc gagcagatca gcgagttctc caagagagtg    3840
atcctggccg acgctaatct ggacaaagtg ctgtccgcct acaacaagca ccgggataag    3900
cccatcagag agcaggccga gaatatcatc cacctgttta ccctgaccaa tctgggagcc    3960
cctcgggcct tcaagtactt tgacaccacc atcgaccgga aggtgtaccg gagcaccaaa    4020
gaggtgctgg acgccaccct gatccaccag agcatcaccg gcctgtacga gacacggatc    4080
gacctgtctc agctgggagg tgac                                          4104
```

<210> SEQ ID NO 32
<211> LENGTH: 4048
<212> TYPE: DNA
<213> ORGANISM: Artificial Sequence
<220> FEATURE:
<223> OTHER INFORMATION: Synthetic Construct

<400> SEQUENCE: 32

```
cgtgatcacc gacgagtaca aggtgcccag caagaaattc aaggtgctgg gcaacaccga    60
```

```
ccggcacagc atcaagaaga acctgatcgg agccctgctg ttcgacagcg gcgaaacagc    120
cgaggccacc cggctgaaga gaaccgccag aagaagatac accagacgga agaaccggat    180
ctgctatctg caagagatct tcagcaacga gatggccaag gtggacgaca gcttcttcca    240
cagactggaa gagtccttcc tggtggaaga ggataagaag cacgagcggc acccccatctt   300
cggcaacatc gtggacgagg tggcctacca cgagaagtac cccaccatct accacctgag    360
aaagaaactg gtggacagca ccgacaaggc cgacctgcgg ctgatctatc tggccctggc    420
ccacatgatc aagttccggg gccacttcct gatcgagggc gacctgaacc ccgacaacag    480
cgacgtggac aagctgttca tccagctggt gcagacctac aaccagctgt tcgaggaaaa    540
ccccatcaac gccagcggcg tggacgccaa ggccatcctg tctgccagac tgagcaagag    600
cagacggctg gaaaatctga tcgcccagct gcccggcgag aagaagaatg cctgttcgg    660
aaacctgatt gccctgagcc tgggcctgac ccccaacttc aagagcaact tcgacctggc    720
cgaggatacc aaactgcagc tgagcaagga cacctacgac gacgacctgg acaacctgct    780
ggcccagatc ggcgaccagt acgccgacct gtttctggcc gccaagaacc tgtccgacgc    840
catcctgctg agcgacatcc tgagagtgaa caccgagatc accaaggccc ccctgagcgc    900
ctctatgatc aagctgtacg acgagcacca ccaggacctg accctgctga agctctcgt    960
gcggcagcag ctgcctgaga gtacaaaga gatttcttc gaccagagca agaacggcta    1020
cgccggctac attgacggcg gagccagcca ggaagagttc tacaagttca tcaagcccat    1080
cctggaaaag atggacggca ccgaggaact gctcgtgaag ctgaacagag aggacctgct    1140
gcggaagcag cggaccttcg acaacggcat catccccac cagatccacc tgggagagct    1200
gcacgccatt ctgcggcggc aggaagattt ttacccattc ctgaaggaca ccgggaaaa    1260
gatcgagaag atcctgacct tccgcatccc ctactacgtg ggccctctgg ccaggggaaa    1320
cagcagattc gcctggatga ccagaaagag cgaggaaacc atcaccccct ggaacttcga    1380
gaaggtggtg acaagggcg cttccgccca gagcttcatc gagcggatga ccaacttcga    1440
taagaacctg cccaacgaga aggtgctgcc caagcacagc ctgctgtacg agtacttcac    1500
cgtgtataac gagctgacca aagtgaaata cgtgaccgag ggaatgagaa agcccgcctt    1560
cctgagcggc gaccagaaaa aggccatcgt ggacctgctg ttcaagacca ccggaaagt    1620
gaccgtgaag cagctgaaag gaactactt caagaaaatc gagtgcttcg actccgtgga    1680
aatctccggc gtgaagatc ggttcaacgc ctccctgggc atacaccacg atctgctgaa    1740
aattatcaag gacaaggact tcctggacaa tgaggaaaac gaggacattc tggaagatat    1800
cgtgctgacc ctgacactgt tgaggacag agatgatc gaggaacggc tgaaaaccta    1860
tgcccacctg ttcgacgaca agtgatgaa gcagctgaag cggcggagat acaccggctg    1920
gggcaggctg agccggaagc tgatcaacgg catccgggac aagcagtccg gcaagacaat    1980
cctggatttc ctgaagtccg acggcttcgc caacagaaac ttcatccagc tgatccacga    2040
cgacagcctg acctttaaag aggacatcca gaaagcccag gtgtccggcc agggcgatag    2100
cctgcacgag cacattgcca atctggccgg cagccccgcc attaagaagg gcatcctgca    2160
gacagtgaag gtggtggacg agctcgtgaa agtgatgggc cggcacaagc ccgagaacat    2220
cgtgatcgaa atggccagag agaaccagac cacccagaag ggacagaaga cagccgcga    2280
gagaatgaag cggatcgaag agggcatcaa agagctgggc agccagatcc tgaaagaaca    2340
ccccgtggaa aacacccagc tgcagaacga gaagctgtac ctgtactacc tgcagaatgg    2400
gcgggatatg tacgtggacc aggaactgga catcaaccgg ctgtccgact acgatgtgga    2460
```

```
ccatatcgtg cctcagagct ttctgaagga cgactccatc gacaacaagg tgctgaccag    2520
aagcgacaag aaccggggca agagcgacaa cgtgccctcc gaagaggtcg tgaagaagat    2580
gaagaactac tggcggcagc tgctgaacgc caagctgatt acccagagaa agttcgacaa    2640
tctgaccaag gccgagagag gcggcctgag cgaactggaa aaggccggct tcatcaagag    2700
acagctggtg gaaacccggc agatcacaaa gcacgtggca cagatcctgg actcccggat    2760
gaacactaag tacgacgaga atgacaagct gatccgggaa gtgaaagtga tcaccctgaa    2820
gtccaagctg gtgtccgatt ccggaaggat tttccagttt tacaaagtgc gcgagatcaa    2880
caactaccac cacgcccacg acgcctacct gaacgccgtc gtgggaaccg ccctgatcaa    2940
aaagtaccct aagctggaaa gcgagttcgt gtacggcgac tacaaggtgt acgacgtgcg    3000
gaagatgatc gccaagagcg agcaggaaat cggcaaggct accgccaagt acttcttcta    3060
cagcaacatc atgaactttt tcaagaccga gattaccctg ccaacggcg agatccggaa     3120 gcggcctctg atcgagacaa acggcgaaac cggggagatc gtgtgggata agggccggga    3180
ttttgccacc gtgcggaaag tgctgagcat gccccaagtg aatatcgtga aaaagaccga    3240
ggtgcagaca ggcggcttca gcaaagagtc tatcctgccc aagaggaaca gcgataagct    3300
gatcgccaga aagaaggact gggaccctaa gaagtacggc ggcttcgaca gccccaccgt    3360
ggcctattct gtgctggtgg tggccaaagt ggaaaagggc aagtccaaga actgaagag    3420 tgtgaaagag ctgctgggga tcaccatcat ggaaagaagc agcttcgaga gaatcccat    3480 cgactttctg gaagccaagg gctacaaaga agtgaaaaag gacctgatca tcaagctgcc    3540
taagtactcc ctgttcgagc tggaaaacgg ccggaagaga atgctggcct ctgccggcgt    3600
gctgcagaag ggaaacgaac tggccctgcc ctccaaatat gtgaacttcc tgtacctggc    3660
cagccactat gagaagctga agggctcccc cgaggataat gagcagaaac agctgtttgt    3720
ggaacagcac aagcactacc tggacgagat catcgagcag atcagcgagt ctccaagag    3780 agtgatcctg gccgacgcta atctggacaa agtgctgtcc gcctacaaca gcaccgggga    3840
taagcccatc agagagcagg ccgagaatat catccacctg tttaccctga ccaatcgg     3900 agcccctgcc gccttcaagt actttgacac caccatcgac cggaagaggt acaccagcac    3960
caaagaggtg ctggacgcca ccctgatcca ccagagcatc accggcctgt acgagacacg    4020
gatcgacctg tctcagctgg gaggcgac                                        4048
```

<210> SEQ ID NO 33
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 33

```
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca cggaagaa ccggatctgc       240 tatctgcaag agatcttcag caacgagatg gccaaggtgg acgacagctt cttccacaga    300
ctggaagagt cctttctggt ggaagaggat aagaagcacg agcggcaccc catcttcggc    360
aacatcgtgg acgaggtggc ctaccacgag aagtaccccc ccatctacca cctgagaaag    420
```

-continued

```
aaactggtgg acagcaccga caaggccgac ctgcggctga tctatctggc cctggcccac    480
atgatcaagt tccggggcca cttcctgatc gagggcgacc tgaaccccga caacagcgac    540
gtggacaagc tgttcatcca gctggtgcag acctacaacc agctgttcga ggaaaacccc    600
atcaacgcca cgggcgtgga cgccaaggcc atcctgtctg ccagactgag caagagcaga    660
cggctggaaa atctgatcgc ccagctgccc ggcgagaaga agaatggcct gttcggaaac    720
ctgattgccc tgagcctggg cctgacccca aacttcaaga gcaacttcga cctggccgag    780
gataccaaac tgcagctgag caaggacacc tacgacgacg acctggacaa cctgctggcc    840
cagatcggcg accagtacgc cgacctgttt ctggccgcca gaaacctgtc cgacgccatc    900
ctgctgagcg acatcctgag agtgaacacc gagatcacca aggccccct gagcgcctct    960 atgatcaagc tgtacgacga gcaccaccag gacctgaccc tgctgaaagc tctcgtgcgg   1020
cagcagctgc ctgagaagta caaagagatt ttcttcgacc agagcaagaa cggctacgcc   1080
ggctacattg acggcggagc cagccaggaa gagttctaca gttcatcaa gcccatcctg   1140 gaaaagatgg acggcaccga ggaactgctc gtgaagctga cagagagga cctgctgcgg   1200 aagcagcgga ccttcgacaa cggcatcatc ccccaccaga tccacctggg agagctgcac   1260
gccattctgc ggcggcagga agattttttac ccattcctga aggacaaccg ggaaaagatc   1320
gagaagatcc tgaccttccg catccctac tacgtgggcc ctctggccag gggaaacagc   1380
agattcgcct ggatgaccag aaagagcgag gaaaccatca cccctggaa cttcgagaag   1440 gtggtggaca agggcgcttc cgcccagagc ttcatcgagc ggatgaccaa cttcgataag   1500
aacctgccca cgagaaggt gctgcccaag cacagcctgc tgtacgagta cttcaccgtg   1560
tataacgagc tgaccaaagt gaaatacgtg accgagggaa tgagaaagcc cgccttcctg   1620
agcggcgacc agaaaaaggc catcgtggac ctgctgttca gaccaaccg gaaagtgacc   1680 gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgaga acggctgaa aacctatgcc   1920 cacctgttcg acgacaaagt gatgaagcag ctgaagcggc ggagatacac cggctgggc   1980 aggctgagcc ggaagctgat caacggcatc cgggacaagc agtccggcaa gacaatcctg   2040
gatttcctga agtccgacgg cttcgccaac agaaacttca tccagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga gaacatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca caaggtgct gaccagaagc   2580 gacaagaacc ggggcaagag cgacaacgtg ccctccgaag aggtcgtgaa gaagatgaag   2640
aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
```

```
actaagtacg acgagaatga caagctgatc cgggaagtga agtgatcac cctgaagtcc    2880 aagctggtgt ccgatttccg gaaggatttc cagttttaca aagtgcgcga gatcaacaac    2940
taccaccacg cccacgacgc ctacctgaac gccgtcgtgg gaaccgccct gatcaaaaag    3000
taccctaagc tggaaagcga gttcgtgtac ggcgactaca aggtgtacga cgtgcggaag    3060
atgatcgcca agagcgagca ggaaatcggc aaggctaccg ccaagtactt cttctacagc    3120
aacatcatga acttttttcaa gaccgagatt accctggcca acggcgagat ccggaagcgg    3180
cctctgatcg agacaaacgg cgaaaccggg gagatcgtgt gggataaggg ccgggatttt    3240
gccaccgtgc ggaaagtgct gagcatgccc caagtgaata tcgtgaaaaa gaccgaggtg    3300
cagacaggcg gcttcagcaa agagtctatc cggcccaaga ggaacagcga taagctgatc    3360
gccagaaaga aggactggga ccctaagaag tacggcggct tcgtcagccc caccgtggcc    3420
tattctgtgc tggtggtggc caaagtggaa aagggcaagt ccaagaaact gaagagtgtg    3480
aaagagctgc tggggatcac catcatgaa agaagcagct cgagaagaa tcccatcgac    3540 tttctggaag ccaagggcta caaagaagtg aaaaaggacc tgatcatcaa gctgcctaag    3600
tactccctgt tcgagctgga aaacggccgg aagagaatgc tggcctctgc ccgctttctg    3660
cagaagggaa acgaactggc cctgccctcc aaatatgtga acttcctgta cctggccagc    3720
cactatgaga agctgaaggg ctccccccgag gataatgagc agaaacagct gtttgtggaa    3780
cagcacaagc actacctgga cgagatcatc gagcagatca gcgagttctc caagagagtg    3840
atcctggccg acgctaatct ggacaaagtg ctgtccgcct acaacaagca ccgggataag    3900
cccatcagag agcaggccga gaatatcatc cacctgtttta ccctgaccaa tctgggagcc    3960
cctcgggcct tcaagtactt tgacaccacc atcgaccgga aggtgtaccg gagcaccaaa    4020
gaggtgctgg acgccaccct gatccaccag agcatcaccg cctgtacga gacacggatc    4080 gacctgtctc agctgggagg tgac                                          4104
```

<210> SEQ ID NO 34
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 34

```
atggacaaga agtacagcat cggcctggcc atcggcacca actctgtggg ctgggccgtg     60
atcaccgacg agtacaaggt gcccagcaag aaattcaagg tgctgggcaa caccgaccgg    120
cacagcatca agaagaacct gatcggagcc ctgctgttcg acagcggcga aacagccgag    180
gccacccggc tgaagagaac cgccagaaga agatacacca cgcggaagaa ccggatctgc    240
tatctgcaag agatcttcag caacgagatg gccaaggtgg acgacagctt cttccacaga    300
ctggaagagt cctttctggt ggaagaggat aagaagcacg agcggcaccc catcttcggc    360
aacatcgtgg acgaggtggc ctaccacgag aagtacccca ccatctacca cctgagaaag    420
aaactggtgg acagcaccga caaggccgac ctgcggctga tctatctggc cctggcccac    480
atgatcaagt tccggggcca cttcctgatc gagggcgacc tgaaccccga caacagcgac    540
gtggacaagc tgttcatcca gctggtgcag acctacaacc agctgttcga ggaaaacccc    600
atcaacgcca gcgcgtgga cgccaaggcc atcctgtctg ccagactgag caagagcaga    660
cggctggaaa atctgatcgc ccagctgccc ggcgagaaga gaatggcct gttcggaaac    720
```

```
ctgattgccc tgagcctggg cctgaccccc aacttcaaga gcaacttcga cctggccgag    780
gatgccaaac tgcagctgag caaggacacc tacgacgacg acctggacaa cctgctggcc    840
cagatcggcg accagtacgc cgacctgttt ctggccgcca agaacctgtc cgacgccatc    900
ctgctgagcg acatcctgag agtgaacacc gagatcacca aggcccccct gagcgcctct    960
atgatcaaga gatacgacga gcaccaccag acctgaccc tgctgaaagc tctcgtgcgg   1020
cagcagctgc ctgagaagta caaagagatt ttcttcgacc agagcaagaa cggctacgcc   1080
ggctacattg acggcggagc cagccaggaa gagttctaca gttcatcaa gcccatcctg   1140
gaaaagatgg acggcaccga ggaactgctc gtgaagctga acagagagga cctgctgcgg   1200
aagcagcgga ccttcgacaa cggcagcatc ccccaccaga tccacctggg agagctgcac   1260
gccattctgc ggcggcagga agatttttac ccattcctga aggacaaccg ggaaaagatc   1320
gagaagatcc tgaccttccg catcccctac tacgtgggcc ctctggccag ggaaacagc   1380
agattcgcct ggatgaccag aaagagcgag gaaaccatca ccccctggaa cttcgaggaa   1440
gtggtggaca agggcgcttc cgcccagagc ttcatcgagc ggatgaccaa cttcgataag   1500
aacctgccca cgagaaggt gctgcccaag cacagcctgc tgtacgagta cttcaccgtg   1560
tataacgagc tgaccaaagt gaaatacgtg accgaggaa tgagaaagcc cgccttcctg   1620
agcggcgagc agaaaaaggc catcgtggac ctgctgttca agaccaaccg gaaagtgacc   1680
gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcggc ggagatacac cggctgggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga acatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca caaggtgct gaccagaagc   2580
gacaagaacc ggggcaagag cgacaacgtg ccctccgaag aggtcgtgaa gaagatgaag   2640
aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cgggaagtga aagtgatcac cctgaagtcc   2880
aagctggtgt ccgatttccg gaaggatttc cagttttaca aagtgcgcga gatcaacaac   2940
taccaccacg cccacgacgc ctacctgaac gccgtcgtgg aaccgccct gatcaaaaag   3000
taccctaagc tggaaagcga gttcgtgtac ggcgactaca aggtgtacga cgtgcggaag   3060
atgatcgcca agagcgagca ggaaatcggc aaggctaccg ccaagtactt cttctacagc   3120
```

```
aacatcatga actttttcaa gaccgagatt accctggcca acggcgagat ccggaagcgg    3180
cctctgatcg agacaaacgg cgaaaccggg gagatcgtgt gggataaggg ccgggatttt    3240
gccaccgtgc ggaaagtgct gagcatgccc caagtgaata tcgtgaaaaa gaccgaggtg    3300
cagacaggcg gcttcagcaa agagtctatc cggcccaaga ggaacagcga taagctgatc    3360
gccagaaaga aggactggga ccctaagaag tacggcggct tcgtcagccc caccgtggcc    3420
tattctgtgc tggtggtggc caaagtggaa aagggcaagt ccaagaaact gaagagtgtg    3480
aaagagctgc tggggatcac catcatggaa agaagcagct tcgagaagaa tcccatcgac    3540
tttctggaag ccaagggcta caagaagtg aaaaaggacc tgatcatcaa gctgcctaag    3600
tactccctgt tcgagctgga aaacggccgg aagagaatgc tggcctctgc ccgctttctg    3660
cagaagggaa acgaactggc cctgccctcc aaatatgtga acttcctgta cctggccagc    3720
cactatgaga agctgaaggg ctcccccgag ataatgagc agaaacagct gtttgtggaa    3780
cagcacaagc actacctgga cgagatcatc gagcagatca gcgagttctc caagagagtg    3840
atcctggccg acgctaatct ggacaaagtg ctgtccgcct acaacaagca ccgggataag    3900
cccatcagag agcaggccga gaatatcatc caacctgttta ccctgaccaa tctgggagcc    3960
cctcgggcct tcaagtactt tgacaccacc atcgaccgga agcagtaccg gagcaccaaa    4020
gaggtgctgg acgccaccct gatccaccag agcataccg gcctgtacga gacacggatc    4080
gacctgtctc agctgggagg tgac                                           4104

<210> SEQ ID NO 35
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 35
atggacaaga agtacagcat cggcctggcc atcggcacca actctgtggg ctgggccgtg      60
atcaccgacg agtacaaggt gcccagcaag aaattcaagg tgctgggcaa caccgaccgg     120
cacagcatca agaagaacct gatcggagcc ctgctgttcg acagcggcga aacagccgag     180
gccacccggc tgaagagaac cgccagaaga agatacacca gacggaagaa ccggatctgc     240
tatctgcaag agatcttcag caacgagatg gccaaggtgg acgacagctt cttccacaga     300
ctggaagagt ccttcctggt ggaagaggat aagaagcacg agcggcaccc catcttcggc     360
aacatcgtgg acgaggtggc ctaccacgag aagtacccc ccatctacca cctgagaaag     420
aaactggtgg acagcaccga caaggccgac ctgcggctga tctatctggc cctggcccac     480
atgatcaagt tccgggggcca cttcctgatc gagggcgacc tgaacccgga caacagcgac     540
gtggacaagc tgttcatcca gctggtgcag acctacaacc agctgttcga ggaaaacccc     600
atcaacgcca gcggcgtgga cgccaaggcc atcctgtctg ccagactgag caagagcaga     660
cggctggaaa atctgatcgc ccagctgccc ggcgagaaga gaatggcct gttcggaaac     720 ctgattgccc tgagcctggg cctgacccc aacttcaaga gcaacttcga cctggccgag     780
gatgccaaac tgcagctgag caaggacacc tacgacgacg acctggacaa cctgctggcc     840
cagatcggcg accagtacgc cgacctgttt ctggccgcca gaaacctgtc cgacgccatc     900
ctgctgagcg acatcctgag agtgaacacc gagatcacca aggccccct gagcgcctct     960 atgatcaaga gatacgacga gcaccaccag gacctgaccc tgctgaaagc tctcgtgcgg    1020
```

-continued

| | |
|---|---|
| cagcagctgc ctgagaagta caaagagatt tcttcgacc agagcaagaa cggctacgcc | 1080 |
| ggctacattg acggcggagc cagccaggaa gagttctaca agttcatcaa gcccatcctg | 1140 |
| gaaaagatgg acggcaccga ggaactgctc gtgaagctga acagagagga cctgctgcgg | 1200 |
| aagcagcgga ccttcgacaa cggcagcatc ccccaccaga tccacctggg agagctgcac | 1260 |
| gccattctgc ggcggcagga agatttttac ccattcctga aggacaaccg ggaaaagatc | 1320 |
| gagaagatcc tgaccttccg catcccctac tacgtgggcc ctctggccag gggaaacagc | 1380 |
| agattcgcct ggatgaccag aaagagcgag gaaaccatca ccccctggaa cttcgaggaa | 1440 |
| gtggtggaca agggcgcttc cgcccagagc ttcatcgagc ggatgaccaa cttcgataag | 1500 |
| aacctgccca acgagaaggt gctgcccaag cacagcctgc tgtacgagta cttcaccgtg | 1560 |
| tataacgagc tgaccaaagt gaaatacgtg accgagggaa tgagaaagcc cgccttcctg | 1620 |
| agcggcgagc agaaaaaggc catcgtggac ctgctgttca gaccaaccg gaaagtgacc | 1680 |
| gtgaagcagc tgaaagagga ctacttcaag aaaatcgagt gcttcgactc cgtggaaatc | 1740 |
| tccggcgtgg aagatcggtt caacgcctcc ctgggcacat accacgatct gctgaaaatt | 1800 |
| atcaaggaca aggacttcct ggacaatgag gaaaacgagg acattctgga agatatcgtg | 1860 |
| ctgaccctga cactgtttga ggacagagag atgatcgagg aacggctgaa aacctatgcc | 1920 |
| cacctgttcg acgacaaagt gatgaagcag ctgaagcggc ggagatacac cggctggggc | 1980 |
| aggctgagcc ggaagctgat caacggcatc cgggacaagc agtccggcaa gacaatcctg | 2040 |
| gatttcctga agtccgacgg cttcgccaac agaaacttca tgcagctgat ccacgacgac | 2100 |
| agcctgacct ttaaagagga catccagaaa gcccaggtgt ccggccaggg cgatagcctg | 2160 |
| cacgagcaca ttgccaatct ggccggcagc cccgccatta agaagggcat cctgcagaca | 2220 |
| gtgaaggtgg tggacgagct cgtgaaagtg atgggccggc acaagcccga gaacatcgtg | 2280 |
| atcgaaatgg ccagagagaa ccagaccacc cagaagggac agaagaacag ccgcgagaga | 2340 |
| atgaagcgga tcgaagaggg catcaaagag ctgggcagcc agatcctgaa agaacacccc | 2400 |
| gtggaaaaca cccagctgca gaacgagaag ctgtacctgt actacctgca gaatgggcgg | 2460 |
| gatatgtacg tggaccagga actggacatc aaccggctgt ccgactacga tgtggaccat | 2520 |
| atcgtgcctc agagctttct gaaggacgac tccatcgaca caaggtgct gaccagaagc | 2580 |
| gacaagaacc ggggcaagag cgacaacgtg ccctccgaag aggtcgtgaa aaagatgaag | 2640 |
| aactactggc ggcagctgct gaacgccaag ctgattaccc agagaaagtt cgacaatctg | 2700 |
| accaaggccg agagaggcgg cctgagcgaa ctggataagg ccggcttcat caagagacag | 2760 |
| ctggtggaaa cccggcagat cacaaagcac gtggcacaga tcctggactc ccggatgaac | 2820 |
| actaagtacg acgagaatga caagctgatc cgggaagtga aagtgatcac cctgaagtcc | 2880 |
| aagctggtgt ccgatttccg gaaggatttc cagttttaca aagtgcgcga gatcaacaac | 2940 |
| taccaccacg cccacgacgc ctacctgaac gccgtcgtgg gaaccgccct gatcaaaaag | 3000 |
| taccctaagc tggaaagcga gttcgtgtac ggcgactaca aggtgtacga cgtgcggaag | 3060 |
| atgatcgcca agagcgagca ggaaatcggc aaggctaccg ccaagtactt cttctacagc | 3120 |
| aacatcatga actttttcaa gaccgagatt accctggcca acggcgagat ccggaagcgg | 3180 |
| cctctgatcg agacaaacgg cgaaaccggg gagatcgtgt gggataaggg ccgggatttt | 3240 |
| gccaccgtgc ggaaagtgct gagcatgccc caagtgaata tcgtgaaaaa gaccgaggtg | 3300 |
| cagacaggcg gcttcagcaa agagtctatc cggcccaaga ggaacagcga taagctgatc | 3360 |
| gccagaaaga aggactggga ccctaagaag tacggcggct tcgtcagccc caccgtggcc | 3420 |

```
tattctgtgc tggtggtggc caaagtggaa aagggcaagt ccaagaaact gaagagtgtg    3480
aaagagctgc tgggatcac catcatgaa agaagcagct tcgagaagaa tcccatcgac     3540
tttctggaag ccaagggcta caagaagtg aaaaaggacc tgatcatcaa gctgcctaag    3600
tactccctgt tcgagctgga aaacggccgg aagagaatgc tggcctctgc ccgctttctg   3660
cagaagggaa acgaactggc cctgccctcc aaatatgtga acttcctgta cctggccagc   3720
cactatgaga agctgaaggg ctcccccgag gataatgagc agaaacagct gtttgtggaa   3780
cagcacaagc actacctgga cgagatcatc gagcagatca gcgagttctc caagagagtg   3840
atcctggccg acgctaatct ggacaaagtg ctgtccgcct acaacaagca ccgggataag   3900
cccatcagag agcaggccga gaatatcatc cacctgttta ccctgaccaa tctgggagcc   3960
cctcgggcct tcaagtactt tgacaccacc atcgaccgga aggagtaccg gagcaccaaa   4020
gaggtgctgg acgccaccct gatccaccag agcatcaccg gcctgtacga gacacggatc   4080
gacctgtctc agctgggagg tgac                                          4104
```

<210> SEQ ID NO 36
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 36

```
atggacaaga agtacagcat cggcctggcc atcggcacca actctgtggg ctgggccgtg     60
atcaccgacg agtacaaggt gcccagcaag aaattcaagg tgctgggcaa caccgaccgg    120
cacagcatca agaagaacct gatcggagcc ctgctgttcg acagcggcga aacagccgag    180
gccacccggc tgaagagaac cgccagaaga agatacacca gacggaagaa ccggatctgc    240
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca ccatctacca cctgagaaag    420
aaactggtgg acagcaccga caaggccgac ctgcggctga tctatctggc cctggcccac    480
atgatcaagt tccgggggcca cttcctgatc gagggcgacc tgaaccccga caacagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa atctgatcgc ccagctgccc ggcgagaaga gaatggcct gttcggaaac     720 ctgattgccc tgagcctggg cctgaccccc aacttcaaga gcaacttcga cctggccgag    780
gataccaaac tgcagctgag caaggacacc tacgacgacg acctggacaa cctgctggcc    840
cagatcggcg accagtacgc cgacctgttt ctggccgcca gaaacctgtc cgacgccatc    900
ctgctgagcg acatcctgag agtgaacacc gagatcacca aggcccccct gagcgcctct    960
atgatcaagc gtacgacga gcaccaccag gacctgaccc tgctgaaagc tctcgtgcgg    1020
cagcagctgc ctgagaagta caaagagatt ttcttcgacc agagcaagaa cggctacgcc   1080
ggctacattg acggcggagc cagccaggaa gagttctaca agttcatcaa gcccatcctg   1140
gaaaagatgg acggcaccga ggaactgctc gtgaagctga acagagagga cctgctgcgg   1200
aagcagcgga ccttcgacaa cggcatcatc ccccaccaga tccacctggg agagctgcac   1260
gccattctgc ggcggcagga agatttttac ccattcctga aggacaaccg ggaaaagatc   1320
```

-continued

```
gagaagatcc tgaccttccg catcccctac tacgtgggcc ctctggccag ggaaacagc     1380 agattcgcct ggatgaccag aaagagcgag gaaaccatca ccccctggaa cttcgagaag    1440
gtggtggaca agggcgcttc cgcccagagc ttcatcgagc ggatgaccaa cttcgataag    1500
aacctgccca cgagaaggt gctgcccaag cacagcctgc tgtacgagta cttcaccgtg     1560
tataacgagc tgaccaaagt gaaatacgtg accgagggaa tgagaaagcc cgccttcctg   1620
agcggcgacc agaaaaaggc catcgtggac ctgctgttca agaccaaccg gaaagtgacc   1680
gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860 ctgacccctga cactgtttga ggacagagag atgatcgagg aacggctgaa aacctatgcc   1920
cacctgttcg acgacaaagt gatgaagcag ctgaagcggc ggagatacac cggctggggc   1980
aggctgagcc ggaagctgat caacggcatc cgggacaagc agtccggcaa gacaatcctg   2040
gatttcctga agtccgacgg cttcgccaac agaaacttca tccagctgat ccacgacgac   2100
agcctgacct ttaaagagga catccagaaa gcccaggtgt ccggccaggg cgatagcctg   2160
cacgagcaca ttgccaatct ggccggcagc cccgccatta gaaagggcat cctgcagaca   2220
gtgaaggtgg tggacgagct cgtgaaagtg atgggccggc acaagcccga gaacatcgtg   2280
atcgaaatgg ccagagagaa ccagaccacc cagaagggac agaagaacag ccgcgagaga   2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca caaggtgct gaccagaagc    2580 gacaagaacc ggggcaagag cgacaacgtg ccctccgaag aggtcgtgaa gaagatgaag   2640
aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cgggaagtga aagtgatcac cctgaagtcc   2880
aagctggtgt ccgatttccg gaaggatttc cagttttaca agtgcgcga tcaacaac     2940 taccaccacg cccacgacgc ctacctgaac gccgtcgtgg gaaccgccct gatcaaaaag   3000
taccctaagc tggaaagcga gttcgtgtac ggcgactaca aggtgtacga cgtgcggaag   3060
atgatcgcca agagcgagca ggaaatcggc aaggctaccg ccaagtactt cttctacagc   3120
aacatcatga cttttttcaa gaccgagatt accctggcca acggcgagat ccggaagcgg   3180
cctctgatcg agacaaacgg cgaaaccggg gagatcgtgt gggataaggg ccgggatttt   3240
gccaccgtgc ggaaagtgct gagcatgccc caagtgaata tcgtgaaaaa gaccgaggtg   3300
cagacaggcg gcttcagcaa agagtctatc cggcccaaga ggaacagcga taagctgatc   3360
gccagaaaga aggactggga ccctaagaag tacggcggct tcgtcagccc caccgtggcc   3420
tattctgtgc tggtggtggc caaagtggaa aagggcaagt ccaagaaact gaagagtgtg   3480
aaagagctgc tggggatcac catcatggaa agaagcagct tcgagaagaa tcccatcgac   3540
tttctggaag ccaagggcta caaagaagtg aaaaaggacc tgatcatcaa gctgcctaag   3600
tactccctgt tcgagctgga aaacggccgg aagagaatgc tggcctctgc cgctttctg    3660 cagaagggaa acgaactggc cctgcctcc aaatatgtga acttcctgta cctggccagc   3720
```

| | |
|---|---|
| cactatgaga agctgaaggg ctcccccgag gataatgagc agaaacagct gtttgtggaa | 3780 |
| cagcacaagc actacctgga cgagatcatc gagcagatca gcgagttctc caagagagtg | 3840 |
| atcctggccg acgctaatct ggacaaagtg ctgtccgcct acaacaagca ccgggataag | 3900 |
| cccatcagag agcaggccga gaatatcatc cacctgttta ccctgaccaa tctgggagcc | 3960 |
| cctcgggcct tcaagtactt tgacaccacc atcgaccgga agcagtaccg gagcaccaaa | 4020 |
| gaggtgctgg acgccaccct gatccaccag agcatcaccg cctgtacga gacacggatc | 4080 |
| gacctgtctc agctgggagg tgac | 4104 |

<210> SEQ ID NO 37
<211> LENGTH: 4104
<212> TYPE: DNA
<213> ORGANISM: Artificial Sequence
<220> FEATURE:
<223> OTHER INFORMATION: Synthetic Construct

<400> SEQUENCE: 37

| | |
|---|---|
| atggacaaga agtacagcat cggcctggcc atcggcacca actctgtggg ctgggccgtg | 60 |
| atcaccgacg agtacaaggt gcccagcaag aaattcaagg tgctgggcaa caccgaccgg | 120 |
| cacagcatca agaagaacct gatcggagcc ctgctgttcg acagcggcga aacagccgag | 180 |
| gccacccggc tgaagagaac cgccagaaga agatacacca cacggaagaa ccggatctgc | 240 |
| tatctgcaag agatcttcag caacgagatg gccaaggtgg acgacagctt cttccacaga | 300 |
| ctggaagagt ccttcctggt ggaagaggat aagaagcacg agcggcaccc catcttcggc | 360 |
| aacatcgtgg acgaggtggc ctaccacgag aagtacccca ccatctacca cctgagaaag | 420 |
| aaactggtgg acagcaccga caaggccgac ctgcggctga tctatctggc cctggcccac | 480 |
| atgatcaagt tccggggcca cttcctgatc gagggcgacc tgaaccccga caacagcgac | 540 |
| gtggacaagc tgttcatcca gctggtgcag acctacaacc agctgttcga ggaaaacccc | 600 |
| atcaacgcca gcggcgtgga cgccaaggcc atcctgtctg ccagactgag caagagcaga | 660 |
| cggctggaaa atctgatcgc ccagctgccc ggcgagaaga gaatggcct gttcggaaac | 720 |
| ctgattgccc tgagcctggg cctgaccccc aacttcaaga gcaacttcga cctggccgag | 780 |
| gataccaaac tgcagctgag caaggacacc tacgacgacg acctggacaa cctgctggcc | 840 |
| cagatcggcg accagtacgc cgacctgttt ctggccgcca gaaacctgtc cgacgccatc | 900 |
| ctgctgagcg acatcctgag agtgaacacc gagatcacca aggcccccct gagcgcctct | 960 |
| atgatcaagc gttacgacga gcaccaccag gacctgaccc tgctgaaagc tctcgtgcgg | 1020 |
| cagcagctgc ctgagaagta caaagagatt ttcttcgacc agagcaagaa cggctacgcc | 1080 |
| ggctacattg acggcggagc cagccaggaa gagttctaca agttcatcaa gcccatcctg | 1140 |
| gaaaagatgg acggcaccga ggaactgctc gtgaagctga acagagagga cctgctgcgg | 1200 |
| aagcagcgga ccttcgacaa cggcatcatc ccccaccaga tccacctggg agagctgcac | 1260 |
| gccattctgc ggcggcagga agatttttac ccattcctga aggacaaccg ggaaaagatc | 1320 |
| gagaagatcc tgaccttccg catcccctac tacgtgggcc ctctggccag gggaaacagc | 1380 |
| agattcgcct ggatgaccag aaagagcgag gaaaccatca cccctggaa cttcgagaag | 1440 |
| gtggtggaca agggcgcttc cgcccagagc ttcatcgagc ggatgaccaa cttcgataag | 1500 |
| aacctgccca cgagaaggt gctgcccaag cacagcctgc tgtacgagta cttcaccgtg | 1560 |
| tataacgagc tgaccaaagt gaaatacgtg accgagggaa tgagaaagcc cgccttcctg | 1620 |

```
agcggcgacc agaaaaaggc catcgtggac ctgctgttca agaccaaccg gaaagtgacc      1680
gtgaagcagc tgaaagagga ctacttcaag aaaatcgagt gcttcgactc cgtggaaatc      1740
tccggcgtgg aagatcggtt caacgcctcc ctgggcacat accacgatct gctgaaaatt      1800
atcaaggaca aggacttcct ggacaatgag gaaaacgagg acattctgga agatatcgtg      1860
ctgaccctga cactgtttga ggacagagag atgatcgagg aacggctgaa aacctatgcc      1920
cacctgttcg acgacaaagt gatgaagcag ctgaagcggc ggagatacac cggctggggc      1980
aggctgagcc ggaagctgat caacggcatc cgggacaagc agtccggcaa gacaatcctg      2040
gatttcctga gtccgacgg cttcgccaac agaaacttca tccagctgat ccacgacgac      2100
agcctgacct ttaaagagga catccagaaa gcccaggtgt ccggccaggg cgatagcctg      2160
cacgagcaca ttgccaatct ggccggcagc cccgccatta agaagggcat cctgcagaca      2220
gtgaaggtgg tggacgagct cgtgaaagtg atgggccggc acaagcccga gaacatcgtg      2280
atcgaaatgg ccagagagaa ccagaccacc cagaagggac agaagaacag ccgcgagaga      2340
atgaagcgga tcgaagaggg catcaaagag ctgggcagcc agatcctgaa agaacacccc      2400
gtggaaaaca cccagctgca gaacgagaag ctgtacctgt actacctgca gaatgggcgg      2460
gatatgtacg tggaccagga actggacatc aaccggctgt ccgactacga tgtggaccat      2520
atcgtgcctc agagctttct gaaggacgac tccatcgaca caaggtgct gaccagaagc      2580 gacaagaacc gggcaagag cgacaacgtg ccctccgaag aggtcgtgaa aagatgaag      2640 aactactggc ggcagctgct gaacgccaag ctgattaccc agagaaagtt cgacaatctg      2700
accaaggccg agagaggcgg cctgagcgaa ctggataagg ccggcttcat caagagacag      2760
ctggtggaaa cccggcagat cacaaagcac gtggcacaga tcctggactc ccggatgaac      2820
actaagtacg acgagaatga caagctgatc cgggaagtga agtgatcac cctgaagtcc      2880 aagctggtgt ccgatttccg gaaggatttc cagttttaca agtgcgcga tcaacaac       2940 taccaccacg cccacgacgc ctacctgaac gccgtcgtgg gaaccgccct gatcaaaaag      3000
taccctaagc tggaaagcga gttcgtgtac ggcgactaca aggtgtacga cgtgcggaag      3060
atgatcgcca agagcgagca ggaaatcggc aaggctaccg ccaagtactt cttctacagc      3120
aacatcatga ctttttcaa gaccgagatt accctggcca acggcgagat ccggaagcgg      3180
cctctgatcg agacaaacgg cgaaaccggg gagatcgtgt gggataaggg ccggatttt       3240 gccaccgtgc ggaaagtgct gagcatgccc caagtgaata tcgtgaaaaa gaccgaggtg      3300
cagacaggcg gcttcagcaa agagtctatc cggcccaaga ggaacagcga taagctgatc      3360
gccagaaaga aggactggga ccctaagaag tacgcggct cgtcagccc caccgtggcc      3420 tattctgtgc tggtggtggc caaagtggaa agggcaagt ccaagaaact gaagagtgtg       3480
aaagagctgc tggggatcac catcatggaa agaagcagct cgagaagaa tcccatcgac      3540 tttctggaag ccaagggcta caaagaagtg aaaaaggacc tgatcatcaa gctgcctaag      3600
tactccctgt tcgagctgga aaacggccgg aagagaatgc tggcctctgc ccgctttctg      3660
cagaagggaa acgaactggc cctgcccctcc aaatatgtga acttcctgta cctggccagc      3720
cactatgaga agctgaaggg ctccccgag gataatgagc agaaacagct gtttgtggaa      3780
cagcacaagc actacctgga cgagatcatc gagcagatca gcgagttctc caagagagtg      3840
atcctggccg acgctaatct ggacaaagtg ctgtccgcct acaacaagca ccgggataag      3900
cccatcagag agcaggccga gaatatcatc cacctgttta ccctgaccaa tctgggagcc      3960
cctcgggcct tcaagtactt tgacaccacc atcgaccgga aggagtaccg gagcaccaaa      4020
```

```
gaggtgctgg acgccaccct gatccaccag agcatcaccg gcctgtacga gacacggatc   4080
gacctgtctc agctgggagg tgac                                         4104

<210> SEQ ID NO 38
<211> LENGTH: 4134
<212> TYPE: DNA
<213> ORGANISM: Artificial Sequence
<220> FEATURE:
<223> OTHER INFORMATION: Synthetic Construct

<400> SEQUENCE: 38
atggacaaga agtacagcat cggcctggcc atcggcacca actctgtggg ctgggccgtg     60
atcaccgacg agtacaaggt gcccagcaag aaattcaagg tgctgggcaa caccgaccgg    120
cacagcatca agaagaacct gatcggagcc ctgctgttcg acagcggcga aacagccgag    180
gccacccggc tgaagagaac cgccagaaga agatacacca gacggaagaa ccggatctgc    240
tatctgcaag agatcttcag caacgagatg gccaaggtgg acgacagctt cttccacaga    300
ctggaagagt ccttcctggt ggaagaggat aagaagcacg agcggcaccc catcttcggc    360
aacatcgtgg acgaggtggc ctaccacgag aagtacccca ccatctacca cctgagaaag    420
aaactggtgg acagcaccga caaggccgac ctgcggctga tctatctggc cctggcccac    480
atgatcaagt tccggggcca cttcctgatc gagggcgacc tgaaccccga caacagcgac    540
gtggacaagc tgttcatcca gctggtgcag acctacaacc agctgttcga ggaaaacccc    600
atcaacgcca gcggcgtgga cgccaaggcc atcctgtctg ccagactgag caagagcaga    660
cggctggaaa atctgatcgc ccagctgccc ggcgagaaga gaatggcct gttcggaaac    720 ctgattgccc tgagcctggg cctgacccc aacttcaaga gcaacttcga cctggccgag    780
gatgccaaac tgcagctgag caaggacacc tacgacgacg acctggacaa cctgctggcc    840
cagatcggcg accagtacgc cgacctgttt ctggccgcca gaaacctgtc cgacgccatc    900
ctgctgagcg acatcctgag agtgaacacc gagatcacca aggcccccct gagcgcctct    960
atgatcaaga gatacgacga gcaccaccag gacctgaccc tgctgaaagc tctcgtgcgg   1020
cagcagctgc ctgagaagta caaagagatt ttcttcgacc agagcaagaa cggctacgcc   1080
ggctacgtgg acggcggcgc aagcgcagct ctaaactggc cacagaggaa   1140
gagttctaca agttcatcaa gcccatcctg gaaaagatgg acggcaccga ggaactgctc   1200
gtgaagctga acagagagga cctgctgcgg aagcagcgga ccttcgacaa cggcagcatc   1260
ccccaccaga tccacctggg agagctgcac gccattctgc ggcggcagga gattttttac   1320
ccattcctga aggacaaccg ggaaaagatc gagaagatcc tgaccttccg catcccctac   1380
tacgtgggcc ctctggccag gggaaacagc agattcgcct ggatgaccag aaagagcgag   1440
gaaaccatca cccctggaa cttcgaggaa gtggtggaca agggcgcttc cgcccagagc   1500
ttcatcgagc ggatgaccaa cttcgataag aacctgccca acgagaaggt gctgcccaag   1560
cacagcctgc tgtacgagta cttcaccgtg tataacgagc tgaccaaagt gaaatacgtg   1620
accgagggaa tgagaaagcc cgccttcctg agcggcgagc agaaaaaggc catcgtggac   1680
ctgctgttca gaccaaccg gaaagtgacc gtgaagcagc tgaaagagga ctacttcaag   1740
aaaatcgagt gcttcgactc cgtggaaatc tccggcgtgg aagatcggtt caacgcctcc   1800
ctgggcacat accacgatct gctgaaaatt atcaaggaca aggacttcct ggacaatgag   1860
gaaaacgagg acattctgga agatatcgtg ctgaccctga cactgtttga ggacagagag   1920
```

```
atgatcgagg aacggctgaa aacctatgcc cacctgttcg acgacaaagt gatgaagcag    1980
ctgaagcggc ggagatacac cggctggggc aggctgagcc ggaagctgat caacggcatc    2040
cgggacaagc agtccggcaa gacaatcctg gatttcctga agtccgacgg cttcgccaac    2100
agaaacttca tgcagctgat ccacgacgac agcctgacct ttaaaggaga catccagaaa    2160
gcccaggtgt ccggccaggg cgatagcctg cacgagcaca ttgccaatct ggccggcagc    2220
cccgccatta gaagggcat cctgcagaca gtgaaggtgg tggacgagct cgtgaaagtg    2280
atgggccggc acaagcccga gaacatcgtg atcgaaatgg ccagagagaa ccagaccacc    2340
cagaagggac agaagaacag ccgcgagaga atgaagcgga tcgagaggg catcaaagag    2400
ctggcagcc agatcctgaa agaacacccc gtggaaaaca cccagctgca gaacgagaag    2460
ctgtacctgt actacctgca gaatgggcgg gatatgtacg tggaccagga actggacatc    2520
aaccggctgt ccgactacga tgtggaccat atcgtgcctc agagctttct gaaggacgac    2580
tccatcgaca caaggtgct gaccagaagc gacaagaacc ggggcaagag cgacaacgtg    2640
ccctccgaag aggtcgtgaa gaagatgaag aactactggc ggcagctgct gaacgccaag    2700
ctgattaccc agagaaagtt cgacaatctg accaaggccg agagaggcgg cctgagcgaa    2760
ctggataagg ccggcttcat caagacacag ctggtgaaaa cccggcagat cacaaagcac    2820
gtggcacaga tcctggactc ccggatgaac actaagtacg acgagaatga caagctgatc    2880
cgggaagtga aagtgatcac cctgaagtcc aagctggtgt ccgatttccg gaaggatttc    2940
cagttttaca agtgcgcga atcaacaac taccaccacg cccacgacgc ctacctgaac    3000
gccgtcgtgg gaaccgccct gatcaaaaag taccctaagc tggaaagcga gttcgtgtac    3060
ggcgactaca aggtgtacga cgtgcggaag atgatcgcca agagcgagca ggaaatcggc    3120
aaggctaccg ccaagtactt cttctacagc aacatcatga actttttcaa gaccgagatt    3180
accctggcca acggcgagat ccggaagcgg cctctgatcg agacaaacgg cgaaaccggg    3240
gagatcgtgt gggataaggg ccgggatttt gccaccgtgc ggaaagtgct gagcatgccc    3300
caagtgaata tcgtgaaaaa gaccgaggtg cagacaggcg gcttcagcaa agagtctatc    3360
cggcccaaga ggaacagcga taagctgatc gccagaaaga aggactggga ccctaagaag    3420
tacggcggct tcgtcagccc caccgtggcc tattctgtgc tggtggtggc caaagtggaa    3480
aagggcaagt ccaagaaact gaagagtgtg aaagagctgc tggggatcac catcatggaa    3540
agaagcagct tcgagaagaa tcccatcgac tttctggaag ccaagggcta caaagaagtg    3600
aaaaaggacc tgatcatcaa gctgcctaag tactccctgt tcgagctgga aaacggccgg    3660
aagagaatgc tggcctctgc ccgctttctg cagaagggaa acgaactggc cctgccctcc    3720
aaatatgtga acttcctgta cctggccagc cactatgaga agctgaaggg ctcccccgag    3780
gataatgagc agaaacagct gtttgtggaa cagcacaagc actacctgga cgagatcatc    3840
gagcagatca gcgagttctc caagagagtg atcctggccg acgctaatct ggacaaagtg    3900
ctgtccgcct acaacaagca ccgggataag cccatcagag caggccga gaatatcatc    3960
cacctgttta ccctgaccaa tctgggagcc cctcgggcct tcaagtactt tgacaccacc    4020
atcgaccgga aggtgtaccg gagcaccaaa gaggtgctgg acgccaccct gatccaccag    4080
agcatcaccg gcctgtacga gacacggatc gacctgtctc agctgggagg tgac        4134
```

<210> SEQ ID NO 39
<211> LENGTH: 4134
<212> TYPE: DNA
<213> ORGANISM: Artificial Sequence -continued
<220> FEATURE:
<223> OTHER INFORMATION: Synthetic Construct

<400> SEQUENCE: 39

| | | | | | |
|---|---|---|---|---|---|
| atggacaaga | agtacagcat | cggcctggcc | atcggcacca | actctgtggg ctgggccgtg | 60 |
| atcaccgacg | agtacaaggt | gcccagcaag | aaattcaagg | tgctgggcaa caccgaccgg | 120 |
| cacagcatca | agaagaacct | gatcggagcc | ctgctgttcg | acagcggcga aacagccgag | 180 |
| gccacccggc | tgaagagaac | cgccagaaga | agatacacca | gacggaagaa ccggatctgc | 240 |
| tatctgcaag | agatcttcag | caacgagatg | gccaaggtgg | acgacagctt cttccacaga | 300 |
| ctggaagagt | ccttcctggt | ggaagaggat | aagaagcacg | agcggcaccc catcttcggc | 360 |
| aacatcgtgg | acgaggtggc | ctaccacgag | aagtacccca | ccatctacca cctgagaaag | 420 |
| aaactggtgg | acagcaccga | caaggccgac | ctgcggctga | tctatctggc cctgcccac | 480 |
| atgatcaagt | ccggggcca | cttcctgatc | gagggcgacc | tgaaccccga acagcgac | 540 |
| gtggacaagc | tgttcatcca | gctggtgcag | acctacaacc | agctgttcga ggaaaacccc | 600 |
| atcaacgcca | gcggcgtgga | cgccaaggcc | atcctgtctg | ccagactgag caagagcaga | 660 |
| cggctggaaa | atctgatcgc | ccagctgccc | ggcgagaaga | agaatggcct gttcggaaac | 720 |
| ctgattgccc | tgagcctggg | cctgaccccc | aacttcaaga | gcaacttcga cctggccgag | 780 |
| gataccaaac | tgcagctgag | caaggacacc | tacgacgacg | acctggacaa cctgctggcc | 840 |
| cagatcggcg | accagtacgc | cgacctgttt | ctggccgcca | gaacctgtc cgacgccatc | 900 |
| ctgctgagcg | acatcctgag | agtgaacacc | gagatcacca | aggcccccct gagcgcctct | 960 |
| atgatcaagc | tgtacgacga | gcaccaccag | gacctgaccc | tgctgaaagc tctcgtgcgg | 1020 |
| cagcagctgc | ctgagaagta | caaagagatt | ttcttcgacc | agagcaagaa cggctacgcc | 1080 |
| ggctacgtgg | gcgccgacaa | gaagctgcgc | aagcgcagct | ctaaactggc cacagaggaa | 1140 |
| gagttctaca | agttcatcaa | gcccatcctg | gaaaagatgg | acggcaccga ggaactgctc | 1200 |
| gtgaagctga | acagagagga | cctgctgcgg | aagcagcgga | ccttcgacaa cggcatcatc | 1260 |
| ccccaccaga | tccacctggg | agagctgcac | gccattctgc | ggcggcagga agattttac | 1320 |
| ccattcctga | aggacaaccg | ggaaaagatc | gagaagatcc | tgaccttccg catcccctac | 1380 |
| tacgtgggcc | ctctggccag | gggaaacagc | agattcgcct | ggatgaccag aaagagcgag | 1440 |
| gaaaccatca | ccccctggaa | cttcgagaag | gtggtggaca | agggcgcttc cgcccagagc | 1500 |
| ttcatcgagc | ggatgaccaa | cttcgataag | aacctgccca | acgagaaggt gctgcccaag | 1560 |
| cacagcctgc | tgtacgagta | cttcaccgtg | tataacgagc | tgaccaaagt gaaatacgtg | 1620 |
| accgagggaa | tgagaaagcc | cgccttcctg | agcggcgacc | agaaaaaggc catcgtggac | 1680 |
| ctgctgttca | agaccaaccg | gaaagtgacc | gtgaagcagc | tgaaagagga ctacttcaag | 1740 |
| aaaatcgagt | gcttcgactc | cgtggaaatc | tccggcgtgg | aagatcggtt caacgcctcc | 1800 |
| ctgggcacat | accacgatct | gctgaaaatt | atcaaggaca | aggacttcct ggacaatgag | 1860 |
| gaaaacgagg | acattctgga | agatatcgtg | ctgaccctga | cactgtttga ggacagagag | 1920 |
| atgatcgagg | aacggctgaa | aacctatgcc | cacctgttcg | acgacaaagt gatgaagcag | 1980 |
| ctgaagcggc | ggagatacac | cggctgggc | aggctgagcc | ggaagctgat caacggcatc | 2040 |
| cgggacaagc | agtccggcaa | gacaatcctg | gatttcctga | agtccgacgg cttcgccaac | 2100 |
| agaaacttca | tccagctgat | ccacgacgac | agcctgacct | ttaaagagga catccagaaa | 2160 |
| gcccaggtgt | ccggccaggg | cgatagcctg | cacgagcaca | ttgccaatct ggccggcagc | 2220 |

```
cccgccatta agaagggcat cctgcagaca gtgaaggtgg tggacgagct cgtgaaagtg    2280
atgggccggc acaagcccga gaacatcgtg atcgaaatgg ccagagagaa ccagaccacc    2340
cagaagggac agaagaacag ccgcgagaga atgaagcgga tcgaagaggg catcaaagag    2400
ctgggcagcc agatcctgaa agaacacccc gtggaaaaca cccagctgca gaacgagaag    2460
ctgtacctgt actacctgca gaatgggcgg gatatgtacg tggaccagga actggacatc    2520
aaccggctgt ccgactacga tgtggaccat atcgtgcctc agagctttct gaaggacgac    2580
tccatcgaca caaggtgct gaccagaagc gacaagaacc ggggcaagag cgacaacgtg    2640
ccctccgaag aggtcgtgaa gaagatgaag aactactggc ggcagctgct gaacgccaag    2700
ctgattaccc agagaaagtt cgacaatctg accaaggccg agagaggcgg cctgagcgaa    2760
ctggataagg ccggcttcat caagagacag ctggtggaaa cccggcagat cacaaagcac    2820
gtggcacaga tcctggactc ccggatgaac actaagtacg acgagaatga caagctgatc    2880
cgggaagtga aagtgatcac cctgaagtcc aagctggtgt ccgatttccg gaaggatttc    2940
cagttttaca agtgcgcga gatcaacaac taccaccacg cccacgacgc ctacctgaac    3000
gccgtcgtgg gaaccgccct gatcaaaaag taccctaagc tggaaagcga gttcgtgtac    3060
ggcgactaca aggtgtacga cgtgcggaag atgatcgcca gagcgagca ggaaatcggc    3120 aaggctaccg ccaagtactt cttctacagc aacatcatga actttttcaa gaccgagatt    3180
accctggcca acgcgagat ccggaagcgg cctctgatcg agacaaacgg cgaaaccggg    3240
gagatcgtgt gggataaggg ccggattttt gccaccgtgc ggaaagtgct gagcatgccc    3300
caagtgaata tcgtgaaaaa gaccgagtg cagacaggcg gcttcagcaa agagtctatc    3360
cggcccaaga ggaacagcga taagctgatc gccagaaaga aggactggga ccctaagaag    3420 tacgcggct tcgtcagccc caccgtggcc tattctgtgc tggtggtggc caaagtggaa    3480
aagggcaagt ccaagaaact gaagagtgtg aaagagctgc tggggatcac catcatggaa    3540
agaagcagct cgagaagaa tcccatcgac tttctggaag ccaagggcta caagaagtg    3600 aaaaaggacc tgatcatcaa gctgcctaag tactccctgt tcgagctgga aaacggccgg    3660
aagagaatgc tggcctctgc ccgctttctg cagaagggaa acgaactggc cctgccctcc    3720
aaatatgtga acttcctgta cctggccagc cactatgaga agctgaaggg ctccccccgag    3780 gataatgagc agaaacagct gtttgtggaa cagcacaagc actacctgga cgagatcatc    3840
gagcagatca gcgagttctc caagagagtg atcctggccg acgctaatct ggacaaagtg    3900
ctgtccgcct acaacaagca ccgggataag cccatcagag agcaggccga gaatatcatc    3960
cacctgttta ccctgaccaa tctgggagcc cctcgggcct tcaagtactt tgacaccacc    4020
atcgaccgga aggtgtaccg gagcaccaaa gaggtgctgg acgccaccct gatccaccag    4080
agcatcaccg gcctgtacga gacacggatc gacctgtctc agctgggagg tgac          4134
```

<210> SEQ ID NO 40
<211> LENGTH: 4125
<212> TYPE: DNA
<213> ORGANISM: Artificial Sequence
<220> FEATURE:
<223> OTHER INFORMATION: Synthetic Construct

<400> SEQUENCE: 40

```
atggagaaga agtacagcat cggcctggcc atcggcacca acagcgtggg ctgggccgtg      60
atcaccgacg actacaaggt gcccagcaag aagttcaagg tgctgggcaa caccaaccgc     120
aagagcatca agaagaacct gatgggcgcc ctgctgttcg acagcggcga gaccgccgag     180
```

```
gccacccgcc tgaagcgcac cgcccgccgc cgctacaccc gccgcaagaa ccgcatccgc    240
tacctgcagg agatattcgc caacgagatg gccaagctgg acgacagctt cttccagcgc    300
ctggaggaga gcttcctggt ggaggaggac aagaagaacg agcgccaccc catcttcggc    360
aacctggccg acgaggtggc ctaccaccgc aactacccca ccatctacca cctgcgcaag    420
aagctggccg acagccccga aaggccgac ctgcgcctga tctacctggc cctggcccac    480
atcatcaagt tccgcggcca cttcctgatc gagggcaagc tgaacgccga aacagcgac    540 gtggccaagc tgttctacca gctgatccag acctacaacc agctgttcga ggagagcccc    600
ctggacgaga tcgaggtgga cgccaagggc atcctgagcg cccgcctgag caagagcaag    660
cgcctggaga agctgatcgc cgtgttcccc aacgagaaga gaacggcct gttcggcaac    720 atcatcgccc tggccctggg cctgaccccc aacttcaaga gcaacttcga cctgaccgag    780
gacgccaagc tgcagctgag caaggacacc tacgacgacg acctggacga gctgctgggc    840
cagatcggcg accagtacgc cgacctgttc agcgccgcca agaacctgag cgacgccatc    900
ctgctgagcg acatcctgcg cagcaacagc gaggtgacca aggcccccct gagcgccagc    960
atggtgaagc gctacgacga gcaccaccag gacctggccc tgctgaagac cctggtgcgc   1020
cagcagttcc ccgagaagta cgccgagata ttcaaggacg acaccaagaa cggctacgcc   1080
ggctacgtgg gcatcggcat caagcaccgc aagcgcacca ccaagctggc cacccaggag   1140
gagttctaca gttcatcaa gcccatcctg gagaagatgg acggcgccga ggagctgctg   1200
gccaagctga accgcgacga cctgctgcgc aagcagcgca ccttcgacaa cggcagcatc   1260
ccccaccaga tccacctgaa ggagctgcac gccatcctgc gccgccagga ggagttctac   1320
cccttcctga aggagaaccg cgagaagatc gagaagatcc tgaccttccg catcccctac   1380
tacgtgggcc ccctggcccg cggcaacagc cgcttcgcct ggctgacccg caagagcgag   1440
gaggccatca cccctggaa cttcgaggag gtggtggaca agggcgccag cgcccagagc   1500
ttcatcgagc gcatgaccaa cttcgacgag cagctgccca caagaaggt gctgcccaag   1560 cacagcctgc tgtacgagta cttcaccgtg tacaacgagc tgaccaaggt gaagtacgtg   1620
accgagcgca tgcgcaagcc cgagttcctg agcggcgagc agaagaaggc catcgtggac   1680
ctgctgttca agaccaaccg caaggtgacc gtgaagcagc tgaaggagga ctacttcaag   1740
aagatcgagt gcttcgacag cgtggagatc atcggcgtgg aggaccgctt caacgccagc   1800
ctgggcacct accacgacct gctgaagatc atcaaggaca aggacttcct ggacaacgag   1860
gagaacgagg acatcctgga ggacatcgtg ctgaccctga ccctgttcga ggaccgcgag   1920
atgatcgagg agcgcctgaa gacctacgcc cacctgttcg acgacaaggt gatgaagcag   1980
ctgaagcgcc gccactacac cggctgggc cgcctgagcc gcaagatgat caacggcatc   2040
cgcgacaagc agagcggcaa gaccatcctg gacttcctga gagcgacgg cttcagcaac   2100 cgcaacttca tgcagctgat ccacgacgac agcctgacct tcaaggagga gatcgagaag   2160
gcccaggtga gcggccaggg cgacagcctg cacgagcaga tcgccgacct ggccggcagc   2220
cccgccatca gaagggcat cctgcagacc gtgaagatcg tggacgagct ggtgaaggtg   2280
atgggccaca gcccgagaa catcgtgatc gagatggccc gcgagaacca gaccaccacc   2340
aagggcctgc agcagagccg cgagcgcaag aagcgcatcg aggagggcat caaggagctg   2400
gagagccaga tcctgaagga gaccccgtg gagaacaccc agctgcagaa cgagaagctg   2460
tacctgtact acctgcagaa cggccgcgac atgtacgtgg accaggagct ggacatcaac   2520
```

| | |
|---|---:|
| cgcctgagcg actacgacgt ggaccacatc gtgccccaga gcttcatcaa ggacgacagc | 2580 |
| atcgacaaca aggtgctgac ccgcagcgtg gagaaccgcg gcaagagcga caacgtgccc | 2640 |
| agcgaggagg tggtgaagaa gatgaagaac tactggcgcc agctgctgaa cgccaagctg | 2700 |
| atcacccagc gcaagttcga caacctgacc aaggccgagc gcggcggcct gagcgaggcc | 2760 |
| gacaaggccg gcttcatcaa gcgccagctg gtggagaccc gccagatcac caagcacgtg | 2820 |
| gcccgcatcc tggacagccg catgaacacc aagcgcgaca gaacgacaa gcccatccgc | 2880 |
| gaggtgaagg tgatcaccct gaagagcaag ctggtgagcg acttccgcaa ggacttccag | 2940 |
| ctgtacaagg tgcgcgacat caacaactac caccacgccc acgacgccta cctgaacgcc | 3000 |
| gtggtgggca ccgccctgat caagaagtac cccaagctgg agagcgagtt cgtgtacggc | 3060 |
| gactacaagg tgtacgacgt gcgcaagatg atcgccaaga gcgagcagga gatcggcaag | 3120 |
| gccaccgcca agcgcttctt ctacagcaac atcatgaact tcttcaagac cgaggtgaag | 3180 |
| ctggccaacg gcgagatccg caagcgcccc ctgatcgaga ccaacggcga gaccggcgag | 3240 |
| gtggtgtgga caaggagaa ggacttcgcc accgtgcgca aggtgctggc catgccccag | 3300 |
| gtgaacatcg tgaagaagac cgaggtgcag accggcggct tcagcaagga gagcatcctg | 3360 |
| agcaagcgcg agagcgccaa gctgatcccc cgcaagaagg gctgggacac ccgcaagtac | 3420 |
| ggcggcttcg gcagccccac cgtggcctac agcatcctgg tggtggccaa ggtggagaag | 3480 |
| ggcaaggcca gaagctgaa gagcgtgaag gtgctggtgg gcatcaccat catggagaag | 3540 |
| ggcagctacg agaaggaccc catcggcttc ctggaggcca agggctacaa ggacatcaag | 3600 |
| aaggagctga tcttcaagct gcccaagtac agcctgttcg agctggagaa cggccgccgc | 3660 |
| cgcatgctgg ccagcgccac cgagctgcag aaggccaacg agctggtgct gccccagcac | 3720 |
| ctggtgcgcc tgctgtacta caccagaac atcagcgcca ccaccggcag caacaacctg | 3780 |
| ggctacatcg agcagcaccg cgaggagttc aaggagatat tcgagaagat catcgacttc | 3840 |
| agcgagaagt acatcctgaa gaacaaggtg aacagcaacc tgaagagcag cttcgacgag | 3900 |
| cagttcgccg tgagcgacag catcctgctg agcaacagct tcgtgagcct gctgaagtac | 3960 |
| accagcttcg cgccagcgg cggcttcacc ttcctggacc tggacgtgaa gcagggccgc | 4020 |
| ctgcgctacc agaccgtgac cgaggtgctg gacgccaccc tgatctacca gagcatcacc | 4080 |
| ggcctgtacg agacccgcac cgacctgagc cagctgggcg gcgac | 4125 |

<210> SEQ ID NO 41
<211> LENGTH: 1092
<212> TYPE: DNA
<213> ORGANISM: Artificial Sequence
<220> FEATURE:
<223> OTHER INFORMATION: Synthetic Construct

<400> SEQUENCE: 41

| | |
|---|---:|
| tctgaagtcg agtttagcca cgagtattgg atgaggcacg cactgaccct ggcaaagcga | 60 |
| gcatgggatg aaagagaagt ccccgtgggc gccgtgctgg tgcacaacaa tagagtgatc | 120 |
| ggagagggat ggaacaggcc aatcggccgc cacgacccta ccgcacacgc agagatcatg | 180 |
| gcactgaggc agggaggcct ggtcatgcag aattaccgcc tgatcgatgc caccctgtat | 240 |
| gtgacactgg agccatgcgt gatgtgcgca ggagcaatga tccacagcag gatcggaaga | 300 |
| gtggtgttcg agcacgggga cgccaagacc ggcgcagcag gctccctgat ggatgtgctg | 360 |
| caccaccccg gcatgaacca ccgggtggag atcacagagg gaatcctggc agacgagtgc | 420 |
| gccgccctgc tgagcgattt ctttagaatg cggagacagg agatcaaggc ccagaagaag | 480 |

-continued

```
gcacagagct ccaccgactc tggaggatct agcggaggat cctctggaag cgagacacca    540
ggcacaagcg agtccgccac accagagagc tccggcggct cctccggagg atcctctgag    600
gtggagtttt cccacgagta ctggatgaga catgccctga ccctggccaa gagggcacgc    660
gatgagaggg aggtgcctgt gggagccgtg ctggtgctga acaatagagt gatcggcgag    720
ggctggaaca gagccatcgg cctgcacgac ccaacagccc atgccgaaat tatggccctg    780
agacagggcg gcctggtcat gcagaactac agactgattg acgccaccct gtacgtgaca    840
ttcgagcctt gcgtgatgtg cgccggcgcc atgatccact ctaggatcgg ccgcgtggtg    900
tttggcgtga ggaacgcaaa aaccggcgcc gcaggctccc tgatggacgt gctgcactac    960
cccggcatga atcaccgcgt cgaaattacc gagggaatcc tggcagatga atgtgccgcc   1020
ctgctgtgct atttctttcg gatgcctaga caggtgttca atgctcagaa gaaggcccag   1080
agctccaccg ac                                                       1092
```

<210> SEQ ID NO 42
<211> LENGTH: 498
<212> TYPE: DNA
<213> ORGANISM: Artificial Sequence
<220> FEATURE:
<223> OTHER INFORMATION: Synthetic Construct

<400> SEQUENCE: 42

```
tctgaggtgg agttttccca cgagtactgg atgagacatg ccctgaccct ggccaagagg     60
gcacgcgatg agagggaggt gcctgtggga gccgtgctgg tgctgaacaa tagagtgatc    120
ggcgagggct ggaacagagc catcggcctg cacgacccaa caggccatgc cgaaattatg    180
gccctgaggc agggcggcct ggtcatgcag aactacagac tgattgacgc caccctgtac    240
gggacattcg agccttgcgt gatgtgcgcc ggcgccatga tccactctag gatcggccgc    300
gtggtgtttg gcgtgaggaa cgcaaaaacc ggcgccgcag gctccctgat ggacgtgctg    360
cactaccccg gcatgaatca ccgcgtcgaa attaccgagg gaatcctggc agatgaatgt    420
gccgccctgc tgtgctattt ctttcggatg cctagacagg tgttcaatgc tcagaagaag    480
gcccagagct ccaccgac                                                  498
```

<210> SEQ ID NO 43
<211> LENGTH: 267
<212> TYPE: DNA
<213> ORGANISM: Artificial Sequence
<220> FEATURE:
<223> OTHER INFORMATION: Synthetic Construct

<400> SEQUENCE: 43

```
tgtttggatc tgaaaacgca agttcaaacg ccacagggta tgaaagaaat atccaatata     60
caggtcggcg atctcgtctt gtctaacact ggctataacg aggtgctgaa tgtatttcca    120
aaaagcaaga aaaaagtta caagataact ctggaagatg aaaagaaat tatctgttct     180 gaggagcatc tgtttccgac ccaaacaggg gagatgaata tcagtggcgg tctcaaagag    240
ggtatgtgtt tgtatgtcaa ggaataa                                        267
```

<210> SEQ ID NO 44
<211> LENGTH: 114
<212> TYPE: DNA
<213> ORGANISM: Artificial Sequence
<220> FEATURE:
<223> OTHER INFORMATION: Synthetic Construct

<400> SEQUENCE: 44
atgatgctca agaagatcct caagattgaa gagttggacg agcgcgagct tatagacata     60
gaagtcagtg gtaatcacct tttctacgca aatgacattt tgactcacaa ctcc          114

<210> SEQ ID NO 45
<211> LENGTH: 306
<212> TYPE: DNA
<213> ORGANISM: Artificial Sequence
<220> FEATURE:
<223> OTHER INFORMATION: Synthetic Construct

<400> SEQUENCE: 45
tgtctcagtt atgacaccga atcctgaca gtcgagtatg gatttctgcc gatcggcaag      60
attgtggagg agagaattga atgtacggtc tatacggtcg acaagaatgg tttcgtctac    120
acccaaccaa ttgctcaatg cataatcga ggggagcagg aggtgtttga gtattgcctg    180
gaggacgggt caatcattag agctacaaag gaccataagt ttatgacaac cgatggtcaa    240
atgctgccga tagatgaaat attcgaaagg ggactggatc ttaagcaagt cgatggcctt    300
ccaaac                                                                306

<210> SEQ ID NO 46
<211> LENGTH: 108
<212> TYPE: DNA
<213> ORGANISM: Artificial Sequence
<220> FEATURE:
<223> OTHER INFORMATION: Synthetic Construct

<400> SEQUENCE: 46
atggtcaaga ttatcagccg caaatccttg gggacacaga atgtatatga catcggcgtg     60
gaaaaggatc acaattttct gctgaagaat ggtcttgttg cttccaat                 108

<210> SEQ ID NO 47
<211> LENGTH: 166
<212> TYPE: PRT
<213> ORGANISM: Artificial Sequence
<220> FEATURE:
<223> OTHER INFORMATION: Synthetic Construct

<400> SEQUENCE: 47

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
            115                 120                 125

Val Glu Ile Thr Glu Gly Ile Leu Ala Asp Glu Cys Ala Ala Leu Leu
        130                 135                 140

```
Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 48
<211> LENGTH: 45
<212> TYPE: DNA
<213> ORGANISM: Artificial Sequence
<220> FEATURE:
<223> OTHER INFORMATION: Synthetic Construct

<400> SEQUENCE: 48
tgagtatcat cgtgtgaaag ctgaggggac gaggcaggcc tataa          45

<210> SEQ ID NO 49
<211> LENGTH: 45
<212> TYPE: DNA
<213> ORGANISM: Artificial Sequence
<220> FEATURE:
<223> OTHER INFORMATION: Synthetic Construct

<400> SEQUENCE: 49
aaaaacatca acttcagcca tccatttctt cagggtttgt atgtg          45

<210> SEQ ID NO 50
<211> LENGTH: 45
<212> TYPE: DNA
<213> ORGANISM: Artificial Sequence
<220> FEATURE:
<223> OTHER INFORMATION: Synthetic Construct

<400> SEQUENCE: 50
tatatcataa tgaaaacgcc gccatttctc aacagatctg tcaaa          45

<210> SEQ ID NO 51
<211> LENGTH: 45
<212> TYPE: DNA
<213> ORGANISM: Artificial Sequence
<220> FEATURE:
<223> OTHER INFORMATION: Synthetic Construct

<400> SEQUENCE: 51
ctgtgtgaaa tggctgcaaa tcgatggttg agctctgaga tttgg          45

<210> SEQ ID NO 52
<211> LENGTH: 45
<212> TYPE: DNA
<213> ORGANISM: Artificial Sequence
<220> FEATURE:
<223> OTHER INFORMATION: Synthetic Construct

<400> SEQUENCE: 52
gttctgcttt tgctactact cacgtttcca tgttgtcccc ctcta          45

<210> SEQ ID NO 53
<211> LENGTH: 45
<212> TYPE: DNA
<213> ORGANISM: Artificial Sequence
<220> FEATURE:
<223> OTHER INFORMATION: Synthetic Construct

<400> SEQUENCE: 53
attttatggc cttttgcaac tcgaccagaa aaaagcagc tttgg           45
```

```
<210> SEQ ID NO 54
<211> LENGTH: 45
<212> TYPE: DNA
<213> ORGANISM: Artificial Sequence
<220> FEATURE:
<223> OTHER INFORMATION: Synthetic Construct

<400> SEQUENCE: 54
tgaggagatc gcccacgggc tgccaggatc ccttgatcac ctcag          45

<210> SEQ ID NO 55
<211> LENGTH: 45
<212> TYPE: DNA
<213> ORGANISM: Artificial Sequence
<220> FEATURE:
<223> OTHER INFORMATION: Synthetic Construct

<400> SEQUENCE: 55
ggctgctctg tcagaaatat tcgtacagtc tcaagagtac tcatg          45

<210> SEQ ID NO 56
<211> LENGTH: 45
<212> TYPE: DNA
<213> ORGANISM: Artificial Sequence
<220> FEATURE:
<223> OTHER INFORMATION: Synthetic Construct

<400> SEQUENCE: 56
gtgtaggcat agctcttgaa tcgaggctta ggggaagaag ttctc          45

<210> SEQ ID NO 57
<211> LENGTH: 45
<212> TYPE: DNA
<213> ORGANISM: Artificial Sequence
<220> FEATURE:
<223> OTHER INFORMATION: Synthetic Construct

<400> SEQUENCE: 57
cctgttcttc agtaagacgt tgccatttga gaaggatgtc ttgta          45

<210> SEQ ID NO 58
<211> LENGTH: 45
<212> TYPE: DNA
<213> ORGANISM: Artificial Sequence
<220> FEATURE:
<223> OTHER INFORMATION: Synthetic Construct

<400> SEQUENCE: 58
gccattttag gcttttact tacttgtctg tagctctttc tctct           45

<210> SEQ ID NO 59
<211> LENGTH: 45
<212> TYPE: DNA
<213> ORGANISM: Artificial Sequence
<220> FEATURE:
<223> OTHER INFORMATION: Synthetic Construct

<400> SEQUENCE: 59
ctagtttctc acacatgaca cacctgttct tcagtaagac gttgc          45

<210> SEQ ID NO 60
<211> LENGTH: 45
<212> TYPE: DNA
<213> ORGANISM: Artificial Sequence
<220> FEATURE:
<223> OTHER INFORMATION: Synthetic Construct
```

<400> SEQUENCE: 60
gtgaagttga ttacattaac ctgtggataa ttacgagttg attgt    45

<210> SEQ ID NO 61
<211> LENGTH: 45
<212> TYPE: DNA
<213> ORGANISM: Artificial Sequence
<220> FEATURE:
<223> OTHER INFORMATION: Synthetic Construct

<400> SEQUENCE: 61
ttttgtatat ctgagttaaa ctgctccaat tccttcaaag gaatg    45

<210> SEQ ID NO 62
<211> LENGTH: 45
<212> TYPE: DNA
<213> ORGANISM: Artificial Sequence
<220> FEATURE:
<223> OTHER INFORMATION: Synthetic Construct

<400> SEQUENCE: 62
tctgcaatat aagctgccaa ctgcttgtca atgaatgtga gggac    45

<210> SEQ ID NO 63
<211> LENGTH: 45
<212> TYPE: DNA
<213> ORGANISM: Artificial Sequence
<220> FEATURE:
<223> OTHER INFORMATION: Synthetic Construct

<400> SEQUENCE: 63
ggactggggt tccagtctca tccagtctag gaagagggcc gcttc    45

<210> SEQ ID NO 64
<211> LENGTH: 45
<212> TYPE: DNA
<213> ORGANISM: Artificial Sequence
<220> FEATURE:
<223> OTHER INFORMATION: Synthetic Construct

<400> SEQUENCE: 64
agtcgttgtg tggctgactg ctggcaaacc acactattcc agtca    45

<210> SEQ ID NO 65
<211> LENGTH: 45
<212> TYPE: DNA
<213> ORGANISM: Artificial Sequence
<220> FEATURE:
<223> OTHER INFORMATION: Synthetic Construct

<400> SEQUENCE: 65
atttgtgtct ttctgagaaa ctgttcagct tctgttagcc actga    45

<210> SEQ ID NO 66
<211> LENGTH: 45
<212> TYPE: DNA
<213> ORGANISM: Artificial Sequence
<220> FEATURE:
<223> OTHER INFORMATION: Synthetic Construct

<400> SEQUENCE: 66
aagaacccag cggtcttctg tccatctaca gatgtttgcc catcg    45

<210> SEQ ID NO 67
<211> LENGTH: 45

```
<212> TYPE: DNA
<213> ORGANISM: Artificial Sequence
<220> FEATURE:
<223> OTHER INFORMATION: Synthetic Construct

<400> SEQUENCE: 67
agactttttc cgaagttcac tccacttgaa gttcatgtta tccaa        45

<210> SEQ ID NO 68
<211> LENGTH: 45
<212> TYPE: DNA
<213> ORGANISM: Artificial Sequence
<220> FEATURE:
<223> OTHER INFORMATION: Synthetic Construct

<400> SEQUENCE: 68
tacctgttgg cacatgtgat cccactgagt gttaagttct ttgag        45

<210> SEQ ID NO 69
<211> LENGTH: 45
<212> TYPE: DNA
<213> ORGANISM: Artificial Sequence
<220> FEATURE:
<223> OTHER INFORMATION: Synthetic Construct

<400> SEQUENCE: 69
caaagggcct tctgcagtct tcggagtttc atggcagtcc tataa        45

<210> SEQ ID NO 70
<211> LENGTH: 45
<212> TYPE: DNA
<213> ORGANISM: Artificial Sequence
<220> FEATURE:
<223> OTHER INFORMATION: Synthetic Construct

<400> SEQUENCE: 70
atggttaatg tctaaccttt atccactgga gatttgtctg cttga        45

<210> SEQ ID NO 71
<211> LENGTH: 45
<212> TYPE: DNA
<213> ORGANISM: Artificial Sequence
<220> FEATURE:
<223> OTHER INFORMATION: Synthetic Construct

<400> SEQUENCE: 71
caaaataatc tgaccttaag ttgttcttcc aaagcagcag ttgcg        45

<210> SEQ ID NO 72
<211> LENGTH: 45
<212> TYPE: DNA
<213> ORGANISM: Artificial Sequence
<220> FEATURE:
<223> OTHER INFORMATION: Synthetic Construct

<400> SEQUENCE: 72
catctacaga tgtttgccca tcgatctccc aatacctgga gaaga        45

<210> SEQ ID NO 73
<211> LENGTH: 45
<212> TYPE: DNA
<213> ORGANISM: Artificial Sequence
<220> FEATURE:
<223> OTHER INFORMATION: Synthetic Construct

<400> SEQUENCE: 73
```
aaggtgttct tgtacttcat cccactgatt ctgaattctt tcaac    45

<210> SEQ ID NO 74
<211> LENGTH: 45
<212> TYPE: DNA
<213> ORGANISM: Artificial Sequence
<220> FEATURE:
<223> OTHER INFORMATION: Synthetic Construct

<400> SEQUENCE: 74
gaaggtgttc ttgtacttca tcccactgat tctgaattct ttcaa    45

<210> SEQ ID NO 75
<211> LENGTH: 45
<212> TYPE: DNA
<213> ORGANISM: Artificial Sequence
<220> FEATURE:
<223> OTHER INFORMATION: Synthetic Construct

<400> SEQUENCE: 75
gctatgcttt gaatttttaa tcgttcaatt tgaggttgaa gatct    45

<210> SEQ ID NO 76
<211> LENGTH: 45
<212> TYPE: DNA
<213> ORGANISM: Artificial Sequence
<220> FEATURE:
<223> OTHER INFORMATION: Synthetic Construct

<400> SEQUENCE: 76
tctaggaggc gcctcccatc ctgtaggtca ctgaagaggt tctca    45

<210> SEQ ID NO 77
<211> LENGTH: 45
<212> TYPE: DNA
<213> ORGANISM: Artificial Sequence
<220> FEATURE:
<223> OTHER INFORMATION: Synthetic Construct

<400> SEQUENCE: 77
gtgtaattac cattcaccat ctgttccacc agggcctgag ctgat    45

<210> SEQ ID NO 78
<211> LENGTH: 45
<212> TYPE: DNA
<213> ORGANISM: Artificial Sequence
<220> FEATURE:
<223> OTHER INFORMATION: Synthetic Construct

<400> SEQUENCE: 78
tgagcatgct ttaccaggat ctgttccctt gtggtcaccg tagtt    45

<210> SEQ ID NO 79
<211> LENGTH: 45
<212> TYPE: DNA
<213> ORGANISM: Artificial Sequence
<220> FEATURE:
<223> OTHER INFORMATION: Synthetic Construct

<400> SEQUENCE: 79
ctactgtata gggaccctcc ttccatgact caagcttggc tctgg    45

<210> SEQ ID NO 80
<211> LENGTH: 45
<212> TYPE: DNA
<213> ORGANISM: Artificial Sequence
<220> FEATURE:
<223> OTHER INFORMATION: Synthetic Construct

<400> SEQUENCE: 80
cagcttcttc cttagcttcc agccattgtg ttgaatcctt taaca         45

<210> SEQ ID NO 81
<211> LENGTH: 45
<212> TYPE: DNA
<213> ORGANISM: Artificial Sequence
<220> FEATURE:
<223> OTHER INFORMATION: Synthetic Construct

<400> SEQUENCE: 81
agctgcccaa ggtcttttat ttgagcttca atttctcctt gtttc         45

<210> SEQ ID NO 82
<211> LENGTH: 45
<212> TYPE: DNA
<213> ORGANISM: Artificial Sequence
<220> FEATURE:
<223> OTHER INFORMATION: Synthetic Construct

<400> SEQUENCE: 82
tgccagtaac aactcacaat tgtgcaaag ttgagtcttc gaaac         45

<210> SEQ ID NO 83
<211> LENGTH: 45
<212> TYPE: DNA
<213> ORGANISM: Artificial Sequence
<220> FEATURE:
<223> OTHER INFORMATION: Synthetic Construct

<400> SEQUENCE: 83
agagtaacag tctgagtagg agctaaaata ttttgggttt ttgca         45

<210> SEQ ID NO 84
<211> LENGTH: 45
<212> TYPE: DNA
<213> ORGANISM: Artificial Sequence
<220> FEATURE:
<223> OTHER INFORMATION: Synthetic Construct

<400> SEQUENCE: 84
cttcagcaaa aaaagtactc acgcagaatc tactggccag aagtt         45

<210> SEQ ID NO 85
<211> LENGTH: 45
<212> TYPE: DNA
<213> ORGANISM: Artificial Sequence
<220> FEATURE:
<223> OTHER INFORMATION: Synthetic Construct

<400> SEQUENCE: 85
acatctacat tgtctgcca ctggcggagg tctttggcca actgc         45

<210> SEQ ID NO 86
<211> LENGTH: 45
<212> TYPE: DNA
<213> ORGANISM: Artificial Sequence
<220> FEATURE:
<223> OTHER INFORMATION: Synthetic Construct

<400> SEQUENCE: 86
ctgagatagt ataggccact tgttgctct tgcagagaac tttgt         45

<210> SEQ ID NO 87
<211> LENGTH: 45
<212> TYPE: DNA
<213> ORGANISM: Artificial Sequence
<220> FEATURE:
<223> OTHER INFORMATION: Synthetic Construct

<400> SEQUENCE: 87
tagctgtcct ttacacactt tacctgttga gaatagtgca tttga    45

<210> SEQ ID NO 88
<211> LENGTH: 45
<212> TYPE: DNA
<213> ORGANISM: Artificial Sequence
<220> FEATURE:
<223> OTHER INFORMATION: Synthetic Construct

<400> SEQUENCE: 88
gcctgggctt cctgaggcat ttgagctgcg tccaccttgt ctgca    45

<210> SEQ ID NO 89
<211> LENGTH: 45
<212> TYPE: DNA
<213> ORGANISM: Artificial Sequence
<220> FEATURE:
<223> OTHER INFORMATION: Synthetic Construct

<400> SEQUENCE: 89
tgcactggca ggtagcccat tcggggatgc ttcgcaaaat acctt    45

<210> SEQ ID NO 90
<211> LENGTH: 45
<212> TYPE: DNA
<213> ORGANISM: Artificial Sequence
<220> FEATURE:
<223> OTHER INFORMATION: Synthetic Construct

<400> SEQUENCE: 90
ttatagttcc acattcaatt acctctgggc tcctggtaga gtttc    45

<210> SEQ ID NO 91
<211> LENGTH: 45
<212> TYPE: DNA
<213> ORGANISM: Artificial Sequence
<220> FEATURE:
<223> OTHER INFORMATION: Synthetic Construct

<400> SEQUENCE: 91
cgtcaggctg gcgtcaaact taccggagtg caatattcca ccatg    45

<210> SEQ ID NO 92
<211> LENGTH: 45
<212> TYPE: DNA
<213> ORGANISM: Artificial Sequence
<220> FEATURE:
<223> OTHER INFORMATION: Synthetic Construct

<400> SEQUENCE: 92
tcatccaaaa gtgtgtcagc ctgaatgatc cactttgtga tgtgg    45

<210> SEQ ID NO 93
<211> LENGTH: 45
<212> TYPE: DNA
<213> ORGANISM: Artificial Sequence
<220> FEATURE:
<223> OTHER INFORMATION: Synthetic Construct

```
<400> SEQUENCE: 93
tgtagccaca ccagaagttc ctgcagagaa aggtgcagac gcttc              45

<210> SEQ ID NO 94
<211> LENGTH: 45
<212> TYPE: DNA
<213> ORGANISM: Artificial Sequence
<220> FEATURE:
<223> OTHER INFORMATION: Synthetic Construct

<400> SEQUENCE: 94
tgtaaggatt tttcagtctc ctgggcagac tggatgctct gttca              45

<210> SEQ ID NO 95
<211> LENGTH: 45
<212> TYPE: DNA
<213> ORGANISM: Artificial Sequence
<220> FEATURE:
<223> OTHER INFORMATION: Synthetic Construct

<400> SEQUENCE: 95
agaatgggat ccagtatact tacaggctcc aatagtggtc agtcc              45

<210> SEQ ID NO 96
<211> LENGTH: 45
<212> TYPE: DNA
<213> ORGANISM: Artificial Sequence
<220> FEATURE:
<223> OTHER INFORMATION: Synthetic Construct

<400> SEQUENCE: 96
ttcagaggcg caatttctcc tcgaagtgcc tgtgtgcaat agtca              45

<210> SEQ ID NO 97
<211> LENGTH: 45
<212> TYPE: DNA
<213> ORGANISM: Artificial Sequence
<220> FEATURE:
<223> OTHER INFORMATION: Synthetic Construct

<400> SEQUENCE: 97
gtttcttcca aagcagcctc tcgctcactc accctgcaaa ggacc              45

<210> SEQ ID NO 98
<211> LENGTH: 45
<212> TYPE: DNA
<213> ORGANISM: Artificial Sequence
<220> FEATURE:
<223> OTHER INFORMATION: Synthetic Construct

<400> SEQUENCE: 98
ctgaacttct cagcttttc tcgctctatg gcctgcagca tgaga               45

<210> SEQ ID NO 99
<211> LENGTH: 45
<212> TYPE: DNA
<213> ORGANISM: Artificial Sequence
<220> FEATURE:
<223> OTHER INFORMATION: Synthetic Construct

<400> SEQUENCE: 99
agatttaacc actcttctgc tcgggaggtg acagctatcc agtta              45

<210> SEQ ID NO 100
```

```
<211> LENGTH: 45
<212> TYPE: DNA
<213> ORGANISM: Artificial Sequence
<220> FEATURE:
<223> OTHER INFORMATION: Synthetic Construct

<400> SEQUENCE: 100
tgttttatct ttatttcctc tcgctttctc tcatctgtga ttctt          45

<210> SEQ ID NO 101
<211> LENGTH: 45
<212> TYPE: DNA
<213> ORGANISM: Artificial Sequence
<220> FEATURE:
<223> OTHER INFORMATION: Synthetic Construct

<400> SEQUENCE: 101
ccagctggga ggagagcttc ttccagcgtc cctcaatttc ttcaa          45

<210> SEQ ID NO 102
<211> LENGTH: 45
<212> TYPE: DNA
<213> ORGANISM: Artificial Sequence
<220> FEATURE:
<223> OTHER INFORMATION: Synthetic Construct

<400> SEQUENCE: 102
acacagcttc tgagcgagta atccagctgt gaagttcagt tatat          45

<210> SEQ ID NO 103
<211> LENGTH: 45
<212> TYPE: DNA
<213> ORGANISM: Artificial Sequence
<220> FEATURE:
<223> OTHER INFORMATION: Synthetic Construct

<400> SEQUENCE: 103
aagtaaacgg tttaccgcct tccactcaga gctcagatct tctaa          45

<210> SEQ ID NO 104
<211> LENGTH: 45
<212> TYPE: DNA
<213> ORGANISM: Artificial Sequence
<220> FEATURE:
<223> OTHER INFORMATION: Synthetic Construct

<400> SEQUENCE: 104
aaatagaaaa attagatgac ttgccaaagg tcacaaaggt aactg          45

<210> SEQ ID NO 105
<211> LENGTH: 45
<212> TYPE: DNA
<213> ORGANISM: Artificial Sequence
<220> FEATURE:
<223> OTHER INFORMATION: Synthetic Construct

<400> SEQUENCE: 105
ttgactttct cgaggtgatc ttggagagag tcaatgagga gatcg          45

<210> SEQ ID NO 106
<211> LENGTH: 45
<212> TYPE: DNA
<213> ORGANISM: Artificial Sequence
<220> FEATURE:
<223> OTHER INFORMATION: Synthetic Construct

<400> SEQUENCE: 106
```
tctaaaatca tcttactttc ttgtagacgc tgctcaaaat tggct                45

<210> SEQ ID NO 107
<211> LENGTH: 45
<212> TYPE: DNA
<213> ORGANISM: Artificial Sequence
<220> FEATURE:
<223> OTHER INFORMATION: Synthetic Construct

<400> SEQUENCE: 107
gaattgaccc tgacttgttc ttgttctaga tcttcttgaa gcacc                45

<210> SEQ ID NO 108
<211> LENGTH: 45
<212> TYPE: DNA
<213> ORGANISM: Artificial Sequence
<220> FEATURE:
<223> OTHER INFORMATION: Synthetic Construct

<400> SEQUENCE: 108
tggatggctt caatgctcac ttgttgaggc aaaacttgga agagt                45

<210> SEQ ID NO 109
<211> LENGTH: 45
<212> TYPE: DNA
<213> ORGANISM: Artificial Sequence
<220> FEATURE:
<223> OTHER INFORMATION: Synthetic Construct

<400> SEQUENCE: 109
aacagtcctc tacttcttcc caccaaagca ttttgaaaag tgtat                45

<210> SEQ ID NO 110
<211> LENGTH: 45
<212> TYPE: DNA
<213> ORGANISM: Artificial Sequence
<220> FEATURE:
<223> OTHER INFORMATION: Synthetic Construct

<400> SEQUENCE: 110
aggcctcctt tctggcatag accttccaca aaacaaacaa acaaa                45

<210> SEQ ID NO 111
<211> LENGTH: 45
<212> TYPE: DNA
<213> ORGANISM: Artificial Sequence
<220> FEATURE:
<223> OTHER INFORMATION: Synthetic Construct

<400> SEQUENCE: 111
tttggtttct gactgctgga cccatgtcct gatggcactc atggt                45

<210> SEQ ID NO 112
<211> LENGTH: 45
<212> TYPE: DNA
<213> ORGANISM: Artificial Sequence
<220> FEATURE:
<223> OTHER INFORMATION: Synthetic Construct

<400> SEQUENCE: 112
atcttacttt cttgtagacg ctgctcaaaa ttggctggtt tctgg                45

<210> SEQ ID NO 113
<211> LENGTH: 45
<212> TYPE: DNA

```
<213> ORGANISM: Artificial Sequence
<220> FEATURE:
<223> OTHER INFORMATION: Synthetic Construct

<400> SEQUENCE: 113
agatttttca cttatcttca tacctcttca tgtagttccc tccaa          45

<210> SEQ ID NO 114
<211> LENGTH: 45
<212> TYPE: DNA
<213> ORGANISM: Artificial Sequence
<220> FEATURE:
<223> OTHER INFORMATION: Synthetic Construct

<400> SEQUENCE: 114
ctgttcagtt gttctgaggc ttgtttgatg ctatctgcat taaca          45

<210> SEQ ID NO 115
<211> LENGTH: 45
<212> TYPE: DNA
<213> ORGANISM: Artificial Sequence
<220> FEATURE:
<223> OTHER INFORMATION: Synthetic Construct

<400> SEQUENCE: 115
cagcattaat atacacgact tacatctgta cttgtcttcc aaatg          45

<210> SEQ ID NO 116
<211> LENGTH: 45
<212> TYPE: DNA
<213> ORGANISM: Artificial Sequence
<220> FEATURE:
<223> OTHER INFORMATION: Synthetic Construct

<400> SEQUENCE: 116
tcatgacttg tcaaatcaga ttggattttc tgttgggagg atagc          45

<210> SEQ ID NO 117
<211> LENGTH: 45
<212> TYPE: DNA
<213> ORGANISM: Artificial Sequence
<220> FEATURE:
<223> OTHER INFORMATION: Synthetic Construct

<400> SEQUENCE: 117
atctgctcca attgttgtag ctgattatag aaagcgatga tgttg          45

<210> SEQ ID NO 118
<211> LENGTH: 45
<212> TYPE: DNA
<213> ORGANISM: Artificial Sequence
<220> FEATURE:
<223> OTHER INFORMATION: Synthetic Construct

<400> SEQUENCE: 118
caaatttgct ctcaatttcc cgccagcgct tgctgagctg gatct          45

<210> SEQ ID NO 119
<211> LENGTH: 45
<212> TYPE: DNA
<213> ORGANISM: Artificial Sequence
<220> FEATURE:
<223> OTHER INFORMATION: Synthetic Construct

<400> SEQUENCE: 119
cattcaaagc caggccatca gaccagctgg tggtgaagtt gatta          45
```

<210> SEQ ID NO 120
<211> LENGTH: 45
<212> TYPE: DNA
<213> ORGANISM: Artificial Sequence
<220> FEATURE:
<223> OTHER INFORMATION: Synthetic Construct

<400> SEQUENCE: 120
ttcatctctt caactgcttt ctgtaattca tctggagttt tatat        45

<210> SEQ ID NO 121
<211> LENGTH: 45
<212> TYPE: DNA
<213> ORGANISM: Artificial Sequence
<220> FEATURE:
<223> OTHER INFORMATION: Synthetic Construct

<400> SEQUENCE: 121
attgaaagct agaaagtaca tacggccagt ttttgaagac ttgat        45

<210> SEQ ID NO 122
<211> LENGTH: 45
<212> TYPE: DNA
<213> ORGANISM: Artificial Sequence
<220> FEATURE:
<223> OTHER INFORMATION: Synthetic Construct

<400> SEQUENCE: 122
ttcaaatact ggccaatact tacagcaaag ggccttctgc agtct        45

<210> SEQ ID NO 123
<211> LENGTH: 45
<212> TYPE: DNA
<213> ORGANISM: Artificial Sequence
<220> FEATURE:
<223> OTHER INFORMATION: Synthetic Construct

<400> SEQUENCE: 123
gttgtctgtg ttagtgatgg ctgagtggtg gtgacagcct gtgaa        45

<210> SEQ ID NO 124
<211> LENGTH: 45
<212> TYPE: DNA
<213> ORGANISM: Artificial Sequence
<220> FEATURE:
<223> OTHER INFORMATION: Synthetic Construct

<400> SEQUENCE: 124
tcatcagcct gcctcttgta ctgataccac tgatgagaaa tttct        45

<210> SEQ ID NO 125
<211> LENGTH: 45
<212> TYPE: DNA
<213> ORGANISM: Artificial Sequence
<220> FEATURE:
<223> OTHER INFORMATION: Synthetic Construct

<400> SEQUENCE: 125
tactgtatag ggaccctcct tccatgactc aagcttggct ctggc        45

<210> SEQ ID NO 126
<211> LENGTH: 45
<212> TYPE: DNA
<213> ORGANISM: Artificial Sequence
<220> FEATURE:

<223> OTHER INFORMATION: Synthetic Construct

<400> SEQUENCE: 126
atgttgaatg catgttccag tcgttgtgtg gctgactgct ggcaa    45

<210> SEQ ID NO 127
<211> LENGTH: 45
<212> TYPE: DNA
<213> ORGANISM: Artificial Sequence
<220> FEATURE:
<223> OTHER INFORMATION: Synthetic Construct

<400> SEQUENCE: 127
tgccatttga aaggatgtc ttgtaaaaga acccagcggt cttct    45

<210> SEQ ID NO 128
<211> LENGTH: 45
<212> TYPE: DNA
<213> ORGANISM: Artificial Sequence
<220> FEATURE:
<223> OTHER INFORMATION: Synthetic Construct

<400> SEQUENCE: 128
gagacttttt ccgaagttca ctccacttga agttcatgtt atcca    45

<210> SEQ ID NO 129
<211> LENGTH: 45
<212> TYPE: DNA
<213> ORGANISM: Artificial Sequence
<220> FEATURE:
<223> OTHER INFORMATION: Synthetic Construct

<400> SEQUENCE: 129
ttagcaactg gcagaattcg atccaccggc tgttcagttg ttctg    45

<210> SEQ ID NO 130
<211> LENGTH: 45
<212> TYPE: DNA
<213> ORGANISM: Artificial Sequence
<220> FEATURE:
<223> OTHER INFORMATION: Synthetic Construct

<400> SEQUENCE: 130
ttgccacatc tacatttgtc tgccactggc ggaggtcttt ggcca    45

<210> SEQ ID NO 131
<211> LENGTH: 45
<212> TYPE: DNA
<213> ORGANISM: Artificial Sequence
<220> FEATURE:
<223> OTHER INFORMATION: Synthetic Construct

<400> SEQUENCE: 131
tcccattcag cctagtgcag agccactggt agttggtggt tagag    45

<210> SEQ ID NO 132
<211> LENGTH: 45
<212> TYPE: DNA
<213> ORGANISM: Artificial Sequence
<220> FEATURE:
<223> OTHER INFORMATION: Synthetic Construct

<400> SEQUENCE: 132
gacttactgg aaagaaagtg ctgagatgct ggaccaaagt ccctg    45

```
<210> SEQ ID NO 133
<211> LENGTH: 45
<212> TYPE: DNA
<213> ORGANISM: Artificial Sequence
<220> FEATURE:
<223> OTHER INFORMATION: Synthetic Construct

<400> SEQUENCE: 133
tttaatcgtt caatttgagg ttgaagatct gatagccggt tgact          45

<210> SEQ ID NO 134
<211> LENGTH: 45
<212> TYPE: DNA
<213> ORGANISM: Artificial Sequence
<220> FEATURE:
<223> OTHER INFORMATION: Synthetic Construct

<400> SEQUENCE: 134
aaagagattg tctatacctg ttggcacatg tgatcccact gagtg          45

<210> SEQ ID NO 135
<211> LENGTH: 45
<212> TYPE: DNA
<213> ORGANISM: Artificial Sequence
<220> FEATURE:
<223> OTHER INFORMATION: Synthetic Construct

<400> SEQUENCE: 135
aagtttttgg actaaattat cccaacaccg ggcaaagtta tccag          45

<210> SEQ ID NO 136
<211> LENGTH: 45
<212> TYPE: DNA
<213> ORGANISM: Artificial Sequence
<220> FEATURE:
<223> OTHER INFORMATION: Synthetic Construct

<400> SEQUENCE: 136
agctcagcat cccgggact ctggggagag gtgggcatca tttca           45

<210> SEQ ID NO 137
<211> LENGTH: 45
<212> TYPE: DNA
<213> ORGANISM: Artificial Sequence
<220> FEATURE:
<223> OTHER INFORMATION: Synthetic Construct

<400> SEQUENCE: 137
ttgtccccct ctaagacagt ctgcactggc aggtagccca ttcgg          45

<210> SEQ ID NO 138
<211> LENGTH: 45
<212> TYPE: DNA
<213> ORGANISM: Artificial Sequence
<220> FEATURE:
<223> OTHER INFORMATION: Synthetic Construct

<400> SEQUENCE: 138
ttcgcaaaat accttttggt tcgaaatttg ttttttagta ccttg          45

<210> SEQ ID NO 139
<211> LENGTH: 45
<212> TYPE: DNA
<213> ORGANISM: Artificial Sequence
<220> FEATURE:
<223> OTHER INFORMATION: Synthetic Construct
```

<400> SEQUENCE: 139
tgcaactcga ccagaaaaaa agcagctttg gcagatgtca taatt            45

<210> SEQ ID NO 140
<211> LENGTH: 45
<212> TYPE: DNA
<213> ORGANISM: Artificial Sequence
<220> FEATURE:
<223> OTHER INFORMATION: Synthetic Construct

<400> SEQUENCE: 140
ttgcagatgt tacatttggc ctgatgcttg gcagtttctg cagca            45

<210> SEQ ID NO 141
<211> LENGTH: 45
<212> TYPE: DNA
<213> ORGANISM: Artificial Sequence
<220> FEATURE:
<223> OTHER INFORMATION: Synthetic Construct

<400> SEQUENCE: 141
aaataaaaac atgccatacg tacgtatcat aaacattcag cagcc            45

<210> SEQ ID NO 142
<211> LENGTH: 45
<212> TYPE: DNA
<213> ORGANISM: Artificial Sequence
<220> FEATURE:
<223> OTHER INFORMATION: Synthetic Construct

<400> SEQUENCE: 142
tacttacagc aaagggcctt ctgcagtctt cggagtttca tggca            45

<210> SEQ ID NO 143
<211> LENGTH: 45
<212> TYPE: DNA
<213> ORGANISM: Artificial Sequence
<220> FEATURE:
<223> OTHER INFORMATION: Synthetic Construct

<400> SEQUENCE: 143
ttgacctcct cagcctgctt tcgtagaagc cgagtgacat tctgg            45

<210> SEQ ID NO 144
<211> LENGTH: 45
<212> TYPE: DNA
<213> ORGANISM: Artificial Sequence
<220> FEATURE:
<223> OTHER INFORMATION: Synthetic Construct

<400> SEQUENCE: 144
attcaattac ctctgggctc ctggtagagt ttctctagtc cttcc            45

<210> SEQ ID NO 145
<211> LENGTH: 45
<212> TYPE: DNA
<213> ORGANISM: Artificial Sequence
<220> FEATURE:
<223> OTHER INFORMATION: Synthetic Construct

<400> SEQUENCE: 145
aatgcctgac ttacttgcca ttgtttcatc agctcttta ctccc             45

<210> SEQ ID NO 146
<211> LENGTH: 45

-continued

```
<212> TYPE: DNA
<213> ORGANISM: Artificial Sequence
<220> FEATURE:
<223> OTHER INFORMATION: Synthetic Construct

<400> SEQUENCE: 146
tgtacttcat cccactgatt ctgaattctt tcaactagaa taaaa            45

<210> SEQ ID NO 147
<211> LENGTH: 45
<212> TYPE: DNA
<213> ORGANISM: Artificial Sequence
<220> FEATURE:
<223> OTHER INFORMATION: Synthetic Construct

<400> SEQUENCE: 147
tgcttcatta ccttcactgg ctgagtggct ggttttcct tgtac             45

<210> SEQ ID NO 148
<211> LENGTH: 45
<212> TYPE: DNA
<213> ORGANISM: Artificial Sequence
<220> FEATURE:
<223> OTHER INFORMATION: Synthetic Construct

<400> SEQUENCE: 148
tttaattgtt tgagaattcc ctggcgcagg ggcaactctt ccacc            45

<210> SEQ ID NO 149
<211> LENGTH: 45
<212> TYPE: DNA
<213> ORGANISM: Artificial Sequence
<220> FEATURE:
<223> OTHER INFORMATION: Synthetic Construct

<400> SEQUENCE: 149
atatgtgtta cctacccttg tcggtccttg tacattttgt taact            45

<210> SEQ ID NO 150
<211> LENGTH: 45
<212> TYPE: DNA
<213> ORGANISM: Artificial Sequence
<220> FEATURE:
<223> OTHER INFORMATION: Synthetic Construct

<400> SEQUENCE: 150
tcaagctggg agagagcttc ctgtagcttc acctttcca caggc             45

<210> SEQ ID NO 151
<211> LENGTH: 45
<212> TYPE: DNA
<213> ORGANISM: Artificial Sequence
<220> FEATURE:
<223> OTHER INFORMATION: Synthetic Construct

<400> SEQUENCE: 151
atgtcaatcc gacctgagct tgttgtaga ctatctttta tattc             45

<210> SEQ ID NO 152
<211> LENGTH: 45
<212> TYPE: DNA
<213> ORGANISM: Artificial Sequence
<220> FEATURE:
<223> OTHER INFORMATION: Synthetic Construct

<400> SEQUENCE: 152
```

```
gttgtagact atcttttata ttctgtaata taaaaatttt aaaac          45

<210> SEQ ID NO 153
<211> LENGTH: 45
<212> TYPE: DNA
<213> ORGANISM: Artificial Sequence
<220> FEATURE:
<223> OTHER INFORMATION: Synthetic Construct

<400> SEQUENCE: 153
tcccgccagc gcttgctgag ctggatctga gttggctcca ctgcc          45

<210> SEQ ID NO 154
<211> LENGTH: 45
<212> TYPE: DNA
<213> ORGANISM: Artificial Sequence
<220> FEATURE:
<223> OTHER INFORMATION: Synthetic Construct

<400> SEQUENCE: 154
ttatgttttg tctgtaacag ctgctgtttt atctttattt cctct          45

<210> SEQ ID NO 155
<211> LENGTH: 45
<212> TYPE: DNA
<213> ORGANISM: Artificial Sequence
<220> FEATURE:
<223> OTHER INFORMATION: Synthetic Construct

<400> SEQUENCE: 155
tgttttgtct gtaacagctg ctgttttatc tttatttcct ctcgc          45

<210> SEQ ID NO 156
<211> LENGTH: 45
<212> TYPE: DNA
<213> ORGANISM: Artificial Sequence
<220> FEATURE:
<223> OTHER INFORMATION: Synthetic Construct

<400> SEQUENCE: 156
tttctctcat ctgtgattct tgttgtaag ttgtctcctc tttgc           45

<210> SEQ ID NO 157
<211> LENGTH: 45
<212> TYPE: DNA
<213> ORGANISM: Artificial Sequence
<220> FEATURE:
<223> OTHER INFORMATION: Synthetic Construct

<400> SEQUENCE: 157
accttaagca cgtcttcttt tgctggggt ttcttttct ctgat            45

<210> SEQ ID NO 158
<211> LENGTH: 45
<212> TYPE: DNA
<213> ORGANISM: Artificial Sequence
<220> FEATURE:
<223> OTHER INFORMATION: Synthetic Construct

<400> SEQUENCE: 158
ttaagcacgt cttctttttg ctggggtttc tttttctctg attca          45

<210> SEQ ID NO 159
<211> LENGTH: 45
<212> TYPE: DNA
<213> ORGANISM: Artificial Sequence
```

```
<220> FEATURE:
<223> OTHER INFORMATION: Synthetic Construct

<400> SEQUENCE: 159
atactcttca ggtgcacctt ctgtttctca atctcttttt gagta          45

<210> SEQ ID NO 160
<211> LENGTH: 45
<212> TYPE: DNA
<213> ORGANISM: Artificial Sequence
<220> FEATURE:
<223> OTHER INFORMATION: Synthetic Construct

<400> SEQUENCE: 160
agctgtgact gtactacttc ctgttccaca ctctttgttt ccaat          45

<210> SEQ ID NO 161
<211> LENGTH: 45
<212> TYPE: DNA
<213> ORGANISM: Artificial Sequence
<220> FEATURE:
<223> OTHER INFORMATION: Synthetic Construct

<400> SEQUENCE: 161
ttggctggtt tctggaataa tcgaaacttc atggagacat cttgt          45

<210> SEQ ID NO 162
<211> LENGTH: 45
<212> TYPE: DNA
<213> ORGANISM: Artificial Sequence
<220> FEATURE:
<223> OTHER INFORMATION: Synthetic Construct

<400> SEQUENCE: 162
tgcatctctg atagatcttt ctggaggctt acagttttct ccaaa          45

<210> SEQ ID NO 163
<211> LENGTH: 45
<212> TYPE: DNA
<213> ORGANISM: Artificial Sequence
<220> FEATURE:
<223> OTHER INFORMATION: Synthetic Construct

<400> SEQUENCE: 163
acagtgaaag agattgtcta tacctgttgg cacatgtgat cccac          45

<210> SEQ ID NO 164
<211> LENGTH: 45
<212> TYPE: DNA
<213> ORGANISM: Artificial Sequence
<220> FEATURE:
<223> OTHER INFORMATION: Synthetic Construct

<400> SEQUENCE: 164
aaggcatcat ataaaaatct tactctgcac tgtttcagct gcttt          45

<210> SEQ ID NO 165
<211> LENGTH: 45
<212> TYPE: DNA
<213> ORGANISM: Artificial Sequence
<220> FEATURE:
<223> OTHER INFORMATION: Synthetic Construct

<400> SEQUENCE: 165
cttactctgc actgtttcag ctgctttttt agaatttctg aatcc          45
```

<210> SEQ ID NO 166
<211> LENGTH: 45
<212> TYPE: DNA
<213> ORGANISM: Artificial Sequence
<220> FEATURE:
<223> OTHER INFORMATION: Synthetic Construct

<400> SEQUENCE: 166
tcttgaatta cctgaatttt tcggagttta ttcatttgct cctct                45

<210> SEQ ID NO 167
<211> LENGTH: 45
<212> TYPE: DNA
<213> ORGANISM: Artificial Sequence
<220> FEATURE:
<223> OTHER INFORMATION: Synthetic Construct

<400> SEQUENCE: 167
tgttgctctt gcagagaact tgtaaagcc taaaaaacaa ttttt                 45

<210> SEQ ID NO 168
<211> LENGTH: 45
<212> TYPE: DNA
<213> ORGANISM: Artificial Sequence
<220> FEATURE:
<223> OTHER INFORMATION: Synthetic Construct

<400> SEQUENCE: 168
attggtggca aagtgtcaaa aactttatca aaagggaaaa aagaa                45

<210> SEQ ID NO 169
<211> LENGTH: 45
<212> TYPE: DNA
<213> ORGANISM: Artificial Sequence
<220> FEATURE:
<223> OTHER INFORMATION: Synthetic Construct

<400> SEQUENCE: 169 taggctttt acttacttgt ctgtagctct ttctctctgg cctgc                 45

<210> SEQ ID NO 170
<211> LENGTH: 45
<212> TYPE: DNA
<213> ORGANISM: Artificial Sequence
<220> FEATURE:
<223> OTHER INFORMATION: Synthetic Construct

<400> SEQUENCE: 170
gcctgcacat cagaaaagac ttgcttaaaa tgatttgtaa aggcc                45

<210> SEQ ID NO 171
<211> LENGTH: 45
<212> TYPE: DNA
<213> ORGANISM: Artificial Sequence
<220> FEATURE:
<223> OTHER INFORMATION: Synthetic Construct

<400> SEQUENCE: 171
atggaaggag aagagattct taccttacaa atttttaact gactt                45

<210> SEQ ID NO 172
<211> LENGTH: 45
<212> TYPE: DNA
<213> ORGANISM: Artificial Sequence
<220> FEATURE:
<223> OTHER INFORMATION: Synthetic Construct

```
<400> SEQUENCE: 172
ggtggtgggt tggattttca accagttttc agcagtagtt gtcat            45

<210> SEQ ID NO 173
<211> LENGTH: 45
<212> TYPE: DNA
<213> ORGANISM: Artificial Sequence
<220> FEATURE:
<223> OTHER INFORMATION: Synthetic Construct

<400> SEQUENCE: 173
tcgatccacc ggctgttcag ttgttctgag gcttgtttga tgcta            45

<210> SEQ ID NO 174
<211> LENGTH: 45
<212> TYPE: DNA
<213> ORGANISM: Artificial Sequence
<220> FEATURE:
<223> OTHER INFORMATION: Synthetic Construct

<400> SEQUENCE: 174
tgagctgatc tgctggcatc ttgcagtttt ctgaacttct cagct            45

<210> SEQ ID NO 175
<211> LENGTH: 45
<212> TYPE: DNA
<213> ORGANISM: Artificial Sequence
<220> FEATURE:
<223> OTHER INFORMATION: Synthetic Construct

<400> SEQUENCE: 175
ataaaagctt aagatgctct cacctttttcc taatttcaga atcca            45

<210> SEQ ID NO 176
<211> LENGTH: 45
<212> TYPE: DNA
<213> ORGANISM: Artificial Sequence
<220> FEATURE:
<223> OTHER INFORMATION: Synthetic Construct

<400> SEQUENCE: 176
atttcagaat ccacagtaat ctgcctcttc ttttggggag gtggt            45

<210> SEQ ID NO 177
<211> LENGTH: 45
<212> TYPE: DNA
<213> ORGANISM: Artificial Sequence
<220> FEATURE:
<223> OTHER INFORMATION: Synthetic Construct

<400> SEQUENCE: 177
tgataattgg tatcactaac ctgtgctgta ctcttttcaa gtttt            45

<210> SEQ ID NO 178
<211> LENGTH: 45
<212> TYPE: DNA
<213> ORGANISM: Artificial Sequence
<220> FEATURE:
<223> OTHER INFORMATION: Synthetic Construct

<400> SEQUENCE: 178
tccagccatg cttccgtctt ctgggtcact gacttattct tcagt            45

<210> SEQ ID NO 179
```

```
<211> LENGTH: 45
<212> TYPE: DNA
<213> ORGANISM: Artificial Sequence
<220> FEATURE:
<223> OTHER INFORMATION: Synthetic Construct

<400> SEQUENCE: 179
gaaggatgtc ttgtaaaaga acccagcggt cttctgtcca tctac            45

<210> SEQ ID NO 180
<211> LENGTH: 45
<212> TYPE: DNA
<213> ORGANISM: Artificial Sequence
<220> FEATURE:
<223> OTHER INFORMATION: Synthetic Construct

<400> SEQUENCE: 180
tgttcttgtt ctagatcttc ttgaagcacc tgaaagataa aatgt            45

<210> SEQ ID NO 181
<211> LENGTH: 45
<212> TYPE: DNA
<213> ORGANISM: Artificial Sequence
<220> FEATURE:
<223> OTHER INFORMATION: Synthetic Construct

<400> SEQUENCE: 181
cctaccttat gttgttgtac ttggcgtttt aggtcttcaa gatca            45

<210> SEQ ID NO 182
<211> LENGTH: 45
<212> TYPE: DNA
<213> ORGANISM: Artificial Sequence
<220> FEATURE:
<223> OTHER INFORMATION: Synthetic Construct

<400> SEQUENCE: 182
tctttcttct gttttgtta gccagtcatt caactctttc agttt            45

<210> SEQ ID NO 183
<211> LENGTH: 45
<212> TYPE: DNA
<213> ORGANISM: Artificial Sequence
<220> FEATURE:
<223> OTHER INFORMATION: Synthetic Construct

<400> SEQUENCE: 183
attaaaaaca aataaggact tacttgcttt gttttccat gctag            45

<210> SEQ ID NO 184
<211> LENGTH: 45
<212> TYPE: DNA
<213> ORGANISM: Artificial Sequence
<220> FEATURE:
<223> OTHER INFORMATION: Synthetic Construct

<400> SEQUENCE: 184
caaataagga cttacttgct tgtttttcc atgctagcta ccctg             45

<210> SEQ ID NO 185
<211> LENGTH: 45
<212> TYPE: DNA
<213> ORGANISM: Artificial Sequence
<220> FEATURE:
<223> OTHER INFORMATION: Synthetic Construct

<400> SEQUENCE: 185
```
tttaggagat tcatctgctc ttgtacttca gtttcttcat cttct          45

<210> SEQ ID NO 186
<211> LENGTH: 45
<212> TYPE: DNA
<213> ORGANISM: Artificial Sequence
<220> FEATURE:
<223> OTHER INFORMATION: Synthetic Construct

<400> SEQUENCE: 186
acatcattag aaatctctcc ttgtgcttgc aatgtgtcct cagca          45

<210> SEQ ID NO 187
<211> LENGTH: 45
<212> TYPE: DNA
<213> ORGANISM: Artificial Sequence
<220> FEATURE:
<223> OTHER INFORMATION: Synthetic Construct

<400> SEQUENCE: 187
tggtagtcca gaaatttacc aaccttcagg atcgagtagt ttctc          45

<210> SEQ ID NO 188
<211> LENGTH: 45
<212> TYPE: DNA
<213> ORGANISM: Artificial Sequence
<220> FEATURE:
<223> OTHER INFORMATION: Synthetic Construct

<400> SEQUENCE: 188
tatttttcat tacatttttg acctacatgt ggaaataaat tttca          45

<210> SEQ ID NO 189
<211> LENGTH: 45
<212> TYPE: DNA
<213> ORGANISM: Artificial Sequence
<220> FEATURE:
<223> OTHER INFORMATION: Synthetic Construct

<400> SEQUENCE: 189
ccattcatca ggattcttac ctgccagtgg aggattatat tccaa          45

<210> SEQ ID NO 190
<211> LENGTH: 45
<212> TYPE: DNA
<213> ORGANISM: Artificial Sequence
<220> FEATURE:
<223> OTHER INFORMATION: Synthetic Construct

<400> SEQUENCE: 190
tttcttaaaa ataagtcaca taccagtttt tgccctgtca ggcct          45

<210> SEQ ID NO 191
<211> LENGTH: 45
<212> TYPE: DNA
<213> ORGANISM: Artificial Sequence
<220> FEATURE:
<223> OTHER INFORMATION: Synthetic Construct

<400> SEQUENCE: 191
aataagtcac ataccagttt tgccctgtc aggccttcga ggagg          45

<210> SEQ ID NO 192
<211> LENGTH: 45
<212> TYPE: DNA

```
<213> ORGANISM: Artificial Sequence
<220> FEATURE:
<223> OTHER INFORMATION: Synthetic Construct

<400> SEQUENCE: 192
gtaaagtaac aaaccattct taccttagaa aattgtgcat ttacc            45

<210> SEQ ID NO 193
<211> LENGTH: 45
<212> TYPE: DNA
<213> ORGANISM: Artificial Sequence
<220> FEATURE:
<223> OTHER INFORMATION: Synthetic Construct

<400> SEQUENCE: 193
tttactaagc aaaataatct gaccttaagt tgttcttcca aagca            45

<210> SEQ ID NO 194
<211> LENGTH: 45
<212> TYPE: DNA
<213> ORGANISM: Artificial Sequence
<220> FEATURE:
<223> OTHER INFORMATION: Synthetic Construct

<400> SEQUENCE: 194
acggatcctc cctgttcgtc ccctattatg aagaatcaaa gcaga            45

<210> SEQ ID NO 195
<211> LENGTH: 45
<212> TYPE: DNA
<213> ORGANISM: Artificial Sequence
<220> FEATURE:
<223> OTHER INFORMATION: Synthetic Construct

<400> SEQUENCE: 195
ttctcaacag atctgtcaaa tcgcctgcag gtaaaagcat atgga            45

<210> SEQ ID NO 196
<211> LENGTH: 45
<212> TYPE: DNA
<213> ORGANISM: Artificial Sequence
<220> FEATURE:
<223> OTHER INFORMATION: Synthetic Construct

<400> SEQUENCE: 196
ctgtcaaatc catcatgtac ccctgacaaa gaaggaagtt aacaa            45

<210> SEQ ID NO 197
<211> LENGTH: 45
<212> TYPE: DNA
<213> ORGANISM: Artificial Sequence
<220> FEATURE:
<223> OTHER INFORMATION: Synthetic Construct

<400> SEQUENCE: 197
tctcaatatg ctgcttccca aactgaaatt aaaaaaaata cactc            45

<210> SEQ ID NO 198
<211> LENGTH: 45
<212> TYPE: DNA
<213> ORGANISM: Artificial Sequence
<220> FEATURE:
<223> OTHER INFORMATION: Synthetic Construct

<400> SEQUENCE: 198
cttaattcat catctttcag ctgtagccac accagaagtt cctgc            45
```

<210> SEQ ID NO 199
<211> LENGTH: 45
<212> TYPE: DNA
<213> ORGANISM: Artificial Sequence
<220> FEATURE:
<223> OTHER INFORMATION: Synthetic Construct

<400> SEQUENCE: 199
gtcaagacat tcatttcctt tcgcatctta cgggacaatt tcaag            45

<210> SEQ ID NO 200
<211> LENGTH: 45
<212> TYPE: DNA
<213> ORGANISM: Artificial Sequence
<220> FEATURE:
<223> OTHER INFORMATION: Synthetic Construct

<400> SEQUENCE: 200
tgtgtcctca gcagaaagaa gccacgataa tacttcttct aaagc            45

<210> SEQ ID NO 201
<211> LENGTH: 45
<212> TYPE: DNA
<213> ORGANISM: Artificial Sequence
<220> FEATURE:
<223> OTHER INFORMATION: Synthetic Construct

<400> SEQUENCE: 201
tagaaagcga tgatgttgtt ctgatactcc agccagttaa gtctc            45

<210> SEQ ID NO 202
<211> LENGTH: 45
<212> TYPE: DNA
<213> ORGANISM: Artificial Sequence
<220> FEATURE:
<223> OTHER INFORMATION: Synthetic Construct

<400> SEQUENCE: 202
ctctctaagg aaatcaagat ctgggcagga ctacgaggct ggctc            45

<210> SEQ ID NO 203
<211> LENGTH: 45
<212> TYPE: DNA
<213> ORGANISM: Artificial Sequence
<220> FEATURE:
<223> OTHER INFORMATION: Synthetic Construct

<400> SEQUENCE: 203
tcaaaagttt ccatgtgttt ctggtattcc ttaattgtac agaga            45

<210> SEQ ID NO 204
<211> LENGTH: 45
<212> TYPE: DNA
<213> ORGANISM: Artificial Sequence
<220> FEATURE:
<223> OTHER INFORMATION: Synthetic Construct

<400> SEQUENCE: 204
actgtttcca ttacagttgt ctgtgttagt gatggctgag tggtg            45

<210> SEQ ID NO 205
<211> LENGTH: 45
<212> TYPE: DNA
<213> ORGANISM: Artificial Sequence
<220> FEATURE:

<223> OTHER INFORMATION: Synthetic Construct

<400> SEQUENCE: 205
tttagtacct tggcaaagtc tcgaacatct tctcctgatg tagtc                45

<210> SEQ ID NO 206
<211> LENGTH: 45
<212> TYPE: DNA
<213> ORGANISM: Artificial Sequence
<220> FEATURE:
<223> OTHER INFORMATION: Synthetic Construct

<400> SEQUENCE: 206
atttgtgcaa agttgagtct tcgaaactga gcaaatttgc tctca                45

<210> SEQ ID NO 207
<211> LENGTH: 45
<212> TYPE: DNA
<213> ORGANISM: Artificial Sequence
<220> FEATURE:
<223> OTHER INFORMATION: Synthetic Construct

<400> SEQUENCE: 207
tggggacgcc tctgttccaa atcctgcatt gttgcctgta agaac                45

<210> SEQ ID NO 208
<211> LENGTH: 45
<212> TYPE: DNA
<213> ORGANISM: Artificial Sequence
<220> FEATURE:
<223> OTHER INFORMATION: Synthetic Construct

<400> SEQUENCE: 208
gtctcctatg aactcgagaa gccgcaaaac caaggaagag aaaga                45

<210> SEQ ID NO 209
<211> LENGTH: 45
<212> TYPE: DNA
<213> ORGANISM: Artificial Sequence
<220> FEATURE:
<223> OTHER INFORMATION: Synthetic Construct

<400> SEQUENCE: 209
gagagtttgg tttctgactg ctggacccat gtcctgatgg cactc                45

<210> SEQ ID NO 210
<211> LENGTH: 45
<212> TYPE: DNA
<213> ORGANISM: Artificial Sequence
<220> FEATURE:
<223> OTHER INFORMATION: Synthetic Construct

<400> SEQUENCE: 210
tgcgtatttg ccaccagaaa tacataccac acaatgattt agctg                45

<210> SEQ ID NO 211
<211> LENGTH: 45
<212> TYPE: DNA
<213> ORGANISM: Artificial Sequence
<220> FEATURE:
<223> OTHER INFORMATION: Synthetic Construct

<400> SEQUENCE: 211
tttgggttat cctctgaatg tcgcatcaaa ttttcaagtg actga                45

```
<210> SEQ ID NO 212
<211> LENGTH: 45
<212> TYPE: DNA
<213> ORGANISM: Artificial Sequence
<220> FEATURE:
<223> OTHER INFORMATION: Synthetic Construct

<400> SEQUENCE: 212
aggacacgga tcctccctgt cgtccccta ttatgaagaa tcaaa          45

<210> SEQ ID NO 213
<211> LENGTH: 45
<212> TYPE: DNA
<213> ORGANISM: Artificial Sequence
<220> FEATURE:
<223> OTHER INFORMATION: Synthetic Construct

<400> SEQUENCE: 213
tgcttgttaa aaaacttact tcgatccgta atgattgttc tagcc          45

<210> SEQ ID NO 214
<211> LENGTH: 45
<212> TYPE: DNA
<213> ORGANISM: Artificial Sequence
<220> FEATURE:
<223> OTHER INFORMATION: Synthetic Construct

<400> SEQUENCE: 214
ttttgctcca catcttttcc tacctaatgt tgagagactt tttcc          45

<210> SEQ ID NO 215
<211> LENGTH: 45
<212> TYPE: DNA
<213> ORGANISM: Artificial Sequence
<220> FEATURE:
<223> OTHER INFORMATION: Synthetic Construct

<400> SEQUENCE: 215
cctgccagtg gaggattata ttccaaatca aaccaagagt cagtt          45

<210> SEQ ID NO 216
<211> LENGTH: 45
<212> TYPE: DNA
<213> ORGANISM: Artificial Sequence
<220> FEATURE:
<223> OTHER INFORMATION: Synthetic Construct

<400> SEQUENCE: 216
ggataattac gagttgattg tcggacccag ctcaggagaa tcttt          45

<210> SEQ ID NO 217
<211> LENGTH: 45
<212> TYPE: DNA
<213> ORGANISM: Artificial Sequence
<220> FEATURE:
<223> OTHER INFORMATION: Synthetic Construct

<400> SEQUENCE: 217
tttagactgg gctgaattgt ctgaatatca ctgactaaaa gctaa          45

<210> SEQ ID NO 218
<211> LENGTH: 45
<212> TYPE: DNA
<213> ORGANISM: Artificial Sequence
<220> FEATURE:
<223> OTHER INFORMATION: Synthetic Construct
```

<400> SEQUENCE: 218
gtactactta cattattgtt ctgcaaaacc cgcagtgcct tgttg           45

<210> SEQ ID NO 219
<211> LENGTH: 45
<212> TYPE: DNA
<213> ORGANISM: Artificial Sequence
<220> FEATURE:
<223> OTHER INFORMATION: Synthetic Construct

<400> SEQUENCE: 219
ttcatttgct cctctagctt ttgacaatgc tcaaccagct gggag           45

<210> SEQ ID NO 220
<211> LENGTH: 45
<212> TYPE: DNA
<213> ORGANISM: Artificial Sequence
<220> FEATURE:
<223> OTHER INFORMATION: Synthetic Construct

<400> SEQUENCE: 220
tcaatctgag acaggactct ttgggcagcc tccttcccct gatta           45

<210> SEQ ID NO 221
<211> LENGTH: 45
<212> TYPE: DNA
<213> ORGANISM: Artificial Sequence
<220> FEATURE:
<223> OTHER INFORMATION: Synthetic Construct

<400> SEQUENCE: 221
ttcagctcct ctttcttctt ctgcaattcc cgatcaattt cctat           45

<210> SEQ ID NO 222
<211> LENGTH: 23
<212> TYPE: DNA
<213> ORGANISM: Artificial Sequence
<220> FEATURE:
<223> OTHER INFORMATION: Synthetic Construct

<400> SEQUENCE: 222
aaagctaagg ggacgaggca ggc           23

<210> SEQ ID NO 223
<211> LENGTH: 23
<212> TYPE: DNA
<213> ORGANISM: Artificial Sequence
<220> FEATURE:
<223> OTHER INFORMATION: Synthetic Construct

<400> SEQUENCE: 223
gaaagctaag gggacgaggc agg           23

<210> SEQ ID NO 224
<211> LENGTH: 23
<212> TYPE: DNA
<213> ORGANISM: Artificial Sequence
<220> FEATURE:
<223> OTHER INFORMATION: Synthetic Construct

<400> SEQUENCE: 224
aaatagatgg ctgaagttga tgt           23

<210> SEQ ID NO 225
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 225
gaaatagatg gctgaagttg atg                                              23

<210> SEQ ID NO 226
<211> LENGTH: 23
<212> TYPE: DNA
<213> ORGANISM: Artificial Sequence
<220> FEATURE:
<223> OTHER INFORMATION: Synthetic Construct

<400> SEQUENCE: 226
aagaaataga tggctgaagt tga                                              23

<210> SEQ ID NO 227
<211> LENGTH: 27
<212> TYPE: DNA
<213> ORGANISM: Artificial Sequence
<220> FEATURE:
<223> OTHER INFORMATION: Synthetic Construct

<400> SEQUENCE: 227
ctgaagaaat agatggctga agttgat                                          27

<210> SEQ ID NO 228
<211> LENGTH: 23
<212> TYPE: DNA
<213> ORGANISM: Artificial Sequence
<220> FEATURE:
<223> OTHER INFORMATION: Synthetic Construct

<400> SEQUENCE: 228
aaatagcggc gttttcatta tga                                              23

<210> SEQ ID NO 229
<211> LENGTH: 27
<212> TYPE: DNA
<213> ORGANISM: Artificial Sequence
<220> FEATURE:
<223> OTHER INFORMATION: Synthetic Construct

<400> SEQUENCE: 229
gagaaatagc ggcgttttca ttatgat                                          27

<210> SEQ ID NO 230
<211> LENGTH: 23
<212> TYPE: DNA
<213> ORGANISM: Artificial Sequence
<220> FEATURE:
<223> OTHER INFORMATION: Synthetic Construct

<400> SEQUENCE: 230
aaatcaatgg ttgagctctg aga                                              23

<210> SEQ ID NO 231
<211> LENGTH: 23
<212> TYPE: DNA
<213> ORGANISM: Artificial Sequence
<220> FEATURE:
<223> OTHER INFORMATION: Synthetic Construct

<400> SEQUENCE: 231
```

```
gcaaatcaat ggttgagctc tga                                    23
```

<210> SEQ ID NO 232
<211> LENGTH: 27
<212> TYPE: DNA
<213> ORGANISM: Artificial Sequence
<220> FEATURE:
<223> OTHER INFORMATION: Synthetic Construct

<400> SEQUENCE: 232

```
tgcaaatcaa tggttgagct ctgagat                                27
```

<210> SEQ ID NO 233
<211> LENGTH: 23
<212> TYPE: DNA
<213> ORGANISM: Artificial Sequence
<220> FEATURE:
<223> OTHER INFORMATION: Synthetic Construct

<400> SEQUENCE: 233

```
aacatgagta gtagcaaaag cag                                    23
```

<210> SEQ ID NO 234
<211> LENGTH: 23
<212> TYPE: DNA
<213> ORGANISM: Artificial Sequence
<220> FEATURE:
<223> OTHER INFORMATION: Synthetic Construct

<400> SEQUENCE: 234

```
gaaacatgag tagtagcaaa agc                                    23
```

<210> SEQ ID NO 235
<211> LENGTH: 23
<212> TYPE: DNA
<213> ORGANISM: Artificial Sequence
<220> FEATURE:
<223> OTHER INFORMATION: Synthetic Construct

<400> SEQUENCE: 235

```
ggaaacatga gtagtagcaa aag                                    23
```

<210> SEQ ID NO 236
<211> LENGTH: 23
<212> TYPE: DNA
<213> ORGANISM: Artificial Sequence
<220> FEATURE:
<223> OTHER INFORMATION: Synthetic Construct

<400> SEQUENCE: 236

```
tggaaacatg agtagtagca aaa                                    23
```

<210> SEQ ID NO 237
<211> LENGTH: 23
<212> TYPE: DNA
<213> ORGANISM: Artificial Sequence
<220> FEATURE:
<223> OTHER INFORMATION: Synthetic Construct

<400> SEQUENCE: 237

```
aactcaacca gaaaaaaagc agc                                    23
```

<210> SEQ ID NO 238
<211> LENGTH: 23
<212> TYPE: DNA
<213> ORGANISM: Artificial Sequence

```
<220> FEATURE:
<223> OTHER INFORMATION: Synthetic Construct

<400> SEQUENCE: 238
caactcaacc agaaaaaaag cag                                              23

<210> SEQ ID NO 239
<211> LENGTH: 27
<212> TYPE: DNA
<213> ORGANISM: Artificial Sequence
<220> FEATURE:
<223> OTHER INFORMATION: Synthetic Construct

<400> SEQUENCE: 239
aagggatcct gacagcccgt gggcgat                                          27

<210> SEQ ID NO 240
<211> LENGTH: 23
<212> TYPE: DNA
<213> ORGANISM: Artificial Sequence
<220> FEATURE:
<223> OTHER INFORMATION: Synthetic Construct

<400> SEQUENCE: 240
aatattcata cagtctcaag agt                                              23

<210> SEQ ID NO 241
<211> LENGTH: 23
<212> TYPE: DNA
<213> ORGANISM: Artificial Sequence
<220> FEATURE:
<223> OTHER INFORMATION: Synthetic Construct

<400> SEQUENCE: 241
aatcaaggct taggggaaga agt                                              23

<210> SEQ ID NO 242
<211> LENGTH: 23
<212> TYPE: DNA
<213> ORGANISM: Artificial Sequence
<220> FEATURE:
<223> OTHER INFORMATION: Synthetic Construct

<400> SEQUENCE: 242
gaatcaaggc ttaggggaag aag                                              23

<210> SEQ ID NO 243
<211> LENGTH: 23
<212> TYPE: DNA
<213> ORGANISM: Artificial Sequence
<220> FEATURE:
<223> OTHER INFORMATION: Synthetic Construct

<400> SEQUENCE: 243
tgaatcaagg cttagggaa gaa                                               23

<210> SEQ ID NO 244
<211> LENGTH: 23
<212> TYPE: DNA
<213> ORGANISM: Artificial Sequence
<220> FEATURE:
<223> OTHER INFORMATION: Synthetic Construct

<400> SEQUENCE: 244
ttgaatcaag gcttaggga aga                                               23
```

<210> SEQ ID NO 245
<211> LENGTH: 27
<212> TYPE: DNA
<213> ORGANISM: Artificial Sequence
<220> FEATURE:
<223> OTHER INFORMATION: Synthetic Construct

<400> SEQUENCE: 245
cttgaatcaa ggcttagggg aagaagt                                27

<210> SEQ ID NO 246
<211> LENGTH: 23
<212> TYPE: DNA
<213> ORGANISM: Artificial Sequence
<220> FEATURE:
<223> OTHER INFORMATION: Synthetic Construct

<400> SEQUENCE: 246
aatgacaacg tcttactgaa gaa                                    23

<210> SEQ ID NO 247
<211> LENGTH: 23
<212> TYPE: DNA
<213> ORGANISM: Artificial Sequence
<220> FEATURE:
<223> OTHER INFORMATION: Synthetic Construct

<400> SEQUENCE: 247
aaatgacaac gtcttactga aga                                    23

<210> SEQ ID NO 248
<211> LENGTH: 23
<212> TYPE: DNA
<213> ORGANISM: Artificial Sequence
<220> FEATURE:
<223> OTHER INFORMATION: Synthetic Construct

<400> SEQUENCE: 248
caaatgacaa cgtcttactg aag                                    23

<210> SEQ ID NO 249
<211> LENGTH: 23
<212> TYPE: DNA
<213> ORGANISM: Artificial Sequence
<220> FEATURE:
<223> OTHER INFORMATION: Synthetic Construct

<400> SEQUENCE: 249
tcaaatgaca acgtcttact gaa                                    23

<210> SEQ ID NO 250
<211> LENGTH: 23
<212> TYPE: DNA
<213> ORGANISM: Artificial Sequence
<220> FEATURE:
<223> OTHER INFORMATION: Synthetic Construct

<400> SEQUENCE: 250
acaaataagt aaaaagccta aaa                                    23

<210> SEQ ID NO 251
<211> LENGTH: 23
<212> TYPE: DNA
<213> ORGANISM: Artificial Sequence
<220> FEATURE:
<223> OTHER INFORMATION: Synthetic Construct

<400> SEQUENCE: 251
acagatgtgt catgtgtgag aaa                                              23

<210> SEQ ID NO 252
<211> LENGTH: 23
<212> TYPE: DNA
<213> ORGANISM: Artificial Sequence
<220> FEATURE:
<223> OTHER INFORMATION: Synthetic Construct

<400> SEQUENCE: 252
aacagatgtg tcatgtgtga gaa                                              23

<210> SEQ ID NO 253
<211> LENGTH: 23
<212> TYPE: DNA
<213> ORGANISM: Artificial Sequence
<220> FEATURE:
<223> OTHER INFORMATION: Synthetic Construct

<400> SEQUENCE: 253
gaacagatgt gtcatgtgtg aga                                              23

<210> SEQ ID NO 254
<211> LENGTH: 23
<212> TYPE: DNA
<213> ORGANISM: Artificial Sequence
<220> FEATURE:
<223> OTHER INFORMATION: Synthetic Construct

<400> SEQUENCE: 254
agaacagatg tgtcatgtgt gag                                              23

<210> SEQ ID NO 255
<211> LENGTH: 23
<212> TYPE: DNA
<213> ORGANISM: Artificial Sequence
<220> FEATURE:
<223> OTHER INFORMATION: Synthetic Construct

<400> SEQUENCE: 255
acctatggat aattacgagt tga                                              23

<210> SEQ ID NO 256
<211> LENGTH: 23
<212> TYPE: DNA
<213> ORGANISM: Artificial Sequence
<220> FEATURE:
<223> OTHER INFORMATION: Synthetic Construct

<400> SEQUENCE: 256
aacctatgga taattacgag ttg                                              23

<210> SEQ ID NO 257
<211> LENGTH: 23
<212> TYPE: DNA
<213> ORGANISM: Artificial Sequence
<220> FEATURE:
<223> OTHER INFORMATION: Synthetic Construct

<400> SEQUENCE: 257
ttaacctatg gataattacg agt                                              23

<210> SEQ ID NO 258

```
<211> LENGTH: 27
<212> TYPE: DNA
<213> ORGANISM: Artificial Sequence
<220> FEATURE:
<223> OTHER INFORMATION: Synthetic Construct

<400> SEQUENCE: 258
ttaacctatg gataattacg agttgat                                              27

<210> SEQ ID NO 259
<211> LENGTH: 23
<212> TYPE: DNA
<213> ORGANISM: Artificial Sequence
<220> FEATURE:
<223> OTHER INFORMATION: Synthetic Construct

<400> SEQUENCE: 259
actactccaa ttccttcaaa gga                                                  23

<210> SEQ ID NO 260
<211> LENGTH: 23
<212> TYPE: DNA
<213> ORGANISM: Artificial Sequence
<220> FEATURE:
<223> OTHER INFORMATION: Synthetic Construct

<400> SEQUENCE: 260
aactactcca attccttcaa agg                                                  23

<210> SEQ ID NO 261
<211> LENGTH: 27
<212> TYPE: DNA
<213> ORGANISM: Artificial Sequence
<220> FEATURE:
<223> OTHER INFORMATION: Synthetic Construct

<400> SEQUENCE: 261
aaactactcc aattccttca aaggaat                                              27

<210> SEQ ID NO 262
<211> LENGTH: 23
<212> TYPE: DNA
<213> ORGANISM: Artificial Sequence
<220> FEATURE:
<223> OTHER INFORMATION: Synthetic Construct

<400> SEQUENCE: 262
actacttgtc aatgaatgtg agg                                                  23

<210> SEQ ID NO 263
<211> LENGTH: 23
<212> TYPE: DNA
<213> ORGANISM: Artificial Sequence
<220> FEATURE:
<223> OTHER INFORMATION: Synthetic Construct

<400> SEQUENCE: 263
aactacttgt caatgaatgt gag                                                  23

<210> SEQ ID NO 264
<211> LENGTH: 23
<212> TYPE: DNA
<213> ORGANISM: Artificial Sequence
<220> FEATURE:
<223> OTHER INFORMATION: Synthetic Construct

<400> SEQUENCE: 264
```
caactacttg tcaatgaatg tga                                          23

<210> SEQ ID NO 265
<211> LENGTH: 23
<212> TYPE: DNA
<213> ORGANISM: Artificial Sequence
<220> FEATURE:
<223> OTHER INFORMATION: Synthetic Construct

<400> SEQUENCE: 265
ccaactactt gtcaatgaat gtg                                          23

<210> SEQ ID NO 266
<211> LENGTH: 23
<212> TYPE: DNA
<213> ORGANISM: Artificial Sequence
<220> FEATURE:
<223> OTHER INFORMATION: Synthetic Construct

<400> SEQUENCE: 266
gccaactact tgtcaatgaa tgt                                          23

<210> SEQ ID NO 267
<211> LENGTH: 23
<212> TYPE: DNA
<213> ORGANISM: Artificial Sequence
<220> FEATURE:
<223> OTHER INFORMATION: Synthetic Construct

<400> SEQUENCE: 267
actagatgag actggaaccc cag                                          23

<210> SEQ ID NO 268
<211> LENGTH: 27
<212> TYPE: DNA
<213> ORGANISM: Artificial Sequence
<220> FEATURE:
<223> OTHER INFORMATION: Synthetic Construct

<400> SEQUENCE: 268
tagactagat gagactggaa ccccagt                                      27

<210> SEQ ID NO 269
<211> LENGTH: 27
<212> TYPE: DNA
<213> ORGANISM: Artificial Sequence
<220> FEATURE:
<223> OTHER INFORMATION: Synthetic Construct

<400> SEQUENCE: 269
actgctagca aaccacacta ttccagt                                      27

<210> SEQ ID NO 270
<211> LENGTH: 23
<212> TYPE: DNA
<213> ORGANISM: Artificial Sequence
<220> FEATURE:
<223> OTHER INFORMATION: Synthetic Construct

<400> SEQUENCE: 270
agaaactatt cagcttctgt tag                                          23

<210> SEQ ID NO 271
<211> LENGTH: 23
<212> TYPE: DNA

```
<213> ORGANISM: Artificial Sequence
<220> FEATURE:
<223> OTHER INFORMATION: Synthetic Construct

<400> SEQUENCE: 271
agatagacag aagaccgctg ggt                                          23

<210> SEQ ID NO 272
<211> LENGTH: 23
<212> TYPE: DNA
<213> ORGANISM: Artificial Sequence
<220> FEATURE:
<223> OTHER INFORMATION: Synthetic Construct

<400> SEQUENCE: 272
tagatagaca gaagaccgct ggg                                          23

<210> SEQ ID NO 273
<211> LENGTH: 23
<212> TYPE: DNA
<213> ORGANISM: Artificial Sequence
<220> FEATURE:
<223> OTHER INFORMATION: Synthetic Construct

<400> SEQUENCE: 273
gtagatagac agaagaccgc tgg                                          23

<210> SEQ ID NO 274
<211> LENGTH: 23
<212> TYPE: DNA
<213> ORGANISM: Artificial Sequence
<220> FEATURE:
<223> OTHER INFORMATION: Synthetic Construct

<400> SEQUENCE: 274
tgtagataga cagaagaccg ctg                                          23

<210> SEQ ID NO 275
<211> LENGTH: 27
<212> TYPE: DNA
<213> ORGANISM: Artificial Sequence
<220> FEATURE:
<223> OTHER INFORMATION: Synthetic Construct

<400> SEQUENCE: 275
ctgtagatag acagaagacc gctgggt                                      27

<210> SEQ ID NO 276
<211> LENGTH: 23
<212> TYPE: DNA
<213> ORGANISM: Artificial Sequence
<220> FEATURE:
<223> OTHER INFORMATION: Synthetic Construct

<400> SEQUENCE: 276
agtagagtga acttcggaaa aag                                          23

<210> SEQ ID NO 277
<211> LENGTH: 23
<212> TYPE: DNA
<213> ORGANISM: Artificial Sequence
<220> FEATURE:
<223> OTHER INFORMATION: Synthetic Construct

<400> SEQUENCE: 277
aagtagagtg aacttcggaa aaa                                          23
```

<210> SEQ ID NO 278
<211> LENGTH: 23
<212> TYPE: DNA
<213> ORGANISM: Artificial Sequence
<220> FEATURE:
<223> OTHER INFORMATION: Synthetic Construct

<400> SEQUENCE: 278
caagtagagt gaacttcgga aaa                                    23

<210> SEQ ID NO 279
<211> LENGTH: 23
<212> TYPE: DNA
<213> ORGANISM: Artificial Sequence
<220> FEATURE:
<223> OTHER INFORMATION: Synthetic Construct

<400> SEQUENCE: 279
tcaagtagag tgaacttcgg aaa                                    23

<210> SEQ ID NO 280
<211> LENGTH: 27
<212> TYPE: DNA
<213> ORGANISM: Artificial Sequence
<220> FEATURE:
<223> OTHER INFORMATION: Synthetic Construct

<400> SEQUENCE: 280
tcaagtagag tgaacttcgg aaaaagt                                27

<210> SEQ ID NO 281
<211> LENGTH: 23
<212> TYPE: DNA
<213> ORGANISM: Artificial Sequence
<220> FEATURE:
<223> OTHER INFORMATION: Synthetic Construct

<400> SEQUENCE: 281
agtaggatca catgtgccaa cag                                    23

<210> SEQ ID NO 282
<211> LENGTH: 23
<212> TYPE: DNA
<213> ORGANISM: Artificial Sequence
<220> FEATURE:
<223> OTHER INFORMATION: Synthetic Construct

<400> SEQUENCE: 282
ctcagtagga tcacatgtgc caa                                    23

<210> SEQ ID NO 283
<211> LENGTH: 27
<212> TYPE: DNA
<213> ORGANISM: Artificial Sequence
<220> FEATURE:
<223> OTHER INFORMATION: Synthetic Construct

<400> SEQUENCE: 283
tcagtaggat cacatgtgcc aacaggt                                27

<210> SEQ ID NO 284
<211> LENGTH: 23
<212> TYPE: DNA
<213> ORGANISM: Artificial Sequence
<220> FEATURE:

<223> OTHER INFORMATION: Synthetic Construct

<400> SEQUENCE: 284
agtcttcaga gtttcatggc agt                                    23

<210> SEQ ID NO 285
<211> LENGTH: 27
<212> TYPE: DNA
<213> ORGANISM: Artificial Sequence
<220> FEATURE:
<223> OTHER INFORMATION: Synthetic Construct

<400> SEQUENCE: 285
ctgcagtctt cagagtttca tggcagt                                27

<210> SEQ ID NO 286
<211> LENGTH: 23
<212> TYPE: DNA
<213> ORGANISM: Artificial Sequence
<220> FEATURE:
<223> OTHER INFORMATION: Synthetic Construct

<400> SEQUENCE: 286
agtgaataaa ggttagacat taa                                    23

<210> SEQ ID NO 287
<211> LENGTH: 23
<212> TYPE: DNA
<213> ORGANISM: Artificial Sequence
<220> FEATURE:
<223> OTHER INFORMATION: Synthetic Construct

<400> SEQUENCE: 287
agttattctt ccaaagcagc agt                                    23

<210> SEQ ID NO 288
<211> LENGTH: 23
<212> TYPE: DNA
<213> ORGANISM: Artificial Sequence
<220> FEATURE:
<223> OTHER INFORMATION: Synthetic Construct

<400> SEQUENCE: 288
aagttattct tccaaagcag cag                                    23

<210> SEQ ID NO 289
<211> LENGTH: 23
<212> TYPE: DNA
<213> ORGANISM: Artificial Sequence
<220> FEATURE:
<223> OTHER INFORMATION: Synthetic Construct

<400> SEQUENCE: 289
ttaagttatt cttccaaagc agc                                    23

<210> SEQ ID NO 290
<211> LENGTH: 27
<212> TYPE: DNA
<213> ORGANISM: Artificial Sequence
<220> FEATURE:
<223> OTHER INFORMATION: Synthetic Construct

<400> SEQUENCE: 290
cttaagttat tcttccaaag cagcagt                                27

```
<210> SEQ ID NO 291
<211> LENGTH: 23
<212> TYPE: DNA
<213> ORGANISM: Artificial Sequence
<220> FEATURE:
<223> OTHER INFORMATION: Synthetic Construct

<400> SEQUENCE: 291
atcaatctcc caatacctgg aga                                              23

<210> SEQ ID NO 292
<211> LENGTH: 23
<212> TYPE: DNA
<213> ORGANISM: Artificial Sequence
<220> FEATURE:
<223> OTHER INFORMATION: Synthetic Construct

<400> SEQUENCE: 292
catcaatctc ccaatacctg gag                                              23

<210> SEQ ID NO 293
<211> LENGTH: 23
<212> TYPE: DNA
<213> ORGANISM: Artificial Sequence
<220> FEATURE:
<223> OTHER INFORMATION: Synthetic Construct

<400> SEQUENCE: 293
ccatcaatct cccaatacct gga                                              23

<210> SEQ ID NO 294
<211> LENGTH: 23
<212> TYPE: DNA
<213> ORGANISM: Artificial Sequence
<220> FEATURE:
<223> OTHER INFORMATION: Synthetic Construct

<400> SEQUENCE: 294
cccatcaatc tcccaatacc tgg                                              23

<210> SEQ ID NO 295
<211> LENGTH: 23
<212> TYPE: DNA
<213> ORGANISM: Artificial Sequence
<220> FEATURE:
<223> OTHER INFORMATION: Synthetic Construct

<400> SEQUENCE: 295
gcccatcaat ctcccaatac ctg                                              23

<210> SEQ ID NO 296
<211> LENGTH: 23
<212> TYPE: DNA
<213> ORGANISM: Artificial Sequence
<220> FEATURE:
<223> OTHER INFORMATION: Synthetic Construct

<400> SEQUENCE: 296
atcagtagga tgaagtacaa gaa                                              23

<210> SEQ ID NO 297
<211> LENGTH: 23
<212> TYPE: DNA
<213> ORGANISM: Artificial Sequence
<220> FEATURE:
<223> OTHER INFORMATION: Synthetic Construct
```

<400> SEQUENCE: 297
aatcagtagg atgaagtaca aga                                            23

<210> SEQ ID NO 298
<211> LENGTH: 23
<212> TYPE: DNA
<213> ORGANISM: Artificial Sequence
<220> FEATURE:
<223> OTHER INFORMATION: Synthetic Construct

<400> SEQUENCE: 298
atcagtgaga tgaagtacaa gaa                                            23

<210> SEQ ID NO 299
<211> LENGTH: 23
<212> TYPE: DNA
<213> ORGANISM: Artificial Sequence
<220> FEATURE:
<223> OTHER INFORMATION: Synthetic Construct

<400> SEQUENCE: 299
atcattcaat tgaggttga aga                                             23

<210> SEQ ID NO 300
<211> LENGTH: 23
<212> TYPE: DNA
<213> ORGANISM: Artificial Sequence
<220> FEATURE:
<223> OTHER INFORMATION: Synthetic Construct

<400> SEQUENCE: 300
aatcattcaa tttgaggttg aag                                            23

<210> SEQ ID NO 301
<211> LENGTH: 23
<212> TYPE: DNA
<213> ORGANISM: Artificial Sequence
<220> FEATURE:
<223> OTHER INFORMATION: Synthetic Construct

<400> SEQUENCE: 301
taatcattca atttgaggtt gaa                                            23

<210> SEQ ID NO 302
<211> LENGTH: 23
<212> TYPE: DNA
<213> ORGANISM: Artificial Sequence
<220> FEATURE:
<223> OTHER INFORMATION: Synthetic Construct

<400> SEQUENCE: 302
ttaatcattc aatttgaggt tga                                            23

<210> SEQ ID NO 303
<211> LENGTH: 23
<212> TYPE: DNA
<213> ORGANISM: Artificial Sequence
<220> FEATURE:
<223> OTHER INFORMATION: Synthetic Construct

<400> SEQUENCE: 303
tttaatcatt caatttgagg ttg                                            23

<210> SEQ ID NO 304
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 304
atcctatagg tcactgaaga ggt                                          23

<210> SEQ ID NO 305
<211> LENGTH: 23
<212> TYPE: DNA
<213> ORGANISM: Artificial Sequence
<220> FEATURE:
<223> OTHER INFORMATION: Synthetic Construct

<400> SEQUENCE: 305
catcctatag gtcactgaag agg                                          23

<210> SEQ ID NO 306
<211> LENGTH: 23
<212> TYPE: DNA
<213> ORGANISM: Artificial Sequence
<220> FEATURE:
<223> OTHER INFORMATION: Synthetic Construct

<400> SEQUENCE: 306
ccatcctata ggtcactgaa gag                                          23

<210> SEQ ID NO 307
<211> LENGTH: 27
<212> TYPE: DNA
<213> ORGANISM: Artificial Sequence
<220> FEATURE:
<223> OTHER INFORMATION: Synthetic Construct

<400> SEQUENCE: 307
tcccatccta taggtcactg aagaggt                                      27

<210> SEQ ID NO 308
<211> LENGTH: 23
<212> TYPE: DNA
<213> ORGANISM: Artificial Sequence
<220> FEATURE:
<223> OTHER INFORMATION: Synthetic Construct

<400> SEQUENCE: 308
atctattcca ccagggcctg agc                                          23

<210> SEQ ID NO 309
<211> LENGTH: 23
<212> TYPE: DNA
<213> ORGANISM: Artificial Sequence
<220> FEATURE:
<223> OTHER INFORMATION: Synthetic Construct

<400> SEQUENCE: 309
accatctatt ccaccagggc ctg                                          23

<210> SEQ ID NO 310
<211> LENGTH: 27
<212> TYPE: DNA
<213> ORGANISM: Artificial Sequence
<220> FEATURE:
<223> OTHER INFORMATION: Synthetic Construct

<400> SEQUENCE: 310
```
atctattcca ccagggcctg agctgat                                                27

<210> SEQ ID NO 311
<211> LENGTH: 23
<212> TYPE: DNA
<213> ORGANISM: Artificial Sequence
<220> FEATURE:
<223> OTHER INFORMATION: Synthetic Construct

<400> SEQUENCE: 311
atctattccc ttgtggtcac cgt                                                    23

<210> SEQ ID NO 312
<211> LENGTH: 23
<212> TYPE: DNA
<213> ORGANISM: Artificial Sequence
<220> FEATURE:
<223> OTHER INFORMATION: Synthetic Construct

<400> SEQUENCE: 312
gatctattcc cttgtggtca ccg                                                    23

<210> SEQ ID NO 313
<211> LENGTH: 27
<212> TYPE: DNA
<213> ORGANISM: Artificial Sequence
<220> FEATURE:
<223> OTHER INFORMATION: Synthetic Construct

<400> SEQUENCE: 313
gatctattcc cttgtggtca ccgtagt                                                27

<210> SEQ ID NO 314
<211> LENGTH: 23
<212> TYPE: DNA
<213> ORGANISM: Artificial Sequence
<220> FEATURE:
<223> OTHER INFORMATION: Synthetic Construct

<400> SEQUENCE: 314
atgaaaggag ggtccctata cag                                                    23

<210> SEQ ID NO 315
<211> LENGTH: 27
<212> TYPE: DNA
<213> ORGANISM: Artificial Sequence
<220> FEATURE:
<223> OTHER INFORMATION: Synthetic Construct

<400> SEQUENCE: 315
gtcatgaaag gagggtccct atacagt                                                27

<210> SEQ ID NO 316
<211> LENGTH: 23
<212> TYPE: DNA
<213> ORGANISM: Artificial Sequence
<220> FEATURE:
<223> OTHER INFORMATION: Synthetic Construct

<400> SEQUENCE: 316
atgactggaa gctaaggaag aag                                                    23

<210> SEQ ID NO 317
<211> LENGTH: 23
<212> TYPE: DNA
<213> ORGANISM: Artificial Sequence
<220> FEATURE:
<223> OTHER INFORMATION: Synthetic Construct

<400> SEQUENCE: 317
aatgactgga agctaaggaa gaa                                               23

<210> SEQ ID NO 318
<211> LENGTH: 23
<212> TYPE: DNA
<213> ORGANISM: Artificial Sequence
<220> FEATURE:
<223> OTHER INFORMATION: Synthetic Construct

<400> SEQUENCE: 318
caatgactgg aagctaagga aga                                               23

<210> SEQ ID NO 319
<211> LENGTH: 23
<212> TYPE: DNA
<213> ORGANISM: Artificial Sequence
<220> FEATURE:
<223> OTHER INFORMATION: Synthetic Construct

<400> SEQUENCE: 319
acaatgactg gaagctaagg aag                                               23

<210> SEQ ID NO 320
<211> LENGTH: 23
<212> TYPE: DNA
<213> ORGANISM: Artificial Sequence
<220> FEATURE:
<223> OTHER INFORMATION: Synthetic Construct

<400> SEQUENCE: 320
cacaatgact ggaagctaag gaa                                               23

<210> SEQ ID NO 321
<211> LENGTH: 23
<212> TYPE: DNA
<213> ORGANISM: Artificial Sequence
<220> FEATURE:
<223> OTHER INFORMATION: Synthetic Construct

<400> SEQUENCE: 321
atttaagctt caatttctcc ttg                                               23

<210> SEQ ID NO 322
<211> LENGTH: 23
<212> TYPE: DNA
<213> ORGANISM: Artificial Sequence
<220> FEATURE:
<223> OTHER INFORMATION: Synthetic Construct

<400> SEQUENCE: 322
atttatgcaa agttgagtct tcg                                               23

<210> SEQ ID NO 323
<211> LENGTH: 23
<212> TYPE: DNA
<213> ORGANISM: Artificial Sequence
<220> FEATURE:
<223> OTHER INFORMATION: Synthetic Construct

<400> SEQUENCE: 323
attttaactc ctactcagac tgt                                               23

<210> SEQ ID NO 324
<211> LENGTH: 23
<212> TYPE: DNA
<213> ORGANISM: Artificial Sequence
<220> FEATURE:
<223> OTHER INFORMATION: Synthetic Construct

<400> SEQUENCE: 324
tattttaact cctactcaga ctg                                          23

<210> SEQ ID NO 325
<211> LENGTH: 23
<212> TYPE: DNA
<213> ORGANISM: Artificial Sequence
<220> FEATURE:
<223> OTHER INFORMATION: Synthetic Construct

<400> SEQUENCE: 325
cacacagaat ctactggcca gaa                                          23

<210> SEQ ID NO 326
<211> LENGTH: 23
<212> TYPE: DNA
<213> ORGANISM: Artificial Sequence
<220> FEATURE:
<223> OTHER INFORMATION: Synthetic Construct

<400> SEQUENCE: 326
ctcacacaga atctactggc cag                                          23

<210> SEQ ID NO 327
<211> LENGTH: 23
<212> TYPE: DNA
<213> ORGANISM: Artificial Sequence
<220> FEATURE:
<223> OTHER INFORMATION: Synthetic Construct

<400> SEQUENCE: 327
cactagcgga ggtctttggc caa                                          23

<210> SEQ ID NO 328
<211> LENGTH: 23
<212> TYPE: DNA
<213> ORGANISM: Artificial Sequence
<220> FEATURE:
<223> OTHER INFORMATION: Synthetic Construct

<400> SEQUENCE: 328
cactttattg ctcttgcaga gaa                                          23

<210> SEQ ID NO 329
<211> LENGTH: 23
<212> TYPE: DNA
<213> ORGANISM: Artificial Sequence
<220> FEATURE:
<223> OTHER INFORMATION: Synthetic Construct

<400> SEQUENCE: 329
ccactttatt gctcttgcag aga                                          23

<210> SEQ ID NO 330
<211> LENGTH: 23
<212> TYPE: DNA
<213> ORGANISM: Artificial Sequence
<220> FEATURE:
<223> OTHER INFORMATION: Synthetic Construct

<400> SEQUENCE: 330
cagataaagt gtgtaaagga cag                                    23

<210> SEQ ID NO 331
<211> LENGTH: 23
<212> TYPE: DNA
<213> ORGANISM: Artificial Sequence
<220> FEATURE:
<223> OTHER INFORMATION: Synthetic Construct

<400> SEQUENCE: 331
caacagataa agtgtgtaaa gga                                    23

<210> SEQ ID NO 332
<211> LENGTH: 23
<212> TYPE: DNA
<213> ORGANISM: Artificial Sequence
<220> FEATURE:
<223> OTHER INFORMATION: Synthetic Construct

<400> SEQUENCE: 332
tcaacagata aagtgtgtaa agg                                    23

<210> SEQ ID NO 333
<211> LENGTH: 23
<212> TYPE: DNA
<213> ORGANISM: Artificial Sequence
<220> FEATURE:
<223> OTHER INFORMATION: Synthetic Construct

<400> SEQUENCE: 333
catttaagct gcgtccacct tgt                                    23

<210> SEQ ID NO 334
<211> LENGTH: 23
<212> TYPE: DNA
<213> ORGANISM: Artificial Sequence
<220> FEATURE:
<223> OTHER INFORMATION: Synthetic Construct

<400> SEQUENCE: 334
gcatttaagc tgcgtccacc ttg                                    23

<210> SEQ ID NO 335
<211> LENGTH: 23
<212> TYPE: DNA
<213> ORGANISM: Artificial Sequence
<220> FEATURE:
<223> OTHER INFORMATION: Synthetic Construct

<400> SEQUENCE: 335
ccattcaggg atgcttcgca aaa                                    23

<210> SEQ ID NO 336
<211> LENGTH: 23
<212> TYPE: DNA
<213> ORGANISM: Artificial Sequence
<220> FEATURE:
<223> OTHER INFORMATION: Synthetic Construct

<400> SEQUENCE: 336
cccattcagg gatgcttcgc aaa                                    23

<210> SEQ ID NO 337

```
<211> LENGTH: 23
<212> TYPE: DNA
<213> ORGANISM: Artificial Sequence
<220> FEATURE:
<223> OTHER INFORMATION: Synthetic Construct

<400> SEQUENCE: 337
cccagaagta attgaatgtg gaa                                              23

<210> SEQ ID NO 338
<211> LENGTH: 23
<212> TYPE: DNA
<213> ORGANISM: Artificial Sequence
<220> FEATURE:
<223> OTHER INFORMATION: Synthetic Construct

<400> SEQUENCE: 338
gcccagaagt aattgaatgt gga                                              23

<210> SEQ ID NO 339
<211> LENGTH: 23
<212> TYPE: DNA
<213> ORGANISM: Artificial Sequence
<220> FEATURE:
<223> OTHER INFORMATION: Synthetic Construct

<400> SEQUENCE: 339
ccgataagtt tgacgccagc ctg                                              23

<210> SEQ ID NO 340
<211> LENGTH: 23
<212> TYPE: DNA
<213> ORGANISM: Artificial Sequence
<220> FEATURE:
<223> OTHER INFORMATION: Synthetic Construct

<400> SEQUENCE: 340
actccgataa gtttgacgcc agc                                              23

<210> SEQ ID NO 341
<211> LENGTH: 23
<212> TYPE: DNA
<213> ORGANISM: Artificial Sequence
<220> FEATURE:
<223> OTHER INFORMATION: Synthetic Construct

<400> SEQUENCE: 341
cactccgata agtttgacgc cag                                              23

<210> SEQ ID NO 342
<211> LENGTH: 23
<212> TYPE: DNA
<213> ORGANISM: Artificial Sequence
<220> FEATURE:
<223> OTHER INFORMATION: Synthetic Construct

<400> SEQUENCE: 342
cctaaatgat ccactttgtg atg                                              23

<210> SEQ ID NO 343
<211> LENGTH: 23
<212> TYPE: DNA
<213> ORGANISM: Artificial Sequence
<220> FEATURE:
<223> OTHER INFORMATION: Synthetic Construct

<400> SEQUENCE: 343
```
cctacagaga aaggtgcaga cgc                                    23

<210> SEQ ID NO 344
<211> LENGTH: 23
<212> TYPE: DNA
<213> ORGANISM: Artificial Sequence
<220> FEATURE:
<223> OTHER INFORMATION: Synthetic Construct

<400> SEQUENCE: 344
tcctacagag aaaggtgcag acg                                    23

<210> SEQ ID NO 345
<211> LENGTH: 23
<212> TYPE: DNA
<213> ORGANISM: Artificial Sequence
<220> FEATURE:
<223> OTHER INFORMATION: Synthetic Construct

<400> SEQUENCE: 345
gttcctacag agaaaggtgc aga                                    23

<210> SEQ ID NO 346
<211> LENGTH: 23
<212> TYPE: DNA
<213> ORGANISM: Artificial Sequence
<220> FEATURE:
<223> OTHER INFORMATION: Synthetic Construct

<400> SEQUENCE: 346
agttcctaca gagaaaggtg cag                                    23

<210> SEQ ID NO 347
<211> LENGTH: 23
<212> TYPE: DNA
<213> ORGANISM: Artificial Sequence
<220> FEATURE:
<223> OTHER INFORMATION: Synthetic Construct

<400> SEQUENCE: 347
cctaggcaga ctggatgctc tgt                                    23

<210> SEQ ID NO 348
<211> LENGTH: 23
<212> TYPE: DNA
<213> ORGANISM: Artificial Sequence
<220> FEATURE:
<223> OTHER INFORMATION: Synthetic Construct

<400> SEQUENCE: 348
tcctaggcag actggatgct ctg                                    23

<210> SEQ ID NO 349
<211> LENGTH: 27
<212> TYPE: DNA
<213> ORGANISM: Artificial Sequence
<220> FEATURE:
<223> OTHER INFORMATION: Synthetic Construct

<400> SEQUENCE: 349
ctattggagc ctataagtat actggat                                27

<210> SEQ ID NO 350
<211> LENGTH: 23
<212> TYPE: DNA

```
<213> ORGANISM: Artificial Sequence
<220> FEATURE:
<223> OTHER INFORMATION: Synthetic Construct

<400> SEQUENCE: 350
ctcaaagtgc ctgtgtgcaa tag                                            23

<210> SEQ ID NO 351
<211> LENGTH: 23
<212> TYPE: DNA
<213> ORGANISM: Artificial Sequence
<220> FEATURE:
<223> OTHER INFORMATION: Synthetic Construct

<400> SEQUENCE: 351
ctcctcaaag tgcctgtgtg caa                                            23

<210> SEQ ID NO 352
<211> LENGTH: 27
<212> TYPE: DNA
<213> ORGANISM: Artificial Sequence
<220> FEATURE:
<223> OTHER INFORMATION: Synthetic Construct

<400> SEQUENCE: 352
ctcctcaaag tgcctgtgtg caatagt                                        27

<210> SEQ ID NO 353
<211> LENGTH: 27
<212> TYPE: DNA
<213> ORGANISM: Artificial Sequence
<220> FEATURE:
<223> OTHER INFORMATION: Synthetic Construct

<400> SEQUENCE: 353
tttctcctca aagtgcctgt gtgcaat                                        27

<210> SEQ ID NO 354
<211> LENGTH: 23
<212> TYPE: DNA
<213> ORGANISM: Artificial Sequence
<220> FEATURE:
<223> OTHER INFORMATION: Synthetic Construct

<400> SEQUENCE: 354
ctcactcact caccctgcaa agg                                            23

<210> SEQ ID NO 355
<211> LENGTH: 23
<212> TYPE: DNA
<213> ORGANISM: Artificial Sequence
<220> FEATURE:
<223> OTHER INFORMATION: Synthetic Construct

<400> SEQUENCE: 355
tctcactcac tcaccctgca aag                                            23

<210> SEQ ID NO 356
<211> LENGTH: 23
<212> TYPE: DNA
<213> ORGANISM: Artificial Sequence
<220> FEATURE:
<223> OTHER INFORMATION: Synthetic Construct

<400> SEQUENCE: 356
ctctcactca ctcaccctgc aaa                                            23
```

<210> SEQ ID NO 357
<211> LENGTH: 23
<212> TYPE: DNA
<213> ORGANISM: Artificial Sequence
<220> FEATURE:
<223> OTHER INFORMATION: Synthetic Construct

<400> SEQUENCE: 357
cctctcactc actcaccctg caa                                          23

<210> SEQ ID NO 358
<211> LENGTH: 23
<212> TYPE: DNA
<213> ORGANISM: Artificial Sequence
<220> FEATURE:
<223> OTHER INFORMATION: Synthetic Construct

<400> SEQUENCE: 358
ctcactctat ggcctgcagc atg                                          23

<210> SEQ ID NO 359
<211> LENGTH: 23
<212> TYPE: DNA
<213> ORGANISM: Artificial Sequence
<220> FEATURE:
<223> OTHER INFORMATION: Synthetic Construct

<400> SEQUENCE: 359
tttctcactc tatggcctgc agc                                          23

<210> SEQ ID NO 360
<211> LENGTH: 23
<212> TYPE: DNA
<213> ORGANISM: Artificial Sequence
<220> FEATURE:
<223> OTHER INFORMATION: Synthetic Construct

<400> SEQUENCE: 360
ttttctcact ctatggcctg cag                                          23

<210> SEQ ID NO 361
<211> LENGTH: 23
<212> TYPE: DNA
<213> ORGANISM: Artificial Sequence
<220> FEATURE:
<223> OTHER INFORMATION: Synthetic Construct

<400> SEQUENCE: 361
ctcaggaggt gacagctatc cag                                          23

<210> SEQ ID NO 362
<211> LENGTH: 27
<212> TYPE: DNA
<213> ORGANISM: Artificial Sequence
<220> FEATURE:
<223> OTHER INFORMATION: Synthetic Construct

<400> SEQUENCE: 362
ctgctcagga ggtgacagct atccagt                                      27

<210> SEQ ID NO 363
<211> LENGTH: 23
<212> TYPE: DNA
<213> ORGANISM: Artificial Sequence
<220> FEATURE:

<223> OTHER INFORMATION: Synthetic Construct

<400> SEQUENCE: 363 ctctcactttctctcatctgtga                                     23

<210> SEQ ID NO 364
<211> LENGTH: 23
<212> TYPE: DNA
<213> ORGANISM: Artificial Sequence
<220> FEATURE:
<223> OTHER INFORMATION: Synthetic Construct

<400> SEQUENCE: 364 cctctcactttctctcatctgtg                                     23

<210> SEQ ID NO 365
<211> LENGTH: 23
<212> TYPE: DNA
<213> ORGANISM: Artificial Sequence
<220> FEATURE:
<223> OTHER INFORMATION: Synthetic Construct

<400> SEQUENCE: 365 tcctctcactttctctcatctgt                                     23

<210> SEQ ID NO 366
<211> LENGTH: 27
<212> TYPE: DNA
<213> ORGANISM: Artificial Sequence
<220> FEATURE:
<223> OTHER INFORMATION: Synthetic Construct

<400> SEQUENCE: 366 ttcctctcactttctctcatctgtgat                                 27

<210> SEQ ID NO 367
<211> LENGTH: 23
<212> TYPE: DNA
<213> ORGANISM: Artificial Sequence
<220> FEATURE:
<223> OTHER INFORMATION: Synthetic Construct

<400> SEQUENCE: 367 ctgaaagaagctctcctcccagc                                     23

<210> SEQ ID NO 368
<211> LENGTH: 23
<212> TYPE: DNA
<213> ORGANISM: Artificial Sequence
<220> FEATURE:
<223> OTHER INFORMATION: Synthetic Construct

<400> SEQUENCE: 368 gctgaaagaagctctcctcccag                                     23

<210> SEQ ID NO 369
<211> LENGTH: 23
<212> TYPE: DNA
<213> ORGANISM: Artificial Sequence
<220> FEATURE:
<223> OTHER INFORMATION: Synthetic Construct

<400> SEQUENCE: 369 ctgaattactcgctcagaagctg                                     23

```
<210> SEQ ID NO 370
<211> LENGTH: 23
<212> TYPE: DNA
<213> ORGANISM: Artificial Sequence
<220> FEATURE:
<223> OTHER INFORMATION: Synthetic Construct

<400> SEQUENCE: 370
agctgaatta ctcgctcaga agc                                              23

<210> SEQ ID NO 371
<211> LENGTH: 23
<212> TYPE: DNA
<213> ORGANISM: Artificial Sequence
<220> FEATURE:
<223> OTHER INFORMATION: Synthetic Construct

<400> SEQUENCE: 371
cagctgaatt actcgctcag aag                                              23

<210> SEQ ID NO 372
<211> LENGTH: 23
<212> TYPE: DNA
<213> ORGANISM: Artificial Sequence
<220> FEATURE:
<223> OTHER INFORMATION: Synthetic Construct

<400> SEQUENCE: 372
acagctgaat tactcgctca gaa                                              23

<210> SEQ ID NO 373
<211> LENGTH: 23
<212> TYPE: DNA
<213> ORGANISM: Artificial Sequence
<220> FEATURE:
<223> OTHER INFORMATION: Synthetic Construct

<400> SEQUENCE: 373
ctgagtagaa ggcggtaaac cgt                                              23

<210> SEQ ID NO 374
<211> LENGTH: 23
<212> TYPE: DNA
<213> ORGANISM: Artificial Sequence
<220> FEATURE:
<223> OTHER INFORMATION: Synthetic Construct

<400> SEQUENCE: 374
tctgagtaga aggcggtaaa ccg                                              23

<210> SEQ ID NO 375
<211> LENGTH: 23
<212> TYPE: DNA
<213> ORGANISM: Artificial Sequence
<220> FEATURE:
<223> OTHER INFORMATION: Synthetic Construct

<400> SEQUENCE: 375
cttaccaaag gtcacaaagg taa                                              23

<210> SEQ ID NO 376
<211> LENGTH: 23
<212> TYPE: DNA
<213> ORGANISM: Artificial Sequence
<220> FEATURE:
<223> OTHER INFORMATION: Synthetic Construct
```

```
<400> SEQUENCE: 376
gacttaccaa aggtcacaaa ggt                                        23

<210> SEQ ID NO 377
<211> LENGTH: 23
<212> TYPE: DNA
<213> ORGANISM: Artificial Sequence
<220> FEATURE:
<223> OTHER INFORMATION: Synthetic Construct

<400> SEQUENCE: 377
tgacttacca aggtcacaa agg                                         23

<210> SEQ ID NO 378
<211> LENGTH: 23
<212> TYPE: DNA
<213> ORGANISM: Artificial Sequence
<220> FEATURE:
<223> OTHER INFORMATION: Synthetic Construct

<400> SEQUENCE: 378
atgacttacc aaaggtcaca aag                                        23

<210> SEQ ID NO 379
<211> LENGTH: 27
<212> TYPE: DNA
<213> ORGANISM: Artificial Sequence
<220> FEATURE:
<223> OTHER INFORMATION: Synthetic Construct

<400> SEQUENCE: 379
agatgactta ccaaaggtca caaaggt                                    27

<210> SEQ ID NO 380
<211> LENGTH: 23
<212> TYPE: DNA
<213> ORGANISM: Artificial Sequence
<220> FEATURE:
<223> OTHER INFORMATION: Synthetic Construct

<400> SEQUENCE: 380
cttagagaga gtcaatgagg aga                                        23

<210> SEQ ID NO 381
<211> LENGTH: 23
<212> TYPE: DNA
<213> ORGANISM: Artificial Sequence
<220> FEATURE:
<223> OTHER INFORMATION: Synthetic Construct

<400> SEQUENCE: 381
tcttagagag agtcaatgag gag                                        23

<210> SEQ ID NO 382
<211> LENGTH: 23
<212> TYPE: DNA
<213> ORGANISM: Artificial Sequence
<220> FEATURE:
<223> OTHER INFORMATION: Synthetic Construct

<400> SEQUENCE: 382
atcttagaga gagtcaatga gga                                        23

<210> SEQ ID NO 383
<211> LENGTH: 23
```

```
<212> TYPE: DNA
<213> ORGANISM: Artificial Sequence
<220> FEATURE:
<223> OTHER INFORMATION: Synthetic Construct

<400> SEQUENCE: 383
gatcttagag agagtcaatg agg                                          23

<210> SEQ ID NO 384
<211> LENGTH: 23
<212> TYPE: DNA
<213> ORGANISM: Artificial Sequence
<220> FEATURE:
<223> OTHER INFORMATION: Synthetic Construct

<400> SEQUENCE: 384
tgatcttaga gagagtcaat gag                                          23

<210> SEQ ID NO 385
<211> LENGTH: 27
<212> TYPE: DNA
<213> ORGANISM: Artificial Sequence
<220> FEATURE:
<223> OTHER INFORMATION: Synthetic Construct

<400> SEQUENCE: 385
gatcttagag agagtcaatg aggagat                                      27

<210> SEQ ID NO 386
<211> LENGTH: 23
<212> TYPE: DNA
<213> ORGANISM: Artificial Sequence
<220> FEATURE:
<223> OTHER INFORMATION: Synthetic Construct

<400> SEQUENCE: 386
cttatagacg ctgctcaaaa ttg                                          23

<210> SEQ ID NO 387
<211> LENGTH: 23
<212> TYPE: DNA
<213> ORGANISM: Artificial Sequence
<220> FEATURE:
<223> OTHER INFORMATION: Synthetic Construct

<400> SEQUENCE: 387
tttcttatag acgctgctca aaa                                          23

<210> SEQ ID NO 388
<211> LENGTH: 23
<212> TYPE: DNA
<213> ORGANISM: Artificial Sequence
<220> FEATURE:
<223> OTHER INFORMATION: Synthetic Construct

<400> SEQUENCE: 388
ctttcttata gacgctgctc aaa                                          23

<210> SEQ ID NO 389
<211> LENGTH: 27
<212> TYPE: DNA
<213> ORGANISM: Artificial Sequence
<220> FEATURE:
<223> OTHER INFORMATION: Synthetic Construct

<400> SEQUENCE: 389
```

```
tactttctta tagacgctgc tcaaaat                                              27
```

<210> SEQ ID NO 390
<211> LENGTH: 23
<212> TYPE: DNA
<213> ORGANISM: Artificial Sequence
<220> FEATURE:
<223> OTHER INFORMATION: Synthetic Construct

<400> SEQUENCE: 390

```
cttattctag atcttcttga agc                                                  23
```

<210> SEQ ID NO 391
<211> LENGTH: 23
<212> TYPE: DNA
<213> ORGANISM: Artificial Sequence
<220> FEATURE:
<223> OTHER INFORMATION: Synthetic Construct

<400> SEQUENCE: 391

```
cttattgagg caaaacttgg aag                                                  23
```

<210> SEQ ID NO 392
<211> LENGTH: 23
<212> TYPE: DNA
<213> ORGANISM: Artificial Sequence
<220> FEATURE:
<223> OTHER INFORMATION: Synthetic Construct

<400> SEQUENCE: 392

```
tcacttattg aggcaaaact tgg                                                  23
```

<210> SEQ ID NO 393
<211> LENGTH: 23
<212> TYPE: DNA
<213> ORGANISM: Artificial Sequence
<220> FEATURE:
<223> OTHER INFORMATION: Synthetic Construct

<400> SEQUENCE: 393

```
ctcacttatt gaggcaaaac ttg                                                  23
```

<210> SEQ ID NO 394
<211> LENGTH: 27
<212> TYPE: DNA
<213> ORGANISM: Artificial Sequence
<220> FEATURE:
<223> OTHER INFORMATION: Synthetic Construct

<400> SEQUENCE: 394

```
acttattgag gcaaaacttg gaagagt                                              27
```

<210> SEQ ID NO 395
<211> LENGTH: 23
<212> TYPE: DNA
<213> ORGANISM: Artificial Sequence
<220> FEATURE:
<223> OTHER INFORMATION: Synthetic Construct

<400> SEQUENCE: 395

```
ctttgatggg aagaagtaga gga                                                  23
```

<210> SEQ ID NO 396
<211> LENGTH: 23
<212> TYPE: DNA
<213> ORGANISM: Artificial Sequence

```
<220> FEATURE:
<223> OTHER INFORMATION: Synthetic Construct

<400> SEQUENCE: 396
gctttgatgg gaagaagtag agg                                              23

<210> SEQ ID NO 397
<211> LENGTH: 23
<212> TYPE: DNA
<213> ORGANISM: Artificial Sequence
<220> FEATURE:
<223> OTHER INFORMATION: Synthetic Construct

<400> SEQUENCE: 397
tgctttgatg ggaagaagta gag                                              23

<210> SEQ ID NO 398
<211> LENGTH: 23
<212> TYPE: DNA
<213> ORGANISM: Artificial Sequence
<220> FEATURE:
<223> OTHER INFORMATION: Synthetic Construct

<400> SEQUENCE: 398
gaaagtctat gccagaaagg agg                                              23

<210> SEQ ID NO 399
<211> LENGTH: 23
<212> TYPE: DNA
<213> ORGANISM: Artificial Sequence
<220> FEATURE:
<223> OTHER INFORMATION: Synthetic Construct

<400> SEQUENCE: 399
ggaaagtcta tgccagaaag gag                                              23

<210> SEQ ID NO 400
<211> LENGTH: 23
<212> TYPE: DNA
<213> ORGANISM: Artificial Sequence
<220> FEATURE:
<223> OTHER INFORMATION: Synthetic Construct

<400> SEQUENCE: 400
tggaaagtct atgccagaaa gga                                              23

<210> SEQ ID NO 401
<211> LENGTH: 23
<212> TYPE: DNA
<213> ORGANISM: Artificial Sequence
<220> FEATURE:
<223> OTHER INFORMATION: Synthetic Construct

<400> SEQUENCE: 401
gtggaaagtc tatgccagaa agg                                              23

<210> SEQ ID NO 402
<211> LENGTH: 23
<212> TYPE: DNA
<213> ORGANISM: Artificial Sequence
<220> FEATURE:
<223> OTHER INFORMATION: Synthetic Construct

<400> SEQUENCE: 402
tgtggaaagt ctatgccaga aag                                              23
```

<210> SEQ ID NO 403
<211> LENGTH: 23
<212> TYPE: DNA
<213> ORGANISM: Artificial Sequence
<220> FEATURE:
<223> OTHER INFORMATION: Synthetic Construct

<400> SEQUENCE: 403
gacataggtc cagcagtcag aaa                                              23

<210> SEQ ID NO 404
<211> LENGTH: 23
<212> TYPE: DNA
<213> ORGANISM: Artificial Sequence
<220> FEATURE:
<223> OTHER INFORMATION: Synthetic Construct

<400> SEQUENCE: 404
ggacataggt ccagcagtca gaa                                              23

<210> SEQ ID NO 405
<211> LENGTH: 23
<212> TYPE: DNA
<213> ORGANISM: Artificial Sequence
<220> FEATURE:
<223> OTHER INFORMATION: Synthetic Construct

<400> SEQUENCE: 405
aggacatagg tccagcagtc aga                                              23

<210> SEQ ID NO 406
<211> LENGTH: 23
<212> TYPE: DNA
<213> ORGANISM: Artificial Sequence
<220> FEATURE:
<223> OTHER INFORMATION: Synthetic Construct

<400> SEQUENCE: 406
gacgctactc aaaattggct ggt                                              23

<210> SEQ ID NO 407
<211> LENGTH: 23
<212> TYPE: DNA
<213> ORGANISM: Artificial Sequence
<220> FEATURE:
<223> OTHER INFORMATION: Synthetic Construct

<400> SEQUENCE: 407
agacgctact caaaattggc tgg                                              23

<210> SEQ ID NO 408
<211> LENGTH: 27
<212> TYPE: DNA
<213> ORGANISM: Artificial Sequence
<220> FEATURE:
<223> OTHER INFORMATION: Synthetic Construct

<400> SEQUENCE: 408
tgtagacgct actcaaaatt ggctggt                                          27

<210> SEQ ID NO 409
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 409
gagatatgaa gataagtgaa aaa                                          23

<210> SEQ ID NO 410
<211> LENGTH: 23
<212> TYPE: DNA
<213> ORGANISM: Artificial Sequence
<220> FEATURE:
<223> OTHER INFORMATION: Synthetic Construct

<400> SEQUENCE: 410
agagatatga agataagtga aaa                                          23

<210> SEQ ID NO 411
<211> LENGTH: 23
<212> TYPE: DNA
<213> ORGANISM: Artificial Sequence
<220> FEATURE:
<223> OTHER INFORMATION: Synthetic Construct

<400> SEQUENCE: 411
aagagatatg aagataagtg aaa                                          23

<210> SEQ ID NO 412
<211> LENGTH: 23
<212> TYPE: DNA
<213> ORGANISM: Artificial Sequence
<220> FEATURE:
<223> OTHER INFORMATION: Synthetic Construct

<400> SEQUENCE: 412
gaagagatat gaagataagt gaa                                          23

<210> SEQ ID NO 413
<211> LENGTH: 23
<212> TYPE: DNA
<213> ORGANISM: Artificial Sequence
<220> FEATURE:
<223> OTHER INFORMATION: Synthetic Construct

<400> SEQUENCE: 413
tgaagagata tgaagataag tga                                          23

<210> SEQ ID NO 414
<211> LENGTH: 27
<212> TYPE: DNA
<213> ORGANISM: Artificial Sequence
<220> FEATURE:
<223> OTHER INFORMATION: Synthetic Construct

<400> SEQUENCE: 414
gaagagatat gaagataagt gaaaaat                                      27

<210> SEQ ID NO 415
<211> LENGTH: 23
<212> TYPE: DNA
<213> ORGANISM: Artificial Sequence
<220> FEATURE:
<223> OTHER INFORMATION: Synthetic Construct

<400> SEQUENCE: 415
gaggcttatt tgatgctatc tgc                                          23

<210> SEQ ID NO 416
```

```
<211> LENGTH: 23
<212> TYPE: DNA
<213> ORGANISM: Artificial Sequence
<220> FEATURE:
<223> OTHER INFORMATION: Synthetic Construct

<400> SEQUENCE: 416
gatataagtc gtgtatatta atg                                              23

<210> SEQ ID NO 417
<211> LENGTH: 23
<212> TYPE: DNA
<213> ORGANISM: Artificial Sequence
<220> FEATURE:
<223> OTHER INFORMATION: Synthetic Construct

<400> SEQUENCE: 417
cagatataag tcgtgtatat taa                                              23

<210> SEQ ID NO 418
<211> LENGTH: 27
<212> TYPE: DNA
<213> ORGANISM: Artificial Sequence
<220> FEATURE:
<223> OTHER INFORMATION: Synthetic Construct

<400> SEQUENCE: 418
gtacagatat aagtcgtgta tattaat                                          27

<210> SEQ ID NO 419
<211> LENGTH: 23
<212> TYPE: DNA
<213> ORGANISM: Artificial Sequence
<220> FEATURE:
<223> OTHER INFORMATION: Synthetic Construct

<400> SEQUENCE: 419
gattagattt tctgttggga gga                                              23

<210> SEQ ID NO 420
<211> LENGTH: 23
<212> TYPE: DNA
<213> ORGANISM: Artificial Sequence
<220> FEATURE:
<223> OTHER INFORMATION: Synthetic Construct

<400> SEQUENCE: 420
agattagatt ttctgttggg agg                                              23

<210> SEQ ID NO 421
<211> LENGTH: 23
<212> TYPE: DNA
<213> ORGANISM: Artificial Sequence
<220> FEATURE:
<223> OTHER INFORMATION: Synthetic Construct

<400> SEQUENCE: 421
cagattagat tttctgttgg gag                                              23

<210> SEQ ID NO 422
<211> LENGTH: 23
<212> TYPE: DNA
<213> ORGANISM: Artificial Sequence
<220> FEATURE:
<223> OTHER INFORMATION: Synthetic Construct

<400> SEQUENCE: 422
```

```
tcagattaga ttttctgttg gga                                              23

<210> SEQ ID NO 423
<211> LENGTH: 27
<212> TYPE: DNA
<213> ORGANISM: Artificial Sequence
<220> FEATURE:
<223> OTHER INFORMATION: Synthetic Construct

<400> SEQUENCE: 423
tcagattaga ttttctgttg ggaggat                                          27

<210> SEQ ID NO 424
<211> LENGTH: 23
<212> TYPE: DNA
<213> ORGANISM: Artificial Sequence
<220> FEATURE:
<223> OTHER INFORMATION: Synthetic Construct

<400> SEQUENCE: 424
gctaattata gaaagcgatg atg                                              23

<210> SEQ ID NO 425
<211> LENGTH: 23
<212> TYPE: DNA
<213> ORGANISM: Artificial Sequence
<220> FEATURE:
<223> OTHER INFORMATION: Synthetic Construct

<400> SEQUENCE: 425
tagctaatta tagaaagcga tga                                              23

<210> SEQ ID NO 426
<211> LENGTH: 23
<212> TYPE: DNA
<213> ORGANISM: Artificial Sequence
<220> FEATURE:
<223> OTHER INFORMATION: Synthetic Construct

<400> SEQUENCE: 426
gtagctaatt atagaaagcg atg                                              23

<210> SEQ ID NO 427
<211> LENGTH: 27
<212> TYPE: DNA
<213> ORGANISM: Artificial Sequence
<220> FEATURE:
<223> OTHER INFORMATION: Synthetic Construct

<400> SEQUENCE: 427
ttgtagctaa ttatagaaag cgatgat                                          27

<210> SEQ ID NO 428
<211> LENGTH: 23
<212> TYPE: DNA
<213> ORGANISM: Artificial Sequence
<220> FEATURE:
<223> OTHER INFORMATION: Synthetic Construct

<400> SEQUENCE: 428
gctgacggga aattgagagc aaa                                              23

<210> SEQ ID NO 429
<211> LENGTH: 23
<212> TYPE: DNA
```

```
<213> ORGANISM: Artificial Sequence
<220> FEATURE:
<223> OTHER INFORMATION: Synthetic Construct

<400> SEQUENCE: 429
cgctgacggg aaattgagag caa                                            23

<210> SEQ ID NO 430
<211> LENGTH: 23
<212> TYPE: DNA
<213> ORGANISM: Artificial Sequence
<220> FEATURE:
<223> OTHER INFORMATION: Synthetic Construct

<400> SEQUENCE: 430
agcgctgacg ggaaattgag agc                                            23

<210> SEQ ID NO 431
<211> LENGTH: 27
<212> TYPE: DNA
<213> ORGANISM: Artificial Sequence
<220> FEATURE:
<223> OTHER INFORMATION: Synthetic Construct

<400> SEQUENCE: 431
agcgctgacg ggaaattgag agcaaat                                        27

<210> SEQ ID NO 432
<211> LENGTH: 23
<212> TYPE: DNA
<213> ORGANISM: Artificial Sequence
<220> FEATURE:
<223> OTHER INFORMATION: Synthetic Construct

<400> SEQUENCE: 432
gctgatctga tggcctggct ttg                                            23

<210> SEQ ID NO 433
<211> LENGTH: 27
<212> TYPE: DNA
<213> ORGANISM: Artificial Sequence
<220> FEATURE:
<223> OTHER INFORMATION: Synthetic Construct

<400> SEQUENCE: 433
agctgatctg atggcctggc tttgaat                                        27

<210> SEQ ID NO 434
<211> LENGTH: 23
<212> TYPE: DNA
<213> ORGANISM: Artificial Sequence
<220> FEATURE:
<223> OTHER INFORMATION: Synthetic Construct

<400> SEQUENCE: 434
gctttctata attcatctgg agt                                            23

<210> SEQ ID NO 435
<211> LENGTH: 27
<212> TYPE: DNA
<213> ORGANISM: Artificial Sequence
<220> FEATURE:
<223> OTHER INFORMATION: Synthetic Construct

<400> SEQUENCE: 435
aactgctttc tataattcat ctggagt                                        27
```

<210> SEQ ID NO 436
<211> LENGTH: 27
<212> TYPE: DNA
<213> ORGANISM: Artificial Sequence
<220> FEATURE:
<223> OTHER INFORMATION: Synthetic Construct

<400> SEQUENCE: 436
ggccatatgt actttctagc tttcaat                                27

<210> SEQ ID NO 437
<211> LENGTH: 27
<212> TYPE: DNA
<213> ORGANISM: Artificial Sequence
<220> FEATURE:
<223> OTHER INFORMATION: Synthetic Construct

<400> SEQUENCE: 437
ggccctttgc tataagtatt ggccagt                                27

<210> SEQ ID NO 438
<211> LENGTH: 23
<212> TYPE: DNA
<213> ORGANISM: Artificial Sequence
<220> FEATURE:
<223> OTHER INFORMATION: Synthetic Construct

<400> SEQUENCE: 438
ggctaagtgg tggtgacagc ctg                                    23

<210> SEQ ID NO 439
<211> LENGTH: 23
<212> TYPE: DNA
<213> ORGANISM: Artificial Sequence
<220> FEATURE:
<223> OTHER INFORMATION: Synthetic Construct

<400> SEQUENCE: 439
gatggctaag tggtggtgac agc                                    23

<210> SEQ ID NO 440
<211> LENGTH: 23
<212> TYPE: DNA
<213> ORGANISM: Artificial Sequence
<220> FEATURE:
<223> OTHER INFORMATION: Synthetic Construct

<400> SEQUENCE: 440
gtactaatac cactgatgag aaa                                    23

<210> SEQ ID NO 441
<211> LENGTH: 23
<212> TYPE: DNA
<213> ORGANISM: Artificial Sequence
<220> FEATURE:
<223> OTHER INFORMATION: Synthetic Construct

<400> SEQUENCE: 441
tgtactaata ccactgatga gaa                                    23

<210> SEQ ID NO 442
<211> LENGTH: 23
<212> TYPE: DNA
<213> ORGANISM: Artificial Sequence
<220> FEATURE:

```
<223> OTHER INFORMATION: Synthetic Construct

<400> SEQUENCE: 442
ttgtactaat accactgatg aga                                              23

<210> SEQ ID NO 443
<211> LENGTH: 27
<212> TYPE: DNA
<213> ORGANISM: Artificial Sequence
<220> FEATURE:
<223> OTHER INFORMATION: Synthetic Construct

<400> SEQUENCE: 443
cttgtactaa taccactgat gagaaat                                          27

<210> SEQ ID NO 444
<211> LENGTH: 27
<212> TYPE: DNA
<213> ORGANISM: Artificial Sequence
<220> FEATURE:
<223> OTHER INFORMATION: Synthetic Construct

<400> SEQUENCE: 444
gtcatagaag gagggtccct atacagt                                          27

<210> SEQ ID NO 445
<211> LENGTH: 23
<212> TYPE: DNA
<213> ORGANISM: Artificial Sequence
<220> FEATURE:
<223> OTHER INFORMATION: Synthetic Construct

<400> SEQUENCE: 445
gtcattgtgt ggctgactgc tgg                                              23

<210> SEQ ID NO 446
<211> LENGTH: 23
<212> TYPE: DNA
<213> ORGANISM: Artificial Sequence
<220> FEATURE:
<223> OTHER INFORMATION: Synthetic Construct

<400> SEQUENCE: 446
agtcattgtg tggctgactg ctg                                              23

<210> SEQ ID NO 447
<211> LENGTH: 23
<212> TYPE: DNA
<213> ORGANISM: Artificial Sequence
<220> FEATURE:
<223> OTHER INFORMATION: Synthetic Construct

<400> SEQUENCE: 447
ccagtcattg tgtggctgac tgc                                              23

<210> SEQ ID NO 448
<211> LENGTH: 23
<212> TYPE: DNA
<213> ORGANISM: Artificial Sequence
<220> FEATURE:
<223> OTHER INFORMATION: Synthetic Construct

<400> SEQUENCE: 448
tccagtcatt gtgtggctga ctg                                              23
```

```
<210> SEQ ID NO 449
<211> LENGTH: 23
<212> TYPE: DNA
<213> ORGANISM: Artificial Sequence
<220> FEATURE:
<223> OTHER INFORMATION: Synthetic Construct

<400> SEQUENCE: 449
gtcttataaa agaacccagc ggt                                              23

<210> SEQ ID NO 450
<211> LENGTH: 23
<212> TYPE: DNA
<213> ORGANISM: Artificial Sequence
<220> FEATURE:
<223> OTHER INFORMATION: Synthetic Construct

<400> SEQUENCE: 450
tgtcttataa aagaacccag cgg                                              23

<210> SEQ ID NO 451
<211> LENGTH: 23
<212> TYPE: DNA
<213> ORGANISM: Artificial Sequence
<220> FEATURE:
<223> OTHER INFORMATION: Synthetic Construct

<400> SEQUENCE: 451
atgtcttata aagaacccca gcg                                              23

<210> SEQ ID NO 452
<211> LENGTH: 27
<212> TYPE: DNA
<213> ORGANISM: Artificial Sequence
<220> FEATURE:
<223> OTHER INFORMATION: Synthetic Construct

<400> SEQUENCE: 452
ggatgtctta taaagaacc cagcggt                                           27

<210> SEQ ID NO 453
<211> LENGTH: 23
<212> TYPE: DNA
<213> ORGANISM: Artificial Sequence
<220> FEATURE:
<223> OTHER INFORMATION: Synthetic Construct

<400> SEQUENCE: 453
gtgaagtgaa cttcggaaaa agt                                              23

<210> SEQ ID NO 454
<211> LENGTH: 23
<212> TYPE: DNA
<213> ORGANISM: Artificial Sequence
<220> FEATURE:
<223> OTHER INFORMATION: Synthetic Construct

<400> SEQUENCE: 454
agtgaagtga acttcggaaa aag                                              23

<210> SEQ ID NO 455
<211> LENGTH: 23
<212> TYPE: DNA
<213> ORGANISM: Artificial Sequence
<220> FEATURE:
<223> OTHER INFORMATION: Synthetic Construct
```

<400> SEQUENCE: 455
aagtgaagtg aacttcggaa aaa                                          23

<210> SEQ ID NO 456
<211> LENGTH: 23
<212> TYPE: DNA
<213> ORGANISM: Artificial Sequence
<220> FEATURE:
<223> OTHER INFORMATION: Synthetic Construct

<400> SEQUENCE: 456
caagtgaagt gaacttcgga aaa                                          23

<210> SEQ ID NO 457
<211> LENGTH: 23
<212> TYPE: DNA
<213> ORGANISM: Artificial Sequence
<220> FEATURE:
<223> OTHER INFORMATION: Synthetic Construct

<400> SEQUENCE: 457
tcaagtgaag tgaacttcgg aaa                                          23

<210> SEQ ID NO 458
<211> LENGTH: 27
<212> TYPE: DNA
<213> ORGANISM: Artificial Sequence
<220> FEATURE:
<223> OTHER INFORMATION: Synthetic Construct

<400> SEQUENCE: 458
tcaagtgaag tgaacttcgg aaaaagt                                      27

<210> SEQ ID NO 459
<211> LENGTH: 23
<212> TYPE: DNA
<213> ORGANISM: Artificial Sequence
<220> FEATURE:
<223> OTHER INFORMATION: Synthetic Construct

<400> SEQUENCE: 459
gtgaatcgaa ttctgccagt tgc                                          23

<210> SEQ ID NO 460
<211> LENGTH: 23
<212> TYPE: DNA
<213> ORGANISM: Artificial Sequence
<220> FEATURE:
<223> OTHER INFORMATION: Synthetic Construct

<400> SEQUENCE: 460
ggtgaatcga attctgccag ttg                                          23

<210> SEQ ID NO 461
<211> LENGTH: 23
<212> TYPE: DNA
<213> ORGANISM: Artificial Sequence
<220> FEATURE:
<223> OTHER INFORMATION: Synthetic Construct

<400> SEQUENCE: 461
gccggtgaat cgaattctgc cag                                          23

<210> SEQ ID NO 462
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 462
gtgacagaca aatgtagatg tgg                                          23

<210> SEQ ID NO 463
<211> LENGTH: 23
<212> TYPE: DNA
<213> ORGANISM: Artificial Sequence
<220> FEATURE:
<223> OTHER INFORMATION: Synthetic Construct

<400> SEQUENCE: 463
agtgacagac aaatgtagat gtg                                          23

<210> SEQ ID NO 464
<211> LENGTH: 23
<212> TYPE: DNA
<213> ORGANISM: Artificial Sequence
<220> FEATURE:
<223> OTHER INFORMATION: Synthetic Construct

<400> SEQUENCE: 464
cagtgacaga caaatgtaga tgt                                          23

<210> SEQ ID NO 465
<211> LENGTH: 23
<212> TYPE: DNA
<213> ORGANISM: Artificial Sequence
<220> FEATURE:
<223> OTHER INFORMATION: Synthetic Construct

<400> SEQUENCE: 465
ccagtgacag acaaatgtag atg                                          23

<210> SEQ ID NO 466
<211> LENGTH: 27
<212> TYPE: DNA
<213> ORGANISM: Artificial Sequence
<220> FEATURE:
<223> OTHER INFORMATION: Synthetic Construct

<400> SEQUENCE: 466
ctccgccagt gacagacaaa tgtagat                                      27

<210> SEQ ID NO 467
<211> LENGTH: 23
<212> TYPE: DNA
<213> ORGANISM: Artificial Sequence
<220> FEATURE:
<223> OTHER INFORMATION: Synthetic Construct

<400> SEQUENCE: 467
gtgactctgc actaggctga atg                                          23

<210> SEQ ID NO 468
<211> LENGTH: 23
<212> TYPE: DNA
<213> ORGANISM: Artificial Sequence
<220> FEATURE:
<223> OTHER INFORMATION: Synthetic Construct

<400> SEQUENCE: 468
```

```
cagtgactct gcactaggct gaa                                          23

<210> SEQ ID NO 469
<211> LENGTH: 23
<212> TYPE: DNA
<213> ORGANISM: Artificial Sequence
<220> FEATURE:
<223> OTHER INFORMATION: Synthetic Construct

<400> SEQUENCE: 469
ccagtgactc tgcactaggc tga                                          23

<210> SEQ ID NO 470
<211> LENGTH: 23
<212> TYPE: DNA
<213> ORGANISM: Artificial Sequence
<220> FEATURE:
<223> OTHER INFORMATION: Synthetic Construct

<400> SEQUENCE: 470
accagtgact ctgcactagg ctg                                          23

<210> SEQ ID NO 471
<211> LENGTH: 27
<212> TYPE: DNA
<213> ORGANISM: Artificial Sequence
<220> FEATURE:
<223> OTHER INFORMATION: Synthetic Construct

<400> SEQUENCE: 471
taccagtgac tctgcactag gctgaat                                      27

<210> SEQ ID NO 472
<211> LENGTH: 23
<212> TYPE: DNA
<213> ORGANISM: Artificial Sequence
<220> FEATURE:
<223> OTHER INFORMATION: Synthetic Construct

<400> SEQUENCE: 472
gtgctaagat gctggaccaa agt                                          23

<210> SEQ ID NO 473
<211> LENGTH: 23
<212> TYPE: DNA
<213> ORGANISM: Artificial Sequence
<220> FEATURE:
<223> OTHER INFORMATION: Synthetic Construct

<400> SEQUENCE: 473
agtgctaaga tgctggacca aag                                          23

<210> SEQ ID NO 474
<211> LENGTH: 23
<212> TYPE: DNA
<213> ORGANISM: Artificial Sequence
<220> FEATURE:
<223> OTHER INFORMATION: Synthetic Construct

<400> SEQUENCE: 474
aagtgctaag atgctggacc aaa                                          23

<210> SEQ ID NO 475
<211> LENGTH: 27
<212> TYPE: DNA
<213> ORGANISM: Artificial Sequence
```

```
<220> FEATURE:
<223> OTHER INFORMATION: Synthetic Construct

<400> SEQUENCE: 475
gaaagtgcta agatgctgga ccaaagt                                27

<210> SEQ ID NO 476
<211> LENGTH: 23
<212> TYPE: DNA
<213> ORGANISM: Artificial Sequence
<220> FEATURE:
<223> OTHER INFORMATION: Synthetic Construct

<400> SEQUENCE: 476
gttaaagatc tgatagccgg ttg                                    23

<210> SEQ ID NO 477
<211> LENGTH: 23
<212> TYPE: DNA
<213> ORGANISM: Artificial Sequence
<220> FEATURE:
<223> OTHER INFORMATION: Synthetic Construct

<400> SEQUENCE: 477
gaggttaaag atctgatagc cgg                                    23

<210> SEQ ID NO 478
<211> LENGTH: 23
<212> TYPE: DNA
<213> ORGANISM: Artificial Sequence
<220> FEATURE:
<223> OTHER INFORMATION: Synthetic Construct

<400> SEQUENCE: 478
tgaggttaaa gatctgatag ccg                                    23

<210> SEQ ID NO 479
<211> LENGTH: 27
<212> TYPE: DNA
<213> ORGANISM: Artificial Sequence
<220> FEATURE:
<223> OTHER INFORMATION: Synthetic Construct

<400> SEQUENCE: 479
tttgaggtta aagatctgat agccggt                                27

<210> SEQ ID NO 480
<211> LENGTH: 23
<212> TYPE: DNA
<213> ORGANISM: Artificial Sequence
<220> FEATURE:
<223> OTHER INFORMATION: Synthetic Construct

<400> SEQUENCE: 480
gttagcacat gtgatcccac tga                                    23

<210> SEQ ID NO 481
<211> LENGTH: 23
<212> TYPE: DNA
<213> ORGANISM: Artificial Sequence
<220> FEATURE:
<223> OTHER INFORMATION: Synthetic Construct

<400> SEQUENCE: 481
tgttagcaca tgtgatccca ctg                                    23
```

<210> SEQ ID NO 482
<211> LENGTH: 27
<212> TYPE: DNA
<213> ORGANISM: Artificial Sequence
<220> FEATURE:
<223> OTHER INFORMATION: Synthetic Construct

<400> SEQUENCE: 482
ctgttagcac atgtgatccc actgagt                                        27

<210> SEQ ID NO 483
<211> LENGTH: 23
<212> TYPE: DNA
<213> ORGANISM: Artificial Sequence
<220> FEATURE:
<223> OTHER INFORMATION: Synthetic Construct

<400> SEQUENCE: 483
gttaggataa tttagtccaa aaa                                            23

<210> SEQ ID NO 484
<211> LENGTH: 23
<212> TYPE: DNA
<213> ORGANISM: Artificial Sequence
<220> FEATURE:
<223> OTHER INFORMATION: Synthetic Construct

<400> SEQUENCE: 484
tgttaggata atttagtcca aaa                                            23

<210> SEQ ID NO 485
<211> LENGTH: 23
<212> TYPE: DNA
<213> ORGANISM: Artificial Sequence
<220> FEATURE:
<223> OTHER INFORMATION: Synthetic Construct

<400> SEQUENCE: 485
gtgttaggat aatttagtcc aaa                                            23

<210> SEQ ID NO 486
<211> LENGTH: 23
<212> TYPE: DNA
<213> ORGANISM: Artificial Sequence
<220> FEATURE:
<223> OTHER INFORMATION: Synthetic Construct

<400> SEQUENCE: 486
ggtgttagga taatttagtc caa                                            23

<210> SEQ ID NO 487
<211> LENGTH: 23
<212> TYPE: DNA
<213> ORGANISM: Artificial Sequence
<220> FEATURE:
<223> OTHER INFORMATION: Synthetic Construct

<400> SEQUENCE: 487
taagatcaga ttattttgct tag                                            23

<210> SEQ ID NO 488
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 488
taataaggga cgaacaggga gga                                                23

<210> SEQ ID NO 489
<211> LENGTH: 23
<212> TYPE: DNA
<213> ORGANISM: Artificial Sequence
<220> FEATURE:
<223> OTHER INFORMATION: Synthetic Construct

<400> SEQUENCE: 489
ataataaggg acgaacaggg agg                                                23

<210> SEQ ID NO 490
<211> LENGTH: 23
<212> TYPE: DNA
<213> ORGANISM: Artificial Sequence
<220> FEATURE:
<223> OTHER INFORMATION: Synthetic Construct

<400> SEQUENCE: 490
cataataagg gacgaacagg gag                                                23

<210> SEQ ID NO 491
<211> LENGTH: 27
<212> TYPE: DNA
<213> ORGANISM: Artificial Sequence
<220> FEATURE:
<223> OTHER INFORMATION: Synthetic Construct

<400> SEQUENCE: 491
tcataataag gacgaacag ggaggat                                             27

<210> SEQ ID NO 492
<211> LENGTH: 23
<212> TYPE: DNA
<213> ORGANISM: Artificial Sequence
<220> FEATURE:
<223> OTHER INFORMATION: Synthetic Construct

<400> SEQUENCE: 492
tcaaatcacc tgcaggtaaa agc                                                23

<210> SEQ ID NO 493
<211> LENGTH: 23
<212> TYPE: DNA
<213> ORGANISM: Artificial Sequence
<220> FEATURE:
<223> OTHER INFORMATION: Synthetic Construct

<400> SEQUENCE: 493
tcaagggtac atgatggatt tga                                                23

<210> SEQ ID NO 494
<211> LENGTH: 23
<212> TYPE: DNA
<213> ORGANISM: Artificial Sequence
<220> FEATURE:
<223> OTHER INFORMATION: Synthetic Construct

<400> SEQUENCE: 494
gtcaagggta catgatggat ttg                                                23

<210> SEQ ID NO 495
```

```
<211> LENGTH: 27
<212> TYPE: DNA
<213> ORGANISM: Artificial Sequence
<220> FEATURE:
<223> OTHER INFORMATION: Synthetic Construct

<400> SEQUENCE: 495
cttctttgtc aagggtacat gatggat                                          27

<210> SEQ ID NO 496
<211> LENGTH: 23
<212> TYPE: DNA
<213> ORGANISM: Artificial Sequence
<220> FEATURE:
<223> OTHER INFORMATION: Synthetic Construct

<400> SEQUENCE: 496
tcaatttggg aagcagcata ttg                                              23

<210> SEQ ID NO 497
<211> LENGTH: 23
<212> TYPE: DNA
<213> ORGANISM: Artificial Sequence
<220> FEATURE:
<223> OTHER INFORMATION: Synthetic Construct

<400> SEQUENCE: 497
tcagctatag ccacaccaga agt                                              23

<210> SEQ ID NO 498
<211> LENGTH: 23
<212> TYPE: DNA
<213> ORGANISM: Artificial Sequence
<220> FEATURE:
<223> OTHER INFORMATION: Synthetic Construct

<400> SEQUENCE: 498
ttcagctata gccacaccag aag                                              23

<210> SEQ ID NO 499
<211> LENGTH: 27
<212> TYPE: DNA
<213> ORGANISM: Artificial Sequence
<220> FEATURE:
<223> OTHER INFORMATION: Synthetic Construct

<400> SEQUENCE: 499
tctttcagct atagccacac cagaagt                                          27

<210> SEQ ID NO 500
<211> LENGTH: 23
<212> TYPE: DNA
<213> ORGANISM: Artificial Sequence
<220> FEATURE:
<223> OTHER INFORMATION: Synthetic Construct

<400> SEQUENCE: 500
tcctttcaca tcttacggga caa                                              23

<210> SEQ ID NO 501
<211> LENGTH: 27
<212> TYPE: DNA
<213> ORGANISM: Artificial Sequence
<220> FEATURE:
<223> OTHER INFORMATION: Synthetic Construct

<400> SEQUENCE: 501
```

-continued atttcctttc acatcttacg ggacaat 27

<210> SEQ ID NO 502
<211> LENGTH: 23
<212> TYPE: DNA
<213> ORGANISM: Artificial Sequence
<220> FEATURE:
<223> OTHER INFORMATION: Synthetic Construct

<400> SEQUENCE: 502
tcgtagcttc tttctgctga gga 23

<210> SEQ ID NO 503
<211> LENGTH: 23
<212> TYPE: DNA
<213> ORGANISM: Artificial Sequence
<220> FEATURE:
<223> OTHER INFORMATION: Synthetic Construct

<400> SEQUENCE: 503
atcgtagctt ctttctgctg agg 23

<210> SEQ ID NO 504
<211> LENGTH: 23
<212> TYPE: DNA
<213> ORGANISM: Artificial Sequence
<220> FEATURE:
<223> OTHER INFORMATION: Synthetic Construct

<400> SEQUENCE: 504
tatcgtagct tctttctgct gag 23

<210> SEQ ID NO 505
<211> LENGTH: 23
<212> TYPE: DNA
<213> ORGANISM: Artificial Sequence
<220> FEATURE:
<223> OTHER INFORMATION: Synthetic Construct

<400> SEQUENCE: 505
ttatcgtagc ttctttctgc tga 23

<210> SEQ ID NO 506
<211> LENGTH: 23
<212> TYPE: DNA
<213> ORGANISM: Artificial Sequence
<220> FEATURE:
<223> OTHER INFORMATION: Synthetic Construct

<400> SEQUENCE: 506
tctaatactc cagccagtta agt 23

<210> SEQ ID NO 507
<211> LENGTH: 23
<212> TYPE: DNA
<213> ORGANISM: Artificial Sequence
<220> FEATURE:
<223> OTHER INFORMATION: Synthetic Construct

<400> SEQUENCE: 507
ttctaatact ccagccagtt aag 23

<210> SEQ ID NO 508
<211> LENGTH: 23
<212> TYPE: DNA

```
<213> ORGANISM: Artificial Sequence
<220> FEATURE:
<223> OTHER INFORMATION: Synthetic Construct

<400> SEQUENCE: 508
gttctaatac tccagccagt taa                                              23

<210> SEQ ID NO 509
<211> LENGTH: 27
<212> TYPE: DNA
<213> ORGANISM: Artificial Sequence
<220> FEATURE:
<223> OTHER INFORMATION: Synthetic Construct

<400> SEQUENCE: 509
ttgttctaat actccagcca gttaagt                                          27

<210> SEQ ID NO 510
<211> LENGTH: 27
<212> TYPE: DNA
<213> ORGANISM: Artificial Sequence
<220> FEATURE:
<223> OTHER INFORMATION: Synthetic Construct

<400> SEQUENCE: 510
tgatgttgtt ctaatactcc agccagt                                          27

<210> SEQ ID NO 511
<211> LENGTH: 23
<212> TYPE: DNA
<213> ORGANISM: Artificial Sequence
<220> FEATURE:
<223> OTHER INFORMATION: Synthetic Construct

<400> SEQUENCE: 511
tctaggcagg actacgaggc tgg                                              23

<210> SEQ ID NO 512
<211> LENGTH: 23
<212> TYPE: DNA
<213> ORGANISM: Artificial Sequence
<220> FEATURE:
<223> OTHER INFORMATION: Synthetic Construct

<400> SEQUENCE: 512
atctaggcag gactacgagg ctg                                              23

<210> SEQ ID NO 513
<211> LENGTH: 23
<212> TYPE: DNA
<213> ORGANISM: Artificial Sequence
<220> FEATURE:
<223> OTHER INFORMATION: Synthetic Construct

<400> SEQUENCE: 513
agatctaggc aggactacga ggc                                              23

<210> SEQ ID NO 514
<211> LENGTH: 23
<212> TYPE: DNA
<213> ORGANISM: Artificial Sequence
<220> FEATURE:
<223> OTHER INFORMATION: Synthetic Construct

<400> SEQUENCE: 514
aagatctagg caggactacg agg                                              23
```

```
<210> SEQ ID NO 515
<211> LENGTH: 23
<212> TYPE: DNA
<213> ORGANISM: Artificial Sequence
<220> FEATURE:
<223> OTHER INFORMATION: Synthetic Construct

<400> SEQUENCE: 515
tctagtattc cttaattgta cag                                              23

<210> SEQ ID NO 516
<211> LENGTH: 23
<212> TYPE: DNA
<213> ORGANISM: Artificial Sequence
<220> FEATURE:
<223> OTHER INFORMATION: Synthetic Construct

<400> SEQUENCE: 516
tgtttctagt attccttaat tgt                                              23

<210> SEQ ID NO 517
<211> LENGTH: 23
<212> TYPE: DNA
<213> ORGANISM: Artificial Sequence
<220> FEATURE:
<223> OTHER INFORMATION: Synthetic Construct

<400> SEQUENCE: 517
tctatgttag tgatggctga gtg                                              23

<210> SEQ ID NO 518
<211> LENGTH: 23
<212> TYPE: DNA
<213> ORGANISM: Artificial Sequence
<220> FEATURE:
<223> OTHER INFORMATION: Synthetic Construct

<400> SEQUENCE: 518
gtctatgtta gtgatggctg agt                                              23

<210> SEQ ID NO 519
<211> LENGTH: 23
<212> TYPE: DNA
<213> ORGANISM: Artificial Sequence
<220> FEATURE:
<223> OTHER INFORMATION: Synthetic Construct

<400> SEQUENCE: 519
tgtctatgtt agtgatggct gag                                              23

<210> SEQ ID NO 520
<211> LENGTH: 23
<212> TYPE: DNA
<213> ORGANISM: Artificial Sequence
<220> FEATURE:
<223> OTHER INFORMATION: Synthetic Construct

<400> SEQUENCE: 520
ttgtctatgt tagtgatggc tga                                              23

<210> SEQ ID NO 521
<211> LENGTH: 23
<212> TYPE: DNA
<213> ORGANISM: Artificial Sequence
<220> FEATURE:
```

<223> OTHER INFORMATION: Synthetic Construct

<400> SEQUENCE: 521
gttgtctatg ttagtgatgg ctg                                              23

<210> SEQ ID NO 522
<211> LENGTH: 27
<212> TYPE: DNA
<213> ORGANISM: Artificial Sequence
<220> FEATURE:
<223> OTHER INFORMATION: Synthetic Construct

<400> SEQUENCE: 522
tgtctatgtt agtgatggct gagtggt                                          27

<210> SEQ ID NO 523
<211> LENGTH: 27
<212> TYPE: DNA
<213> ORGANISM: Artificial Sequence
<220> FEATURE:
<223> OTHER INFORMATION: Synthetic Construct

<400> SEQUENCE: 523
agttgtctat gttagtgatg gctgagt                                          27

<210> SEQ ID NO 524
<211> LENGTH: 23
<212> TYPE: DNA
<213> ORGANISM: Artificial Sequence
<220> FEATURE:
<223> OTHER INFORMATION: Synthetic Construct

<400> SEQUENCE: 524
tctcaaacat cttctcctga tgt                                              23

<210> SEQ ID NO 525
<211> LENGTH: 23
<212> TYPE: DNA
<213> ORGANISM: Artificial Sequence
<220> FEATURE:
<223> OTHER INFORMATION: Synthetic Construct

<400> SEQUENCE: 525
gtctcaaaca tcttctcctg atg                                              23

<210> SEQ ID NO 526
<211> LENGTH: 23
<212> TYPE: DNA
<213> ORGANISM: Artificial Sequence
<220> FEATURE:
<223> OTHER INFORMATION: Synthetic Construct

<400> SEQUENCE: 526
aagtctcaaa catcttctcc tga                                              23

<210> SEQ ID NO 527
<211> LENGTH: 27
<212> TYPE: DNA
<213> ORGANISM: Artificial Sequence
<220> FEATURE:
<223> OTHER INFORMATION: Synthetic Construct

<400> SEQUENCE: 527
gtctcaaaca tcttctcctg atgtagt                                          27

```
<210> SEQ ID NO 528
<211> LENGTH: 23
<212> TYPE: DNA
<213> ORGANISM: Artificial Sequence
<220> FEATURE:
<223> OTHER INFORMATION: Synthetic Construct

<400> SEQUENCE: 528
tcttcaaaac tgagcaaatt tgc                                              23

<210> SEQ ID NO 529
<211> LENGTH: 23
<212> TYPE: DNA
<213> ORGANISM: Artificial Sequence
<220> FEATURE:
<223> OTHER INFORMATION: Synthetic Construct

<400> SEQUENCE: 529
gtcttcaaaa ctgagcaaat ttg                                              23

<210> SEQ ID NO 530
<211> LENGTH: 23
<212> TYPE: DNA
<213> ORGANISM: Artificial Sequence
<220> FEATURE:
<223> OTHER INFORMATION: Synthetic Construct

<400> SEQUENCE: 530
tgcagaattt ggaacagagg cgt                                              23

<210> SEQ ID NO 531
<211> LENGTH: 23
<212> TYPE: DNA
<213> ORGANISM: Artificial Sequence
<220> FEATURE:
<223> OTHER INFORMATION: Synthetic Construct

<400> SEQUENCE: 531
atgcagaatt tggaacagag gcg                                              23

<210> SEQ ID NO 532
<211> LENGTH: 23
<212> TYPE: DNA
<213> ORGANISM: Artificial Sequence
<220> FEATURE:
<223> OTHER INFORMATION: Synthetic Construct

<400> SEQUENCE: 532
aatgcagaat ttggaacaga ggc                                              23

<210> SEQ ID NO 533
<211> LENGTH: 23
<212> TYPE: DNA
<213> ORGANISM: Artificial Sequence
<220> FEATURE:
<223> OTHER INFORMATION: Synthetic Construct

<400> SEQUENCE: 533
tgcagcttct cgagttcata gga                                              23

<210> SEQ ID NO 534
<211> LENGTH: 23
<212> TYPE: DNA
<213> ORGANISM: Artificial Sequence
<220> FEATURE:
<223> OTHER INFORMATION: Synthetic Construct
```

```
<400> SEQUENCE: 534
ttgcagcttc tcgagttcat agg                                              23

<210> SEQ ID NO 535
<211> LENGTH: 23
<212> TYPE: DNA
<213> ORGANISM: Artificial Sequence
<220> FEATURE:
<223> OTHER INFORMATION: Synthetic Construct

<400> SEQUENCE: 535
tgctagaccc atgtcctgat ggc                                              23

<210> SEQ ID NO 536
<211> LENGTH: 23
<212> TYPE: DNA
<213> ORGANISM: Artificial Sequence
<220> FEATURE:
<223> OTHER INFORMATION: Synthetic Construct

<400> SEQUENCE: 536
ctgctagacc catgtcctga tgg                                              23

<210> SEQ ID NO 537
<211> LENGTH: 23
<212> TYPE: DNA
<213> ORGANISM: Artificial Sequence
<220> FEATURE:
<223> OTHER INFORMATION: Synthetic Construct

<400> SEQUENCE: 537
actgctagac ccatgtcctg atg                                              23

<210> SEQ ID NO 538
<211> LENGTH: 27
<212> TYPE: DNA
<213> ORGANISM: Artificial Sequence
<220> FEATURE:
<223> OTHER INFORMATION: Synthetic Construct

<400> SEQUENCE: 538
ttctgactgc tagacccatg tcctgat                                          27

<210> SEQ ID NO 539
<211> LENGTH: 23
<212> TYPE: DNA
<213> ORGANISM: Artificial Sequence
<220> FEATURE:
<223> OTHER INFORMATION: Synthetic Construct

<400> SEQUENCE: 539
tggtatatat ttctggtggc aaa                                              23

<210> SEQ ID NO 540
<211> LENGTH: 23
<212> TYPE: DNA
<213> ORGANISM: Artificial Sequence
<220> FEATURE:
<223> OTHER INFORMATION: Synthetic Construct

<400> SEQUENCE: 540
gtggtatata tttctggtgg caa                                              23

<210> SEQ ID NO 541
<211> LENGTH: 27
```

```
<212> TYPE: DNA
<213> ORGANISM: Artificial Sequence
<220> FEATURE:
<223> OTHER INFORMATION: Synthetic Construct

<400> SEQUENCE: 541
gtgtggtata tatttctggt ggcaaat                                          27

<210> SEQ ID NO 542
<211> LENGTH: 23
<212> TYPE: DNA
<213> ORGANISM: Artificial Sequence
<220> FEATURE:
<223> OTHER INFORMATION: Synthetic Construct

<400> SEQUENCE: 542
tgtcacatca aattttcaag tga                                              23

<210> SEQ ID NO 543
<211> LENGTH: 23
<212> TYPE: DNA
<213> ORGANISM: Artificial Sequence
<220> FEATURE:
<223> OTHER INFORMATION: Synthetic Construct

<400> SEQUENCE: 543
atgtcacatc aaattttcaa gtg                                              23

<210> SEQ ID NO 544
<211> LENGTH: 23
<212> TYPE: DNA
<213> ORGANISM: Artificial Sequence
<220> FEATURE:
<223> OTHER INFORMATION: Synthetic Construct

<400> SEQUENCE: 544
tgttcatccc ctattatgaa gaa                                              23

<210> SEQ ID NO 545
<211> LENGTH: 23
<212> TYPE: DNA
<213> ORGANISM: Artificial Sequence
<220> FEATURE:
<223> OTHER INFORMATION: Synthetic Construct

<400> SEQUENCE: 545
ctgttcatcc cctattatga aga                                              23

<210> SEQ ID NO 546
<211> LENGTH: 23
<212> TYPE: DNA
<213> ORGANISM: Artificial Sequence
<220> FEATURE:
<223> OTHER INFORMATION: Synthetic Construct

<400> SEQUENCE: 546
cctgttcatc ccctattatg aag                                              23

<210> SEQ ID NO 547
<211> LENGTH: 27
<212> TYPE: DNA
<213> ORGANISM: Artificial Sequence
<220> FEATURE:
<223> OTHER INFORMATION: Synthetic Construct

<400> SEQUENCE: 547
```

```
ccctgttcat cccctattat gaagaat                                          27
```

<210> SEQ ID NO 548
<211> LENGTH: 23
<212> TYPE: DNA
<213> ORGANISM: Artificial Sequence
<220> FEATURE:
<223> OTHER INFORMATION: Synthetic Construct

<400> SEQUENCE: 548

```
ttacttcaat ccgtaatgat tgt                                              23
```

<210> SEQ ID NO 549
<211> LENGTH: 23
<212> TYPE: DNA
<213> ORGANISM: Artificial Sequence
<220> FEATURE:
<223> OTHER INFORMATION: Synthetic Construct

<400> SEQUENCE: 549

```
ttagatagga aaagatgtgg agc                                              23
```

<210> SEQ ID NO 550
<211> LENGTH: 23
<212> TYPE: DNA
<213> ORGANISM: Artificial Sequence
<220> FEATURE:
<223> OTHER INFORMATION: Synthetic Construct

<400> SEQUENCE: 550

```
attagatagg aaaagatgtg gag                                              23
```

<210> SEQ ID NO 551
<211> LENGTH: 23
<212> TYPE: DNA
<213> ORGANISM: Artificial Sequence
<220> FEATURE:
<223> OTHER INFORMATION: Synthetic Construct

<400> SEQUENCE: 551

```
cattagatag gaaaagatgt gga                                              23
```

<210> SEQ ID NO 552
<211> LENGTH: 23
<212> TYPE: DNA
<213> ORGANISM: Artificial Sequence
<220> FEATURE:
<223> OTHER INFORMATION: Synthetic Construct

<400> SEQUENCE: 552

```
acattagata ggaaaagatg tgg                                              23
```

<210> SEQ ID NO 553
<211> LENGTH: 23
<212> TYPE: DNA
<213> ORGANISM: Artificial Sequence
<220> FEATURE:
<223> OTHER INFORMATION: Synthetic Construct

<400> SEQUENCE: 553

```
ttgaaatata atcctccact ggc                                              23
```

<210> SEQ ID NO 554
<211> LENGTH: 23
<212> TYPE: DNA
<213> ORGANISM: Artificial Sequence

```
<220> FEATURE:
<223> OTHER INFORMATION: Synthetic Construct

<400> SEQUENCE: 554
tttgaaatat aatcctccac tgg                                          23

<210> SEQ ID NO 555
<211> LENGTH: 23
<212> TYPE: DNA
<213> ORGANISM: Artificial Sequence
<220> FEATURE:
<223> OTHER INFORMATION: Synthetic Construct

<400> SEQUENCE: 555
atttgaaata taatcctcca ctg                                          23

<210> SEQ ID NO 556
<211> LENGTH: 23
<212> TYPE: DNA
<213> ORGANISM: Artificial Sequence
<220> FEATURE:
<223> OTHER INFORMATION: Synthetic Construct

<400> SEQUENCE: 556
ttgtcagacc cagctcagga gaa                                          23

<210> SEQ ID NO 557
<211> LENGTH: 23
<212> TYPE: DNA
<213> ORGANISM: Artificial Sequence
<220> FEATURE:
<223> OTHER INFORMATION: Synthetic Construct

<400> SEQUENCE: 557
attgtcagac ccagctcagg aga                                          23

<210> SEQ ID NO 558
<211> LENGTH: 23
<212> TYPE: DNA
<213> ORGANISM: Artificial Sequence
<220> FEATURE:
<223> OTHER INFORMATION: Synthetic Construct

<400> SEQUENCE: 558
gattgtcaga cccagctcag gag                                          23

<210> SEQ ID NO 559
<211> LENGTH: 27
<212> TYPE: DNA
<213> ORGANISM: Artificial Sequence
<220> FEATURE:
<223> OTHER INFORMATION: Synthetic Construct

<400> SEQUENCE: 559
tgattgtcag acccagctca ggagaat                                      27

<210> SEQ ID NO 560
<211> LENGTH: 23
<212> TYPE: DNA
<213> ORGANISM: Artificial Sequence
<220> FEATURE:
<223> OTHER INFORMATION: Synthetic Construct

<400> SEQUENCE: 560
ttgtctaaat atcactgact aaa                                          23
```

<210> SEQ ID NO 561
<211> LENGTH: 23
<212> TYPE: DNA
<213> ORGANISM: Artificial Sequence
<220> FEATURE:
<223> OTHER INFORMATION: Synthetic Construct

<400> SEQUENCE: 561
attgtctaaa tatcactgac taa                                              23

<210> SEQ ID NO 562
<211> LENGTH: 23
<212> TYPE: DNA
<213> ORGANISM: Artificial Sequence
<220> FEATURE:
<223> OTHER INFORMATION: Synthetic Construct

<400> SEQUENCE: 562
ttgttctaca aacccgcag tgc                                               23

<210> SEQ ID NO 563
<211> LENGTH: 23
<212> TYPE: DNA
<213> ORGANISM: Artificial Sequence
<220> FEATURE:
<223> OTHER INFORMATION: Synthetic Construct

<400> SEQUENCE: 563
tttaacaatg ctcaaccagc tgg                                              23

<210> SEQ ID NO 564
<211> LENGTH: 23
<212> TYPE: DNA
<213> ORGANISM: Artificial Sequence
<220> FEATURE:
<223> OTHER INFORMATION: Synthetic Construct

<400> SEQUENCE: 564
ttttaacaat gctcaaccag ctg                                              23

<210> SEQ ID NO 565
<211> LENGTH: 23
<212> TYPE: DNA
<213> ORGANISM: Artificial Sequence
<220> FEATURE:
<223> OTHER INFORMATION: Synthetic Construct

<400> SEQUENCE: 565
gcttttaaca atgctcaacc agc                                              23

<210> SEQ ID NO 566
<211> LENGTH: 23
<212> TYPE: DNA
<213> ORGANISM: Artificial Sequence
<220> FEATURE:
<223> OTHER INFORMATION: Synthetic Construct

<400> SEQUENCE: 566
agcttttaac aatgctcaac cag                                              23

<210> SEQ ID NO 567
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 567
tttaggcagc ctccttcccc tga                                       23

<210> SEQ ID NO 568
<211> LENGTH: 23
<212> TYPE: DNA
<213> ORGANISM: Artificial Sequence
<220> FEATURE:
<223> OTHER INFORMATION: Synthetic Construct

<400> SEQUENCE: 568
ctttaggcag cctccttccc ctg                                       23

<210> SEQ ID NO 569
<211> LENGTH: 27
<212> TYPE: DNA
<213> ORGANISM: Artificial Sequence
<220> FEATURE:
<223> OTHER INFORMATION: Synthetic Construct

<400> SEQUENCE: 569
tttcttcttc tacaattccc gatcaat                                   27

<210> SEQ ID NO 570
<211> LENGTH: 20
<212> TYPE: DNA
<213> ORGANISM: Artificial Sequence
<220> FEATURE:
<223> OTHER INFORMATION: Synthetic Construct

<400> SEQUENCE: 570
gttatctcct gttctgcagc                                           20

<210> SEQ ID NO 571
<211> LENGTH: 20
<212> TYPE: DNA
<213> ORGANISM: Artificial Sequence
<220> FEATURE:
<223> OTHER INFORMATION: Synthetic Construct

<400> SEQUENCE: 571
gtttatgtca ccagagtaac                                           20

<210> SEQ ID NO 572
<211> LENGTH: 21
<212> TYPE: DNA
<213> ORGANISM: Artificial Sequence
<220> FEATURE:
<223> OTHER INFORMATION: Synthetic Construct

<400> SEQUENCE: 572
gaggtaatag agccaagccc t                                         21

<210> SEQ ID NO 573
<211> LENGTH: 25
<212> TYPE: DNA
<213> ORGANISM: Artificial Sequence
<220> FEATURE:
<223> OTHER INFORMATION: Synthetic Construct

<400> SEQUENCE: 573
gcaagaattc cacttttcac ttcct                                     25

<210> SEQ ID NO 574
```

```
<211> LENGTH: 24
<212> TYPE: DNA
<213> ORGANISM: Artificial Sequence
<220> FEATURE:
<223> OTHER INFORMATION: Synthetic Construct

<400> SEQUENCE: 574
ctgtcatctc caaactagaa atgc                                          24

<210> SEQ ID NO 575
<211> LENGTH: 22
<212> TYPE: DNA
<213> ORGANISM: Artificial Sequence
<220> FEATURE:
<223> OTHER INFORMATION: Synthetic Construct

<400> SEQUENCE: 575
gcagcctctt gctcacttac tc                                            22

<210> SEQ ID NO 576
<211> LENGTH: 20
<212> TYPE: DNA
<213> ORGANISM: Artificial Sequence
<220> FEATURE:
<223> OTHER INFORMATION: Synthetic Construct

<400> SEQUENCE: 576
gatgacaggc aggggcaccg                                               20

<210> SEQ ID NO 577
<211> LENGTH: 20
<212> TYPE: DNA
<213> ORGANISM: Artificial Sequence
<220> FEATURE:
<223> OTHER INFORMATION: Synthetic Construct

<400> SEQUENCE: 577
ttccagtggt tcaatggtca                                               20

<210> SEQ ID NO 578
<211> LENGTH: 20
<212> TYPE: DNA
<213> ORGANISM: Artificial Sequence
<220> FEATURE:
<223> OTHER INFORMATION: Synthetic Construct

<400> SEQUENCE: 578
ctttcaaccc gaacggagac                                               20

<210> SEQ ID NO 579
<211> LENGTH: 20
<212> TYPE: DNA
<213> ORGANISM: Artificial Sequence
<220> FEATURE:
<223> OTHER INFORMATION: Synthetic Construct

<400> SEQUENCE: 579
gagcgagcag cgtcttcgag                                               20

<210> SEQ ID NO 580
<211> LENGTH: 20
<212> TYPE: DNA
<213> ORGANISM: Artificial Sequence
<220> FEATURE:
<223> OTHER INFORMATION: Synthetic Construct

<400> SEQUENCE: 580
```
gcagacggca gtcactaggg                                               20

<210> SEQ ID NO 581
<211> LENGTH: 20
<212> TYPE: DNA
<213> ORGANISM: Artificial Sequence
<220> FEATURE:
<223> OTHER INFORMATION: Synthetic Construct

<400> SEQUENCE: 581
gggaagctgg gtgaatggag                                               20

<210> SEQ ID NO 582
<211> LENGTH: 20
<212> TYPE: DNA
<213> ORGANISM: Artificial Sequence
<220> FEATURE:
<223> OTHER INFORMATION: Synthetic Construct

<400> SEQUENCE: 582
agctgtttgg gaggtcagaa                                               20

<210> SEQ ID NO 583
<211> LENGTH: 20
<212> TYPE: DNA
<213> ORGANISM: Artificial Sequence
<220> FEATURE:
<223> OTHER INFORMATION: Synthetic Construct

<400> SEQUENCE: 583
agggagcagg aaagtgaggt                                               20

<210> SEQ ID NO 584
<211> LENGTH: 20
<212> TYPE: DNA
<213> ORGANISM: Artificial Sequence
<220> FEATURE:
<223> OTHER INFORMATION: Synthetic Construct

<400> SEQUENCE: 584
gtcgcaggac agcttttcct                                               20

<210> SEQ ID NO 585
<211> LENGTH: 20
<212> TYPE: DNA
<213> ORGANISM: Artificial Sequence
<220> FEATURE:
<223> OTHER INFORMATION: Synthetic Construct

<400> SEQUENCE: 585
tgtagctacg cctgtgatgg                                               20

<210> SEQ ID NO 586
<211> LENGTH: 20
<212> TYPE: DNA
<213> ORGANISM: Artificial Sequence
<220> FEATURE:
<223> OTHER INFORMATION: Synthetic Construct

<400> SEQUENCE: 586
tgccctgaga tcttttcctc                                               20

<210> SEQ ID NO 587
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 587
gatccaggtg ctgcagaagg                                              20

<210> SEQ ID NO 588
<211> LENGTH: 20
<212> TYPE: DNA
<213> ORGANISM: Artificial Sequence
<220> FEATURE:
<223> OTHER INFORMATION: Synthetic Construct

<400> SEQUENCE: 588
ctcttgcctc cactggttgt                                              20

<210> SEQ ID NO 589
<211> LENGTH: 20
<212> TYPE: DNA
<213> ORGANISM: Artificial Sequence
<220> FEATURE:
<223> OTHER INFORMATION: Synthetic Construct

<400> SEQUENCE: 589
tcggtaggat gccctacatc                                              20

<210> SEQ ID NO 590
<211> LENGTH: 20
<212> TYPE: DNA
<213> ORGANISM: Artificial Sequence
<220> FEATURE:
<223> OTHER INFORMATION: Synthetic Construct

<400> SEQUENCE: 590
atcctacagc atggtggctg                                              20

<210> SEQ ID NO 591
<211> LENGTH: 32
<212> TYPE: DNA
<213> ORGANISM: Artificial Sequence
<220> FEATURE:
<223> OTHER INFORMATION: Synthetic Construct

<400> SEQUENCE: 591
agtggtctcc ggaaacctcc gcgccccgca ac                                32

<210> SEQ ID NO 592
<211> LENGTH: 20
<212> TYPE: DNA
<213> ORGANISM: Artificial Sequence
<220> FEATURE:
<223> OTHER INFORMATION: Synthetic Construct

<400> SEQUENCE: 592
tccttgaaga agatggtgcg                                              20

<210> SEQ ID NO 593
<211> LENGTH: 55
<212> TYPE: DNA
<213> ORGANISM: Artificial Sequence
<220> FEATURE:
<223> OTHER INFORMATION: Synthetic Construct

<400> SEQUENCE: 593
acactctttc cctacacgac gctcttccga tctgaactca ttactgctgc ccaga        55
```

<210> SEQ ID NO 594
<211> LENGTH: 55
<212> TYPE: DNA
<213> ORGANISM: Artificial Sequence
<220> FEATURE:
<223> OTHER INFORMATION: Synthetic Construct

<400> SEQUENCE: 594
gtgactggag ttcagacgtg tgctcttccg atcgacctgt tcggcttctt cctta    55

<210> SEQ ID NO 595
<211> LENGTH: 58
<212> TYPE: DNA
<213> ORGANISM: Artificial Sequence
<220> FEATURE:
<223> OTHER INFORMATION: Synthetic Construct

<400> SEQUENCE: 595
acactctttc cctacacgac gctcttccga tctaaatttc cactgtcttc tcttgagt    58

<210> SEQ ID NO 596
<211> LENGTH: 55
<212> TYPE: DNA
<213> ORGANISM: Artificial Sequence
<220> FEATURE:
<223> OTHER INFORMATION: Synthetic Construct

<400> SEQUENCE: 596
gtgactggag ttcagacgtg tgctcttccg atcgcttgcc tctgacctgt cctat    55

<210> SEQ ID NO 597
<211> LENGTH: 55
<212> TYPE: DNA
<213> ORGANISM: Artificial Sequence
<220> FEATURE:
<223> OTHER INFORMATION: Synthetic Construct

<400> SEQUENCE: 597
acactctttc cctacacgac gctcttccga tctgtgacta ggggcaaagc aagat    55

<210> SEQ ID NO 598
<211> LENGTH: 55
<212> TYPE: DNA
<213> ORGANISM: Artificial Sequence
<220> FEATURE:
<223> OTHER INFORMATION: Synthetic Construct

<400> SEQUENCE: 598
gtgactggag ttcagacgtg tgctcttccg atccttccaa actttctgcc cattc    55

<210> SEQ ID NO 599
<211> LENGTH: 56
<212> TYPE: DNA
<213> ORGANISM: Artificial Sequence
<220> FEATURE:
<223> OTHER INFORMATION: Synthetic Construct

<400> SEQUENCE: 599
acactctttc cctacacgac gctcttccga tctaacacag cgtgctcttt ccttac    56

<210> SEQ ID NO 600
<211> LENGTH: 56
<212> TYPE: DNA
<213> ORGANISM: Artificial Sequence
<220> FEATURE:

<223> OTHER INFORMATION: Synthetic Construct

<400> SEQUENCE: 600
gtgactggag ttcagacgtg tgctcttccg atcgttcaga agaacatccc gttgac        56

<210> SEQ ID NO 601
<211> LENGTH: 45
<212> TYPE: DNA
<213> ORGANISM: Artificial Sequence
<220> FEATURE:
<223> OTHER INFORMATION: Synthetic Construct

<400> SEQUENCE: 601
aatgatacgg cgaccaccga gatctacact ctttccctac acgac        45

<210> SEQ ID NO 602
<211> LENGTH: 49
<212> TYPE: DNA
<213> ORGANISM: Artificial Sequence
<220> FEATURE:
<223> OTHER INFORMATION: Synthetic Construct

<400> SEQUENCE: 602
caagcagaag acggcatacg agatcttgta gtgactggag ttcagacgt        49

<210> SEQ ID NO 603
<211> LENGTH: 49
<212> TYPE: DNA
<213> ORGANISM: Artificial Sequence
<220> FEATURE:
<223> OTHER INFORMATION: Synthetic Construct

<400> SEQUENCE: 603
caagcagaag acggcatacg agatcagatc gtgactggag ttcagacgt        49

<210> SEQ ID NO 604
<211> LENGTH: 49
<212> TYPE: DNA
<213> ORGANISM: Artificial Sequence
<220> FEATURE:
<223> OTHER INFORMATION: Synthetic Construct

<400> SEQUENCE: 604
caagcagaag acggcatacg agatccgtcc gtgactggag ttcagacgt        49

<210> SEQ ID NO 605
<211> LENGTH: 49
<212> TYPE: DNA
<213> ORGANISM: Artificial Sequence
<220> FEATURE:
<223> OTHER INFORMATION: Synthetic Construct

<400> SEQUENCE: 605
caagcagaag acggcatacg agatatgtca gtgactggag ttcagacgt        49

<210> SEQ ID NO 606
<211> LENGTH: 49
<212> TYPE: DNA
<213> ORGANISM: Artificial Sequence
<220> FEATURE:
<223> OTHER INFORMATION: Synthetic Construct

<400> SEQUENCE: 606
caagcagaag acggcatacg agatgtccgc gtgactggag ttcagacgt        49

```
<210> SEQ ID NO 607
<211> LENGTH: 49
<212> TYPE: DNA
<213> ORGANISM: Artificial Sequence
<220> FEATURE:
<223> OTHER INFORMATION: Synthetic Construct

<400> SEQUENCE: 607
caagcagaag acggcatacg agatttaggc gtgactggag ttcagacgt            49

<210> SEQ ID NO 608
<211> LENGTH: 49
<212> TYPE: DNA
<213> ORGANISM: Artificial Sequence
<220> FEATURE:
<223> OTHER INFORMATION: Synthetic Construct

<400> SEQUENCE: 608
caagcagaag acggcatacg agatcgatgt gtgactggag ttcagacgt            49

<210> SEQ ID NO 609
<211> LENGTH: 49
<212> TYPE: DNA
<213> ORGANISM: Artificial Sequence
<220> FEATURE:
<223> OTHER INFORMATION: Synthetic Construct

<400> SEQUENCE: 609
caagcagaag acggcatacg agattgacca gtgactggag ttcagacgt            49

<210> SEQ ID NO 610
<211> LENGTH: 49
<212> TYPE: DNA
<213> ORGANISM: Artificial Sequence
<220> FEATURE:
<223> OTHER INFORMATION: Synthetic Construct

<400> SEQUENCE: 610
caagcagaag acggcatacg agatagtcaa gtgactggag ttcagacgt            49

<210> SEQ ID NO 611
<211> LENGTH: 49
<212> TYPE: DNA
<213> ORGANISM: Artificial Sequence
<220> FEATURE:
<223> OTHER INFORMATION: Synthetic Construct

<400> SEQUENCE: 611
caagcagaag acggcatacg agatagttcc gtgactggag ttcagacgt            49

<210> SEQ ID NO 612
<211> LENGTH: 49
<212> TYPE: DNA
<213> ORGANISM: Artificial Sequence
<220> FEATURE:
<223> OTHER INFORMATION: Synthetic Construct

<400> SEQUENCE: 612
caagcagaag acggcatacg agatgatcag gtgactggag ttcagacgt            49

<210> SEQ ID NO 613
<211> LENGTH: 49
<212> TYPE: DNA
<213> ORGANISM: Artificial Sequence
<220> FEATURE:
<223> OTHER INFORMATION: Synthetic Construct
```

```
<400> SEQUENCE: 613
caagcagaag acggcatacg agatacagtg gtgactggag ttcagacgt        49

<210> SEQ ID NO 614
<211> LENGTH: 49
<212> TYPE: DNA
<213> ORGANISM: Artificial Sequence
<220> FEATURE:
<223> OTHER INFORMATION: Synthetic Construct

<400> SEQUENCE: 614
caagcagaag acggcatacg agattatact gtgactggag ttcagacgt        49

<210> SEQ ID NO 615
<211> LENGTH: 49
<212> TYPE: DNA
<213> ORGANISM: Artificial Sequence
<220> FEATURE:
<223> OTHER INFORMATION: Synthetic Construct

<400> SEQUENCE: 615
caagcagaag acggcatacg agatcaacaa gtgactggag ttcagacgt        49

<210> SEQ ID NO 616
<211> LENGTH: 49
<212> TYPE: DNA
<213> ORGANISM: Artificial Sequence
<220> FEATURE:
<223> OTHER INFORMATION: Synthetic Construct

<400> SEQUENCE: 616
caagcagaag acggcatacg agatgttgtt gtgactggag ttcagacgt        49

<210> SEQ ID NO 617
<211> LENGTH: 49
<212> TYPE: DNA
<213> ORGANISM: Artificial Sequence
<220> FEATURE:
<223> OTHER INFORMATION: Synthetic Construct

<400> SEQUENCE: 617
caagcagaag acggcatacg agattcggtt gtgactggag ttcagacgt        49

<210> SEQ ID NO 618
<211> LENGTH: 49
<212> TYPE: DNA
<213> ORGANISM: Artificial Sequence
<220> FEATURE:
<223> OTHER INFORMATION: Synthetic Construct

<400> SEQUENCE: 618
caagcagaag acggcatacg agatagtatt gtgactggag ttcagacgt        49

<210> SEQ ID NO 619
<211> LENGTH: 49
<212> TYPE: DNA
<213> ORGANISM: Artificial Sequence
<220> FEATURE:
<223> OTHER INFORMATION: Synthetic Construct

<400> SEQUENCE: 619
caagcagaag acggcatacg agattcttgt gtgactggag ttcagacgt        49

<210> SEQ ID NO 620
<211> LENGTH: 27
```

```
<212> TYPE: DNA
<213> ORGANISM: Artificial Sequence
<220> FEATURE:
<223> OTHER INFORMATION: Synthetic Construct

<400> SEQUENCE: 620
gaacagctgc agaacaggag ataacag                                          27

<210> SEQ ID NO 621
<211> LENGTH: 23
<212> TYPE: DNA
<213> ORGANISM: Artificial Sequence
<220> FEATURE:
<223> OTHER INFORMATION: Synthetic Construct

<400> SEQUENCE: 621
gttatctcct gttctgcagc tgt                                              23

<210> SEQ ID NO 622
<211> LENGTH: 22
<212> TYPE: DNA
<213> ORGANISM: Artificial Sequence
<220> FEATURE:
<223> OTHER INFORMATION: Synthetic Construct

<400> SEQUENCE: 622
atgacaggca ggggcaccgc gg                                               22

<210> SEQ ID NO 623
<211> LENGTH: 23
<212> TYPE: DNA
<213> ORGANISM: Artificial Sequence
<220> FEATURE:
<223> OTHER INFORMATION: Synthetic Construct

<400> SEQUENCE: 623
gagcgagcag cgtcttcgag agt                                              23

<210> SEQ ID NO 624
<211> LENGTH: 23
<212> TYPE: DNA
<213> ORGANISM: Artificial Sequence
<220> FEATURE:
<223> OTHER INFORMATION: Synthetic Construct

<400> SEQUENCE: 624
gcagacggca gtcactaggg ggc                                              23

<210> SEQ ID NO 625
<211> LENGTH: 23
<212> TYPE: DNA
<213> ORGANISM: Artificial Sequence
<220> FEATURE:
<223> OTHER INFORMATION: Synthetic Construct

<400> SEQUENCE: 625
gtcgcaggac agcttttcct aga                                              23

<210> SEQ ID NO 626
<211> LENGTH: 23
<212> TYPE: DNA
<213> ORGANISM: Artificial Sequence
<220> FEATURE:
<223> OTHER INFORMATION: Synthetic Construct

<400> SEQUENCE: 626
```

```
gggaagctgg gtgaatggag cga                                              23
```

<210> SEQ ID NO 627
<211> LENGTH: 23
<212> TYPE: DNA
<213> ORGANISM: Artificial Sequence
<220> FEATURE:
<223> OTHER INFORMATION: Synthetic Construct

<400> SEQUENCE: 627

```
gatccaggtg ctgcagaagg gat                                              23
```

<210> SEQ ID NO 628
<211> LENGTH: 23
<212> TYPE: DNA
<213> ORGANISM: Artificial Sequence
<220> FEATURE:
<223> OTHER INFORMATION: Synthetic Construct

<400> SEQUENCE: 628

```
gttatctcct gctctgcagc aga                                              23
```

<210> SEQ ID NO 629
<211> LENGTH: 23
<212> TYPE: DNA
<213> ORGANISM: Artificial Sequence
<220> FEATURE:
<223> OTHER INFORMATION: Synthetic Construct

<400> SEQUENCE: 629

```
gatatctcct gttctgcagg aga                                              23
```

<210> SEQ ID NO 630
<211> LENGTH: 20
<212> TYPE: DNA
<213> ORGANISM: Artificial Sequence
<220> FEATURE:
<223> OTHER INFORMATION: Synthetic Construct

<400> SEQUENCE: 630

```
ggatttccaa gtctccaccc                                                  20
```

<210> SEQ ID NO 631
<211> LENGTH: 19
<212> TYPE: DNA
<213> ORGANISM: Artificial Sequence
<220> FEATURE:
<223> OTHER INFORMATION: Synthetic Construct

<400> SEQUENCE: 631

```
tcccaccgta cacgcctac                                                   19
```

<210> SEQ ID NO 632
<211> LENGTH: 54
<212> TYPE: DNA
<213> ORGANISM: Artificial Sequence
<220> FEATURE:
<223> OTHER INFORMATION: Synthetic Construct

<400> SEQUENCE: 632

```
ggtttcagac aaaatcaaaa agaaggaagg tgctcacatt ccttaaatta agga            54
```

<210> SEQ ID NO 633
<211> LENGTH: 54
<212> TYPE: DNA
<213> ORGANISM: Artificial Sequence

```
<220> FEATURE:
<223> OTHER INFORMATION: Synthetic Construct

<400> SEQUENCE: 633
ggttttagac aaaatcaaaa agaaggaagg tgctcacatt ccttaaatta agga        54

<210> SEQ ID NO 634
<211> LENGTH: 24
<212> TYPE: DNA
<213> ORGANISM: Artificial Sequence
<220> FEATURE:
<223> OTHER INFORMATION: Synthetic Construct

<400> SEQUENCE: 634
gtgctcacat tccttaaatt aagg        24

<210> SEQ ID NO 635
<211> LENGTH: 24
<212> TYPE: DNA
<213> ORGANISM: Artificial Sequence
<220> FEATURE:
<223> OTHER INFORMATION: Synthetic Construct

<400> SEQUENCE: 635
ggctcacatt ccttaaatta agga        24
```